US010954497B2

(12) United States Patent
Gjermansen et al.

(10) Patent No.: US 10,954,497 B2
(45) Date of Patent: Mar. 23, 2021

(54) POLYPEPTIDES

(71) Applicant: NOVOZYMES A/S, Bagsvaerd (DK)

(72) Inventors: Morten Gjermansen, Greve (DK); Klaus Gori, Copenhagen (DK); Henrik Marcus Geertz-Hansen, Copenhagen (DK); Jesper Salomon, Holte (DK); Thomas Holberg Blicher, Copenhagen (DK); Mary Ann Stringer, Soborg (DK); Nikolaj Spodsberg, Holte (DK); Tianqi Sun, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/766,894

(22) PCT Filed: Oct. 7, 2016

(86) PCT No.: PCT/EP2016/074079
§ 371 (c)(1),
(2) Date: Apr. 9, 2018

(87) PCT Pub. No.: WO2017/060475
PCT Pub. Date: Apr. 13, 2017

(65) Prior Publication Data

US 2020/0123476 A1 Apr. 23, 2020

(30) Foreign Application Priority Data

Oct. 7, 2015 (DK) .......................... PA 2015 00615
Oct. 7, 2015 (DK) .......................... PA 2015 00617
Oct. 7, 2015 (DK) .......................... PA 2015 00618

(51) Int. Cl.

| | |
|---|---|
| ***C12N 9/22*** | (2006.01) |
| ***C11D 3/386*** | (2006.01) |
| ***C11D 3/20*** | (2006.01) |
| ***C11D 3/22*** | (2006.01) |
| ***C11D 3/37*** | (2006.01) |
| ***C11D 11/00*** | (2006.01) |

(52) U.S. Cl.
CPC .............. *C12N 9/22* (2013.01); *C11D 3/2065* (2013.01); *C11D 3/22* (2013.01); *C11D 3/3707* (2013.01); *C11D 3/38627* (2013.01); *C11D 3/38636* (2013.01); *C11D 3/38681* (2013.01); *C11D 11/0017* (2013.01); *C12Y 301/21* (2013.01); *C12Y 301/21001* (2013.01)

(58) Field of Classification Search
CPC ........................................................ C12N 9/22
USPC ........................................................ 435/199
See application file for complete search history.

(56) References Cited

U.S. PATENT DOCUMENTS

| | | | |
|---|---|---|---|
| 6,340,566 | B1 | 1/2002 | McCutchen-Maloney |
| 6,365,355 | B1 | 4/2002 | McCutchen-Maloney |
| 2012/0060300 | A1 | 3/2012 | Kim et al. |
| 2013/0189760 | A1 | 7/2013 | Mori |

FOREIGN PATENT DOCUMENTS

| | | | |
|---|---|---|---|
| EP | 2617824 | A1 | 7/2013 |
| WO | 01/98214 | A1 | 12/2001 |
| WO | 2009/107091 | A2 | 9/2009 |
| WO | 2009/111258 | A2 | 9/2009 |
| WO | 2011/015327 | A1 | 2/2011 |
| WO | 2011/098579 | A1 | 8/2011 |
| WO | 2014/087011 | A1 | 6/2014 |
| WO | 2015/181286 | A1 | 12/2015 |
| WO | 2017162836 | A1 | 9/2017 |
| WO | 2018/011276 | A1 | 1/2018 |

OTHER PUBLICATIONS

Anonymous, NCBI Accession No. WP_004251670 (2013).
Anonymous, UniParc Accession No. UPI0003A82032 (2013).
Anonymous, NCBI Accession No. WP_0275722554 (2014).
Anonymous, NCBI Accession No. WP_029440352 (2014).
Anonymous, NCBI Accession No. WP_034664156 (2014).
Anonymous, NCBI Accession No. WP_027924635 (2014).
Anonymous, NCBI Accession No. WP_039304398 (2015).
Anonymous, NCBI Accession No. WP_041089515 (2015).
Anonymous, NCBI Accession No. WP_045521827 (2015).
Anonymous, NCBI Accession No. WP_047969415 (2015).
Anonymous, NCBI Accession No. WP_051450038 (2015).
Anonymous, NCBI Accession No. WP_030603405 (2016).
Anonymous, NCBI Accession No. WP_031424130 (2016).
Anonymous, NCBI Accession No. WP_034817012 (2016).
Anonymous, NCBI Accession No. WP_035510436 (2016).
Feldgarden et al., GenBank Accession No. EJR08198 (2012).
Franco et al., UniProt Accession No. AOAOL1HKH6 (2015).
Gao et al., PloS Genetics, vol. 7, Issue 1, article E1001264, pp. 1-18 (2011).
Gori et al., IP.com No. IPCOM000237363D, pp. 1-94 (2014).
Greiner-Stoefelle et al., EBI Accession No. JA286954 (2011).
Kwak et al., UniProt Accession No. A0A086GGG3 (2014).
Lian et al., GenBank Accession No. AFK65439 (2013).
Liu et al., GenBank Accession No. KMY52255 (2015).
McCuthchen-Mulaney, EBI Accession No. AAE89259 (2014).
McCuthchen-Mulaney, EBI Accession No. AAM56188 (2014).
Murphy et al., UniProt Accession No. AOAOT9L4U8 (2015).

(Continued)

*Primary Examiner* — Tekchand Saidha
(74) *Attorney, Agent, or Firm* — Elias Lambiris

(57) ABSTRACT

The present invention relates to polypeptides, nucleotides encoding the polypeptide, as well as methods of producing the polypeptides. The present invention also relates to detergent composition comprising polypeptides, a laundering method and the use of polypeptides.

15 Claims, 3 Drawing Sheets

Specification includes a Sequence Listing.

(56) References Cited

OTHER PUBLICATIONS

Neafsey et al., UniProt Accession No. AOAOJ8TUN1 (2010).
Nijland et al., PLoS One, vol. 5, No. 12, article E15668, pp. 1-7 (2010).
O'Connell et al., UniProt Accession No. H1V7F8 (2012).
Osei et al., UniProt Accession No. AOAOP8GOA5 (2016).
Sharma et al., UniProt Accession No. AOAOF5R1U3 (2015).
Shields et al., PLoS One, vol. 8, No. 2, article E55339, pp. 1-13 (2013).
Tran et al., UniProt Accession No. A0A0K6K3H5 (2015).
Vandeputte et al., UniProt Accession No. A0A084G9H5 (2014).
Wang et al., GenBank Accession No. AJK28734 (2015).
Wang et al., UniProt Accession No. A0A0C5AGR7 (2015).
Yoon et al., UniProt Accession No. A0A084H293 (2005).
Zhu et al., UniProt Accession No. A0A0F7TT23 (2014).
Anonymous, 2014, NCBI Accession No. WP_028551502.
Baumgarten et al, 2015, Genbank Accession No. KXJ07836.
Chancey et al, 2012, Uniprot accession No. J1GWI8.
Chen et al, 2013, Uniprot accession No. S3D1S1.
Chen et al, 2013, Uniprot accession No. S3DWR8.
Coleman et al, 2009, EBI Accession No. C7YPZ7.
Daniel, 2015, Uniprot accession No. A0A0E4HDQ4.
Gostin et al, 2014, EBI Accession No. A0A074YFK3.
Hymes et al, 2013, Journal of Infectious Disease 207(10), 1491-1497.
Ma et al, 2012, EBI Accession No. H6NAU2.
Marincowitz et al, Genbank accession No. EU552123.
Martin et al, 1996, Trends in biochemical sciences 21(8), 283-285.
Ngo et al, 1994, The Protein Folding Problem and Tertiary Structure Prediction, vol. 433 ABD pp. 492-495.
Anonymous, Merriam-Webster Dictionary, definition of granule (2020).
Birren et al., EBI Accession No. Q5ARC4 (2005).
Birren et al., EBI Accession No. Q2GRF9 (2006).
Cuomo et al., EBI Accession No. U7Q814 (2014).
Cuomo et al., EBI Accession No. A0A0D2ITS4 (2015).
Fedorova et al., EBI Accession No. A1D7D1 (2007).
Gibson, EBI Accession No. A0A0A1V6B7 (2015).
Hane et al., EBI Accession No. QOU4Q1 (2006).
Klosterman et al., EBI Accession No. G2WSK6 (2011).
Lawrence et al., EBI Accession No. A0A0G2FAG3 (2015).
Ohm et al., EBI Accession No. M2N7N4 (2013).
Ohm et al., EBI Access No. M2S5C4 (2013).
Pei et al., EBI Accession No. A2QFZ2 (2007).
Traeger et al., EBI Accession No. U4LM18 (2013).
Wang et al, 2014, EBI Accession No. W3WUK5 (2014).
Goh et al., UniProt Accession No. A0A0C2VMI6 (2015).
Yaakop et al., UniProt Accession No. A0A0B5ASW2 (2015).
Birren et al., GenBank Accession No. EAT79147.2 (2007).
Birren et al., GenBank Accession No. EAQ85431.1 (2015).
Cuomo et al., GenBank Accession No. ERT03205.1 (2015).
Cuomo et al., GenBank Accession No. KIX09484.1 (2015).
Giuliano et al., GenBank Accession No. EXV05759.1 (2014).
Liu et al., GenBank Accession No. ETS77558.1 (2014).
Ma et al., GenBank Accession No. EGY17920.1 (2011).
Ma et al., GenBank Accession No. CCF36160.1 (2012).
Morales-Cruz et al., GenBank Accession No. KKY31181.1 (2015).
Nierman, GenBank Accession No. EAW21625.1 (2006).
Ohm et al., GenBank Accession No. EMC94815.1 (2013).
Ohm et al., GenBank Accession No. EMD62363.1 (2013).
Pel et al., GenBank Accession No. CAK38102.1 (2011).
Vandeputte et al., GenBank Accession No. KEZ43987.1 (2014).
Wortman et al., GenBank Accession No. CBF82427.1 (2015).
Yoon et al., GenBank Accession No. KEZ53705.1 (2014).

GYS –clade alignment

Alignment of polypeptides in the NAWK clade

Alignment of polypeptides in the KNAW clade

SEQUENCE LISTING

```
<160> NUMBER OF SEQ ID NOS: 210

<210> SEQ ID NO 1
<211> LENGTH: 633
<212> TYPE: DNA
<213> ORGANISM: Bacillus species

<400> SEQUENCE: 1

atgttgaaaa agtcgttgct gttctctttg tcgcttgttt tatcattgct tgtttttcag      60

tatgatttat tatccgcttc tgccttgcct ccagatttgc catccaaatc tactacccaa     120

gcacaactta attcgttaaa tgtgaaaaat gaagaatcca tgagtggcta tagtcgagaa     180

aaattccctc actggattag tcaaggggat ggttgtgata caaggcaagt gatccttaag     240

cgtgatgccg acaattatag tggtaattgt ccagtgactt caggtaaatg gtatagctat     300

tatgatggca tcactttcaa tgacccctca caattagata ttgaccatgt cgttccactc     360

gcagaagcat ggcgttctgg ggcaagtagt tggtcaactg ctaaaagaga ggacttcgcc     420

aatgacctca atggaccaca actcatcgca gtatcagcca gctcaaatcg atccaaaggt     480

gaccaagatc catccacatg gcaaccacct cgtgcaggtg caaattgtgc ttatgctaaa     540

atgtggatca atacaaaata caattggggt ttgcatttgc agagttctga aaaaacagct     600

cttcaaggaa tgctcaatag ttgctcctat taa                                  633


<210> SEQ ID NO 2
<211> LENGTH: 210
<212> TYPE: PRT
<213> ORGANISM: Bacillus species

<400> SEQUENCE: 2
```

-continued

```
Met Leu Lys Lys Ser Leu Leu Phe Ser Leu Ser Leu Val Leu Ser Leu
1               5                   10                  15

Leu Val Phe Gln Tyr Asp Leu Leu Ser Ala Ser Ala Leu Pro Pro Asp
            20                  25                  30

Leu Pro Ser Lys Ser Thr Thr Gln Ala Gln Leu Asn Ser Leu Asn Val
        35                  40                  45

Lys Asn Glu Glu Ser Met Ser Gly Tyr Ser Arg Glu Lys Phe Pro His
    50                  55                  60

Trp Ile Ser Gln Gly Asp Gly Cys Asp Thr Arg Gln Val Ile Leu Lys
65                  70                  75                  80

Arg Asp Ala Asp Asn Tyr Ser Gly Asn Cys Pro Val Thr Ser Gly Lys
                85                  90                  95

Trp Tyr Ser Tyr Tyr Asp Gly Ile Thr Phe Asn Asp Pro Ser Gln Leu
            100                 105                 110

Asp Ile Asp His Val Val Pro Leu Ala Glu Ala Trp Arg Ser Gly Ala
        115                 120                 125

Ser Ser Trp Ser Thr Ala Lys Arg Glu Asp Phe Ala Asn Asp Leu Asn
    130                 135                 140

Gly Pro Gln Leu Ile Ala Val Ser Ala Ser Ser Asn Arg Ser Lys Gly
145                 150                 155                 160

Asp Gln Asp Pro Ser Thr Trp Gln Pro Pro Arg Ala Gly Ala Asn Cys
                165                 170                 175

Ala Tyr Ala Lys Met Trp Ile Asn Thr Lys Tyr Asn Trp Gly Leu His
            180                 185                 190

Leu Gln Ser Ser Glu Lys Thr Ala Leu Gln Gly Met Leu Asn Ser Cys
        195                 200                 205

Ser Tyr
    210
```

<210> SEQ ID NO 3
<211> LENGTH: 633
<212> TYPE: DNA
<213> ORGANISM: Bacillus horikoshii

<400> SEQUENCE: 3

```
atgcttaaaa aatccatgtt ggttgttttt gcatttatcc tgtcgttctc agccctgcag      60

cttgacccac aaaccgtctc tgcacttccc cctggcacac cgaccaagtc tgaagcgcaa     120

aaccaattga actccttgac cgtaaaatcg gagggctcta tgaccgggta ctcgagggac     180

ttattcccac actggagcgg ccaaggcaat ggttgcgata cccgccaaat cgtcttgcaa     240

cgcgatgccg actattacac tggtacctgt cccactactt ccggaaaatg gtatagttat     300

tttgatggtg tcattgtgta ttctccgtct gagattgaca ttgatcacat tgttcctttg     360

gcagaggctt ggcgttctgg tgccagtagc tggacaaccg aacagcgccg tgcgtttgct     420

aacgacctca acggcccaca gttgattgcc gtgacagcta gcgttaaccg ttccaaagga     480

gaccaagacc catccacatg gcagccacct cgtgccggcg ctcgctgtgc ctatgcaaaa     540

tggtggatca atacgaaaca ccgctggaac ctacaccttc agtcatctga gaaatcttct     600

ttgcaaacga tgcttaacgg ctgcgcttac taa                                  633
```

<210> SEQ ID NO 4
<211> LENGTH: 210
<212> TYPE: PRT
<213> ORGANISM: Bacillus horikoshii

<400> SEQUENCE: 4

```
Met Leu Lys Lys Ser Met Leu Val Val Phe Ala Phe Ile Leu Ser Phe
1               5                   10                  15

Ser Ala Leu Gln Leu Asp Pro Gln Thr Val Ser Ala Leu Pro Pro Gly
            20                  25                  30

Thr Pro Thr Lys Ser Glu Ala Gln Asn Gln Leu Asn Ser Leu Thr Val
        35                  40                  45

Lys Ser Glu Gly Ser Met Thr Gly Tyr Ser Arg Asp Leu Phe Pro His
    50                  55                  60

Trp Ser Gly Gln Gly Asn Gly Cys Asp Thr Arg Gln Ile Val Leu Gln
65                  70                  75                  80

Arg Asp Ala Asp Tyr Tyr Thr Gly Thr Cys Pro Thr Thr Ser Gly Lys
                85                  90                  95

Trp Tyr Ser Tyr Phe Asp Gly Val Ile Val Tyr Ser Pro Ser Glu Ile
            100                 105                 110

Asp Ile Asp His Ile Val Pro Leu Ala Glu Ala Trp Arg Ser Gly Ala
        115                 120                 125

Ser Ser Trp Thr Thr Glu Gln Arg Arg Ala Phe Ala Asn Asp Leu Asn
    130                 135                 140

Gly Pro Gln Leu Ile Ala Val Thr Ala Ser Val Asn Arg Ser Lys Gly
145                 150                 155                 160

Asp Gln Asp Pro Ser Thr Trp Gln Pro Pro Arg Ala Gly Ala Arg Cys
                165                 170                 175

Ala Tyr Ala Lys Trp Trp Ile Asn Thr Lys His Arg Trp Asn Leu His
            180                 185                 190

Leu Gln Ser Ser Glu Lys Ser Ser Leu Gln Thr Met Leu Asn Gly Cys
        195                 200                 205

Ala Tyr
    210
```

<210> SEQ ID NO 5
<211> LENGTH: 609
<212> TYPE: DNA
<213> ORGANISM: Paenibacillus species

<400> SEQUENCE: 5

```
ttgaaacgac ggcttattcc tttccttctt gtcctcgtcc tggttgcgac cgggtgcgca     60

ctggcgcaga agccccttgc cgacgcgccg cggcagacgg agcacgacga ttacgactac    120

gagctgatct ttccaagcga cgactatccc gaaacggcgc tgcacattct cggggcgatc    180

gagcaagggt attccgacgt atgcacgatc gaccgcggcg gggcggaaga gaaccgcaag    240

caatcgctgg ccggaataga gacgcgctcg ggctacgacc gcgacgaatg gccgatggcg    300

atgtgcgagg aaggcggagc gggcgcaagc gtcgcctaca tcgatgccag cgacaaccgg    360

ggagccggca gctgggtcgg gcatcagctg tcggcctatg aagacggcac gaaaattttg    420

tttatcgtag agaaacccaa agttctgttt ccgaaccagc cggcaaccgc ggctccggcc    480

ggcaacaacg aggttcgcta tcccaattgc gccgccgtgc gcgaggcggg caaagcgcct    540

ctgcgcaagg gagatcccgg ctactccgct aaattggacc gggacggcga cggcgtcgct    600

tgcgaatag                                                            609
```

<210> SEQ ID NO 6
<211> LENGTH: 202
<212> TYPE: PRT
<213> ORGANISM: Paenibacillus species

<400> SEQUENCE: 6

Met Lys Arg Arg Leu Ile Pro Phe Leu Leu Val Leu Val Leu Val Ala
1 5 10 15

Thr Gly Cys Ala Leu Ala Gln Lys Pro Leu Ala Asp Ala Pro Arg Gln
20 25 30

Thr Glu His Asp Asp Tyr Asp Tyr Glu Leu Ile Phe Pro Ser Asp Asp
35 40 45

Tyr Pro Glu Thr Ala Leu His Ile Leu Gly Ala Ile Glu Gln Gly Tyr
50 55 60

Ser Asp Val Cys Thr Ile Asp Arg Gly Gly Ala Glu Glu Asn Arg Lys
65 70 75 80

Gln Ser Leu Ala Gly Ile Glu Thr Arg Ser Gly Tyr Asp Arg Asp Glu
85 90 95

Trp Pro Met Ala Met Cys Glu Glu Gly Gly Ala Gly Ala Ser Val Ala
100 105 110

Tyr Ile Asp Ala Ser Asp Asn Arg Gly Ala Gly Ser Trp Val Gly His
115 120 125

Gln Leu Ser Ala Tyr Glu Asp Gly Thr Lys Ile Leu Phe Ile Val Glu
130 135 140

Lys Pro Lys Val Leu Phe Pro Asn Gln Pro Ala Thr Ala Ala Pro Ala
145 150 155 160

Gly Asn Asn Glu Val Arg Tyr Pro Asn Cys Ala Ala Val Arg Glu Ala
165 170 175

Gly Lys Ala Pro Leu Arg Lys Gly Asp Pro Gly Tyr Ser Ala Lys Leu
180 185 190

Asp Arg Asp Gly Asp Gly Val Ala Cys Glu
195 200

<210> SEQ ID NO 7
<211> LENGTH: 245
<212> TYPE: PRT
<213> ORGANISM: Serratia marcescens

<400> SEQUENCE: 7

Asp Thr Leu Glu Ser Ile Asp Asn Cys Ala Val Gly Cys Pro Thr Gly
1 5 10 15

Gly Ser Ser Asn Val Ser Ile Val Arg His Ala Tyr Thr Leu Asn Asn
20 25 30

Asn Ser Thr Thr Lys Phe Ala Asn Trp Val Ala Tyr His Ile Thr Lys
35 40 45

Asp Thr Pro Ala Ser Gly Lys Thr Arg Asn Trp Lys Thr Asp Pro Ala
50 55 60

Leu Asn Pro Ala Asp Thr Leu Ala Pro Ala Asp Tyr Thr Gly Ala Asn
65 70 75 80

Ala Ala Leu Lys Val Asp Arg Gly His Gln Ala Pro Leu Ala Ser Leu
85 90 95

Ala Gly Val Ser Asp Trp Glu Ser Leu Asn Tyr Leu Ser Asn Ile Thr
100 105 110

Pro Gln Lys Ser Asp Leu Asn Gln Gly Ala Trp Ala Arg Leu Glu Asp
115 120 125

Gln Glu Arg Lys Leu Ile Asp Arg Ala Asp Ile Ser Ser Val Tyr Thr
130 135 140

Val Thr Gly Pro Leu Tyr Glu Arg Asp Met Gly Lys Leu Pro Gly Thr
145 150 155 160

```
Gln Lys Ala His Thr Ile Pro Ser Ala Tyr Trp Lys Val Ile Phe Ile
                165                 170                 175

Asn Asn Ser Pro Ala Val Asn His Tyr Ala Ala Phe Leu Phe Asp Gln
            180                 185                 190

Asn Thr Pro Lys Gly Ala Asp Phe Cys Gln Phe Arg Val Thr Val Asp
        195                 200                 205

Glu Ile Glu Lys Arg Thr Gly Leu Ile Ile Trp Ala Gly Leu Pro Asp
    210                 215                 220

Asp Val Gln Ala Ser Leu Lys Ser Lys Pro Gly Val Leu Pro Glu Leu
225                 230                 235                 240

Met Gly Cys Lys Asn
                245


<210> SEQ ID NO 8
<211> LENGTH: 182
<212> TYPE: PRT
<213> ORGANISM: Bacillus species

<400> SEQUENCE: 8

Leu Pro Pro Asp Leu Pro Ser Lys Ser Thr Thr Gln Ala Gln Leu Asn
1               5                   10                  15

Ser Leu Asn Val Lys Asn Glu Glu Ser Met Ser Gly Tyr Ser Arg Glu
            20                  25                  30

Lys Phe Pro His Trp Ile Ser Gln Gly Asp Gly Cys Asp Thr Arg Gln
        35                  40                  45

Val Ile Leu Lys Arg Asp Ala Asp Asn Tyr Ser Gly Asn Cys Pro Val
    50                  55                  60

Thr Ser Gly Lys Trp Tyr Ser Tyr Tyr Asp Gly Ile Thr Phe Asn Asp
65                  70                  75                  80

Pro Ser Gln Leu Asp Ile Asp His Val Val Pro Leu Ala Glu Ala Trp
                85                  90                  95

Arg Ser Gly Ala Ser Ser Trp Ser Thr Ala Lys Arg Glu Asp Phe Ala
            100                 105                 110

Asn Asp Leu Asn Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Asn Cys Ala Tyr Ala Lys Met Trp Ile Asn Thr Lys Tyr Asn
145                 150                 155                 160

Trp Gly Leu His Leu Gln Ser Ser Glu Lys Thr Ala Leu Gln Gly Met
                165                 170                 175

Leu Asn Ser Cys Ser Tyr
            180


<210> SEQ ID NO 9
<211> LENGTH: 182
<212> TYPE: PRT
<213> ORGANISM: Bacillus horikoshii

<400> SEQUENCE: 9

Leu Pro Pro Gly Thr Pro Thr Lys Ser Glu Ala Gln Asn Gln Leu Asn
1               5                   10                  15

Ser Leu Thr Val Lys Ser Glu Gly Ser Met Thr Gly Tyr Ser Arg Asp
            20                  25                  30

Leu Phe Pro His Trp Ser Gly Gln Gly Asn Gly Cys Asp Thr Arg Gln
        35                  40                  45
```

```
Ile Val Leu Gln Arg Asp Ala Asp Tyr Tyr Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ser Leu Gln Thr Met
                165                 170                 175

Leu Asn Gly Cys Ala Tyr
            180
```

<210> SEQ ID NO 10
<211> LENGTH: 180
<212> TYPE: PRT
<213> ORGANISM: Paenibacillus species

<400> SEQUENCE: 10

```
Gln Lys Pro Leu Ala Asp Ala Pro Arg Gln Thr Glu His Asp Asp Tyr
1               5                   10                  15

Asp Tyr Glu Leu Ile Phe Pro Ser Asp Asp Tyr Pro Glu Thr Ala Leu
            20                  25                  30

His Ile Leu Gly Ala Ile Glu Gln Gly Tyr Ser Asp Val Cys Thr Ile
        35                  40                  45

Asp Arg Gly Gly Ala Glu Glu Asn Arg Lys Gln Ser Leu Ala Gly Ile
    50                  55                  60

Glu Thr Arg Ser Gly Tyr Asp Arg Asp Glu Trp Pro Met Ala Met Cys
65                  70                  75                  80

Glu Glu Gly Gly Ala Gly Ala Ser Val Ala Tyr Ile Asp Ala Ser Asp
                85                  90                  95

Asn Arg Gly Ala Gly Ser Trp Val Gly His Gln Leu Ser Ala Tyr Glu
            100                 105                 110

Asp Gly Thr Lys Ile Leu Phe Ile Val Glu Lys Pro Lys Val Leu Phe
        115                 120                 125

Pro Asn Gln Pro Ala Thr Ala Ala Pro Ala Gly Asn Asn Glu Val Arg
    130                 135                 140

Tyr Pro Asn Cys Ala Ala Val Arg Glu Ala Gly Lys Ala Pro Leu Arg
145                 150                 155                 160

Lys Gly Asp Pro Gly Tyr Ser Ala Lys Leu Asp Arg Asp Gly Asp Gly
                165                 170                 175

Val Ala Cys Glu
            180
```

<210> SEQ ID NO 11
<211> LENGTH: 182
<212> TYPE: PRT
<213> ORGANISM: Bacillus species

<400> SEQUENCE: 11

```
Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180


<210> SEQ ID NO 12
<211> LENGTH: 182
<212> TYPE: PRT
<213> ORGANISM: Bacillus species

<400> SEQUENCE: 12

Leu Pro Pro Gly Thr Pro Ser Lys Ser Glu Ala Gln Ser Gln Leu Asn
1               5                   10                  15

Ala Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Ala Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180
```

<210> SEQ ID NO 13
<211> LENGTH: 182
<212> TYPE: PRT
<213> ORGANISM: Bacillus horikoshii

<400> SEQUENCE: 13

```
Leu Pro Pro Gly Thr Pro Ser Lys Ser Glu Ala Gln Ser Gln Leu Asn
1               5                   10                  15

Ser Leu Thr Val Lys Ser Glu Asp Pro Met Thr Gly Tyr Ser Arg Asp
            20                  25                  30

His Phe Pro His Trp Ser Gly Gln Gly Asn Gly Cys Asp Thr Arg Gln
        35                  40                  45

Ile Val Leu Gln Arg Asp Ala Asp Tyr Tyr Ser Gly Asn Cys Pro Val
    50                  55                  60

Thr Ser Gly Lys Trp Tyr Ser Tyr Phe Asp Gly Val Ile Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Glu Gln Arg Arg Ser Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140

Gly Ala Arg Cys Ala Tyr Ala Lys Trp Trp Ile Asn Thr Lys His Arg
145                 150                 155                 160

Trp Asn Leu His Leu Gln Ser Ser Glu Lys Ser Ala Leu Gln Thr Met
                165                 170                 175

Leu Asn Gly Cys Val Tyr
            180
```

<210> SEQ ID NO 14
<211> LENGTH: 182
<212> TYPE: PRT
<213> ORGANISM: Bacillus horikoshii

<400> SEQUENCE: 14

```
Leu Pro Pro Gly Thr Pro Ser Lys Ser Glu Ala Gln Ser Gln Leu Asn
1               5                   10                  15

Ser Leu Thr Val Lys Thr Glu Asp Pro Met Thr Gly Tyr Ser Arg Asp
            20                  25                  30

Leu Phe Pro His Trp Ser Gly Gln Gly Ser Gly Cys Asp Thr Arg Gln
        35                  40                  45

Ile Val Leu Gln Arg Asp Ala Asp Tyr Phe Thr Gly Thr Cys Pro Thr
    50                  55                  60

Thr Ser Gly Lys Trp Tyr Ser Tyr Phe Asp Gly Val Ile Val Tyr Ser
65                  70                  75                  80

Pro Ser Glu Ile Asp Val Asp His Ile Val Pro Leu Ala Glu Ala Trp
                85                  90                  95

Arg Ser Gly Ala Ser Ser Trp Thr Thr Glu Gln Arg Arg Ala Phe Ala
            100                 105                 110

Asn Asp Leu Thr Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ala
    130                 135                 140
```

Gly Ala Arg Cys Ala Tyr Ala Lys Trp Trp Ile Asn Thr Lys His Arg
145 150 155 160

Trp Asn Leu His Leu Gln Ser Ser Glu Lys Ser Ser Leu Gln Thr Met
165 170 175

Leu Asn Gly Cys Ala Tyr
180

<210> SEQ ID NO 15
<211> LENGTH: 182
<212> TYPE: PRT
<213> ORGANISM: Bacillus species

<400> SEQUENCE: 15

Leu Pro Pro Gly Thr Pro Ser Lys Ser Glu Ala Gln Ser Gln Leu Asn
1 5 10 15

Ala Leu Thr Val Lys Ala Glu Asp Pro Met Thr Gly Tyr Ser Arg Asn
20 25 30

Leu Phe Pro His Trp Asn Ser Gln Gly Asn Gly Cys Asn Thr Arg Gln
35 40 45

Leu Val Leu Gln Arg Asp Ala Asp Tyr Tyr Ser Gly Asn Cys Pro Val
50 55 60

Thr Ser Gly Arg Trp Tyr Ser Tyr Phe Asp Gly Val Val Val Thr Ser
65 70 75 80

Pro Ser Glu Ile Asp Ile Asp His Ile Val Pro Leu Ala Glu Ala Trp
85 90 95

Arg Ser Gly Ala Ser Ser Trp Thr Thr Glu Lys Arg Lys Glu Phe Ala
100 105 110

Asn Asp Leu Asn Gly Pro Gln Leu Ile Ala Val Thr Ala Ser Val Asn
115 120 125

Arg Ser Lys Gly Asp Gln Asp Pro Ser Thr Trp Gln Pro Pro Arg Ala
130 135 140

Ala Ala Arg Cys Gly Tyr Ala Lys Trp Trp Ile Asn Thr Lys Tyr Arg
145 150 155 160

Trp Asp Leu Ser Leu Gln Ser Ser Glu Lys Ser Ser Leu Gln Thr Met
165 170 175

Leu Asn Thr Cys Ser Tyr
180

<210> SEQ ID NO 16
<211> LENGTH: 182
<212> TYPE: PRT
<213> ORGANISM: Bacillus species

<400> SEQUENCE: 16

Leu Pro Pro Gly Thr Pro Ser Lys Ser Gln Ala Gln Ser Gln Leu Asn
1 5 10 15

Ala Leu Thr Val Lys Ala Glu Asp Pro Met Thr Gly Tyr Ser Arg Asn
20 25 30

Leu Phe Pro His Trp Ser Ser Gln Gly Asn Gly Cys Asn Thr Arg Gln
35 40 45

Leu Val Leu Gln Arg Asp Ala Asp Tyr Tyr Ser Gly Asn Cys Pro Val
50 55 60

Thr Ser Gly Arg Trp Tyr Ser Tyr Phe Asp Gly Val Val Val Thr Ser
65 70 75 80

Pro Ser Glu Ile Asp Ile Asp His Ile Val Pro Leu Ala Glu Ala Trp
85 90 95

```
Arg Ser Gly Ala Ser Ser Trp Thr Thr Glu Lys Arg Arg Glu Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Val
    130                 135                 140

Ala Ala Arg Cys Gly Tyr Ala Lys Trp Trp Ile Asn Thr Lys Tyr Arg
145                 150                 155                 160

Trp Asp Leu Ser Leu Gln Ser Ser Glu Lys Ser Ser Leu Gln Thr Met
                165                 170                 175

Leu Asn Thr Cys Ser Tyr
            180


<210> SEQ ID NO 17
<211> LENGTH: 182
<212> TYPE: PRT
<213> ORGANISM: Bacillus species

<400> SEQUENCE: 17

Leu Pro Pro Gly Thr Pro Ser Lys Ser Glu Ala Gln Ser Gln Leu Thr
1               5                   10                  15

Ser Leu Thr Val Lys Pro Glu Asp Pro Met Thr Gly Tyr Ser Arg Asp
            20                  25                  30

His Phe Pro His Trp Ile Ser Gln Gly Asn Gly Cys Asn Thr Arg Gln
        35                  40                  45

Ile Val Leu Gln Arg Asp Ala Asp Tyr Tyr Ser Gly Asn Cys Pro Val
    50                  55                  60

Thr Thr Gly Lys Trp Tyr Ser Tyr Phe Asp Gly Val Ile Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Ala Glu Gln Arg Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Thr
    130                 135                 140

Gly Ala Arg Cys Ala Tyr Ala Lys Trp Trp Ile Asn Thr Lys Tyr Arg
145                 150                 155                 160

Trp Gly Leu His Leu Gln Ser Ser Glu Lys Ser Ser Leu Gln Ser Met
                165                 170                 175

Leu Asn Gly Cys Ala Tyr
            180


<210> SEQ ID NO 18
<211> LENGTH: 185
<212> TYPE: PRT
<213> ORGANISM: Bacillus species

<400> SEQUENCE: 18

Ala Ser Ala Phe Pro Pro Gly Thr Pro Ser Lys Ser Thr Ala Gln Ser
1               5                   10                  15

Gln Leu Asn Ser Leu Pro Val Lys Ser Glu Gly Ser Met Asn Gly Tyr
            20                  25                  30

Ser Arg Asp Lys Phe Pro His Trp Ile Ser Gln Gly Asp Gly Cys Asp
        35                  40                  45
```

Thr Arg Gln Leu Val Leu Lys Arg Asp Gly Asp Tyr Tyr Ser Gly Ser
50 55 60

Cys Pro Val Thr Ser Gly Lys Trp Tyr Ser Tyr Tyr Asp Gly Ile Thr
65 70 75 80

Val Tyr Ser Pro Ser Glu Ile Asp Ile Asp His Ile Val Pro Leu Ala
85 90 95

Glu Ala Trp Arg Ser Gly Ala Ser Gly Trp Thr Thr Glu Lys Arg Gln
100 105 110

Ser Phe Ala Asn Asp Leu Asn Gly Pro Gln Leu Ile Ala Val Thr Ala
115 120 125

Ser Val Asn Arg Ser Lys Gly Asp Gln Asp Pro Ser Thr Trp Gln Pro
130 135 140

Pro Arg Ser Gly Ser His Cys Ala Tyr Ala Lys Met Trp Val Asn Thr
145 150 155 160

Lys Tyr Arg Trp Gly Leu His Leu Gln Ser Ala Glu Lys Ser Ala Leu
165 170 175

Gln Ser Met Leu Asn Ala Cys Ser Tyr
180 185

<210> SEQ ID NO 19
<211> LENGTH: 185
<212> TYPE: PRT
<213> ORGANISM: Bacillus horneckiae

<400> SEQUENCE: 19

Ala Ser Ala Phe Pro Pro Gly Thr Pro Ser Lys Ser Thr Ala Gln Ser
1 5 10 15

Gln Leu Asn Ser Leu Thr Val Lys Ser Glu Gly Ser Met Thr Gly Tyr
20 25 30

Ser Arg Asp Lys Phe Pro His Trp Ile Ser Gln Gly Asp Gly Cys Asp
35 40 45

Thr Arg Gln Leu Val Leu Lys Arg Asp Gly Asp Tyr Tyr Ser Gly Asn
50 55 60

Cys Pro Val Thr Ser Gly Lys Trp Tyr Ser Tyr Tyr Asp Gly Ile Thr
65 70 75 80

Val Tyr Ser Pro Ser Glu Ile Asp Ile Asp His Ile Val Pro Leu Ala
85 90 95

Glu Ala Trp Arg Ser Gly Ala Ser Gly Trp Thr Thr Glu Lys Arg Gln
100 105 110

Ser Phe Ala Asn Asp Leu Asn Gly Pro Gln Leu Ile Ala Val Thr Ala
115 120 125

Ser Val Asn Arg Ser Lys Gly Asp Gln Asp Pro Ser Thr Trp Gln Pro
130 135 140

Pro Arg Ser Gly Ser His Cys Ala Tyr Ala Lys Met Trp Val Asn Thr
145 150 155 160

Lys Tyr Arg Trp Gly Leu His Val Gln Ser Ala Glu Lys Ser Ala Leu
165 170 175

Gln Ser Met Leu Asn Ala Cys Ser Tyr
180 185

<210> SEQ ID NO 20
<211> LENGTH: 182
<212> TYPE: PRT
<213> ORGANISM: Bacillus species

<400> SEQUENCE: 20

```
Phe Pro Pro Glu Ile Pro Ser Lys Ser Thr Ala Gln Ser Gln Leu Asn
1               5                   10                  15

Ser Leu Thr Val Lys Ser Glu Asp Ala Met Thr Gly Tyr Ser Arg Asp
            20                  25                  30

Lys Phe Pro His Trp Ile Ser Gln Gly Asp Gly Cys Asp Thr Arg Gln
        35                  40                  45

Met Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Arg Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Ser
    130                 135                 140

Gly Ala Arg Cys Ala Tyr Ala Lys Met Trp Val Asn Thr Lys Tyr Arg
145                 150                 155                 160

Trp Gly Leu His Leu Gln Ser Ala Glu Lys Ser Gly Leu Glu Ser Met
                165                 170                 175

Leu Asn Thr Cys Ser Tyr
            180


<210> SEQ ID NO 21
<211> LENGTH: 182
<212> TYPE: PRT
<213> ORGANISM: Bacillus cibi

<400> SEQUENCE: 21

Thr Pro Pro Gly Thr Pro Ser Lys Ser Ala Ala Gln Ser Gln Leu Asn
1               5                   10                  15

Ala Leu Thr Val Lys Thr Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
```

180

<210> SEQ ID NO 22
<211> LENGTH: 182
<212> TYPE: PRT
<213> ORGANISM: Bacillus species

<400> SEQUENCE: 22

```
Phe Pro Pro Gly Thr Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Gly Gln Gly Ser Gly Cys Asp Thr Arg Gln
        35                  40                  45

Leu Val Leu Gln Arg Asp Ala Asp Tyr Tyr Ser Gly Ser Cys Pro Val
    50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Ser Thr Gln Lys Arg Lys Asp Phe Ala
            100                 105                 110

Asn Asp Leu Ser Gly Pro Gln Leu Ile Ala Val Ser Ala Ser Ser Asn
        115                 120                 125

Arg Ser Lys Gly Asp Gln Asp Pro Ser Thr Trp Gln Pro Thr Arg Ser
    130                 135                 140

Gly Ala Ala Cys Gly Tyr Ser Lys Trp Trp Ile Ser Thr Lys His Lys
145                 150                 155                 160

Trp Gly Leu Ser Leu Gln Ser Ser Glu Lys Asn Ala Leu Gln Gly Met
                165                 170                 175

Leu Asn Ser Cys Val Tyr
            180
```

<210> SEQ ID NO 23
<211> LENGTH: 182
<212> TYPE: PRT
<213> ORGANISM: Bacillus idriensis

<400> SEQUENCE: 23

```
Leu Pro Pro Gly Thr Pro Ser Lys Ser Thr Ala Gln Ser Gln Leu Asn
1               5                   10                  15

Ala Leu Thr Val Gln Thr Glu Gly Ser Met Thr Gly Tyr Ser Arg Asp
            20                  25                  30

Lys Phe Pro His Trp Ile Ser Gln Gly Asn Gly Cys Asp Thr Arg Gln
        35                  40                  45

Val Val Leu Gln Arg Asp Ala Asp Tyr Tyr Ser Gly Thr Cys Pro Val
    50                  55                  60

Thr Ser Gly Lys Trp Tyr Ser Tyr Tyr Asp Gly Val Thr Leu Tyr Asn
65                  70                  75                  80

Pro Ser Asp Leu Asp Ile Asp His Val Val Ala Leu Ala Glu Ala Trp
                85                  90                  95

Arg Ser Gly Ala Ser Ser Trp Thr Thr Asp Lys Arg Glu Asp Phe Ala
            100                 105                 110

Asn Asp Leu Ser Gly Thr Gln Leu Ile Ala Val Ser Ala Ser Thr Asn
        115                 120                 125

Arg Ser Lys Gly Asp Gln Asp Pro Ser Thr Trp Gln Pro Pro Arg Ser
```

```
    130                 135                 140

Gly Ala Ala Cys Gly Tyr Ala Lys Trp Trp Ile Ser Thr Lys Tyr Lys
145                 150                 155                 160

Trp Asn Leu Asn Leu Gln Ser Ser Glu Lys Thr Ala Leu Gln Ser Met
                165                 170                 175

Leu Asn Ser Cys Ser Tyr
            180


<210> SEQ ID NO 24
<211> LENGTH: 27
<212> TYPE: PRT
<213> ORGANISM: Artificial sequence
<220> FEATURE:
<223> OTHER INFORMATION: Bacillus clausii

<400> SEQUENCE: 24

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25


<210> SEQ ID NO 25
<211> LENGTH: 1633
<212> TYPE: DNA
<213> ORGANISM: bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 25

agaaaatggg gtttgttcaa acgggagccc actcttttta tatgggagat gaagaacaaa      60

ttgacattat catgaccaag acactgtaat tacagggacg gttcttttcc ttcttatcta     120

agaagccaaa gaaccgtccc tttacgtcgg aaatctatta gttgcctata gcttttgcct     180

tttaagtttt ccattatcat ttgtatagat atctctcctc ataaggcctc cgttccttta     240

ctagccattt aatcatagtc cccattactt tttgctctcc tagtggttca aaggatgcgg     300

gaggtccgtt ctatttttc atttttacaa aaacttaact tgagtagctt cttaaatgta      360

ctatcatttc aagtagatac atatttcatt tgcttccccg cagagaactt ctttgccgtg     420

ccgttttgac ttcgaaacta ttaaaatctt attttacatg agattttgat ataaaaaatt     480

aaatagtagg aggcatctct atg ttt aaa aaa tca ttg tcg att gtt ttt gca     533
                      Met Phe Lys Lys Ser Leu Ser Ile Val Phe Ala
                                  -25                 -20

ttt ctc ctt tcg ttt tct gtt ttt cat ttt gac cct gaa acg gtc tcg       581
Phe Leu Leu Ser Phe Ser Val Phe His Phe Asp Pro Glu Thr Val Ser
        -15                 -10                 -5

gca ctt cct ccg gga aca ccg tcc aag tcc gaa gcc caa tca caa ttg       629
Ala Leu Pro Pro Gly Thr Pro Ser Lys Ser Glu Ala Gln Ser Gln Leu
-1  1               5                   10                  15

aac gct ctg act gtg aaa cct gaa gac ccc atg acc ggc tac tcg cgg       677
Asn Ala Leu Thr Val Lys Pro Glu Asp Pro Met Thr Gly Tyr Ser Arg
                20                  25                  30

gat cat ttc ccg cac tgg atc agc caa gga aac ggc tgc aac acc cgc       725
Asp His Phe Pro His Trp Ile Ser Gln Gly Asn Gly Cys Asn Thr Arg
            35                  40                  45
```

```
cag att gta ctt caa cgg gac gcc gac tac tac agc ggg gcc tgc ccc      773
Gln Ile Val Leu Gln Arg Asp Ala Asp Tyr Tyr Ser Gly Ala Cys Pro
        50                  55                  60

gtc act acc gga aag tgg tac agt tac ttt gat ggc gtc att gtg tac      821
Val Thr Thr Gly Lys Trp Tyr Ser Tyr Phe Asp Gly Val Ile Val Tyr
    65                  70                  75

tcg cca tca gaa att gat att gat cac att gtt cct ttg gcc gaa gcc      869
Ser Pro Ser Glu Ile Asp Ile Asp His Ile Val Pro Leu Ala Glu Ala
80                  85                  90                  95

tgg cgt tcc ggt gcc agc agc tgg acc aca gaa aag cgc cgc agt ttc      917
Trp Arg Ser Gly Ala Ser Ser Trp Thr Thr Glu Lys Arg Arg Ser Phe
                100                 105                 110

gca aat gac ctc aac ggc cca cag ctg att gca gtg aca gca agc gtt      965
Ala Asn Asp Leu Asn Gly Pro Gln Leu Ile Ala Val Thr Ala Ser Val
            115                 120                 125

aat cgc tcc aaa ggg gac cag gat cct tcc aca tgg cag ccg ccg cgt     1013
Asn Arg Ser Lys Gly Asp Gln Asp Pro Ser Thr Trp Gln Pro Pro Arg
        130                 135                 140

gcc ggt gca cgc tgc gct tat gca aag tgg tgg att aac acg aag cac     1061
Ala Gly Ala Arg Cys Ala Tyr Ala Lys Trp Trp Ile Asn Thr Lys His
    145                 150                 155

cgc tgg gga ctg cac ctt cag tca tcg gaa aaa tcg tct ctg caa agc     1109
Arg Trp Gly Leu His Leu Gln Ser Ser Glu Lys Ser Ser Leu Gln Ser
160                 165                 170                 175

atg ctg aac ggc tgc gct tac taagatagaa aggagtcatt cttatggaaa        1160
Met Leu Asn Gly Cys Ala Tyr
                180

agaaatcatc tgttttcaaa gcaacccatg gagtcatgac agcggaggtt ggtgtcatca   1220

gcggagagct cgaactgcgc accacctgcg aggaagatgg tgtcctctcg ctagctatca   1280

cctatgtcgg tgccgaggaa tggtacaccc tccccggtga ggactaccgc ctgcacgatc   1340

cgcgtgacca cgaggttgtt caccgcatgc ttgttaaggt gttagaacgg aattgaggag   1400

agtgggtcag agggacatgt tccttgaccc gctctcatta aattaccaag ttttattaaa   1460

ccaccacaca ataaggaata tactcgttat cccccaagct atagttccca ctaaccacca   1520

aataataaat gaaagtgtac tttcatggcg ttccactttt cttttcataa atgtgagaac   1580

aacaaatccg attaagaaaa aaacaactgt aaaccagagt aatacatcca ctt          1633


<210> SEQ ID NO 26
<211> LENGTH: 210
<212> TYPE: PRT
<213> ORGANISM: bacillus species

<400> SEQUENCE: 26

Met Phe Lys Lys Ser Leu Ser Ile Val Phe Ala Phe Leu Leu Ser Phe
            -25                 -20                 -15

Ser Val Phe His Phe Asp Pro Glu Thr Val Ser Ala Leu Pro Pro Gly
        -10                 -5              -1  1

Thr Pro Ser Lys Ser Glu Ala Gln Ser Gln Leu Asn Ala Leu Thr Val
5                   10                  15                  20

Lys Pro Glu Asp Pro Met Thr Gly Tyr Ser Arg Asp His Phe Pro His
                25                  30                  35

Trp Ile Ser Gln Gly Asn Gly Cys Asn Thr Arg Gln Ile Val Leu Gln
            40                  45                  50

Arg Asp Ala Asp Tyr Tyr Ser Gly Ala Cys Pro Val Thr Thr Gly Lys
        55                  60                  65
```

```
Trp Tyr Ser Tyr Phe Asp Gly Val Ile Val Tyr Ser Pro Ser Glu Ile
    70                  75                  80

Asp Ile Asp His Ile Val Pro Leu Ala Glu Ala Trp Arg Ser Gly Ala
85                  90                  95                  100

Ser Ser Trp Thr Thr Glu Lys Arg Arg Ser Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Ala Gly Ala Arg Cys
        135                 140                 145

Ala Tyr Ala Lys Trp Trp Ile Asn Thr Lys His Arg Trp Gly Leu His
    150                 155                 160

Leu Gln Ser Ser Glu Lys Ser Ser Leu Gln Ser Met Leu Asn Gly Cys
165                 170                 175                 180

Ala Tyr


<210> SEQ ID NO 27
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 27

agaaaatggg gtttgttcaa acgggagctc actcttttta tatgggagat gaagaacaaa      60

ttgacattat catgaccaag acactgtaat tacagggacg gttcttttcc ttcttatcta     120

agaagccaaa gaaccgtccc tttacgtcgg aaatctatta gttgcctata gcttttgcct     180

tttaagtttt ccattatcat ttgtatagat atctctcctc ataaggcctc cgttccttta     240

ctagccattt aatcatagtc cccattactt tttgctctcc tagtggttca aaggatgcgg     300

gaggtccgtt ctatttttc atttttacaa aaacttaact tgagtagctt cttaaatgta     360

ctatcatttc aagtagatac atatttcatt tgcttccccg cagagaactt ctttgccgtg     420

ccgttttgac ttcgaaacta ttaaaatctt attttacatg agattttgat ataaaaaatt     480

aaatagtagg aggcatctct atg ttt aaa aaa tca ttg tcg att gtt ttt gca     533
                      Met Phe Lys Lys Ser Leu Ser Ile Val Phe Ala
                                      -25                 -20

ttt ctc ctt tcg ttt tct gtt ttt cat ttt gac cct gaa acg gtc tcg      581
Phe Leu Leu Ser Phe Ser Val Phe His Phe Asp Pro Glu Thr Val Ser
        -15                 -10                 -5

gca ctt cct ccg gga aca ccg tcc aag tcc gaa gcc caa tca caa ttg      629
Ala Leu Pro Pro Gly Thr Pro Ser Lys Ser Glu Ala Gln Ser Gln Leu
-1  1               5                   10                  15

aac gct ctg act gtg aaa cct gaa gac ccc atg acc ggc tac tcg cgg      677
Asn Ala Leu Thr Val Lys Pro Glu Asp Pro Met Thr Gly Tyr Ser Arg
                20                  25                  30

gat cat ttc ccg cac tgg atc agc caa gga aac ggc tgc aac acc cgc      725
Asp His Phe Pro His Trp Ile Ser Gln Gly Asn Gly Cys Asn Thr Arg
            35                  40                  45

cag att gta ctt caa cgg gac gcc gac tac tac agc ggg gcc tgc ccc      773
Gln Ile Val Leu Gln Arg Asp Ala Asp Tyr Tyr Ser Gly Ala Cys Pro
        50                  55                  60
```

```
gtc act acc gga aag tgg tac agt tac ttt gat ggc gtc att gtg tac      821
Val Thr Thr Gly Lys Trp Tyr Ser Tyr Phe Asp Gly Val Ile Val Tyr
    65                  70                  75

tcg cca tcc gaa att gat att gat cac att gtt cct ttg gcc gaa gct      869
Ser Pro Ser Glu Ile Asp Ile Asp His Ile Val Pro Leu Ala Glu Ala
80                  85                  90                  95

tgg cgt tcc ggt gcc agc agc tgg acc acc gaa cag cgc cgc agt ttc      917
Trp Arg Ser Gly Ala Ser Ser Trp Thr Thr Glu Gln Arg Arg Ser Phe
                100                 105                 110

gca aat gac ctc aac ggg cca cag ctg att gca gtg aca gca agc gtt      965
Ala Asn Asp Leu Asn Gly Pro Gln Leu Ile Ala Val Thr Ala Ser Val
            115                 120                 125

aat cgc tcc aaa ggg gac cag gat cct tcc aca tgg cag ccc cct cgt     1013
Asn Arg Ser Lys Gly Asp Gln Asp Pro Ser Thr Trp Gln Pro Pro Arg
        130                 135                 140

gcc ggt gca cgt tgc gct tat gca aag tgg tgg att aac acg aag cac     1061
Ala Gly Ala Arg Cys Ala Tyr Ala Lys Trp Trp Ile Asn Thr Lys His
    145                 150                 155

cgc tgg gga tta cac ctt cag tca tcg gaa aaa tcg tct ctg caa agc     1109
Arg Trp Gly Leu His Leu Gln Ser Ser Glu Lys Ser Ser Leu Gln Ser
160                 165                 170                 175

atg ctg aac ggc tgc gct tac taagatagaa aggagtcatt cttatggaaa        1160
Met Leu Asn Gly Cys Ala Tyr
                180

agaaatcatc tgttttcaaa gcaacccatg gagtcatgac agcggaggtt ggtgtcatca   1220

gcggagagct cgaactgcgc accacctgcg aggaagatgg tgtcctcttt ctagctatca   1280

cctatgtcgg tgccgaggaa tggtacaccc tccccggtga ggactaccgc ctgcacgatc   1340

cgcgtgacca cgaggttgtt caccgcatgc ttgttaaggt gttagaacgg aattgaggag   1400

aatgggtcag agggacatgt tccttgaccc gctctcatta aattaccaag ttttattaaa   1460

ccaccacaca ataaggaata tactcgttat cccccaagct atagttccca ctaaccacca   1520

aataataaat gaaagggtgc tttcatggtg ttcccctttt cttttcataa gtgtgagaac   1580

aacaaagccg attaagaaaa aaacaactgt aaaccagagt aatacatcca ctt          1633


<210> SEQ ID NO 28
<211> LENGTH: 210
<212> TYPE: PRT
<213> ORGANISM: Bacillus species

<400> SEQUENCE: 28

Met Phe Lys Lys Ser Leu Ser Ile Val Phe Ala Phe Leu Leu Ser Phe
            -25                 -20                 -15

Ser Val Phe His Phe Asp Pro Glu Thr Val Ser Ala Leu Pro Pro Gly
        -10                 -5                  -1  1

Thr Pro Ser Lys Ser Glu Ala Gln Ser Gln Leu Asn Ala Leu Thr Val
5                   10                  15                  20

Lys Pro Glu Asp Pro Met Thr Gly Tyr Ser Arg Asp His Phe Pro His
                25                  30                  35

Trp Ile Ser Gln Gly Asn Gly Cys Asn Thr Arg Gln Ile Val Leu Gln
            40                  45                  50

Arg Asp Ala Asp Tyr Tyr Ser Gly Ala Cys Pro Val Thr Thr Gly Lys
        55                  60                  65

Trp Tyr Ser Tyr Phe Asp Gly Val Ile Val Tyr Ser Pro Ser Glu Ile
    70                  75                  80

Asp Ile Asp His Ile Val Pro Leu Ala Glu Ala Trp Arg Ser Gly Ala
```

```
85                  90                  95                  100

Ser Ser Trp Thr Thr Glu Gln Arg Arg Ser Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Ala Gly Ala Arg Cys
        135                 140                 145

Ala Tyr Ala Lys Trp Trp Ile Asn Thr Lys His Arg Trp Gly Leu His
    150                 155                 160

Leu Gln Ser Ser Glu Lys Ser Ser Leu Gln Ser Met Leu Asn Gly Cys
165                 170                 175                 180

Ala Tyr


<210> SEQ ID NO 29
<211> LENGTH: 1633
<212> TYPE: DNA
<213> ORGANISM: Bacillus horikoshii
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 29

gttaaggaga aattctcatg actcggaaag tgctgaagcc acatgtatcc atcatccacg      60

atgcatacac ttttttcttc atagtgcact gttaatggat ccgtcacttt atgaatgttg     120

agtaaggtaa tatgcccttt gaaacccttt gtatccatat atttctgagt gtactgccgt     180

tttaatatcc gtttccattc tgagcggtct ccgtatcttc tttttaacat tggcatcccc     240

ctcttcgata cagacttatt gtactacttt tcagacaaat gatgggtata tcactccttt     300

cttcattcaa aggtagtagg agcactgtac cctttcttaa tatttacaat attttaactt     360

gttaaaaaat ttttatgtac tattatttca agtagataca tagctcatat cctgtcctcg     420

attgaagcgt gattaagtta ttaaaatctc atccatcaat gagattttga tataaaaatt     480

gtatactagg aggcatacct atg ctg aag aaa ccc ctg tta ttg gtg ttt gca     533
                      Met Leu Lys Lys Pro Leu Leu Leu Val Phe Ala
                                      -25                 -20

ttt atc ctg tcg ttt tca aca cta cag ctt gac cct caa acg gtc tcg       581
Phe Ile Leu Ser Phe Ser Thr Leu Gln Leu Asp Pro Gln Thr Val Ser
        -15                 -10                 -5

gca ctc ccc cct gga aca ccg tcc aag tca gaa gca caa tct caa ttg       629
Ala Leu Pro Pro Gly Thr Pro Ser Lys Ser Glu Ala Gln Ser Gln Leu
-1  1               5                   10                  15

aac tcg ttg act gtg aaa tcc gaa gac ccc atg acc ggt tac tcc cgg       677
Asn Ser Leu Thr Val Lys Ser Glu Asp Pro Met Thr Gly Tyr Ser Arg
                20                  25                  30

gac cat ttc cca cat tgg agc ggc caa ggg aat ggc tgt gac acc cgc       725
Asp His Phe Pro His Trp Ser Gly Gln Gly Asn Gly Cys Asp Thr Arg
            35                  40                  45

caa att gtc ctg caa cgc gat gcc gac tat tac agc ggc aac tgt ccc       773
Gln Ile Val Leu Gln Arg Asp Ala Asp Tyr Tyr Ser Gly Asn Cys Pro
        50                  55                  60

gtc act tct gga aaa tgg tat agt tat ttc gat ggt gtc ata gtg tat       821
Val Thr Ser Gly Lys Trp Tyr Ser Tyr Phe Asp Gly Val Ile Val Tyr
    65                  70                  75
```

```
tct ccg tct gaa att gat att gat cac gtt gtt cct tta gcc gag gct      869
Ser Pro Ser Glu Ile Asp Ile Asp His Val Val Pro Leu Ala Glu Ala
80                  85                  90                  95

tgg cgt tcc ggt gcc agc agc tgg acg acc gaa cag cgt cgt agt ttt      917
Trp Arg Ser Gly Ala Ser Ser Trp Thr Thr Glu Gln Arg Arg Ser Phe
                100                 105                 110

gcc aac gat ctc aac ggg ccg caa ctg att gca gta aca gca agc gtc      965
Ala Asn Asp Leu Asn Gly Pro Gln Leu Ile Ala Val Thr Ala Ser Val
            115                 120                 125

aat cga tcc aaa ggt gac cag gac ccg tcg aca tgg caa cca cca cgt     1013
Asn Arg Ser Lys Gly Asp Gln Asp Pro Ser Thr Trp Gln Pro Pro Arg
        130                 135                 140

gcc ggc gct cgt tgt gca tat gca aaa tgg tgg atc aat acg aaa cac     1061
Ala Gly Ala Arg Cys Ala Tyr Ala Lys Trp Trp Ile Asn Thr Lys His
    145                 150                 155

cgt tgg aac tta cac ctt cag tca tct gag aaa tct gct ttg caa acg     1109
Arg Trp Asn Leu His Leu Gln Ser Ser Glu Lys Ser Ala Leu Gln Thr
160                 165                 170                 175

atg ctt aac ggc tgc gtt tac taattatttt atgtgacatg actgcaagta        1160
Met Leu Asn Gly Cys Val Tyr
                180

ttgctgcttg cagtcatgct atctaagaga ggagtcttat ctatggaaaa gctttcatct   1220

acttttactg catctcacgg agttatgaca gccgaggttg gagtcatcag cggagaacta   1280

gaactacgca ccacctgcga tgaagaaggc gtgctctcgc ttgccatcac ctatgtcggt   1340

gcagaagagt ggtacaccct gcctggagaa gactaccgcc tgcatgattc gcgggatcat   1400

gaggtcgtgc accgtatgct tgtgaaagtg ttggagcggg gttgaggagg taccgtgacc   1460

cacctcaaaa agttgcatta aaccaccaaa caacaaggaa aatggtcact atcccccaaa   1520

ctgtagtacc tacaataaac catacgcctg attgtgtagc ttctttctta ctctgtaggt   1580

tcctcttcag aaaggaaagc accacaaagc caattacgaa gaaagcaatg gta          1633


<210> SEQ ID NO 30
<211> LENGTH: 210
<212> TYPE: PRT
<213> ORGANISM: Bacillus horikoshii

<400> SEQUENCE: 30

Met Leu Lys Lys Pro Leu Leu Leu Val Phe Ala Phe Ile Leu Ser Phe
            -25                 -20                 -15

Ser Thr Leu Gln Leu Asp Pro Gln Thr Val Ser Ala Leu Pro Pro Gly
        -10                 -5              -1  1

Thr Pro Ser Lys Ser Glu Ala Gln Ser Gln Leu Asn Ser Leu Thr Val
5                   10                  15                  20

Lys Ser Glu Asp Pro Met Thr Gly Tyr Ser Arg Asp His Phe Pro His
                25                  30                  35

Trp Ser Gly Gln Gly Asn Gly Cys Asp Thr Arg Gln Ile Val Leu Gln
            40                  45                  50

Arg Asp Ala Asp Tyr Tyr Ser Gly Asn Cys Pro Val Thr Ser Gly Lys
        55                  60                  65

Trp Tyr Ser Tyr Phe Asp Gly Val Ile Val Tyr Ser Pro Ser Glu Ile
    70                  75                  80

Asp Ile Asp His Val Val Pro Leu Ala Glu Ala Trp Arg Ser Gly Ala
85                  90                  95                  100

Ser Ser Trp Thr Thr Glu Gln Arg Arg Ser Phe Ala Asn Asp Leu Asn
                105                 110                 115
```

```
Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Ala Gly Ala Arg Cys
        135                 140                 145

Ala Tyr Ala Lys Trp Trp Ile Asn Thr Lys His Arg Trp Asn Leu His
    150                 155                 160

Leu Gln Ser Ser Glu Lys Ser Ala Leu Gln Thr Met Leu Asn Gly Cys
165                 170                 175                 180

Val Tyr


<210> SEQ ID NO 31
<211> LENGTH: 1633
<212> TYPE: DNA
<213> ORGANISM: Bacillus horikoshii
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 31

ctccactgtc atcacctaaa ttcttattaa aattcctaag tgtgattttg ccatccccat      60

caacggaaag tcactgttct tcgtgggttg tagggacagg catggcgacg ccaatgacca     120

tttattaggt aaatttagtt tctctcactt acaatatatg gattgtcgtc aatttcaact     180

gatttattga atacttttag tggttaagcg tatacttcgt gccatttatt gagtaattgg     240

aagtgtttat tgaataatta agggcttggg tagcgcaccc cgctaaacac tgggtcaacg     300

gacctgtccc ctcgactctt ccccgccctc tctggtccat caggcgcagg aggaccgtac     360

cttttcttaa catttacaat attttaactt attaaagcac ttttatgtat tattatttca     420

agtagataca tagtcgacta ttaaaatctc gtccttccac gaggttttga tataaaaatt     480

ttatagtagg aggcatttct atg ctg aaa aag tcc atg ttg gtt gtt ttt gca     533
                      Met Leu Lys Lys Ser Met Leu Val Val Phe Ala
                                  -25                 -20

ttc atc ctg tcg ttc tct gca att caa ctt gat cca caa acc gtc tcg       581
Phe Ile Leu Ser Phe Ser Ala Ile Gln Leu Asp Pro Gln Thr Val Ser
        -15                 -10                 -5

gca ctt ccc cct gga aca ccg tcc aag tca gaa gct caa tct caa ttg       629
Ala Leu Pro Pro Gly Thr Pro Ser Lys Ser Glu Ala Gln Ser Gln Leu
-1  1               5                   10                  15

aac tcg ttg act gta aaa aca gaa gac ccc atg acc ggg tat tcg cgg       677
Asn Ser Leu Thr Val Lys Thr Glu Asp Pro Met Thr Gly Tyr Ser Arg
                20                  25                  30

gat tta ttc cca cat tgg agc ggc cag ggc agt ggc tgt gat act cgc       725
Asp Leu Phe Pro His Trp Ser Gly Gln Gly Ser Gly Cys Asp Thr Arg
            35                  40                  45

caa atc gtc ctt caa cgc gat gca gac tat ttc act ggc acc tgt ccc       773
Gln Ile Val Leu Gln Arg Asp Ala Asp Tyr Phe Thr Gly Thr Cys Pro
        50                  55                  60

aca acg tct gga aaa tgg tat agt tac ttc gat ggc gtc att gtc tat       821
Thr Thr Ser Gly Lys Trp Tyr Ser Tyr Phe Asp Gly Val Ile Val Tyr
    65                  70                  75

tct ccg tct gaa att gat gtt gat cac atc gtt cca ttg gct gaa gct       869
Ser Pro Ser Glu Ile Asp Val Asp His Ile Val Pro Leu Ala Glu Ala
80                  85                  90                  95
```

```
tgg cgt tct ggt gcc agc agc tgg aca act gaa cag cga cgt gct ttt      917
Trp Arg Ser Gly Ala Ser Ser Trp Thr Thr Glu Gln Arg Arg Ala Phe
                100                 105                 110

gcc aac gac ctc aca ggt ccg caa ctg atc gca gta aca gca agc gtc      965
Ala Asn Asp Leu Thr Gly Pro Gln Leu Ile Ala Val Thr Ala Ser Val
            115                 120                 125

aac cgt tcc aaa ggg gac caa gat ccg tct act tgg caa cca cct cgt     1013
Asn Arg Ser Lys Gly Asp Gln Asp Pro Ser Thr Trp Gln Pro Pro Arg
        130                 135                 140

gcc ggt gct cgc tgt gcc tat gca aaa tgg tgg att aac aca aaa cac     1061
Ala Gly Ala Arg Cys Ala Tyr Ala Lys Trp Trp Ile Asn Thr Lys His
    145                 150                 155

cgt tgg aac tta cac ctt cag tca tct gag aaa tct tct tta caa acg     1109
Arg Trp Asn Leu His Leu Gln Ser Ser Glu Lys Ser Ser Leu Gln Thr
160                 165                 170                 175

atg ctt aac ggc tgc gct tac taaattagag attgcgtctg caggcggagt        1160
Met Leu Asn Gly Cys Ala Tyr
                180

tgaatatgtt tgcagacgcg ttatagatta attgaaacgg aaggagtttt tacatatgga   1220

aaagaaatca tctattttta cagcatcaca cggcgtcatg acagccgagg ttggtgtcat   1280

cagtggcgag ctcgaactgc aaaccacctg tgatgaggac ggttccctct cgctcgccat   1340

cacctacgtc ggtgctgcag aatggtacac cttgcctggt gaagactatc gcctgcatga   1400

tttacgtgat catgaggtaa ttcaccgcat gcttgttaag gtgttggagc ggaaatgatg   1460

gggtgggtcg tgggggacag gcaccgcgac ccgcttttca cacacattaa ttctctagct   1520

caatatattc cctcaaaagc ttccattggt ttgcttcaag tctccagata aacatacact   1580

gtgcagtaaa aggtttccct ccaataacgt ttgtttccct acccattaca act          1633
```

<210> SEQ ID NO 32
<211> LENGTH: 210
<212> TYPE: PRT
<213> ORGANISM: Bacillus horikoshii

<400> SEQUENCE: 32

```
Met Leu Lys Lys Ser Met Leu Val Val Phe Ala Phe Ile Leu Ser Phe
            -25                 -20                 -15

Ser Ala Ile Gln Leu Asp Pro Gln Thr Val Ser Ala Leu Pro Pro Gly
        -10                 -5              -1  1

Thr Pro Ser Lys Ser Glu Ala Gln Ser Gln Leu Asn Ser Leu Thr Val
5                   10                  15                  20

Lys Thr Glu Asp Pro Met Thr Gly Tyr Ser Arg Asp Leu Phe Pro His
                25                  30                  35

Trp Ser Gly Gln Gly Ser Gly Cys Asp Thr Arg Gln Ile Val Leu Gln
            40                  45                  50

Arg Asp Ala Asp Tyr Phe Thr Gly Thr Cys Pro Thr Thr Ser Gly Lys
        55                  60                  65

Trp Tyr Ser Tyr Phe Asp Gly Val Ile Val Tyr Ser Pro Ser Glu Ile
    70                  75                  80

Asp Val Asp His Ile Val Pro Leu Ala Glu Ala Trp Arg Ser Gly Ala
85                  90                  95                  100

Ser Ser Trp Thr Thr Glu Gln Arg Arg Ala Phe Ala Asn Asp Leu Thr
                105                 110                 115

Gly Pro Gln Leu Ile Ala Val Thr Ala Ser Val Asn Arg Ser Lys Gly
            120                 125                 130
```

```
Asp Gln Asp Pro Ser Thr Trp Gln Pro Pro Arg Ala Gly Ala Arg Cys
        135                 140                 145

Ala Tyr Ala Lys Trp Trp Ile Asn Thr Lys His Arg Trp Asn Leu His
    150                 155                 160

Leu Gln Ser Ser Glu Lys Ser Ser Leu Gln Thr Met Leu Asn Gly Cys
165                 170                 175                 180

Ala Tyr


<210> SEQ ID NO 33
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 33

gagagttagt ggtgacgcac ctgttattta cacggttcaa tcaggagaca cactttgggc      60

gattgctcag cgttataata cgacagttgc agatgttcgc caactaaatg ggcttactag     120

tgatgttatt caaccaggac aaagactaag agtaaggtaa caaaaaccct cacttcggtg     180

ggggcctatt taagttttat tttgctcatt catgcccctt aaaaacagaa ccagttaata     240

ccgtttaaaa ccaaaataga agaagttagt ctacatactt atacttattt caagaactgt     300

aacctcgaat aaattatgta tatatgaatc tattattggg gttgattaaa ttaaagtatt     360

ttatttgtaa acgtgacttt ctattaaaaa acctttacaa atatttacaa actattaact     420

tgtggcaatt ctcacccctg tactatcatt attaatagag tttatcaaca ttttaaaagt     480

acatataggg aggtaattct atg tta aga aaa tcc ttg atc ttt att ttt acg     533
                      Met Leu Arg Lys Ser Leu Ile Phe Ile Phe Thr
                                  -25                 -20

ttg ctt ata ttg ttt acc gca tta caa ttt gac atc caa cca gca tca       581
Leu Leu Ile Leu Phe Thr Ala Leu Gln Phe Asp Ile Gln Pro Ala Ser
        -15                 -10                 -5

gca tta cca cct gga aca ccg tcc aag tca gag gca caa tcc cag tta       629
Ala Leu Pro Pro Gly Thr Pro Ser Lys Ser Glu Ala Gln Ser Gln Leu
-1  1               5                   10                  15

aac gct ttg acc gtg aag gcc gaa gat cca atg act ggt tac tcg cgc       677
Asn Ala Leu Thr Val Lys Ala Glu Asp Pro Met Thr Gly Tyr Ser Arg
                20                  25                  30

aat tta ttt cca cac tgg aac agc cag ggc aat ggg tgt aac acc cga       725
Asn Leu Phe Pro His Trp Asn Ser Gln Gly Asn Gly Cys Asn Thr Arg
            35                  40                  45

cag ttg gtg ctc cag cgt gac gct gac tac tac agt gga aac tgt cct       773
Gln Leu Val Leu Gln Arg Asp Ala Asp Tyr Tyr Ser Gly Asn Cys Pro
        50                  55                  60

gta act tcc ggc aga tgg tac agc tac ttc gac ggc gtc gta gta acc       821
Val Thr Ser Gly Arg Trp Tyr Ser Tyr Phe Asp Gly Val Val Val Thr
    65                  70                  75

tca ccg tcc gaa atc gac att gat cac att gta cct tta gct gaa gcg       869
Ser Pro Ser Glu Ile Asp Ile Asp His Ile Val Pro Leu Ala Glu Ala
80                  85                  90                  95

tgg cgt tct gga gct agt agc tgg acg acg gaa aag cgt aag gaa ttc       917
Trp Arg Ser Gly Ala Ser Ser Trp Thr Thr Glu Lys Arg Lys Glu Phe
                100                 105                 110
```

```
gct aat gat ctc aac ggt ccg cag ctg atc gca gtt act gcg agt gtc      965
Ala Asn Asp Leu Asn Gly Pro Gln Leu Ile Ala Val Thr Ala Ser Val
            115                 120                 125

aac cgc tct aaa ggt gat caa gat cct tca aca tgg cag cca cct cgt     1013
Asn Arg Ser Lys Gly Asp Gln Asp Pro Ser Thr Trp Gln Pro Pro Arg
        130                 135                 140

gca gcc gca cgt tgc gga tac gct aag tgg tgg att aac act aag tac     1061
Ala Ala Ala Arg Cys Gly Tyr Ala Lys Trp Trp Ile Asn Thr Lys Tyr
    145                 150                 155

cgc tgg gat tta agc ttg cag tct tct gag aag tct tca ctg caa act     1109
Arg Trp Asp Leu Ser Leu Gln Ser Ser Glu Lys Ser Ser Leu Gln Thr
160                 165                 170                 175

atg ctt aac act tgc tca tac taagtttaat agtgtaccct acaaaggctg       1160
Met Leu Asn Thr Cys Ser Tyr
                180

taaattattt ggaagtcttg cgacgtaatt cttcaatctc agaaaggagt cacttatatg   1220

gataagaagt cgaccatttt taccgcaacc cacggtgtaa tgaccaagga ggttggcgtc   1280

attagcgggg aacttgaact gcttactacc tgtgatgaca acggagttct cacactcgcc   1340

attacttatg taggagctat ggattggtac acgctgcctg gtgaagacta ccgcctaaat   1400

gacctaaggg atcacgaggt cgtccaccgc atgctcgcca ctgttcttga gcgcccttga   1460

taccatatca agggggcttt ttttaagaat gtaaaaaggc aatacagtta tgtgattttt   1520

aacctaaaac aagcatagac ccgttcttta tttttttgaa agtctagaag atatttaaaa   1580

acgttagaat ttgaattaat ttaatgtcac tcatttaata agtttaaaag aaa           1633


<210> SEQ ID NO 34
<211> LENGTH: 210
<212> TYPE: PRT
<213> ORGANISM: Bacillus species

<400> SEQUENCE: 34

Met Leu Arg Lys Ser Leu Ile Phe Ile Phe Thr Leu Leu Ile Leu Phe
            -25                 -20                 -15

Thr Ala Leu Gln Phe Asp Ile Gln Pro Ala Ser Ala Leu Pro Pro Gly
        -10                 -5              -1  1

Thr Pro Ser Lys Ser Glu Ala Gln Ser Gln Leu Asn Ala Leu Thr Val
5                   10                  15                  20

Lys Ala Glu Asp Pro Met Thr Gly Tyr Ser Arg Asn Leu Phe Pro His
                25                  30                  35

Trp Asn Ser Gln Gly Asn Gly Cys Asn Thr Arg Gln Leu Val Leu Gln
            40                  45                  50

Arg Asp Ala Asp Tyr Tyr Ser Gly Asn Cys Pro Val Thr Ser Gly Arg
        55                  60                  65

Trp Tyr Ser Tyr Phe Asp Gly Val Val Val Thr Ser Pro Ser Glu Ile
    70                  75                  80

Asp Ile Asp His Ile Val Pro Leu Ala Glu Ala Trp Arg Ser Gly Ala
85                  90                  95                  100

Ser Ser Trp Thr Thr Glu Lys Arg Lys Glu Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Ala Ala Ala Arg Cys
        135                 140                 145

Gly Tyr Ala Lys Trp Trp Ile Asn Thr Lys Tyr Arg Trp Asp Leu Ser
```

```
    150                 155                 160

Leu Gln Ser Ser Glu Lys Ser Ser Leu Gln Thr Met Leu Asn Thr Cys
165                 170                 175                 180

Ser Tyr


<210> SEQ ID NO 35
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 35

accgtcataa atacgataat ccataaagta atcgaggtat atatcaggat aagaccagtc      60

taaatccgtt agtagccaat tatattcttt ttcaagacca ttaaaggaat tcaaaatttc     120

ttttaactct aaaaagtcct ctaaaataga attcatcttg cacctcaatt tatatttccc     180

tttaatctac aactaatgat accaaagaat agtaaataaa tcccttttat attcaataac     240

taacaaaaag agccctcact cttgtgggag ctttttaaag tccttatttt gctaataaaa     300

ttcaactaac ttcaaagcat tatctagagt aatcctactg atctcaaatc ccccccttctt    360

caaccacttc aaactaactt ttttaataaa acatttacaa atatttacaa actattaact     420

tgtgaaaaaa ttcaccactg tactatcatt gttaatagag tttatcaaca ttttaaaagt     480

acatataggg aggtaattct atg tta aga aaa tcc ttg atc ttt att ttt acg     533
                      Met Leu Arg Lys Ser Leu Ile Phe Ile Phe Thr
                                  -25                 -20

ttg ctt ata ttg ttt acc gca tta caa ttt gac atc caa cca gca tca       581
Leu Leu Ile Leu Phe Thr Ala Leu Gln Phe Asp Ile Gln Pro Ala Ser
        -15                 -10                 -5

gca tta cca cct gga aca ccg tcc aag tca cag gca caa tcc cag tta       629
Ala Leu Pro Pro Gly Thr Pro Ser Lys Ser Gln Ala Gln Ser Gln Leu
-1  1               5                   10                  15

aac gct ttg acc gtg aag gcc gaa gat cca atg act ggt tac tcg cgc       677
Asn Ala Leu Thr Val Lys Ala Glu Asp Pro Met Thr Gly Tyr Ser Arg
                20                  25                  30

aac ttg ttt cca cac tgg agt agt cag ggc aat ggg tgt aac acc cga       725
Asn Leu Phe Pro His Trp Ser Ser Gln Gly Asn Gly Cys Asn Thr Arg
            35                  40                  45

cag ttg gtg ctc cag cgt gac gct gac tac tac agt gga aac tgt cct       773
Gln Leu Val Leu Gln Arg Asp Ala Asp Tyr Tyr Ser Gly Asn Cys Pro
        50                  55                  60

gta act tcc ggc aga tgg tac agc tac ttc gac ggc gtc gta gta acc       821
Val Thr Ser Gly Arg Trp Tyr Ser Tyr Phe Asp Gly Val Val Val Thr
    65                  70                  75

tct cca tcc gaa atc gac att gat cac att gta cct tta gct gaa gca       869
Ser Pro Ser Glu Ile Asp Ile Asp His Ile Val Pro Leu Ala Glu Ala
80                  85                  90                  95

tgg cgt tcc gga gct agc agc tgg acg acg gaa aag cgt aga gaa ttc       917
Trp Arg Ser Gly Ala Ser Ser Trp Thr Thr Glu Lys Arg Arg Glu Phe
                100                 105                 110

gct aat gat ctc aac ggt ccg cag ctg atc gct gta act gcg agt gtc       965
Ala Asn Asp Leu Asn Gly Pro Gln Leu Ile Ala Val Thr Ala Ser Val
            115                 120                 125
```

```
aac cgc tct aaa ggt gat caa gat cct tcg aca tgg cag cca cct cgt      1013
Asn Arg Ser Lys Gly Asp Gln Asp Pro Ser Thr Trp Gln Pro Pro Arg
        130                 135                 140

gta gcc gca cgt tgc gga tac gct aaa tgg tgg att aac aca aag tac      1061
Val Ala Ala Arg Cys Gly Tyr Ala Lys Trp Trp Ile Asn Thr Lys Tyr
    145                 150                 155

cgc tgg gac cta agc ttg cag tct tct gag aag tca tca ctg caa acc      1109
Arg Trp Asp Leu Ser Leu Gln Ser Ser Glu Lys Ser Ser Leu Gln Thr
160                 165                 170                 175

atg ctc aac act tgc tca tac taagtttaat agtgtaacct actaaggctg        1160
Met Leu Asn Thr Cys Ser Tyr
                180

tcaattatat ggcagtcttg cgacgtaatt cttcaatctc agaaaggagt cactcgtatg   1220

gataagaagt ccaccatttt taccgcaacc cacggtgtaa tgaccaagga ggttggcgtc   1280

attagcgggg aacttgaact gctcactacc tgtgatgaca acggagtact cacactcgcc   1340

attacgtatg taggagctat ggattggtac acactgcctg gtgaaggcta ccgcctgaat   1400

gatcgacgcg atcacgaagt cgtccaccgc atgctcgcca ctgtacttga gcgcccttga   1460

taccatatca agggggcttt ttttaagaat gtaaaaaggc aataaggtta tgtgattttt   1520

aaactaaaac aagcatagcc ccgttcttta ttttttttga aagtctagaa gatatttaaa   1580

aacgttataa attaaattaa ttcaatgtca ctcatttaat aagtttaaaa gaa           1633


<210> SEQ ID NO 36
<211> LENGTH: 210
<212> TYPE: PRT
<213> ORGANISM: Bacillus species

<400> SEQUENCE: 36

Met Leu Arg Lys Ser Leu Ile Phe Ile Phe Thr Leu Leu Ile Leu Phe
            -25                 -20                 -15

Thr Ala Leu Gln Phe Asp Ile Gln Pro Ala Ser Ala Leu Pro Pro Gly
        -10                 -5              -1  1

Thr Pro Ser Lys Ser Gln Ala Gln Ser Gln Leu Asn Ala Leu Thr Val
5                   10                  15                  20

Lys Ala Glu Asp Pro Met Thr Gly Tyr Ser Arg Asn Leu Phe Pro His
                25                  30                  35

Trp Ser Ser Gln Gly Asn Gly Cys Asn Thr Arg Gln Leu Val Leu Gln
            40                  45                  50

Arg Asp Ala Asp Tyr Tyr Ser Gly Asn Cys Pro Val Thr Ser Gly Arg
        55                  60                  65

Trp Tyr Ser Tyr Phe Asp Gly Val Val Val Thr Ser Pro Ser Glu Ile
    70                  75                  80

Asp Ile Asp His Ile Val Pro Leu Ala Glu Ala Trp Arg Ser Gly Ala
85                  90                  95                  100

Ser Ser Trp Thr Thr Glu Lys Arg Arg Glu Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Val Ala Ala Arg Cys
        135                 140                 145

Gly Tyr Ala Lys Trp Trp Ile Asn Thr Lys Tyr Arg Trp Asp Leu Ser
    150                 155                 160

Leu Gln Ser Ser Glu Lys Ser Ser Leu Gln Thr Met Leu Asn Thr Cys
165                 170                 175                 180
```

Ser Tyr

<210> SEQ ID NO 37
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 37

```
cgtcgtttcc cattcccgtt gaatttttct ttcaagtaaa tgaccttcaa tttcagctat      60

gaaactctca acataagcaa gacgctcttc ttcaatctcc atcatttgtc tattctccac     120

aaatgcaaaa cggtcagaat gttttgctag gaaatctatt agttgcttat agcttttgcc     180

ttttatgttt tccgttatca tttgcataga gatctctcct aataaggcct tagttccttt     240

actagccatt taatcatagt tttctttact ttatgctccc ctagtggttc aaaggatgca     300

ggaggtccgt tctgtttttt catttttaca aaaacttaac ttgagtagca acttaaatgt     360

actattattt caagtagata catagttcat ttatttcccc gacgagaacc ttcttgccat     420

gccgttttga ctttgaaact attaaaatct cattcatcat gagattttga tataaaaaat     480

ttatagtagg aggcacctct atg ctg cag aaa tca ttg tcg gtt gtt ttt gca     533
                      Met Leu Gln Lys Ser Leu Ser Val Val Phe Ala
                                      -25                 -20

ttt gtc ctg tcg ttc tct gtt ttt cat ttt gac cca caa acg gtc tcg       581
Phe Val Leu Ser Phe Ser Val Phe His Phe Asp Pro Gln Thr Val Ser
        -15                 -10                 -5

gca ctt ccc ccg gga aca ccg tcc aag tcc gaa gcc caa tcc caa ttg       629
Ala Leu Pro Pro Gly Thr Pro Ser Lys Ser Glu Ala Gln Ser Gln Leu
-1  1               5                   10                  15

acc tct ctg act gtg aaa cct gaa gat ccc atg acc ggc tac tca cgg       677
Thr Ser Leu Thr Val Lys Pro Glu Asp Pro Met Thr Gly Tyr Ser Arg
                20                  25                  30

gac cat ttc cca cac tgg att agc caa gga aac ggc tgc aac acc cgc       725
Asp His Phe Pro His Trp Ile Ser Gln Gly Asn Gly Cys Asn Thr Arg
            35                  40                  45

cag att gta ctt caa cgg gac gct gac tac tac agc ggg aac tgc ccc       773
Gln Ile Val Leu Gln Arg Asp Ala Asp Tyr Tyr Ser Gly Asn Cys Pro
        50                  55                  60

gtc act acc gga aag tgg tac agt tac ttt gat ggc gtc att gtg tac       821
Val Thr Thr Gly Lys Trp Tyr Ser Tyr Phe Asp Gly Val Ile Val Tyr
    65                  70                  75

tcg cca tcc gaa att gat att gat cac att gtt cct ttg gcc gaa gct       869
Ser Pro Ser Glu Ile Asp Ile Asp His Ile Val Pro Leu Ala Glu Ala
80                  85                  90                  95

tgg cgt tcc ggt gcc agc agc tgg acc gcc gaa cag cgt cgc aat ttt       917
Trp Arg Ser Gly Ala Ser Ser Trp Thr Ala Glu Gln Arg Arg Asn Phe
                100                 105                 110

gcc aat gat ctc aac ggc cca cag ctg att gcc gtg aca gca agc gtc       965
Ala Asn Asp Leu Asn Gly Pro Gln Leu Ile Ala Val Thr Ala Ser Val
            115                 120                 125

aat cgt tcc aaa gga gac caa gat cct tcc aca tgg caa cct ccg cgt      1013
Asn Arg Ser Lys Gly Asp Gln Asp Pro Ser Thr Trp Gln Pro Pro Arg
        130                 135                 140
```

```
acc ggt gca cgc tgc gct tat gca aag tgg tgg att aac acg aag tac    1061
Thr Gly Ala Arg Cys Ala Tyr Ala Lys Trp Trp Ile Asn Thr Lys Tyr
145                 150                 155

cgc tgg gga tta cat ctt cag tca tcg gaa aaa tcc tct ttg caa agt    1109
Arg Trp Gly Leu His Leu Gln Ser Ser Glu Lys Ser Ser Leu Gln Ser
160                 165                 170                 175

atg ctt aac ggc tgc gct tac taaattcgta tatgcgtctg caagcacagt       1160
Met Leu Asn Gly Cys Ala Tyr
                180

actagtacct gtactttaag atgcattatt tatctacaga aaggagtcat tcgtatggaa  1220

aagaaatcat ctgttttcac tgcaacccat ggagtcatga cagccgaggt tggtgtcatc  1280

agcggagagc tcgaactgcg caccacctgc gatgaagatg gtattctctc gctagctatc  1340

acctatgtcg gggccgaaga gtggtacacc ctccctggcg aagactaccg cctgcacgat  1400

tcgcgtgacc acgaggttgt ccaccgcatg cttgttaagg tgttagaacg aaattgaggg  1460

gagtgggtca gagggacagg ttcctcgacc cactctcttt ttcaatctcc taattttgca  1520

gcatagtcaa ttaaagaatg aaggacgata agtggcaaga tagagccaat tccaatataa  1580

agaatggaga atattattcc aaatatagtt gttcttacta ctcctgttgt gaa         1633

<210> SEQ ID NO 38
<211> LENGTH: 210
<212> TYPE: PRT
<213> ORGANISM: Bacillus species

<400> SEQUENCE: 38

Met Leu Gln Lys Ser Leu Ser Val Val Phe Ala Phe Val Leu Ser Phe
            -25                 -20                 -15

Ser Val Phe His Phe Asp Pro Gln Thr Val Ser Ala Leu Pro Pro Gly
        -10                  -5              -1   1

Thr Pro Ser Lys Ser Glu Ala Gln Ser Gln Leu Thr Ser Leu Thr Val
5                10                  15                   20

Lys Pro Glu Asp Pro Met Thr Gly Tyr Ser Arg Asp His Phe Pro His
                25                  30                  35

Trp Ile Ser Gln Gly Asn Gly Cys Asn Thr Arg Gln Ile Val Leu Gln
            40                  45                  50

Arg Asp Ala Asp Tyr Tyr Ser Gly Asn Cys Pro Val Thr Thr Gly Lys
        55                  60                  65

Trp Tyr Ser Tyr Phe Asp Gly Val Ile Val Tyr Ser Pro Ser Glu Ile
    70                  75                  80

Asp Ile Asp His Ile Val Pro Leu Ala Glu Ala Trp Arg Ser Gly Ala
85                  90                  95                  100

Ser Ser Trp Thr Ala Glu Gln Arg Arg Asn Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Thr Gly Ala Arg Cys
        135                 140                 145

Ala Tyr Ala Lys Trp Trp Ile Asn Thr Lys Tyr Arg Trp Gly Leu His
    150                 155                 160

Leu Gln Ser Ser Glu Lys Ser Ser Leu Gln Ser Met Leu Asn Gly Cys
165                 170                 175                 180

Ala Tyr
```

```
<210> SEQ ID NO 39
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(581)
<220> FEATURE:
<221> NAME/KEY: mat_peptide
<222> LOCATION: (582)..(1130)

<400> SEQUENCE: 39

aaggtatgta gtttattaat ttatctatct atgttttgaa aaatagggtg cttaaataaa     60

ggggttagta taacaaaaaa cacagttgat ataactaaac attttctgga atgggtatat    120

acggtgcctt aatgataagc ccattattca ttaacacttc tttaacttgt tctatcaaat    180

ctaagttggc atctatacaa tatctaaaga attcttttac atttgtccta tttacaagaa    240

ttatagctac aaaatagact gattatttac aaatttttaa ctttaaagaa aataatctgt    300

gtaatattat tgcaagtaga agcattttca atcacagata cctagtttat gttactttac    360

gcaatagaca ttaaaaataa tgaaagctga tgcgctccat ttcgctttaa ttgcaatctt    420

tttcttacta ttaacatcta tcacaagaaa atgaacatag atgttagtat ataaaaccat    480

tacgtatagg aggaatttga atg ctg aaa aaa tcg gtg tgg ttt gtt ttt tcg    533
                      Met Leu Lys Lys Ser Val Trp Phe Val Phe Ser
                                  -25                 -20

ttg gtt ttg acg ttt gct gtt ttt cta tat gac ata ccg gcg gca gcg      581
Leu Val Leu Thr Phe Ala Val Phe Leu Tyr Asp Ile Pro Ala Ala Ala
    -15                 -10                 -5                  -1

gca ttt ccg ccc ggt aca ccg tcc aag tcc acc gcc caa tca cag tta      629
Ala Phe Pro Pro Gly Thr Pro Ser Lys Ser Thr Ala Gln Ser Gln Leu
1               5                   10                  15

aac tcg ctg acc gtt aaa tcc gaa ggt tct atg acc ggc tac tcg cga      677
Asn Ser Leu Thr Val Lys Ser Glu Gly Ser Met Thr Gly Tyr Ser Arg
            20                  25                  30

gac aag ttt cca cat tgg atc agc caa ggt gat ggc tgt gat act cgc      725
Asp Lys Phe Pro His Trp Ile Ser Gln Gly Asp Gly Cys Asp Thr Arg
        35                  40                  45

cag ctg gtg ctt aag cgt gat ggc gac tac tac agt ggg aac tgt cct      773
Gln Leu Val Leu Lys Arg Asp Gly Asp Tyr Tyr Ser Gly Asn Cys Pro
    50                  55                  60

gtc acg tcg ggt aag tgg tac agc tac tac gac ggc atc gcc gtg tac      821
Val Thr Ser Gly Lys Trp Tyr Ser Tyr Tyr Asp Gly Ile Ala Val Tyr
65                  70                  75                  80

tca ccg tct gaa atc gac atc gat cac atc gtc ccg tta gca gaa gca      869
Ser Pro Ser Glu Ile Asp Ile Asp His Ile Val Pro Leu Ala Glu Ala
                85                  90                  95

tgg cgt tct ggc gct agc ggc tgg act acg gaa aag cgc cag aat ttc      917
Trp Arg Ser Gly Ala Ser Gly Trp Thr Thr Glu Lys Arg Gln Asn Phe
            100                 105                 110

gca aac gac ctc aac ggc cca cag cta atc gcg gta acc gct agt gta      965
Ala Asn Asp Leu Asn Gly Pro Gln Leu Ile Ala Val Thr Ala Ser Val
        115                 120                 125

aat cga tcc aag gga gat cag gat ccg tcg acg tgg cag cca ccg cgt     1013
Asn Arg Ser Lys Gly Asp Gln Asp Pro Ser Thr Trp Gln Pro Pro Arg
    130                 135                 140

tct ggt tca cac tgc gcg tac gca aag atg tgg gtc aac acc aag tat     1061
Ser Gly Ser His Cys Ala Tyr Ala Lys Met Trp Val Asn Thr Lys Tyr
145                 150                 155                 160
```

```
cgc tgg ggc ctg cac ttg cag tcg gcg gaa aag tcc gcg ctg cag agc      1109
Arg Trp Gly Leu His Leu Gln Ser Ala Glu Lys Ser Ala Leu Gln Ser
                165                 170                 175

atg ctc aat gcc tgc tcc tac tagtctgtta ttctttgcag agaaaccatt        1160
Met Leu Asn Ala Cys Ser Tyr
            180

ctgccccaga aaggagtcta ctcgtatgga aaagaagtcg tcaatcttca ccgcaacaca   1220

cggtgtaatg acagcggagg tcggcgtaat cagtggggag ctcgaacttc acagcacctg   1280

tgatgacgac ggcaccctca cactagccat cacctatgtc ggcgccgagg aatggtacac   1340

gttgccaggg ggtgattacc tcctgcacga cttgcgtgac cacgaagtcg tccaccgcct   1400

gctcaccgcc gtacttgagc gctcatgagt tggaatgctc tatcaaaggg tgctttcgtt   1460

taattatgca taagatcagc tgcctagtaa ggcagcgatt tttttataat taaagccgta   1520

tagctgaaga agagtttagt ttagtaagaa cacccaattt ttaaaatgta tagaaaatga   1580

tgagataaca tttaatttca tgacttatca actaactttt aaaataggta att          1633


<210> SEQ ID NO 40
<211> LENGTH: 210
<212> TYPE: PRT
<213> ORGANISM: Bacillus species

<400> SEQUENCE: 40

Met Leu Lys Lys Ser Val Trp Phe Val Phe Ser Leu Val Leu Thr Phe
        -25                 -20                 -15

Ala Val Phe Leu Tyr Asp Ile Pro Ala Ala Ala Ala Phe Pro Pro Gly
    -10                 -5              -1  1               5

Thr Pro Ser Lys Ser Thr Ala Gln Ser Gln Leu Asn Ser Leu Thr Val
                10                  15                  20

Lys Ser Glu Gly Ser Met Thr Gly Tyr Ser Arg Asp Lys Phe Pro His
            25                  30                  35

Trp Ile Ser Gln Gly Asp Gly Cys Asp Thr Arg Gln Leu Val Leu Lys
        40                  45                  50

Arg Asp Gly Asp Tyr Tyr Ser Gly Asn Cys Pro Val Thr Ser Gly Lys
    55                  60                  65

Trp Tyr Ser Tyr Tyr Asp Gly Ile Ala Val Tyr Ser Pro Ser Glu Ile
70                  75                  80                  85

Asp Ile Asp His Ile Val Pro Leu Ala Glu Ala Trp Arg Ser Gly Ala
                90                  95                  100

Ser Gly Trp Thr Thr Glu Lys Arg Gln Asn Phe Ala Asn Asp Leu Asn
            105                 110                 115

Gly Pro Gln Leu Ile Ala Val Thr Ala Ser Val Asn Arg Ser Lys Gly
        120                 125                 130

Asp Gln Asp Pro Ser Thr Trp Gln Pro Pro Arg Ser Gly Ser His Cys
    135                 140                 145

Ala Tyr Ala Lys Met Trp Val Asn Thr Lys Tyr Arg Trp Gly Leu His
150                 155                 160                 165

Leu Gln Ser Ala Glu Lys Ser Ala Leu Gln Ser Met Leu Asn Ala Cys
                170                 175                 180

Ser Tyr


<210> SEQ ID NO 41
<211> LENGTH: 1633
<212> TYPE: DNA
<213> ORGANISM: Bacillus horneckiae
```

```
<220> FEATURE:
<221> NAME/KEY: CDS
<222> LOCATION: (501)..(1130)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1130)

<400> SEQUENCE: 41

actttggtaa atccattaat cagtgcctta cttgttgcct gcgtttccat aatattaaag      60

agctgggcaa tttctaatgc gcgcaatagc cgtacatgtc caaagaatcc gtttgaaaaa     120

tcttgatgaa cgaacgaaac attttctgga attggtatat acggtgcctt aatgatatgc     180

ccattattca ttaacacttc tttaacttgt tctatcaaat ttaagttggc atctatacaa     240

tatctaaaga attcttttac gtctgtccta tttacaagaa ttatagctat aaaaaagact     300

gattatttac aaatttttaa ctttaaagaa aaaaatctgt gtaatattat tgcaagtaga     360

agcattttca atcagacatt aaaaataatg cgcgctccat ttcgctttaa ttgcaatctt     420

tttcttacta ttaacatcta tcacaaaaaa atgaacatag atgttagtat ataaaaccat     480

tacgtatagg aggaatttac atg ctg aag aaa tcg gtg ttg ttt gtt ttt tcg     533
                      Met Leu Lys Lys Ser Val Leu Phe Val Phe Ser
                      -25                 -20                 -15

ttg gct ttg aca ttt gct gtt ttt ctt tat gac ata ccg gcg gca tcg       581
Leu Ala Leu Thr Phe Ala Val Phe Leu Tyr Asp Ile Pro Ala Ala Ser
                -10                 -5              -1  1

gca ttt ccg ccc ggt aca ccg tcc aag tcc acc gcc caa tca cag ttg       629
Ala Phe Pro Pro Gly Thr Pro Ser Lys Ser Thr Ala Gln Ser Gln Leu
        5                   10                  15

aat tcg ctg acc gtt aaa tcc gaa ggt tct atg acc ggc tac tcg cga       677
Asn Ser Leu Thr Val Lys Ser Glu Gly Ser Met Thr Gly Tyr Ser Arg
    20                  25                  30

gac aag ttt cca cat tgg atc agc caa ggt gat ggc tgt gac act cgc       725
Asp Lys Phe Pro His Trp Ile Ser Gln Gly Asp Gly Cys Asp Thr Arg
35                  40                  45                  50

cag ctg gtg ctt aag cgt gac ggc gac tac tac agt ggt aac tgt ccc       773
Gln Leu Val Leu Lys Arg Asp Gly Asp Tyr Tyr Ser Gly Asn Cys Pro
                55                  60                  65

gtc aca tcg ggt aag tgg tac agc tac tac gac ggc atc acc gtg tac       821
Val Thr Ser Gly Lys Trp Tyr Ser Tyr Tyr Asp Gly Ile Thr Val Tyr
            70                  75                  80

tca ccg tct gaa atc gac atc gat cac atc gtc ccg tta gca gaa gca       869
Ser Pro Ser Glu Ile Asp Ile Asp His Ile Val Pro Leu Ala Glu Ala
        85                  90                  95

tgg cgt tcg ggc gct agc ggc tgg aca acg gaa aag cgc cag agc ttc       917
Trp Arg Ser Gly Ala Ser Gly Trp Thr Thr Glu Lys Arg Gln Ser Phe
    100                 105                 110

gca aac gac ctc aac ggc cca cag cta atc gcg gta acc gct agt gta       965
Ala Asn Asp Leu Asn Gly Pro Gln Leu Ile Ala Val Thr Ala Ser Val
115                 120                 125                 130

aat cga tcc aag gga gac cag gat ccg tcg acg tgg cag cca ccg cgt      1013
Asn Arg Ser Lys Gly Asp Gln Asp Pro Ser Thr Trp Gln Pro Pro Arg
                135                 140                 145

tct ggt tca cac tgc gcg tac gca aag atg tgg gtc aac acc aag tat      1061
Ser Gly Ser His Cys Ala Tyr Ala Lys Met Trp Val Asn Thr Lys Tyr
            150                 155                 160

cgc tgg ggc ctg cac gtg cag tcg gcg gaa aag tcc gcg ctg cag agc      1109
Arg Trp Gly Leu His Val Gln Ser Ala Glu Lys Ser Ala Leu Gln Ser
        165                 170                 175
```

```
atg ctc aat gcc tgc tcc tac tagtctgtta ttatttgcag agaaaccatt       1160
Met Leu Asn Ala Cys Ser Tyr
    180                185

ctgcccagaa aggagtctac tcgtatggaa aagaaatcgt ccatcttcac cgcaacacac   1220

ggtgtaatga cagcagaagt cggcgtaatc agtggggagc tcgaacttcg cagcacctgt   1280

gatgacgacg gcaccctcac attagccatc acctatgttg gcgccgagga atggtacacg   1340

ttgccagggg atgattacca cctgcacgac ttgcgtgacc acgaagtcgt ccaccgcctg   1400

ctcaccgccg tacttgagcg ctcatgagct ggtatgctct atcaaagggt gctttcgttt   1460

aattatgcat aagatcagct gcctagttag gcagcgattt tttttataat taaagcagta   1520

tagccgaaga agagtttagc tcagtaagaa cacccaattt ttaaaatgta taggagataa   1580

caattaaatt catgacttat caactaactt ttaaaatagg taatttaagg tat          1633


<210> SEQ ID NO 42
<211> LENGTH: 210
<212> TYPE: PRT
<213> ORGANISM: Bacillus horneckiae

<400> SEQUENCE: 42

Met Leu Lys Lys Ser Val Leu Phe Val Phe Ser Leu Ala Leu Thr Phe
-25                 -20                 -15                 -10

Ala Val Phe Leu Tyr Asp Ile Pro Ala Ala Ser Ala Phe Pro Pro Gly
                -5              -1  1               5

Thr Pro Ser Lys Ser Thr Ala Gln Ser Gln Leu Asn Ser Leu Thr Val
        10                  15                  20

Lys Ser Glu Gly Ser Met Thr Gly Tyr Ser Arg Asp Lys Phe Pro His
    25                  30                  35

Trp Ile Ser Gln Gly Asp Gly Cys Asp Thr Arg Gln Leu Val Leu Lys
40                  45                  50                  55

Arg Asp Gly Asp Tyr Tyr Ser Gly Asn Cys Pro Val Thr Ser Gly Lys
                60                  65                  70

Trp Tyr Ser Tyr Tyr Asp Gly Ile Thr Val Tyr Ser Pro Ser Glu Ile
            75                  80                  85

Asp Ile Asp His Ile Val Pro Leu Ala Glu Ala Trp Arg Ser Gly Ala
        90                  95                  100

Ser Gly Trp Thr Thr Glu Lys Arg Gln Ser Phe Ala Asn Asp Leu Asn
    105                 110                 115

Gly Pro Gln Leu Ile Ala Val Thr Ala Ser Val Asn Arg Ser Lys Gly
120                 125                 130                 135

Asp Gln Asp Pro Ser Thr Trp Gln Pro Pro Arg Ser Gly Ser His Cys
                140                 145                 150

Ala Tyr Ala Lys Met Trp Val Asn Thr Lys Tyr Arg Trp Gly Leu His
            155                 160                 165

Val Gln Ser Ala Glu Lys Ser Ala Leu Gln Ser Met Leu Asn Ala Cys
        170                 175                 180

Ser Tyr
    185


<210> SEQ ID NO 43
<211> LENGTH: 1633
<212> TYPE: DNA
<213> ORGANISM: Bacillus species
<220> FEATURE:
<221> NAME/KEY: CDS
<222> LOCATION: (501)..(1130)
```

```
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 43

ggatatagaa aaagtatttc cttttcttcg agaaaacgaa actctcatac gcatttggat      60

tgaacctaaa gaaattcaat acgttttaaa tgaccatgaa ttatcaaccc acgtaataaa     120

tgaagcatta aaaatctctg attcatacat ttagcttagt gtatgttaaa gtttacactt     180

gctgaacaaa cggggcaggt tggtttaaaa tggaaaaatt gctgaaggaa gagaaaaaac     240

tatgtttttt tctaaaatag acagattatt tacaaatttt taactttaaa gaaaataatc     300

cgtgtaatat tattacaagt agaggcgttt tcaacttatt accttatttc attaaaaact     360

aaaagaaaca ttaaaagtaa tgaatcgttg acgtgctcta tttcgctttg attgcaattt     420

ttttcttact attaacatct attcattaaa aatgaacata gatgttagta tataaaacaa     480

ttattatagg aggaatttct atg ttg aag aaa tcg atg ttg ttt gtt ttt tcg     533
                      Met Leu Lys Lys Ser Met Leu Phe Val Phe Ser
                                  -25                 -20

ttg gtt ttg tcg ttt gct gtt ttt caa tat gac ata cca acg gca tcg      581
Leu Val Leu Ser Phe Ala Val Phe Gln Tyr Asp Ile Pro Thr Ala Ser
        -15                 -10                 -5

gct ttt ccg cct gaa ata ccg tcc aag tct acc gcc caa tcc cag ttg      629
Ala Phe Pro Pro Glu Ile Pro Ser Lys Ser Thr Ala Gln Ser Gln Leu
-1  1               5                   10                  15

aat tcg ctg acc gtt aag tcc gaa gac gct atg acc ggc tac tcg cga      677
Asn Ser Leu Thr Val Lys Ser Glu Asp Ala Met Thr Gly Tyr Ser Arg
                20                  25                  30

gac aag ttt ccg cat tgg att agc caa ggc gat ggc tgt gac act cgc      725
Asp Lys Phe Pro His Trp Ile Ser Gln Gly Asp Gly Cys Asp Thr Arg
            35                  40                  45

cag atg gtg ctc aag cgt gac gct gac tac tac agt ggg agc tgc ccc      773
Gln Met Val Leu Lys Arg Asp Ala Asp Tyr Tyr Ser Gly Ser Cys Pro
        50                  55                  60

gtc acg tct ggt aag tgg tac agc tac tac gac ggt atc acc gtg tac      821
Val Thr Ser Gly Lys Trp Tyr Ser Tyr Tyr Asp Gly Ile Thr Val Tyr
    65                  70                  75

tca ccg tct gaa atc gac atc gat cac atc gtc ccg tta gca gaa gcg      869
Ser Pro Ser Glu Ile Asp Ile Asp His Ile Val Pro Leu Ala Glu Ala
80                  85                  90                  95

tgg cgt tcc ggc gct agc agc tgg acc acg gaa aag cgc cgg aac ttc      917
Trp Arg Ser Gly Ala Ser Ser Trp Thr Thr Glu Lys Arg Arg Asn Phe
                100                 105                 110

gca aac gac ctc aac ggc cca cag cta att gcg gtg acc gcc agc gtt      965
Ala Asn Asp Leu Asn Gly Pro Gln Leu Ile Ala Val Thr Ala Ser Val
            115                 120                 125

aac cgg tcc aag ggc gac cag gat cca tcg acg tgg cag cca ccg cgt     1013
Asn Arg Ser Lys Gly Asp Gln Asp Pro Ser Thr Trp Gln Pro Pro Arg
        130                 135                 140

tcc ggc gcc cgc tgc gca tac gcg aag atg tgg gtc aac acc aag tac     1061
Ser Gly Ala Arg Cys Ala Tyr Ala Lys Met Trp Val Asn Thr Lys Tyr
    145                 150                 155

cgc tgg ggc ctg cac ctg cag tcg gcg gag aag tcc ggg ctg gag agc     1109
Arg Trp Gly Leu His Leu Gln Ser Ala Glu Lys Ser Gly Leu Glu Ser
160                 165                 170                 175

atg ctc aac acc tgc tcc tac taagtctgtt agaacttgca gtgaaaccat        1160
Met Leu Asn Thr Cys Ser Tyr
```

180 ccaacctcag aagggagtct actcgtatgg aaaagaaatc gtcaatcttc accgcaactc 1220 acggtgtaat gaccgctgag gtcggcgtga tcagtgggga actcgaactt cgcacaacct 1280 gtgatgatga cggctttctc acgctcgcca tcacgtatgt cggcgccgag gagtggtaca 1340 cgctgccggg taaagattac cacctgcacg atccgcgtga ccatgaagtc gtccaccgca 1400 tgctcaccgc cgtactagag cgcccatgag atcgactgct taactatcaa gaaaagggta 1460 ctttcgttta actatgcata agatcagctg cctaatcggg cagcgatttt ctttttgaac 1520 taaagtggga gtttagaata agagttaatc attcttctat aatttgatta atactgtata 1580 tatagtgtgg gggatgctgt gtgattatta aacagataac atgtgaagtg aaa 1633

<210> SEQ ID NO 44
<211> LENGTH: 210
<212> TYPE: PRT
<213> ORGANISM: Bacillus species

<400> SEQUENCE: 44

Met Leu Lys Lys Ser Met Leu Phe Val Phe Ser Leu Val Leu Ser Phe
-25 -20 -15

Ala Val Phe Gln Tyr Asp Ile Pro Thr Ala Ser Ala Phe Pro Pro Glu
-10 -5 -1 1

Ile Pro Ser Lys Ser Thr Ala Gln Ser Gln Leu Asn Ser Leu Thr Val
5 10 15 20

Lys Ser Glu Asp Ala Met Thr Gly Tyr Ser Arg Asp Lys Phe Pro His
25 30 35

Trp Ile Ser Gln Gly Asp Gly Cys Asp Thr Arg Gln Met Val Leu Lys
40 45 50

Arg Asp Ala Asp Tyr Tyr Ser Gly Ser Cys Pro Val Thr Ser Gly Lys
55 60 65

Trp Tyr Ser Tyr Tyr Asp Gly Ile Thr Val Tyr Ser Pro Ser Glu Ile
70 75 80

Asp Ile Asp His Ile Val Pro Leu Ala Glu Ala Trp Arg Ser Gly Ala
85 90 95 100

Ser Ser Trp Thr Thr Glu Lys Arg Arg Asn Phe Ala Asn Asp Leu Asn
105 110 115

Gly Pro Gln Leu Ile Ala Val Thr Ala Ser Val Asn Arg Ser Lys Gly
120 125 130

Asp Gln Asp Pro Ser Thr Trp Gln Pro Pro Arg Ser Gly Ala Arg Cys
135 140 145

Ala Tyr Ala Lys Met Trp Val Asn Thr Lys Tyr Arg Trp Gly Leu His
150 155 160

Leu Gln Ser Ala Glu Lys Ser Gly Leu Glu Ser Met Leu Asn Thr Cys
165 170 175 180

Ser Tyr

<210> SEQ ID NO 45
<211> LENGTH: 1624
<212> TYPE: DNA
<213> ORGANISM: Bacillus cibi
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:

```
<221> NAME/KEY: mat_peptide
<222> LOCATION: (576)..(1121)

<400> SEQUENCE: 45

cctcaacggg agacgcatcc ccggtgagtt tgatttttct tgctttatcc tattcccaat     60

agacctctga gaaaaagggt ttcctatgaa cttatgggga aacctttttta attttcaaga    120

gcttctgcct gcatctgctc ggaaacacct gtatcattgg actcattttt attccccatt    180

gtaaatttgc agacggaagg gttttgattc ctttttctca ccttaaatga aattgtttca    240

tgacatatgg cctcaaattt ataaatacct ctattcattc ccttcctttg gaacttaaaa    300

tcagcgtaaa ttccatcata catgttaagg agtttacatt tgattaactt gtagaaatct    360

ctcttttcat actatgattt ctaatagaga gataaatttc catctttctt atccgccctc    420

atttcctttt gtgctgtcta ttaatctcac tgactactgg ttatgggatt agtataaaat    480

tttttacagg aggcatctac atg ctg aaa aaa gct tca tta tct gtt ttt gca    533
                      Met Leu Lys Lys Ala Ser Leu Ser Val Phe Ala
                      -25                 -20                 -15

ctg ctt ctc tca ttc act ttg ttt ctc ccg gaa acc cat gct acg ccg      581
Leu Leu Leu Ser Phe Thr Leu Phe Leu Pro Glu Thr His Ala Thr Pro
                -10                 -5                  -1  1

ccg ggc act ccg tca aag tcc gca gca caa tcc cag ctt aac gcg ctg      629
Pro Gly Thr Pro Ser Lys Ser Ala Ala Gln Ser Gln Leu Asn Ala Leu
        5                   10                  15

acc gtt aag aca gaa ggc tcc atg agc ggc tac tca cgt gat tta ttc      677
Thr Val Lys Thr Glu Gly Ser Met Ser Gly Tyr Ser Arg Asp Leu Phe
    20                  25                  30

cct cac tgg atc agt cag gga agc ggc tgt gac acc cgc caa gtt gtt      725
Pro His Trp Ile Ser Gln Gly Ser Gly Cys Asp Thr Arg Gln Val Val
35                  40                  45                  50

ctt aaa cgt gac gca gac tcc tac agc ggt aat tgc ccc gta aca tca      773
Leu Lys Arg Asp Ala Asp Ser Tyr Ser Gly Asn Cys Pro Val Thr Ser
                55                  60                  65

ggc agc tgg tac agc tat tac gac ggt gta acg ttc acc aat cct tct      821
Gly Ser Trp Tyr Ser Tyr Tyr Asp Gly Val Thr Phe Thr Asn Pro Ser
            70                  75                  80

gat ctt gat atc gat cat atc gtc cct ctt gca gaa gca tgg aga tcc      869
Asp Leu Asp Ile Asp His Ile Val Pro Leu Ala Glu Ala Trp Arg Ser
        85                  90                  95

ggt gcc agc agc tgg aca acg tcc aag cgc cag gat ttt gca aac gat      917
Gly Ala Ser Ser Trp Thr Thr Ser Lys Arg Gln Asp Phe Ala Asn Asp
    100                 105                 110

tta agc gga cct cag cta att gca gta agt gcc agc acc aac cgt tcc      965
Leu Ser Gly Pro Gln Leu Ile Ala Val Ser Ala Ser Thr Asn Arg Ser
115                 120                 125                 130

aaa ggt gac cag gat cct tct aca tgg cag cca cca cgc tca ggt gca     1013
Lys Gly Asp Gln Asp Pro Ser Thr Trp Gln Pro Pro Arg Ser Gly Ala
                135                 140                 145

gcg tgc ggg tat tca aaa tgg tgg atc agc aca aaa tac aaa tgg gga     1061
Ala Cys Gly Tyr Ser Lys Trp Trp Ile Ser Thr Lys Tyr Lys Trp Gly
            150                 155                 160

tta agc ctt cag tct tca gaa aag acc gcg ctt caa ggc atg ctc aat     1109
Leu Ser Leu Gln Ser Ser Glu Lys Thr Ala Leu Gln Gly Met Leu Asn
        165                 170                 175

agc tgt tct tat taagggttta actaaaaaaa cgagcagcca aaagcggctg         1161
Ser Cys Ser Tyr
    180

ctcgtttatg ctataatcta agcaaatgat ggaggtgaca agcatggaga agaaatcaac   1221
```

```
ggtttttacc gccacccacg gtgtcatgac agcagaagtc ggcgtcatca gcggcgagct   1281

tgaacttgtc acagcctgca gagaagacgg cgttcttact ctttccatta catacaatgg   1341

ggctgcagag tggtactctc ttccgggtga ggaataccgg ctgtatgatg tgcgggatca   1401

tgaagtggtt catgagatgc ttgtcagagt gcttgagcgt ccttgattca cctagaacct   1461

agaggatcat aaaaatgaaa gccgcctgac aagtccagtt acggtcctat caggcggctc   1521

tttgtatgct tcaaacttcc agcagaaatt catgctccgc aaaagattgc tcaatctaaa   1581

tcgaatccga caaacccatt atcctctcct gaaaaacaaa acg                     1624
```

<210> SEQ ID NO 46
<211> LENGTH: 207
<212> TYPE: PRT
<213> ORGANISM: Bacillus cibi

<400> SEQUENCE: 46

```
Met Leu Lys Lys Ala Ser Leu Ser Val Phe Ala Leu Leu Leu Ser Phe
-25                 -20                 -15                 -10

Thr Leu Phe Leu Pro Glu Thr His Ala Thr Pro Pro Gly Thr Pro Ser
                -5              -1  1               5

Lys Ser Ala Ala Gln Ser Gln Leu Asn Ala Leu Thr Val Lys Thr Glu
        10                  15                  20

Gly Ser Met Ser Gly Tyr Ser Arg Asp Leu Phe Pro His Trp Ile Ser
    25                  30                  35

Gln Gly Ser Gly Cys Asp Thr Arg Gln Val Val Leu Lys Arg Asp Ala
40                  45                  50                  55

Asp Ser Tyr Ser Gly Asn Cys Pro Val Thr Ser Gly Ser Trp Tyr Ser
                60                  65                  70

Tyr Tyr Asp Gly Val Thr Phe Thr Asn Pro Ser Asp Leu Asp Ile Asp
            75                  80                  85

His Ile Val Pro Leu Ala Glu Ala Trp Arg Ser Gly Ala Ser Ser Trp
        90                  95                  100

Thr Thr Ser Lys Arg Gln Asp Phe Ala Asn Asp Leu Ser Gly Pro Gln
    105                 110                 115

Leu Ile Ala Val Ser Ala Ser Thr Asn Arg Ser Lys Gly Asp Gln Asp
120                 125                 130                 135

Pro Ser Thr Trp Gln Pro Pro Arg Ser Gly Ala Ala Cys Gly Tyr Ser
                140                 145                 150

Lys Trp Trp Ile Ser Thr Lys Tyr Lys Trp Gly Leu Ser Leu Gln Ser
            155                 160                 165

Ser Glu Lys Thr Ala Leu Gln Gly Met Leu Asn Ser Cys Ser Tyr
        170                 175                 180
```

<210> SEQ ID NO 47
<211> LENGTH: 1624
<212> TYPE: DNA
<213> ORGANISM: Bacillus species
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 47

```
cgtattttta aaatgctgca cgtaaatgtg gaaagtggaa tgtatttttc aaaagtggaa     60
```

-continued

```
cgtaaatgca ggaattggat tgtattttca atttatatgg aattgacttc tcccgaacgt    120

ttcataagcc aaatttcata gtgggatcga aacgtaaagt gaggatatta gatgacgcca    180

ccatttactt cgggcttttt ctctctcaag taggcacaac gtatcacaag tttagtgctc    240

acagtgaacc cataatcctg agggaccagg aacatagttt caacctttgt aaagcatacc    300

aatttacaaa attttaactt gttagaaggt tattccatcc actatcattc aagtagaagc    360

aaacccgctt ctatccgatc ctcacaaaat tgattcaacc tgaacttaat tcaaagtctg    420

actacatcga ttcactatta acattccatt ctctgagaat gagatgttga tataaaaaaa    480

tacatacagg aggcattatc atg cta aag aaa tcg atg ctg ttt gtt gtt gcg    533
                      Met Leu Lys Lys Ser Met Leu Phe Val Val Ala
                      -25                 -20                 -15

cta ctt ctt tcg ttc act tta ttc ctg ccg acc gcc ttt gca ttc ccg      581
Leu Leu Leu Ser Phe Thr Leu Phe Leu Pro Thr Ala Phe Ala Phe Pro
                -10                 -5              -1   1

cct ggt aca ccg tcc aaa tct acg gca caa tcg caa ctg aac tca ctc      629
Pro Gly Thr Pro Ser Lys Ser Thr Ala Gln Ser Gln Leu Asn Ser Leu
        5                   10                  15

act gtt aaa tct gaa ggc tcc atg acc ggt tat tcg cgg gac aag ttc      677
Thr Val Lys Ser Glu Gly Ser Met Thr Gly Tyr Ser Arg Asp Lys Phe
    20                  25                  30

ccc cat tgg atc ggt caa ggg agc gga tgt gac acc cgc cag ctc gtt      725
Pro His Trp Ile Gly Gln Gly Ser Gly Cys Asp Thr Arg Gln Leu Val
35                  40                  45                  50

ctc cag cgt gac gcc gac tat tac agc ggc agt tgc cca gta acg tca      773
Leu Gln Arg Asp Ala Asp Tyr Tyr Ser Gly Ser Cys Pro Val Thr Ser
                55                  60                  65

ggt aaa tgg tac agc tac tat gac gga gtc aca ttt tac gat ccg tcc      821
Gly Lys Trp Tyr Ser Tyr Tyr Asp Gly Val Thr Phe Tyr Asp Pro Ser
            70                  75                  80

gac ctt gat atc gat cac gtc gtt ccg ctt gcc gaa gcg tgg cgt tcc      869
Asp Leu Asp Ile Asp His Val Val Pro Leu Ala Glu Ala Trp Arg Ser
        85                  90                  95

ggt gcg agc agt tgg agc aca cag aag cgt aaa gac ttc gcc aac gat      917
Gly Ala Ser Ser Trp Ser Thr Gln Lys Arg Lys Asp Phe Ala Asn Asp
    100                 105                 110

ctc agt ggc ccg cag ctg atc gcc gtc agc gca agc tcc aat cgg tct      965
Leu Ser Gly Pro Gln Leu Ile Ala Val Ser Ala Ser Ser Asn Arg Ser
115                 120                 125                 130

aaa ggc gac cag gat cca tcc aca tgg cag cca aca cga tca ggc gca     1013
Lys Gly Asp Gln Asp Pro Ser Thr Trp Gln Pro Thr Arg Ser Gly Ala
                135                 140                 145

gcc tgc ggt tac tcg aag tgg tgg atc agc acg aag cac aag tgg gga     1061
Ala Cys Gly Tyr Ser Lys Trp Trp Ile Ser Thr Lys His Lys Trp Gly
            150                 155                 160

tta agt ctt cag tct tca gag aag aac gca ctt caa ggc atg ctg aac     1109
Leu Ser Leu Gln Ser Ser Glu Lys Asn Ala Leu Gln Gly Met Leu Asn
        165                 170                 175

agc tgc gtt tac tgattggaac catgaggatc cccgtacgct ctgcacgtac         1161
Ser Cys Val Tyr
    180

gggaattgtt cacatccaac cattagaatg gaggaatata tgtggaaagg aaatcaacta   1221

tttttacagc aacccatggc gtcatgacct cagaggtggg tgtaattagc ggagaccttg   1281

agcttgtcac cacctgtgat gattctggcg ttctgacact ttcaatcacg tatgttggag   1341

ctgatgaatg gtatacacta cctggtgagg aatatcgact tcatgatacg cgagatcatg   1401
```

-continued

```
aggtcgtgca caaaatgctt tctgcggtgt tggagcgtcc ttgaagttgg ggcaatgtac   1461

gtatcatttt gagaaatcat tcggggttcc gaatgatttt ttttgaagcg aatagcttgg   1521

tcaagcggcc tgttccccga tccataggat taaggtcggt tggaggtgtg gcccccgcat   1581

ttcattggac gtgaatatcc atgacctgtg atttttcgac aag                     1624


<210> SEQ ID NO 48
<211> LENGTH: 207
<212> TYPE: PRT
<213> ORGANISM: Bacillus species

<400> SEQUENCE: 48

Met Leu Lys Lys Ser Met Leu Phe Val Val Ala Leu Leu Leu Ser Phe
-25                 -20                 -15                 -10

Thr Leu Phe Leu Pro Thr Ala Phe Ala Phe Pro Pro Gly Thr Pro Ser
                -5              -1  1               5

Lys Ser Thr Ala Gln Ser Gln Leu Asn Ser Leu Thr Val Lys Ser Glu
        10                  15                  20

Gly Ser Met Thr Gly Tyr Ser Arg Asp Lys Phe Pro His Trp Ile Gly
    25                  30                  35

Gln Gly Ser Gly Cys Asp Thr Arg Gln Leu Val Leu Gln Arg Asp Ala
40                  45                  50                  55

Asp Tyr Tyr Ser Gly Ser Cys Pro Val Thr Ser Gly Lys Trp Tyr Ser
                60                  65                  70

Tyr Tyr Asp Gly Val Thr Phe Tyr Asp Pro Ser Asp Leu Asp Ile Asp
            75                  80                  85

His Val Val Pro Leu Ala Glu Ala Trp Arg Ser Gly Ala Ser Ser Trp
        90                  95                  100

Ser Thr Gln Lys Arg Lys Asp Phe Ala Asn Asp Leu Ser Gly Pro Gln
    105                 110                 115

Leu Ile Ala Val Ser Ala Ser Ser Asn Arg Ser Lys Gly Asp Gln Asp
120                 125                 130                 135

Pro Ser Thr Trp Gln Pro Thr Arg Ser Gly Ala Ala Cys Gly Tyr Ser
                140                 145                 150

Lys Trp Trp Ile Ser Thr Lys His Lys Trp Gly Leu Ser Leu Gln Ser
            155                 160                 165

Ser Glu Lys Asn Ala Leu Gln Gly Met Leu Asn Ser Cys Val Tyr
        170                 175                 180


<210> SEQ ID NO 49
<211> LENGTH: 1624
<212> TYPE: DNA
<213> ORGANISM: Bacillus idriensis
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 49

gaatgaagcg acctatccta gagcaaagag aacagcccgc ccgaccattt atgacctcaa     60

tttatttgta tggatctgca aaattcttcc acaagcgaaa atctttgcat caatttcagc    120

tgaaataaat ccaatccaac tcctccttct atgtactcat tttctgatta tattttttaa    180

aatggaacct cttcaatcag agaactttg atacaacatc ctcattttca gaaaaaaact     240
```

-continued

```
cattactaat taccctgatt atttaaggag ttatatcgtt actcttcctt atgtacttcc    300

tttctccccc taaatgttaa gggatttaca aatgcttaac ttgttaaaaa ttcaattatt    360

atactatcat ttctaatgaa gaaacaaatt tccatttacc tgtgaaatac agtccagtgg    420

cttgctgcgc gtttgatgtt aacctctcac ctatcaaaaa tgagagattg atataaaaat    480

tacatacagg aggcatttaa atg ctg aaa aaa atg atg ttg ttt gtt ttt gca    533
                      Met Leu Lys Lys Met Met Leu Phe Val Phe Ala
                      -25                 -20                 -15

cta gtt ctc tcg ttt aca tta ttc ttg cca gac gcc tat gca ctg cca      581
Leu Val Leu Ser Phe Thr Leu Phe Leu Pro Asp Ala Tyr Ala Leu Pro
                -10                 -5              -1   1

ccc gga act ccg tcc aaa tcc act gca caa tcc cag ctg aac gcg ttg      629
Pro Gly Thr Pro Ser Lys Ser Thr Ala Gln Ser Gln Leu Asn Ala Leu
        5                   10                  15

acc gtg cag aca gaa ggc tct atg acc ggc tac tct cgt gac aaa ttt      677
Thr Val Gln Thr Glu Gly Ser Met Thr Gly Tyr Ser Arg Asp Lys Phe
    20                  25                  30

ccc cat tgg atc agt caa gga aac ggc tgt gac acc cgt cag gtg gtg      725
Pro His Trp Ile Ser Gln Gly Asn Gly Cys Asp Thr Arg Gln Val Val
35                  40                  45                  50

ctt cag cgt gat gcc gat tac tac agc ggc acc tgc cct gtg aca tcc      773
Leu Gln Arg Asp Ala Asp Tyr Tyr Ser Gly Thr Cys Pro Val Thr Ser
                55                  60                  65

ggc aag tgg tac agt tac tac gac ggt gtt acg ctg tac aat ccg tcg      821
Gly Lys Trp Tyr Ser Tyr Tyr Asp Gly Val Thr Leu Tyr Asn Pro Ser
            70                  75                  80

gac ctt gac atc gat cat gtc gtc gct ctt gct gag gcg tgg cgt tcc      869
Asp Leu Asp Ile Asp His Val Val Ala Leu Ala Glu Ala Trp Arg Ser
        85                  90                  95

ggc gca agc agc tgg aca acg gac aaa cgt gag gac ttt gcc aac gac      917
Gly Ala Ser Ser Trp Thr Thr Asp Lys Arg Glu Asp Phe Ala Asn Asp
    100                 105                 110

tta agc ggc acg cag ctg att gcg gta agc gcc agc acc aat cgt tcc      965
Leu Ser Gly Thr Gln Leu Ile Ala Val Ser Ala Ser Thr Asn Arg Ser
115                 120                 125                 130

aaa ggt gac caa gat ccg tct acg tgg cag ccg cct cgt tcc ggt gca     1013
Lys Gly Asp Gln Asp Pro Ser Thr Trp Gln Pro Pro Arg Ser Gly Ala
                135                 140                 145

gca tgc gga tat gca aag tgg tgg atc agt acg aag tac aaa tgg aat     1061
Ala Cys Gly Tyr Ala Lys Trp Trp Ile Ser Thr Lys Tyr Lys Trp Asn
            150                 155                 160

tta aac ctg caa tct tca gag aag acc gcg ctt caa agc atg ctc aat     1109
Leu Asn Leu Gln Ser Ser Glu Lys Thr Ala Leu Gln Ser Met Leu Asn
        165                 170                 175

agt tgc tct tat tgattatata gctgttcgaa cgaacgattc acagttgatt         1161
Ser Cys Ser Tyr
    180

gttcgttcgt acagtaaata atggaggtgc ttttatggaa aagaagtcaa ctgcttttac   1221

agcaacccac ggtgtcatga cctctgaggt tggtgttatc agcggtgagc ttgagcttgt   1281

tacaacgtgc ggtgatgacg gtgacctaac tctcgccatc acatatgttg gggctgagga   1341

gtggtattcc cttcccgggg agaaatacaa gttgtatgac ttgcgtgatc acggggtcat   1401

tcacgagatg cttgtgaggg tacttgagcg cccttaaggc attgggtcat ttagattatg   1461

gtggaattat tgcgtgaggt atataaaaac aggcaatctt tcgaaataac tcaagagaca   1521

tgaaatgact tcatgtctct ttttctgtta aaaaataatc cccaatcctg caaaagcaag   1581
```

atcctcacaa tctacttttt gaacataact ttctttttca aac 1624

<210> SEQ ID NO 50
<211> LENGTH: 207
<212> TYPE: PRT
<213> ORGANISM: Bacillus idriensis

<400> SEQUENCE: 50

```
Met Leu Lys Lys Met Met Leu Phe Val Phe Ala Leu Val Leu Ser Phe
-25                 -20                 -15                 -10

Thr Leu Phe Leu Pro Asp Ala Tyr Ala Leu Pro Pro Gly Thr Pro Ser
                -5                  -1  1               5

Lys Ser Thr Ala Gln Ser Gln Leu Asn Ala Leu Thr Val Gln Thr Glu
        10                  15                  20

Gly Ser Met Thr Gly Tyr Ser Arg Asp Lys Phe Pro His Trp Ile Ser
    25                  30                  35

Gln Gly Asn Gly Cys Asp Thr Arg Gln Val Val Leu Gln Arg Asp Ala
40                  45                  50                  55

Asp Tyr Tyr Ser Gly Thr Cys Pro Val Thr Ser Gly Lys Trp Tyr Ser
                60                  65                  70

Tyr Tyr Asp Gly Val Thr Leu Tyr Asn Pro Ser Asp Leu Asp Ile Asp
            75                  80                  85

His Val Val Ala Leu Ala Glu Ala Trp Arg Ser Gly Ala Ser Ser Trp
        90                  95                  100

Thr Thr Asp Lys Arg Glu Asp Phe Ala Asn Asp Leu Ser Gly Thr Gln
    105                 110                 115

Leu Ile Ala Val Ser Ala Ser Thr Asn Arg Ser Lys Gly Asp Gln Asp
120                 125                 130                 135

Pro Ser Thr Trp Gln Pro Pro Arg Ser Gly Ala Ala Cys Gly Tyr Ala
                140                 145                 150

Lys Trp Trp Ile Ser Thr Lys Tyr Lys Trp Asn Leu Asn Leu Gln Ser
            155                 160                 165

Ser Glu Lys Thr Ala Leu Gln Ser Met Leu Asn Ser Cys Ser Tyr
        170                 175                 180
```

<210> SEQ ID NO 51
<211> LENGTH: 1633
<212> TYPE: DNA
<213> ORGANISM: Bacillus algicola
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 51

```
aaacgatcag ctagtgaatc acccatccga ttcaacaggt gaacggccag tgtcagatgg     60

gattctcatt tttgaataga aattttggga cgaaaatata gagtctacta tttcgatagt    120

aggcagcaag ccgagggtaa ttcctcggct ttttctaatt catccaaagg tcacactttt    180

tattaagctt gtaaaatttg taggtaatat ctacttaaaa ttgaaataac cttcactagc    240

tcatatgaac caactttact tttatggcta tgaactatag aacattgctg gatagatatg    300

ctagatttaa gtcgcgctaa tggaaagatg aaccatctat acataaaaga aacacaaacc    360

tatttcgctt gctaaagagg tcacctcctc ttgttctgtc tcaatttttt gcatgaacta    420
```

```
tgaaactatt actatcacct tcacctaaaa gtgaacggtg atgttagtac ataaataaac    480

aaaaaatagg aggctccacc atg ctt aag aag tcg ttt ttg att gtt ttt acg    533
                      Met Leu Lys Lys Ser Phe Leu Ile Val Phe Thr
                                  -25                 -20

ttg gtt ctg ttg ttt gct ggg ttt caa ctt ggt ctg ccg tca gct ctt      581
Leu Val Leu Leu Phe Ala Gly Phe Gln Leu Gly Leu Pro Ser Ala Leu
        -15                 -10                 -5

gcg ttt ccc cca ggt aca ccg tct aaa tct gaa gct caa tct cag ttg      629
Ala Phe Pro Pro Gly Thr Pro Ser Lys Ser Glu Ala Gln Ser Gln Leu
-1  1               5                   10                  15

aat tcc ctc act gta cag tca gaa ggc tcg atg tcc ggc tat tcg cgc      677
Asn Ser Leu Thr Val Gln Ser Glu Gly Ser Met Ser Gly Tyr Ser Arg
                20                  25                  30

gat aag ttc cca cac tgg att ggt cag ggt aat ggg tgt gat aca cgt      725
Asp Lys Phe Pro His Trp Ile Gly Gln Gly Asn Gly Cys Asp Thr Arg
            35                  40                  45

cag tta gtg ctt cag cgt gat gcg gat tac tac agt gga gat tgt cct      773
Gln Leu Val Leu Gln Arg Asp Ala Asp Tyr Tyr Ser Gly Asp Cys Pro
        50                  55                  60

gtt acg tcc ggt aag tgg tac agc tac ttc gat ggt gtg acg gtg tat      821
Val Thr Ser Gly Lys Trp Tyr Ser Tyr Phe Asp Gly Val Thr Val Tyr
    65                  70                  75

gat ccg tct gat cta gac atc gat cat atg gta ccg atg gca gag gcg      869
Asp Pro Ser Asp Leu Asp Ile Asp His Met Val Pro Met Ala Glu Ala
80                  85                  90                  95

tgg cgt tca ggg gca agc agt tgg agt aca cag aag cgt gaa gat ttc      917
Trp Arg Ser Gly Ala Ser Ser Trp Ser Thr Gln Lys Arg Glu Asp Phe
                100                 105                 110

gcg aac gac ctt agt ggt cct cac ctc att gca gta aca gca agc agc      965
Ala Asn Asp Leu Ser Gly Pro His Leu Ile Ala Val Thr Ala Ser Ser
            115                 120                 125

aat cgc tcc aag ggt gac cag gat cct tct aca tgg aag ccg acg cgt     1013
Asn Arg Ser Lys Gly Asp Gln Asp Pro Ser Thr Trp Lys Pro Thr Arg
        130                 135                 140

tac ggg gca cat tgc ggg tat gcg aag tgg tgg atc aat acg aaa tat     1061
Tyr Gly Ala His Cys Gly Tyr Ala Lys Trp Trp Ile Asn Thr Lys Tyr
    145                 150                 155

gtg tat gac cta acc ctt cag tcc tcg gaa aaa act gag ctt caa agc     1109
Val Tyr Asp Leu Thr Leu Gln Ser Ser Glu Lys Thr Glu Leu Gln Ser
160                 165                 170                 175

atg ctt aat acg tgt agt tat taagtcgttt cgttgctagt gttatagttt        1160
Met Leu Asn Thr Cys Ser Tyr
                180

gaataaactt ggtcagaagg gagccactca tatggagaag tcatcgatct tcacggcaac   1220

gcatggtgtg atgacggaag aagttggtgt gattagcggg gaactcgagc tgcgcacatc   1280

gtgtgatgaa gaaggtaaca tttcgcttag catcacatac gtaggtgctg aggagtggta   1340

ctcactccct ggtaaagaat atcgcctaca cgatgtgcgt gatcacgaag tcgttcatca   1400

catactcgta tccgtgctgg agcgtcgcta attttcgaca cgtgcctggc accatagtgc   1460

aaaagaagga tagcccactg ggctatcctt ctttaaactt ctcaatctgg tgaatcaaat   1520

caacataatc aatttcattt aggtctggat aatcatcgaa tttcttctaa acaaactcaa   1580

gttcaggggg gagttccttt ttcctattca aattatggac gcaacgaaat cag          1633
```

<210> SEQ ID NO 52
<211> LENGTH: 210
<212> TYPE: PRT

```
<213> ORGANISM: Bacillus algicola

<400> SEQUENCE: 52

Met Leu Lys Lys Ser Phe Leu Ile Val Phe Thr Leu Val Leu Leu Phe
            -25                 -20                 -15

Ala Gly Phe Gln Leu Gly Leu Pro Ser Ala Leu Ala Phe Pro Pro Gly
        -10                 -5                  -1  1

Thr Pro Ser Lys Ser Glu Ala Gln Ser Gln Leu Asn Ser Leu Thr Val
5                   10                  15                  20

Gln Ser Glu Gly Ser Met Ser Gly Tyr Ser Arg Asp Lys Phe Pro His
                25                  30                  35

Trp Ile Gly Gln Gly Asn Gly Cys Asp Thr Arg Gln Leu Val Leu Gln
            40                  45                  50

Arg Asp Ala Asp Tyr Tyr Ser Gly Asp Cys Pro Val Thr Ser Gly Lys
        55                  60                  65

Trp Tyr Ser Tyr Phe Asp Gly Val Thr Val Tyr Asp Pro Ser Asp Leu
    70                  75                  80

Asp Ile Asp His Met Val Pro Met Ala Glu Ala Trp Arg Ser Gly Ala
85                  90                  95                  100

Ser Ser Trp Ser Thr Gln Lys Arg Glu Asp Phe Ala Asn Asp Leu Ser
                105                 110                 115

Gly Pro His Leu Ile Ala Val Thr Ala Ser Ser Asn Arg Ser Lys Gly
            120                 125                 130

Asp Gln Asp Pro Ser Thr Trp Lys Pro Thr Arg Tyr Gly Ala His Cys
        135                 140                 145

Gly Tyr Ala Lys Trp Trp Ile Asn Thr Lys Tyr Val Tyr Asp Leu Thr
    150                 155                 160

Leu Gln Ser Ser Glu Lys Thr Glu Leu Gln Ser Met Leu Asn Thr Cys
165                 170                 175                 180

Ser Tyr


<210> SEQ ID NO 53
<211> LENGTH: 182
<212> TYPE: PRT
<213> ORGANISM: Bacillus algicola

<400> SEQUENCE: 53

Phe Pro Pro Gly Thr Pro Ser Lys Ser Glu Ala Gln Ser Gln Leu Asn
1               5                   10                  15

Ser Leu Thr Val Gln Ser Glu Gly Ser Met Ser Gly Tyr Ser Arg Asp
            20                  25                  30

Lys Phe Pro His Trp Ile Gly Gln Gly Asn Gly Cys Asp Thr Arg Gln
        35                  40                  45

Leu Val Leu Gln Arg Asp Ala Asp Tyr Tyr Ser Gly Asp Cys Pro Val
    50                  55                  60

Thr Ser Gly Lys Trp Tyr Ser Tyr Phe Asp Gly Val Thr Val Tyr Asp
65                  70                  75                  80

Pro Ser Asp Leu Asp Ile Asp His Met Val Pro Met Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Ser Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140
```

```
Gly Ala His Cys Gly Tyr Ala Lys Trp Trp Ile Asn Thr Lys Tyr Val
145                 150                 155                 160

Tyr Asp Leu Thr Leu Gln Ser Ser Glu Lys Thr Glu Leu Gln Ser Met
                165                 170                 175

Leu Asn Thr Cys Ser Tyr
            180


<210> SEQ ID NO 54
<211> LENGTH: 1633
<212> TYPE: DNA
<213> ORGANISM: Xanthan alkaline
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 54

caggttccgg gtgttggaac ttcacctcga acagtttctc gtccatcttc ccgccgagca      60

ctttttgaa attggtgagg aacagctctt ggtgttcctg ctctaaaaaa gggaatgagc     120

gcaattcttc atgaaaaatc tcattgctgt cttgtcgaat ataaatatta taaatgtcgg    180

cgatttgac cgcctcggca ttcaatttga aatgtttgcg gatggccgcg atgtcttttt     240

gattcatgta tccccactcc ttcgttcttt cctacaaacc gactccatta taccaatagt    300

tcgggtccac gcgaggatgt atagtgctaa agccgggacg tctgatgtca tatattatgt    360

ctctcatctt aacttttata atctttctat tcatttttgt aaatttcaca ctttcttcat    420

cgtagcccat gtatagtcga tgtgcgtcca tcgattggat gcgctcgatt cggttgtcat    480

acatatgagg aggctcaccc atg ttg aag aaa atg ctc agt tct cta ttc gcc    533
                      Met Leu Lys Lys Met Leu Ser Ser Leu Phe Ala
                                  -25                 -20

atc gtt ctc gtt ttg acc acg ctg cac ttc agt acg cct acc gct tcg      581
Ile Val Leu Val Leu Thr Thr Leu His Phe Ser Thr Pro Thr Ala Ser
        -15                 -10                 -5

gcc ttg ccg ccg aac atc cca tca aaa gcc gac gcg ctc acg aaa ctg      629
Ala Leu Pro Pro Asn Ile Pro Ser Lys Ala Asp Ala Leu Thr Lys Leu
-1  1               5                   10                  15

aac gcg ttg acc gtt caa aca gaa ggg ccg atg acc ggc tac agc cgt      677
Asn Ala Leu Thr Val Gln Thr Glu Gly Pro Met Thr Gly Tyr Ser Arg
                20                  25                  30

gat ttg ttc ccg cat tgg agc agc caa ggg aac ggc tgt aac acc cgt      725
Asp Leu Phe Pro His Trp Ser Ser Gln Gly Asn Gly Cys Asn Thr Arg
            35                  40                  45

cac gtc gtc ttg aag cga gat gcc gat tcg gtc gtc gac act tgc ccg      773
His Val Val Leu Lys Arg Asp Ala Asp Ser Val Val Asp Thr Cys Pro
        50                  55                  60

gtc acg act gga aga tgg tac agt tac tat gac gga ctc gtc ttc acg      821
Val Thr Thr Gly Arg Trp Tyr Ser Tyr Tyr Asp Gly Leu Val Phe Thr
    65                  70                  75

tcc gct tcc gat atc gac atc gac cac gtc gtc ccg ctc gct gaa gcg      869
Ser Ala Ser Asp Ile Asp Ile Asp His Val Val Pro Leu Ala Glu Ala
80                  85                  90                  95

tgg cgc tca ggt gcg agc agc tgg aca tcg acg aag cgt caa agc ttc      917
Trp Arg Ser Gly Ala Ser Ser Trp Thr Ser Thr Lys Arg Gln Ser Phe
                100                 105                 110
```

-continued

```
gcc aac gat ttg aac gga ccg cag ttg att gcc gtt tca gcc acg tca      965
Ala Asn Asp Leu Asn Gly Pro Gln Leu Ile Ala Val Ser Ala Thr Ser
            115                 120                 125

aac cgt tca aaa ggg gac caa gac cca tcg aca tgg caa ccg ccg cgt     1013
Asn Arg Ser Lys Gly Asp Gln Asp Pro Ser Thr Trp Gln Pro Pro Arg
        130                 135                 140

gcc ggt gcg cgc tgt gcg tat gcg aag atg tgg gtc gag acg aag agc     1061
Ala Gly Ala Arg Cys Ala Tyr Ala Lys Met Trp Val Glu Thr Lys Ser
    145                 150                 155

cgt tgg ggg ctc acg ctc caa tcg tca gaa aaa gca gcg ctt caa acg     1109
Arg Trp Gly Leu Thr Leu Gln Ser Ser Glu Lys Ala Ala Leu Gln Thr
160                 165                 170                 175

gcc atc aac gct tgc agc tat tgatgtagaa aggagttcgt tatggatcaa        1160
Ala Ile Asn Ala Cys Ser Tyr
                180

caatcatcta tctttaaagc ctctcacggg gtcatgaccg aagaagtcgg cgtcatcagt   1220

ggagaactcg aactgaagac gacgtgccaa gaggacggca cgctcgagct cgccatcacc   1280

tatgtcggcg ccgccgaatg gtatacatta cccgggaaag attacaagct tcacgacgtg   1340

cgtgaccacg acgtcgtgca tcaactgctc gtaaacgttc tcgagcgagc gtaaatgtaa   1400

aggagtctcg acacctcatt tgggtgacga gactcctttt tgtttggtgc ttacttcacc   1460

attttaatga tggcacgaat gacaaggaaa atgaccccga tcatgattcc tgccaacagc   1520

aagctggcgc caccgacaat gccgagtgtg aacataacgg tcctccgtgg tgatgtgatg   1580

attacttctc tacgatatca tctgtctcac aatagcataa gctgagtcta ttt          1633


<210> SEQ ID NO 55
<211> LENGTH: 210
<212> TYPE: PRT
<213> ORGANISM: Xanthan alkaline

<400> SEQUENCE: 55

Met Leu Lys Lys Met Leu Ser Ser Leu Phe Ala Ile Val Leu Val Leu
            -25                 -20                 -15

Thr Thr Leu His Phe Ser Thr Pro Thr Ala Ser Ala Leu Pro Pro Asn
        -10                 -5                  -1  1

Ile Pro Ser Lys Ala Asp Ala Leu Thr Lys Leu Asn Ala Leu Thr Val
5                   10                  15                  20

Gln Thr Glu Gly Pro Met Thr Gly Tyr Ser Arg Asp Leu Phe Pro His
                25                  30                  35

Trp Ser Ser Gln Gly Asn Gly Cys Asn Thr Arg His Val Val Leu Lys
            40                  45                  50

Arg Asp Ala Asp Ser Val Val Asp Thr Cys Pro Val Thr Thr Gly Arg
        55                  60                  65

Trp Tyr Ser Tyr Tyr Asp Gly Leu Val Phe Thr Ser Ala Ser Asp Ile
    70                  75                  80

Asp Ile Asp His Val Val Pro Leu Ala Glu Ala Trp Arg Ser Gly Ala
85                  90                  95                  100

Ser Ser Trp Thr Ser Thr Lys Arg Gln Ser Phe Ala Asn Asp Leu Asn
                105                 110                 115

Gly Pro Gln Leu Ile Ala Val Ser Ala Thr Ser Asn Arg Ser Lys Gly
            120                 125                 130

Asp Gln Asp Pro Ser Thr Trp Gln Pro Pro Arg Ala Gly Ala Arg Cys
        135                 140                 145

Ala Tyr Ala Lys Met Trp Val Glu Thr Lys Ser Arg Trp Gly Leu Thr
    150                 155                 160
```

Leu Gln Ser Ser Glu Lys Ala Ala Leu Gln Thr Ala Ile Asn Ala Cys
165 170 175 180

Ser Tyr

<210> SEQ ID NO 56
<211> LENGTH: 182
<212> TYPE: PRT
<213> ORGANISM: Xanthan alkaline

<400> SEQUENCE: 56

Leu Pro Pro Asn Ile Pro Ser Lys Ala Asp Ala Leu Thr Lys Leu Asn
1 5 10 15

Ala Leu Thr Val Gln Thr Glu Gly Pro Met Thr Gly Tyr Ser Arg Asp
20 25 30

Leu Phe Pro His Trp Ser Ser Gln Gly Asn Gly Cys Asn Thr Arg His
35 40 45

Val Val Leu Lys Arg Asp Ala Asp Ser Val Val Asp Thr Cys Pro Val
50 55 60

Thr Thr Gly Arg Trp Tyr Ser Tyr Tyr Asp Gly Leu Val Phe Thr Ser
65 70 75 80

Ala Ser Asp Ile Asp Ile Asp His Val Val Pro Leu Ala Glu Ala Trp
85 90 95

Arg Ser Gly Ala Ser Ser Trp Thr Ser Thr Lys Arg Gln Ser Phe Ala
100 105 110

Asn Asp Leu Asn Gly Pro Gln Leu Ile Ala Val Ser Ala Thr Ser Asn
115 120 125

Arg Ser Lys Gly Asp Gln Asp Pro Ser Thr Trp Gln Pro Pro Arg Ala
130 135 140

Gly Ala Arg Cys Ala Tyr Ala Lys Met Trp Val Glu Thr Lys Ser Arg
145 150 155 160

Trp Gly Leu Thr Leu Gln Ser Ser Glu Lys Ala Ala Leu Gln Thr Ala
165 170 175

Ile Asn Ala Cys Ser Tyr
180

<210> SEQ ID NO 57
<211> LENGTH: 1624
<212> TYPE: DNA
<213> ORGANISM: Bacillus vietnamensis
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 57
gacttcttgg tcggtaacct tttcagcatc ttcaaatgta ctatcgtatt cttgaatggt 60
catgcttttc acgccggaaa aaccgttata taacacggaa tagcttatcc atccaaatac 120
aatgacaaaa aggacagtta ggatgatttt tttcattgtt ccccctccct ttatccaatt 180
atttcaaact ccttctgtca tatccacaca tttctccttg tagtcattac gtcacacaaa 240
tcgctcactc ccgatgaccg tctgattctg aaggaacagg cataaagttt catctttcta 300
aatagcccct gatttacaaa atattaactt gttagaagag ctttccatcc cctatcattt 360

-continued

```
taggtagaag cgaacacaac tgatgccaaa tcctcaataa gaatcctttc tcactgcctg    420

actacgttgt ttaactatta acatgctatt ccattaagaa tgacatgttg atataaaaaa    480

tacatacagg aggcatcccc atg cta aag aaa tca ttg atg ttt gtc gtt gcc    533
                      Met Leu Lys Lys Ser Leu Met Phe Val Val Ala
                      -25                 -20                 -15

ctg ctt ctc tcg ttc gct tta ttc ctg ccg tct gca ctc gca ttc cca      581
Leu Leu Leu Ser Phe Ala Leu Phe Leu Pro Ser Ala Leu Ala Phe Pro
                -10                 -5                  -1   1

ccc ggc acc ccg tcc aag tcc acg gcc caa tca cag ttg aac gcg ttg      629
Pro Gly Thr Pro Ser Lys Ser Thr Ala Gln Ser Gln Leu Asn Ala Leu
        5                   10                  15

aca gta aag tcg gaa agc tcc atg acc gga tac tcc cgt gat aag ttc      677
Thr Val Lys Ser Glu Ser Ser Met Thr Gly Tyr Ser Arg Asp Lys Phe
    20                  25                  30

ccc cac tgg atc ggc cag agg aac gga tgt gac aca aga cag ctc gtc      725
Pro His Trp Ile Gly Gln Arg Asn Gly Cys Asp Thr Arg Gln Leu Val
35                  40                  45                  50

ctg cag cgt gac gct gac agc tac agt ggc agc tgc ccg gtg aca tcc      773
Leu Gln Arg Asp Ala Asp Ser Tyr Ser Gly Ser Cys Pro Val Thr Ser
                55                  60                  65

gga tca tgg tac agt tat tac gac gga gtc aca ttt acg gat cca tcc      821
Gly Ser Trp Tyr Ser Tyr Tyr Asp Gly Val Thr Phe Thr Asp Pro Ser
            70                  75                  80

gat ctt gac atc gat cac gtt gtc ccc ctt gca gaa gca tgg cgc tcc      869
Asp Leu Asp Ile Asp His Val Val Pro Leu Ala Glu Ala Trp Arg Ser
        85                  90                  95

gga gcc agc agc tgg acg aca gct aag cgc gaa gac ttc gcc aac gac      917
Gly Ala Ser Ser Trp Thr Thr Ala Lys Arg Glu Asp Phe Ala Asn Asp
    100                 105                 110

ctg agc ggt cca cag ctg att gcc gtc agc gca agc tca aac cgc tcc      965
Leu Ser Gly Pro Gln Leu Ile Ala Val Ser Ala Ser Ser Asn Arg Ser
115                 120                 125                 130

aaa gga gat cag gat cca tcc act tgg cag cca ccg cgt tcc ggc gca     1013
Lys Gly Asp Gln Asp Pro Ser Thr Trp Gln Pro Pro Arg Ser Gly Ala
                135                 140                 145

gcc tgc ggt tac tcc aaa tgg tgg atc agc acg aaa tac aaa tgg ggc     1061
Ala Cys Gly Tyr Ser Lys Trp Trp Ile Ser Thr Lys Tyr Lys Trp Gly
            150                 155                 160

tta agc ctg caa tct tca gaa aaa acc gcc ctt caa ggt atg cta aac     1109
Leu Ser Leu Gln Ser Ser Glu Lys Thr Ala Leu Gln Gly Met Leu Asn
        165                 170                 175

agc tgt att tac tgatgtagag gggagcacgg ggacggttct cgtgctccct         1161
Ser Cys Ile Tyr
    180

tttcattcaa cattgattat atctacacat cgaaagggag gaatgcatat ggaaaagaaa   1221

tcaacggttt tcacggcaac acacggggtc atgacgtctg aagtaggcgt gatcagtgga   1281

gaacttgagc tggtgacgac atgtgatgaa gatggtgtgc taaaactagc tatcacctat   1341

gtaggggccg aggaatggta ttcgctgccc ggtgaggagt accacttgca tgacgtccgg   1401

gatcatgaga ttgtgcataa aatgcttgct gctgtgttgg agcgacctta agaaggaagc   1461

acggggacgg ttcccgtgct tctttttttcg attaagaaga agcagtagaa ccgtcccccct  1521

gcttctactt cctctccatc accgcaaaat aattttcttc atgatcggca aagttaaata   1581

ctctgccccc aggcatatcg acgatttccc ctaccttgac ctt                     1624
```

<210> SEQ ID NO 58
<211> LENGTH: 207

```
<212> TYPE: PRT
<213> ORGANISM: Bacillus vietnamensis

<400> SEQUENCE: 58

Met Leu Lys Lys Ser Leu Met Phe Val Val Ala Leu Leu Leu Ser Phe
-25                 -20                 -15                 -10

Ala Leu Phe Leu Pro Ser Ala Leu Ala Phe Pro Pro Gly Thr Pro Ser
                -5                  -1  1               5

Lys Ser Thr Ala Gln Ser Gln Leu Asn Ala Leu Thr Val Lys Ser Glu
        10                  15                  20

Ser Ser Met Thr Gly Tyr Ser Arg Asp Lys Phe Pro His Trp Ile Gly
    25                  30                  35

Gln Arg Asn Gly Cys Asp Thr Arg Gln Leu Val Leu Gln Arg Asp Ala
40                  45                  50                  55

Asp Ser Tyr Ser Gly Ser Cys Pro Val Thr Ser Gly Ser Trp Tyr Ser
                60                  65                  70

Tyr Tyr Asp Gly Val Thr Phe Thr Asp Pro Ser Asp Leu Asp Ile Asp
            75                  80                  85

His Val Val Pro Leu Ala Glu Ala Trp Arg Ser Gly Ala Ser Ser Trp
        90                  95                  100

Thr Thr Ala Lys Arg Glu Asp Phe Ala Asn Asp Leu Ser Gly Pro Gln
    105                 110                 115

Leu Ile Ala Val Ser Ala Ser Ser Asn Arg Ser Lys Gly Asp Gln Asp
120                 125                 130                 135

Pro Ser Thr Trp Gln Pro Pro Arg Ser Gly Ala Ala Cys Gly Tyr Ser
                140                 145                 150

Lys Trp Trp Ile Ser Thr Lys Tyr Lys Trp Gly Leu Ser Leu Gln Ser
            155                 160                 165

Ser Glu Lys Thr Ala Leu Gln Gly Met Leu Asn Ser Cys Ile Tyr
        170                 175                 180


<210> SEQ ID NO 59
<211> LENGTH: 182
<212> TYPE: PRT
<213> ORGANISM: Bacillus vietnamensis

<400> SEQUENCE: 59

Phe Pro Pro Gly Thr Pro Ser Lys Ser Thr Ala Gln Ser Gln Leu Asn
1               5                   10                  15

Ala Leu Thr Val Lys Ser Glu Ser Ser Met Thr Gly Tyr Ser Arg Asp
            20                  25                  30

Lys Phe Pro His Trp Ile Gly Gln Arg Asn Gly Cys Asp Thr Arg Gln
        35                  40                  45

Leu Val Leu Gln Arg Asp Ala Asp Ser Tyr Ser Gly Ser Cys Pro Val
    50                  55                  60

Thr Ser Gly Ser Trp Tyr Ser Tyr Tyr Asp Gly Val Thr Phe Thr Asp
65                  70                  75                  80

Pro Ser Asp Leu Asp Ile Asp His Val Val Pro Leu Ala Glu Ala Trp
                85                  90                  95

Arg Ser Gly Ala Ser Ser Trp Thr Thr Ala Lys Arg Glu Asp Phe Ala
            100                 105                 110

Asn Asp Leu Ser Gly Pro Gln Leu Ile Ala Val Ser Ala Ser Ser Asn
        115                 120                 125

Arg Ser Lys Gly Asp Gln Asp Pro Ser Thr Trp Gln Pro Pro Arg Ser
    130                 135                 140
```

```
Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ile Tyr
            180


<210> SEQ ID NO 60
<211> LENGTH: 1633
<212> TYPE: DNA
<213> ORGANISM: Bacillus hwajinpoensis
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 60

aaaaagggta aaaggagcat taattattcc aataattaat gctccttttt ttgatggaat      60

caacagaacc gtcccgacga ttactaaatg acggagcgga aaacaagaag aagccacggt     120

ccctttacct gaaagccatg ggttattccc tcggattttt ttatacaaac caaaggtcac     180

gctttttatt aagcttgtaa aaattgttgg gaacatttac ttataaatga tagaacgctt     240

actagctcat atgaaccaac tttcatttta tgtcttagag ctatagaaca ttgctagaaa     300

ggtgtgctag atttaaggcg cactaatgaa agaatgaaga accagcgata aataaaaacaa    360

gcaaattgct tgataaaaga gagcacaagg ctttgttatg tcttactttt cttgtttacc     420

ttaagaacga ttactatctc cttcactcaa agtgaacgga agggtaatac ataaataatc     480

aaaaagtagg aggcattatt gtg tta aag aaa tcg att tta gtt ctt ttt acg     533
                      Val Leu Lys Lys Ser Ile Leu Val Leu Phe Thr
                                  -25                 -20

ttg gtt ctg ttg ttt agt ggc tat caa ttt ggt ctc ccg tcc gct ctt       581
Leu Val Leu Leu Phe Ser Gly Tyr Gln Phe Gly Leu Pro Ser Ala Leu
        -15                 -10                 -5

gca atc cct cct gga aca ccg tca aag tct gcc gct caa tct caa ttg       629
Ala Ile Pro Pro Gly Thr Pro Ser Lys Ser Ala Ala Gln Ser Gln Leu
-1  1               5                   10                  15

gat tca cta gct gta cag tct gaa ggt tcc atg tcc gga tac tcg cgt       677
Asp Ser Leu Ala Val Gln Ser Glu Gly Ser Met Ser Gly Tyr Ser Arg
                20                  25                  30

gat aaa ttc cca cac tgg atc ggg cag ggg aat ggc tgt gac acc cgt       725
Asp Lys Phe Pro His Trp Ile Gly Gln Gly Asn Gly Cys Asp Thr Arg
            35                  40                  45

cag tta gtg cta cag cgg gat gct gat tat tac agc ggt gac tgt cct       773
Gln Leu Val Leu Gln Arg Asp Ala Asp Tyr Tyr Ser Gly Asp Cys Pro
        50                  55                  60

gta acg tct ggt aaa tgg tat agc tac ttt gat ggc gta cag gtg tat       821
Val Thr Ser Gly Lys Trp Tyr Ser Tyr Phe Asp Gly Val Gln Val Tyr
    65                  70                  75

gac cca tct tat ctc gat atc gac cac atg gtg ccg tta gca gag gca       869
Asp Pro Ser Tyr Leu Asp Ile Asp His Met Val Pro Leu Ala Glu Ala
80                  85                  90                  95

tgg cgt tca gga gca agt agt tgg agt aca caa aag cgt gag gat ttc       917
Trp Arg Ser Gly Ala Ser Ser Trp Ser Thr Gln Lys Arg Glu Asp Phe
                100                 105                 110

gcg aat gac ctt gat ggt cct cat ctc att gca gta acg gcg agc agc       965
```

```
Ala Asn Asp Leu Asp Gly Pro His Leu Ile Ala Val Thr Ala Ser Ser
            115                 120                 125

aac cgt tcc aag ggc gac caa gat ccg tct aca tgg aag cca acg cgt     1013
Asn Arg Ser Lys Gly Asp Gln Asp Pro Ser Thr Trp Lys Pro Thr Arg
        130                 135                 140

tac agt gct cac tgc ggt tat gct aag tgg tgg atc aat acg aag tat     1061
Tyr Ser Ala His Cys Gly Tyr Ala Lys Trp Trp Ile Asn Thr Lys Tyr
    145                 150                 155

gtc tat gat tta aac ctt cag tct tca gag aaa tct gct ctt caa agc     1109
Val Tyr Asp Leu Asn Leu Gln Ser Ser Glu Lys Ser Ala Leu Gln Ser
160                 165                 170                 175

atg ctg aat acg tgt agt tat taagtcgggg tagttgatag tatgatagtt        1160
Met Leu Asn Thr Cys Ser Tyr
                180

tcttaatggc tagttgagga ggtgcactca aatggaacag aagtcatcaa ttttcactgc   1220

aactcatggt gttatgaccg aagaagtggg tgtaattagc ggagagcttg aactgcgtac   1280

ttcctgtgat aaggaaggcg atctcacgct acgcattacg tatgtaggag cagaggagtg   1340

gtacacgctg cctggtaaag aatatcgttt acacgacgcg cgtgaccatg aagtcgttca   1400

ccgtttgctc gtatcggtgc ttgagcgtca ttaaaattcg acaagtgaca ggcaccatgg   1460

tcgagcggta ccttatttaa gcatatttcg tattaaagtg aaaaggagca ttaattattt   1520

caataattaa tgctcttttt attttgagat ggaattatca gaaccgttcc gacgataccc   1580

catcaacact cctttttagg taattagtcc agggtaaccc attttgcaat agg          1633


<210> SEQ ID NO 61
<211> LENGTH: 210
<212> TYPE: PRT
<213> ORGANISM: Bacillus hwajinpoensis

<400> SEQUENCE: 61

Val Leu Lys Lys Ser Ile Leu Val Leu Phe Thr Leu Val Leu Leu Phe
            -25                 -20                 -15

Ser Gly Tyr Gln Phe Gly Leu Pro Ser Ala Leu Ala Ile Pro Pro Gly
        -10                 -5                  -1  1

Thr Pro Ser Lys Ser Ala Ala Gln Ser Gln Leu Asp Ser Leu Ala Val
5                   10                  15                  20

Gln Ser Glu Gly Ser Met Ser Gly Tyr Ser Arg Asp Lys Phe Pro His
                25                  30                  35

Trp Ile Gly Gln Gly Asn Gly Cys Asp Thr Arg Gln Leu Val Leu Gln
            40                  45                  50

Arg Asp Ala Asp Tyr Tyr Ser Gly Asp Cys Pro Val Thr Ser Gly Lys
        55                  60                  65

Trp Tyr Ser Tyr Phe Asp Gly Val Gln Val Tyr Asp Pro Ser Tyr Leu
    70                  75                  80

Asp Ile Asp His Met Val Pro Leu Ala Glu Ala Trp Arg Ser Gly Ala
85                  90                  95                  100

Ser Ser Trp Ser Thr Gln Lys Arg Glu Asp Phe Ala Asn Asp Leu Asp
                105                 110                 115

Gly Pro His Leu Ile Ala Val Thr Ala Ser Ser Asn Arg Ser Lys Gly
            120                 125                 130

Asp Gln Asp Pro Ser Thr Trp Lys Pro Thr Arg Tyr Ser Ala His Cys
        135                 140                 145

Gly Tyr Ala Lys Trp Trp Ile Asn Thr Lys Tyr Val Tyr Asp Leu Asn
    150                 155                 160
```

```
Leu Gln Ser Ser Glu Lys Ser Ala Leu Gln Ser Met Leu Asn Thr Cys
165                 170                 175                 180

Ser Tyr


<210> SEQ ID NO 62
<211> LENGTH: 182
<212> TYPE: PRT
<213> ORGANISM: Bacillus hwajinpoensis

<400> SEQUENCE: 62

Ile Pro Pro Gly Thr Pro Ser Lys Ser Ala Ala Gln Ser Gln Leu Asp
1               5                   10                  15

Ser Leu Ala Val Gln Ser Glu Gly Ser Met Ser Gly Tyr Ser Arg Asp
            20                  25                  30

Lys Phe Pro His Trp Ile Gly Gln Gly Asn Gly Cys Asp Thr Arg Gln
        35                  40                  45

Leu Val Leu Gln Arg Asp Ala Asp Tyr Tyr Ser Gly Asp Cys Pro Val
    50                  55                  60

Thr Ser Gly Lys Trp Tyr Ser Tyr Phe Asp Gly Val Gln Val Tyr Asp
65                  70                  75                  80

Pro Ser Tyr Leu Asp Ile Asp His Met Val Pro Leu Ala Glu Ala Trp
                85                  90                  95

Arg Ser Gly Ala Ser Ser Trp Ser Thr Gln Lys Arg Glu Asp Phe Ala
            100                 105                 110

Asn Asp Leu Asp Gly Pro His Leu Ile Ala Val Thr Ala Ser Ser Asn
        115                 120                 125

Arg Ser Lys Gly Asp Gln Asp Pro Ser Thr Trp Lys Pro Thr Arg Tyr
    130                 135                 140

Ser Ala His Cys Gly Tyr Ala Lys Trp Trp Ile Asn Thr Lys Tyr Val
145                 150                 155                 160

Tyr Asp Leu Asn Leu Gln Ser Ser Glu Lys Ser Ala Leu Gln Ser Met
                165                 170                 175

Leu Asn Thr Cys Ser Tyr
            180


<210> SEQ ID NO 63
<211> LENGTH: 1633
<212> TYPE: DNA
<213> ORGANISM: Paenibacillus mucilaginosus
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 63

tcccgatgaa atcccggcct gcccggccga gattcgctcc cactgctttt gaccttgatc     60

caaccgaacc aatcccctct ttgagcaatt cttccgacca ataatcccgt atacatccaa    120

tccactgatg tggagatggt cactttatta tggggcataa aaacacaaaa aagttaatct    180

ttcatgcgca ctttagctgt tcaattcatt attgttgtcg gattctgact atgcaaagga    240

cgcatggaca gagataccac atacagaccg agtcattgat acacatgcat cgaaacgcga    300

cagaggatct atgcagtaac tttgttccgt ccatctcatc ctaaaatacc caattgaatg    360

acatattcta ggccctcatt gttcggagta ttgactccat acctgatacc gtttacaaac    420
```

```
tattaacttg tacgaaattc tagcgagatg ttacgatctt cacggaatta ttatcatgat    480

ttgggggta tttcctttcc atg gtg aag aaa tca agg ttg ttt gtt ttt gcg    533
                     Met Val Lys Lys Ser Arg Leu Phe Val Phe Ala
                                 -25                 -20

ttg gtt ctg tcg ctg tct gct ggt ttt tat ggc acg cct acg gcc tcg     581
Leu Val Leu Ser Leu Ser Ala Gly Phe Tyr Gly Thr Pro Thr Ala Ser
        -15                 -10                 -5

gcg ctt ccg ccg gga aca cca tcc aag tcc acc gcc caa tcc cag ctg     629
Ala Leu Pro Pro Gly Thr Pro Ser Lys Ser Thr Ala Gln Ser Gln Leu
-1  1               5                   10                  15

aac tcc ctg act gtg aag tcc gaa agc acc atg act ggc tac tcg cgc     677
Asn Ser Leu Thr Val Lys Ser Glu Ser Thr Met Thr Gly Tyr Ser Arg
                20                  25                  30

gac aag ttc ccg cac tgg acc agt caa ggc ggt ggc tgc gat acc cgc     725
Asp Lys Phe Pro His Trp Thr Ser Gln Gly Gly Gly Cys Asp Thr Arg
            35                  40                  45

cag gtg gtg ctc aag cga gac gcc gac tac tac agc ggg agc tgc ccc     773
Gln Val Val Leu Lys Arg Asp Ala Asp Tyr Tyr Ser Gly Ser Cys Pro
        50                  55                  60

gtc acg tcc ggc aag tgg tac agc tac tac gac ggc att acc gtg tac     821
Val Thr Ser Gly Lys Trp Tyr Ser Tyr Tyr Asp Gly Ile Thr Val Tyr
    65                  70                  75

tca ccc tct gaa att gac atc gat cat att gtg ccg ctg gcc gag gca     869
Ser Pro Ser Glu Ile Asp Ile Asp His Ile Val Pro Leu Ala Glu Ala
80                  85                  90                  95

tgg cgt tcc ggt gct agc agc tgg acc act gaa aag cgt cag aac ttc     917
Trp Arg Ser Gly Ala Ser Ser Trp Thr Thr Glu Lys Arg Gln Asn Phe
                100                 105                 110

gcc aac gac ctg ggc ggc ccg cag ctg atc gcg gtg acc gcc agc tcc     965
Ala Asn Asp Leu Gly Gly Pro Gln Leu Ile Ala Val Thr Ala Ser Ser
            115                 120                 125

aac cgg gcc aag ggt gac cag gat cca tcg act tgg aag ccg acg cgt    1013
Asn Arg Ala Lys Gly Asp Gln Asp Pro Ser Thr Trp Lys Pro Thr Arg
        130                 135                 140

tcc ggc gcc cac tgt gcg tat gcg aag tgg tgg atc aat acc aaa tac    1061
Ser Gly Ala His Cys Ala Tyr Ala Lys Trp Trp Ile Asn Thr Lys Tyr
    145                 150                 155

cgc tgg ggc ttg cac ctg cag tcg tcg gag aag acc gct ttg caa agc    1109
Arg Trp Gly Leu His Leu Gln Ser Ser Glu Lys Thr Ala Leu Gln Ser
160                 165                 170                 175

atg ctc aac act tgc tcc tac tgagtccgta gtgcgtctgc aaggtttgcc       1160
Met Leu Asn Thr Cys Ser Tyr
                180

aaccgttggc agtacacttg cagcgcagcc atcataaccg agaagggagt cacctgaatg  1220

gaagagaagt cgtcaatctt catcgcaacc cacggtgtga tgaccgttga ggtcggcgtg  1280

atcagcgggg aactcgaact gcgtacgacc tgcgatgacg agggtgccct cacgctcgcc  1340

atcacgtatg tcggcgccga ggagtggtat acgctgccag gtgagcacta tcgcctgcac  1400

gatccgcgtg accacgaagt cgtccaccgc atgctcgtca ccgtactaga gcgcccttga  1460

gacagactga cccgccggtc cggtaactta acaagcgttc tgccgtgcgc ctggcacgtt  1520

tgtctgtgct agatacattt actccactta aaaagggatg ctctccgaca cctaatctgg  1580

agagcatccc tttttacgg cagaacgcac gcagttttca acccagcgtc ccc          1633
```

<210> SEQ ID NO 64
<211> LENGTH: 210
<212> TYPE: PRT

<213> ORGANISM: Paenibacillus mucilaginosus

<400> SEQUENCE: 64

```
Met Val Lys Lys Ser Arg Leu Phe Val Phe Ala Leu Val Leu Ser Leu
            -25                 -20                 -15

Ser Ala Gly Phe Tyr Gly Thr Pro Thr Ala Ser Ala Leu Pro Pro Gly
        -10                 -5              -1  1

Thr Pro Ser Lys Ser Thr Ala Gln Ser Gln Leu Asn Ser Leu Thr Val
5                   10                  15                  20

Lys Ser Glu Ser Thr Met Thr Gly Tyr Ser Arg Asp Lys Phe Pro His
                25                  30                  35

Trp Thr Ser Gln Gly Gly Gly Cys Asp Thr Arg Gln Val Val Leu Lys
            40                  45                  50

Arg Asp Ala Asp Tyr Tyr Ser Gly Ser Cys Pro Val Thr Ser Gly Lys
        55                  60                  65

Trp Tyr Ser Tyr Tyr Asp Gly Ile Thr Val Tyr Ser Pro Ser Glu Ile
    70                  75                  80

Asp Ile Asp His Ile Val Pro Leu Ala Glu Ala Trp Arg Ser Gly Ala
85                  90                  95                  100

Ser Ser Trp Thr Thr Glu Lys Arg Gln Asn Phe Ala Asn Asp Leu Gly
                105                 110                 115

Gly Pro Gln Leu Ile Ala Val Thr Ala Ser Ser Asn Arg Ala Lys Gly
            120                 125                 130

Asp Gln Asp Pro Ser Thr Trp Lys Pro Thr Arg Ser Gly Ala His Cys
        135                 140                 145

Ala Tyr Ala Lys Trp Trp Ile Asn Thr Lys Tyr Arg Trp Gly Leu His
    150                 155                 160

Leu Gln Ser Ser Glu Lys Thr Ala Leu Gln Ser Met Leu Asn Thr Cys
165                 170                 175                 180

Ser Tyr
```

<210> SEQ ID NO 65
<211> LENGTH: 182
<212> TYPE: PRT
<213> ORGANISM: Paenibacillus mucilaginosus

<400> SEQUENCE: 65

```
Leu Pro Pro Gly Thr Pro Ser Lys Ser Thr Ala Gln Ser Gln Leu Asn
1               5                   10                  15

Ser Leu Thr Val Lys Ser Glu Ser Thr Met Thr Gly Tyr Ser Arg Asp
            20                  25                  30

Lys Phe Pro His Trp Thr Ser Gln Gly Gly Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Ile Thr Val Tyr Ser
65                  70                  75                  80

Pro Ser Glu Ile Asp Ile Asp His Ile Val Pro Leu Ala Glu Ala Trp
                85                  90                  95

Arg Ser Gly Ala Ser Ser Trp Thr Thr Glu Lys Arg Gln Asn Phe Ala
            100                 105                 110

Asn Asp Leu Gly Gly Pro Gln Leu Ile Ala Val Thr Ala Ser Ser Asn
        115                 120                 125

Arg Ala Lys Gly Asp Gln Asp Pro Ser Thr Trp Lys Pro Thr Arg Ser
    130                 135                 140
```

```
Gly Ala His Cys Ala Tyr Ala Lys Trp Trp Ile Asn Thr Lys Tyr Arg
145                 150                 155                 160

Trp Gly Leu His Leu Gln Ser Ser Glu Lys Thr Ala Leu Gln Ser Met
                165                 170                 175

Leu Asn Thr Cys Ser Tyr
            180


<210> SEQ ID NO 66
<211> LENGTH: 1624
<212> TYPE: DNA
<213> ORGANISM: Bacillus indicus
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 66

atatttctga agcactgttt tacatggttg cattctttca gtttgatacc ccatatttct      60

gccgcatcgt tttataggga tgcaaatcac attttaaaac agaggacacc tcctccccat     120

ccaaaatttg caaaaactcc aataaacacc tgcttcgatg gactcatttt tattttccat     180

tgtaaatcat catactaaag agttttgatg ccttttcctt acctatatta aaaatgtttc     240

atgacatatg gcctcaatct cataaatacc tctattcatc ctcttccttt tggacttaaa     300

atcagcgcaa atccgaacat aaatgttaag aggtttacat ttccttaact tgaagaaatc     360

tctcttttca tactatgatt tctaatagag aaacaaattt ccatcacttt ttccctcttc     420

ttccatcgtt ctgtctatta atctcactga ctataagtta tgagattgat atataaaaat     480

ttcatacagg aggcatctac atg ctg aaa aaa gct tca tta tct gtt ttt gca     533
                      Met Leu Lys Lys Ala Ser Leu Ser Val Phe Ala
                      -25                 -20                 -15

ctg ctg ctc tca ttc act tta ttt ctg ccg gaa aca cat gct act ccg       581
Leu Leu Leu Ser Phe Thr Leu Phe Leu Pro Glu Thr His Ala Thr Pro
                -10                 -5              -1  1

ccg ggc act ccg tcg aag tcc acg gca caa acc cag ctc aat gct ttg       629
Pro Gly Thr Pro Ser Lys Ser Thr Ala Gln Thr Gln Leu Asn Ala Leu
        5                   10                  15

aca gtc aag aca gaa ggt tcc atg acc gga tac tcg cgt gat tta ttt       677
Thr Val Lys Thr Glu Gly Ser Met Thr Gly Tyr Ser Arg Asp Leu Phe
    20                  25                  30

ccc cat tgg att agc caa gga agc ggc tgt gac acc cgt cag gtt gtg       725
Pro His Trp Ile Ser Gln Gly Ser Gly Cys Asp Thr Arg Gln Val Val
35                  40                  45                  50

ctt aag cgt gac gct gac tac tac agc ggc agt tgc cct gtg acc tca       773
Leu Lys Arg Asp Ala Asp Tyr Tyr Ser Gly Ser Cys Pro Val Thr Ser
                55                  60                  65

gga aaa tgg tac agc tac tat gat ggt gtt aca ttc tat gac cca tct       821
Gly Lys Trp Tyr Ser Tyr Tyr Asp Gly Val Thr Phe Tyr Asp Pro Ser
            70                  75                  80

gac ctt gac atc gac cat att gtc cct ctt gct gaa gct tgg cgt tca       869
Asp Leu Asp Ile Asp His Ile Val Pro Leu Ala Glu Ala Trp Arg Ser
        85                  90                  95

ggc gca agc agc tgg aca acg tcc aag cgc cag gat ttt gca aac gac       917
Gly Ala Ser Ser Trp Thr Thr Ser Lys Arg Gln Asp Phe Ala Asn Asp
    100                 105                 110
```

```
tta agc gga cct cag ctg att gcg gta agc gcc agc acc aat cgt tcc      965
Leu Ser Gly Pro Gln Leu Ile Ala Val Ser Ala Ser Thr Asn Arg Ser
115                 120                 125                 130

aaa ggt gac cag gat cca tct aca tgg cag cct cca cga gcc ggt gca     1013
Lys Gly Asp Gln Asp Pro Ser Thr Trp Gln Pro Pro Arg Ala Gly Ala
                135                 140                 145

gcc tgc gga tac tca aaa tgg tgg atc agc acg aaa tac aaa tgg ggc     1061
Ala Cys Gly Tyr Ser Lys Trp Trp Ile Ser Thr Lys Tyr Lys Trp Gly
            150                 155                 160

ttg agc ctt cag tct tca gaa aaa acc gcg cta cag ggc atg ctt aat     1109
Leu Ser Leu Gln Ser Ser Glu Lys Thr Ala Leu Gln Gly Met Leu Asn
        165                 170                 175

agc tgt tct tac taatgcttaa ctgaaaacga gcagccaaaa gcggctgctc         1161
Ser Cys Ser Tyr
    180

gtttatgcta taatctaagc aaatgacgga ggtgacagca tggagaagaa atcaacggtt   1221

tttaccgcaa cccacggtgt catgacgaca gaagtcggcg tcatcagcgg cgagcttgaa   1281

cttgtcactg cctgcgatga agacggggtc ctgaatctcg ctattacata cgccggggct   1341

gcggaatggt acactcttcc tggtgaggaa taccggctgc atgatgtgcg tgatcatgag   1401

gttgtgcatg aaatgcttgt aagagtgctt gagcgtccgt aattcaataa gctgtaaata   1461

aagtgacagc cgcctgttaa gtcgatattc ggacttatca ggcggctttt ttaatgtgct   1521

taaaatgaaa aatcattttt taagataact cttcaggaat atctaaatca attccaataa   1581

accctttata ctcgtcttcc gcaaaacaaa acgtaacttc aga                     1624


<210> SEQ ID NO 67
<211> LENGTH: 207
<212> TYPE: PRT
<213> ORGANISM: Bacillus indicus

<400> SEQUENCE: 67

Met Leu Lys Lys Ala Ser Leu Ser Val Phe Ala Leu Leu Leu Ser Phe
-25                 -20                 -15                 -10

Thr Leu Phe Leu Pro Glu Thr His Ala Thr Pro Pro Gly Thr Pro Ser
                -5                  -1  1               5

Lys Ser Thr Ala Gln Thr Gln Leu Asn Ala Leu Thr Val Lys Thr Glu
        10                  15                  20

Gly Ser Met Thr Gly Tyr Ser Arg Asp Leu Phe Pro His Trp Ile Ser
    25                  30                  35

Gln Gly Ser Gly Cys Asp Thr Arg Gln Val Val Leu Lys Arg Asp Ala
40                  45                  50                  55

Asp Tyr Tyr Ser Gly Ser Cys Pro Val Thr Ser Gly Lys Trp Tyr Ser
                60                  65                  70

Tyr Tyr Asp Gly Val Thr Phe Tyr Asp Pro Ser Asp Leu Asp Ile Asp
            75                  80                  85

His Ile Val Pro Leu Ala Glu Ala Trp Arg Ser Gly Ala Ser Ser Trp
        90                  95                  100

Thr Thr Ser Lys Arg Gln Asp Phe Ala Asn Asp Leu Ser Gly Pro Gln
    105                 110                 115

Leu Ile Ala Val Ser Ala Ser Thr Asn Arg Ser Lys Gly Asp Gln Asp
120                 125                 130                 135

Pro Ser Thr Trp Gln Pro Pro Arg Ala Gly Ala Ala Cys Gly Tyr Ser
                140                 145                 150

Lys Trp Trp Ile Ser Thr Lys Tyr Lys Trp Gly Leu Ser Leu Gln Ser
            155                 160                 165
```

```
Ser Glu Lys Thr Ala Leu Gln Gly Met Leu Asn Ser Cys Ser Tyr
        170                 175                 180


<210> SEQ ID NO 68
<211> LENGTH: 182
<212> TYPE: PRT
<213> ORGANISM: Bacillus indicus

<400> SEQUENCE: 68

Thr Pro Pro Gly Thr Pro Ser Lys Ser Thr Ala Gln Thr Gln Leu Asn
1               5                   10                  15

Ala Leu Thr Val Lys Thr Glu Gly Ser Met Thr Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Tyr Tyr Ser Gly Ser Cys Pro Val
    50                  55                  60

Thr Ser Gly Lys Trp Tyr Ser Tyr Tyr Asp Gly Val Thr Phe Tyr Asp
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ala
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180


<210> SEQ ID NO 69
<211> LENGTH: 1624
<212> TYPE: DNA
<213> ORGANISM: Bacillus marisflavi
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 69

ttacaaagaa tcagataaat tcggtggatt tccagtccct caattggcga aaaaaacagt      60

gagtcgggat gactttgaat cgtacacatg ggctggtact tctgaagcga aggaggatgg     120

acttcccttc ctttaccgtt cacatatcaa agcgggtgga tggaaaaaaa cgtttcaaga     180

aggaacgctg acgacgtatg aaaaaggtga acataaaatt gacgtaatcg cacaaacaag     240

ttatctttcc ataaacgtta gtagagagta gccgtgtatt ctgcatgaac caatccctta     300

atgataaggc ggttggttct ttttcatttc aagacattcg tttatcatca attttaaaaa     360

tccgaaagaa gtctgaatct ttacaaaaaa cctcttgtaa acctctctct ccctccccta     420
```

```
tcatggcagt agaggcacct tatcccagta tgcgcatcca ccagatgttc atataaaaaa    480

ctacatacag gaggctctcc atg ttc aag aaa acc atg ttg ttt gtc gtt gcc    533
                      Met Phe Lys Lys Thr Met Leu Phe Val Val Ala
                      -25                 -20                 -15

ctt gtc ctt tcc ttc tcg ctg ttc ctg ccg tcc gcg ttt gcc act ccg      581
Leu Val Leu Ser Phe Ser Leu Phe Leu Pro Ser Ala Phe Ala Thr Pro
                -10                 -5              -1   1

cct gtc acg ccg tcg aaa gcg acg tcc caa tcc cag ttg aac gga ctc      629
Pro Val Thr Pro Ser Lys Ala Thr Ser Gln Ser Gln Leu Asn Gly Leu
        5                   10                  15

acg gtg aag acc gag ggg gcg atg acc ggc tac tcc cgg gac aag ttc      677
Thr Val Lys Thr Glu Gly Ala Met Thr Gly Tyr Ser Arg Asp Lys Phe
    20                  25                  30

ccc cac tgg agc agt cag ggc ggc ggc tgt gat acc cgc cag gtc gtc      725
Pro His Trp Ser Ser Gln Gly Gly Gly Cys Asp Thr Arg Gln Val Val
35                  40                  45                  50

ctg aag cgc gat gcc gat tcg tac agc ggc aac tgc ccg gtg acg tcg      773
Leu Lys Arg Asp Ala Asp Ser Tyr Ser Gly Asn Cys Pro Val Thr Ser
                55                  60                  65

gga agc tgg tac agc tac tat gac ggc gtt aag ttt acc aat cct tcc      821
Gly Ser Trp Tyr Ser Tyr Tyr Asp Gly Val Lys Phe Thr Asn Pro Ser
            70                  75                  80

gac ctc gat atc gat cac atc gtg cct ctt gcc gaa gca tgg cgc tcg      869
Asp Leu Asp Ile Asp His Ile Val Pro Leu Ala Glu Ala Trp Arg Ser
        85                  90                  95

ggt gcc agc agc tgg acc acc gcc cag cgc gag gca ttc gcc aat gat      917
Gly Ala Ser Ser Trp Thr Thr Ala Gln Arg Glu Ala Phe Ala Asn Asp
    100                 105                 110

ctg agc ggc tcc cag ctc atc gcc gtc tcc gcg agc agc aac cgc tcc      965
Leu Ser Gly Ser Gln Leu Ile Ala Val Ser Ala Ser Ser Asn Arg Ser
115                 120                 125                 130

aag ggc gac cag gac cca tcc acc tgg cag cca ccc cgt gcc ggt gca     1013
Lys Gly Asp Gln Asp Pro Ser Thr Trp Gln Pro Pro Arg Ala Gly Ala
                135                 140                 145

aaa tgt ggc tat gcg aaa tgg tgg atc agc acc aag tct aaa tgg aac     1061
Lys Cys Gly Tyr Ala Lys Trp Trp Ile Ser Thr Lys Ser Lys Trp Asn
            150                 155                 160

ctg agc ctg caa tcg tcc gag aag acc gcc ctt caa ggg atg ctg aac     1109
Leu Ser Leu Gln Ser Ser Glu Lys Thr Ala Leu Gln Gly Met Leu Asn
        165                 170                 175

agc tgc gta tac tgatagaata aaagaaaaac ggacgatcct caccgggatc         1161
Ser Cys Val Tyr
    180

gtccgtttca aacaggaggc caaaccatgg aaaccaaatc aaccacgttc aacgcaagcc   1221

acggcgtcat gaccgaagaa gtcggcgtcg tcagcgggga gcttgagctt gtcaccacct   1281

gcgatgaaga gggcatcctc tccctcaaga tcacctatgt gggtgccgaa gaatggtaca   1341

ccctgcccgg tgaggagtat cggctgtttg atgcgaggga tcatgaggtg attcatggga   1401

tgctggtgaa ggtattggaa agaagttgat tctctactat aaaaagagta aagacgcttg   1461

gactccaagc gtctttgtca attctatctt ctactgaaat agggttcgag ccaatcggtc   1521

tcatgcgtga ggacgaacat ccaacggtgt atacaacata gatggcccac cccacttcac   1581

aacattcttc ttagtgagct cactagttaa ggaacttcaa tct                     1624
```

<210> SEQ ID NO 70
<211> LENGTH: 207
<212> TYPE: PRT
<213> ORGANISM: Bacillus marisflavi

<400> SEQUENCE: 70

```
Met Phe Lys Lys Thr Met Leu Phe Val Val Ala Leu Val Leu Ser Phe
-25                 -20                 -15                 -10

Ser Leu Phe Leu Pro Ser Ala Phe Ala Thr Pro Pro Val Thr Pro Ser
                -5              -1  1               5

Lys Ala Thr Ser Gln Ser Gln Leu Asn Gly Leu Thr Val Lys Thr Glu
        10                  15                  20

Gly Ala Met Thr Gly Tyr Ser Arg Asp Lys Phe Pro His Trp Ser Ser
    25                  30                  35

Gln Gly Gly Gly Cys Asp Thr Arg Gln Val Val Leu Lys Arg Asp Ala
40                  45                  50                  55

Asp Ser Tyr Ser Gly Asn Cys Pro Val Thr Ser Gly Ser Trp Tyr Ser
                60                  65                  70

Tyr Tyr Asp Gly Val Lys Phe Thr Asn Pro Ser Asp Leu Asp Ile Asp
            75                  80                  85

His Ile Val Pro Leu Ala Glu Ala Trp Arg Ser Gly Ala Ser Ser Trp
        90                  95                  100

Thr Thr Ala Gln Arg Glu Ala Phe Ala Asn Asp Leu Ser Gly Ser Gln
    105                 110                 115

Leu Ile Ala Val Ser Ala Ser Ser Asn Arg Ser Lys Gly Asp Gln Asp
120                 125                 130                 135

Pro Ser Thr Trp Gln Pro Pro Arg Ala Gly Ala Lys Cys Gly Tyr Ala
                140                 145                 150

Lys Trp Trp Ile Ser Thr Lys Ser Lys Trp Asn Leu Ser Leu Gln Ser
            155                 160                 165

Ser Glu Lys Thr Ala Leu Gln Gly Met Leu Asn Ser Cys Val Tyr
        170                 175                 180
```

<210> SEQ ID NO 71
<211> LENGTH: 182
<212> TYPE: PRT
<213> ORGANISM: Bacillus marisflavi

<400> SEQUENCE: 71

```
Thr Pro Pro Val Thr Pro Ser Lys Ala Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160
```

```
Trp Asn Leu Ser Leu Gln Ser Ser Glu Lys Thr Ala Leu Gln Gly Met
                165                 170                 175

Leu Asn Ser Cys Val Tyr
            180


<210> SEQ ID NO 72
<211> LENGTH: 1633
<212> TYPE: DNA
<213> ORGANISM: Bacillus luciferensis
<220> FEATURE:
<221> NAME/KEY: CDS
<222> LOCATION: (501)..(1130)
<220> FEATURE:
<221> NAME/KEY: sig_peptide
<222> LOCATION: (501)..(578)
<220> FEATURE:
<221> NAME/KEY: mat_peptide
<222> LOCATION: (579)..(1130)

<400> SEQUENCE: 72

tggattaatt tttttatcta ttgttatttt tgtattagtg ttaataacac caataaatga      60

tttaattaca atagcgttgt aatctcttat ttttgttgta tcaatgttta tgttatttag     120

aaaagaaata gaacttattg aactaactgg cgcgatagtt acaaactaac tctcagcttt     180

aatagaaaat taagagttgt caatggcaac tctttttttt gctaaccggc aggtgaacaa     240

ggattccatt aaatcatgtt gaatattatc taataaaata aatattatca ggacagaaaa     300

atgaaaagaa tttcatatat atagttataa cacaaattat tctttattta ttttaatact     360

tctatccatg gttggaatca catgaataat acatttgagc cccatattgc aattttaatc     420

ttattattaa catctctttc attaaaattg taagtagatg ttagtatata aaaaaattaa     480

tacatatagg aggaatttct atg ctg aaa aaa tcg atg ttg att gtt ttt gcg     533
                      Met Leu Lys Lys Ser Met Leu Ile Val Phe Ala
                          -25                 -20

ttg gtt ctg acg ttt act gtt tta cag ttt gaa act gcg aag gcc gca       581
Leu Val Leu Thr Phe Thr Val Leu Gln Phe Glu Thr Ala Lys Ala Ala
-15                 -10                 -5                  -1  1

tcg tta ccg ccc gga ata cca tcc tta tcc aca gcc caa tcc cag ctg       629
Ser Leu Pro Pro Gly Ile Pro Ser Leu Ser Thr Ala Gln Ser Gln Leu
            5                   10                  15

aat tca ttg acc gtt aag tca gaa ggt tcc ctg act ggc tac tct cgc       677
Asn Ser Leu Thr Val Lys Ser Glu Gly Ser Leu Thr Gly Tyr Ser Arg
        20                  25                  30

gac gtt ttc cct cac tgg atc agc caa gga agt ggc tgc gat aca cgt       725
Asp Val Phe Pro His Trp Ile Ser Gln Gly Ser Gly Cys Asp Thr Arg
    35                  40                  45

cag gtg gtg ctc aag cgt gat gcc gac tac tat agc ggg aac tgc cct       773
Gln Val Val Leu Lys Arg Asp Ala Asp Tyr Tyr Ser Gly Asn Cys Pro
50                  55                  60                  65

gta acg tcc ggt aaa tgg tac agc tac tac gac ggg gtc aca gtg tac       821
Val Thr Ser Gly Lys Trp Tyr Ser Tyr Tyr Asp Gly Val Thr Val Tyr
                70                  75                  80

tcg ccg tcc gaa atc gac att gat cat gtc gtc cca ttg gca gag gcg       869
Ser Pro Ser Glu Ile Asp Ile Asp His Val Val Pro Leu Ala Glu Ala
            85                  90                  95

tgg cgt tct ggt gcc agc agt tgg acc aca gaa aag cgt cag aac ttc       917
Trp Arg Ser Gly Ala Ser Ser Trp Thr Thr Glu Lys Arg Gln Asn Phe
        100                 105                 110

gcc aac gac ctt aat ggt ccg cag ttg ata gca gtg act gct agc tct       965
Ala Asn Asp Leu Asn Gly Pro Gln Leu Ile Ala Val Thr Ala Ser Ser
    115                 120                 125
```

```
aac cgc tca aag ggt gac caa gat cct tct aca tgg cag cca act cgt      1013
Asn Arg Ser Lys Gly Asp Gln Asp Pro Ser Thr Trp Gln Pro Thr Arg
130                 135                 140                 145

acc ggt gca cgc tgc gcg tat gcg aag atg tgg ata aac acc aag tac      1061
Thr Gly Ala Arg Cys Ala Tyr Ala Lys Met Trp Ile Asn Thr Lys Tyr
                150                 155                 160

cgc tgg gga ttg cac cta caa tca tct gag aag tcc gca ctg cag agc      1109
Arg Trp Gly Leu His Leu Gln Ser Ser Glu Lys Ser Ala Leu Gln Ser
            165                 170                 175

atg ctc aat acc tgc tct tat tgatttcatt attcgtctac aaataatatc        1160
Met Leu Asn Thr Cys Ser Tyr
        180

accgaccgtt ggtagtactt gcatcgcaac cattcaaacc cagatgggag gaggcactcg   1220

tatggaaaag aagtctacaa tcttcaccgc aactcacggt gtaatgacca cagaggtcgg   1280

tgtaatcagt ggggagctcg aactacgcac cacctgcgat gacggaggag cactcacact   1340

tgccatcacg tatgttggtg ctgaggagtg gtacactctg cctgggaaag attaccacct   1400

gttcgattcg cgtgatcatc aagtcgtcca ccgcatgctc gccacggtgc tagctcgtcc   1460

ttgagacaga ctgacaactc tgcataagtc taatggctcg tactactggg cattgtggtt   1520

gaaaaaacaa aaattgaaat taagtgcagg atctataagg attctgtgct tttttattga   1580

agcattagta aaatgaacag gagtaatcta attccttatt caactaactg gcg          1633


<210> SEQ ID NO 73
<211> LENGTH: 210
<212> TYPE: PRT
<213> ORGANISM: Bacillus luciferensis

<400> SEQUENCE: 73

Met Leu Lys Lys Ser Met Leu Ile Val Phe Ala Leu Val Leu Thr Phe
    -25                 -20                 -15

Thr Val Leu Gln Phe Glu Thr Ala Lys Ala Ala Ser Leu Pro Pro Gly
-10                 -5              -1  1               5

Ile Pro Ser Leu Ser Thr Ala Gln Ser Gln Leu Asn Ser Leu Thr Val
            10                  15                  20

Lys Ser Glu Gly Ser Leu Thr Gly Tyr Ser Arg Asp Val Phe Pro His
        25                  30                  35

Trp Ile Ser Gln Gly Ser Gly Cys Asp Thr Arg Gln Val Val Leu Lys
    40                  45                  50

Arg Asp Ala Asp Tyr Tyr Ser Gly Asn Cys Pro Val Thr Ser Gly Lys
55                  60                  65                  70

Trp Tyr Ser Tyr Tyr Asp Gly Val Thr Val Tyr Ser Pro Ser Glu Ile
                75                  80                  85

Asp Ile Asp His Val Val Pro Leu Ala Glu Ala Trp Arg Ser Gly Ala
            90                  95                  100

Ser Ser Trp Thr Thr Glu Lys Arg Gln Asn Phe Ala Asn Asp Leu Asn
        105                 110                 115

Gly Pro Gln Leu Ile Ala Val Thr Ala Ser Ser Asn Arg Ser Lys Gly
    120                 125                 130

Asp Gln Asp Pro Ser Thr Trp Gln Pro Thr Arg Thr Gly Ala Arg Cys
135                 140                 145                 150

Ala Tyr Ala Lys Met Trp Ile Asn Thr Lys Tyr Arg Trp Gly Leu His
                155                 160                 165

Leu Gln Ser Ser Glu Lys Ser Ala Leu Gln Ser Met Leu Asn Thr Cys
            170                 175                 180
```

Ser Tyr

<210> SEQ ID NO 74
<211> LENGTH: 184
<212> TYPE: PRT
<213> ORGANISM: Bacillus luciferensis

<400> SEQUENCE: 74

Ala Ser Leu Pro Pro Gly Ile Pro Ser Leu Ser Thr Ala Gln Ser Gln
1 5 10 15

Leu Asn Ser Leu Thr Val Lys Ser Glu Gly Ser Leu Thr Gly Tyr Ser
20 25 30

Arg Asp Val Phe Pro His Trp Ile Ser Gln Gly Ser Gly Cys Asp Thr
35 40 45

Arg Gln Val Val Leu Lys Arg Asp Ala Asp Tyr Tyr Ser Gly Asn Cys
50 55 60

Pro Val Thr Ser Gly Lys Trp Tyr Ser Tyr Tyr Asp Gly Val Thr Val
65 70 75 80

Tyr Ser Pro Ser Glu Ile Asp Ile Asp His Val Val Pro Leu Ala Glu
85 90 95

Ala Trp Arg Ser Gly Ala Ser Ser Trp Thr Thr Glu Lys Arg Gln Asn
100 105 110

Phe Ala Asn Asp Leu Asn Gly Pro Gln Leu Ile Ala Val Thr Ala Ser
115 120 125

Ser Asn Arg Ser Lys Gly Asp Gln Asp Pro Ser Thr Trp Gln Pro Thr
130 135 140

Arg Thr Gly Ala Arg Cys Ala Tyr Ala Lys Met Trp Ile Asn Thr Lys
145 150 155 160

Tyr Arg Trp Gly Leu His Leu Gln Ser Ser Glu Lys Ser Ala Leu Gln
165 170 175

Ser Met Leu Asn Thr Cys Ser Tyr
180

<210> SEQ ID NO 75
<211> LENGTH: 1624
<212> TYPE: DNA
<213> ORGANISM: Bacillus marisflavi
<220> FEATURE:
<221> NAME/KEY: CDS
<222> LOCATION: (501)..(1121)
<220> FEATURE:
<221> NAME/KEY: sig_peptide
<222> LOCATION: (501)..(575)
<220> FEATURE:
<221> NAME/KEY: mat_peptide
<222> LOCATION: (576)..(1121)

<400> SEQUENCE: 75
tcattttaac aatgcaatgc cccagcaaaa tcacgcgtta tttcacaccc caaaaaaata 60
ctcatacttc ttaaaatcca tcctatgctt cagaaaggaa tggaacaagt ccttatgtgg 120
ccttcccttc ctttaccgtt cgcatatcaa agcggggggt tggaaaaaaa cgtttcaaga 180
aggaacgctg acgacgtatg aaaaaggtga acataaaatt gatgtgatct cacaaacagg 240
ctatctttcc ataaacgtta gtagagagta gtcgggtatt ctgcatgaac caatccctta 300
ataataaggt ggttggttct ttttcatttc aagatattct ttcatcacca attttaaaaa 360
tccaaaagaa gtctgaatct ttacaaaaaa actcttgtaa acctctcact ccctccccta 420
tcatggcagt agaggcacct tatcacagta tgcgcatcgt gctgatgttc atataaaaaa 480

```
ctacatacag gaggctctcc atg ttc aag aaa acc atg ttg ttt gtc gtt gcc    533
                      Met Phe Lys Lys Thr Met Leu Phe Val Val Ala
                      -25                 -20                 -15

ctt gtc ctt tcc ttc tcc ctg ttc cta ccg tcc gcc ttt gcc act ccg      581
Leu Val Leu Ser Phe Ser Leu Phe Leu Pro Ser Ala Phe Ala Thr Pro
                -10                 -5              -1   1

cct gtt acg ccg tcg aaa gag acg tcc cag tcc cag ctg aat ggg ctc      629
Pro Val Thr Pro Ser Lys Glu Thr Ser Gln Ser Gln Leu Asn Gly Leu
        5                   10                  15

acg gtg aag acc gag ggg gcg atg acc ggc tac tcc cgg gac aag ttc      677
Thr Val Lys Thr Glu Gly Ala Met Thr Gly Tyr Ser Arg Asp Lys Phe
    20                  25                  30

ccc cac tgg agc agt cag ggc ggc gga tgt gat acc cgc cag gtc gtc      725
Pro His Trp Ser Ser Gln Gly Gly Gly Cys Asp Thr Arg Gln Val Val
35                  40                  45                  50

ctg aag cgc gat gcc gat tcg tac agc ggc aac tgc ccg gtg acg tct      773
Leu Lys Arg Asp Ala Asp Ser Tyr Ser Gly Asn Cys Pro Val Thr Ser
                55                  60                  65

gga agc tgg tac agc tac tat gac ggc gtt aag ttt acc cat ccg tct      821
Gly Ser Trp Tyr Ser Tyr Tyr Asp Gly Val Lys Phe Thr His Pro Ser
            70                  75                  80

gac ctc gat atc gac cac atc gtc cca cta gct gaa gca tgg cgc tcc      869
Asp Leu Asp Ile Asp His Ile Val Pro Leu Ala Glu Ala Trp Arg Ser
        85                  90                  95

ggg gcc agc agc tgg acc acc gcc cag cgc gaa gca ttc gcc aat gac      917
Gly Ala Ser Ser Trp Thr Thr Ala Gln Arg Glu Ala Phe Ala Asn Asp
    100                 105                 110

ctg agc ggt tcc cag ctc atc gcc gtc tcc gca agc agc aac cgc tcc      965
Leu Ser Gly Ser Gln Leu Ile Ala Val Ser Ala Ser Ser Asn Arg Ser
115                 120                 125                 130

aag ggt gac cag gat cca tcc acc tgg cag ccg ccc cgt gcc ggt gca     1013
Lys Gly Asp Gln Asp Pro Ser Thr Trp Gln Pro Pro Arg Ala Gly Ala
                135                 140                 145

aaa tgt ggc tac gcc aaa tgg tgg atc agc acc aag tcc aaa tgg aac     1061
Lys Cys Gly Tyr Ala Lys Trp Trp Ile Ser Thr Lys Ser Lys Trp Asn
            150                 155                 160

ctg agc ctg cag tca tcc gag aaa acc gcc ctt cag ggg atg ctg aac     1109
Leu Ser Leu Gln Ser Ser Glu Lys Thr Ala Leu Gln Gly Met Leu Asn
        165                 170                 175

agc tgc gta tac tgatagaata aaagaaaaac ggacgatcct caccgggatc         1161
Ser Cys Val Tyr
    180

gtccgtttca aacaggaggc caaaccatgg aaaccaaatc aaccacgttc aacgcaagcc   1221

acggcgtcat gaccgaggaa gtcggcgtca tcagcgggga gcttgagctc gtcaccacct   1281

gcgatgaaaa tggcatcctc tccctcaaga tcacctatgt gggtgcagaa gaatggtaca   1341

ccctgcccgg tgaggagtat cgactgtttg atgcaaggga tcatgaggtg gttcatggga   1401

ttcttgtgaa ggtattggaa agaagttgag tttctactag agtacgatca atgacaaaga   1461

cgcttggaat ctcaagcttc tttgtcttct ctatctccta ctgaaataag gtccgagcca   1521

atcggtttca tgcgtgagca cgaacgtcca acggaactgt ttatctacga catagatgtc   1581

ccgccccacc tcacttgata ggtcgatcac atcaaacccc gat                     1624
```

<210> SEQ ID NO 76
<211> LENGTH: 207
<212> TYPE: PRT
<213> ORGANISM: Bacillus marisflavi

<400> SEQUENCE: 76

```
Met Phe Lys Lys Thr Met Leu Phe Val Val Ala Leu Val Leu Ser Phe
-25                 -20                 -15                 -10

Ser Leu Phe Leu Pro Ser Ala Phe Ala Thr Pro Pro Val Thr Pro Ser
                -5              -1   1               5

Lys Glu Thr Ser Gln Ser Gln Leu Asn Gly Leu Thr Val Lys Thr Glu
        10                  15                  20

Gly Ala Met Thr Gly Tyr Ser Arg Asp Lys Phe Pro His Trp Ser Ser
    25                  30                  35

Gln Gly Gly Gly Cys Asp Thr Arg Gln Val Val Leu Lys Arg Asp Ala
40                  45                  50                  55

Asp Ser Tyr Ser Gly Asn Cys Pro Val Thr Ser Gly Ser Trp Tyr Ser
                60                  65                  70

Tyr Tyr Asp Gly Val Lys Phe Thr His Pro Ser Asp Leu Asp Ile Asp
            75                  80                  85

His Ile Val Pro Leu Ala Glu Ala Trp Arg Ser Gly Ala Ser Ser Trp
        90                  95                  100

Thr Thr Ala Gln Arg Glu Ala Phe Ala Asn Asp Leu Ser Gly Ser Gln
    105                 110                 115

Leu Ile Ala Val Ser Ala Ser Ser Asn Arg Ser Lys Gly Asp Gln Asp
120                 125                 130                 135

Pro Ser Thr Trp Gln Pro Pro Arg Ala Gly Ala Lys Cys Gly Tyr Ala
                140                 145                 150

Lys Trp Trp Ile Ser Thr Lys Ser Lys Trp Asn Leu Ser Leu Gln Ser
            155                 160                 165

Ser Glu Lys Thr Ala Leu Gln Gly Met Leu Asn Ser Cys Val Tyr
        170                 175                 180
```

<210> SEQ ID NO 77
<211> LENGTH: 182
<212> TYPE: PRT
<213> ORGANISM: Bacillus marisflavi

<400> SEQUENCE: 77

```
Thr Pro Pro Val Thr Pro Ser Lys Glu Thr Ser Gln Ser Gln Leu Asn
1               5                   10                  15

Gly Leu Thr Val Lys Thr Glu Gly Ala Met Thr Gly Tyr Ser Arg Asp
            20                  25                  30

Lys Phe Pro His Trp Ser Ser Gln Gly Gly Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Lys Phe Thr His
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ala Gln Arg Glu Ala Phe Ala
            100                 105                 110

Asn Asp Leu Ser Gly Ser Gln Leu Ile Ala Val Ser Ala Ser Ser Asn
        115                 120                 125

Arg Ser Lys Gly Asp Gln Asp Pro Ser Thr Trp Gln Pro Pro Arg Ala
    130                 135                 140

Gly Ala Lys Cys Gly Tyr Ala Lys Trp Trp Ile Ser Thr Lys Ser Lys
145                 150                 155                 160
```

```
Trp Asn Leu Ser Leu Gln Ser Ser Glu Lys Thr Ala Leu Gln Gly Met
                165                 170                 175

Leu Asn Ser Cys Val Tyr
            180


<210> SEQ ID NO 78
<211> LENGTH: 1633
<212> TYPE: DNA
<213> ORGANISM: Bacillus species
<220> FEATURE:
<221> NAME/KEY: CDS
<222> LOCATION: (501)..(1130)
<220> FEATURE:
<221> NAME/KEY: sig_peptide
<222> LOCATION: (501)..(584)
<220> FEATURE:
<221> NAME/KEY: mat_peptide
<222> LOCATION: (585)..(1130)

<400> SEQUENCE: 78

agcgttgact tttgtttcat ccctgtcgat gcaaacgact tcgtgaccca tttccgcaag      60

gcaaactcca tttaccagtc ctacataccc agttccagca acagtgattt tcattcaatc     120

cctcccgaaa gtaatgcttg cttatttcca ttttattaga agaacatgca tactttcttg     180

aggcagcgta aagggattgt aaaattgttg taacattttc aaattttctg tgttttccca     240

ggtgggtttc atgaaagaat actttcggcc tatcactatc attccttttg atgcctctct     300

aaaatatcaa gatttttaag atttggtata caggttggag gaagcaaact gagaatttat     360

aaatgagaaa gagtttttga accaactgct gactttacaa tttacggaat atttacaaat     420

atttaacttt taatcaggta atttatcaac tatcatttct agtggaggaa tagtaaaaat     480

acatactggg aggaaatttt atg atg aag aaa tgg ata ggg ttg gtt ttt gcg     533
                      Met Met Lys Lys Trp Ile Gly Leu Val Phe Ala
                                  -25                 -20

ctc gtt ttg tcg gtg gtt gtt ttt cat ttt gat att cct act gca tcc       581
Leu Val Leu Ser Val Val Val Phe His Phe Asp Ile Pro Thr Ala Ser
        -15                 -10                 -5

gct tta ccg tca gga att ccg tcc aag tcc acc gcc caa tct cag ttg       629
Ala Leu Pro Ser Gly Ile Pro Ser Lys Ser Thr Ala Gln Ser Gln Leu
-1  1               5                   10                  15

aac tcg ctg acc gtc aag tcc gaa ggt tcc atg acc ggt tac tcg cgg       677
Asn Ser Leu Thr Val Lys Ser Glu Gly Ser Met Thr Gly Tyr Ser Arg
                20                  25                  30

gac aag ttc ccg cac tgg atc agc cag ggc ggc ggc tgt gat acc cgt       725
Asp Lys Phe Pro His Trp Ile Ser Gln Gly Gly Gly Cys Asp Thr Arg
            35                  40                  45

cag gtg gtg ctc aag cgt gat gcg gac tac tac agc ggg aat tgc ccc       773
Gln Val Val Leu Lys Arg Asp Ala Asp Tyr Tyr Ser Gly Asn Cys Pro
        50                  55                  60

gtc aca tcc ggc aaa tgg tac agc tac tat gat ggc atc tcc gtg tac       821
Val Thr Ser Gly Lys Trp Tyr Ser Tyr Tyr Asp Gly Ile Ser Val Tyr
    65                  70                  75

tca cct tcc gaa atc gac atc gac cac gtc gtc ccg ctt gca gaa gca       869
Ser Pro Ser Glu Ile Asp Ile Asp His Val Val Pro Leu Ala Glu Ala
80                  85                  90                  95

tgg cgt tcc ggc gcc agc agc tgg act acg aca aag cgc cag aat ttt       917
Trp Arg Ser Gly Ala Ser Ser Trp Thr Thr Thr Lys Arg Gln Asn Phe
                100                 105                 110

gca aac gac ctc aac ggc ccg cag ctc att gcg gtg acc gcg agc gtt       965
Ala Asn Asp Leu Asn Gly Pro Gln Leu Ile Ala Val Thr Ala Ser Val
            115                 120                 125
```

```
aac cgg tcc aag ggt gac cag gat ccg tca acc tgg cag cca ccg cgt      1013
Asn Arg Ser Lys Gly Asp Gln Asp Pro Ser Thr Trp Gln Pro Pro Arg
        130                 135                 140

tat gga gca cgc tgt gca tac gcc aag atg tgg atc aac acc aag tac      1061
Tyr Gly Ala Arg Cys Ala Tyr Ala Lys Met Trp Ile Asn Thr Lys Tyr
    145                 150                 155

cgc tgg gac ctg aac ctg caa tca tcg gag aag tct tcc ctg caa agc      1109
Arg Trp Asp Leu Asn Leu Gln Ser Ser Glu Lys Ser Ser Leu Gln Ser
160                 165                 170                 175

atg ctt gac acc tgc tcc tat taagactgtt ataatatttt aaagtattac         1160
Met Leu Asp Thr Cys Ser Tyr
                180

caagctaaaa ctgttatagc ccaatcatta gcatagaagg gagacaacca tatggaaacg   1220

aagtcgtcaa ttttccacgc aacccatggg gtaatgacca aggaggtcgg cgtgatcagt   1280

ggggacctcg aacttcgcac cacatgcagc gacaatggtg tccttacact cgccattacc   1340

tatgttggcg ctgaagaatg gtatacgctg ccgggtgaaa attatcatct gcacgatccg   1400

cgtgaccatg aagtcgtcca ccgcatgctc actgctgtcc ttgagcgctc ttgagatgga   1460

aatatatacg gtgcatgttc agggtgtcat aaatttcggg ttgtgacagg cacttttttta   1520

atacgagtac tcggcttata tgcgatactg gtgcacagtc acaaccaggg agtgtctaat   1580

aaatagagga gccttatcct ttggtggata aggctctttt gtagcgtatt gct           1633
```

<210> SEQ ID NO 79
<211> LENGTH: 210
<212> TYPE: PRT
<213> ORGANISM: Bacillus species

<400> SEQUENCE: 79

```
Met Met Lys Lys Trp Ile Gly Leu Val Phe Ala Leu Val Leu Ser Val
            -25                 -20                 -15

Val Val Phe His Phe Asp Ile Pro Thr Ala Ser Ala Leu Pro Ser Gly
        -10                 -5              -1  1

Ile Pro Ser Lys Ser Thr Ala Gln Ser Gln Leu Asn Ser Leu Thr Val
5                   10                  15                  20

Lys Ser Glu Gly Ser Met Thr Gly Tyr Ser Arg Asp Lys Phe Pro His
                25                  30                  35

Trp Ile Ser Gln Gly Gly Gly Cys Asp Thr Arg Gln Val Val Leu Lys
            40                  45                  50

Arg Asp Ala Asp Tyr Tyr Ser Gly Asn Cys Pro Val Thr Ser Gly Lys
        55                  60                  65

Trp Tyr Ser Tyr Tyr Asp Gly Ile Ser Val Tyr Ser Pro Ser Glu Ile
    70                  75                  80

Asp Ile Asp His Val Val Pro Leu Ala Glu Ala Trp Arg Ser Gly Ala
85                  90                  95                  100

Ser Ser Trp Thr Thr Thr Lys Arg Gln Asn Phe Ala Asn Asp Leu Asn
                105                 110                 115

Gly Pro Gln Leu Ile Ala Val Thr Ala Ser Val Asn Arg Ser Lys Gly
            120                 125                 130

Asp Gln Asp Pro Ser Thr Trp Gln Pro Pro Arg Tyr Gly Ala Arg Cys
        135                 140                 145

Ala Tyr Ala Lys Met Trp Ile Asn Thr Lys Tyr Arg Trp Asp Leu Asn
    150                 155                 160

Leu Gln Ser Ser Glu Lys Ser Ser Leu Gln Ser Met Leu Asp Thr Cys
165                 170                 175                 180
```

Ser Tyr

<210> SEQ ID NO 80
<211> LENGTH: 182
<212> TYPE: PRT
<213> ORGANISM: Bacillus species

<400> SEQUENCE: 80

Leu Pro Ser Gly Ile Pro Ser Lys Ser Thr Ala Gln Ser Gln Leu Asn
1               5                   10                  15

Ser Leu Thr Val Lys Ser Glu Gly Ser Met Thr Gly Tyr Ser Arg Asp
            20                  25                  30

Lys Phe Pro His Trp Ile Ser Gln Gly Gly Gly Cys Asp Thr Arg Gln
        35                  40                  45

Val Val Leu Lys Arg Asp Ala Asp Tyr Tyr Ser Gly Asn Cys Pro Val
    50                  55                  60

Thr Ser Gly Lys Trp Tyr Ser Tyr Tyr Asp Gly Ile Ser Val Tyr Ser
65                  70                  75                  80

Pro Ser Glu Ile Asp Ile Asp His Val Val Pro Leu Ala Glu Ala Trp
                85                  90                  95

Arg Ser Gly Ala Ser Ser Trp Thr Thr Thr Lys Arg Gln Asn Phe Ala
            100                 105                 110

Asn Asp Leu Asn Gly Pro Gln Leu Ile Ala Val Thr Ala Ser Val Asn
        115                 120                 125

Arg Ser Lys Gly Asp Gln Asp Pro Ser Thr Trp Gln Pro Pro Arg Tyr
    130                 135                 140

Gly Ala Arg Cys Ala Tyr Ala Lys Met Trp Ile Asn Thr Lys Tyr Arg
145                 150                 155                 160

Trp Asp Leu Asn Leu Gln Ser Ser Glu Lys Ser Ser Leu Gln Ser Met
                165                 170                 175

Leu Asp Thr Cys Ser Tyr
            180

<210> SEQ ID NO 81
<211> LENGTH: 912
<212> TYPE: DNA
<213> ORGANISM: Pyrenochaetosis species
<220> FEATURE:
<221> NAME/KEY: CDS
<222> LOCATION: (1)..(369)
<220> FEATURE:
<221> NAME/KEY: sig_peptide
<222> LOCATION: (1)..(45)
<220> FEATURE:
<221> NAME/KEY: mat_peptide
<222> LOCATION: (46)..(909)
<220> FEATURE:
<221> NAME/KEY: CDS
<222> LOCATION: (559)..(690)
<220> FEATURE:
<221> NAME/KEY: CDS
<222> LOCATION: (793)..(909)

<400> SEQUENCE: 81 atg aag tcc ctc gtc ctc ctc agc ctc gcc tcc ctc atc gcc gcc ctc       48
Met Lys Ser Leu Val Leu Leu Ser Leu Ala Ser Leu Ile Ala Ala Leu
-15                 -10                 -5                  -1  1 ccc tcc ccc ctc ctc atc gcc cgc tcc cca ccc aac atc ccc agc gcc       96
Pro Ser Pro Leu Leu Ile Ala Arg Ser Pro Pro Asn Ile Pro Ser Ala
            5                   10                  15 acc acc gcc aaa acc caa ctc gcc ggc ctc acc gtc gca ccc caa gga      144
Thr Thr Ala Lys Thr Gln Leu Ala Gly Leu Thr Val Ala Pro Gln Gly

```
        20                  25                  30

ccc cag aca ggc tac tcg cgc gac cta ttc ccg cac tgg atc acg cag      192
Pro Gln Thr Gly Tyr Ser Arg Asp Leu Phe Pro His Trp Ile Thr Gln
    35                  40                  45

tcg gga aca tgc aac acg cgc gag gtc gtc ttg aag cgc gat ggt acc      240
Ser Gly Thr Cys Asn Thr Arg Glu Val Val Leu Lys Arg Asp Gly Thr
50                  55                  60                  65

aac gtg gtt acg aac tct gcg tgc gcg agt acg agc ggg agc tgg ttg      288
Asn Val Val Thr Asn Ser Ala Cys Ala Ser Thr Ser Gly Ser Trp Leu
            70                  75                  80

agt ccg tat gat ggc aag acg tgg gac tcg gcg agt gat att cag att      336
Ser Pro Tyr Asp Gly Lys Thr Trp Asp Ser Ala Ser Asp Ile Gln Ile
            85                  90                  95

gat cat ctt gtg ccg ttg agt aat gcg tgg aag gtatgttcat agtctccttt    389
Asp His Leu Val Pro Leu Ser Asn Ala Trp Lys
        100                 105

tactgttttg tctaggtgct ttacgctctg ttcggacttt gtgatatgtg atcacgtgcg    449

tcaccgaaga gacgagaata cgaaatcaga tggaaagcaa tatgaacaca actctaggaa    509

ggatctagag cgactgaatg ttgaggaatt caactaacca actccccag tcc gga gca    567
                                                      Ser Gly Ala
                                                          110

gca gcc tgg acc acc gcc cag cgt caa gcc ttc gcc aac gac cta acc      615
Ala Ala Trp Thr Thr Ala Gln Arg Gln Ala Phe Ala Asn Asp Leu Thr
            115                 120                 125

cac cca caa ctc gtc gcc gta aca ggc agc gtc aat gaa tcc aag gga      663
His Pro Gln Leu Val Ala Val Thr Gly Ser Val Asn Glu Ser Lys Gly
        130                 135                 140

gac gat ggg ccg gaa gac tgg aag cct gtgagttcct gctctccacc            710
Asp Asp Gly Pro Glu Asp Trp Lys Pro
    145                 150

aatttacttc aattccacgc cacatgacca aaatgagaca tatcgagtat aagggacgat    770

ggctaacgat ctataccaac ag ccg cta gca agc tac tac tgc acc tac gca     822
                         Pro Leu Ala Ser Tyr Tyr Cys Thr Tyr Ala
                                 155                 160

tcg atg tgg acg gcg gtg aaa tct aac tat aag ctg acg att acg agt      870
Ser Met Trp Thr Ala Val Lys Ser Asn Tyr Lys Leu Thr Ile Thr Ser
        165                 170                 175

gca gag aag agc gcg ttg acg agt atg ttg gca act tgc tag              912
Ala Glu Lys Ser Ala Leu Thr Ser Met Leu Ala Thr Cys
    180                 185                 190


<210> SEQ ID NO 82
<211> LENGTH: 206
<212> TYPE: PRT
<213> ORGANISM: Pyrenochaetosis species

<400> SEQUENCE: 82

Met Lys Ser Leu Val Leu Leu Ser Leu Ala Ser Leu Ile Ala Ala Leu
-15                 -10                 -5                  -1  1

Pro Ser Pro Leu Leu Ile Ala Arg Ser Pro Pro Asn Ile Pro Ser Ala
            5                   10                  15

Thr Thr Ala Lys Thr Gln Leu Ala Gly Leu Thr Val Ala Pro Gln Gly
        20                  25                  30

Pro Gln Thr Gly Tyr Ser Arg Asp Leu Phe Pro His Trp Ile Thr Gln
    35                  40                  45

Ser Gly Thr Cys Asn Thr Arg Glu Val Val Leu Lys Arg Asp Gly Thr
50                  55                  60                  65
```

```
Asn Val Val Thr Asn Ser Ala Cys Ala Ser Thr Ser Gly Ser Trp Leu
                70                  75                  80

Ser Pro Tyr Asp Gly Lys Thr Trp Asp Ser Ala Ser Asp Ile Gln Ile
            85                  90                  95

Asp His Leu Val Pro Leu Ser Asn Ala Trp Lys Ser Gly Ala Ala Ala
        100                 105                 110

Trp Thr Thr Ala Gln Arg Gln Ala Phe Ala Asn Asp Leu Thr His Pro
    115                 120                 125

Gln Leu Val Ala Val Thr Gly Ser Val Asn Glu Ser Lys Gly Asp Asp
130                 135                 140                 145

Gly Pro Glu Asp Trp Lys Pro Pro Leu Ala Ser Tyr Tyr Cys Thr Tyr
                150                 155                 160

Ala Ser Met Trp Thr Ala Val Lys Ser Asn Tyr Lys Leu Thr Ile Thr
            165                 170                 175

Ser Ala Glu Lys Ser Ala Leu Thr Ser Met Leu Ala Thr Cys
        180                 185                 190


<210> SEQ ID NO 83
<211> LENGTH: 191
<212> TYPE: PRT
<213> ORGANISM: Pyrenochaetopsis species

<400> SEQUENCE: 83

Leu Pro Ser Pro Leu Leu Ile Ala Arg Ser Pro Pro Asn Ile Pro Ser
1               5                   10                  15

Ala Thr Thr Ala Lys Thr Gln Leu Ala Gly Leu Thr Val Ala Pro Gln
            20                  25                  30

Gly Pro Gln Thr Gly Tyr Ser Arg Asp Leu Phe Pro His Trp Ile Thr
        35                  40                  45

Gln Ser Gly Thr Cys Asn Thr Arg Glu Val Val Leu Lys Arg Asp Gly
    50                  55                  60

Thr Asn Val Val Thr Asn Ser Ala Cys Ala Ser Thr Ser Gly Ser Trp
65                  70                  75                  80

Leu Ser Pro Tyr Asp Gly Lys Thr Trp Asp Ser Ala Ser Asp Ile Gln
                85                  90                  95

Ile Asp His Leu Val Pro Leu Ser Asn Ala Trp Lys Ser Gly Ala Ala
            100                 105                 110

Ala Trp Thr Thr Ala Gln Arg Gln Ala Phe Ala Asn Asp Leu Thr His
        115                 120                 125

Pro Gln Leu Val Ala Val Thr Gly Ser Val Asn Glu Ser Lys Gly Asp
    130                 135                 140

Asp Gly Pro Glu Asp Trp Lys Pro Pro Leu Ala Ser Tyr Tyr Cys Thr
145                 150                 155                 160

Tyr Ala Ser Met Trp Thr Ala Val Lys Ser Asn Tyr Lys Leu Thr Ile
                165                 170                 175

Thr Ser Ala Glu Lys Ser Ala Leu Thr Ser Met Leu Ala Thr Cys
            180                 185                 190


<210> SEQ ID NO 84
<211> LENGTH: 831
<212> TYPE: DNA
<213> ORGANISM: Vibrissea flavovires
<220> FEATURE:
<221> NAME/KEY: CDS
<222> LOCATION: (1)..(379)
<220> FEATURE:
<221> NAME/KEY: sig_peptide
<222> LOCATION: (1)..(57)
```

```
<220> FEATURE:
<221> NAME/KEY: mat_peptide
<222> LOCATION: (58)..(828)
<220> FEATURE:
<221> NAME/KEY: CDS
<222> LOCATION: (507)..(644)
<220> FEATURE:
<221> NAME/KEY: CDS
<222> LOCATION: (719)..(828)

<400> SEQUENCE: 84

atg tat acc tcc ctc ctc gtc tct gtc ctc ctc tcc tcc ctc cct ctc       48
Met Tyr Thr Ser Leu Leu Val Ser Val Leu Leu Ser Ser Leu Pro Leu
                -15                 -10                 -5

gtc ctc acc acc ccc ctc ccc atc atc gcg cgg aca ccg ccc aat atc       96
Val Leu Thr Thr Pro Leu Pro Ile Ile Ala Arg Thr Pro Pro Asn Ile
        -1  1               5                   10

ccc aca acc gct acc gcg aag tcc cag ctc gcg gcc ttg act gtt gcg      144
Pro Thr Thr Ala Thr Ala Lys Ser Gln Leu Ala Ala Leu Thr Val Ala
    15                  20                  25

gcc gcg ggt ccg cag acc ggg tac tcg cgt gac ctg ttt ccg acc tgg      192
Ala Ala Gly Pro Gln Thr Gly Tyr Ser Arg Asp Leu Phe Pro Thr Trp
30                  35                  40                  45

atc acg atc tct ggg acg tgt aat acg agg gag acg gtg ctg aag agg      240
Ile Thr Ile Ser Gly Thr Cys Asn Thr Arg Glu Thr Val Leu Lys Arg
                50                  55                  60

gat ggg acg aat gtg gta gtt gat tcg gcg tgt gtg gct acg agt ggg      288
Asp Gly Thr Asn Val Val Val Asp Ser Ala Cys Val Ala Thr Ser Gly
            65                  70                  75

agt tgg tat agt ccg tat gat ggg gcg act tgg acg gcg gct agt gat      336
Ser Trp Tyr Ser Pro Tyr Asp Gly Ala Thr Trp Thr Ala Ala Ser Asp
        80                  85                  90

gtt gat att gat cat atg gtt ccg ttg agt aat gct tgg aag a            379
Val Asp Ile Asp His Met Val Pro Leu Ser Asn Ala Trp Lys
    95                  100                 105

gtgagtgctt tccacaatta tctgaagtcc gagatcttgt caagttgtcc atgtccagtt    439

cgagtgctgg gtttgagtct gggatttgga agctcaatgt actggatggt tattgacttt    499

gtgatag gt  ggt gcg agt gcc tgg aca aca gca cag aga cag act ttt      547
        Ser Gly Ala Ser Ala Trp Thr Thr Ala Gln Arg Gln Thr Phe
                110                 115                 120

gcc aat gat ctg act aat cct caa cta ttg gcc gtt acg gac aat gtc      595
Ala Asn Asp Leu Thr Asn Pro Gln Leu Leu Ala Val Thr Asp Asn Val
            125                 130                 135

aat caa gct aag ggt gat agt gga ccg gag gac tgg aag cca tcg ttg a    644
Asn Gln Ala Lys Gly Asp Ser Gly Pro Glu Asp Trp Lys Pro Ser Leu
        140                 145                 150

gtatgtcttg tgatctagat ctctcctggg agataaataa tttgcgatgg cgaacaatag    704

ctaatgatat atag cc  tca tac tgg tgc aca tat gcc aaa atg tgg gtt      753
                Thr Ser Tyr Trp Cys Thr Tyr Ala Lys Met Trp Val
                    155                 160                 165

aag gtc aag act gtt tat gat ctt acg atc acg tcg gct gag aag act      801
Lys Val Lys Thr Val Tyr Asp Leu Thr Ile Thr Ser Ala Glu Lys Thr
                170                 175                 180

gct ttg act act atg ctg aac act tgt tga                              831
Ala Leu Thr Thr Met Leu Asn Thr Cys
            185                 190


<210> SEQ ID NO 85
<211> LENGTH: 209
<212> TYPE: PRT
<213> ORGANISM: Vibrissea flavovires
```

<400> SEQUENCE: 85

```
Met Tyr Thr Ser Leu Leu Val Ser Val Leu Leu Ser Ser Leu Pro Leu
                -15                 -10                 -5

Val Leu Thr Thr Pro Leu Pro Ile Ile Ala Arg Thr Pro Pro Asn Ile
        -1  1               5                   10

Pro Thr Thr Ala Thr Ala Lys Ser Gln Leu Ala Ala Leu Thr Val Ala
    15                  20                  25

Ala Ala Gly Pro Gln Thr Gly Tyr Ser Arg Asp Leu Phe Pro Thr Trp
30                  35                  40                  45

Ile Thr Ile Ser Gly Thr Cys Asn Thr Arg Glu Thr Val Leu Lys Arg
                50                  55                  60

Asp Gly Thr Asn Val Val Val Asp Ser Ala Cys Val Ala Thr Ser Gly
            65                  70                  75

Ser Trp Tyr Ser Pro Tyr Asp Gly Ala Thr Trp Thr Ala Ala Ser Asp
        80                  85                  90

Val Asp Ile Asp His Met Val Pro Leu Ser Asn Ala Trp Lys Ser Gly
    95                  100                 105

Ala Ser Ala Trp Thr Thr Ala Gln Arg Gln Thr Phe Ala Asn Asp Leu
110                 115                 120                 125

Thr Asn Pro Gln Leu Leu Ala Val Thr Asp Asn Val Asn Gln Ala Lys
                130                 135                 140

Gly Asp Ser Gly Pro Glu Asp Trp Lys Pro Ser Leu Thr Ser Tyr Trp
            145                 150                 155

Cys Thr Tyr Ala Lys Met Trp Val Lys Val Lys Thr Val Tyr Asp Leu
        160                 165                 170

Thr Ile Thr Ser Ala Glu Lys Thr Ala Leu Thr Thr Met Leu Asn Thr
    175                 180                 185

Cys
190
```

<210> SEQ ID NO 86
<211> LENGTH: 190
<212> TYPE: PRT
<213> ORGANISM: Vibrissea flavovirens

<400> SEQUENCE: 86

```
Thr Pro Leu Pro Ile Ile Ala Arg Thr Pro Pro Asn Ile Pro Thr Thr
1               5                   10                  15

Ala Thr Ala Lys Ser Gln Leu Ala Ala Leu Thr Val Ala Ala Ala Gly
            20                  25                  30

Pro Gln Thr Gly Tyr Ser Arg Asp Leu Phe Pro Thr Trp Ile Thr Ile
        35                  40                  45

Ser Gly Thr Cys Asn Thr Arg Glu Thr Val Leu Lys Arg Asp Gly Thr
    50                  55                  60

Asn Val Val Val Asp Ser Ala Cys Val Ala Thr Ser Gly Ser Trp Tyr
65                  70                  75                  80

Ser Pro Tyr Asp Gly Ala Thr Trp Thr Ala Ala Ser Asp Val Asp Ile
                85                  90                  95

Asp His Met Val Pro Leu Ser Asn Ala Trp Lys Ser Gly Ala Ser Ala
            100                 105                 110

Trp Thr Thr Ala Gln Arg Gln Thr Phe Ala Asn Asp Leu Thr Asn Pro
        115                 120                 125

Gln Leu Leu Ala Val Thr Asp Asn Val Asn Gln Ala Lys Gly Asp Ser
    130                 135                 140
```

```
Gly Pro Glu Asp Trp Lys Pro Ser Leu Thr Ser Tyr Trp Cys Thr Tyr
145                 150                 155                 160

Ala Lys Met Trp Val Lys Val Lys Thr Val Tyr Asp Leu Thr Ile Thr
                165                 170                 175

Ser Ala Glu Lys Thr Ala Leu Thr Thr Met Leu Asn Thr Cys
            180                 185                 190


<210> SEQ ID NO 87
<211> LENGTH: 727
<212> TYPE: DNA
<213> ORGANISM: Setosphaeria rostrate
<220> FEATURE:
<221> NAME/KEY: CDS
<222> LOCATION: (1)..(378)
<220> FEATURE:
<221> NAME/KEY: sig_peptide
<222> LOCATION: (1)..(51)
<220> FEATURE:
<221> NAME/KEY: mat_peptide
<222> LOCATION: (52)..(724)
<220> FEATURE:
<221> NAME/KEY: CDS
<222> LOCATION: (476)..(724)

<400> SEQUENCE: 87

atg aag gcc tct ctt atc att gcc gcc gct tcc cta gcc ctc acc tcc       48
Met Lys Ala Ser Leu Ile Ile Ala Ala Ala Ser Leu Ala Leu Thr Ser
        -15                 -10                 -5

gcg gct ccc acc tca tca ccc ctc gtc gct cgt gct cct ccc aat gtc       96
Ala Ala Pro Thr Ser Ser Pro Leu Val Ala Arg Ala Pro Pro Asn Val
-1  1               5                   10                  15

ccc agc aaa gcc gag gca acc tcc caa ctc gca ggc ctg acc gtc gca      144
Pro Ser Lys Ala Glu Ala Thr Ser Gln Leu Ala Gly Leu Thr Val Ala
                20                  25                  30

cct caa ggt ccg caa acc ggt tac tcg cgc gac ctg ttt ccc cac tgg      192
Pro Gln Gly Pro Gln Thr Gly Tyr Ser Arg Asp Leu Phe Pro His Trp
            35                  40                  45

atc act cag tcc ggc acg tgc aac acc cga gag act gtc ctg aag cgc      240
Ile Thr Gln Ser Gly Thr Cys Asn Thr Arg Glu Thr Val Leu Lys Arg
        50                  55                  60

gac ggc aca aac gtc gtt acc aac agc gcg tgc gca tcc acc tct ggc      288
Asp Gly Thr Asn Val Val Thr Asn Ser Ala Cys Ala Ser Thr Ser Gly
    65                  70                  75

tcc tgg ttc agc cca tac gac gga gcg aca tgg aca gcc gcc agt gac      336
Ser Trp Phe Ser Pro Tyr Asp Gly Ala Thr Trp Thr Ala Ala Ser Asp
80                  85                  90                  95

gta gac att gac cac atg gtc cca ttg agc aac gcc tgg aag              378
Val Asp Ile Asp His Met Val Pro Leu Ser Asn Ala Trp Lys
                100                 105

gtgagttttc tttttccttt tccttcgtta ttccccgcat tctaagtatc acacatacct    438

ccatgtaacc atgtatgcta acacatctct ccaccag tct ggt gcc gca tcc tgg     493
                                         Ser Gly Ala Ala Ser Trp
                                         110                 115

acc act gcc cgc cgc cag gcc ttt gcc aac gac ctt acc aac ccc cag      541
Thr Thr Ala Arg Arg Gln Ala Phe Ala Asn Asp Leu Thr Asn Pro Gln
                120                 125                 130

ctg ctc gct gtc acc gac aac gtg aac caa gcc aag ggc gac aag ggc      589
Leu Leu Ala Val Thr Asp Asn Val Asn Gln Ala Lys Gly Asp Lys Gly
            135                 140                 145

ccc gag gac tgg aag ccc ccg cta acc agc tac tac tgc act tac agc      637
Pro Glu Asp Trp Lys Pro Pro Leu Thr Ser Tyr Tyr Cys Thr Tyr Ser
        150                 155                 160
```

```
aag atg tgg atc aag gtt aag agc gtg tgg ggc ttg acg att acg agt      685
Lys Met Trp Ile Lys Val Lys Ser Val Trp Gly Leu Thr Ile Thr Ser
    165                 170                 175

gcc gag aag agt gcg ttg acg agc atg ttg gcg acg tgc tag              727
Ala Glu Lys Ser Ala Leu Thr Ser Met Leu Ala Thr Cys
180                 185                 190


<210> SEQ ID NO 88
<211> LENGTH: 209
<212> TYPE: PRT
<213> ORGANISM: Setosphaeria rostrate

<400> SEQUENCE: 88

Met Lys Ala Ser Leu Ile Ile Ala Ala Ala Ser Leu Ala Leu Thr Ser
        -15                 -10                 -5

Ala Ala Pro Thr Ser Ser Pro Leu Val Ala Arg Ala Pro Pro Asn Val
-1  1               5                   10                  15

Pro Ser Lys Ala Glu Ala Thr Ser Gln Leu Ala Gly Leu Thr Val Ala
                20                  25                  30

Pro Gln Gly Pro Gln Thr Gly Tyr Ser Arg Asp Leu Phe Pro His Trp
            35                  40                  45

Ile Thr Gln Ser Gly Thr Cys Asn Thr Arg Glu Thr Val Leu Lys Arg
        50                  55                  60

Asp Gly Thr Asn Val Val Thr Asn Ser Ala Cys Ala Ser Thr Ser Gly
    65                  70                  75

Ser Trp Phe Ser Pro Tyr Asp Gly Ala Thr Trp Thr Ala Ala Ser Asp
80                  85                  90                  95

Val Asp Ile Asp His Met Val Pro Leu Ser Asn Ala Trp Lys Ser Gly
                100                 105                 110

Ala Ala Ser Trp Thr Thr Ala Arg Arg Gln Ala Phe Ala Asn Asp Leu
            115                 120                 125

Thr Asn Pro Gln Leu Leu Ala Val Thr Asp Asn Val Asn Gln Ala Lys
        130                 135                 140

Gly Asp Lys Gly Pro Glu Asp Trp Lys Pro Pro Leu Thr Ser Tyr Tyr
    145                 150                 155

Cys Thr Tyr Ser Lys Met Trp Ile Lys Val Lys Ser Val Trp Gly Leu
160                 165                 170                 175

Thr Ile Thr Ser Ala Glu Lys Ser Ala Leu Thr Ser Met Leu Ala Thr
                180                 185                 190

Cys


<210> SEQ ID NO 89
<211> LENGTH: 192
<212> TYPE: PRT
<213> ORGANISM: Setosphaeria rostrata

<400> SEQUENCE: 89

Ala Pro Thr Ser Ser Pro Leu Val Ala Arg Ala Pro Pro Asn Val Pro
1               5                   10                  15

Ser Lys Ala Glu Ala Thr Ser Gln Leu Ala Gly Leu Thr Val Ala Pro
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Val Thr Asn Ser Ala Cys Ala Ser Thr Ser Gly Ser
```

```
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ser Lys Met Trp Ile Lys Val Lys Ser Val Trp Gly Leu Thr
                165                 170                 175

Ile Thr Ser Ala Glu Lys Ser Ala Leu Thr Ser Met Leu Ala Thr Cys
            180                 185                 190


<210> SEQ ID NO 90
<211> LENGTH: 838
<212> TYPE: DNA
<213> ORGANISM: Endophragmiella valdina
<220> FEATURE:
<221> NAME/KEY: CDS
<222> LOCATION: (1)..(203)
<220> FEATURE:
<221> NAME/KEY: sig_peptide
<222> LOCATION: (1)..(48)
<220> FEATURE:
<221> NAME/KEY: mat_peptide
<222> LOCATION: (49)..(835)
<220> FEATURE:
<221> NAME/KEY: CDS
<222> LOCATION: (263)..(434)
<220> FEATURE:
<221> NAME/KEY: CDS
<222> LOCATION: (521)..(659)
<220> FEATURE:
<221> NAME/KEY: CDS
<222> LOCATION: (726)..(835)

<400> SEQUENCE: 90

atg aag tac ctc gcc ctc acc atg gcc ttt gcg gcc gta tca atg gcc       48
Met Lys Tyr Leu Ala Leu Thr Met Ala Phe Ala Ala Val Ser Met Ala
    -15                 -10                 -5                  -1

gcc ccc gtg cca ggc cat ctg atg cct cgc gca ccg cca aac gtc ccc       96
Ala Pro Val Pro Gly His Leu Met Pro Arg Ala Pro Pro Asn Val Pro
1               5                   10                  15

acc acc gct gcc gcg aag acc gcc ctc gcc ggc ctc acc gtc cag gcc      144
Thr Thr Ala Ala Ala Lys Thr Ala Leu Ala Gly Leu Thr Val Gln Ala
            20                  25                  30

cag ggc tcc cag acc ggc tac tcg cgt gat ctg ttc ccc cat tgg atc      192
Gln Gly Ser Gln Thr Gly Tyr Ser Arg Asp Leu Phe Pro His Trp Ile
        35                  40                  45

acc cag agc gg  gtaaggctat gctctccctt tttatgccat tatcggacgt          243
Thr Gln Ser Gly
    50

aaactcaccg ttttaatag a acc tgc aac acc cgt gag gtc gtg ctc aag       293
                       Thr Cys Asn Thr Arg Glu Val Val Leu Lys
                               55                  60

cgt gat ggt acc aac gta gtc acc gac tct gcc tgc gct gcc aca tcc      341
Arg Asp Gly Thr Asn Val Val Thr Asp Ser Ala Cys Ala Ala Thr Ser
        65                  70                  75

gga acc tgg gtg tcg ccc tac gac ggc gct acc tgg acc gcc gcc agc      389
Gly Thr Trp Val Ser Pro Tyr Asp Gly Ala Thr Trp Thr Ala Ala Ser
```

```
    80                  85                  90

gac gtc gac att gac cac atg gtc cct ctg tcc aac gcc tgg aag           434
Asp Val Asp Ile Asp His Met Val Pro Leu Ser Asn Ala Trp Lys
95                  100                 105

gtgcgtattt ttcttttctt ccttttctgt tcttgatcca gccattccct ctgcgaaaaa    494

ttacatgcta acagaacccc tgatag tct ggc gcc gcc tcc tgg act acc gcc      547
                             Ser Gly Ala Ala Ser Trp Thr Thr Ala
                             110                 115

cag agg cag gca ttc gca aac gac ttg acg aac ccc cag ctg ctg gct       595
Gln Arg Gln Ala Phe Ala Asn Asp Leu Thr Asn Pro Gln Leu Leu Ala
    120                 125                 130

gtg acg gac aac gtc aac cag tcc aag ggc gac aag ggc cct gag gac       643
Val Thr Asp Asn Val Asn Gln Ser Lys Gly Asp Lys Gly Pro Glu Asp
135                 140                 145                 150

tgg aag ccc cca ctt a gtaagtgttt ccccagggga gatgtgagcc atggcatgtt    699
Trp Lys Pro Pro Leu
                155

tcggccggct aacggcttgt ttctag ct  tcg tac tac tgc acc tat gcc aag      751
                             Thr Ser Tyr Tyr Cys Thr Tyr Ala Lys
                                             160

atg tgg gtc aag gtc aag agc gtg tat tcg ctc acc atc acc agc gct       799
Met Trp Val Lys Val Lys Ser Val Tyr Ser Leu Thr Ile Thr Ser Ala
165                 170                 175                 180

gag aag acg gcg ctt acg agc atg ttg aac act tgc tag                   838
Glu Lys Thr Ala Leu Thr Ser Met Leu Asn Thr Cys
                185                 190


<210> SEQ ID NO 91
<211> LENGTH: 208
<212> TYPE: PRT
<213> ORGANISM: Endophragmiella valdina

<400> SEQUENCE: 91

Met Lys Tyr Leu Ala Leu Thr Met Ala Phe Ala Ala Val Ser Met Ala
    -15                 -10                 -5              -1

Ala Pro Val Pro Gly His Leu Met Pro Arg Ala Pro Pro Asn Val Pro
1               5                   10                  15

Thr Thr Ala Ala Ala Lys Thr Ala Leu Ala Gly Leu Thr Val Gln Ala
            20                  25                  30

Gln Gly Ser Gln Thr Gly Tyr Ser Arg Asp Leu Phe Pro His Trp Ile
        35                  40                  45

Thr Gln Ser Gly Thr Cys Asn Thr Arg Glu Val Val Leu Lys Arg Asp
    50                  55                  60

Gly Thr Asn Val Val Thr Asp Ser Ala Cys Ala Ala Thr Ser Gly Thr
65                  70                  75                  80

Trp Val Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Gln Arg Gln Ala Phe Ala Asn Asp Leu Thr
        115                 120                 125

Asn Pro Gln Leu Leu Ala Val Thr Asp Asn Val Asn Gln Ser Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175
```

Ile Thr Ser Ala Glu Lys Thr Ala Leu Thr Ser Met Leu Asn Thr Cys
180 185 190

<210> SEQ ID NO 92
<211> LENGTH: 192
<212> TYPE: PRT
<213> ORGANISM: Endophragmiella valdina

<400> SEQUENCE: 92

Ala Pro Val Pro Gly His Leu Met Pro Arg Ala Pro Pro Asn Val Pro
1 5 10 15

Thr Thr Ala Ala Ala Lys Thr Ala Leu Ala Gly Leu Thr Val Gln Ala
20 25 30

Gln Gly Ser Gln Thr Gly Tyr Ser Arg Asp Leu Phe Pro His Trp Ile
35 40 45

Thr Gln Ser Gly Thr Cys Asn Thr Arg Glu Val Val Leu Lys Arg Asp
50 55 60

Gly Thr Asn Val Val Thr Asp Ser Ala Cys Ala Ala Thr Ser Gly Thr
65 70 75 80

Trp Val Ser Pro Tyr Asp Gly Ala Thr Trp Thr Ala Ala Ser Asp Val
85 90 95

Asp Ile Asp His Met Val Pro Leu Ser Asn Ala Trp Lys Ser Gly Ala
100 105 110

Ala Ser Trp Thr Thr Ala Gln Arg Gln Ala Phe Ala Asn Asp Leu Thr
115 120 125

Asn Pro Gln Leu Leu Ala Val Thr Asp Asn Val Asn Gln Ser Lys Gly
130 135 140

Asp Lys Gly Pro Glu Asp Trp Lys Pro Pro Leu Thr Ser Tyr Tyr Cys
145 150 155 160

Thr Tyr Ala Lys Met Trp Val Lys Val Lys Ser Val Tyr Ser Leu Thr
165 170 175

Ile Thr Ser Ala Glu Lys Thr Ala Leu Thr Ser Met Leu Asn Thr Cys
180 185 190

<210> SEQ ID NO 93
<211> LENGTH: 735
<212> TYPE: DNA
<213> ORGANISM: Corynespora cassiicola
<220> FEATURE:
<221> NAME/KEY: CDS
<222> LOCATION: (1)..(369)
<220> FEATURE:
<221> NAME/KEY: sig_peptide
<222> LOCATION: (1)..(48)
<220> FEATURE:
<221> NAME/KEY: mat_peptide
<222> LOCATION: (49)..(732)
<220> FEATURE:
<221> NAME/KEY: CDS
<222> LOCATION: (431)..(569)
<220> FEATURE:
<221> NAME/KEY: CDS
<222> LOCATION: (623)..(732)

<400> SEQUENCE: 93 atg aag tgc ctc ctc ctt gct ctg gcc tcc acc gcc ctg gtg tcc gcc 48
Met Lys Cys Leu Leu Leu Ala Leu Ala Ser Thr Ala Leu Val Ser Ala
-15 -10 -5 -1 ctc ccc gct ccg ctt gtg cct cgc gcc cct ccc ggc atc ccc acc acc 96
Leu Pro Ala Pro Leu Val Pro Arg Ala Pro Pro Gly Ile Pro Thr Thr
1 5 10 15

```
tcg gcc gcc agg tcc cag ctt gct ggc ctc acc gtc gct gcc cag ggc      144
Ser Ala Ala Arg Ser Gln Leu Ala Gly Leu Thr Val Ala Ala Gln Gly
            20                  25                  30

cct cag acc ggc tac tcc cgt gat ctg ttc ccc cac tgg atc acc cag      192
Pro Gln Thr Gly Tyr Ser Arg Asp Leu Phe Pro His Trp Ile Thr Gln
        35                  40                  45

agc gga agc tgc aac acg cgc gag gtg gtc ctc gcc cgc gac ggc acc      240
Ser Gly Ser Cys Asn Thr Arg Glu Val Val Leu Ala Arg Asp Gly Thr
    50                  55                  60

ggc gtt gtc cag gac tct tcc tgt gcc gcc acc tcg gga acc tgg cgc      288
Gly Val Val Gln Asp Ser Ser Cys Ala Ala Thr Ser Gly Thr Trp Arg
65                  70                  75                  80

tcg ccc ttc gac ggc gcc act tgg acc gct gct agc gac gtc gac att      336
Ser Pro Phe Asp Gly Ala Thr Trp Thr Ala Ala Ser Asp Val Asp Ile
                85                  90                  95

gac cac atg gtt cct ctc tcc aat gct tgg aag gtatgggcag ccgtgtacct    389
Asp His Met Val Pro Leu Ser Asn Ala Trp Lys
            100                 105

actacatctg tgcacaaaga cactgtgcta accgcctgca g tct gga gcc gca tcc    445
                                              Ser Gly Ala Ala Ser
                                                      110

tgg acc acg tcc cgc cgc cag gca ttt gcc aac gac ttg acc aac cct      493
Trp Thr Thr Ser Arg Arg Gln Ala Phe Ala Asn Asp Leu Thr Asn Pro
        115                 120                 125

cag ctg att gct gtg acg gac aac gtt aac cag tcc aag ggt gac aag      541
Gln Leu Ile Ala Val Thr Asp Asn Val Asn Gln Ser Lys Gly Asp Lys
    130                 135                 140

ggc ccg gaa gac tgg aag ccg ccg ctc a gtacgccatg ccccgcctca          589
Gly Pro Glu Asp Trp Lys Pro Pro Leu
145                 150

tcctacgaga acgccacact gactagccta cag cc  tcg tac tac tgc acc tat     642
                                     Thr Ser Tyr Tyr Cys Thr Tyr
                                         155                 160

gcc aag atg tgg gtg agg gtc aag agc gtg tac tct ttg acc att acc      690
Ala Lys Met Trp Val Arg Val Lys Ser Val Tyr Ser Leu Thr Ile Thr
                165                 170                 175

agc gct gag aag agt gcg ctc acg agc atg ttg gac act tgc tag          735
Ser Ala Glu Lys Ser Ala Leu Thr Ser Met Leu Asp Thr Cys
            180                 185                 190


<210> SEQ ID NO 94
<211> LENGTH: 206
<212> TYPE: PRT
<213> ORGANISM: Corynespora cassiicola

<400> SEQUENCE: 94

Met Lys Cys Leu Leu Leu Ala Leu Ala Ser Thr Ala Leu Val Ser Ala
    -15                 -10                 -5                  -1

Leu Pro Ala Pro Leu Val Pro Arg Ala Pro Pro Gly Ile Pro Thr Thr
1               5                   10                  15

Ser Ala Ala Arg Ser Gln Leu Ala Gly Leu Thr Val Ala Ala Gln Gly
            20                  25                  30

Pro Gln Thr Gly Tyr Ser Arg Asp Leu Phe Pro His Trp Ile Thr Gln
        35                  40                  45

Ser Gly Ser Cys Asn Thr Arg Glu Val Val Leu Ala Arg Asp Gly Thr
    50                  55                  60

Gly Val Val Gln Asp Ser Ser Cys Ala Ala Thr Ser Gly Thr Trp Arg
65                  70                  75                  80

Ser Pro Phe Asp Gly Ala Thr Trp Thr Ala Ala Ser Asp Val Asp Ile
```

```
                85                  90                  95

Asp His Met Val Pro Leu Ser Asn Ala Trp Lys Ser Gly Ala Ala Ser
            100                 105                 110

Trp Thr Thr Ser Arg Arg Gln Ala Phe Ala Asn Asp Leu Thr Asn Pro
        115                 120                 125

Gln Leu Ile Ala Val Thr Asp Asn Val Asn Gln Ser Lys Gly Asp Lys
    130                 135                 140

Gly Pro Glu Asp Trp Lys Pro Pro Leu Thr Ser Tyr Tyr Cys Thr Tyr
145                 150                 155                 160

Ala Lys Met Trp Val Arg Val Lys Ser Val Tyr Ser Leu Thr Ile Thr
                165                 170                 175

Ser Ala Glu Lys Ser Ala Leu Thr Ser Met Leu Asp Thr Cys
            180                 185                 190


<210> SEQ ID NO 95
<211> LENGTH: 190
<212> TYPE: PRT
<213> ORGANISM: Corynespora cassiicola

<400> SEQUENCE: 95

Leu Pro Ala Pro Leu Val Pro Arg Ala Pro Pro Gly Ile Pro Thr Thr
1               5                   10                  15

Ser Ala Ala Arg Ser Gln Leu Ala Gly Leu Thr Val Ala Ala Gln Gly
            20                  25                  30

Pro Gln Thr Gly Tyr Ser Arg Asp Leu Phe Pro His Trp Ile Thr Gln
        35                  40                  45

Ser Gly Ser Cys Asn Thr Arg Glu Val Val Leu Ala Arg Asp Gly Thr
    50                  55                  60

Gly Val Val Gln Asp Ser Ser Cys Ala Ala Thr Ser Gly Thr Trp Arg
65                  70                  75                  80

Ser Pro Phe Asp Gly Ala Thr Trp Thr Ala Ala Ser Asp Val Asp Ile
                85                  90                  95

Asp His Met Val Pro Leu Ser Asn Ala Trp Lys Ser Gly Ala Ala Ser
            100                 105                 110

Trp Thr Thr Ser Arg Arg Gln Ala Phe Ala Asn Asp Leu Thr Asn Pro
        115                 120                 125

Gln Leu Ile Ala Val Thr Asp Asn Val Asn Gln Ser Lys Gly Asp Lys
    130                 135                 140

Gly Pro Glu Asp Trp Lys Pro Pro Leu Thr Ser Tyr Tyr Cys Thr Tyr
145                 150                 155                 160

Ala Lys Met Trp Val Arg Val Lys Ser Val Tyr Ser Leu Thr Ile Thr
                165                 170                 175

Ser Ala Glu Lys Ser Ala Leu Thr Ser Met Leu Asp Thr Cys
            180                 185                 190


<210> SEQ ID NO 96
<211> LENGTH: 703
<212> TYPE: DNA
<213> ORGANISM: Paraphoma species
<220> FEATURE:
<221> NAME/KEY: CDS
<222> LOCATION: (1)..(378)
<220> FEATURE:
<221> NAME/KEY: sig_peptide
<222> LOCATION: (1)..(51)
<220> FEATURE:
<221> NAME/KEY: mat_peptide
<222> LOCATION: (52)..(700)
<220> FEATURE:
```

```
<221> NAME/KEY: CDS
<222> LOCATION: (452)..(700)

<400> SEQUENCE: 96

atg aag tcc acc atc ctt ctc gcg ctg gct tca gcg gcc ttc gtc tcc       48
Met Lys Ser Thr Ile Leu Leu Ala Leu Ala Ser Ala Ala Phe Val Ser
        -15                 -10                 -5

gcg gca cca gca cca gtt cac ctc gtt gct cgc gcg cca ccc aat gtc       96
Ala Ala Pro Ala Pro Val His Leu Val Ala Arg Ala Pro Pro Asn Val
-1  1               5                   10                  15

cca acc gcc gcc caa gca caa act caa ctt gcc ggc ctc act gtt gct      144
Pro Thr Ala Ala Gln Ala Gln Thr Gln Leu Ala Gly Leu Thr Val Ala
                20                  25                  30

gct caa ggt ccc cag act ggc tac agc cgc gat ctc ttc ccc cat tgg      192
Ala Gln Gly Pro Gln Thr Gly Tyr Ser Arg Asp Leu Phe Pro His Trp
            35                  40                  45

atc acc cag tcc ggt gcc tgc aac acg cgt gag act gtc ctc aag cgt      240
Ile Thr Gln Ser Gly Ala Cys Asn Thr Arg Glu Thr Val Leu Lys Arg
        50                  55                  60

gat ggc acc ggc gtc gtg caa gac tcc gca tgt gct gcc acc agc gga      288
Asp Gly Thr Gly Val Val Gln Asp Ser Ala Cys Ala Ala Thr Ser Gly
    65                  70                  75

acc tgg aag agt cca tac gac ggc gca aca tgg acc gct gcc agc gac      336
Thr Trp Lys Ser Pro Tyr Asp Gly Ala Thr Trp Thr Ala Ala Ser Asp
80                  85                  90                  95

gtc gac att gac cac atg gtc ccc ttg agc aac gcc tgg aag              378
Val Asp Ile Asp His Met Val Pro Leu Ser Asn Ala Trp Lys
                100                 105

gtccgtctca tcccacccca attcccacat tgcttccatt tccaacgaac aaaatcgcta    438

acttatcatc tag tcc ggc gca gca tcc tgg acc acg gcc cgc cgc cag       487
               Ser Gly Ala Ala Ser Trp Thr Thr Ala Arg Arg Gln
               110                 115                 120

gcc ttc gcc aat gac ttg acc aac ccc caa ctc cta gcc gtc acc gac      535
Ala Phe Ala Asn Asp Leu Thr Asn Pro Gln Leu Leu Ala Val Thr Asp
            125                 130                 135

aac gtc aac cag gcc aag ggc gac aag ggc ccc gaa gac tgg aag ccc      583
Asn Val Asn Gln Ala Lys Gly Asp Lys Gly Pro Glu Asp Trp Lys Pro
        140                 145                 150

ccg cta acg agc tac tac tgc atc tac gcc cgc atg tgg atc aag gtc      631
Pro Leu Thr Ser Tyr Tyr Cys Ile Tyr Ala Arg Met Trp Ile Lys Val
    155                 160                 165

aag agc gtg tac agc ctt act atc aca agt gct gag aag tcg gcg ttg      679
Lys Ser Val Tyr Ser Leu Thr Ile Thr Ser Ala Glu Lys Ser Ala Leu
170                 175                 180                 185

acg agc atg ttg ggc acc tgc tga                                      703
Thr Ser Met Leu Gly Thr Cys
                190


<210> SEQ ID NO 97
<211> LENGTH: 209
<212> TYPE: PRT
<213> ORGANISM: Paraphoma species

<400> SEQUENCE: 97

Met Lys Ser Thr Ile Leu Leu Ala Leu Ala Ser Ala Ala Phe Val Ser
        -15                 -10                 -5

Ala Ala Pro Ala Pro Val His Leu Val Ala Arg Ala Pro Pro Asn Val
-1  1               5                   10                  15

Pro Thr Ala Ala Gln Ala Gln Thr Gln Leu Ala Gly Leu Thr Val Ala
                20                  25                  30
```

```
Ala Gln Gly Pro Gln Thr Gly Tyr Ser Arg Asp Leu Phe Pro His Trp
            35                  40                  45

Ile Thr Gln Ser Gly Ala Cys Asn Thr Arg Glu Thr Val Leu Lys Arg
        50                  55                  60

Asp Gly Thr Gly Val Val Gln Asp Ser Ala Cys Ala Ala Thr Ser Gly
    65                  70                  75

Thr Trp Lys Ser Pro Tyr Asp Gly Ala Thr Trp Thr Ala Ala Ser Asp
80                  85                  90                  95

Val Asp Ile Asp His Met Val Pro Leu Ser Asn Ala Trp Lys Ser Gly
                100                 105                 110

Ala Ala Ser Trp Thr Thr Ala Arg Arg Gln Ala Phe Ala Asn Asp Leu
            115                 120                 125

Thr Asn Pro Gln Leu Leu Ala Val Thr Asp Asn Val Asn Gln Ala Lys
        130                 135                 140

Gly Asp Lys Gly Pro Glu Asp Trp Lys Pro Pro Leu Thr Ser Tyr Tyr
    145                 150                 155

Cys Ile Tyr Ala Arg Met Trp Ile Lys Val Lys Ser Val Tyr Ser Leu
160                 165                 170                 175

Thr Ile Thr Ser Ala Glu Lys Ser Ala Leu Thr Ser Met Leu Gly Thr
                180                 185                 190

Cys


<210> SEQ ID NO 98
<211> LENGTH: 192
<212> TYPE: PRT
<213> ORGANISM: Paraphoma species

<400> SEQUENCE: 98

Ala Pro Ala Pro Val His Leu Val Ala Arg Ala Pro Pro Asn Val Pro
1               5                   10                  15

Thr Ala Ala Gln Ala Gln Thr Gln Leu Ala Gly Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Ala Cys Asn Thr Arg Glu Thr Val Leu Lys Arg Asp
    50                  55                  60

Gly Thr Gly Val Val Gln Asp Ser Ala Cys Ala Ala Thr Ser Gly Thr
65                  70                  75                  80

Trp Lys Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Ile Tyr Ala Arg Met Trp Ile Lys Val Lys Ser Val Tyr Ser Leu Thr
                165                 170                 175

Ile Thr Ser Ala Glu Lys Ser Ala Leu Thr Ser Met Leu Gly Thr Cys
            180                 185                 190


<210> SEQ ID NO 99
```

```
<211> LENGTH: 795
<212> TYPE: DNA
<213> ORGANISM: Monilinia fructicola
<220> FEATURE:
<221> NAME/KEY: CDS
<222> LOCATION: (1)..(174)
<220> FEATURE:
<221> NAME/KEY: sig_peptide
<222> LOCATION: (1)..(54)
<220> FEATURE:
<221> NAME/KEY: mat_peptide
<222> LOCATION: (55)..(792)
<220> FEATURE:
<221> NAME/KEY: CDS
<222> LOCATION: (280)..(607)
<220> FEATURE:
<221> NAME/KEY: CDS
<222> LOCATION: (683)..(792)

<400> SEQUENCE: 99

atg gtt ccg act ctt ctc ctc agt atc cta gca aca gga ctc ctc gtt       48
Met Val Pro Thr Leu Leu Leu Ser Ile Leu Ala Thr Gly Leu Leu Val
            -15                 -10                 -5

cac gca act ccg gtc cca gca cca act ggt att cca tct act tct gtt       96
His Ala Thr Pro Val Pro Ala Pro Thr Gly Ile Pro Ser Thr Ser Val
    -1  1               5                   10

gcc aat act caa ctt gct gct ttg aca gtg gct gcc gct gga agt caa      144
Ala Asn Thr Gln Leu Ala Ala Leu Thr Val Ala Ala Ala Gly Ser Gln
15                  20                  25                  30

gac ggt tat tca aga gat ttg ttt cct cac gtccgttcac ctgaacactt        194
Asp Gly Tyr Ser Arg Asp Leu Phe Pro His
                35                  40

ttctctccat tccatcccca acgcggcccc cccccccac acacatctcc acaaactaaa    254

ctaaccctcc ctacccctga tttag tgg ata acc atc tcc ggc gcc tgc aac      306
                            Trp Ile Thr Ile Ser Gly Ala Cys Asn
                                            45

acg cgc gaa acc gtc ctc aag cgc gac ggc acc aac gtc gtc gtt aat      354
Thr Arg Glu Thr Val Leu Lys Arg Asp Gly Thr Asn Val Val Val Asn
50                  55                  60                  65

tct gcc tgt gca gcc aca tct ggc aca tgg gtc tct ccc tac gac ggc      402
Ser Ala Cys Ala Ala Thr Ser Gly Thr Trp Val Ser Pro Tyr Asp Gly
                70                  75                  80

gct acc tgg acc gcc gca tcc gac gtt gat atc gat cat ctt gtc cct      450
Ala Thr Trp Thr Ala Ala Ser Asp Val Asp Ile Asp His Leu Val Pro
            85                  90                  95

cta agc aat gca tgg aaa gct ggg gct tct tca tgg acc acg gcc caa      498
Leu Ser Asn Ala Trp Lys Ala Gly Ala Ser Ser Trp Thr Thr Ala Gln
        100                 105                 110

cgt caa gca ttc gct aac gat ctt gtg aac ccg caa ctg ctg gcc gtg      546
Arg Gln Ala Phe Ala Asn Asp Leu Val Asn Pro Gln Leu Leu Ala Val
    115                 120                 125

acg gac agc gtt aat cag gga aaa tcg gat agc gga cct gaa gcg tgg      594
Thr Asp Ser Val Asn Gln Gly Lys Ser Asp Ser Gly Pro Glu Ala Trp
130                 135                 140                 145

aaa cca agt ttg a gtatgtttct ctttggactg tggatattgg atggggggaa        647
Lys Pro Ser Leu

gtgggatcca agacaattgc taatgagaaa attag aa  tct tac tgg tgc aca       699
                                       Lys Ser Tyr Trp Cys Thr
                                       150                 155

tat gct aag atg tgg att aaa gtt aaa tat gtg tat gat ctc aca att      747
Tyr Ala Lys Met Trp Ile Lys Val Lys Tyr Val Tyr Asp Leu Thr Ile
                160                 165                 170

acg agt gcg gag aaa tcg gcc ttg gtt act atg atg gat act tgt tag      795
```

```
Thr Ser Ala Glu Lys Ser Ala Leu Val Thr Met Met Asp Thr Cys
            175                 180                 185


<210> SEQ ID NO 100
<211> LENGTH: 204
<212> TYPE: PRT
<213> ORGANISM: Monilinia fructicola

<400> SEQUENCE: 100

Met Val Pro Thr Leu Leu Leu Ser Ile Leu Ala Thr Gly Leu Leu Val
            -15                 -10                 -5

His Ala Thr Pro Val Pro Ala Pro Thr Gly Ile Pro Ser Thr Ser Val
    -1  1               5                   10

Ala Asn Thr Gln Leu Ala Ala Leu Thr Val Ala Ala Ala Gly Ser Gln
15                  20                  25                  30

Asp Gly Tyr Ser Arg Asp Leu Phe Pro His Trp Ile Thr Ile Ser Gly
                35                  40                  45

Ala Cys Asn Thr Arg Glu Thr Val Leu Lys Arg Asp Gly Thr Asn Val
            50                  55                  60

Val Val Asn Ser Ala Cys Ala Ala Thr Ser Gly Thr Trp Val Ser Pro
        65                  70                  75

Tyr Asp Gly Ala Thr Trp Thr Ala Ala Ser Asp Val Asp Ile Asp His
    80                  85                  90

Leu Val Pro Leu Ser Asn Ala Trp Lys Ala Gly Ala Ser Ser Trp Thr
95                  100                 105                 110

Thr Ala Gln Arg Gln Ala Phe Ala Asn Asp Leu Val Asn Pro Gln Leu
                115                 120                 125

Leu Ala Val Thr Asp Ser Val Asn Gln Gly Lys Ser Asp Ser Gly Pro
            130                 135                 140

Glu Ala Trp Lys Pro Ser Leu Lys Ser Tyr Trp Cys Thr Tyr Ala Lys
        145                 150                 155

Met Trp Ile Lys Val Lys Tyr Val Tyr Asp Leu Thr Ile Thr Ser Ala
    160                 165                 170

Glu Lys Ser Ala Leu Val Thr Met Met Asp Thr Cys
175                 180                 185


<210> SEQ ID NO 101
<211> LENGTH: 186
<212> TYPE: PRT
<213> ORGANISM: Monilinia fructicola

<400> SEQUENCE: 101

Thr Pro Val Pro Ala Pro Thr Gly Ile Pro Ser Thr Ser Val Ala Asn
1               5                   10                  15

Thr Gln Leu Ala Ala Leu Thr Val Ala Ala Ala Gly Ser Gln Asp Gly
            20                  25                  30

Tyr Ser Arg Asp Leu Phe Pro His Trp Ile Thr Ile Ser Gly Ala Cys
        35                  40                  45

Asn Thr Arg Glu Thr Val Leu Lys Arg Asp Gly Thr Asn Val Val Val
    50                  55                  60

Asn Ser Ala Cys Ala Ala Thr Ser Gly Thr Trp Val Ser Pro Tyr Asp
65                  70                  75                  80

Gly Ala Thr Trp Thr Ala Ala Ser Asp Val Asp Ile Asp His Leu Val
                85                  90                  95

Pro Leu Ser Asn Ala Trp Lys Ala Gly Ala Ser Ser Trp Thr Thr Ala
            100                 105                 110
```

```
Gln Arg Gln Ala Phe Ala Asn Asp Leu Val Asn Pro Gln Leu Leu Ala
        115                 120                 125

Val Thr Asp Ser Val Asn Gln Gly Lys Ser Asp Ser Gly Pro Glu Ala
    130                 135                 140

Trp Lys Pro Ser Leu Lys Ser Tyr Trp Cys Thr Tyr Ala Lys Met Trp
145                 150                 155                 160

Ile Lys Val Lys Tyr Val Tyr Asp Leu Thr Ile Thr Ser Ala Glu Lys
                165                 170                 175

Ser Ala Leu Val Thr Met Met Asp Thr Cys
            180                 185


<210> SEQ ID NO 102
<211> LENGTH: 692
<212> TYPE: DNA
<213> ORGANISM: Curvularia lunata
<220> FEATURE:
<221> NAME/KEY: CDS
<222> LOCATION: (1)..(372)
<220> FEATURE:
<221> NAME/KEY: sig_peptide
<222> LOCATION: (1)..(51)
<220> FEATURE:
<221> NAME/KEY: mat_peptide
<222> LOCATION: (52)..(689)
<220> FEATURE:
<221> NAME/KEY: CDS
<222> LOCATION: (441)..(689)

<400> SEQUENCE: 102

atg aag gcc gct ctc ctc ctt gct gcc gtc tcc gca gcc ctc acc tcg       48
Met Lys Ala Ala Leu Leu Leu Ala Ala Val Ser Ala Ala Leu Thr Ser
        -15                 -10                 -5

gcg gca ccc gcc ccc ctc tct gct cgc gca ccc ccc aat att ccc agc       96
Ala Ala Pro Ala Pro Leu Ser Ala Arg Ala Pro Pro Asn Ile Pro Ser
-1  1               5                   10                  15

aaa gct gat gcc acc tct caa ctc gcc ggc ctg acc gtc gcc gcc caa      144
Lys Ala Asp Ala Thr Ser Gln Leu Ala Gly Leu Thr Val Ala Ala Gln
                20                  25                  30

ggc cct cag act ggc tac tct cgc gat ctc ttc ccc cac tgg atc act      192
Gly Pro Gln Thr Gly Tyr Ser Arg Asp Leu Phe Pro His Trp Ile Thr
            35                  40                  45

cag tct gga acc tgc aat acg cgc gaa acc gtg ctc aag cgt gac ggc      240
Gln Ser Gly Thr Cys Asn Thr Arg Glu Thr Val Leu Lys Arg Asp Gly
        50                  55                  60

aca aac gtc gtc acg agc agc tcc tgc gcc gcg aca tct gga aca tgg      288
Thr Asn Val Val Thr Ser Ser Ser Cys Ala Ala Thr Ser Gly Thr Trp
    65                  70                  75

ttt agt ccc tat gac ggc gcg acg tgg acg gcg gcc agt gat gtc gat      336
Phe Ser Pro Tyr Asp Gly Ala Thr Trp Thr Ala Ala Ser Asp Val Asp
80                  85                  90                  95

atc gac cat gtg gtg ccg ttg agt aac gcg tgg aag gtacattgtc           382
Ile Asp His Val Val Pro Leu Ser Asn Ala Trp Lys
                100                 105

tccctctctc ttcctatttc cctatctcga agtaaacggt gactaacgaa acaaatag      440

tcc ggt gcc gca tcc tgg act acg gcc cgc cgc cag gcc ttt gcc aat      488
Ser Gly Ala Ala Ser Trp Thr Thr Ala Arg Arg Gln Ala Phe Ala Asn
        110                 115                 120

gac ttg acg aac ccg cag ttg att gcc gtg acc gac agc gtc aac cag      536
Asp Leu Thr Asn Pro Gln Leu Ile Ala Val Thr Asp Ser Val Asn Gln
    125                 130                 135

gcc aag ggc gac aag ggc cct gag gat tgg aag cct ccg cta tcg agc      584
Ala Lys Gly Asp Lys Gly Pro Glu Asp Trp Lys Pro Pro Leu Ser Ser
```

```
140                 145                 150                 155

tac tac tgc aca tac agt aag atg tgg att aag gtt aag agc gtg tac      632
Tyr Tyr Cys Thr Tyr Ser Lys Met Trp Ile Lys Val Lys Ser Val Tyr
                160                 165                 170

ggg ttg acg gtg aca agc gcg gag aag agt gcg ctg tcg agt atg ctt      680
Gly Leu Thr Val Thr Ser Ala Glu Lys Ser Ala Leu Ser Ser Met Leu
            175                 180                 185

gcg act tgc tag                                                      692
Ala Thr Cys
        190


<210> SEQ ID NO 103
<211> LENGTH: 207
<212> TYPE: PRT
<213> ORGANISM: Curvularia lunata

<400> SEQUENCE: 103

Met Lys Ala Ala Leu Leu Leu Ala Ala Val Ser Ala Ala Leu Thr Ser
        -15                 -10                 -5

Ala Ala Pro Ala Pro Leu Ser Ala Arg Ala Pro Pro Asn Ile Pro Ser
-1  1               5                   10                  15

Lys Ala Asp Ala Thr Ser Gln Leu Ala Gly Leu Thr Val Ala Ala Gln
                20                  25                  30

Gly Pro Gln Thr Gly Tyr Ser Arg Asp Leu Phe Pro His Trp Ile Thr
            35                  40                  45

Gln Ser Gly Thr Cys Asn Thr Arg Glu Thr Val Leu Lys Arg Asp Gly
        50                  55                  60

Thr Asn Val Val Thr Ser Ser Ser Cys Ala Ala Thr Ser Gly Thr Trp
    65                  70                  75

Phe Ser Pro Tyr Asp Gly Ala Thr Trp Thr Ala Ala Ser Asp Val Asp
80                  85                  90                  95

Ile Asp His Val Val Pro Leu Ser Asn Ala Trp Lys Ser Gly Ala Ala
                100                 105                 110

Ser Trp Thr Thr Ala Arg Arg Gln Ala Phe Ala Asn Asp Leu Thr Asn
            115                 120                 125

Pro Gln Leu Ile Ala Val Thr Asp Ser Val Asn Gln Ala Lys Gly Asp
        130                 135                 140

Lys Gly Pro Glu Asp Trp Lys Pro Pro Leu Ser Ser Tyr Tyr Cys Thr
    145                 150                 155

Tyr Ser Lys Met Trp Ile Lys Val Lys Ser Val Tyr Gly Leu Thr Val
160                 165                 170                 175

Thr Ser Ala Glu Lys Ser Ala Leu Ser Ser Met Leu Ala Thr Cys
                180                 185                 190


<210> SEQ ID NO 104
<211> LENGTH: 190
<212> TYPE: PRT
<213> ORGANISM: Curvularia lunata

<400> SEQUENCE: 104

Ala Pro Ala Pro Leu Ser Ala Arg Ala Pro Pro Asn Ile Pro Ser Lys
1               5                   10                  15

Ala Asp Ala Thr Ser Gln Leu Ala Gly Leu Thr Val Ala Ala Gln Gly
            20                  25                  30

Pro Gln Thr Gly Tyr Ser Arg Asp Leu Phe Pro His Trp Ile Thr Gln
        35                  40                  45

Ser Gly Thr Cys Asn Thr Arg Glu Thr Val Leu Lys Arg Asp Gly Thr
```

```
    50                  55                  60

Asn Val Val Thr Ser Ser Ser Cys Ala Ala Thr Ser Gly Thr Trp Phe
65                  70                  75                  80

Ser Pro Tyr Asp Gly Ala Thr Trp Thr Ala Ala Ser Asp Val Asp Ile
                85                  90                  95

Asp His Val Val Pro Leu Ser Asn Ala Trp Lys Ser Gly Ala Ala Ser
            100                 105                 110

Trp Thr Thr Ala Arg Arg Gln Ala Phe Ala Asn Asp Leu Thr Asn Pro
        115                 120                 125

Gln Leu Ile Ala Val Thr Asp Ser Val Asn Gln Ala Lys Gly Asp Lys
    130                 135                 140

Gly Pro Glu Asp Trp Lys Pro Pro Leu Ser Ser Tyr Tyr Cys Thr Tyr
145                 150                 155                 160

Ser Lys Met Trp Ile Lys Val Lys Ser Val Tyr Gly Leu Thr Val Thr
                165                 170                 175

Ser Ala Glu Lys Ser Ala Leu Ser Ser Met Leu Ala Thr Cys
            180                 185                 190


<210> SEQ ID NO 105
<211> LENGTH: 807
<212> TYPE: DNA
<213> ORGANISM: Penicillium reticulisporum
<220> FEATURE:
<221> NAME/KEY: CDS
<222> LOCATION: (1)..(218)
<220> FEATURE:
<221> NAME/KEY: sig_peptide
<222> LOCATION: (1)..(69)
<220> FEATURE:
<221> NAME/KEY: mat_peptide
<222> LOCATION: (70)..(804)
<220> FEATURE:
<221> NAME/KEY: CDS
<222> LOCATION: (272)..(446)
<220> FEATURE:
<221> NAME/KEY: CDS
<222> LOCATION: (503)..(641)
<220> FEATURE:
<221> NAME/KEY: CDS
<222> LOCATION: (695)..(804)

<400> SEQUENCE: 105

atg aga ttt tct caa ctc aca cag acc ttg ata ggt ctt ttg gct ttt       48
Met Arg Phe Ser Gln Leu Thr Gln Thr Leu Ile Gly Leu Leu Ala Phe
            -20                 -15                 -10

cag cct gct ctg atc gca gga ctc ccg gcc ccg gaa gct ctc cca gcc       96
Gln Pro Ala Leu Ile Ala Gly Leu Pro Ala Pro Glu Ala Leu Pro Ala
        -5              -1  1               5

cct cct ggc gtc cct agt gct tca act gcc cag agc gaa ctg gct gca      144
Pro Pro Gly Val Pro Ser Ala Ser Thr Ala Gln Ser Glu Leu Ala Ala
10                  15                  20                  25

ctg aca gtc gcc gct caa gga tcg caa gat ggt tat tct cga agc aag      192
Leu Thr Val Ala Ala Gln Gly Ser Gln Asp Gly Tyr Ser Arg Ser Lys
                30                  35                  40

ttc cct cac tgg atc aca caa tct gg  gtaagagaat ttaatttcac            238
Phe Pro His Trp Ile Thr Gln Ser Gly
            45                  50

agttcgtgta tggcgcgctc attatccatg cag g agc tgc gac acc cgg gat       290
                                       Ser Cys Asp Thr Arg Asp
                                                       55

gta gtg ctg aag cgt gac ggg aca aat gtg gta caa agc gcg agt gga      338
Val Val Leu Lys Arg Asp Gly Thr Asn Val Val Gln Ser Ala Ser Gly
            60                  65                  70
```

```
tgt acc att acc agc ggt aaa tgg gtt tca cca tat gac ggt gca acc      386
Cys Thr Ile Thr Ser Gly Lys Trp Val Ser Pro Tyr Asp Gly Ala Thr
        75                  80                  85

tgg act gcc tcg agc gat gtc gac att gac cac ctt gtc ccg ctg tcc      434
Trp Thr Ala Ser Ser Asp Val Asp Ile Asp His Leu Val Pro Leu Ser
    90                  95                  100

aat gcc tgg aag gtaagaatat cccccaagta gtgaaaccgg gtcaagacga          486
Asn Ala Trp Lys
105

ctgatgtgtt tgatag tcg ggt gct tct gga tgg acc acc gca gcg cga cag    538
                  Ser Gly Ala Ser Gly Trp Thr Thr Ala Ala Arg Gln
                      110                 115                 120

gcc ttt gcg aat gac ctg acc aat cca caa ctc ctg gtc gtg act gac      586
Ala Phe Ala Asn Asp Leu Thr Asn Pro Gln Leu Leu Val Val Thr Asp
                125                 130                 135

aat gtc aac gag tcc aag ggc gat aaa ggt ccc gag gaa tgg aaa cct      634
Asn Val Asn Glu Ser Lys Gly Asp Lys Gly Pro Glu Glu Trp Lys Pro
            140                 145                 150

cca ctt a gtatgtgtgg ctttttataa cggccattga agatatagct aacctgggaa     691
Pro Leu

tag cc  tcg tac tat tgc acc tac gct gag atg tgg gtg aag gtc aag      738
    Thr Ser Tyr Tyr Cys Thr Tyr Ala Glu Met Trp Val Lys Val Lys
    155                 160                 165

tcg gtc tac aaa ctc act atc acg tcc gct gag aaa tcc gcc ctg acg      786
Ser Val Tyr Lys Leu Thr Ile Thr Ser Ala Glu Lys Ser Ala Leu Thr
170                 175                 180                 185

agc atg ctc agt act tgc tag                                          807
Ser Met Leu Ser Thr Cys
                190
```

<210> SEQ ID NO 106
<211> LENGTH: 214
<212> TYPE: PRT
<213> ORGANISM: Penicillium reticulisporum

<400> SEQUENCE: 106

```
Met Arg Phe Ser Gln Leu Thr Gln Thr Leu Ile Gly Leu Leu Ala Phe
            -20                 -15                 -10

Gln Pro Ala Leu Ile Ala Gly Leu Pro Ala Pro Glu Ala Leu Pro Ala
        -5              -1  1               5

Pro Pro Gly Val Pro Ser Ala Ser Thr Ala Gln Ser Glu Leu Ala Ala
10                  15                  20                  25

Leu Thr Val Ala Ala Gln Gly Ser Gln Asp Gly Tyr Ser Arg Ser Lys
                30                  35                  40

Phe Pro His Trp Ile Thr Gln Ser Gly Ser Cys Asp Thr Arg Asp Val
            45                  50                  55

Val Leu Lys Arg Asp Gly Thr Asn Val Val Gln Ser Ala Ser Gly Cys
        60                  65                  70

Thr Ile Thr Ser Gly Lys Trp Val Ser Pro Tyr Asp Gly Ala Thr Trp
    75                  80                  85

Thr Ala Ser Ser Asp Val Asp Ile Asp His Leu Val Pro Leu Ser Asn
90                  95                  100                 105

Ala Trp Lys Ser Gly Ala Ser Gly Trp Thr Thr Ala Ala Arg Gln Ala
                110                 115                 120

Phe Ala Asn Asp Leu Thr Asn Pro Gln Leu Leu Val Val Thr Asp Asn
            125                 130                 135

Val Asn Glu Ser Lys Gly Asp Lys Gly Pro Glu Glu Trp Lys Pro Pro
```

```
        140                 145                 150

Leu Thr Ser Tyr Tyr Cys Thr Tyr Ala Glu Met Trp Val Lys Val Lys
    155                 160                 165

Ser Val Tyr Lys Leu Thr Ile Thr Ser Ala Glu Lys Ser Ala Leu Thr
170                 175                 180                 185

Ser Met Leu Ser Thr Cys
                190


<210> SEQ ID NO 107
<211> LENGTH: 191
<212> TYPE: PRT
<213> ORGANISM: Penicillium reticulisporum

<400> SEQUENCE: 107

Leu Pro Ala Pro Glu Ala Leu Pro Ala Pro Pro Gly Val Pro Ser Ala
1               5                   10                  15

Ser Thr Ala Gln Ser Glu Leu Ala Ala Leu Thr Val Ala Ala Gln Gly
            20                  25                  30

Ser Gln Asp Gly Tyr Ser Arg Ser Lys Phe Pro His Trp Ile Thr Gln
        35                  40                  45

Ser Gly Ser Cys Asp Thr Arg Asp Val Val Leu Lys Arg Asp Gly Thr
    50                  55                  60

Asn Val Val Gln Ser Ala Ser Gly Cys Thr Ile Thr Ser Gly Lys Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
            100                 105                 110

Gly Trp Thr Thr Ala Ala Arg Gln Ala Phe Ala Asn Asp Leu Thr Asn
        115                 120                 125

Pro Gln Leu Leu Val Val Thr Asp Asn Val Asn Glu Ser Lys Gly Asp
    130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175

Thr Ser Ala Glu Lys Ser Ala Leu Thr Ser Met Leu Ser Thr Cys
            180                 185                 190


<210> SEQ ID NO 108
<211> LENGTH: 814
<212> TYPE: DNA
<213> ORGANISM: Penicillium quercetorum
<220> FEATURE:
<221> NAME/KEY: CDS
<222> LOCATION: (1)..(218)
<220> FEATURE:
<221> NAME/KEY: sig_peptide
<222> LOCATION: (1)..(69)
<220> FEATURE:
<221> NAME/KEY: mat_peptide
<222> LOCATION: (70)..(811)
<220> FEATURE:
<221> NAME/KEY: CDS
<222> LOCATION: (271)..(445)
<220> FEATURE:
<221> NAME/KEY: CDS
<222> LOCATION: (504)..(642)
<220> FEATURE:
<221> NAME/KEY: CDS
<222> LOCATION: (702)..(811)
```

```
<400> SEQUENCE: 108

atg ggc ttt gca caa gta tct caa gtc ttg atc ggt ctt ttg gct ctc       48
Met Gly Phe Ala Gln Val Ser Gln Val Leu Ile Gly Leu Leu Ala Leu
            -20                 -15                 -10

cag cca ggt ctg att gca ggc ctt ccc gct cct gaa cct gct ccg tct       96
Gln Pro Gly Leu Ile Ala Gly Leu Pro Ala Pro Glu Pro Ala Pro Ser
        -5              -1  1               5

ccc ccg ggg atc ccg tct gct tca acc gcg cga agc gag ctg gct agt      144
Pro Pro Gly Ile Pro Ser Ala Ser Thr Ala Arg Ser Glu Leu Ala Ser
10                  15                  20                  25

ttg acg gtg gct ccc caa gga tct caa gat ggt tat tct cga gcc aag      192
Leu Thr Val Ala Pro Gln Gly Ser Gln Asp Gly Tyr Ser Arg Ala Lys
                30                  35                  40

ttt cct cac tgg atc aag cag agc gg  gtgagacatt cacgtccaca            238
Phe Pro His Trp Ile Lys Gln Ser Gly
            45                  50

tctcttcctg gtcgtactga tcgattttgc ag g agt tgt gac acc cga gac gtt    292
                                      Ser Cys Asp Thr Arg Asp Val
                                                      55

gtc ctc gag cgt gat ggg aca aac gta gtc cag agt tcg act ggc tgc      340
Val Leu Glu Arg Asp Gly Thr Asn Val Val Gln Ser Ser Thr Gly Cys
        60                  65                  70

acc att acc ggt ggc aca tgg gtc tca cca tat gat ggt gca acc tgg      388
Thr Ile Thr Gly Gly Thr Trp Val Ser Pro Tyr Asp Gly Ala Thr Trp
    75                  80                  85

act gcc tcg agc gat gtc gac att gat cat ctt gtt ccg ctg tcg aat      436
Thr Ala Ser Ser Asp Val Asp Ile Asp His Leu Val Pro Leu Ser Asn
90                  95                  100                 105

gcc tgg aag gtacgcatat tctctagcca gcgaagcttt tgtcagagga              485
Ala Trp Lys

ctgacatgtt ttcgatag tcg ggt gcc tct gca tgg acc aca gcc caa cga      536
                    Ser Gly Ala Ser Ala Trp Thr Thr Ala Gln Arg
                        110                 115

caa gcc ttt gcc aat gac ttg acc aat cca caa ctc gtc gca gtg aca      584
Gln Ala Phe Ala Asn Asp Leu Thr Asn Pro Gln Leu Val Ala Val Thr
120                 125                 130                 135

gac aat gtc aat gag gca aag ggt gat aaa ggc ccc gag gaa tgg aag      632
Asp Asn Val Asn Glu Ala Lys Gly Asp Lys Gly Pro Glu Glu Trp Lys
                140                 145                 150

cct cct ctt a gtatgttaca tgtatacctc ttgtgacttg ttcatccaca            682
Pro Pro Leu

cattactgac tggaacaag ca  tcg tac tat tgc acg tac gcg gaa atg tgg     733
                     Thr Ser Tyr Tyr Cys Thr Tyr Ala Glu Met Trp
                     155                 160                 165

gtg aag gtc aag tcc gtc tac aag ctc acc atc aca tcc gcc gag aag      781
Val Lys Val Lys Ser Val Tyr Lys Leu Thr Ile Thr Ser Ala Glu Lys
                170                 175                 180

tcc gcc ctc tcg agc atg ctt aat act tgc tag                          814
Ser Ala Leu Ser Ser Met Leu Asn Thr Cys
            185                 190


<210> SEQ ID NO 109
<211> LENGTH: 214
<212> TYPE: PRT
<213> ORGANISM: Penicillium quercetorum

<400> SEQUENCE: 109

Met Gly Phe Ala Gln Val Ser Gln Val Leu Ile Gly Leu Leu Ala Leu
            -20                 -15                 -10
```

```
Gln Pro Gly Leu Ile Ala Gly Leu Pro Ala Pro Glu Pro Ala Pro Ser
        -5              -1  1               5

Pro Pro Gly Ile Pro Ser Ala Ser Thr Ala Arg Ser Glu Leu Ala Ser
10                  15                  20                  25

Leu Thr Val Ala Pro Gln Gly Ser Gln Asp Gly Tyr Ser Arg Ala Lys
                30                  35                  40

Phe Pro His Trp Ile Lys Gln Ser Gly Ser Cys Asp Thr Arg Asp Val
            45                  50                  55

Val Leu Glu Arg Asp Gly Thr Asn Val Val Gln Ser Ser Thr Gly Cys
        60                  65                  70

Thr Ile Thr Gly Gly Thr Trp Val Ser Pro Tyr Asp Gly Ala Thr Trp
    75                  80                  85

Thr Ala Ser Ser Asp Val Asp Ile Asp His Leu Val Pro Leu Ser Asn
90                  95                  100                 105

Ala Trp Lys Ser Gly Ala Ser Ala Trp Thr Thr Ala Gln Arg Gln Ala
                110                 115                 120

Phe Ala Asn Asp Leu Thr Asn Pro Gln Leu Val Ala Val Thr Asp Asn
            125                 130                 135

Val Asn Glu Ala Lys Gly Asp Lys Gly Pro Glu Glu Trp Lys Pro Pro
        140                 145                 150

Leu Thr Ser Tyr Tyr Cys Thr Tyr Ala Glu Met Trp Val Lys Val Lys
    155                 160                 165

Ser Val Tyr Lys Leu Thr Ile Thr Ser Ala Glu Lys Ser Ala Leu Ser
170                 175                 180                 185

Ser Met Leu Asn Thr Cys
                190
```

<210> SEQ ID NO 110
<211> LENGTH: 191
<212> TYPE: PRT
<213> ORGANISM: Penicillium quercetorum

<400> SEQUENCE: 110

```
Leu Pro Ala Pro Glu Pro Ala Pro Ser Pro Pro Gly Ile Pro Ser Ala
1               5                   10                  15

Ser Thr Ala Arg Ser Glu Leu Ala Ser Leu Thr Val Ala Pro Gln Gly
            20                  25                  30

Ser Gln Asp Gly Tyr Ser Arg Ala Lys Phe Pro His Trp Ile Lys Gln
        35                  40                  45

Ser Gly Ser Cys Asp Thr Arg Asp Val Val Leu Glu Arg Asp Gly Thr
    50                  55                  60

Asn Val Val Gln Ser Ser Thr Gly Cys Thr Ile Thr Gly Gly Thr Trp
65                  70                  75                  80

Val Ser Pro Tyr Asp Gly Ala Thr Trp Thr Ala Ser Ser Asp Val Asp
                85                  90                  95

Ile Asp His Leu Val Pro Leu Ser Asn Ala Trp Lys Ser Gly Ala Ser
            100                 105                 110

Ala Trp Thr Thr Ala Gln Arg Gln Ala Phe Ala Asn Asp Leu Thr Asn
        115                 120                 125

Pro Gln Leu Val Ala Val Thr Asp Asn Val Asn Glu Ala Lys Gly Asp
    130                 135                 140

Lys Gly Pro Glu Glu Trp Lys Pro Pro Leu Thr Ser Tyr Tyr Cys Thr
145                 150                 155                 160

Tyr Ala Glu Met Trp Val Lys Val Lys Ser Val Tyr Lys Leu Thr Ile
                165                 170                 175
```

```
Thr Ser Ala Glu Lys Ser Ala Leu Ser Ser Met Leu Asn Thr Cys
            180                 185                 190


<210> SEQ ID NO 111
<211> LENGTH: 808
<212> TYPE: DNA
<213> ORGANISM: Setophaeosphaeria species
<220> FEATURE:
<221> NAME/KEY: CDS
<222> LOCATION: (1)..(378)
<220> FEATURE:
<221> NAME/KEY: sig_peptide
<222> LOCATION: (1)..(51)
<220> FEATURE:
<221> NAME/KEY: mat_peptide
<222> LOCATION: (52)..(805)
<220> FEATURE:
<221> NAME/KEY: CDS
<222> LOCATION: (438)..(569)
<220> FEATURE:
<221> NAME/KEY: CDS
<222> LOCATION: (622)..(655)
<220> FEATURE:
<221> NAME/KEY: CDS
<222> LOCATION: (723)..(805)

<400> SEQUENCE: 111

atg agg tcc tcc atc ctc gtt gct ctt tct tca ctg gct ctt gtc tct       48
Met Arg Ser Ser Ile Leu Val Ala Leu Ser Ser Leu Ala Leu Val Ser
        -15                 -10                 -5

gct ttg cca gca cca gtg aca ctt gaa gcc cgt gct cca cct aac att       96
Ala Leu Pro Ala Pro Val Thr Leu Glu Ala Arg Ala Pro Pro Asn Ile
-1  1               5                   10                  15

ccc tcc acg gca tca gcc aac acc ttg ctt gca ggc ctc act gtc gct      144
Pro Ser Thr Ala Ser Ala Asn Thr Leu Leu Ala Gly Leu Thr Val Ala
                20                  25                  30

gct caa ggc tct cag acc ggc tac tct cgt gat ctg ttc cct cat tgg      192
Ala Gln Gly Ser Gln Thr Gly Tyr Ser Arg Asp Leu Phe Pro His Trp
            35                  40                  45

atc acc caa tct gga acc tgc aat acc cgc gag act gtc ctg aag cgt      240
Ile Thr Gln Ser Gly Thr Cys Asn Thr Arg Glu Thr Val Leu Lys Arg
        50                  55                  60

gat ggt acc ggg gtt gtc act gat tct gcg tgt gct tca acc tct ggc      288
Asp Gly Thr Gly Val Val Thr Asp Ser Ala Cys Ala Ser Thr Ser Gly
    65                  70                  75

agt tgg tac tct gtc tat gat gga gca act tgg act gcg gca agc gat      336
Ser Trp Tyr Ser Val Tyr Asp Gly Ala Thr Trp Thr Ala Ala Ser Asp
80                  85                  90                  95

gtc gac att gac cac gtc gtg cca ttg agc aat gcc tgg aag              378
Val Asp Ile Asp His Val Val Pro Leu Ser Asn Ala Trp Lys
                100                 105

gttcgtagct cagccttctg gagggagttt agaatacaag gtcactaacg aaaaaacag     437

tct ggt gcc gca agc tgg acg acc gca cgc cgc caa agc ttt gca aat      485
Ser Gly Ala Ala Ser Trp Thr Thr Ala Arg Arg Gln Ser Phe Ala Asn
110                 115                 120                 125

gac ttg acc aat ccc cag ctc att gct gtg aca gat aat gtc aac cag      533
Asp Leu Thr Asn Pro Gln Leu Ile Ala Val Thr Asp Asn Val Asn Gln
                130                 135                 140

gct aag gga gac aag ggt ccc gag gac tgg aag ccc gtaagttatg           579
Ala Lys Gly Asp Lys Gly Pro Glu Asp Trp Lys Pro
            145                 150

aaactagtca aagcatattt caaaatgact gacgtatagc ag ccg cta acc agc       633
                                               Pro Leu Thr Ser
                                                   155
```

```
tac tac tgc acc tat gcg aag a gtaagtgcct tgcattttct agcagtgccg       685
Tyr Tyr Cys Thr Tyr Ala Lys
        160

cttccactaa gaagacgtat gctgactaca taaatag tg  tgg gtc aaa gtc aag     739
                                        Met Trp Val Lys Val Lys
                                        165                 170

agt gtg tac agc ctg acc atc aca agt gcg gag aag act gct ctg aca      787
Ser Val Tyr Ser Leu Thr Ile Thr Ser Ala Glu Lys Thr Ala Leu Thr
                175                 180                 185

agc atg ttg aac act tgc taa                                          808
Ser Met Leu Asn Thr Cys
            190


<210> SEQ ID NO 112
<211> LENGTH: 209
<212> TYPE: PRT
<213> ORGANISM: Setophaeosphaeria species

<400> SEQUENCE: 112

Met Arg Ser Ser Ile Leu Val Ala Leu Ser Ser Leu Ala Leu Val Ser
        -15                 -10                 -5

Ala Leu Pro Ala Pro Val Thr Leu Glu Ala Arg Ala Pro Pro Asn Ile
-1  1               5                   10                  15

Pro Ser Thr Ala Ser Ala Asn Thr Leu Leu Ala Gly Leu Thr Val Ala
                20                  25                  30

Ala Gln Gly Ser Gln Thr Gly Tyr Ser Arg Asp Leu Phe Pro His Trp
            35                  40                  45

Ile Thr Gln Ser Gly Thr Cys Asn Thr Arg Glu Thr Val Leu Lys Arg
        50                  55                  60

Asp Gly Thr Gly Val Val Thr Asp Ser Ala Cys Ala Ser Thr Ser Gly
    65                  70                  75

Ser Trp Tyr Ser Val Tyr Asp Gly Ala Thr Trp Thr Ala Ala Ser Asp
80                  85                  90                  95

Val Asp Ile Asp His Val Val Pro Leu Ser Asn Ala Trp Lys Ser Gly
                100                 105                 110

Ala Ala Ser Trp Thr Thr Ala Arg Arg Gln Ser Phe Ala Asn Asp Leu
            115                 120                 125

Thr Asn Pro Gln Leu Ile Ala Val Thr Asp Asn Val Asn Gln Ala Lys
        130                 135                 140

Gly Asp Lys Gly Pro Glu Asp Trp Lys Pro Pro Leu Thr Ser Tyr Tyr
    145                 150                 155

Cys Thr Tyr Ala Lys Met Trp Val Lys Val Lys Ser Val Tyr Ser Leu
160                 165                 170                 175

Thr Ile Thr Ser Ala Glu Lys Thr Ala Leu Thr Ser Met Leu Asn Thr
                180                 185                 190

Cys


<210> SEQ ID NO 113
<211> LENGTH: 192
<212> TYPE: PRT
<213> ORGANISM: Setophaeosphaeria species

<400> SEQUENCE: 113

Leu Pro Ala Pro Val Thr Leu Glu Ala Arg Ala Pro Pro Asn Ile Pro
1               5                   10                  15

Ser Thr Ala Ser Ala Asn Thr Leu Leu Ala Gly Leu Thr Val Ala Ala
            20                  25                  30
```

```
Gln Gly Ser Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Gly Val Val Thr Asp Ser Ala Cys Ala Ser Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Thr Ala Leu Thr Ser Met Leu Asn Thr Cys
            180                 185                 190


<210> SEQ ID NO 114
<211> LENGTH: 819
<212> TYPE: DNA
<213> ORGANISM: Alternaria species
<220> FEATURE:
<221> NAME/KEY: CDS
<222> LOCATION: (1)..(378)
<220> FEATURE:
<221> NAME/KEY: sig_peptide
<222> LOCATION: (1)..(51)
<220> FEATURE:
<221> NAME/KEY: mat_peptide
<222> LOCATION: (52)..(816)
<220> FEATURE:
<221> NAME/KEY: CDS
<222> LOCATION: (448)..(579)
<220> FEATURE:
<221> NAME/KEY: CDS
<222> LOCATION: (635)..(668)
<220> FEATURE:
<221> NAME/KEY: CDS
<222> LOCATION: (734)..(816)

<400> SEQUENCE: 114

atg aag tcc tcc atc ctc gtt gcc ctc tct tca att gct ctc gtc tct       48
Met Lys Ser Ser Ile Leu Val Ala Leu Ser Ser Ile Ala Leu Val Ser
        -15                 -10                 -5

gct ctg cca gca cca gtg acc ctc gaa gcc cga gct ccc ccc aac atc       96
Ala Leu Pro Ala Pro Val Thr Leu Glu Ala Arg Ala Pro Pro Asn Ile
-1  1               5                   10                  15

ccc acg acc gca gca gcc aaa acc cag ctt gcc ggc ctc act gtt gcc      144
Pro Thr Thr Ala Ala Ala Lys Thr Gln Leu Ala Gly Leu Thr Val Ala
                20                  25                  30

gct caa ggc cct cag acc ggc tac tcc cgt gac ctc ttc cct cac tgg      192
Ala Gln Gly Pro Gln Thr Gly Tyr Ser Arg Asp Leu Phe Pro His Trp
            35                  40                  45

atc act caa tct ggc acc tgc aac acg cgc gag act gtc ctc aag cgc      240
Ile Thr Gln Ser Gly Thr Cys Asn Thr Arg Glu Thr Val Leu Lys Arg
        50                  55                  60

gac ggc acc ggc gtt gtc act gat tcc gcg tgc gcc tca acc tct ggc      288
Asp Gly Thr Gly Val Val Thr Asp Ser Ala Cys Ala Ser Thr Ser Gly
```

```
    65                  70                  75

agc tgg ttc tcg gtc tac gat ggt gct acg tgg act gcg gcg tca gat      336
Ser Trp Phe Ser Val Tyr Asp Gly Ala Thr Trp Thr Ala Ala Ser Asp
80                  85                  90                  95

gtc gat atc gac cat gtc gtg cca ttg agc aat gcc tgg aag              378
Val Asp Ile Asp His Val Val Pro Leu Ser Asn Ala Trp Lys
                100                 105

gttcgtgtga agccccaagt gaacgtgaaa ccatatttag tacagagaca ctaacatatg    438

ccaaaacag tct gga gca gca agc tgg acc acc gca cgc cgc cag tct ttt    489
          Ser Gly Ala Ala Ser Trp Thr Thr Ala Arg Arg Gln Ser Phe
          110                 115                 120

gcc aat gac ctc acc aac ccg cag ctc atc gct gtc acc gac aac gtc      537
Ala Asn Asp Leu Thr Asn Pro Gln Leu Ile Ala Val Thr Asp Asn Val
    125                 130                 135

aac cag gcc aag ggc gac aag ggc ccc gag gac tgg aag ccc              579
Asn Gln Ala Lys Gly Asp Lys Gly Pro Glu Asp Trp Lys Pro
140                 145                 150

gtaagttttt ctatgccagc gagatgagac cttcagagag actgacgtat cgtag ccg     637
                                                             Pro

cta acc agc tat tac tgc act tat gcg aag a gtaagtcttt cctttcccca      688
Leu Thr Ser Tyr Tyr Cys Thr Tyr Ala Lys
155                 160

agatcaccgt actcgtcacg ggaatctaag ctaattattg gacag tg  tgg gtc aag    744
                                                  Met Trp Val Lys
                                                  165

gtc aag agc gtg tac gcc ctt acc atc acc agc gcc gag aag acg gcc      792
Val Lys Ser Val Tyr Ala Leu Thr Ile Thr Ser Ala Glu Lys Thr Ala
    170                 175                 180

ctg acg agc atg ttg aac acg tgc taa                                  819
Leu Thr Ser Met Leu Asn Thr Cys
185                 190


<210> SEQ ID NO 115
<211> LENGTH: 209
<212> TYPE: PRT
<213> ORGANISM: Alternaria species

<400> SEQUENCE: 115

Met Lys Ser Ser Ile Leu Val Ala Leu Ser Ser Ile Ala Leu Val Ser
        -15                 -10                 -5

Ala Leu Pro Ala Pro Val Thr Leu Glu Ala Arg Ala Pro Pro Asn Ile
-1  1               5                   10                  15

Pro Thr Thr Ala Ala Ala Lys Thr Gln Leu Ala Gly Leu Thr Val Ala
                20                  25                  30

Ala Gln Gly Pro Gln Thr Gly Tyr Ser Arg Asp Leu Phe Pro His Trp
            35                  40                  45

Ile Thr Gln Ser Gly Thr Cys Asn Thr Arg Glu Thr Val Leu Lys Arg
        50                  55                  60

Asp Gly Thr Gly Val Val Thr Asp Ser Ala Cys Ala Ser Thr Ser Gly
    65                  70                  75

Ser Trp Phe Ser Val Tyr Asp Gly Ala Thr Trp Thr Ala Ala Ser Asp
80                  85                  90                  95

Val Asp Ile Asp His Val Val Pro Leu Ser Asn Ala Trp Lys Ser Gly
                100                 105                 110

Ala Ala Ser Trp Thr Thr Ala Arg Arg Gln Ser Phe Ala Asn Asp Leu
            115                 120                 125

Thr Asn Pro Gln Leu Ile Ala Val Thr Asp Asn Val Asn Gln Ala Lys
```

```
        130                 135                 140

Gly Asp Lys Gly Pro Glu Asp Trp Lys Pro Pro Leu Thr Ser Tyr Tyr
    145                 150                 155

Cys Thr Tyr Ala Lys Met Trp Val Lys Val Lys Ser Val Tyr Ala Leu
160                 165                 170                 175

Thr Ile Thr Ser Ala Glu Lys Thr Ala Leu Thr Ser Met Leu Asn Thr
                180                 185                 190

Cys


<210> SEQ ID NO 116
<211> LENGTH: 192
<212> TYPE: PRT
<213> ORGANISM: Alternaria species

<400> SEQUENCE: 116

Leu Pro Ala Pro Val Thr Leu Glu Ala Arg Ala Pro Pro Asn Ile Pro
1               5                   10                  15

Thr Thr Ala Ala Ala Lys Thr Gln Leu Ala Gly Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Gly Val Val Thr Asp Ser Ala Cys Ala Ser Thr Ser Gly Ser
65                  70                  75                  80

Trp Phe Ser Val Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175

Ile Thr Ser Ala Glu Lys Thr Ala Leu Thr Ser Met Leu Asn Thr Cys
            180                 185                 190


<210> SEQ ID NO 117
<211> LENGTH: 810
<212> TYPE: DNA
<213> ORGANISM: Alternaria species
<220> FEATURE:
<221> NAME/KEY: CDS
<222> LOCATION: (1)..(378)
<220> FEATURE:
<221> NAME/KEY: sig_peptide
<222> LOCATION: (1)..(51)
<220> FEATURE:
<221> NAME/KEY: mat_peptide
<222> LOCATION: (52)..(807)
<220> FEATURE:
<221> NAME/KEY: CDS
<222> LOCATION: (446)..(577)
<220> FEATURE:
<221> NAME/KEY: CDS
<222> LOCATION: (637)..(670)
<220> FEATURE:
<221> NAME/KEY: CDS
```

```
<222> LOCATION: (725)..(807)

<400> SEQUENCE: 117

atg aag tcc tcc atc ctc gtt gcc ctc tct tca atc gct ctc gtc tct       48
Met Lys Ser Ser Ile Leu Val Ala Leu Ser Ser Ile Ala Leu Val Ser
        -15                 -10                 -5

gct ctg cca gca cca gtg acc ctc gaa gcc cga gct cct ccc aac atc       96
Ala Leu Pro Ala Pro Val Thr Leu Glu Ala Arg Ala Pro Pro Asn Ile
-1  1               5                   10                  15

ccc acg acc gca gca gcc aaa acc cag ctc gcc ggc ctc act gtc gct      144
Pro Thr Thr Ala Ala Ala Lys Thr Gln Leu Ala Gly Leu Thr Val Ala
                20                  25                  30

gct caa ggc cct cag acc ggc tat tcc cgt gac ctc ttc cct cac tgg      192
Ala Gln Gly Pro Gln Thr Gly Tyr Ser Arg Asp Leu Phe Pro His Trp
            35                  40                  45

atc acc cag tcc ggc tcc tgc aac acg cgc gag gtc gtc ctc cag cgc      240
Ile Thr Gln Ser Gly Ser Cys Asn Thr Arg Glu Val Val Leu Gln Arg
        50                  55                  60

gat ggt act ggc gtt gtc act gat tcc gcg tgc gcc gcg acc tct ggc      288
Asp Gly Thr Gly Val Val Thr Asp Ser Ala Cys Ala Ala Thr Ser Gly
    65                  70                  75

agc tgg tac tcg gtc tac gat ggt gct acc tgg act gcg gcg tca gat      336
Ser Trp Tyr Ser Val Tyr Asp Gly Ala Thr Trp Thr Ala Ala Ser Asp
80                  85                  90                  95

gtc gac atc gac cat atg gtg cca ttg agc aat gcc tgg aag              378
Val Asp Ile Asp His Met Val Pro Leu Ser Asn Ala Trp Lys
                100                 105

gttcgtgtgc tgccccaagt gaatgtcaag ctacaattag tacaaagaca ctgacatgat    438

aaaatag tct gga gca gcg agc tgg acc acc gca cgc cgc cag gcg ttc      487
        Ser Gly Ala Ala Ser Trp Thr Thr Ala Arg Arg Gln Ala Phe
        110                 115                 120

gcc aac gac ctc acc aac ccg cag ctc ctc gcc gtg acc gac aac gtc      535
Ala Asn Asp Leu Thr Asn Pro Gln Leu Leu Ala Val Thr Asp Asn Val
    125                 130                 135

aac cag gcc aag ggc gac aag ggc ccc gag gac tgg aag ccc              577
Asn Gln Ala Lys Gly Asp Lys Gly Pro Glu Asp Trp Lys Pro
140                 145                 150

gtaagttctt tgctgccaac gagatgagcc tacagaaacc agtaactgat gcttcatag     636

ccg ctg acc agc tat tac tgc act tat gcg aag a gtaagtcttt              680
Pro Leu Thr Ser Tyr Tyr Cys Thr Tyr Ala Lys
    155                 160

cctttcctca agattgcggg aatacatgct gattgattga acag tg  tgg gtc aag     735
                                                 Met Trp Val Lys
                                                 165

gtc aag agc gtg tac gcc ctt acc att acc agc gcc gag aag acg gcc      783
Val Lys Ser Val Tyr Ala Leu Thr Ile Thr Ser Ala Glu Lys Thr Ala
    170                 175                 180

ctg acg agc atg ttg aac acg tgc taa                                  810
Leu Thr Ser Met Leu Asn Thr Cys
185                 190


<210> SEQ ID NO 118
<211> LENGTH: 209
<212> TYPE: PRT
<213> ORGANISM: Alternaria species

<400> SEQUENCE: 118

Met Lys Ser Ser Ile Leu Val Ala Leu Ser Ser Ile Ala Leu Val Ser
        -15                 -10                 -5
```

-continued

```
Ala Leu Pro Ala Pro Val Thr Leu Glu Ala Arg Ala Pro Pro Asn Ile
-1  1               5                   10                  15

Pro Thr Thr Ala Ala Ala Lys Thr Gln Leu Ala Gly Leu Thr Val Ala
                20                  25                  30

Ala Gln Gly Pro Gln Thr Gly Tyr Ser Arg Asp Leu Phe Pro His Trp
            35                  40                  45

Ile Thr Gln Ser Gly Ser Cys Asn Thr Arg Glu Val Val Leu Gln Arg
        50                  55                  60

Asp Gly Thr Gly Val Val Thr Asp Ser Ala Cys Ala Ala Thr Ser Gly
    65                  70                  75

Ser Trp Tyr Ser Val Tyr Asp Gly Ala Thr Trp Thr Ala Ala Ser Asp
80                  85                  90                  95

Val Asp Ile Asp His Met Val Pro Leu Ser Asn Ala Trp Lys Ser Gly
                100                 105                 110

Ala Ala Ser Trp Thr Thr Ala Arg Arg Gln Ala Phe Ala Asn Asp Leu
            115                 120                 125

Thr Asn Pro Gln Leu Leu Ala Val Thr Asp Asn Val Asn Gln Ala Lys
        130                 135                 140

Gly Asp Lys Gly Pro Glu Asp Trp Lys Pro Pro Leu Thr Ser Tyr Tyr
    145                 150                 155

Cys Thr Tyr Ala Lys Met Trp Val Lys Val Lys Ser Val Tyr Ala Leu
160                 165                 170                 175

Thr Ile Thr Ser Ala Glu Lys Thr Ala Leu Thr Ser Met Leu Asn Thr
                180                 185                 190

Cys
```

```
<210> SEQ ID NO 119
<211> LENGTH: 192
<212> TYPE: PRT
<213> ORGANISM: Alternaria species

<400> SEQUENCE: 119

Leu Pro Ala Pro Val Thr Leu Glu Ala Arg Ala Pro Pro Asn Ile Pro
1               5                   10                  15

Thr Thr Ala Ala Ala Lys Thr Gln Leu Ala Gly Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Ser Cys Asn Thr Arg Glu Val Val Leu Gln Arg Asp
    50                  55                  60

Gly Thr Gly Val Val Thr Asp Ser Ala Cys Ala Ala Thr Ser Gly Ser
65                  70                  75                  80

Trp Tyr Ser Val Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ala Leu Thr
                165                 170                 175
```

```
Ile Thr Ser Ala Glu Lys Thr Ala Leu Thr Ser Met Leu Asn Thr Cys
            180                 185                 190


<210> SEQ ID NO 120
<211> LENGTH: 1004
<212> TYPE: DNA
<213> ORGANISM: Trichoderma reesei
<220> FEATURE:
<221> NAME/KEY: CDS
<222> LOCATION: (1)..(75)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1001)
<220> FEATURE:
<221> NAME/KEY: CDS
<222> LOCATION: (157)..(290)
<220> FEATURE:
<221> NAME/KEY: CDS
<222> LOCATION: (360)..(516)
<220> FEATURE:
<221> NAME/KEY: CDS
<222> LOCATION: (753)..(1001)

<400> SEQUENCE: 120

atg aag ctg tct ttc tct att gcc ctc gcc tcg gcc atc gcg gct ctc       48
Met Lys Leu Ser Phe Ser Ile Ala Leu Ala Ser Ala Ile Ala Ala Leu
                -15                 -10                 -5

gct gct ccg gct cct cta cct gca ccg gtgcgtaact tctcctccga             95
Ala Ala Pro Ala Pro Leu Pro Ala Pro
        -1  1               5

ccagtctcag caccataaat ctacatacac atcagatata ctgacgaccc aactgtaata    155

g ccc ggg atc cca tcc gaa gac acg gcg aga acc cag ctc gcc ggc ctc    204
  Pro Gly Ile Pro Ser Glu Asp Thr Ala Arg Thr Gln Leu Ala Gly Leu
              10                  15                  20

aca gtc gcc gtt gtt ggt tct ggc acg ggc tac tcc cgc gac ttg ttt      252
Thr Val Ala Val Val Gly Ser Gly Thr Gly Tyr Ser Arg Asp Leu Phe
        25                  30                  35

cct acc tgg gat gcc atc tcc ggc aac tgc aat gct cg  gtacgtcaag       300
Pro Thr Trp Asp Ala Ile Ser Gly Asn Cys Asn Ala Arg
    40                  45                  50

cttccttgga ttcctactga taaaatacga agaggctgac tggcatattg ccataacag     359

c gag tac gtg ttg aag cga gat ggc gag ggc gtc cag gtc aac aat gcc    408
  Glu Tyr Val Leu Lys Arg Asp Gly Glu Gly Val Gln Val Asn Asn Ala
              55                  60                  65

tgc gag gcc cag tct ggg agc tgg atc agc ccc tat gac aat gcc agt      456
Cys Glu Ala Gln Ser Gly Ser Trp Ile Ser Pro Tyr Asp Asn Ala Ser
        70                  75                  80

ttc aca aac gcg tcc agc ctg gac att gac cac atg gtg cct ctg aag      504
Phe Thr Asn Ala Ser Ser Leu Asp Ile Asp His Met Val Pro Leu Lys
    85                  90                  95

aat gcc tgg att gtgagtctgc catcttgctt ctccgtggtc tcagtctcca          556
Asn Ala Trp Ile
100

tgtccctctc tgtccatcgt tgccctctga tatacccctg gaactgtttt cacctctgcc    616

tcacacccac ataacctcag catctttgtc acactcatca cttcactaca gttcttctac    676

ttactttatt ctccccttcg acctttcttt ccaccccctc tcatctcatc tcattacacc    736

aactgactcg acccag tcc ggc gcc tca acc tgg acc acc gcc cag cgc gag    788
                  Ser Gly Ala Ser Thr Trp Thr Thr Ala Gln Arg Glu
                      105                 110                 115
```

-continued

```
gcc ctc gcc aac gac gtc tcc cgc ccg cag ctc tgg gcc gtc tcc gcg      836
Ala Leu Ala Asn Asp Val Ser Arg Pro Gln Leu Trp Ala Val Ser Ala
                120                 125                 130

agc tcc aac cgc tcc aag ggc gac cgc agc ccc gac cag tgg aag ccc      884
Ser Ser Asn Arg Ser Lys Gly Asp Arg Ser Pro Asp Gln Trp Lys Pro
            135                 140                 145

ccg ctg acc agc ttc tac tgc acg tac gcc aag tcg tgg att gac gtc      932
Pro Leu Thr Ser Phe Tyr Cys Thr Tyr Ala Lys Ser Trp Ile Asp Val
        150                 155                 160

aag agc tat tac aag ttg act att acg agc gcg gag aag acg gcg ctg      980
Lys Ser Tyr Tyr Lys Leu Thr Ile Thr Ser Ala Glu Lys Thr Ala Leu
    165                 170                 175

agc agc atg ttg gat acc tgc tag                                      1004
Ser Ser Met Leu Asp Thr Cys
180                 185


<210> SEQ ID NO 121
<211> LENGTH: 205
<212> TYPE: PRT
<213> ORGANISM: Trichoderma reesei

<400> SEQUENCE: 121

Met Lys Leu Ser Phe Ser Ile Ala Leu Ala Ser Ala Ile Ala Ala Leu
                -15                 -10                 -5

Ala Ala Pro Ala Pro Leu Pro Ala Pro Pro Gly Ile Pro Ser Glu Asp
        -1  1               5                   10

Thr Ala Arg Thr Gln Leu Ala Gly Leu Thr Val Ala Val Val Gly Ser
    15                  20                  25

Gly Thr Gly Tyr Ser Arg Asp Leu Phe Pro Thr Trp Asp Ala Ile Ser
30                  35                  40                  45

Gly Asn Cys Asn Ala Arg Glu Tyr Val Leu Lys Arg Asp Gly Glu Gly
                50                  55                  60

Val Gln Val Asn Asn Ala Cys Glu Ala Gln Ser Gly Ser Trp Ile Ser
            65                  70                  75

Pro Tyr Asp Asn Ala Ser Phe Thr Asn Ala Ser Ser Leu Asp Ile Asp
        80                  85                  90

His Met Val Pro Leu Lys Asn Ala Trp Ile Ser Gly Ala Ser Thr Trp
    95                  100                 105

Thr Thr Ala Gln Arg Glu Ala Leu Ala Asn Asp Val Ser Arg Pro Gln
110                 115                 120                 125

Leu Trp Ala Val Ser Ala Ser Ser Asn Arg Ser Lys Gly Asp Arg Ser
                130                 135                 140

Pro Asp Gln Trp Lys Pro Pro Leu Thr Ser Phe Tyr Cys Thr Tyr Ala
            145                 150                 155

Lys Ser Trp Ile Asp Val Lys Ser Tyr Tyr Lys Leu Thr Ile Thr Ser
        160                 165                 170

Ala Glu Lys Thr Ala Leu Ser Ser Met Leu Asp Thr Cys
    175                 180                 185


<210> SEQ ID NO 122
<211> LENGTH: 186
<212> TYPE: PRT
<213> ORGANISM: Trichoderma reesei

<400> SEQUENCE: 122

Ala Pro Leu Pro Ala Pro Pro Gly Ile Pro Ser Glu Asp Thr Ala Arg
1               5                   10                  15

Thr Gln Leu Ala Gly Leu Thr Val Ala Val Val Gly Ser Gly Thr Gly
```

```
            20                  25                  30

Tyr Ser Arg Asp Leu Phe Pro Thr Trp Asp Ala Ile Ser Gly Asn Cys
        35                  40                  45

Asn Ala Arg Glu Tyr Val Leu Lys Arg Asp Gly Glu Gly Val Gln Val
    50                  55                  60

Asn Asn Ala Cys Glu Ala Gln Ser Gly Ser Trp Ile Ser Pro Tyr Asp
65                  70                  75                  80

Asn Ala Ser Phe Thr Asn Ala Ser Ser Leu Asp Ile Asp His Met Val
                85                  90                  95

Pro Leu Lys Asn Ala Trp Ile Ser Gly Ala Ser Thr Trp Thr Thr Ala
            100                 105                 110

Gln Arg Glu Ala Leu Ala Asn Asp Val Ser Arg Pro Gln Leu Trp Ala
        115                 120                 125

Val Ser Ala Ser Ser Asn Arg Ser Lys Gly Asp Arg Ser Pro Asp Gln
    130                 135                 140

Trp Lys Pro Pro Leu Thr Ser Phe Tyr Cys Thr Tyr Ala Lys Ser Trp
145                 150                 155                 160

Ile Asp Val Lys Ser Tyr Tyr Lys Leu Thr Ile Thr Ser Ala Glu Lys
                165                 170                 175

Thr Ala Leu Ser Ser Met Leu Asp Thr Cys
            180                 185


<210> SEQ ID NO 123
<211> LENGTH: 1049
<212> TYPE: DNA
<213> ORGANISM: Chaetomium thermophilum
<220> FEATURE:
<221> NAME/KEY: CDS
<222> LOCATION: (1)..(72)
<220> FEATURE:
<221> NAME/KEY: sig_peptide
<222> LOCATION: (1)..(48)
<220> FEATURE:
<221> NAME/KEY: mat_peptide
<222> LOCATION: (49)..(1046)
<220> FEATURE:
<221> NAME/KEY: CDS
<222> LOCATION: (170)..(303)
<220> FEATURE:
<221> NAME/KEY: CDS
<222> LOCATION: (563)..(719)
<220> FEATURE:
<221> NAME/KEY: CDS
<222> LOCATION: (798)..(1046)

<400> SEQUENCE: 123

atg aag ttt gtc acg att ttc tct tta ctt gcc gct gtt gtt tca gcc       48
Met Lys Phe Val Thr Ile Phe Ser Leu Leu Ala Ala Val Val Ser Ala
    -15                 -10                 -5                  -1

gcc cct gcg ccg cag ccg act cct gtacgtaaag ctcaagccaa cttccagtct     102
Ala Pro Ala Pro Gln Pro Thr Pro
1               5

tttgttcttc gattcgactc ttgtcctccg tttggaaata cttgttcggt cgactaacag    162

cacgcag ccg ggc atc ccg agt agg tcg act gct cag agc tat ctc aat      211
        Pro Gly Ile Pro Ser Arg Ser Thr Ala Gln Ser Tyr Leu Asn
            10                  15                  20

tct ctg aca gtt gct gcc tcg tac gac gat ggg aat tac aac cgc gac      259
Ser Leu Thr Val Ala Ala Ser Tyr Asp Asp Gly Asn Tyr Asn Arg Asp
        25                  30                  35

ttg ttc ccc cac tgg aac act gtt agc ggg acc tgt aat act cg           303
Leu Phe Pro His Trp Asn Thr Val Ser Gly Thr Cys Asn Thr Arg
    40                  45                  50
```

```
gtaagtcacc cagctgtgaa agttgtcggg tgatgatgct ggcacgctgt gcaatgagag    363

tggtggaaga tgcgagccgc aggtgtgctc cacttctgcc tcgtgcaact ttggacgtcc    423

tgctttccat ctccagcgtc tttgcgaaag tgatgatcgc cactcatggt cgcttttgcg    483

acacatcgcc tgtcttgtta tttgcacgat taaaagctct atgcttccat ccgaccttca    543

taactaacga ttgacccag c gag tat gtc ctc aag cgc gat ggc tcc aat       593
                       Glu Tyr Val Leu Lys Arg Asp Gly Ser Asn
                           55                  60

gtc gtg acg aac tcg gcc tgc cag gct act tct ggc aca tgg tac agc      641
Val Val Thr Asn Ser Ala Cys Gln Ala Thr Ser Gly Thr Trp Tyr Ser
    65                  70                  75

ccg tat gac ggc gct acg tgg aca gca gca tca gat atc gat atc gat      689
Pro Tyr Asp Gly Ala Thr Trp Thr Ala Ala Ser Asp Ile Asp Ile Asp
80                  85                  90                  95

cat atg gtc ccc ttg aag aat gct tgg att gtaggtctcc agcaacttag        739
His Met Val Pro Leu Lys Asn Ala Trp Ile
                100                 105

caagattggc gtcgtgctgt gtcccggcta gacgttggtg gctaacgcat agagacag      797

tct ggc gcc aac acc tgg tcg tcc tcg aag cgg tcc tcc ttt gcc aac      845
Ser Gly Ala Asn Thr Trp Ser Ser Ser Lys Arg Ser Ser Phe Ala Asn
                110                 115                 120

gac att aat agc cca cag ctc tgg gct gtc act gac agt gtc aac cag      893
Asp Ile Asn Ser Pro Gln Leu Trp Ala Val Thr Asp Ser Val Asn Gln
            125                 130                 135

tct aag ggc gac aag agc cct gac aag tgg aag cct cct ctc acc acg      941
Ser Lys Gly Asp Lys Ser Pro Asp Lys Trp Lys Pro Pro Leu Thr Thr
        140                 145                 150

ttt tac tgc acc tat gcc aag agt tgg atc acg gtg aag tac aac tat      989
Phe Tyr Cys Thr Tyr Ala Lys Ser Trp Ile Thr Val Lys Tyr Asn Tyr
    155                 160                 165

aat ttg acc atc aca tct gca gag aag tct gct cta cag aac atg att     1037
Asn Leu Thr Ile Thr Ser Ala Glu Lys Ser Ala Leu Gln Asn Met Ile
170                 175                 180                 185

aat acg tgc taa                                                     1049
Asn Thr Cys


<210> SEQ ID NO 124
<211> LENGTH: 204
<212> TYPE: PRT
<213> ORGANISM: Chaetomium thermophilum

<400> SEQUENCE: 124

Met Lys Phe Val Thr Ile Phe Ser Leu Leu Ala Ala Val Val Ser Ala
    -15                 -10                 -5              -1

Ala Pro Ala Pro Gln Pro Thr Pro Pro Gly Ile Pro Ser Arg Ser Thr
1               5                   10                  15

Ala Gln Ser Tyr Leu Asn Ser Leu Thr Val Ala Ala Ser Tyr Asp Asp
            20                  25                  30

Gly Asn Tyr Asn Arg Asp Leu Phe Pro His Trp Asn Thr Val Ser Gly
        35                  40                  45

Thr Cys Asn Thr Arg Glu Tyr Val Leu Lys Arg Asp Gly Ser Asn Val
    50                  55                  60

Val Thr Asn Ser Ala Cys Gln Ala Thr Ser Gly Thr Trp Tyr Ser Pro
65                  70                  75                  80

Tyr Asp Gly Ala Thr Trp Thr Ala Ala Ser Asp Ile Asp Ile Asp His
                85                  90                  95
```

-continued

Met Val Pro Leu Lys Asn Ala Trp Ile Ser Gly Ala Asn Thr Trp Ser
100 105 110

Ser Ser Lys Arg Ser Ser Phe Ala Asn Asp Ile Asn Ser Pro Gln Leu
115 120 125

Trp Ala Val Thr Asp Ser Val Asn Gln Ser Lys Gly Asp Lys Ser Pro
130 135 140

Asp Lys Trp Lys Pro Pro Leu Thr Thr Phe Tyr Cys Thr Tyr Ala Lys
145 150 155 160

Ser Trp Ile Thr Val Lys Tyr Asn Tyr Asn Leu Thr Ile Thr Ser Ala
165 170 175

Glu Lys Ser Ala Leu Gln Asn Met Ile Asn Thr Cys
180 185

<210> SEQ ID NO 125
<211> LENGTH: 188
<212> TYPE: PRT
<213> ORGANISM: Chaetomium thermophilum

<400> SEQUENCE: 125

Ala Pro Ala Pro Gln Pro Thr Pro Pro Gly Ile Pro Ser Arg Ser Thr
1 5 10 15

Ala Gln Ser Tyr Leu Asn Ser Leu Thr Val Ala Ala Ser Tyr Asp Asp
20 25 30

Gly Asn Tyr Asn Arg Asp Leu Phe Pro His Trp Asn Thr Val Ser Gly
35 40 45

Thr Cys Asn Thr Arg Glu Tyr Val Leu Lys Arg Asp Gly Ser Asn Val
50 55 60

Val Thr Asn Ser Ala Cys Gln Ala Thr Ser Gly Thr Trp Tyr Ser Pro
65 70 75 80

Tyr Asp Gly Ala Thr Trp Thr Ala Ala Ser Asp Ile Asp Ile Asp His
85 90 95

Met Val Pro Leu Lys Asn Ala Trp Ile Ser Gly Ala Asn Thr Trp Ser
100 105 110

Ser Ser Lys Arg Ser Ser Phe Ala Asn Asp Ile Asn Ser Pro Gln Leu
115 120 125

Trp Ala Val Thr Asp Ser Val Asn Gln Ser Lys Gly Asp Lys Ser Pro
130 135 140

Asp Lys Trp Lys Pro Pro Leu Thr Thr Phe Tyr Cys Thr Tyr Ala Lys
145 150 155 160

Ser Trp Ile Thr Val Lys Tyr Asn Tyr Asn Leu Thr Ile Thr Ser Ala
165 170 175

Glu Lys Ser Ala Leu Gln Asn Met Ile Asn Thr Cys
180 185

<210> SEQ ID NO 126
<211> LENGTH: 873
<212> TYPE: DNA
<213> ORGANISM: Scytalidium thermophilum
<220> FEATURE:
<221> NAME/KEY: CDS
<222> LOCATION: (1)..(78)
<220> FEATURE:
<221> NAME/KEY: sig_peptide
<222> LOCATION: (1)..(48)
<220> FEATURE:
<221> NAME/KEY: mat_peptide
<222> LOCATION: (49)..(870)
<220> FEATURE:
<221> NAME/KEY: CDS
<222> LOCATION: (179)..(312)

```
<220> FEATURE:
<221> NAME/KEY: CDS
<222> LOCATION: (373)..(529)
<220> FEATURE:
<221> NAME/KEY: CDS
<222> LOCATION: (622)..(870)

<400> SEQUENCE: 126

atg aag tcc ttt att gtc tat tct ttc ctc gcc gcg gtg gct acg gcc       48
Met Lys Ser Phe Ile Val Tyr Ser Phe Leu Ala Ala Val Ala Thr Ala
    -15                 -10                 -5              -1

ttg ccg gcc ccg gcg ccg atg cct act ccc gtaagcccta ttactgctcg         98
Leu Pro Ala Pro Ala Pro Met Pro Thr Pro
1               5                   10

agtcaatctg aggcgttctc gaaaggatta ttatgcatga ggataacctc caatgctaac    158

atggacgtct taatacccag ccg ggc att ccc tca aaa tca acg gcc cag tcc    211
                      Pro Gly Ile Pro Ser Lys Ser Thr Ala Gln Ser
                                      15                  20

cag ctg aac gcc ctg acg gtc aag gcc tcc tat gac gat ggc aag tat      259
Gln Leu Asn Ala Leu Thr Val Lys Ala Ser Tyr Asp Asp Gly Lys Tyr
            25                  30                  35

aag cgc gac ctg ttc cct cac tgg aac acc gtc agc ggg act tgc aac      307
Lys Arg Asp Leu Phe Pro His Trp Asn Thr Val Ser Gly Thr Cys Asn
        40                  45                  50

acc cg  gtaggttgat ctttatgtgg ttgagattct cagcagaacg cagtctgact       362
Thr Arg
    55

gtcgcaacag c gaa tat gtc ctg aag cgc gac ggg gtc aac gtc gtc acc     412
             Glu Tyr Val Leu Lys Arg Asp Gly Val Asn Val Val Thr
                             60                  65

aac tcg gcc tgc gct gcc acc tcg ggc aca tgg tac tcg cct ttc gac      460
Asn Ser Ala Cys Ala Ala Thr Ser Gly Thr Trp Tyr Ser Pro Phe Asp
    70                  75                  80

ggc gcc acc tgg act gcg gca tct gat gtc gat att gac cac atg gtg      508
Gly Ala Thr Trp Thr Ala Ala Ser Asp Val Asp Ile Asp His Met Val
85                  90                  95                  100

ccc ctg aag aat gcc tgg att gtaagcttct gctcaccgtc caactgttta         559
Pro Leu Lys Asn Ala Trp Ile
                105

aatgacagtt gtcgtgtcat aagaatgatt gagacctata ctcacgctcg ttgacaatgc    619

ag tcc ggc gca aac aac tgg acc tca acc aag cgg acg cag ttc gcc       666
   Ser Gly Ala Asn Asn Trp Thr Ser Thr Lys Arg Thr Gln Phe Ala
           110                 115                 120

aac gac atc aac ctg ccc cag ctg tgg gcg gtc acg gac gac gtg aac      714
Asn Asp Ile Asn Leu Pro Gln Leu Trp Ala Val Thr Asp Asp Val Asn
        125                 130                 135

cag gcc aag ggc gac aag tct ccc gac aag tgg aag cct cct ctc acc      762
Gln Ala Lys Gly Asp Lys Ser Pro Asp Lys Trp Lys Pro Pro Leu Thr
    140                 145                 150

tcc ttc tac tgc acc tac gcc aag agc tgg atc acg gtc aag tac aac      810
Ser Phe Tyr Cys Thr Tyr Ala Lys Ser Trp Ile Thr Val Lys Tyr Asn
155                 160                 165                 170

tac ggc ctc agc atc acg tcg gcc gag aag tcg gcg ttg act agc atg      858
Tyr Gly Leu Ser Ile Thr Ser Ala Glu Lys Ser Ala Leu Thr Ser Met
                175                 180                 185

atc aac act tgc tga                                                  873
Ile Asn Thr Cys
            190


<210> SEQ ID NO 127
```

<211> LENGTH: 206
<212> TYPE: PRT
<213> ORGANISM: Scytalidium thermophilum

<400> SEQUENCE: 127

```
Met Lys Ser Phe Ile Val Tyr Ser Phe Leu Ala Ala Val Ala Thr Ala
    -15                 -10                 -5                  -1

Leu Pro Ala Pro Ala Pro Met Pro Thr Pro Pro Gly Ile Pro Ser Lys
1               5                   10                  15

Ser Thr Ala Gln Ser Gln Leu Asn Ala Leu Thr Val Lys Ala Ser Tyr
            20                  25                  30

Asp Asp Gly Lys Tyr Lys Arg Asp Leu Phe Pro His Trp Asn Thr Val
        35                  40                  45

Ser Gly Thr Cys Asn Thr Arg Glu Tyr Val Leu Lys Arg Asp Gly Val
    50                  55                  60

Asn Val Val Thr Asn Ser Ala Cys Ala Ala Thr Ser Gly Thr Trp Tyr
65                  70                  75                  80

Ser Pro Phe Asp Gly Ala Thr Trp Thr Ala Ala Ser Asp Val Asp Ile
                85                  90                  95

Asp His Met Val Pro Leu Lys Asn Ala Trp Ile Ser Gly Ala Asn Asn
            100                 105                 110

Trp Thr Ser Thr Lys Arg Thr Gln Phe Ala Asn Asp Ile Asn Leu Pro
        115                 120                 125

Gln Leu Trp Ala Val Thr Asp Asp Val Asn Gln Ala Lys Gly Asp Lys
    130                 135                 140

Ser Pro Asp Lys Trp Lys Pro Pro Leu Thr Ser Phe Tyr Cys Thr Tyr
145                 150                 155                 160

Ala Lys Ser Trp Ile Thr Val Lys Tyr Asn Tyr Gly Leu Ser Ile Thr
                165                 170                 175

Ser Ala Glu Lys Ser Ala Leu Thr Ser Met Ile Asn Thr Cys
            180                 185                 190
```

<210> SEQ ID NO 128
<211> LENGTH: 190
<212> TYPE: PRT
<213> ORGANISM: Scytalidium thermophilum

<400> SEQUENCE: 128

```
Leu Pro Ala Pro Ala Pro Met Pro Thr Pro Pro Gly Ile Pro Ser Lys
1               5                   10                  15

Ser Thr Ala Gln Ser Gln Leu Asn Ala Leu Thr Val Lys Ala Ser Tyr
            20                  25                  30

Asp Asp Gly Lys Tyr Lys Arg Asp Leu Phe Pro His Trp Asn Thr Val
        35                  40                  45

Ser Gly Thr Cys Asn Thr Arg Glu Tyr Val Leu Lys Arg Asp Gly Val
    50                  55                  60

Asn Val Val Thr Asn Ser Ala Cys Ala Ala Thr Ser Gly Thr Trp Tyr
65                  70                  75                  80

Ser Pro Phe Asp Gly Ala Thr Trp Thr Ala Ala Ser Asp Val Asp Ile
                85                  90                  95

Asp His Met Val Pro Leu Lys Asn Ala Trp Ile Ser Gly Ala Asn Asn
            100                 105                 110

Trp Thr Ser Thr Lys Arg Thr Gln Phe Ala Asn Asp Ile Asn Leu Pro
        115                 120                 125

Gln Leu Trp Ala Val Thr Asp Asp Val Asn Gln Ala Lys Gly Asp Lys
    130                 135                 140
```

```
Ser Pro Asp Lys Trp Lys Pro Pro Leu Thr Ser Phe Tyr Cys Thr Tyr
145                 150                 155                 160

Ala Lys Ser Trp Ile Thr Val Lys Tyr Asn Tyr Gly Leu Ser Ile Thr
                165                 170                 175

Ser Ala Glu Lys Ser Ala Leu Thr Ser Met Ile Asn Thr Cys
            180                 185                 190


<210> SEQ ID NO 129
<211> LENGTH: 802
<212> TYPE: DNA
<213> ORGANISM: Metapochonia suchlasporia
<220> FEATURE:
<221> NAME/KEY: CDS
<222> LOCATION: (1)..(72)
<220> FEATURE:
<221> NAME/KEY: sig_peptide
<222> LOCATION: (1)..(54)
<220> FEATURE:
<221> NAME/KEY: mat_peptide
<222> LOCATION: (55)..(799)
<220> FEATURE:
<221> NAME/KEY: CDS
<222> LOCATION: (143)..(276)
<220> FEATURE:
<221> NAME/KEY: CDS
<222> LOCATION: (329)..(485)
<220> FEATURE:
<221> NAME/KEY: CDS
<222> LOCATION: (551)..(799)

<400> SEQUENCE: 129

atg aag ttc tct tcg gca tct ctc gtc gtg tcc gcc gcc gcg ctt gtc       48
Met Lys Phe Ser Ser Ala Ser Leu Val Val Ser Ala Ala Ala Leu Val
            -15                 -10                 -5

ctc ggt gtg cct gtg cct gcg ccc gtaagcaatc ccactcctga cacgctgtca     102
Leu Gly Val Pro Val Pro Ala Pro
    -1  1               5

ttgtgtaaca aagcctgata atgttttctt gctcttctag ccg ggt atc cca agc      157
                                            Pro Gly Ile Pro Ser
                                                            10

act tcg aca gcc aag act ctt ctt gct ggc ctc aag gtt gct gtt cca      205
Thr Ser Thr Ala Lys Thr Leu Leu Ala Gly Leu Lys Val Ala Val Pro
            15                  20                  25

ttg agt ggc gat ggg tac agt cgt gag aag ttc cct ctt tgg gag acc      253
Leu Ser Gly Asp Gly Tyr Ser Arg Glu Lys Phe Pro Leu Trp Glu Thr
        30                  35                  40

att cag gga act tgc aat gct cg  gtgggtttat cacatcttct cttattcctt     306
Ile Gln Gly Thr Cys Asn Ala Arg
    45                  50

tcatgttgct aatgccatgt ag c gag ttt gtc ctt aag cga gac gga aca       356
                           Glu Phe Val Leu Lys Arg Asp Gly Thr
                                       55                  60

gac gtc aag acc aac aac gca tgt gtc gca gag tct ggc aac tgg gtc      404
Asp Val Lys Thr Asn Asn Ala Cys Val Ala Glu Ser Gly Asn Trp Val
                65                  70                  75

tct ccg tat gac ggg gtc aag ttc acc gca gca cgc gat ctc gac att      452
Ser Pro Tyr Asp Gly Val Lys Phe Thr Ala Ala Arg Asp Leu Asp Ile
            80                  85                  90

gac cac atg gtt cca ctg aag aac gcc tgg att gtaagactac tgcccaactc    505
Asp His Met Val Pro Leu Lys Asn Ala Trp Ile
        95                  100

tttctctcct caacttcacc tactctgtct aactttcctt gccag tcc ggt gcc tca    562
                                                  Ser Gly Ala Ser
                                                      105
```

```
caa tgg acc acc gag cgg cgc aaa gct ctg gcc aac gac atc acc cgc      610
Gln Trp Thr Thr Glu Arg Arg Lys Ala Leu Ala Asn Asp Ile Thr Arg
        110                 115                 120

ccc cag ctt tgg gct gta tca gcc cat gcc aac cgc ggc aag agt gac      658
Pro Gln Leu Trp Ala Val Ser Ala His Ala Asn Arg Gly Lys Ser Asp
    125                 130                 135

gat agc ccc gat gag tgg aag cct cct ctg aag acg ttt tgg tgc aca      706
Asp Ser Pro Asp Glu Trp Lys Pro Pro Leu Lys Thr Phe Trp Cys Thr
140                 145                 150                 155

tac gcc aag agt tgg gtc caa gtg aag agc ttt tat gag ctg act att      754
Tyr Ala Lys Ser Trp Val Gln Val Lys Ser Phe Tyr Glu Leu Thr Ile
                160                 165                 170

acg gat gcc gag aag ggt gct ctg gct ggc atg ctg gat tca tgc taa      802
Thr Asp Ala Glu Lys Gly Ala Leu Ala Gly Met Leu Asp Ser Cys
            175                 180                 185


<210> SEQ ID NO 130
<211> LENGTH: 204
<212> TYPE: PRT
<213> ORGANISM: Metapochonia suchlasporia

<400> SEQUENCE: 130

Met Lys Phe Ser Ser Ala Ser Leu Val Val Ser Ala Ala Ala Leu Val
            -15                 -10                 -5

Leu Gly Val Pro Val Pro Ala Pro Pro Gly Ile Pro Ser Thr Ser Thr
    -1  1               5                   10

Ala Lys Thr Leu Leu Ala Gly Leu Lys Val Ala Val Pro Leu Ser Gly
15                  20                  25                  30

Asp Gly Tyr Ser Arg Glu Lys Phe Pro Leu Trp Glu Thr Ile Gln Gly
                35                  40                  45

Thr Cys Asn Ala Arg Glu Phe Val Leu Lys Arg Asp Gly Thr Asp Val
            50                  55                  60

Lys Thr Asn Asn Ala Cys Val Ala Glu Ser Gly Asn Trp Val Ser Pro
        65                  70                  75

Tyr Asp Gly Val Lys Phe Thr Ala Ala Arg Asp Leu Asp Ile Asp His
    80                  85                  90

Met Val Pro Leu Lys Asn Ala Trp Ile Ser Gly Ala Ser Gln Trp Thr
95                  100                 105                 110

Thr Glu Arg Arg Lys Ala Leu Ala Asn Asp Ile Thr Arg Pro Gln Leu
                115                 120                 125

Trp Ala Val Ser Ala His Ala Asn Arg Gly Lys Ser Asp Asp Ser Pro
            130                 135                 140

Asp Glu Trp Lys Pro Pro Leu Lys Thr Phe Trp Cys Thr Tyr Ala Lys
        145                 150                 155

Ser Trp Val Gln Val Lys Ser Phe Tyr Glu Leu Thr Ile Thr Asp Ala
    160                 165                 170

Glu Lys Gly Ala Leu Ala Gly Met Leu Asp Ser Cys
175                 180                 185


<210> SEQ ID NO 131
<211> LENGTH: 186
<212> TYPE: PRT
<213> ORGANISM: Metapochonia suchlasporia

<400> SEQUENCE: 131

Val Pro Val Pro Ala Pro Pro Gly Ile Pro Ser Thr Ser Thr Ala Lys
1               5                   10                  15
```

```
Thr Leu Leu Ala Gly Leu Lys Val Ala Val Pro Leu Ser Gly Asp Gly
            20                  25                  30

Tyr Ser Arg Glu Lys Phe Pro Leu Trp Glu Thr Ile Gln Gly Thr Cys
        35                  40                  45

Asn Ala Arg Glu Phe Val Leu Lys Arg Asp Gly Thr Asp Val Lys Thr
    50                  55                  60

Asn Asn Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
            100                 105                 110

Arg Arg Lys Ala Leu Ala Asn Asp Ile Thr Arg Pro Gln Leu Trp Ala
        115                 120                 125

Val Ser Ala His Ala Asn Arg Gly Lys Ser Asp Asp Ser Pro Asp Glu
    130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Glu Leu Thr Ile Thr Asp Ala Glu Lys
                165                 170                 175

Gly Ala Leu Ala Gly Met Leu Asp Ser Cys
            180                 185


<210> SEQ ID NO 132
<211> LENGTH: 771
<212> TYPE: DNA
<213> ORGANISM: Daldinia fissa
<220> FEATURE:
<221> NAME/KEY: CDS
<222> LOCATION: (1)..(108)
<220> FEATURE:
<221> NAME/KEY: sig_peptide
<222> LOCATION: (1)..(54)
<220> FEATURE:
<221> NAME/KEY: mat_peptide
<222> LOCATION: (55)..(768)
<220> FEATURE:
<221> NAME/KEY: CDS
<222> LOCATION: (177)..(467)
<220> FEATURE:
<221> NAME/KEY: CDS
<222> LOCATION: (520)..(768)

<400> SEQUENCE: 132

atg agg ttc tca ttc acc ctt ggc agt ctc cta tcc gcg agc gcc gtg       48
Met Arg Phe Ser Phe Thr Leu Gly Ser Leu Leu Ser Ala Ser Ala Val
            -15                 -10                 -5

ctc gcc gcg ccg gcg cca att ccg gtt gcc gag ccc gcc ccc atg ccc       96
Leu Ala Ala Pro Ala Pro Ile Pro Val Ala Glu Pro Ala Pro Met Pro
    -1  1               5                   10

atg cct act ccc gttcgtaatc accttgccct atccataaac gcaacaacag          148
Met Pro Thr Pro
15

ctctttcaaa actgacagat gtaattag cct ggc atc cca tct gcc tcg tca       200
                               Pro Gly Ile Pro Ser Ala Ser Ser
                                   20                  25

gct aaa tct caa ctc gca agc ttg acc gtc aag gcg gcg gtc gac gac      248
Ala Lys Ser Gln Leu Ala Ser Leu Thr Val Lys Ala Ala Val Asp Asp
            30                  35                  40

gga gga tac cag cgg gac ttg ttc ccg acg tgg gac acc atc acg gga      296
Gly Gly Tyr Gln Arg Asp Leu Phe Pro Thr Trp Asp Thr Ile Thr Gly
        45                  50                  55
```

```
acc tgt aac acg cgc gag tac gtc ctc aag cgc gac ggc gcc aac gtc      344
Thr Cys Asn Thr Arg Glu Tyr Val Leu Lys Arg Asp Gly Ala Asn Val
    60                  65                  70

cag gtc ggc tct gac tgt tat ccg acg agc ggc aca tgg acc agt ccc      392
Gln Val Gly Ser Asp Cys Tyr Pro Thr Ser Gly Thr Trp Thr Ser Pro
75                  80                  85                  90

tac gat ggt ggg aag tgg aca tca ccg tct gat gtg gat atc gac cac      440
Tyr Asp Gly Gly Lys Trp Thr Ser Pro Ser Asp Val Asp Ile Asp His
                95                  100                 105

atg gta cct ttg aag aat gcc tgg gtt gtatgtattt catgctttac            487
Met Val Pro Leu Lys Asn Ala Trp Val
            110                 115

ctgtttatca ccgtttaact aattatatgt ag tcc ggg gcg aac aaa tgg aca      540
                                    Ser Gly Ala Asn Lys Trp Thr
                                                    120

act gcc aag cgc gag caa ttc gcc aac gat gtt gat cga cca cag ctc      588
Thr Ala Lys Arg Glu Gln Phe Ala Asn Asp Val Asp Arg Pro Gln Leu
        125                 130                 135

tgg gcc gta acg gat aac gtt aat tca tct aag ggc gac aaa tct ccc      636
Trp Ala Val Thr Asp Asn Val Asn Ser Ser Lys Gly Asp Lys Ser Pro
    140                 145                 150

gat acc tgg aag ccg cct cta aca agc ttc tat tgc act tat gcg agc      684
Asp Thr Trp Lys Pro Pro Leu Thr Ser Phe Tyr Cys Thr Tyr Ala Ser
155                 160                 165                 170

gct tac gtc gcc gtc aag agc tat tgg ggc tta act atc acg tcg gct      732
Ala Tyr Val Ala Val Lys Ser Tyr Trp Gly Leu Thr Ile Thr Ser Ala
                175                 180                 185

gag aaa tcg gct cta agt gac atg tta gga act tgt tag                  771
Glu Lys Ser Ala Leu Ser Asp Met Leu Gly Thr Cys
            190                 195


<210> SEQ ID NO 133
<211> LENGTH: 216
<212> TYPE: PRT
<213> ORGANISM: Daldinia fissa

<400> SEQUENCE: 133

Met Arg Phe Ser Phe Thr Leu Gly Ser Leu Leu Ser Ala Ser Ala Val
            -15                 -10                 -5

Leu Ala Ala Pro Ala Pro Ile Pro Val Ala Glu Pro Ala Pro Met Pro
    -1  1               5                   10

Met Pro Thr Pro Pro Gly Ile Pro Ser Ala Ser Ser Ala Lys Ser Gln
15                  20                  25                  30

Leu Ala Ser Leu Thr Val Lys Ala Ala Val Asp Asp Gly Gly Tyr Gln
                35                  40                  45

Arg Asp Leu Phe Pro Thr Trp Asp Thr Ile Thr Gly Thr Cys Asn Thr
            50                  55                  60

Arg Glu Tyr Val Leu Lys Arg Asp Gly Ala Asn Val Gln Val Gly Ser
        65                  70                  75

Asp Cys Tyr Pro Thr Ser Gly Thr Trp Thr Ser Pro Tyr Asp Gly Gly
    80                  85                  90

Lys Trp Thr Ser Pro Ser Asp Val Asp Ile Asp His Met Val Pro Leu
95                  100                 105                 110

Lys Asn Ala Trp Val Ser Gly Ala Asn Lys Trp Thr Thr Ala Lys Arg
                115                 120                 125

Glu Gln Phe Ala Asn Asp Val Asp Arg Pro Gln Leu Trp Ala Val Thr
            130                 135                 140
```

```
Asp Asn Val Asn Ser Ser Lys Gly Asp Lys Ser Pro Asp Thr Trp Lys
        145                 150                 155

Pro Pro Leu Thr Ser Phe Tyr Cys Thr Tyr Ala Ser Ala Tyr Val Ala
    160                 165                 170

Val Lys Ser Tyr Trp Gly Leu Thr Ile Thr Ser Ala Glu Lys Ser Ala
175                 180                 185                 190

Leu Ser Asp Met Leu Gly Thr Cys
                195


<210> SEQ ID NO 134
<211> LENGTH: 198
<212> TYPE: PRT
<213> ORGANISM: Daldinia fissa

<400> SEQUENCE: 134

Ala Pro Ala Pro Ile Pro Val Ala Glu Pro Ala Pro Met Pro Met Pro
1               5                   10                  15

Thr Pro Pro Gly Ile Pro Ser Ala Ser Ser Ala Lys Ser Gln Leu Ala
            20                  25                  30

Ser Leu Thr Val Lys Ala Ala Val Asp Asp Gly Gly Tyr Gln Arg Asp
        35                  40                  45

Leu Phe Pro Thr Trp Asp Thr Ile Thr Gly Thr Cys Asn Thr Arg Glu
    50                  55                  60

Tyr Val Leu Lys Arg Asp Gly Ala Asn Val Gln Val Gly Ser Asp Cys
65                  70                  75                  80

Tyr Pro Thr Ser Gly Thr Trp Thr Ser Pro Tyr Asp Gly Gly Lys Trp
                85                  90                  95

Thr Ser Pro Ser Asp Val Asp Ile Asp His Met Val Pro Leu Lys Asn
            100                 105                 110

Ala Trp Val Ser Gly Ala Asn Lys Trp Thr Thr Ala Lys Arg Glu Gln
        115                 120                 125

Phe Ala Asn Asp Val Asp Arg Pro Gln Leu Trp Ala Val Thr Asp Asn
    130                 135                 140

Val Asn Ser Ser Lys Gly Asp Lys Ser Pro Asp Thr Trp Lys Pro Pro
145                 150                 155                 160

Leu Thr Ser Phe Tyr Cys Thr Tyr Ala Ser Ala Tyr Val Ala Val Lys
                165                 170                 175

Ser Tyr Trp Gly Leu Thr Ile Thr Ser Ala Glu Lys Ser Ala Leu Ser
            180                 185                 190

Asp Met Leu Gly Thr Cys
        195


<210> SEQ ID NO 135
<211> LENGTH: 805
<212> TYPE: DNA
<213> ORGANISM: Acremonium species
<220> FEATURE:
<221> NAME/KEY: CDS
<222> LOCATION: (1)..(75)
<220> FEATURE:
<221> NAME/KEY: sig_peptide
<222> LOCATION: (1)..(51)
<220> FEATURE:
<221> NAME/KEY: mat_peptide
<222> LOCATION: (52)..(802)
<220> FEATURE:
<221> NAME/KEY: CDS
<222> LOCATION: (152)..(442)
<220> FEATURE:
<221> NAME/KEY: CDS
<222> LOCATION: (554)..(802)
```

<400> SEQUENCE: 135

```
atg aag ttc tcc atc gca acc ctc ctc acg gcc gtg tcc acc atc acc       48
Met Lys Phe Ser Ile Ala Thr Leu Leu Thr Ala Val Ser Thr Ile Thr
        -15                 -10                 -5

gcc ctc ccg ctc caa tct cgt gac ccc gtacgtattt tatccccttc             95
Ala Leu Pro Leu Gln Ser Arg Asp Pro
-1  1               5

tccaactcat aatcccatat cgtcaagacc tctcagacta aacatcgtca aaacag ccc    154
                                                              Pro

ggc att ccc tcc acc gca acc gcc aaa tct ctc ctc aac ggc ctc acc      202
Gly Ile Pro Ser Thr Ala Thr Ala Lys Ser Leu Leu Asn Gly Leu Thr
10                  15                  20                  25

gta aag gca tgg tcc aac gaa gga acc tat gat cgt gac ctc ttt cct      250
Val Lys Ala Trp Ser Asn Glu Gly Thr Tyr Asp Arg Asp Leu Phe Pro
                30                  35                  40

cac tgg cag acc atc gag ggg acg tgc aac gcg agg gaa tac gtt ctc      298
His Trp Gln Thr Ile Glu Gly Thr Cys Asn Ala Arg Glu Tyr Val Leu
            45                  50                  55

aag agg gat ggc cag aat gtt gtg gta aac agt gct tgc acg gca cag      346
Lys Arg Asp Gly Gln Asn Val Val Val Asn Ser Ala Cys Thr Ala Gln
        60                  65                  70

tct ggg acg tgg aag agt gtt tat gat ggg gag act acc aac tct gca      394
Ser Gly Thr Trp Lys Ser Val Tyr Asp Gly Glu Thr Thr Asn Ser Ala
    75                  80                  85

tcg gat ctt gac att gat cac atg atc ccc ttg aag aat gct tgg atc      442
Ser Asp Leu Asp Ile Asp His Met Ile Pro Leu Lys Asn Ala Trp Ile
90                  95                  100                 105

gtgagttccc cccctcccct tcgcagcatt ctcaaaaaaa aaaacaatgt ctacccacat    502

ccctcgcatc ttcaaagctt gcccaactaa caaacaaccc ccccaaccca g tcc ggc     559
                                                        Ser Gly

gcc gcc acc tgg acc acc gca cag cgc acc tcc ttt gca aac gac att      607
Ala Ala Thr Trp Thr Thr Ala Gln Arg Thr Ser Phe Ala Asn Asp Ile
        110                 115                 120

tcc tcc ccc cag ctc tgg gcc gtc acc gcg ggc gtc aac cgc tcg aaa      655
Ser Ser Pro Gln Leu Trp Ala Val Thr Ala Gly Val Asn Arg Ser Lys
    125                 130                 135

tct gac cgc tcg ccg gat acc tgg gtg ccc ccc ctg gcc agc ttc cac      703
Ser Asp Arg Ser Pro Asp Thr Trp Val Pro Pro Leu Ala Ser Phe His
140                 145                 150                 155

tgc acg tat ggc aaa gcg tgg gtg cag gtc aag agc aag tgg gcg ttg      751
Cys Thr Tyr Gly Lys Ala Trp Val Gln Val Lys Ser Lys Trp Ala Leu
                160                 165                 170

agc atc acg agc gcg gag aag agt gcg ctt acg ggg ttg ttg aac aag      799
Ser Ile Thr Ser Ala Glu Lys Ser Ala Leu Thr Gly Leu Leu Asn Lys
            175                 180                 185

tgc taa                                                              805
Cys
```

<210> SEQ ID NO 136
<211> LENGTH: 205
<212> TYPE: PRT
<213> ORGANISM: Acremonium species

<400> SEQUENCE: 136

```
Met Lys Phe Ser Ile Ala Thr Leu Leu Thr Ala Val Ser Thr Ile Thr
        -15                 -10                 -5

Ala Leu Pro Leu Gln Ser Arg Asp Pro Pro Gly Ile Pro Ser Thr Ala
-1  1               5                   10                  15
```

Thr Ala Lys Ser Leu Leu Asn Gly Leu Thr Val Lys Ala Trp Ser Asn
20 25 30

Glu Gly Thr Tyr Asp Arg Asp Leu Phe Pro His Trp Gln Thr Ile Glu
35 40 45

Gly Thr Cys Asn Ala Arg Glu Tyr Val Leu Lys Arg Asp Gly Gln Asn
50 55 60

Val Val Val Asn Ser Ala Cys Thr Ala Gln Ser Gly Thr Trp Lys Ser
65 70 75

Val Tyr Asp Gly Glu Thr Thr Asn Ser Ala Ser Asp Leu Asp Ile Asp
80 85 90 95

His Met Ile Pro Leu Lys Asn Ala Trp Ile Ser Gly Ala Ala Thr Trp
100 105 110

Thr Thr Ala Gln Arg Thr Ser Phe Ala Asn Asp Ile Ser Ser Pro Gln
115 120 125

Leu Trp Ala Val Thr Ala Gly Val Asn Arg Ser Lys Ser Asp Arg Ser
130 135 140

Pro Asp Thr Trp Val Pro Pro Leu Ala Ser Phe His Cys Thr Tyr Gly
145 150 155

Lys Ala Trp Val Gln Val Lys Ser Lys Trp Ala Leu Ser Ile Thr Ser
160 165 170 175

Ala Glu Lys Ser Ala Leu Thr Gly Leu Leu Asn Lys Cys
180 185

<210> SEQ ID NO 137
<211> LENGTH: 188
<212> TYPE: PRT
<213> ORGANISM: Acremonium species

<400> SEQUENCE: 137

Leu Pro Leu Gln Ser Arg Asp Pro Pro Gly Ile Pro Ser Thr Ala Thr
1 5 10 15

Ala Lys Ser Leu Leu Asn Gly Leu Thr Val Lys Ala Trp Ser Asn Glu
20 25 30

Gly Thr Tyr Asp Arg Asp Leu Phe Pro His Trp Gln Thr Ile Glu Gly
35 40 45

Thr Cys Asn Ala Arg Glu Tyr Val Leu Lys Arg Asp Gly Gln Asn Val
50 55 60

Val Val Asn Ser Ala Cys Thr Ala Gln Ser Gly Thr Trp Lys Ser Val
65 70 75 80

Tyr Asp Gly Glu Thr Thr Asn Ser Ala Ser Asp Leu Asp Ile Asp His
85 90 95

Met Ile Pro Leu Lys Asn Ala Trp Ile Ser Gly Ala Ala Thr Trp Thr
100 105 110

Thr Ala Gln Arg Thr Ser Phe Ala Asn Asp Ile Ser Ser Pro Gln Leu
115 120 125

Trp Ala Val Thr Ala Gly Val Asn Arg Ser Lys Ser Asp Arg Ser Pro
130 135 140

Asp Thr Trp Val Pro Pro Leu Ala Ser Phe His Cys Thr Tyr Gly Lys
145 150 155 160

Ala Trp Val Gln Val Lys Ser Lys Trp Ala Leu Ser Ile Thr Ser Ala
165 170 175

Glu Lys Ser Ala Leu Thr Gly Leu Leu Asn Lys Cys
180 185

```
<210> SEQ ID NO 138
<211> LENGTH: 663
<212> TYPE: DNA
<213> ORGANISM: Acremonium dichromosporum
<220> FEATURE:
<221> NAME/KEY: CDS
<222> LOCATION: (1)..(348)
<220> FEATURE:
<221> NAME/KEY: sig_peptide
<222> LOCATION: (1)..(51)
<220> FEATURE:
<221> NAME/KEY: mat_peptide
<222> LOCATION: (52)..(660)
<220> FEATURE:
<221> NAME/KEY: CDS
<222> LOCATION: (412)..(660)

<400> SEQUENCE: 138

atg agg gct gta ctc gct gcc gtg ctc tac tcc gct gtc gcg gtt gtt       48
Met Arg Ala Val Leu Ala Ala Val Leu Tyr Ser Ala Val Ala Val Val
        -15                 -10                 -5

gcc att cct cct ggt att ccc agt gag gcg act gcg cgc tcg ctt ctc       96
Ala Ile Pro Pro Gly Ile Pro Ser Glu Ala Thr Ala Arg Ser Leu Leu
-1  1               5                   10                  15

agc agc ctg act gtg gcg ccc acc gtt gac gat ggc acc tac gat cgc      144
Ser Ser Leu Thr Val Ala Pro Thr Val Asp Asp Gly Thr Tyr Asp Arg
                20                  25                  30

gac ctg ttc cct cac tgg tct tca gtc gag ggc aac tgc aac gcg cga      192
Asp Leu Phe Pro His Trp Ser Ser Val Glu Gly Asn Cys Asn Ala Arg
            35                  40                  45

gag ttc gtt ctc cgt cgt gat ggt gac ggt gtc tcg gtt gga aat gac      240
Glu Phe Val Leu Arg Arg Asp Gly Asp Gly Val Ser Val Gly Asn Asp
        50                  55                  60

tgc tat ccc acc gct ggc acc tgg acg tgc cca tat gat gga aag aga      288
Cys Tyr Pro Thr Ala Gly Thr Trp Thr Cys Pro Tyr Asp Gly Lys Arg
    65                  70                  75

cac agc gtg ccc agc gat gtc tca atc gac cac atg gtg cct ctg cac      336
His Ser Val Pro Ser Asp Val Ser Ile Asp His Met Val Pro Leu His
80                  85                  90                  95

aac gcg tgg atg gtacgttgcc tcatcgtaga aaacatgcac gattcgcccc          388
Asn Ala Trp Met

tgctgacatg attctccaaa aag act ggt gct tct gag tgg acc acg gcg gaa    441
                          Thr Gly Ala Ser Glu Trp Thr Thr Ala Glu
                          100                 105

cgc gag gcg ttt gcc aat gac att gac ggg ccc cag ctg tgg gct gtc      489
Arg Glu Ala Phe Ala Asn Asp Ile Asp Gly Pro Gln Leu Trp Ala Val
110                 115                 120                 125

act agc acg acc aac tcg caa aag ggg tcg gac gcg cca gat gag tgg      537
Thr Ser Thr Thr Asn Ser Gln Lys Gly Ser Asp Ala Pro Asp Glu Trp
                130                 135                 140

cag cct ccc cag acg agc att cac tgc aag tac gct gct gcg tgg atc      585
Gln Pro Pro Gln Thr Ser Ile His Cys Lys Tyr Ala Ala Ala Trp Ile
            145                 150                 155

cag gtc aag agc acc tac gac ctg act gtg agc tcg gca gag cag gcc      633
Gln Val Lys Ser Thr Tyr Asp Leu Thr Val Ser Ser Ala Glu Gln Ala
        160                 165                 170

gct ctg gag gaa atg ctg ggc agg tgc tga                              663
Ala Leu Glu Glu Met Leu Gly Arg Cys
    175                 180


<210> SEQ ID NO 139
<211> LENGTH: 199
<212> TYPE: PRT
<213> ORGANISM: Acremonium dichromosporum
```

<400> SEQUENCE: 139

Met Arg Ala Val Leu Ala Ala Val Leu Tyr Ser Ala Val Ala Val Val
-15 -10 -5

Ala Ile Pro Pro Gly Ile Pro Ser Glu Ala Thr Ala Arg Ser Leu Leu
-1 1 5 10 15

Ser Ser Leu Thr Val Ala Pro Thr Val Asp Asp Gly Thr Tyr Asp Arg
20 25 30

Asp Leu Phe Pro His Trp Ser Ser Val Glu Gly Asn Cys Asn Ala Arg
35 40 45

Glu Phe Val Leu Arg Arg Asp Gly Asp Gly Val Ser Val Gly Asn Asp
50 55 60

Cys Tyr Pro Thr Ala Gly Thr Trp Thr Cys Pro Tyr Asp Gly Lys Arg
65 70 75

His Ser Val Pro Ser Asp Val Ser Ile Asp His Met Val Pro Leu His
80 85 90 95

Asn Ala Trp Met Thr Gly Ala Ser Glu Trp Thr Thr Ala Glu Arg Glu
100 105 110

Ala Phe Ala Asn Asp Ile Asp Gly Pro Gln Leu Trp Ala Val Thr Ser
115 120 125

Thr Thr Asn Ser Gln Lys Gly Ser Asp Ala Pro Asp Glu Trp Gln Pro
130 135 140

Pro Gln Thr Ser Ile His Cys Lys Tyr Ala Ala Ala Trp Ile Gln Val
145 150 155

Lys Ser Thr Tyr Asp Leu Thr Val Ser Ser Ala Glu Gln Ala Ala Leu
160 165 170 175

Glu Glu Met Leu Gly Arg Cys
180

<210> SEQ ID NO 140
<211> LENGTH: 182
<212> TYPE: PRT
<213> ORGANISM: Acremonium dichromosporum

<400> SEQUENCE: 140

Ile Pro Pro Gly Ile Pro Ser Glu Ala Thr Ala Arg Ser Leu Leu Ser
1 5 10 15

Ser Leu Thr Val Ala Pro Thr Val Asp Asp Gly Thr Tyr Asp Arg Asp
20 25 30

Leu Phe Pro His Trp Ser Ser Val Glu Gly Asn Cys Asn Ala Arg Glu
35 40 45

Phe Val Leu Arg Arg Asp Gly Asp Gly Val Ser Val Gly Asn Asp Cys
50 55 60

Tyr Pro Thr Ala Gly Thr Trp Thr Cys Pro Tyr Asp Gly Lys Arg His
65 70 75 80

Ser Val Pro Ser Asp Val Ser Ile Asp His Met Val Pro Leu His Asn
85 90 95

Ala Trp Met Thr Gly Ala Ser Glu Trp Thr Thr Ala Glu Arg Glu Ala
100 105 110

Phe Ala Asn Asp Ile Asp Gly Pro Gln Leu Trp Ala Val Thr Ser Thr
115 120 125

Thr Asn Ser Gln Lys Gly Ser Asp Ala Pro Asp Glu Trp Gln Pro Pro
130 135 140

Gln Thr Ser Ile His Cys Lys Tyr Ala Ala Ala Trp Ile Gln Val Lys
145 150 155 160

```
Ser Thr Tyr Asp Leu Thr Val Ser Ser Ala Glu Gln Ala Ala Leu Glu
                165                 170                 175

Glu Met Leu Gly Arg Cys
            180


<210> SEQ ID NO 141
<211> LENGTH: 802
<212> TYPE: DNA
<213> ORGANISM: Sarocladium species
<220> FEATURE:
<221> NAME/KEY: CDS
<222> LOCATION: (1)..(75)
<220> FEATURE:
<221> NAME/KEY: sig_peptide
<222> LOCATION: (1)..(51)
<220> FEATURE:
<221> NAME/KEY: mat_peptide
<222> LOCATION: (52)..(799)
<220> FEATURE:
<221> NAME/KEY: CDS
<222> LOCATION: (141)..(274)
<220> FEATURE:
<221> NAME/KEY: CDS
<222> LOCATION: (331)..(487)
<220> FEATURE:
<221> NAME/KEY: CDS
<222> LOCATION: (551)..(799)

<400> SEQUENCE: 141

atg aag ttc ttc att cct acc ttg ttg tcg gcg gtg gtg acc gtt ctg       48
Met Lys Phe Phe Ile Pro Thr Leu Leu Ser Ala Val Val Thr Val Leu
        -15                 -10                 -5

gcg gtg ccg att cct ctc cct gat ccg gtaagcatct tctcgtcttg             95
Ala Val Pro Ile Pro Leu Pro Asp Pro
-1  1               5

gctttgtctt cacatgtgtc gagcaggagc ttatctcgag tatag ccg ggc att cct    152
                                                  Pro Gly Ile Pro
                                                      10

agc tct tcg act gcg aat acg ttg ctg gcc ggc ctg aca gtt cgt gcc      200
Ser Ser Ser Thr Ala Asn Thr Leu Leu Ala Gly Leu Thr Val Arg Ala
        15                  20                  25

tct agc aat gag gac act tac aac cgt gat ctg ttc ccg cac tgg gtc      248
Ser Ser Asn Glu Asp Thr Tyr Asn Arg Asp Leu Phe Pro His Trp Val
    30                  35                  40

gcc att tcg ggc aac tgc aac gct cg  gtgagttttc caatgctgga            294
Ala Ile Ser Gly Asn Cys Asn Ala Arg
45                  50

tcgacttcac atggcattga cggactgcgc ctctag t gaa tat gtt ctt cgg cgt    349
                                          Glu Tyr Val Leu Arg Arg
                                              55

gat ggc acc aat gtg gta gtc aat act gcc tgc gtc ccg cag tcc ggc      397
Asp Gly Thr Asn Val Val Val Asn Thr Ala Cys Val Pro Gln Ser Gly
60                  65                  70                  75

aca tgg cgc agt cct tac gat ggc gag tcg acc acc aac gca agt gac      445
Thr Trp Arg Ser Pro Tyr Asp Gly Glu Ser Thr Thr Asn Ala Ser Asp
                80                  85                  90

ctc gac att gac cac atg gtc cct ctc aag aac gca tgg atc              487
Leu Asp Ile Asp His Met Val Pro Leu Lys Asn Ala Trp Ile
            95                  100                 105

gtaagtcttc cccgtctcct caatcacact acataatctc ttgctaacac cacctgtgca    547

aag tcc ggc gct gct tcc tgg acc acc gcc aag cgc cag gac ttc gcc      595
    Ser Gly Ala Ala Ser Trp Thr Thr Ala Lys Arg Gln Asp Phe Ala
                    110                 115                 120
```

```
aac gac gtg tcc ggc ccc cag ctg tgg gct gtc act gcc ggt gtg aac      643
Asn Asp Val Ser Gly Pro Gln Leu Trp Ala Val Thr Ala Gly Val Asn
                125                 130                 135

cgg tcc aag ggt gac aag agc cct gat tca tgg gtg ccg ccg ttg gcg      691
Arg Ser Lys Gly Asp Lys Ser Pro Asp Ser Trp Val Pro Pro Leu Ala
            140                 145                 150

agt ttc cat tgc aca tat gca agg tct tgg atc cag gtg aag agc tca      739
Ser Phe His Cys Thr Tyr Ala Arg Ser Trp Ile Gln Val Lys Ser Ser
        155                 160                 165

tgg gcc ctg agc gtg acg agc gcg gag aag gct gct ttg acc gac ttg      787
Trp Ala Leu Ser Val Thr Ser Ala Glu Lys Ala Ala Leu Thr Asp Leu
    170                 175                 180

ctg agc act tgc tga                                                  802
Leu Ser Thr Cys
185


<210> SEQ ID NO 142
<211> LENGTH: 205
<212> TYPE: PRT
<213> ORGANISM: Sarocladium species

<400> SEQUENCE: 142

Met Lys Phe Phe Ile Pro Thr Leu Leu Ser Ala Val Val Thr Val Leu
        -15                 -10                 -5

Ala Val Pro Ile Pro Leu Pro Asp Pro Pro Gly Ile Pro Ser Ser Ser
-1  1               5                   10                  15

Thr Ala Asn Thr Leu Leu Ala Gly Leu Thr Val Arg Ala Ser Ser Asn
                20                  25                  30

Glu Asp Thr Tyr Asn Arg Asp Leu Phe Pro His Trp Val Ala Ile Ser
            35                  40                  45

Gly Asn Cys Asn Ala Arg Glu Tyr Val Leu Arg Arg Asp Gly Thr Asn
        50                  55                  60

Val Val Val Asn Thr Ala Cys Val Pro Gln Ser Gly Thr Trp Arg Ser
    65                  70                  75

Pro Tyr Asp Gly Glu Ser Thr Thr Asn Ala Ser Asp Leu Asp Ile Asp
80                  85                  90                  95

His Met Val Pro Leu Lys Asn Ala Trp Ile Ser Gly Ala Ala Ser Trp
                100                 105                 110

Thr Thr Ala Lys Arg Gln Asp Phe Ala Asn Asp Val Ser Gly Pro Gln
            115                 120                 125

Leu Trp Ala Val Thr Ala Gly Val Asn Arg Ser Lys Gly Asp Lys Ser
        130                 135                 140

Pro Asp Ser Trp Val Pro Pro Leu Ala Ser Phe His Cys Thr Tyr Ala
    145                 150                 155

Arg Ser Trp Ile Gln Val Lys Ser Ser Trp Ala Leu Ser Val Thr Ser
160                 165                 170                 175

Ala Glu Lys Ala Ala Leu Thr Asp Leu Leu Ser Thr Cys
                180                 185


<210> SEQ ID NO 143
<211> LENGTH: 188
<212> TYPE: PRT
<213> ORGANISM: Sarocladium species

<400> SEQUENCE: 143

Val Pro Ile Pro Leu Pro Asp Pro Pro Gly Ile Pro Ser Ser Ser Thr
1               5                   10                  15

Ala Asn Thr Leu Leu Ala Gly Leu Thr Val Arg Ala Ser Ser Asn Glu
```

```
            20                  25                  30

Asp Thr Tyr Asn Arg Asp Leu Phe Pro His Trp Val Ala Ile Ser Gly
        35                  40                  45

Asn Cys Asn Ala Arg Glu Tyr Val Leu Arg Arg Asp Gly Thr Asn Val
    50                  55                  60

Val Val Asn Thr Ala Cys Val Pro Gln Ser Gly Thr Trp Arg Ser Pro
65                  70                  75                  80

Tyr Asp Gly Glu Ser Thr Thr Asn Ala Ser Asp Leu Asp Ile Asp His
                85                  90                  95

Met Val Pro Leu Lys Asn Ala Trp Ile Ser Gly Ala Ala Ser Trp Thr
            100                 105                 110

Thr Ala Lys Arg Gln Asp Phe Ala Asn Asp Val Ser Gly Pro Gln Leu
        115                 120                 125

Trp Ala Val Thr Ala Gly Val Asn Arg Ser Lys Gly Asp Lys Ser Pro
    130                 135                 140

Asp Ser Trp Val Pro Pro Leu Ala Ser Phe His Cys Thr Tyr Ala Arg
145                 150                 155                 160

Ser Trp Ile Gln Val Lys Ser Ser Trp Ala Leu Ser Val Thr Ser Ala
                165                 170                 175

Glu Lys Ala Ala Leu Thr Asp Leu Leu Ser Thr Cys
            180                 185


<210> SEQ ID NO 144
<211> LENGTH: 815
<212> TYPE: DNA
<213> ORGANISM: Metarhizium species
<220> FEATURE:
<221> NAME/KEY: CDS
<222> LOCATION: (1)..(75)
<220> FEATURE:
<221> NAME/KEY: sig_peptide
<222> LOCATION: (1)..(57)
<220> FEATURE:
<221> NAME/KEY: mat_peptide
<222> LOCATION: (58)..(812)
<220> FEATURE:
<221> NAME/KEY: CDS
<222> LOCATION: (160)..(293)
<220> FEATURE:
<221> NAME/KEY: CDS
<222> LOCATION: (348)..(504)
<220> FEATURE:
<221> NAME/KEY: CDS
<222> LOCATION: (564)..(812)

<400> SEQUENCE: 144

atg agg ttc tcc tcg gca tca ttt ctt gtc gtg tct gcc gct gcg gtt       48
Met Arg Phe Ser Ser Ala Ser Phe Leu Val Val Ser Ala Ala Ala Val
                -15                 -10                 -5

gtc ctc ggt gtg cct gtg cct gcg ccc gtaagccctc tcccgcctgt             95
Val Leu Gly Val Pro Val Pro Ala Pro
        -1  1               5

cctatgccat gccatgccat ccatcttgtg taacaagaag aaacaaaacg ctgacgcttt    155

tcag ccg ggt atc cca act gct tcc acc gcc agg act ctt ctt gct ggc     204
     Pro Gly Ile Pro Thr Ala Ser Thr Ala Arg Thr Leu Leu Ala Gly
                 10                  15                  20

ctc aag gtt gct acg ccg ttg agc ggt gat ggc tac tct cgc acc ctg      252
Leu Lys Val Ala Thr Pro Leu Ser Gly Asp Gly Tyr Ser Arg Thr Leu
            25                  30                  35

ttc cct acg tgg gag acc atc gag gga acc tgc aac gct cg               293
Phe Pro Thr Trp Glu Thr Ile Glu Gly Thr Cys Asn Ala Arg
        40                  45                  50
```

```
gtaggctttt tcttctcttc tctgtcagag acaaggtact aaacatgtat gtag c gag     351
                                                              Glu

ttt gta ctc aag cga gat gga aca gac gtc cag acc aac acc gca tgt      399
Phe Val Leu Lys Arg Asp Gly Thr Asp Val Gln Thr Asn Thr Ala Cys
        55                  60                  65

gtc gcc cag tct ggc aac tgg gtt tct ccg tat gac ggc gtc gca ttc      447
Val Ala Gln Ser Gly Asn Trp Val Ser Pro Tyr Asp Gly Val Ala Phe
    70                  75                  80

act gcc gcc tcg gat ctc gac att gac cac atg gtt cca ctg aag aat      495
Thr Ala Ala Ser Asp Leu Asp Ile Asp His Met Val Pro Leu Lys Asn
85                  90                  95                  100

gcc tgg att gtaagaccaa agacagcatt gataacaagg agtcaccctg              544
Ala Trp Ile

tctaactctc atctcacag tcc ggc gcc tcg caa tgg acc acg gac aag cgc     596
                     Ser Gly Ala Ser Gln Trp Thr Thr Asp Lys Arg
                         105                 110

aaa ggt ctc gcc aac gac atc acc cgt cct cag ctc tgg gcc gtc tct      644
Lys Gly Leu Ala Asn Asp Ile Thr Arg Pro Gln Leu Trp Ala Val Ser
115                 120                 125                 130

gcc cat gcc aac cgc gcc aag ggc gac agc agc ccc gac gag tgg aag      692
Ala His Ala Asn Arg Ala Lys Gly Asp Ser Ser Pro Asp Glu Trp Lys
                135                 140                 145

cct cct ctg aag acg ttc tgg tgt act tac gcg agg agt tgg gtc cag      740
Pro Pro Leu Lys Thr Phe Trp Cys Thr Tyr Ala Arg Ser Trp Val Gln
            150                 155                 160

gtc aag agc tat tat gcg ctg acc att act gat gct gag aag ggc gcg      788
Val Lys Ser Tyr Tyr Ala Leu Thr Ile Thr Asp Ala Glu Lys Gly Ala
        165                 170                 175

ctg tca ggc atg ctg gat tct tgc taa                                  815
Leu Ser Gly Met Leu Asp Ser Cys
    180                 185


<210> SEQ ID NO 145
<211> LENGTH: 205
<212> TYPE: PRT
<213> ORGANISM: Metarhizium species

<400> SEQUENCE: 145

Met Arg Phe Ser Ser Ala Ser Phe Leu Val Val Ser Ala Ala Ala Val
                -15                 -10                 -5

Val Leu Gly Val Pro Val Pro Ala Pro Pro Gly Ile Pro Thr Ala Ser
        -1  1               5                   10

Thr Ala Arg Thr Leu Leu Ala Gly Leu Lys Val Ala Thr Pro Leu Ser
    15                  20                  25

Gly Asp Gly Tyr Ser Arg Thr Leu Phe Pro Thr Trp Glu Thr Ile Glu
30                  35                  40                  45

Gly Thr Cys Asn Ala Arg Glu Phe Val Leu Lys Arg Asp Gly Thr Asp
                50                  55                  60

Val Gln Thr Asn Thr Ala Cys Val Ala Gln Ser Gly Asn Trp Val Ser
            65                  70                  75

Pro Tyr Asp Gly Val Ala Phe Thr Ala Ala Ser Asp Leu Asp Ile Asp
        80                  85                  90

His Met Val Pro Leu Lys Asn Ala Trp Ile Ser Gly Ala Ser Gln Trp
    95                  100                 105

Thr Thr Asp Lys Arg Lys Gly Leu Ala Asn Asp Ile Thr Arg Pro Gln
110                 115                 120                 125

Leu Trp Ala Val Ser Ala His Ala Asn Arg Ala Lys Gly Asp Ser Ser
```

```
                130                 135                 140

Pro Asp Glu Trp Lys Pro Pro Leu Lys Thr Phe Trp Cys Thr Tyr Ala
            145                 150                 155

Arg Ser Trp Val Gln Val Lys Ser Tyr Tyr Ala Leu Thr Ile Thr Asp
        160                 165                 170

Ala Glu Lys Gly Ala Leu Ser Gly Met Leu Asp Ser Cys
    175                 180                 185


<210> SEQ ID NO 146
<211> LENGTH: 186
<212> TYPE: PRT
<213> ORGANISM: Metarhizium species

<400> SEQUENCE: 146

Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Gln Ser Gly Asn Trp Val Ser Pro Tyr Asp
65                  70                  75                  80

Gly Val Ala Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Gly Leu Ala Asn Asp Ile Thr Arg Pro Gln Leu Trp Ala
        115                 120                 125

Val Ser Ala His Ala Asn Arg Ala Lys Gly Asp Ser Ser Pro Asp Glu
    130                 135                 140

Trp Lys Pro Pro Leu Lys Thr Phe Trp Cys Thr Tyr Ala Arg Ser Trp
145                 150                 155                 160

Val Gln Val Lys Ser Tyr Tyr Ala Leu Thr Ile Thr Asp Ala Glu Lys
                165                 170                 175

Gly Ala Leu Ser Gly Met Leu Asp Ser Cys
            180                 185


<210> SEQ ID NO 147
<211> LENGTH: 794
<212> TYPE: DNA
<213> ORGANISM: Acremonium species
<220> FEATURE:
<221> NAME/KEY: CDS
<222> LOCATION: (1)..(75)
<220> FEATURE:
<221> NAME/KEY: sig_peptide
<222> LOCATION: (1)..(51)
<220> FEATURE:
<221> NAME/KEY: mat_peptide
<222> LOCATION: (52)..(791)
<220> FEATURE:
<221> NAME/KEY: CDS
<222> LOCATION: (136)..(269)
<220> FEATURE:
<221> NAME/KEY: CDS
<222> LOCATION: (326)..(482)
<220> FEATURE:
<221> NAME/KEY: CDS
<222> LOCATION: (543)..(791)
```

<400> SEQUENCE: 147

```
atg agg ttc atc att ccg act ttc ttg gcc act gcg gcc act gtg ctg       48
Met Arg Phe Ile Ile Pro Thr Phe Leu Ala Thr Ala Ala Thr Val Leu
        -15                 -10                 -5

gca gcg ccg atc gct gtc cgg gac cca gttagctctc actccccgtc             95
Ala Ala Pro Ile Ala Val Arg Asp Pro
-1  1               5

tcaggcatgt aacgagagta aggagctaac ttatatacag cct ggt atc cca agt      150
                                            Pro Gly Ile Pro Ser
                                                10

gca tcg acg gcc aac acg ttg ctg gcg ggt ctg acg gtt agg gct tca      198
Ala Ser Thr Ala Asn Thr Leu Leu Ala Gly Leu Thr Val Arg Ala Ser
    15                  20                  25

agc aac gaa gac agt tat gat cgc aac ctc ttc ccc cac tgg tct gcc      246
Ser Asn Glu Asp Ser Tyr Asp Arg Asn Leu Phe Pro His Trp Ser Ala
30                  35                  40                  45

ata tcc gga aat tgc aac gct cg  gtaggacaac gcccccaagc actgcgatgg     299
Ile Ser Gly Asn Cys Asn Ala Arg
                50

aacgaacgcc gcttaccaaa tattag t gag ttc gtc ctc gag cgc gac ggc       350
                               Glu Phe Val Leu Glu Arg Asp Gly
                                   55                  60

acc aac gtc gtg gtc aac aac gcc tgc gtc gcc cag tcg ggg act tgg      398
Thr Asn Val Val Val Asn Asn Ala Cys Val Ala Gln Ser Gly Thr Trp
            65                  70                  75

cgc agc cct tat gac ggc gag acg acg ggt aat gcc agt gac ctg gac      446
Arg Ser Pro Tyr Asp Gly Glu Thr Thr Gly Asn Ala Ser Asp Leu Asp
        80                  85                  90

atc gac cac atg gtg cct ctc aag aac gcc tgg atc gtaggtgtcc           492
Ile Asp His Met Val Pro Leu Lys Asn Ala Trp Ile
    95                  100                 105

cgtactcgat cacccgagtt agtaggccgg agctgaccat gtctctgcag tct ggc       548
                                                       Ser Gly

gcc tct tca tgg agc acc acg aga cgt cag gag ttt gcc aac gat gtc      596
Ala Ser Ser Trp Ser Thr Thr Arg Arg Gln Glu Phe Ala Asn Asp Val
        110                 115                 120

tcc ggg cct cag ctg tgg gcc gtc acc gcg ggt gtg aac cgc tcc aag      644
Ser Gly Pro Gln Leu Trp Ala Val Thr Ala Gly Val Asn Arg Ser Lys
    125                 130                 135

ggt gac agg agc ccc gac tcg tgg gtg ccg cct ctg gct agc ttc cac      692
Gly Asp Arg Ser Pro Asp Ser Trp Val Pro Pro Leu Ala Ser Phe His
140                 145                 150                 155

tgc acg tac gcg aag tct tgg gtg cag gtg aag agc tca tgg tcc ttg      740
Cys Thr Tyr Ala Lys Ser Trp Val Gln Val Lys Ser Ser Trp Ser Leu
                160                 165                 170

agt gtg acg agc gcg gaa aag gcg gcg cta tcg gac ctc ctg ggt act      788
Ser Val Thr Ser Ala Glu Lys Ala Ala Leu Ser Asp Leu Leu Gly Thr
            175                 180                 185

tgc tga                                                              794
Cys
```

<210> SEQ ID NO 148
<211> LENGTH: 205
<212> TYPE: PRT
<213> ORGANISM: Acremonium species

<400> SEQUENCE: 148

```
Met Arg Phe Ile Ile Pro Thr Phe Leu Ala Thr Ala Ala Thr Val Leu
        -15                 -10                 -5
```

-continued

```
Ala Ala Pro Ile Ala Val Arg Asp Pro Pro Gly Ile Pro Ser Ala Ser
-1  1               5                   10                  15

Thr Ala Asn Thr Leu Leu Ala Gly Leu Thr Val Arg Ala Ser Ser Asn
                20                  25                  30

Glu Asp Ser Tyr Asp Arg Asn Leu Phe Pro His Trp Ser Ala Ile Ser
            35                  40                  45

Gly Asn Cys Asn Ala Arg Glu Phe Val Leu Glu Arg Asp Gly Thr Asn
        50                  55                  60

Val Val Val Asn Asn Ala Cys Val Ala Gln Ser Gly Thr Trp Arg Ser
    65                  70                  75

Pro Tyr Asp Gly Glu Thr Thr Gly Asn Ala Ser Asp Leu Asp Ile Asp
80                  85                  90                  95

His Met Val Pro Leu Lys Asn Ala Trp Ile Ser Gly Ala Ser Ser Trp
                100                 105                 110

Ser Thr Thr Arg Arg Gln Glu Phe Ala Asn Asp Val Ser Gly Pro Gln
            115                 120                 125

Leu Trp Ala Val Thr Ala Gly Val Asn Arg Ser Lys Gly Asp Arg Ser
        130                 135                 140

Pro Asp Ser Trp Val Pro Pro Leu Ala Ser Phe His Cys Thr Tyr Ala
    145                 150                 155

Lys Ser Trp Val Gln Val Lys Ser Ser Trp Ser Leu Ser Val Thr Ser
160                 165                 170                 175

Ala Glu Lys Ala Ala Leu Ser Asp Leu Leu Gly Thr Cys
                180                 185


<210> SEQ ID NO 149
<211> LENGTH: 188
<212> TYPE: PRT
<213> ORGANISM: Acremonium species

<400> SEQUENCE: 149

Ala Pro Ile Ala Val Arg Asp Pro Pro Gly Ile Pro Ser Ala Ser Thr
1               5                   10                  15

Ala Asn Thr Leu Leu Ala Gly Leu Thr Val Arg Ala Ser Ser Asn Glu
            20                  25                  30

Asp Ser Tyr Asp Arg Asn Leu Phe Pro His Trp Ser Ala Ile Ser Gly
        35                  40                  45

Asn Cys Asn Ala Arg Glu Phe Val Leu Glu Arg Asp Gly Thr Asn Val
    50                  55                  60

Val Val Asn Asn Ala Cys Val Ala Gln Ser Gly Thr Trp Arg Ser Pro
65                  70                  75                  80

Tyr Asp Gly Glu Thr Thr Gly Asn Ala Ser Asp Leu Asp Ile Asp His
                85                  90                  95

Met Val Pro Leu Lys Asn Ala Trp Ile Ser Gly Ala Ser Ser Trp Ser
            100                 105                 110

Thr Thr Arg Arg Gln Glu Phe Ala Asn Asp Val Ser Gly Pro Gln Leu
        115                 120                 125

Trp Ala Val Thr Ala Gly Val Asn Arg Ser Lys Gly Asp Arg Ser Pro
    130                 135                 140

Asp Ser Trp Val Pro Pro Leu Ala Ser Phe His Cys Thr Tyr Ala Lys
145                 150                 155                 160

Ser Trp Val Gln Val Lys Ser Ser Trp Ser Leu Ser Val Thr Ser Ala
                165                 170                 175

Glu Lys Ala Ala Leu Ser Asp Leu Leu Gly Thr Cys
            180                 185
```

<210> SEQ ID NO 150
<211> LENGTH: 964
<212> TYPE: DNA
<213> ORGANISM: Isaria tenuipes
<220> FEATURE:
<221> NAME/KEY: CDS
<222> LOCATION: (1)..(63)
<220> FEATURE:
<221> NAME/KEY: sig_peptide
<222> LOCATION: (1)..(45)
<220> FEATURE:
<221> NAME/KEY: mat_peptide
<222> LOCATION: (46)..(961)
<220> FEATURE:
<221> NAME/KEY: CDS
<222> LOCATION: (126)..(259)
<220> FEATURE:
<221> NAME/KEY: CDS
<222> LOCATION: (393)..(549)
<220> FEATURE:
<221> NAME/KEY: CDS
<222> LOCATION: (713)..(961)

<400> SEQUENCE: 150

```
atg cgc atc tct ggc ctc ctc gcc gct gcc aca atc gcc ctc gcg gct       48
Met Arg Ile Ser Gly Leu Leu Ala Ala Ala Thr Ile Ala Leu Ala Ala
-15                 -10                 -5              -1  1

ccc gtg ccg gag cct gtaagagccc tccctctccg ttggccacct tctcgcgtat      103
Pro Val Pro Glu Pro
            5

aagccactaa cagacgacgc ag ccc ggg atc ccc agc acc agc acc gcc caa     155
                         Pro Gly Ile Pro Ser Thr Ser Thr Ala Gln
                                     10                  15

agc gac ctc aac agc ctc cag gtc gct gcc tct ggc tcc ggt gat ggc      203
Ser Asp Leu Asn Ser Leu Gln Val Ala Ala Ser Gly Ser Gly Asp Gly
            20                  25                  30

tac tcg cgc gcc gag ttc cct cac tgg gtc tcg gtt gag ggc agc tgt      251
Tyr Ser Arg Ala Glu Phe Pro His Trp Val Ser Val Glu Gly Ser Cys
        35                  40                  45

gac tct cg  gtatgaacca gcctcccccc caagttccac cgcatgggtc              299
Asp Ser Arg
    50

atgtttccca cgttttgttt ctggccgacg caacgttgtg ctccctgacc acaaacgcta    359

acggcccttt tcttcttctg tccattcatg tag t gaa tac gtc ctg aag cgt       411
                                       Glu Tyr Val Leu Lys Arg
                                                   55

gac ggc cag gac gtc cag gcc gac tcg tcc tgc aag att act tcc ggc      459
Asp Gly Gln Asp Val Gln Ala Asp Ser Ser Cys Lys Ile Thr Ser Gly
        60                  65                  70

acc tgg gtc agt ccc tac gac gcg acc acc tgg acc aac agc tcc aag      507
Thr Trp Val Ser Pro Tyr Asp Ala Thr Thr Trp Thr Asn Ser Ser Lys
    75                  80                  85

gtc gac att gac cac ctg gtg cct ctc aag aat gcc tgg att              549
Val Asp Ile Asp His Leu Val Pro Leu Lys Asn Ala Trp Ile
90                  95                  100

gtacgtctct gccctttccc ctttgctctc ctcatctctc agcgctgtgt ctttcccccca   609

aaagctcaca acgcccaaca tccctcatcg agtggcccgg gggggggca caacatctct     669

gctgtgcgag taaacaacgt ttcgccaact aaccctctcc cag tct ggt gcc tcg      724
                                                Ser Gly Ala Ser
                                                    105

agc tgg acc aag gca cag cgt caa gac ttt gcc aac gac atc aag cgc      772
Ser Trp Thr Lys Ala Gln Arg Gln Asp Phe Ala Asn Asp Ile Lys Arg
```

```
        110                 115                 120

ccc cag ctc tac gcc gtc agc gag aac gcc aac cgc tcc aag ggc gac      820
Pro Gln Leu Tyr Ala Val Ser Glu Asn Ala Asn Arg Ser Lys Gly Asp
    125                 130                 135

cgc agc ccg gac ggc tgg aag ccc ccg ctg aag agc ttc tac tgc acc      868
Arg Ser Pro Asp Gly Trp Lys Pro Pro Leu Lys Ser Phe Tyr Cys Thr
140                 145                 150                 155

tat gcc aag tcc tgg gtc gcc gtc aag agc tac tac aag ctg acc att      916
Tyr Ala Lys Ser Trp Val Ala Val Lys Ser Tyr Tyr Lys Leu Thr Ile
                160                 165                 170

acc tcg gcc gag aag tcg gcc ctg ggc gac atg ctc gac act tgc tga      964
Thr Ser Ala Glu Lys Ser Ala Leu Gly Asp Met Leu Asp Thr Cys
            175                 180                 185


<210> SEQ ID NO 151
<211> LENGTH: 201
<212> TYPE: PRT
<213> ORGANISM: Isaria tenuipes

<400> SEQUENCE: 151

Met Arg Ile Ser Gly Leu Leu Ala Ala Ala Thr Ile Ala Leu Ala Ala
-15                 -10                 -5                  -1  1

Pro Val Pro Glu Pro Pro Gly Ile Pro Ser Thr Ser Thr Ala Gln Ser
            5                   10                  15

Asp Leu Asn Ser Leu Gln Val Ala Ala Ser Gly Ser Gly Asp Gly Tyr
        20                  25                  30

Ser Arg Ala Glu Phe Pro His Trp Val Ser Val Glu Gly Ser Cys Asp
    35                  40                  45

Ser Arg Glu Tyr Val Leu Lys Arg Asp Gly Gln Asp Val Gln Ala Asp
50                  55                  60                  65

Ser Ser Cys Lys Ile Thr Ser Gly Thr Trp Val Ser Pro Tyr Asp Ala
                70                  75                  80

Thr Thr Trp Thr Asn Ser Ser Lys Val Asp Ile Asp His Leu Val Pro
            85                  90                  95

Leu Lys Asn Ala Trp Ile Ser Gly Ala Ser Ser Trp Thr Lys Ala Gln
        100                 105                 110

Arg Gln Asp Phe Ala Asn Asp Ile Lys Arg Pro Gln Leu Tyr Ala Val
    115                 120                 125

Ser Glu Asn Ala Asn Arg Ser Lys Gly Asp Arg Ser Pro Asp Gly Trp
130                 135                 140                 145

Lys Pro Pro Leu Lys Ser Phe Tyr Cys Thr Tyr Ala Lys Ser Trp Val
                150                 155                 160

Ala Val Lys Ser Tyr Tyr Lys Leu Thr Ile Thr Ser Ala Glu Lys Ser
            165                 170                 175

Ala Leu Gly Asp Met Leu Asp Thr Cys
        180                 185


<210> SEQ ID NO 152
<211> LENGTH: 186
<212> TYPE: PRT
<213> ORGANISM: Isaria tenuipes

<400> SEQUENCE: 152

Ala Pro Val Pro Glu Pro Pro Gly Ile Pro Ser Thr Ser Thr Ala Gln
1               5                   10                  15

Ser Asp Leu Asn Ser Leu Gln Val Ala Ala Ser Gly Ser Gly Asp Gly
            20                  25                  30
```

```
Tyr Ser Arg Ala Glu Phe Pro His Trp Val Ser Val Glu Gly Ser Cys
        35                  40                  45

Asp Ser Arg Glu Tyr Val Leu Lys Arg Asp Gly Gln Asp Val Gln Ala
    50                  55                  60

Asp Ser Ser Cys Lys Ile Thr Ser Gly Thr Trp Val Ser Pro Tyr Asp
65                  70                  75                  80

Ala Thr Thr Trp Thr Asn Ser Ser Lys Val Asp Ile Asp His Leu Val
                85                  90                  95

Pro Leu Lys Asn Ala Trp Ile Ser Gly Ala Ser Ser Trp Thr Lys Ala
            100                 105                 110

Gln Arg Gln Asp Phe Ala Asn Asp Ile Lys Arg Pro Gln Leu Tyr Ala
        115                 120                 125

Val Ser Glu Asn Ala Asn Arg Ser Lys Gly Asp Arg Ser Pro Asp Gly
    130                 135                 140

Trp Lys Pro Pro Leu Lys Ser Phe Tyr Cys Thr Tyr Ala Lys Ser Trp
145                 150                 155                 160

Val Ala Val Lys Ser Tyr Tyr Lys Leu Thr Ile Thr Ser Ala Glu Lys
                165                 170                 175

Ser Ala Leu Gly Asp Met Leu Asp Thr Cys
            180                 185


<210> SEQ ID NO 153
<211> LENGTH: 779
<212> TYPE: DNA
<213> ORGANISM: Scytalidium circinatum
<220> FEATURE:
<221> NAME/KEY: CDS
<222> LOCATION: (1)..(57)
<220> FEATURE:
<221> NAME/KEY: sig_peptide
<222> LOCATION: (1)..(51)
<220> FEATURE:
<221> NAME/KEY: mat_peptide
<222> LOCATION: (52)..(776)
<220> FEATURE:
<221> NAME/KEY: CDS
<222> LOCATION: (112)..(251)
<220> FEATURE:
<221> NAME/KEY: CDS
<222> LOCATION: (316)..(472)
<220> FEATURE:
<221> NAME/KEY: CDS
<222> LOCATION: (528)..(776)

<400> SEQUENCE: 153

atg aag ttc gag ctc gct gcc ctc gtc tcc gcc gcc tct ctg gct gtt       48
Met Lys Phe Glu Leu Ala Ala Leu Val Ser Ala Ala Ser Leu Ala Val
        -15                 -10                 -5

gcc gct ccc gtatgctcgt ctcgatccaa catcctctta atagatgctg               97
Ala Ala Pro
-1  1

accaagctgt ctag ccc ggc att ccc agc gcc tcc act gcc agc tcc ctc      147
                Pro Gly Ile Pro Ser Ala Ser Thr Ala Ser Ser Leu
                        5                   10

ctt ggt gaa ctg gcc gtc gct gag cca gtg gac gac ggc agc tat gac      195
Leu Gly Glu Leu Ala Val Ala Glu Pro Val Asp Asp Gly Ser Tyr Asp
15                  20                  25                  30

cgt gac ctg ttc ccc cac tgg gag ccc atc cct ggc gag act gcc tgc      243
Arg Asp Leu Phe Pro His Trp Glu Pro Ile Pro Gly Glu Thr Ala Cys
                35                  40                  45

agt gct cg  gtaggttacg ccattatgtt ctaagccgta ctgcctcgac              291
Ser Ala Arg
```

```
cgcccactga cagattctca acag c gag tat gtt ctg cgc cgt gat ggc acc      343
                             Glu Tyr Val Leu Arg Arg Asp Gly Thr
                             50                  55

ggc gtt gag acc ggc agc gac tgc tat ccg act tcg ggc aca tgg tcc      391
Gly Val Glu Thr Gly Ser Asp Cys Tyr Pro Thr Ser Gly Thr Trp Ser
    60                  65                  70

agc ccc tac gat ggc ggc agc tgg acc gct ccc agc gac gtg gac att      439
Ser Pro Tyr Asp Gly Gly Ser Trp Thr Ala Pro Ser Asp Val Asp Ile
75                  80                  85                  90

gac cac atg gtt cct ctg aag aac gcc tgg atc gtatgtcttg cattcgaacc    492
Asp His Met Val Pro Leu Lys Asn Ala Trp Ile
                95                  100

cacatgaaag gcaggcccat gctaacttta cccag tct ggt gcc tcc gag tgg       545
                                       Ser Gly Ala Ser Glu Trp
                                                   105

act acc gct gag cgc gag gcc ttt gcc aac gac atc gat gga ccc cag      593
Thr Thr Ala Glu Arg Glu Ala Phe Ala Asn Asp Ile Asp Gly Pro Gln
        110                 115                 120

cta tgg gcc gtc acc gac gag gtc aac cag agc aag agt gac cag agc      641
Leu Trp Ala Val Thr Asp Glu Val Asn Gln Ser Lys Ser Asp Gln Ser
    125                 130                 135

ccc gac gag tgg aag ccc cct ctg tcc agc ttc tac tgc acc tat gcc      689
Pro Asp Glu Trp Lys Pro Pro Leu Ser Ser Phe Tyr Cys Thr Tyr Ala
140                 145                 150                 155

tgc gcc tgg atc cag gtc aag agc acc tac agc ctg tcc atc agc tct      737
Cys Ala Trp Ile Gln Val Lys Ser Thr Tyr Ser Leu Ser Ile Ser Ser
                160                 165                 170

gcc gag cag gct gcc ttg gaa gat atg ctc ggt agc tgc tag              779
Ala Glu Gln Ala Ala Leu Glu Asp Met Leu Gly Ser Cys
            175                 180
```

<210> SEQ ID NO 154
<211> LENGTH: 201
<212> TYPE: PRT
<213> ORGANISM: Scytalidium circinatum

<400> SEQUENCE: 154

```
Met Lys Phe Glu Leu Ala Ala Leu Val Ser Ala Ala Ser Leu Ala Val
        -15                 -10                 -5

Ala Ala Pro Pro Gly Ile Pro Ser Ala Ser Thr Ala Ser Ser Leu Leu
-1  1               5                   10                  15

Gly Glu Leu Ala Val Ala Glu Pro Val Asp Asp Gly Ser Tyr Asp Arg
                20                  25                  30

Asp Leu Phe Pro His Trp Glu Pro Ile Pro Gly Glu Thr Ala Cys Ser
            35                  40                  45

Ala Arg Glu Tyr Val Leu Arg Arg Asp Gly Thr Gly Val Glu Thr Gly
        50                  55                  60

Ser Asp Cys Tyr Pro Thr Ser Gly Thr Trp Ser Ser Pro Tyr Asp Gly
    65                  70                  75

Gly Ser Trp Thr Ala Pro Ser Asp Val Asp Ile Asp His Met Val Pro
80                  85                  90                  95

Leu Lys Asn Ala Trp Ile Ser Gly Ala Ser Glu Trp Thr Thr Ala Glu
                100                 105                 110

Arg Glu Ala Phe Ala Asn Asp Ile Asp Gly Pro Gln Leu Trp Ala Val
            115                 120                 125

Thr Asp Glu Val Asn Gln Ser Lys Ser Asp Gln Ser Pro Asp Glu Trp
        130                 135                 140

Lys Pro Pro Leu Ser Ser Phe Tyr Cys Thr Tyr Ala Cys Ala Trp Ile
```

```
    145                 150                 155

Gln Val Lys Ser Thr Tyr Ser Leu Ser Ile Ser Ser Ala Glu Gln Ala
160                 165                 170                 175

Ala Leu Glu Asp Met Leu Gly Ser Cys
                180


<210> SEQ ID NO 155
<211> LENGTH: 184
<212> TYPE: PRT
<213> ORGANISM: Scytalidium circinatum

<400> SEQUENCE: 155

Ala Pro Pro Gly Ile Pro Ser Ala Ser Thr Ala Ser Ser Leu Leu Gly
1               5                   10                  15

Glu Leu Ala Val Ala Glu Pro Val Asp Asp Gly Ser Tyr Asp Arg Asp
            20                  25                  30

Leu Phe Pro His Trp Glu Pro Ile Pro Gly Glu Thr Ala Cys Ser Ala
        35                  40                  45

Arg Glu Tyr Val Leu Arg Arg Asp Gly Thr Gly Val Glu Thr Gly Ser
    50                  55                  60

Asp Cys Tyr Pro Thr Ser Gly Thr Trp Ser Ser Pro Tyr Asp Gly Gly
65                  70                  75                  80

Ser Trp Thr Ala Pro Ser Asp Val Asp Ile Asp His Met Val Pro Leu
                85                  90                  95

Lys Asn Ala Trp Ile Ser Gly Ala Ser Glu Trp Thr Thr Ala Glu Arg
            100                 105                 110

Glu Ala Phe Ala Asn Asp Ile Asp Gly Pro Gln Leu Trp Ala Val Thr
        115                 120                 125

Asp Glu Val Asn Gln Ser Lys Ser Asp Gln Ser Pro Asp Glu Trp Lys
    130                 135                 140

Pro Pro Leu Ser Ser Phe Tyr Cys Thr Tyr Ala Cys Ala Trp Ile Gln
145                 150                 155                 160

Val Lys Ser Thr Tyr Ser Leu Ser Ile Ser Ser Ala Glu Gln Ala Ala
                165                 170                 175

Leu Glu Asp Met Leu Gly Ser Cys
            180


<210> SEQ ID NO 156
<211> LENGTH: 805
<212> TYPE: DNA
<213> ORGANISM: Metarhizium lepidiotae
<220> FEATURE:
<221> NAME/KEY: CDS
<222> LOCATION: (1)..(75)
<220> FEATURE:
<221> NAME/KEY: sig_peptide
<222> LOCATION: (1)..(57)
<220> FEATURE:
<221> NAME/KEY: mat_peptide
<222> LOCATION: (58)..(802)
<220> FEATURE:
<221> NAME/KEY: CDS
<222> LOCATION: (133)..(266)
<220> FEATURE:
<221> NAME/KEY: CDS
<222> LOCATION: (338)..(494)
<220> FEATURE:
<221> NAME/KEY: CDS
<222> LOCATION: (554)..(802)

<400> SEQUENCE: 156

atg aag ttc tcc tcg gca tca ttt ctc gtc gtg tct gcc gct gcg gtt       48
```

```
Met Lys Phe Ser Ser Ala Ser Phe Leu Val Val Ser Ala Ala Ala Val
                -15                 -10                 -5

gtc ctt ggt gtg cct gtg cct gcg ccc gtaagccctc ccatcttgtg           95
Val Leu Gly Val Pro Val Pro Ala Pro
        -1  1               5

taacaagggg aaacaaaaaa atgctgactc tttccag ccg ggt att cca act gct     150
                                         Pro Gly Ile Pro Thr Ala
                                                     10

tcg acc gcc agg act ctt ctt gct ggc ctc aag gtt gct acg ccg ttg      198
Ser Thr Ala Arg Thr Leu Leu Ala Gly Leu Lys Val Ala Thr Pro Leu
        15                  20                  25

agc ggt gat ggc tac tct cgc acc ctg ttc cct acg tgg gag acc atc      246
Ser Gly Asp Gly Tyr Ser Arg Thr Leu Phe Pro Thr Trp Glu Thr Ile
    30                  35                  40

gag gga act tgc aac gct cg  gtgggcattt ctttttcttc tttttcttct         296
Glu Gly Thr Cys Asn Ala Arg
45                  50

tctcttctct gtcagagaca aggtgctaaa catgaatcta g c gag ttt gta ctc      350
                                                Glu Phe Val Leu
                                                            55

aag cga gat gga aca gac gtc cag acc aac acg gca tgt gtc gcc gag      398
Lys Arg Asp Gly Thr Asp Val Gln Thr Asn Thr Ala Cys Val Ala Glu
                60                  65                  70

tct ggc aac tgg gtt tct ccg tat gac ggc gtc tca ttc acc gcc gcc      446
Ser Gly Asn Trp Val Ser Pro Tyr Asp Gly Val Ser Phe Thr Ala Ala
            75                  80                  85

tcg gat ctc gac att gac cac atg gtt cca ctc aag aat gcc tgg att      494
Ser Asp Leu Asp Ile Asp His Met Val Pro Leu Lys Asn Ala Trp Ile
        90                  95                  100

gtaagaccca agaccgcatt gataccaagg agcctccctg tctaactctc gtctcccag     553

tcc ggc gcc tcg caa tgg acc acg gac aag cgc aaa gat ctc gcc aac      601
Ser Gly Ala Ser Gln Trp Thr Thr Asp Lys Arg Lys Asp Leu Ala Asn
    105                 110                 115

gac atc acc cgt cct cag ctc tgg gcc gtc tct gcc cat gcc aac cgt      649
Asp Ile Thr Arg Pro Gln Leu Trp Ala Val Ser Ala His Ala Asn Arg
120                 125                 130                 135

tcc aag ggc gac agc agc ccc gac gag tgg aag cct ccc ctg cag acc      697
Ser Lys Gly Asp Ser Ser Pro Asp Glu Trp Lys Pro Pro Leu Gln Thr
                140                 145                 150

ttc tgg tgc acc tac tcc aag agc tgg atc cag gtc aag agc cat tac      745
Phe Trp Cys Thr Tyr Ser Lys Ser Trp Ile Gln Val Lys Ser His Tyr
            155                 160                 165

tca ctg acc att acc gat gct gag aag ggc gcg ctg tca ggc atg cta      793
Ser Leu Thr Ile Thr Asp Ala Glu Lys Gly Ala Leu Ser Gly Met Leu
        170                 175                 180

gac tct tgc taa                                                      805
Asp Ser Cys
    185


<210> SEQ ID NO 157
<211> LENGTH: 205
<212> TYPE: PRT
<213> ORGANISM: Metarhizium lepidiotae

<400> SEQUENCE: 157

Met Lys Phe Ser Ser Ala Ser Phe Leu Val Val Ser Ala Ala Ala Val
                -15                 -10                 -5

Val Leu Gly Val Pro Val Pro Ala Pro Pro Gly Ile Pro Thr Ala Ser
        -1  1               5                   10
```

```
Thr Ala Arg Thr Leu Leu Ala Gly Leu Lys Val Ala Thr Pro Leu Ser
    15                  20                  25

Gly Asp Gly Tyr Ser Arg Thr Leu Phe Pro Thr Trp Glu Thr Ile Glu
30                  35                  40                  45

Gly Thr Cys Asn Ala Arg Glu Phe Val Leu Lys Arg Asp Gly Thr Asp
                50                  55                  60

Val Gln Thr Asn Thr Ala Cys Val Ala Glu Ser Gly Asn Trp Val Ser
            65                  70                  75

Pro Tyr Asp Gly Val Ser Phe Thr Ala Ala Ser Asp Leu Asp Ile Asp
        80                  85                  90

His Met Val Pro Leu Lys Asn Ala Trp Ile Ser Gly Ala Ser Gln Trp
    95                  100                 105

Thr Thr Asp Lys Arg Lys Asp Leu Ala Asn Asp Ile Thr Arg Pro Gln
110                 115                 120                 125

Leu Trp Ala Val Ser Ala His Ala Asn Arg Ser Lys Gly Asp Ser Ser
                130                 135                 140

Pro Asp Glu Trp Lys Pro Pro Leu Gln Thr Phe Trp Cys Thr Tyr Ser
            145                 150                 155

Lys Ser Trp Ile Gln Val Lys Ser His Tyr Ser Leu Thr Ile Thr Asp
        160                 165                 170

Ala Glu Lys Gly Ala Leu Ser Gly Met Leu Asp Ser Cys
    175                 180                 185


<210> SEQ ID NO 158
<211> LENGTH: 186
<212> TYPE: PRT
<213> ORGANISM: Metarhizium lepidiotae

<400> SEQUENCE: 158

Val Pro Val Pro Ala Pro Pro Gly Ile Pro Thr Ala Ser Thr Ala Arg
1               5                   10                  15

Thr Leu Leu Ala Gly Leu Lys Val Ala Thr Pro Leu Ser Gly Asp Gly
            20                  25                  30

Tyr Ser Arg Thr Leu Phe Pro Thr Trp Glu Thr Ile Glu Gly Thr Cys
        35                  40                  45

Asn Ala Arg Glu Phe Val Leu Lys Arg Asp Gly Thr Asp Val Gln Thr
    50                  55                  60

Asn Thr Ala Cys Val Ala Glu Ser Gly Asn Trp Val Ser Pro Tyr Asp
65                  70                  75                  80

Gly Val Ser Phe Thr Ala Ala Ser Asp Leu Asp Ile Asp His Met Val
                85                  90                  95

Pro Leu Lys Asn Ala Trp Ile Ser Gly Ala Ser Gln Trp Thr Thr Asp
            100                 105                 110

Lys Arg Lys Asp Leu Ala Asn Asp Ile Thr Arg Pro Gln Leu Trp Ala
        115                 120                 125

Val Ser Ala His Ala Asn Arg Ser Lys Gly Asp Ser Ser Pro Asp Glu
    130                 135                 140

Trp Lys Pro Pro Leu Gln Thr Phe Trp Cys Thr Tyr Ser Lys Ser Trp
145                 150                 155                 160

Ile Gln Val Lys Ser His Tyr Ser Leu Thr Ile Thr Asp Ala Glu Lys
                165                 170                 175

Gly Ala Leu Ser Gly Met Leu Asp Ser Cys
            180                 185


<210> SEQ ID NO 159
```

```
<211> LENGTH: 1759
<212> TYPE: DNA
<213> ORGANISM: Thermobispora bispora
<220> FEATURE:
<221> NAME/KEY: CDS
<222> LOCATION: (501)..(1256)
<220> FEATURE:
<221> NAME/KEY: sig_peptide
<222> LOCATION: (501)..(578)
<220> FEATURE:
<221> NAME/KEY: mat_peptide
<222> LOCATION: (579)..(1256)

<400> SEQUENCE: 159

ccgccgtacg ccctgggctg tgacaaggat ccggagcggg tggcctgcga ctacccgccg      60

tacctgctgg acaagatcgt cagcgcgcgg ttcgcggaga acggcggcaa ggcctacgag     120

ctcatcaaga acttcacctg gaccaacgag gaccagagcg cggtcgcgta cgacatggcg     180

gtgaacaaca tgtccgccga cgacgcggcg cggaagtgga tcgaggcgaa caaggtcgtc     240

tggcagtcct ggctcccgtc ctgagcggtg ggcccgtgga accggcccgg ccggagcctc     300

gccggaggcc atgagcgcgt tgcgctgccc gctgtgcccg cgtacccgct gtgcccgccc     360

acccggcgtc ccgggcttcc ggcccggtga tctcgacgcg cccgggcggg gccacaccct     420

gacgaccggg gtgatttctc ccgcttattt gcctttgcta tagataccta ggtcaagatc     480

accaagacct agggggccca ttg ggc ggg aga cga tcc ctg atc gcg agc gcg     533
                      Leu Gly Gly Arg Arg Ser Leu Ile Ala Ser Ala
                          -25                 -20

gcc ctt gcg ctg gcc gtg ctg acc gga tgc gga acg gcg gac ggc ctc       581
Ala Leu Ala Leu Ala Val Leu Thr Gly Cys Gly Thr Ala Asp Gly Leu
-15                 -10                 -5                  -1  1

gac atc gcc gac ggc cgc ccg gcg ggc ggg aag gcc gcc gag gcg gcg       629
Asp Ile Ala Asp Gly Arg Pro Ala Gly Gly Lys Ala Ala Glu Ala Ala
            5                   10                  15

acc ggc acc agc ccg ctg gcg aat ccg gac ggc acg cgt ccc ggg ctg       677
Thr Gly Thr Ser Pro Leu Ala Asn Pro Asp Gly Thr Arg Pro Gly Leu
        20                  25                  30

gcc gcg atc acc tcg gcc gat gag cgg gcc gag gca cgg gct ctg atc       725
Ala Ala Ile Thr Ser Ala Asp Glu Arg Ala Glu Ala Arg Ala Leu Ile
    35                  40                  45

gag cgg ctc cgg acc aag ggg cga gga ccg aag acc ggc tac gag cgg       773
Glu Arg Leu Arg Thr Lys Gly Arg Gly Pro Lys Thr Gly Tyr Glu Arg
50                  55                  60                  65

gag aag ttc ggg tac gcc tgg gcc gac tcc gtg gac ggc atc ccg ttc       821
Glu Lys Phe Gly Tyr Ala Trp Ala Asp Ser Val Asp Gly Ile Pro Phe
                70                  75                  80

ggg cgc aac gga tgc gac acc cgc aac gac gtg ctg aag cgg gac ggc       869
Gly Arg Asn Gly Cys Asp Thr Arg Asn Asp Val Leu Lys Arg Asp Gly
            85                  90                  95

cag cgg ctg cag ttc cgg agc ggg tcg gac tgc gtg gtg atc tcg atg       917
Gln Arg Leu Gln Phe Arg Ser Gly Ser Asp Cys Val Val Ile Ser Met
        100                 105                 110

acc ctg ttc gac ccg tac acc ggc aag acc atc gag tgg acc aag cag       965
Thr Leu Phe Asp Pro Tyr Thr Gly Lys Thr Ile Glu Trp Thr Lys Gln
    115                 120                 125

aac gcg gcc gag gtg cag atc gac cac gtg gtg ccg ctc tcc tac tcc      1013
Asn Ala Ala Glu Val Gln Ile Asp His Val Val Pro Leu Ser Tyr Ser
130                 135                 140                 145

tgg cag atg ggc gcg tcc cgg tgg agt gac gag aag cgc cgg cag ctc      1061
Trp Gln Met Gly Ala Ser Arg Trp Ser Asp Glu Lys Arg Arg Gln Leu
                150                 155                 160
```

```
gcc aac gac ccg ctc aac ctc atg ccg gtc gac ggc gcc acg aac tcg     1109
Ala Asn Asp Pro Leu Asn Leu Met Pro Val Asp Gly Ala Thr Asn Ser
            165                 170                 175

cgg aag ggc gac tcc ggc ccg gcg tcc tgg ctg ccg ccg cgc cgg gag     1157
Arg Lys Gly Asp Ser Gly Pro Ala Ser Trp Leu Pro Pro Arg Arg Glu
        180                 185                 190

atc cgc tgc gcg tac gtg gtc cgg ttc gcc cag gtg gcg ctc aag tac     1205
Ile Arg Cys Ala Tyr Val Val Arg Phe Ala Gln Val Ala Leu Lys Tyr
    195                 200                 205

gac ctg ccc gtc acc acc gcg gac aag gag acc atg ctg cag cag tgc     1253
Asp Leu Pro Val Thr Thr Ala Asp Lys Glu Thr Met Leu Gln Gln Cys
210                 215                 220                 225

tcc tgagcgcggc cgccgcgcgg ccggacaggg gcgccgccgg ggaccggggg          1306
Ser

cgtcgccggg acgggaggca gggccgctcg gccgtgggcc ggtgacgtgc gcgcgccggg   1366

gccggcgtcg gcgggtgccg tcgccgcgcc gcgccccgcg ccggccgcag cgccccgcgc   1426

cggccgcacg gtggccgggc cgcgccccgg tcggccagtg gccggaactg cgctccccgg   1486

tcagccggtg gccgaggggc tccgctcccg gtcagccggt ggcgcggccg aggctcccgg   1546

ccggcctgcc gcggagcgac gcgtcgagca cctcggcggt gtgcgcgacc ctgagcggcc   1606

ccttgccggc ccgccggacc gcggcggcga tctgcagggt gcaccccggg ttcgcggaga   1666

cgagcaggtc ggcaccggtg gcgagcacgt gcccggcctt ccgggcgccg agctcccggg   1726

ccgcctccgg ctggaacagg ttgtaggtgc cgg                                1759


<210> SEQ ID NO 160
<211> LENGTH: 252
<212> TYPE: PRT
<213> ORGANISM: Thermobispora bispora

<400> SEQUENCE: 160

Leu Gly Gly Arg Arg Ser Leu Ile Ala Ser Ala Ala Leu Ala Leu Ala
    -25                 -20                 -15

Val Leu Thr Gly Cys Gly Thr Ala Asp Gly Leu Asp Ile Ala Asp Gly
-10                 -5              -1  1               5

Arg Pro Ala Gly Gly Lys Ala Ala Glu Ala Ala Thr Gly Thr Ser Pro
            10                  15                  20

Leu Ala Asn Pro Asp Gly Thr Arg Pro Gly Leu Ala Ala Ile Thr Ser
        25                  30                  35

Ala Asp Glu Arg Ala Glu Ala Arg Ala Leu Ile Glu Arg Leu Arg Thr
    40                  45                  50

Lys Gly Arg Gly Pro Lys Thr Gly Tyr Glu Arg Glu Lys Phe Gly Tyr
55                  60                  65                  70

Ala Trp Ala Asp Ser Val Asp Gly Ile Pro Phe Gly Arg Asn Gly Cys
                75                  80                  85

Asp Thr Arg Asn Asp Val Leu Lys Arg Asp Gly Gln Arg Leu Gln Phe
            90                  95                  100

Arg Ser Gly Ser Asp Cys Val Val Ile Ser Met Thr Leu Phe Asp Pro
        105                 110                 115

Tyr Thr Gly Lys Thr Ile Glu Trp Thr Lys Gln Asn Ala Ala Glu Val
    120                 125                 130

Gln Ile Asp His Val Val Pro Leu Ser Tyr Ser Trp Gln Met Gly Ala
135                 140                 145                 150

Ser Arg Trp Ser Asp Glu Lys Arg Arg Gln Leu Ala Asn Asp Pro Leu
                155                 160                 165
```

Asn Leu Met Pro Val Asp Gly Ala Thr Asn Ser Arg Lys Gly Asp Ser
170 175 180

Gly Pro Ala Ser Trp Leu Pro Pro Arg Arg Glu Ile Arg Cys Ala Tyr
185 190 195

Val Val Arg Phe Ala Gln Val Ala Leu Lys Tyr Asp Leu Pro Val Thr
200 205 210

Thr Ala Asp Lys Glu Thr Met Leu Gln Gln Cys Ser
215 220 225

<210> SEQ ID NO 161
<211> LENGTH: 226
<212> TYPE: PRT
<213> ORGANISM: Thermobispora bispora

<400> SEQUENCE: 161

Leu Asp Ile Ala Asp Gly Arg Pro Ala Gly Gly Lys Ala Ala Glu Ala
1 5 10 15

Ala Thr Gly Thr Ser Pro Leu Ala Asn Pro Asp Gly Thr Arg Pro Gly
20 25 30

Leu Ala Ala Ile Thr Ser Ala Asp Glu Arg Ala Glu Ala Arg Ala Leu
35 40 45

Ile Glu Arg Leu Arg Thr Lys Gly Arg Gly Pro Lys Thr Gly Tyr Glu
50 55 60

Arg Glu Lys Phe Gly Tyr Ala Trp Ala Asp Ser Val Asp Gly Ile Pro
65 70 75 80

Phe Gly Arg Asn Gly Cys Asp Thr Arg Asn Asp Val Leu Lys Arg Asp
85 90 95

Gly Gln Arg Leu Gln Phe Arg Ser Gly Ser Asp Cys Val Val Ile Ser
100 105 110

Met Thr Leu Phe Asp Pro Tyr Thr Gly Lys Thr Ile Glu Trp Thr Lys
115 120 125

Gln Asn Ala Ala Glu Val Gln Ile Asp His Val Val Pro Leu Ser Tyr
130 135 140

Ser Trp Gln Met Gly Ala Ser Arg Trp Ser Asp Glu Lys Arg Arg Gln
145 150 155 160

Leu Ala Asn Asp Pro Leu Asn Leu Met Pro Val Asp Gly Ala Thr Asn
165 170 175

Ser Arg Lys Gly Asp Ser Gly Pro Ala Ser Trp Leu Pro Pro Arg Arg
180 185 190

Glu Ile Arg Cys Ala Tyr Val Val Arg Phe Ala Gln Val Ala Leu Lys
195 200 205

Tyr Asp Leu Pro Val Thr Thr Ala Asp Lys Glu Thr Met Leu Gln Gln
210 215 220

Cys Ser
225

<210> SEQ ID NO 162
<211> LENGTH: 925
<212> TYPE: DNA
<213> ORGANISM: Sporormia fimetaria
<220> FEATURE:
<221> NAME/KEY: CDS
<222> LOCATION: (1)..(200)
<220> FEATURE:
<221> NAME/KEY: sig_peptide
<222> LOCATION: (1)..(48)
<220> FEATURE:
<221> NAME/KEY: mat_peptide
<222> LOCATION: (49)..(922)

<220> FEATURE:
<221> NAME/KEY: CDS
<222> LOCATION: (353)..(524)
<220> FEATURE:
<221> NAME/KEY: CDS
<222> LOCATION: (616)..(754)
<220> FEATURE:
<221> NAME/KEY: CDS
<222> LOCATION: (813)..(922)

<400> SEQUENCE: 162 atg aaa tac ctc ctc gtc acc ctc gcc tcc acg ctc ctc gcc act gcc 48
Met Lys Tyr Leu Leu Val Thr Leu Ala Ser Thr Leu Leu Ala Thr Ala
-15 -10 -5 -1 ctc cca gca ccc gtt ctg gag aaa agg act ccg cca aat att ccc tca 96
Leu Pro Ala Pro Val Leu Glu Lys Arg Thr Pro Pro Asn Ile Pro Ser
1 5 10 15 acg tcc act gca cag agt ctt ctt tct gga tta acc gtt gcc cca caa 144
Thr Ser Thr Ala Gln Ser Leu Leu Ser Gly Leu Thr Val Ala Pro Gln
20 25 30 gga tcg cag acc ggg tat tcg cgt gat ttg ttt cca cac tgg atc aca 192
Gly Ser Gln Thr Gly Tyr Ser Arg Asp Leu Phe Pro His Trp Ile Thr
35 40 45 gtg agc gg gtatgtacga aacgctgatc atatgtgtac atcttgcaca 240
Val Ser Gly
50 ttaccttaaa acattctgtg tcaattttcc tatttgaaag atccatccat tgtccccttc 300 tgtctttttt tggcgatcat tgctcgatgt gccaactgac tccattccgc ag a aca 356
Thr tgc aac act cgc gaa acc gtc ctc aag cgc gac ggc tca aac gta gtc 404
Cys Asn Thr Arg Glu Thr Val Leu Lys Arg Asp Gly Ser Asn Val Val
55 60 65 aca gac tct gct tgc gca tca gta tcc ggc tcg tgg tac tca acg tac 452
Thr Asp Ser Ala Cys Ala Ser Val Ser Gly Ser Trp Tyr Ser Thr Tyr
70 75 80 gac ggt gcg acg tgg acg gcg gct agc gac gtc gat att gat cat gtt 500
Asp Gly Ala Thr Trp Thr Ala Ala Ser Asp Val Asp Ile Asp His Val
85 90 95 100 gtg ccc ctt tcc aat gct tgg aag gtgtgtaaat cctctacttc cccgtttcca 554
Val Pro Leu Ser Asn Ala Trp Lys
105 ttgaaatgaa cccactactt ggtagaaggg aaagagattt gtaactgaca ctgtttacaa 614 g tcc ggc gca gca tcc tgg acc act gcc cgc cgc cag gcc ttc gcc aac 663
Ser Gly Ala Ala Ser Trp Thr Thr Ala Arg Arg Gln Ala Phe Ala Asn
110 115 120 gac ctg act aac ccg caa ctc att gcc gtg acc gac aat gtt aat caa 711
Asp Leu Thr Asn Pro Gln Leu Ile Ala Val Thr Asp Asn Val Asn Gln
125 130 135 140 gcg aag ggt gac cag ggg cca gag tcg tgg aaa ccg cca cta a 754
Ala Lys Gly Asp Gln Gly Pro Glu Ser Trp Lys Pro Pro Leu
145 150 gtgagtcttt tcaccaatgg tatgaaactg aaaatgcatg tggctaatat gtgtttag 812 ct tcg tac tac tgc act tac gcc aag atg tgg gtc aag gtc aag agt 859
Thr Ser Tyr Tyr Cys Thr Tyr Ala Lys Met Trp Val Lys Val Lys Ser
155 160 165 170 gtg tac tct ttg act gtc act tcg gca gag aag agc gcg ctg tcg agt 907
Val Tyr Ser Leu Thr Val Thr Ser Ala Glu Lys Ser Ala Leu Ser Ser
175 180 185 atg ttg ggg act tgc taa 925
Met Leu Gly Thr Cys

190

<210> SEQ ID NO 163
<211> LENGTH: 207
<212> TYPE: PRT
<213> ORGANISM: Sporormia fimetaria

<400> SEQUENCE: 163

Met Lys Tyr Leu Leu Val Thr Leu Ala Ser Thr Leu Leu Ala Thr Ala
    -15                 -10                 -5                  -1

Leu Pro Ala Pro Val Leu Glu Lys Arg Thr Pro Pro Asn Ile Pro Ser
1               5                   10                  15

Thr Ser Thr Ala Gln Ser Leu Leu Ser Gly Leu Thr Val Ala Pro Gln
            20                  25                  30

Gly Ser Gln Thr Gly Tyr Ser Arg Asp Leu Phe Pro His Trp Ile Thr
        35                  40                  45

Val Ser Gly Thr Cys Asn Thr Arg Glu Thr Val Leu Lys Arg Asp Gly
    50                  55                  60

Ser Asn Val Val Thr Asp Ser Ala Cys Ala Ser Val Ser Gly Ser Trp
65                  70                  75                  80

Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ala Phe Ala Asn Asp Leu Thr Asn
        115                 120                 125

Pro Gln Leu Ile Ala Val Thr Asp Asn Val Asn Gln Ala Lys Gly Asp
    130                 135                 140

Gln Gly Pro Glu Ser Trp Lys Pro Pro Leu Thr Ser Tyr Tyr Cys Thr
145                 150                 155                 160

Tyr Ala Lys Met Trp Val Lys Val Lys Ser Val Tyr Ser Leu Thr Val
                165                 170                 175

Thr Ser Ala Glu Lys Ser Ala Leu Ser Ser Met Leu Gly Thr Cys
            180                 185                 190

<210> SEQ ID NO 164
<211> LENGTH: 191
<212> TYPE: PRT
<213> ORGANISM: Sporormia fimetaria

<400> SEQUENCE: 164

Leu Pro Ala Pro Val Leu Glu Lys Arg Thr Pro Pro Asn Ile Pro Ser
1               5                   10                  15

Thr Ser Thr Ala Gln Ser Leu Leu Ser Gly Leu Thr Val Ala Pro Gln
            20                  25                  30

Gly Ser Gln Thr Gly Tyr Ser Arg Asp Leu Phe Pro His Trp Ile Thr
        35                  40                  45

Val Ser Gly Thr Cys Asn Thr Arg Glu Thr Val Leu Lys Arg Asp Gly
    50                  55                  60

Ser Asn Val Val Thr Asp Ser Ala Cys Ala Ser Val Ser Gly Ser Trp
65                  70                  75                  80

Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ala Phe Ala Asn Asp Leu Thr Asn

```
        115                 120                 125

Pro Gln Leu Ile Ala Val Thr Asp Asn Val Asn Gln Ala Lys Gly Asp
    130                 135                 140

Gln Gly Pro Glu Ser Trp Lys Pro Pro Leu Thr Ser Tyr Tyr Cys Thr
145                 150                 155                 160

Tyr Ala Lys Met Trp Val Lys Val Lys Ser Val Tyr Ser Leu Thr Val
                165                 170                 175

Thr Ser Ala Glu Lys Ser Ala Leu Ser Ser Met Leu Gly Thr Cys
            180                 185                 190


<210> SEQ ID NO 165
<211> LENGTH: 814
<212> TYPE: DNA
<213> ORGANISM: Pycnidiophora cf.dispera
<220> FEATURE:
<221> NAME/KEY: CDS
<222> LOCATION: (1)..(206)
<220> FEATURE:
<221> NAME/KEY: sig_peptide
<222> LOCATION: (1)..(48)
<220> FEATURE:
<221> NAME/KEY: mat_peptide
<222> LOCATION: (49)..(811)
<220> FEATURE:
<221> NAME/KEY: CDS
<222> LOCATION: (264)..(435)
<220> FEATURE:
<221> NAME/KEY: CDS
<222> LOCATION: (507)..(645)
<220> FEATURE:
<221> NAME/KEY: CDS
<222> LOCATION: (702)..(811)

<400> SEQUENCE: 165

atg aag tcc ctc ctc ctc acc ctc gcc gcc gct acc ctg ggc ctt gcc       48
Met Lys Ser Leu Leu Leu Thr Leu Ala Ala Ala Thr Leu Gly Leu Ala
    -15                 -10                 -5                  -1

ctc ccg gct cct gca ccc gtc ctg gtg gct cgc gag ccc cca aac att       96
Leu Pro Ala Pro Ala Pro Val Leu Val Ala Arg Glu Pro Pro Asn Ile
1               5                   10                  15

cct tcc acc tcg tcg gcc cag agc atg ctc tct ggt ctc acc gtc aag      144
Pro Ser Thr Ser Ser Ala Gln Ser Met Leu Ser Gly Leu Thr Val Lys
            20                  25                  30

gcc cag gga cct cag gat ggg tac tcg agg gat ctg ttc ccg cac tgg      192
Ala Gln Gly Pro Gln Asp Gly Tyr Ser Arg Asp Leu Phe Pro His Trp
        35                  40                  45

atc acc atc agc gg  gtagccactc cagaatctat ccaagaggaa caatgagctg      246
Ile Thr Ile Ser Gly
    50

atcatcctcc aatccag g acc tgc aac acc cgt gag acc gtc ctg aag cgt      297
                     Thr Cys Asn Thr Arg Glu Thr Val Leu Lys Arg
                         55                  60

gat ggc aca aac gtc gtc acc aac tcg gcc tgc gcc tcc acc tcg ggc      345
Asp Gly Thr Asn Val Val Thr Asn Ser Ala Cys Ala Ser Thr Ser Gly
65                  70                  75                  80

tcc tgg tac tcg ccc tat gac ggt gca acc tgg act gcc gcc agc gat      393
Ser Trp Tyr Ser Pro Tyr Asp Gly Ala Thr Trp Thr Ala Ala Ser Asp
                85                  90                  95

gtc gac atc gat cac atc gtc ccg ctg tcc aat gct tgg aag              435
Val Asp Ile Asp His Ile Val Pro Leu Ser Asn Ala Trp Lys
            100                 105                 110

gtgcgcattc gcacccgaag ctccccagtg cactgtcaaa gtgctcatca tgctgattcc    495

cttctttcta g tcc ggc gct gcg agc tgg acc aca tct cgc cgc cag cag     545
```

```
            Ser Gly Ala Ala Ser Trp Thr Thr Ser Arg Arg Gln Gln
                            115                 120

ttc gcc aac gac ctg acc aac ccc cag ctc att gct gtg acc gac agc      593
Phe Ala Asn Asp Leu Thr Asn Pro Gln Leu Ile Ala Val Thr Asp Ser
    125                 130                 135

gtt aac cag gcc aag ggt gac aag ggc cct gag gac tgg aag ccg tcc      641
Val Asn Gln Ala Lys Gly Asp Lys Gly Pro Glu Asp Trp Lys Pro Ser
140                 145                 150                 155

cga a gtaggtttcg gatgcaacgt ttccccttc gaactagaga agctgacagt         695
Arg

gtccag ct  tcg tac cac tgc act tat gcc aag atg tgg atc aag gtc       742
       Thr Ser Tyr His Cys Thr Tyr Ala Lys Met Trp Ile Lys Val
                   160                 165                 170

aag agc gtg tat tcc ctg acg gtg act tcg gct gag aag agc gct ttg      790
Lys Ser Val Tyr Ser Leu Thr Val Thr Ser Ala Glu Lys Ser Ala Leu
                175                 180                 185

acg acc atg ctc aat acg tgc tga                                      814
Thr Thr Met Leu Asn Thr Cys
            190


<210> SEQ ID NO 166
<211> LENGTH: 209
<212> TYPE: PRT
<213> ORGANISM: Pycnidiophora cf.dispera

<400> SEQUENCE: 166

Met Lys Ser Leu Leu Leu Thr Leu Ala Ala Ala Thr Leu Gly Leu Ala
    -15                 -10                 -5                  -1

Leu Pro Ala Pro Ala Pro Val Leu Val Ala Arg Glu Pro Pro Asn Ile
1               5                   10                  15

Pro Ser Thr Ser Ser Ala Gln Ser Met Leu Ser Gly Leu Thr Val Lys
            20                  25                  30

Ala Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Thr Asn Val Val Thr Asn Ser Ala Cys Ala Ser Thr Ser Gly
65                  70                  75                  80

Ser Trp Tyr Ser Pro Tyr Asp Gly Ala Thr Trp Thr Ala Ala Ser Asp
                85                  90                  95

Val Asp Ile Asp His Ile Val Pro Leu Ser Asn Ala Trp Lys Ser Gly
            100                 105                 110

Ala Ala Ser Trp Thr Thr Ser Arg Arg Gln Gln Phe Ala Asn Asp Leu
        115                 120                 125

Thr Asn Pro Gln Leu Ile Ala Val Thr Asp Ser Val Asn Gln Ala Lys
    130                 135                 140

Gly Asp Lys Gly Pro Glu Asp Trp Lys Pro Ser Arg Thr Ser Tyr His
145                 150                 155                 160

Cys Thr Tyr Ala Lys Met Trp Ile Lys Val Lys Ser Val Tyr Ser Leu
                165                 170                 175

Thr Val Thr Ser Ala Glu Lys Ser Ala Leu Thr Thr Met Leu Asn Thr
            180                 185                 190

Cys


<210> SEQ ID NO 167
<211> LENGTH: 193
<212> TYPE: PRT
```

<213> ORGANISM: Pycnidiophora cf.dispera

<400> SEQUENCE: 167

```
Leu Pro Ala Pro Ala Pro Val Leu Val Ala Arg Glu Pro Pro Asn Ile
1               5                   10                  15

Pro Ser Thr Ser Ser Ala Gln Ser Met Leu Ser Gly Leu Thr Val Lys
            20                  25                  30

Ala Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Thr Asn Val Val Thr Asn Ser Ala Cys Ala Ser Thr Ser Gly
65                  70                  75                  80

Ser Trp Tyr Ser Pro Tyr Asp Gly Ala Thr Trp Thr Ala Ala Ser Asp
                85                  90                  95

Val Asp Ile Asp His Ile Val Pro Leu Ser Asn Ala Trp Lys Ser Gly
            100                 105                 110

Ala Ala Ser Trp Thr Thr Ser Arg Arg Gln Gln Phe Ala Asn Asp Leu
        115                 120                 125

Thr Asn Pro Gln Leu Ile Ala Val Thr Asp Ser Val Asn Gln Ala Lys
    130                 135                 140

Gly Asp Lys Gly Pro Glu Asp Trp Lys Pro Ser Arg Thr Ser Tyr His
145                 150                 155                 160

Cys Thr Tyr Ala Lys Met Trp Ile Lys Val Lys Ser Val Tyr Ser Leu
                165                 170                 175

Thr Val Thr Ser Ala Glu Lys Ser Ala Leu Thr Thr Met Leu Asn Thr
            180                 185                 190

Cys
```

<210> SEQ ID NO 168
<211> LENGTH: 1714
<212> TYPE: DNA
<213> ORGANISM: Xanthan alkaline
<220> FEATURE:
<221> NAME/KEY: CDS
<222> LOCATION: (501)..(1211)
<220> FEATURE:
<221> NAME/KEY: sig_peptide
<222> LOCATION: (501)..(614)
<220> FEATURE:
<221> NAME/KEY: mat_peptide
<222> LOCATION: (615)..(1211)

<400> SEQUENCE: 168

```
aggccgtggc gcccagggcg agcggcttgt ccaccacgac ggggacgcct gcgcgcacga      60

gcgccgtcgc gtggtccgcg tggagcgcgg acgggctggc cacgaccacg acgtcgtagg     120

ccgcgcggtc ggcgaggagc gcctcgacgt cgtcgtgcag gtgcacgccg ggccagtcct     180

cggcggcggc ggcgcgtcgc tccggcgagc gcacgacgac ggccgtgacg gtgtgcccgg     240

cctcgcgcac gagacgtgcg tggatgccgc ggccggcccc tccgtacccg acgatcccga     300

ccctgagcgt gcgtgcggcg gtgtccatgc cgaccaatct agccgcgtcg cggccgggcg     360

ccgggggcgc acggggcacg tcgggcgcgg gccggagcac tccgggcgac ctggcagaat     420

gtgcgcgttg gtccgatatg gagcgctgcg taccgtctcg cgggggtcgg gccgagaatc     480

ggtttcggga aggtcgaccc ttg agc acc acg agc cgc cag gtc cct cgt cgg     533
                      Leu Ser Thr Thr Ser Arg Gln Val Pro Arg Arg
                                  -35                 -30
```

-continued

```
agc gtc ctg cgc tac gtc ctc atc gcc ctg gcg atc gcg atc gtc gtc       581
Ser Val Leu Arg Tyr Val Leu Ile Ala Leu Ala Ile Ala Ile Val Val
        -25                 -20                 -15

gcg aac gtc atc aac cag cgg tcc gtc gcg gcg gac acc gac ccg gag       629
Ala Asn Val Ile Asn Gln Arg Ser Val Ala Ala Asp Thr Asp Pro Glu
    -10                 -5              -1  1               5

ccg gtc gcc ggg agc gcg ctc gag gcc ctc gcc ggc ctc gag gtc aag       677
Pro Val Ala Gly Ser Ala Leu Glu Ala Leu Ala Gly Leu Glu Val Lys
                10                  15                  20

ggc ccc ggc ccg gac acc ggc tac gag cgc gcg ttg ttc ggt ccg ccg       725
Gly Pro Gly Pro Asp Thr Gly Tyr Glu Arg Ala Leu Phe Gly Pro Pro
            25                  30                  35

tgg gcc gac gtc gac ggc aac ggg tgc gac act cgc aac gac atc ctc       773
Trp Ala Asp Val Asp Gly Asn Gly Cys Asp Thr Arg Asn Asp Ile Leu
        40                  45                  50

gcg cgc gac ctc acg gac ctg acc ttc tcg acg cgc ggc gac gtc tgc       821
Ala Arg Asp Leu Thr Asp Leu Thr Phe Ser Thr Arg Gly Asp Val Cys
    55                  60                  65

gag gtc cgc acc ggg acc ttc gac gac ccc tac acg ggc gag acg atc       869
Glu Val Arg Thr Gly Thr Phe Asp Asp Pro Tyr Thr Gly Glu Thr Ile
70                  75                  80                  85

gac ttc cgc cgc ggc aac gcg acg agc gcg gcg gtc cag atc gac cac       917
Asp Phe Arg Arg Gly Asn Ala Thr Ser Ala Ala Val Gln Ile Asp His
                90                  95                  100

gtc gtg ccg ctg ctc gac gcg tgg cgc aag ggc gct cgc gcc tgg gac       965
Val Val Pro Leu Leu Asp Ala Trp Arg Lys Gly Ala Arg Ala Trp Asp
            105                 110                 115

gac gag acg cgt cgg cag ttc gcg aac gac ccc ctc aac ctg ctc gcg      1013
Asp Glu Thr Arg Arg Gln Phe Ala Asn Asp Pro Leu Asn Leu Leu Ala
        120                 125                 130

tca gac ggc ccg gcg aac cag tcg aag ggc gcg cgc gac gcg tcg gcg      1061
Ser Asp Gly Pro Ala Asn Gln Ser Lys Gly Ala Arg Asp Ala Ser Ala
    135                 140                 145

tgg ctg ccc ccg aac cac gcg ttc cgg tgc ccg tac gtc gcc cgg cag      1109
Trp Leu Pro Pro Asn His Ala Phe Arg Cys Pro Tyr Val Ala Arg Gln
150                 155                 160                 165

atc gcc gtg aag gcg gcc tac gag ctc tcg gtc acg ccg tcg gag tcg      1157
Ile Ala Val Lys Ala Ala Tyr Glu Leu Ser Val Thr Pro Ser Glu Ser
                170                 175                 180

gag gcg atg gcg cgc gtg ctg gcg gac tgc ccc gcc gag ccg ctc ccg      1205
Glu Ala Met Ala Arg Val Leu Ala Asp Cys Pro Ala Glu Pro Leu Pro
            185                 190                 195

gcg ggc tgagccggct cccccggtcc gcggtccaga cgcccgaggg cgctcggcca       1261
Ala Gly

ccaggcgcga cggccgacgt cgtgcacgag ggcgggcacg aggagcgacc gcaccacgag    1321

ggtgtcgacg aggacgccga acgcgacgat gaacgcgagc tgggcgagga agagcagcgg    1381

gatgatcccg agcgcggcga acgtggccgc gagcacgacg cccgcggacg tgatgaccga    1441

ccccgtgacc gcgagcccgc gcagcacgcc gcgccgcgtc ccgacgcgca ggctctcctc    1501

gcgcacccgc gtcatgagga agatcgagta gtccacgccc agcgcgacga ggaagcagaa    1561

cgcgtagagc gggacggccg ggtccgcgcc ggggaagtcg agcacgtggt tgaagacgat    1621

cgcggcgacg ccgagcgcgg ccccgaacga cagcacgttc gcgagcatga gcagcacggg    1681

cgcgagcacg gaccgcagca gcaggacgag gat                                 1714


<210> SEQ ID NO 169
<211> LENGTH: 237
<212> TYPE: PRT
```

<213> ORGANISM: Xanthan alkaline

<400> SEQUENCE: 169

```
Leu Ser Thr Thr Ser Arg Gln Val Pro Arg Arg Ser Val Leu Arg Tyr
            -35                 -30                 -25

Val Leu Ile Ala Leu Ala Ile Ala Ile Val Val Ala Asn Val Ile Asn
        -20                 -15                 -10

Gln Arg Ser Val Ala Ala Asp Thr Asp Pro Glu Pro Val Ala Gly Ser
    -5              -1  1               5                   10

Ala Leu Glu Ala Leu Ala Gly Leu Glu Val Lys Gly Pro Gly Pro Asp
                15                  20                  25

Thr Gly Tyr Glu Arg Ala Leu Phe Gly Pro Pro Trp Ala Asp Val Asp
            30                  35                  40

Gly Asn Gly Cys Asp Thr Arg Asn Asp Ile Leu Ala Arg Asp Leu Thr
        45                  50                  55

Asp Leu Thr Phe Ser Thr Arg Gly Asp Val Cys Glu Val Arg Thr Gly
    60                  65                  70

Thr Phe Asp Asp Pro Tyr Thr Gly Glu Thr Ile Asp Phe Arg Arg Gly
75                  80                  85                  90

Asn Ala Thr Ser Ala Ala Val Gln Ile Asp His Val Val Pro Leu Leu
                95                  100                 105

Asp Ala Trp Arg Lys Gly Ala Arg Ala Trp Asp Asp Glu Thr Arg Arg
            110                 115                 120

Gln Phe Ala Asn Asp Pro Leu Asn Leu Leu Ala Ser Asp Gly Pro Ala
        125                 130                 135

Asn Gln Ser Lys Gly Ala Arg Asp Ala Ser Ala Trp Leu Pro Pro Asn
    140                 145                 150

His Ala Phe Arg Cys Pro Tyr Val Ala Arg Gln Ile Ala Val Lys Ala
155                 160                 165                 170

Ala Tyr Glu Leu Ser Val Thr Pro Ser Glu Ser Glu Ala Met Ala Arg
                175                 180                 185

Val Leu Ala Asp Cys Pro Ala Glu Pro Leu Pro Ala Gly
            190                 195
```

<210> SEQ ID NO 170
<211> LENGTH: 199
<212> TYPE: PRT
<213> ORGANISM: Xanthan alkaline

<400> SEQUENCE: 170

```
Asp Thr Asp Pro Glu Pro Val Ala Gly Ser Ala Leu Glu Ala Leu Ala
1               5                   10                  15

Gly Leu Glu Val Lys Gly Pro Gly Pro Asp Thr Gly Tyr Glu Arg Ala
            20                  25                  30

Leu Phe Gly Pro Pro Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Asp Val Cys Glu Val Arg Thr Gly Thr Phe Asp Asp Pro Tyr
65                  70                  75                  80

Thr Gly Glu Thr Ile Asp Phe Arg Arg Gly Asn Ala Thr Ser Ala Ala
                85                  90                  95

Val Gln Ile Asp His Val Val Pro Leu Leu Asp Ala Trp Arg Lys Gly
            100                 105                 110

Ala Arg Ala Trp Asp Asp Glu Thr Arg Arg Gln Phe Ala Asn Asp Pro
```

```
        115                 120                 125

Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Ala Ala Tyr Glu Leu Ser Val
                165                 170                 175

Thr Pro Ser Glu Ser Glu Ala Met Ala Arg Val Leu Ala Asp Cys Pro
            180                 185                 190

Ala Glu Pro Leu Pro Ala Gly
        195


<210> SEQ ID NO 171
<211> LENGTH: 1714
<212> TYPE: DNA
<213> ORGANISM: Xanthan alkaline
<220> FEATURE:
<221> NAME/KEY: CDS
<222> LOCATION: (501)..(1211)
<220> FEATURE:
<221> NAME/KEY: sig_peptide
<222> LOCATION: (501)..(614)
<220> FEATURE:
<221> NAME/KEY: mat_peptide
<222> LOCATION: (615)..(1211)

<400> SEQUENCE: 171

ggcgcgggac gccgtggcgc cgagcgcgag cggcttgtcg acgacgaccg gcacgccggc      60

ccgggcgagc gcggtggcgt ggtcggcgtg cagggcggac gggctcgcga ccacgacgac     120

gtcgtaggcc gtccggtcgg cgaggagcgc gtcgaggtcg tcgtgcaggt gcacgtccgg     180

ccagtcctcg accgcggcgg cgcggcgctc gggcgaccgg accacgaccg ccgtgacgac     240

gtgcccggcc tcgcggacga ggcgtgcgtg gatgccgcgg cccgctcctc cgtacccgac     300

gatcccgacc ctgagcgtgc gtgcggcggt gtccatggcg accaatctag ccgcgccgtc     360

gaccggtacc cgcggggtcc tgtcggagtg gtctgagcac tctccgcaac ctggcagaat     420

gtgcgcgttg gtccggtatg gagcgctgcg taccgtctcg cgcgggtcgg gccgagaatc     480

ggtttcggga aggtcgtccc ttg agc acc acg agc cgc cgc gtc cct cgt cgg     533
                      Leu Ser Thr Thr Ser Arg Arg Val Pro Arg Arg
                                  -35                 -30

agc gtc ctg cgc tac gtc ctg atc gcg ttg gcg gtc gcc atc gtg gtc      581
Ser Val Leu Arg Tyr Val Leu Ile Ala Leu Ala Val Ala Ile Val Val
        -25                 -20                 -15

gcg aac gtc atc aac cag cag tcg gtc gcc gcc gac gac gag ccg gaa      629
Ala Asn Val Ile Asn Gln Gln Ser Val Ala Ala Asp Asp Glu Pro Glu
    -10                 -5              -1  1               5

ccc gcc cgg ggc agc gcg ctc gag gcg ctg gcg cgc ctc gag gtc gtg      677
Pro Ala Arg Gly Ser Ala Leu Glu Ala Leu Ala Arg Leu Glu Val Val
                10                  15                  20

ggg ccc ggc ccg gac acg ggc tac gag cgg gag ctc ttc ggt ccc gcg      725
Gly Pro Gly Pro Asp Thr Gly Tyr Glu Arg Glu Leu Phe Gly Pro Ala
            25                  30                  35

tgg gcc gac gtc gac ggc aac ggg tgc gac acc cgc aac gac atc ctc      773
Trp Ala Asp Val Asp Gly Asn Gly Cys Asp Thr Arg Asn Asp Ile Leu
        40                  45                  50

gcg cgc gac ctc acc gac ctc acc ttc tcg acg cgg ggc gag gtc tgc      821
Ala Arg Asp Leu Thr Asp Leu Thr Phe Ser Thr Arg Gly Glu Val Cys
    55                  60                  65

gag gta cgg acg ggc acg ttc cag gac ccg tac acc ggc gag acc atc      869
```

```
Glu Val Arg Thr Gly Thr Phe Gln Asp Pro Tyr Thr Gly Glu Thr Ile
70                  75                  80                  85

gac ttc cgc cgc ggc aac gcg acc agc atg gcg gtc cag atc gac cac      917
Asp Phe Arg Arg Gly Asn Ala Thr Ser Met Ala Val Gln Ile Asp His
                90                  95                  100

gtg gtc ccg ctg atg gac gcg tgg cgc aag ggc gcg cgc gcc tgg gac      965
Val Val Pro Leu Met Asp Ala Trp Arg Lys Gly Ala Arg Ala Trp Asp
            105                 110                 115

gac gag acg cgt cgg cag ttc gcc aac gac ccg ctc aac ctg ctc gcg     1013
Asp Glu Thr Arg Arg Gln Phe Ala Asn Asp Pro Leu Asn Leu Leu Ala
        120                 125                 130

tcc gac ggc ccc gcg aac cag tcc aag ggc gcg cgc gac gcg tcc gcg     1061
Ser Asp Gly Pro Ala Asn Gln Ser Lys Gly Ala Arg Asp Ala Ser Ala
    135                 140                 145

tgg ctc ccc ccg aac cac gcg ttc cgc tgc ccg tac gtc gcg cgg cag     1109
Trp Leu Pro Pro Asn His Ala Phe Arg Cys Pro Tyr Val Ala Arg Gln
150                 155                 160                 165

atc gcg gtg aag acc gcc tac gag ctc tcg gtg acg ccg tcc gag tcg     1157
Ile Ala Val Lys Thr Ala Tyr Glu Leu Ser Val Thr Pro Ser Glu Ser
                170                 175                 180

gag gcg atg gcg cgc gtg ctc gag gac tgc ccg gcc gag ccc gtc ccc     1205
Glu Ala Met Ala Arg Val Leu Glu Asp Cys Pro Ala Glu Pro Val Pro
            185                 190                 195

gcg ggc tgacccttct cccccggccc ccggtcggcg cgcccgaggg cgctcggcca      1261
Ala Gly

ccaggcccga cgaccgacgt cgtgcacgag cgcgggcacc agcagcgacc gcacgacgag   1321

cgtgtcgacg aggacgccga acgcgacgat gaacgcgagc tgggcgagga acagcagcgg   1381

gatgatcccg agcgcggcga acgtcgtcgc gaggaccacg cctgcggacg tgatgaccga   1441

cccggtgacc gcgagaccgc gcagcacgcc gcgccgcgtc ccgacccgca ggctctcctc   1501

ccgcacgcgc gtcatgagga agatcgagta gtcgaccccg agcgcgacga ggaagcagaa   1561

cgcgtagagc gggacggccg ggtcggcgcc cgggaagtcg agcacgtggt tgaagacgat   1621

cgcggcgacg ccgagcgctg cgccgaacga cagcacgttg gcgagcatga gcaggaccgg   1681

cgcgacgatc gaccgcagca gcaggatgag gat                                1714


<210> SEQ ID NO 172
<211> LENGTH: 237
<212> TYPE: PRT
<213> ORGANISM: Xanthan alkaline

<400> SEQUENCE: 172

Leu Ser Thr Thr Ser Arg Arg Val Pro Arg Arg Ser Val Leu Arg Tyr
            -35                 -30                 -25

Val Leu Ile Ala Leu Ala Val Ala Ile Val Val Ala Asn Val Ile Asn
        -20                 -15                 -10

Gln Gln Ser Val Ala Ala Asp Asp Glu Pro Glu Pro Ala Arg Gly Ser
    -5              -1  1               5                   10

Ala Leu Glu Ala Leu Ala Arg Leu Glu Val Val Gly Pro Gly Pro Asp
                15                  20                  25

Thr Gly Tyr Glu Arg Glu Leu Phe Gly Pro Ala Trp Ala Asp Val Asp
            30                  35                  40

Gly Asn Gly Cys Asp Thr Arg Asn Asp Ile Leu Ala Arg Asp Leu Thr
        45                  50                  55

Asp Leu Thr Phe Ser Thr Arg Gly Glu Val Cys Glu Val Arg Thr Gly
    60                  65                  70
```

-continued

```
Thr Phe Gln Asp Pro Tyr Thr Gly Glu Thr Ile Asp Phe Arg Arg Gly
75                  80                  85                  90

Asn Ala Thr Ser Met Ala Val Gln Ile Asp His Val Val Pro Leu Met
                95                  100                 105

Asp Ala Trp Arg Lys Gly Ala Arg Ala Trp Asp Asp Glu Thr Arg Arg
            110                 115                 120

Gln Phe Ala Asn Asp Pro Leu Asn Leu Leu Ala Ser Asp Gly Pro Ala
        125                 130                 135

Asn Gln Ser Lys Gly Ala Arg Asp Ala Ser Ala Trp Leu Pro Pro Asn
    140                 145                 150

His Ala Phe Arg Cys Pro Tyr Val Ala Arg Gln Ile Ala Val Lys Thr
155                 160                 165                 170

Ala Tyr Glu Leu Ser Val Thr Pro Ser Glu Ser Glu Ala Met Ala Arg
                175                 180                 185

Val Leu Glu Asp Cys Pro Ala Glu Pro Val Pro Ala Gly
            190                 195
```

<210> SEQ ID NO 173
<211> LENGTH: 199
<212> TYPE: PRT
<213> ORGANISM: Xanthan alkaline

<400> SEQUENCE: 173

```
Asp Asp Glu Pro Glu Pro Ala Arg Gly Ser Ala Leu Glu Ala Leu Ala
1               5                   10                  15

Arg Leu Glu Val Val Gly Pro Gly Pro Asp Thr Gly Tyr Glu Arg Glu
            20                  25                  30

Leu Phe Gly Pro Ala Trp Ala Asp Val Asp Gly Asn Gly Cys Asp Thr
        35                  40                  45

Arg Asn Asp Ile Leu Ala Arg Asp Leu Thr Asp Leu Thr Phe Ser Thr
    50                  55                  60

Arg Gly Glu Val Cys Glu Val Arg Thr Gly Thr Phe Gln Asp Pro Tyr
65                  70                  75                  80

Thr Gly Glu Thr Ile Asp Phe Arg Arg Gly Asn Ala Thr Ser Met Ala
                85                  90                  95

Val Gln Ile Asp His Val Val Pro Leu Met Asp Ala Trp Arg Lys Gly
            100                 105                 110

Ala Arg Ala Trp Asp Asp Glu Thr Arg Arg Gln Phe Ala Asn Asp Pro
        115                 120                 125

Leu Asn Leu Leu Ala Ser Asp Gly Pro Ala Asn Gln Ser Lys Gly Ala
    130                 135                 140

Arg Asp Ala Ser Ala Trp Leu Pro Pro Asn His Ala Phe Arg Cys Pro
145                 150                 155                 160

Tyr Val Ala Arg Gln Ile Ala Val Lys Thr Ala Tyr Glu Leu Ser Val
                165                 170                 175

Thr Pro Ser Glu Ser Glu Ala Met Ala Arg Val Leu Glu Asp Cys Pro
            180                 185                 190

Ala Glu Pro Val Pro Ala Gly
        195
```

<210> SEQ ID NO 174
<211> LENGTH: 800
<212> TYPE: DNA
<213> ORGANISM: Clavicipitaceae species
<220> FEATURE:
<221> NAME/KEY: CDS
<222> LOCATION: (1)..(72)

```
<220> FEATURE:
<221> NAME/KEY: sig_peptide
<222> LOCATION: (1)..(54)
<220> FEATURE:
<221> NAME/KEY: mat_peptide
<222> LOCATION: (55)..(797)
<220> FEATURE:
<221> NAME/KEY: CDS
<222> LOCATION: (142)..(275)
<220> FEATURE:
<221> NAME/KEY: CDS
<222> LOCATION: (329)..(485)
<220> FEATURE:
<221> NAME/KEY: CDS
<222> LOCATION: (549)..(797)

<400> SEQUENCE: 174

atg aag ttc tct tcg gca tct ctc gtc gtg tcc gct gct gcg ctt gtc       48
Met Lys Phe Ser Ser Ala Ser Leu Val Val Ser Ala Ala Ala Leu Val
            -15                 -10                 -5

ctc ggt gtg cct gtg cct gcg ccc gtaagcaatc ctactcctga cacgctgtca     102
Leu Gly Val Pro Val Pro Ala Pro
    -1  1               5

tcgtgtaaca aagcctaact cttttttttg ttcttctag ccc ggc atc cca agc       156
                                           Pro Gly Ile Pro Ser
                                                       10

acg tcg aca gcc aag act ctt ctt gct ggc ctc aag gtt gct acc ccg      204
Thr Ser Thr Ala Lys Thr Leu Leu Ala Gly Leu Lys Val Ala Thr Pro
            15                  20                  25

ttg agt ggt gat ggg tac tct cgt gat aag ttc cct act tgg gag acc      252
Leu Ser Gly Asp Gly Tyr Ser Arg Asp Lys Phe Pro Thr Trp Glu Thr
        30                  35                  40

att cag gga act tgc aat gct cg  gtgagtttgc ccatctcctt ttgttcttgt     305
Ile Gln Gly Thr Cys Asn Ala Arg
    45                  50

caggttgcta atgcccatgg tag c gag ttt gtc att aag cga gac gga aca      356
                            Glu Phe Val Ile Lys Arg Asp Gly Thr
                                        55                  60

gac gtc aag acc aac agc gca tgc gtc gca gag tcc ggc aac tgg gtc      404
Asp Val Lys Thr Asn Ser Ala Cys Val Ala Glu Ser Gly Asn Trp Val
                65                  70                  75

tct ccg tat gac ggg gtc aag ttc acc gca gca cgc gat ctc gac att      452
Ser Pro Tyr Asp Gly Val Lys Phe Thr Ala Ala Arg Asp Leu Asp Ile
            80                  85                  90

gac cac atg gtt cca ctg aag aat gcc tgg att gtaagacgac tacctaacca    505
Asp His Met Val Pro Leu Lys Asn Ala Trp Ile
        95                  100

tcttgtcctc aattccacgt accttgtcta acttgcttgt cag tcc ggt gcc tca      560
                                                Ser Gly Ala Ser
                                                    105

caa tgg acc acc gag cag cgc aaa gct ctc gcc aac gac att acc cgt      608
Gln Trp Thr Thr Glu Gln Arg Lys Ala Leu Ala Asn Asp Ile Thr Arg
        110                 115                 120

ccc cag ctc tgg gcc gta tca gcc cat gcc aac cgc ggc aag agt gac      656
Pro Gln Leu Trp Ala Val Ser Ala His Ala Asn Arg Gly Lys Ser Asp
    125                 130                 135

gat agc ccc gac gag tgg aag cct cct ctg aag act ttc tgg tgc aca      704
Asp Ser Pro Asp Glu Trp Lys Pro Pro Leu Lys Thr Phe Trp Cys Thr
140                 145                 150                 155

tac gcc aag agt tgg gtg cag gtg aag agc ttc tat aag ttg act att      752
Tyr Ala Lys Ser Trp Val Gln Val Lys Ser Phe Tyr Lys Leu Thr Ile
                160                 165                 170

acg gat acc gag aaa ggt gct ttg gct ggc atg ctg gat act tgc taa      800
```

```
Thr Asp Thr Glu Lys Gly Ala Leu Ala Gly Met Leu Asp Thr Cys
            175                 180                 185


<210> SEQ ID NO 175
<211> LENGTH: 204
<212> TYPE: PRT
<213> ORGANISM: Clavicipitaceae species

<400> SEQUENCE: 175

Met Lys Phe Ser Ser Ala Ser Leu Val Val Ser Ala Ala Ala Leu Val
            -15                 -10                 -5

Leu Gly Val Pro Val Pro Ala Pro Pro Gly Ile Pro Ser Thr Ser Thr
    -1  1               5                   10

Ala Lys Thr Leu Leu Ala Gly Leu Lys Val Ala Thr Pro Leu Ser Gly
15                  20                  25                  30

Asp Gly Tyr Ser Arg Asp Lys Phe Pro Thr Trp Glu Thr Ile Gln Gly
                35                  40                  45

Thr Cys Asn Ala Arg Glu Phe Val Ile Lys Arg Asp Gly Thr Asp Val
            50                  55                  60

Lys Thr Asn Ser Ala Cys Val Ala Glu Ser Gly Asn Trp Val Ser Pro
        65                  70                  75

Tyr Asp Gly Val Lys Phe Thr Ala Ala Arg Asp Leu Asp Ile Asp His
    80                  85                  90

Met Val Pro Leu Lys Asn Ala Trp Ile Ser Gly Ala Ser Gln Trp Thr
95                  100                 105                 110

Thr Glu Gln Arg Lys Ala Leu Ala Asn Asp Ile Thr Arg Pro Gln Leu
                115                 120                 125

Trp Ala Val Ser Ala His Ala Asn Arg Gly Lys Ser Asp Asp Ser Pro
            130                 135                 140

Asp Glu Trp Lys Pro Pro Leu Lys Thr Phe Trp Cys Thr Tyr Ala Lys
        145                 150                 155

Ser Trp Val Gln Val Lys Ser Phe Tyr Lys Leu Thr Ile Thr Asp Thr
    160                 165                 170

Glu Lys Gly Ala Leu Ala Gly Met Leu Asp Thr Cys
175                 180                 185


<210> SEQ ID NO 176
<211> LENGTH: 186
<212> TYPE: PRT
<213> ORGANISM: Clavicipitaceae species

<400> SEQUENCE: 176

Val Pro Val Pro Ala Pro Pro Gly Ile Pro Ser Thr Ser Thr Ala Lys
1               5                   10                  15

Thr Leu Leu Ala Gly Leu Lys Val Ala Thr Pro Leu Ser Gly Asp Gly
            20                  25                  30

Tyr Ser Arg Asp Lys Phe Pro Thr Trp Glu Thr Ile Gln Gly Thr Cys
        35                  40                  45

Asn Ala Arg Glu Phe Val Ile Lys Arg Asp Gly Thr Asp Val Lys Thr
    50                  55                  60

Asn Ser Ala Cys Val Ala Glu Ser Gly Asn Trp Val Ser Pro Tyr Asp
65                  70                  75                  80

Gly Val Lys Phe Thr Ala Ala Arg Asp Leu Asp Ile Asp His Met Val
                85                  90                  95

Pro Leu Lys Asn Ala Trp Ile Ser Gly Ala Ser Gln Trp Thr Thr Glu
            100                 105                 110
```

```
Gln Arg Lys Ala Leu Ala Asn Asp Ile Thr Arg Pro Gln Leu Trp Ala
        115                 120                 125

Val Ser Ala His Ala Asn Arg Gly Lys Ser Asp Asp Ser Pro Asp Glu
    130                 135                 140

Trp Lys Pro Pro Leu Lys Thr Phe Trp Cys Thr Tyr Ala Lys Ser Trp
145                 150                 155                 160

Val Gln Val Lys Ser Phe Tyr Lys Leu Thr Ile Thr Asp Thr Glu Lys
                165                 170                 175

Gly Ala Leu Ala Gly Met Leu Asp Thr Cys
            180                 185


<210> SEQ ID NO 177
<211> LENGTH: 897
<212> TYPE: DNA
<213> ORGANISM: Westerdykella species
<220> FEATURE:
<221> NAME/KEY: CDS
<222> LOCATION: (1)..(206)
<220> FEATURE:
<221> NAME/KEY: sig_peptide
<222> LOCATION: (1)..(48)
<220> FEATURE:
<221> NAME/KEY: mat_peptide
<222> LOCATION: (49)..(894)
<220> FEATURE:
<221> NAME/KEY: CDS
<222> LOCATION: (290)..(461)
<220> FEATURE:
<221> NAME/KEY: CDS
<222> LOCATION: (535)..(673)
<220> FEATURE:
<221> NAME/KEY: CDS
<222> LOCATION: (727)..(773)
<220> FEATURE:
<221> NAME/KEY: CDS
<222> LOCATION: (850)..(894)

<400> SEQUENCE: 177

atg aag tcc ctc ctc gtc acc ctc gct gct gca aca ctg ggt gct gcc       48
Met Lys Ser Leu Leu Val Thr Leu Ala Ala Ala Thr Leu Gly Ala Ala
    -15                 -10                 -5              -1

ttc cca gca ccc gcg tcc gtc ctg gag gct cgc gct ccg ccg aac atc       96
Phe Pro Ala Pro Ala Ser Val Leu Glu Ala Arg Ala Pro Pro Asn Ile
1               5                   10                  15

cct tcg gcg tcg acc gct cag agc ctg ctg gtt ggg ttg acg gtc cag      144
Pro Ser Ala Ser Thr Ala Gln Ser Leu Leu Val Gly Leu Thr Val Gln
            20                  25                  30

cct cag ggt cca caa gat ggg tac tcg agg gat ctc ttc cca cat tgg      192
Pro Gln Gly Pro Gln Asp Gly Tyr Ser Arg Asp Leu Phe Pro His Trp
        35                  40                  45

atc acc ata agt gg  gtaggtggac catgtcccct attgttccgt gctctttgag      246
Ile Thr Ile Ser Gly
    50

acaccattgc agagaaaaca cgggctaatc atggcccacc cag g acc tgc aac acc    302
                                                  Thr Cys Asn Thr
                                                      55

cgc gag acg gtc ctg aag cgc gac ggc agc aac gtc gtc acc aac tcg      350
Arg Glu Thr Val Leu Lys Arg Asp Gly Ser Asn Val Val Thr Asn Ser
        60                  65                  70

gcc tgc gcg gcc acc tcc ggg acc tgg tac tcg ccc tat gac ggc gca      398
Ala Cys Ala Ala Thr Ser Gly Thr Trp Tyr Ser Pro Tyr Asp Gly Ala
    75                  80                  85

aca tgg act tct gcc agc gac gtc gac atc gat cac ctg gtg ccg ctt      446
Thr Trp Thr Ser Ala Ser Asp Val Asp Ile Asp His Leu Val Pro Leu
90                  95                  100                 105
```

```
tcc aat gct tgg aag gtatgtagcc cgtctctccg ctttcgcatg tagcagtaga      501
Ser Asn Ala Trp Lys
                110

aggtgaacgt actgaccgtg agaacttccc cag tcc ggt gct gcc agc tgg acc     555
                                     Ser Gly Ala Ala Ser Trp Thr
                                                     115

acg gcc aaa cgc cag caa ttc gcc aat gac ctg aca aat cca cag ctc      603
Thr Ala Lys Arg Gln Gln Phe Ala Asn Asp Leu Thr Asn Pro Gln Leu
        120                 125                 130

ctt gct gtg act gac agg gtc aac caa gcc aag ggc gac aag ggc ccc      651
Leu Ala Val Thr Asp Arg Val Asn Gln Ala Lys Gly Asp Lys Gly Pro
    135                 140                 145

gag gcc tgg aag ccg tcg tta g gtagaccact ccgtcactct cgcgtgcaac       703
Glu Ala Trp Lys Pro Ser Leu
150                 155

aagtgatggc taatggcttc tag ct  tcg tac cac tgc acc tat gcc aag atg    755
                          Ala Ser Tyr His Cys Thr Tyr Ala Lys Met
                                      160                 165

tgg gtc aag gtt aag agc gtatgggctt tgaccgtaac gtcggctgag             803
Trp Val Lys Val Lys Ser
            170

aagagcgctc taacaacaat gttggctacg tgctgaacac gcgcag aag gac gtt       858
                                                   Lys Asp Val
                                                           175

cgg ctg acc ggg aat tgg acg aag gac gac ggc tgg tga                  897
Arg Leu Thr Gly Asn Trp Thr Lys Asp Asp Gly Trp
                180                 185


<210> SEQ ID NO 178
<211> LENGTH: 203
<212> TYPE: PRT
<213> ORGANISM: Westerdykella species

<400> SEQUENCE: 178

Met Lys Ser Leu Leu Val Thr Leu Ala Ala Ala Thr Leu Gly Ala Ala
    -15                 -10                 -5              -1

Phe Pro Ala Pro Ala Ser Val Leu Glu Ala Arg Ala Pro Pro Asn Ile
1               5                   10                  15

Pro Ser Ala Ser Thr Ala Gln Ser Leu Leu Val Gly Leu Thr Val Gln
            20                  25                  30

Pro Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Ser Asn Val Val Thr Asn Ser Ala Cys Ala Ala Thr Ser Gly
65                  70                  75                  80

Thr Trp Tyr Ser Pro Tyr Asp Gly Ala Thr Trp Thr Ser Ala Ser Asp
                85                  90                  95

Val Asp Ile Asp His Leu Val Pro Leu Ser Asn Ala Trp Lys Ser Gly
            100                 105                 110

Ala Ala Ser Trp Thr Thr Ala Lys Arg Gln Gln Phe Ala Asn Asp Leu
        115                 120                 125

Thr Asn Pro Gln Leu Leu Ala Val Thr Asp Arg Val Asn Gln Ala Lys
    130                 135                 140

Gly Asp Lys Gly Pro Glu Ala Trp Lys Pro Ser Leu Ala Ser Tyr His
145                 150                 155                 160

Cys Thr Tyr Ala Lys Met Trp Val Lys Val Lys Ser Lys Asp Val Arg
```

```
                165                 170                 175

Leu Thr Gly Asn Trp Thr Lys Asp Asp Gly Trp
            180                 185
```

<210> SEQ ID NO 179
<211> LENGTH: 187
<212> TYPE: PRT
<213> ORGANISM: Westerdykella species

<400> SEQUENCE: 179

```
Phe Pro Ala Pro Ala Ser Val Leu Glu Ala Arg Ala Pro Pro Asn Ile
1               5                   10                  15

Pro Ser Ala Ser Thr Ala Gln Ser Leu Leu Val Gly Leu Thr Val Gln
            20                  25                  30

Pro Gln Gly Pro Gln Asp Gly Tyr Ser Arg Asp Leu Phe Pro His Trp
        35                  40                  45

Ile Thr Ile Ser Gly Thr Cys Asn Thr Arg Glu Thr Val Leu Lys Arg
    50                  55                  60

Asp Gly Ser Asn Val Val Thr Asn Ser Ala Cys Ala Ala Thr Ser Gly
65                  70                  75                  80

Thr Trp Tyr Ser Pro Tyr Asp Gly Ala Thr Trp Thr Ser Ala Ser Asp
                85                  90                  95

Val Asp Ile Asp His Leu Val Pro Leu Ser Asn Ala Trp Lys Ser Gly
            100                 105                 110

Ala Ala Ser Trp Thr Thr Ala Lys Arg Gln Gln Phe Ala Asn Asp Leu
        115                 120                 125

Thr Asn Pro Gln Leu Leu Ala Val Thr Asp Arg Val Asn Gln Ala Lys
    130                 135                 140

Gly Asp Lys Gly Pro Glu Ala Trp Lys Pro Ser Leu Ala Ser Tyr His
145                 150                 155                 160

Cys Thr Tyr Ala Lys Met Trp Val Lys Val Lys Ser Lys Asp Val Arg
                165                 170                 175

Leu Thr Gly Asn Trp Thr Lys Asp Asp Gly Trp
            180                 185
```

<210> SEQ ID NO 180
<211> LENGTH: 781
<212> TYPE: DNA
<213> ORGANISM: Humicolopsis cephalosporioides
<220> FEATURE:
<221> NAME/KEY: CDS
<222> LOCATION: (1)..(390)
<220> FEATURE:
<221> NAME/KEY: sig_peptide
<222> LOCATION: (1)..(57)
<220> FEATURE:
<221> NAME/KEY: mat_peptide
<222> LOCATION: (58)..(778)
<220> FEATURE:
<221> NAME/KEY: CDS
<222> LOCATION: (450)..(588)
<220> FEATURE:
<221> NAME/KEY: CDS
<222> LOCATION: (669)..(778)

<400> SEQUENCE: 180

```
atg aag acc act tgg atc ctc acc agc ctt ttg gca caa gct ttc ctc       48
Met Lys Thr Thr Trp Ile Leu Thr Ser Leu Leu Ala Gln Ala Phe Leu
                -15                 -10                 -5

tcc ttg gct gct cct acg cct gcc cca gtg gag cta gag cgt cgc act       96
Ser Leu Ala Ala Pro Thr Pro Ala Pro Val Glu Leu Glu Arg Arg Thr
        -1  1               5                   10
```

```
cct cca aat atc cca acc act gct tcg gcg aag tct ctt ctc gct ggc      144
Pro Pro Asn Ile Pro Thr Thr Ala Ser Ala Lys Ser Leu Leu Ala Gly
    15                  20                  25

ctg act gtt gct gct caa ggt cca caa act ggc tac agt cgt gac ctt      192
Leu Thr Val Ala Ala Gln Gly Pro Gln Thr Gly Tyr Ser Arg Asp Leu
30                  35                  40                  45

ttc cct cac tgg atc aca atc tct ggc tct tgc aac act cgc gaa acg      240
Phe Pro His Trp Ile Thr Ile Ser Gly Ser Cys Asn Thr Arg Glu Thr
                50                  55                  60

gtc ctc aag cgc gac ggc acc ggt gtc gtg aca gat tcc gct tgc gct      288
Val Leu Lys Arg Asp Gly Thr Gly Val Val Thr Asp Ser Ala Cys Ala
            65                  70                  75

tcg aca gct ggc agt tgg tac agc cct tat gat gga gct act tgg act      336
Ser Thr Ala Gly Ser Trp Tyr Ser Pro Tyr Asp Gly Ala Thr Trp Thr
        80                  85                  90

gct gca agt gat gtg gat atc gac cat atg gtt cct ttg tcc aat gct      384
Ala Ala Ser Asp Val Asp Ile Asp His Met Val Pro Leu Ser Asn Ala
    95                  100                 105

tgg aag gtgaatatcg caacaaatca attatgggat atatcgaata atttgctgac       440
Trp Lys
110

ttgacatag tcc ggt gct gcc caa tgg acc acc gct cgc agg cag gat ttc    491
          Ser Gly Ala Ala Gln Trp Thr Thr Ala Arg Arg Gln Asp Phe
                      115                 120                 125

gcc aat gat ctg acc aat ccc cag ctc ttc gcg gtg act gat aat gtc      539
Ala Asn Asp Leu Thr Asn Pro Gln Leu Phe Ala Val Thr Asp Asn Val
                130                 135                 140

aac cag gag aag ggc gac aag gga cca gaa gac tgg aag cct tct ttg a    588
Asn Gln Glu Lys Gly Asp Lys Gly Pro Glu Asp Trp Lys Pro Ser Leu
            145                 150                 155

gtaagtatag atttacttgc agccttcaag ctccgccgtg gaagcttagt atctagtgct    648

cgtcctaaca tgctatctag ct  tcc tat tac tgc act tac gcc aaa gct tgg    700
                      Thr Ser Tyr Tyr Cys Thr Tyr Ala Lys Ala Trp
                              160                 165

gtt aaa gtc aag agt gta tgg gct tta act att aca tcg gcc gaa aag      748
Val Lys Val Lys Ser Val Trp Ala Leu Thr Ile Thr Ser Ala Glu Lys
    170                 175                 180

tct gcg ttg act act atg ctc aat acc tgc tga                          781
Ser Ala Leu Thr Thr Met Leu Asn Thr Cys
185                 190


<210> SEQ ID NO 181
<211> LENGTH: 213
<212> TYPE: PRT
<213> ORGANISM: Humicolopsis cephalosporioides

<400> SEQUENCE: 181

Met Lys Thr Thr Trp Ile Leu Thr Ser Leu Leu Ala Gln Ala Phe Leu
                -15                 -10                 -5

Ser Leu Ala Ala Pro Thr Pro Ala Pro Val Glu Leu Glu Arg Arg Thr
        -1  1               5                   10

Pro Pro Asn Ile Pro Thr Thr Ala Ser Ala Lys Ser Leu Leu Ala Gly
    15                  20                  25

Leu Thr Val Ala Ala Gln Gly Pro Gln Thr Gly Tyr Ser Arg Asp Leu
30                  35                  40                  45

Phe Pro His Trp Ile Thr Ile Ser Gly Ser Cys Asn Thr Arg Glu Thr
                50                  55                  60

Val Leu Lys Arg Asp Gly Thr Gly Val Val Thr Asp Ser Ala Cys Ala
```

65 70 75

Ser Thr Ala Gly Ser Trp Tyr Ser Pro Tyr Asp Gly Ala Thr Trp Thr
80 85 90

Ala Ala Ser Asp Val Asp Ile Asp His Met Val Pro Leu Ser Asn Ala
95 100 105

Trp Lys Ser Gly Ala Ala Gln Trp Thr Thr Ala Arg Arg Gln Asp Phe
110 115 120 125

Ala Asn Asp Leu Thr Asn Pro Gln Leu Phe Ala Val Thr Asp Asn Val
130 135 140

Asn Gln Glu Lys Gly Asp Lys Gly Pro Glu Asp Trp Lys Pro Ser Leu
145 150 155

Thr Ser Tyr Tyr Cys Thr Tyr Ala Lys Ala Trp Val Lys Val Lys Ser
160 165 170

Val Trp Ala Leu Thr Ile Thr Ser Ala Glu Lys Ser Ala Leu Thr Thr
175 180 185

Met Leu Asn Thr Cys
190

<210> SEQ ID NO 182
<211> LENGTH: 194
<212> TYPE: PRT
<213> ORGANISM: Humicolopsis cephalosporioides

<400> SEQUENCE: 182

Ala Pro Thr Pro Ala Pro Val Glu Leu Glu Arg Arg Thr Pro Pro Asn
1 5 10 15

Ile Pro Thr Thr Ala Ser Ala Lys Ser Leu Leu Ala Gly Leu Thr Val
20 25 30

Ala Ala Gln Gly Pro Gln Thr Gly Tyr Ser Arg Asp Leu Phe Pro His
35 40 45

Trp Ile Thr Ile Ser Gly Ser Cys Asn Thr Arg Glu Thr Val Leu Lys
50 55 60

Arg Asp Gly Thr Gly Val Val Thr Asp Ser Ala Cys Ala Ser Thr Ala
65 70 75 80

Gly Ser Trp Tyr Ser Pro Tyr Asp Gly Ala Thr Trp Thr Ala Ala Ser
85 90 95

Asp Val Asp Ile Asp His Met Val Pro Leu Ser Asn Ala Trp Lys Ser
100 105 110

Gly Ala Ala Gln Trp Thr Thr Ala Arg Arg Gln Asp Phe Ala Asn Asp
115 120 125

Leu Thr Asn Pro Gln Leu Phe Ala Val Thr Asp Asn Val Asn Gln Glu
130 135 140

Lys Gly Asp Lys Gly Pro Glu Asp Trp Lys Pro Ser Leu Thr Ser Tyr
145 150 155 160

Tyr Cys Thr Tyr Ala Lys Ala Trp Val Lys Val Lys Ser Val Trp Ala
165 170 175

Leu Thr Ile Thr Ser Ala Glu Lys Ser Ala Leu Thr Thr Met Leu Asn
180 185 190

Thr Cys

<210> SEQ ID NO 183
<211> LENGTH: 769
<212> TYPE: DNA
<213> ORGANISM: Neosartorya massa
<220> FEATURE:
<221> NAME/KEY: CDS

```
<222> LOCATION: (1)..(200)
<220> FEATURE:
<221> NAME/KEY: sig_peptide
<222> LOCATION: (1)..(51)
<220> FEATURE:
<221> NAME/KEY: mat_peptide
<222> LOCATION: (52)..(766)
<220> FEATURE:
<221> NAME/KEY: CDS
<222> LOCATION: (245)..(416)
<220> FEATURE:
<221> NAME/KEY: CDS
<222> LOCATION: (465)..(603)
<220> FEATURE:
<221> NAME/KEY: CDS
<222> LOCATION: (657)..(766)

<400> SEQUENCE: 183

atg act cgc ctt ctc ctc gca gcc ctt ctg ggc acc tct ctt gtc aca       48
Met Thr Arg Leu Leu Leu Ala Ala Leu Leu Gly Thr Ser Leu Val Thr
        -15                 -10                 -5

gcc atc ccg gca cca gtt gct ctc cca act ccc cca gga atc ccc tct       96
Ala Ile Pro Ala Pro Val Ala Leu Pro Thr Pro Pro Gly Ile Pro Ser
-1  1               5                   10                  15

gcc gct acc gca gag tcc gag ctg gct gct ctg act gtc gcg gcg caa      144
Ala Ala Thr Ala Glu Ser Glu Leu Ala Ala Leu Thr Val Ala Ala Gln
                20                  25                  30

ggc tcc agc tct gga tac tct cgc gac ctc ttc ccc cac tgg atc agt      192
Gly Ser Ser Ser Gly Tyr Ser Arg Asp Leu Phe Pro His Trp Ile Ser
            35                  40                  45

caa ggc gg  gtacgtacag cccttcttcc tagcaagcta agctaacagc ccag c       245
Gln Gly Gly
        50

tcc tgc aac acc cgc gag gtc gtc ctc gcc cgc gac ggc agc ggc gtc      293
Ser Cys Asn Thr Arg Glu Val Val Leu Ala Arg Asp Gly Ser Gly Val
                55                  60                  65

gtc aag gat tcc aac tgc tat ccc acc agc gga tca tgg tac tcg ccc      341
Val Lys Asp Ser Asn Cys Tyr Pro Thr Ser Gly Ser Trp Tyr Ser Pro
            70                  75                  80

tac gac gga gcc acc tgg acg cag gcc agc gat gta gac att gac cat      389
Tyr Asp Gly Ala Thr Trp Thr Gln Ala Ser Asp Val Asp Ile Asp His
        85                  90                  95

gtc gtt cct ctc gcc aac gcc tgg aga gtaagaccat cccctattcc            436
Val Val Pro Leu Ala Asn Ala Trp Arg
    100                 105

tatcgccgat ccagctaact tgcgatag tcc ggc gca tct aaa tgg act acc       488
                               Ser Gly Ala Ser Lys Trp Thr Thr
                                       110                 115

tcg cag cgg cag gcg ttt gcc aac gac ctg acc aac ccg cag ctg atg      536
Ser Gln Arg Gln Ala Phe Ala Asn Asp Leu Thr Asn Pro Gln Leu Met
                120                 125                 130

gcg gtg acg gat aac gtc aac cag gcc aag ggc gac gat gga ccg gag      584
Ala Val Thr Asp Asn Val Asn Gln Ala Lys Gly Asp Asp Gly Pro Glu
            135                 140                 145

gcg tgg aag cct cct ctt a gtaagttccc tttcctgtct tctctggggt           633
Ala Trp Lys Pro Pro Leu
        150

ggatggtgat gctaacgggc tag ct  tcg tat tat tgc acg tat gcg aag atg    685
                          Thr Ser Tyr Tyr Cys Thr Tyr Ala Lys Met
                              155                 160

tgg gtt agg gtc aag tat gtg tat gat ttg acc att acc tcg gcg gag      733
Trp Val Arg Val Lys Tyr Val Tyr Asp Leu Thr Ile Thr Ser Ala Glu
    165                 170                 175
```

```
aag agt gct ctg gtg agc atg ttg gat act tgc tag                  769
Lys Ser Ala Leu Val Ser Met Leu Asp Thr Cys
180                 185                 190


<210> SEQ ID NO 184
<211> LENGTH: 207
<212> TYPE: PRT
<213> ORGANISM: Neosartorya massa

<400> SEQUENCE: 184

Met Thr Arg Leu Leu Leu Ala Ala Leu Leu Gly Thr Ser Leu Val Thr
        -15                 -10                 -5

Ala Ile Pro Ala Pro Val Ala Leu Pro Thr Pro Pro Gly Ile Pro Ser
-1  1               5                   10                  15

Ala Ala Thr Ala Glu Ser Glu Leu Ala Ala Leu Thr Val Ala Ala Gln
                20                  25                  30

Gly Ser Ser Ser Gly Tyr Ser Arg Asp Leu Phe Pro His Trp Ile Ser
            35                  40                  45

Gln Gly Gly Ser Cys Asn Thr Arg Glu Val Val Leu Ala Arg Asp Gly
        50                  55                  60

Ser Gly Val Val Lys Asp Ser Asn Cys Tyr Pro Thr Ser Gly Ser Trp
    65                  70                  75

Tyr Ser Pro Tyr Asp Gly Ala Thr Trp Thr Gln Ala Ser Asp Val Asp
80                  85                  90                  95

Ile Asp His Val Val Pro Leu Ala Asn Ala Trp Arg Ser Gly Ala Ser
                100                 105                 110

Lys Trp Thr Thr Ser Gln Arg Gln Ala Phe Ala Asn Asp Leu Thr Asn
            115                 120                 125

Pro Gln Leu Met Ala Val Thr Asp Asn Val Asn Gln Ala Lys Gly Asp
        130                 135                 140

Asp Gly Pro Glu Ala Trp Lys Pro Pro Leu Thr Ser Tyr Tyr Cys Thr
    145                 150                 155

Tyr Ala Lys Met Trp Val Arg Val Lys Tyr Val Tyr Asp Leu Thr Ile
160                 165                 170                 175

Thr Ser Ala Glu Lys Ser Ala Leu Val Ser Met Leu Asp Thr Cys
                180                 185                 190


<210> SEQ ID NO 185
<211> LENGTH: 190
<212> TYPE: PRT
<213> ORGANISM: Neosartorya massa

<400> SEQUENCE: 185

Ile Pro Ala Pro Val Ala Leu Pro Thr Pro Pro Gly Ile Pro Ser Ala
1               5                   10                  15

Ala Thr Ala Glu Ser Glu Leu Ala Ala Leu Thr Val Ala Ala Gln Gly
            20                  25                  30

Ser Ser Ser Gly Tyr Ser Arg Asp Leu Phe Pro His Trp Ile Ser Gln
        35                  40                  45

Gly Gly Ser Cys Asn Thr Arg Glu Val Val Leu Ala Arg Asp Gly Ser
    50                  55                  60

Gly Val Val Lys Asp Ser Asn Cys Tyr Pro Thr Ser Gly Ser Trp Tyr
65                  70                  75                  80

Ser Pro Tyr Asp Gly Ala Thr Trp Thr Gln Ala Ser Asp Val Asp Ile
                85                  90                  95

Asp His Val Val Pro Leu Ala Asn Ala Trp Arg Ser Gly Ala Ser Lys
            100                 105                 110
```

```
Trp Thr Thr Ser Gln Arg Gln Ala Phe Ala Asn Asp Leu Thr Asn Pro
        115                 120                 125

Gln Leu Met Ala Val Thr Asp Asn Val Asn Gln Ala Lys Gly Asp Asp
    130                 135                 140

Gly Pro Glu Ala Trp Lys Pro Pro Leu Thr Ser Tyr Tyr Cys Thr Tyr
145                 150                 155                 160

Ala Lys Met Trp Val Arg Val Lys Tyr Val Tyr Asp Leu Thr Ile Thr
                165                 170                 175

Ser Ala Glu Lys Ser Ala Leu Val Ser Met Leu Asp Thr Cys
            180                 185                 190


<210> SEQ ID NO 186
<211> LENGTH: 828
<212> TYPE: DNA
<213> ORGANISM: Roussoella intermedia
<220> FEATURE:
<221> NAME/KEY: CDS
<222> LOCATION: (1)..(200)
<220> FEATURE:
<221> NAME/KEY: sig_peptide
<222> LOCATION: (1)..(48)
<220> FEATURE:
<221> NAME/KEY: mat_peptide
<222> LOCATION: (49)..(825)
<220> FEATURE:
<221> NAME/KEY: CDS
<222> LOCATION: (269)..(440)
<220> FEATURE:
<221> NAME/KEY: CDS
<222> LOCATION: (511)..(649)
<220> FEATURE:
<221> NAME/KEY: CDS
<222> LOCATION: (716)..(825)

<400> SEQUENCE: 186

atg aag tac atc ctc atc gcc ctc aca tct gcc atc ctc gcc tct gcc       48
Met Lys Tyr Ile Leu Ile Ala Leu Thr Ser Ala Ile Leu Ala Ser Ala
    -15                 -10                 -5                  -1

gcc cct aca ccg gcg ctc ctc ccc cgt gca cca cca aac atc cct tcc       96
Ala Pro Thr Pro Ala Leu Leu Pro Arg Ala Pro Pro Asn Ile Pro Ser
1               5                   10                  15

acc gca aca gca aag tca cag ctt gcc gcc ttg acc gtc gca gca caa      144
Thr Ala Thr Ala Lys Ser Gln Leu Ala Ala Leu Thr Val Ala Ala Gln
            20                  25                  30

ggc cct caa gat ggc tat tcc cgt gac ttg ttc cct cac tgg atc aca      192
Gly Pro Gln Asp Gly Tyr Ser Arg Asp Leu Phe Pro His Trp Ile Thr
        35                  40                  45

cag agc gg  gtacgccgac gaatccccac aagatgtttg tcccacccgg              240
Gln Ser Gly
    50

gcggatgctg acataggtac cgtcgcag g tcc tgc aac acc cgc gag gta gta     293
                                 Ser Cys Asn Thr Arg Glu Val Val
                                             55

ctc aag cgt gac ggc acc aac gtc gtg caa gac tcc tct tgt gct gcc      341
Leu Lys Arg Asp Gly Thr Asn Val Val Gln Asp Ser Ser Cys Ala Ala
60                  65                  70                  75

acg tcc ggc aca tgg gtt tct ccc ttc gac ggt gcc acc tgg aca gcc      389
Thr Ser Gly Thr Trp Val Ser Pro Phe Asp Gly Ala Thr Trp Thr Ala
                80                  85                  90

gca agc gac gtc gac atc gat cat ctc gtc ccc ttg agc aat gcc tgg      437
Ala Ser Asp Val Asp Ile Asp His Leu Val Pro Leu Ser Asn Ala Trp
            95                  100                 105

aag gttcgtccct aatcttttct ttctgtattc cgctctgggg agtcaagaag           490
```

```
Lys

acactaatag tacaccacag agc ggc gcc gcc tcc tgg acg act gct cgc cgc     543
                      Ser Gly Ala Ala Ser Trp Thr Thr Ala Arg Arg
                          110                 115

cag tcc ttc gcc aac gac ctc acc aac ccc cag ctc ctc gcc gtc acc       591
Gln Ser Phe Ala Asn Asp Leu Thr Asn Pro Gln Leu Leu Ala Val Thr
120                 125                 130                 135

gac gaa gtg aac caa gct aag ggc gac aag ggc ccc gag gcc tgg aag       639
Asp Glu Val Asn Gln Ala Lys Gly Asp Lys Gly Pro Glu Ala Trp Lys
                140                 145                 150

cct ccg cta g gtcagttctc ttcctcctct cttccaacat ctttcagtct             689
Pro Pro Leu

ctagatggat gctaacgacc acccag ca  agc tac cac tgc acc tac gcc aag      741
                             Ala Ser Tyr His Cys Thr Tyr Ala Lys
                             155                 160

atg tgg gtc aag gtc aag agc acg tac agc ctg acc atc acg tcg gct       789
Met Trp Val Lys Val Lys Ser Thr Tyr Ser Leu Thr Ile Thr Ser Ala
    165                 170                 175

gag aag agc gcc ttg acg act atg ttg aac act tgc tag                   828
Glu Lys Ser Ala Leu Thr Thr Met Leu Asn Thr Cys
180                 185                 190


<210> SEQ ID NO 187
<211> LENGTH: 207
<212> TYPE: PRT
<213> ORGANISM: Roussoella intermedia

<400> SEQUENCE: 187

Met Lys Tyr Ile Leu Ile Ala Leu Thr Ser Ala Ile Leu Ala Ser Ala
    -15                 -10                 -5              -1

Ala Pro Thr Pro Ala Leu Leu Pro Arg Ala Pro Pro Asn Ile Pro Ser
1               5                   10                  15

Thr Ala Thr Ala Lys Ser Gln Leu Ala Ala Leu Thr Val Ala Ala Gln
            20                  25                  30

Gly Pro Gln Asp Gly Tyr Ser Arg Asp Leu Phe Pro His Trp Ile Thr
        35                  40                  45

Gln Ser Gly Ser Cys Asn Thr Arg Glu Val Val Leu Lys Arg Asp Gly
    50                  55                  60

Thr Asn Val Val Gln Asp Ser Ser Cys Ala Ala Thr Ser Gly Thr Trp
65                  70                  75                  80

Val Ser Pro Phe Asp Gly Ala Thr Trp Thr Ala Ala Ser Asp Val Asp
                85                  90                  95

Ile Asp His Leu Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Leu Ala Val Thr Asp Glu Val Asn Gln Ala Lys Gly Asp
    130                 135                 140

Lys Gly Pro Glu Ala Trp Lys Pro Pro Leu Ala Ser Tyr His Cys Thr
145                 150                 155                 160

Tyr Ala Lys Met Trp Val Lys Val Lys Ser Thr Tyr Ser Leu Thr Ile
                165                 170                 175

Thr Ser Ala Glu Lys Ser Ala Leu Thr Thr Met Leu Asn Thr Cys
            180                 185                 190


<210> SEQ ID NO 188
<211> LENGTH: 191
```

```
<212> TYPE: PRT
<213> ORGANISM: Roussoella intermedia

<400> SEQUENCE: 188

Ala Pro Thr Pro Ala Leu Leu Pro Arg Ala Pro Pro Asn Ile Pro Ser
1               5                   10                  15

Thr Ala Thr Ala Lys Ser Gln Leu Ala Ala Leu Thr Val Ala Ala Gln
            20                  25                  30

Gly Pro Gln Asp Gly Tyr Ser Arg Asp Leu Phe Pro His Trp Ile Thr
        35                  40                  45

Gln Ser Gly Ser Cys Asn Thr Arg Glu Val Val Leu Lys Arg Asp Gly
    50                  55                  60

Thr Asn Val Val Gln Asp Ser Ser Cys Ala Ala Thr Ser Gly Thr Trp
65                  70                  75                  80

Val Ser Pro Phe Asp Gly Ala Thr Trp Thr Ala Ala Ser Asp Val Asp
                85                  90                  95

Ile Asp His Leu Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Leu Ala Val Thr Asp Glu Val Asn Gln Ala Lys Gly Asp
    130                 135                 140

Lys Gly Pro Glu Ala Trp Lys Pro Pro Leu Ala Ser Tyr His Cys Thr
145                 150                 155                 160

Tyr Ala Lys Met Trp Val Lys Val Lys Ser Thr Tyr Ser Leu Thr Ile
                165                 170                 175

Thr Ser Ala Glu Lys Ser Ala Leu Thr Thr Met Leu Asn Thr Cys
            180                 185                 190


<210> SEQ ID NO 189
<211> LENGTH: 792
<212> TYPE: DNA
<213> ORGANISM: Pleosporales species
<220> FEATURE:
<221> NAME/KEY: CDS
<222> LOCATION: (1)..(200)
<220> FEATURE:
<221> NAME/KEY: sig_peptide
<222> LOCATION: (1)..(48)
<220> FEATURE:
<221> NAME/KEY: mat_peptide
<222> LOCATION: (49)..(789)
<220> FEATURE:
<221> NAME/KEY: CDS
<222> LOCATION: (271)..(442)
<220> FEATURE:
<221> NAME/KEY: CDS
<222> LOCATION: (492)..(630)
<220> FEATURE:
<221> NAME/KEY: CDS
<222> LOCATION: (680)..(789)

<400> SEQUENCE: 189

atg aag tac acc atc ctc gct acg gcc ttt gtg gcc ctc gct gcg gcc       48
Met Lys Tyr Thr Ile Leu Ala Thr Ala Phe Val Ala Leu Ala Ala Ala
    -15                 -10                 -5                  -1

ctc ccg aca cct agt ctg gtc aag cga aca ccg cca aac atc ccg tcg       96
Leu Pro Thr Pro Ser Leu Val Lys Arg Thr Pro Pro Asn Ile Pro Ser
1               5                   10                  15

acc acc tcg gcc aag tct ctt ctt gct ggc ttg acc gtc gcc gct cag      144
Thr Thr Ser Ala Lys Ser Leu Leu Ala Gly Leu Thr Val Ala Ala Gln
            20                  25                  30
```

```
gga ccc cag gat ggc tac tcc cgt gac ttg ttc cct cac tgg atc act       192
Gly Pro Gln Asp Gly Tyr Ser Arg Asp Leu Phe Pro His Trp Ile Thr
        35                  40                  45

ata agc gg  gtaagcaagc ttcatctcca gtttcaatca tcaccagcat               240
Ile Ser Gly
    50

tgggagcata ttctgacgag ggggacatag a acg tgc aac acc cgc gag acg        292
                                   Thr Cys Asn Thr Arg Glu Thr
                                               55

gtt ctc aag cgc gac ggt acc aac gtc gta acc gac tcc gct tgc gcc       340
Val Leu Lys Arg Asp Gly Thr Asn Val Val Thr Asp Ser Ala Cys Ala
        60                  65                  70

tct acc tcc gga tct tgg tac tcg acc tac gac ggc gct acc tgg acc       388
Ser Thr Ser Gly Ser Trp Tyr Ser Thr Tyr Asp Gly Ala Thr Trp Thr
75                  80                  85                  90

gcc gct tct gac gtc gac att gac cac gtc gtt cct ctc tcg aat gct       436
Ala Ala Ser Asp Val Asp Ile Asp His Val Val Pro Leu Ser Asn Ala
                95                  100                 105

tgg aag gtattgtact cgtctatttc cctcaacttc ccacgctgac ccagaccag tcc     494
Trp Lys                                                         Ser

gga gcc gcg tcc tgg acc acc gcc cgc cgc cag tct ttc gct aac gac       542
Gly Ala Ala Ser Trp Thr Thr Ala Arg Arg Gln Ser Phe Ala Asn Asp
110                 115                 120                 125

ctg act aac cct caa ctg att gcc gtg acc gac agc gtc aac cag tcc       590
Leu Thr Asn Pro Gln Leu Ile Ala Val Thr Asp Ser Val Asn Gln Ser
                130                 135                 140

aag ggc gac aag ggc ccc gag tcc tgg aag ccc ccg cta a gtgagtcctg      640
Lys Gly Asp Lys Gly Pro Glu Ser Trp Lys Pro Pro Leu
                145                 150

gtctaatagt ttcgtagtcc tatgctgatg acaatatag cc  tcg tac cac tgc        693
                                              Thr Ser Tyr His Cys
                                                    155

acc tac gca aag atg tgg gtc aag gtc aag gac gtg tac agt ctg acc       741
Thr Tyr Ala Lys Met Trp Val Lys Val Lys Asp Val Tyr Ser Leu Thr
160                 165                 170                 175

gtc acg tct gcc gag aag tct gcc ttg acg acc atg ttg aac acc tgc       789
Val Thr Ser Ala Glu Lys Ser Ala Leu Thr Thr Met Leu Asn Thr Cys
                180                 185                 190

tga                                                                   792
```

<210> SEQ ID NO 190
<211> LENGTH: 207
<212> TYPE: PRT
<213> ORGANISM: Pleosporales species

<400> SEQUENCE: 190

```
Met Lys Tyr Thr Ile Leu Ala Thr Ala Phe Val Ala Leu Ala Ala Ala
        -15                 -10                 -5              -1

Leu Pro Thr Pro Ser Leu Val Lys Arg Thr Pro Pro Asn Ile Pro Ser
1               5                   10                  15

Thr Thr Ser Ala Lys Ser Leu Leu Ala Gly Leu Thr Val Ala Ala Gln
                20                  25                  30

Gly Pro Gln Asp Gly Tyr Ser Arg Asp Leu Phe Pro His Trp Ile Thr
                35                  40                  45

Ile Ser Gly Thr Cys Asn Thr Arg Glu Thr Val Leu Lys Arg Asp Gly
            50                  55                  60

Thr Asn Val Val Thr Asp Ser Ala Cys Ala Ser Thr Ser Gly Ser Trp
65                  70                  75                  80
```

```
Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Ile Ala Val Thr Asp Ser Val Asn Gln Ser Lys Gly Asp
    130                 135                 140

Lys Gly Pro Glu Ser Trp Lys Pro Pro Leu Thr Ser Tyr His Cys Thr
145                 150                 155                 160

Tyr Ala Lys Met Trp Val Lys Val Lys Asp Val Tyr Ser Leu Thr Val
                165                 170                 175

Thr Ser Ala Glu Lys Ser Ala Leu Thr Thr Met Leu Asn Thr Cys
            180                 185                 190


<210> SEQ ID NO 191
<211> LENGTH: 191
<212> TYPE: PRT
<213> ORGANISM: Pleosporales species

<400> SEQUENCE: 191

Leu Pro Thr Pro Ser Leu Val Lys Arg Thr Pro Pro Asn Ile Pro Ser
1               5                   10                  15

Thr Thr Ser Ala Lys Ser Leu Leu Ala Gly Leu Thr Val Ala Ala Gln
            20                  25                  30

Gly Pro Gln Asp Gly Tyr Ser Arg Asp Leu Phe Pro His Trp Ile Thr
        35                  40                  45

Ile Ser Gly Thr Cys Asn Thr Arg Glu Thr Val Leu Lys Arg Asp Gly
    50                  55                  60

Thr Asn Val Val Thr Asp Ser Ala Cys Ala Ser Thr Ser Gly Ser Trp
65                  70                  75                  80

Tyr Ser Thr Tyr Asp Gly Ala Thr Trp Thr Ala Ala Ser Asp Val Asp
                85                  90                  95

Ile Asp His Val Val Pro Leu Ser Asn Ala Trp Lys Ser Gly Ala Ala
            100                 105                 110

Ser Trp Thr Thr Ala Arg Arg Gln Ser Phe Ala Asn Asp Leu Thr Asn
        115                 120                 125

Pro Gln Leu Ile Ala Val Thr Asp Ser Val Asn Gln Ser Lys Gly Asp
    130                 135                 140

Lys Gly Pro Glu Ser Trp Lys Pro Pro Leu Thr Ser Tyr His Cys Thr
145                 150                 155                 160

Tyr Ala Lys Met Trp Val Lys Val Lys Asp Val Tyr Ser Leu Thr Val
                165                 170                 175

Thr Ser Ala Glu Lys Ser Ala Leu Thr Thr Met Leu Asn Thr Cys
            180                 185                 190


<210> SEQ ID NO 192
<211> LENGTH: 704
<212> TYPE: DNA
<213> ORGANISM: Phaeosphaeria species
<220> FEATURE:
<221> NAME/KEY: CDS
<222> LOCATION: (1)..(381)
<220> FEATURE:
<221> NAME/KEY: sig_peptide
<222> LOCATION: (1)..(54)
<220> FEATURE:
<221> NAME/KEY: mat_peptide
<222> LOCATION: (55)..(701)
```

```
<220> FEATURE:
<221> NAME/KEY: CDS
<222> LOCATION: (453)..(701)

<400> SEQUENCE: 192

atg aaa tcc gcc ctc ctt ctt gcc atc gcc tca acg gca acc ctc atc       48
Met Lys Ser Ala Leu Leu Leu Ala Ile Ala Ser Thr Ala Thr Leu Ile
            -15                 -10                 -5

tct gcc ctc cct gcc cct atc cac ctc act gct cgg gca cca cca aac       96
Ser Ala Leu Pro Ala Pro Ile His Leu Thr Ala Arg Ala Pro Pro Asn
    -1  1               5                   10

atc ccg tcc gcc tcc gaa gct cgc act caa ctt gcc ggc ctg acc gtc      144
Ile Pro Ser Ala Ser Glu Ala Arg Thr Gln Leu Ala Gly Leu Thr Val
15                  20                  25                  30

gcc gct caa ggc ccg cag gat ggc tac tcg cgc gac ctc ttc ccg cac      192
Ala Ala Gln Gly Pro Gln Asp Gly Tyr Ser Arg Asp Leu Phe Pro His
                35                  40                  45

tgg atc acg caa tct ggg aca tgt aac acg cga gaa acc gtg ctc aag      240
Trp Ile Thr Gln Ser Gly Thr Cys Asn Thr Arg Glu Thr Val Leu Lys
            50                  55                  60

cgg gac ggc acg aac gtc gtt acg aac tcc gcc tgc gcg agc acc agt      288
Arg Asp Gly Thr Asn Val Val Thr Asn Ser Ala Cys Ala Ser Thr Ser
        65                  70                  75

gga agc tgg ttc agc ccg tac gac gga gcg aca tgg aca gca gcg tct      336
Gly Ser Trp Phe Ser Pro Tyr Asp Gly Ala Thr Trp Thr Ala Ala Ser
    80                  85                  90

gac gtc gac att gac cat atg gta ccg ttg agc aat gcc tgg aaa          381
Asp Val Asp Ile Asp His Met Val Pro Leu Ser Asn Ala Trp Lys
95                  100                 105

gtacgtcttc agccttcccc tttttcccat tccaatttcc cctcttgtac atccgctaat    441

caacattgca g tcc ggt gcc gcg tcc tgg acc acg gcc cgc cgc cag gcc     491
             Ser Gly Ala Ala Ser Trp Thr Thr Ala Arg Arg Gln Ala
             110                 115                 120

ttt gca aac gac ctg act aac ccg cag ctc ctc gcc gtc acg gac aac      539
Phe Ala Asn Asp Leu Thr Asn Pro Gln Leu Leu Ala Val Thr Asp Asn
        125                 130                 135

gtc aac caa gca aaa ggc gac aag ggc ccc gag gac tgg aaa ccc ccg      587
Val Asn Gln Ala Lys Gly Asp Lys Gly Pro Glu Asp Trp Lys Pro Pro
    140                 145                 150

ctt aca agc tac tac tgc acg tat gcg cgg atg tgg gtc aag gta aag      635
Leu Thr Ser Tyr Tyr Cys Thr Tyr Ala Arg Met Trp Val Lys Val Lys
155                 160                 165                 170

agt gtg tat gcc ctg acg gta acg agc gcg gag aag agc gct ttg acg      683
Ser Val Tyr Ala Leu Thr Val Thr Ser Ala Glu Lys Ser Ala Leu Thr
                175                 180                 185

agc atg ttg ggc act tgt tga                                          704
Ser Met Leu Gly Thr Cys
            190


<210> SEQ ID NO 193
<211> LENGTH: 210
<212> TYPE: PRT
<213> ORGANISM: Phaeosphaeria species

<400> SEQUENCE: 193

Met Lys Ser Ala Leu Leu Leu Ala Ile Ala Ser Thr Ala Thr Leu Ile
            -15                 -10                 -5

Ser Ala Leu Pro Ala Pro Ile His Leu Thr Ala Arg Ala Pro Pro Asn
    -1  1               5                   10

Ile Pro Ser Ala Ser Glu Ala Arg Thr Gln Leu Ala Gly Leu Thr Val
```

```
15                  20                  25                  30

Ala Ala Gln Gly Pro Gln Asp Gly Tyr Ser Arg Asp Leu Phe Pro His
                35                  40                  45

Trp Ile Thr Gln Ser Gly Thr Cys Asn Thr Arg Glu Thr Val Leu Lys
            50                  55                  60

Arg Asp Gly Thr Asn Val Val Thr Asn Ser Ala Cys Ala Ser Thr Ser
        65                  70                  75

Gly Ser Trp Phe Ser Pro Tyr Asp Gly Ala Thr Trp Thr Ala Ala Ser
    80                  85                  90

Asp Val Asp Ile Asp His Met Val Pro Leu Ser Asn Ala Trp Lys Ser
95                  100                 105                 110

Gly Ala Ala Ser Trp Thr Thr Ala Arg Arg Gln Ala Phe Ala Asn Asp
                115                 120                 125

Leu Thr Asn Pro Gln Leu Leu Ala Val Thr Asp Asn Val Asn Gln Ala
            130                 135                 140

Lys Gly Asp Lys Gly Pro Glu Asp Trp Lys Pro Pro Leu Thr Ser Tyr
        145                 150                 155

Tyr Cys Thr Tyr Ala Arg Met Trp Val Lys Val Lys Ser Val Tyr Ala
    160                 165                 170

Leu Thr Val Thr Ser Ala Glu Lys Ser Ala Leu Thr Ser Met Leu Gly
175                 180                 185                 190

Thr Cys


<210> SEQ ID NO 194
<211> LENGTH: 192
<212> TYPE: PRT
<213> ORGANISM: Phaeosphaeria species

<400> SEQUENCE: 194

Leu Pro Ala Pro Ile His Leu Thr Ala Arg Ala Pro Pro Asn Ile Pro
1               5                   10                  15

Ser Ala Ser Glu Ala Arg Thr Gln Leu Ala Gly Leu Thr Val Ala Ala
            20                  25                  30

Gln Gly Pro Gln Asp Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Val Thr Asn Ser Ala Cys Ala Ser Thr Ser Gly Ser
65                  70                  75                  80

Trp Phe Ser Pro Tyr Asp Gly Ala Thr Trp Thr Ala Ala Ser Asp Val
                85                  90                  95

Asp Ile Asp His Met Val Pro Leu Ser Asn Ala Trp Lys Ser Gly Ala
            100                 105                 110

Ala Ser Trp Thr Thr Ala Arg Arg Gln Ala Phe Ala Asn Asp Leu Thr
        115                 120                 125

Asn Pro Gln Leu Leu Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Arg Met Trp Val Lys Val Lys Ser Val Tyr Ala Leu Thr
                165                 170                 175

Val Thr Ser Ala Glu Lys Ser Ala Leu Thr Ser Met Leu Gly Thr Cys
            180                 185                 190
```

```
<210> SEQ ID NO 195
<211> LENGTH: 889
<212> TYPE: DNA
<213> ORGANISM: Didymosphaeria futilis
<220> FEATURE:
<221> NAME/KEY: CDS
<222> LOCATION: (1)..(237)
<220> FEATURE:
<221> NAME/KEY: sig_peptide
<222> LOCATION: (1)..(51)
<220> FEATURE:
<221> NAME/KEY: mat_peptide
<222> LOCATION: (52)..(886)
<220> FEATURE:
<221> NAME/KEY: CDS
<222> LOCATION: (297)..(437)
<220> FEATURE:
<221> NAME/KEY: CDS
<222> LOCATION: (491)..(622)
<220> FEATURE:
<221> NAME/KEY: CDS
<222> LOCATION: (679)..(712)
<220> FEATURE:
<221> NAME/KEY: CDS
<222> LOCATION: (772)..(837)
<220> FEATURE:
<221> NAME/KEY: CDS
<222> LOCATION: (879)..(886)

<400> SEQUENCE: 195

atg aag tcc act ctt ctc att gct ctg ttc tct cca gcc tta gtg gca       48
Met Lys Ser Thr Leu Leu Ile Ala Leu Phe Ser Pro Ala Leu Val Ala
        -15                 -10                 -5

gcc ttg ccc acg cct aac acc ctt gag gct cgt gca ccc cca aac att       96
Ala Leu Pro Thr Pro Asn Thr Leu Glu Ala Arg Ala Pro Pro Asn Ile
-1  1               5                   10                  15

cct tca aca tca gcc gcc caa tct cag ctt tct gca tta acg gta gct      144
Pro Ser Thr Ser Ala Ala Gln Ser Gln Leu Ser Ala Leu Thr Val Ala
                20                  25                  30

gct cag gga cca caa aca ggt tac tct cgt gat ctc ttt cct cac tgg      192
Ala Gln Gly Pro Gln Thr Gly Tyr Ser Arg Asp Leu Phe Pro His Trp
            35                  40                  45

atc acc cag tct gga act tgc aac aca agg gag aca gtc ttg aag          237
Ile Thr Gln Ser Gly Thr Cys Asn Thr Arg Glu Thr Val Leu Lys
        50                  55                  60

gtcagtcgaa ggtcccgata tgagtggcgt ctatttcatt tgaataacgc agtatgcag     296

cgc gac ggc acg aac gtt cta act gac tct gcg tgt gcg tca act tct      344
Arg Asp Gly Thr Asn Val Leu Thr Asp Ser Ala Cys Ala Ser Thr Ser
        65                  70                  75

ggg tca tgg aag agt cca tat gac ggt gca acg tgg act gct gcc agc      392
Gly Ser Trp Lys Ser Pro Tyr Asp Gly Ala Thr Trp Thr Ala Ala Ser
    80                  85                  90

gac gtc gac atc gac cac gtc gtc cca ttg agc aac gct tgg aag          437
Asp Val Asp Ile Asp His Val Val Pro Leu Ser Asn Ala Trp Lys
95                  100                 105

gtgcggaccg tacaaataag ttaatagtgc ttgtgtgtct aacgaaagta cag tcc       493
                                                           Ser
                                                           110

gga gca gca agc tgg act act gct cgc cgc cag tca ttt gcc aac gac      541
Gly Ala Ala Ser Trp Thr Thr Ala Arg Arg Gln Ser Phe Ala Asn Asp
                115                 120                 125

ctg acc aac cca cag ctg att gca gta aca gat aat gtg aac caa gct      589
Leu Thr Asn Pro Gln Leu Ile Ala Val Thr Asp Asn Val Asn Gln Ala
            130                 135                 140

aag ggt gat aag gga ccc gaa gac tgg aag cca gtacgtttca aatgtcctca    642
Lys Gly Asp Lys Gly Pro Glu Asp Trp Lys Pro
```

```
        145                 150

ggttcacgag acattggtca tactaacctt cgtcag ccg cta aca agc tac tac      696
                                        Pro Leu Thr Ser Tyr Tyr
                                            155

tgc acc tat gca aag a gtaagtgctc catattacgt tgacatacca tttgacttca    752
Cys Thr Tyr Ala Lys
160

gttctaatta tgcggacag tg  tgg gtt aag gtc aag agc gtc tac agc ctg     803
                     Met Trp Val Lys Val Lys Ser Val Tyr Ser Leu
                     165                 170                 175

aca att aca agt gct gag aag agt gca ctg acg a gtatgttgaa             847
Thr Ile Thr Ser Ala Glu Lys Ser Ala Leu Thr
                180                 185

cacctgttag ttggctctaa taggttgcca g tg  ttg gca tag                   889
                                   Met Leu Ala
```

<210> SEQ ID NO 196
<211> LENGTH: 206
<212> TYPE: PRT
<213> ORGANISM: Didymosphaeria futilis

<400> SEQUENCE: 196

```
Met Lys Ser Thr Leu Leu Ile Ala Leu Phe Ser Pro Ala Leu Val Ala
        -15                 -10                 -5

Ala Leu Pro Thr Pro Asn Thr Leu Glu Ala Arg Ala Pro Pro Asn Ile
-1  1               5                   10                  15

Pro Ser Thr Ser Ala Ala Gln Ser Gln Leu Ser Ala Leu Thr Val Ala
                20                  25                  30

Ala Gln Gly Pro Gln Thr Gly Tyr Ser Arg Asp Leu Phe Pro His Trp
            35                  40                  45

Ile Thr Gln Ser Gly Thr Cys Asn Thr Arg Glu Thr Val Leu Lys Arg
        50                  55                  60

Asp Gly Thr Asn Val Leu Thr Asp Ser Ala Cys Ala Ser Thr Ser Gly
    65                  70                  75

Ser Trp Lys Ser Pro Tyr Asp Gly Ala Thr Trp Thr Ala Ala Ser Asp
80                  85                  90                  95

Val Asp Ile Asp His Val Val Pro Leu Ser Asn Ala Trp Lys Ser Gly
                100                 105                 110

Ala Ala Ser Trp Thr Thr Ala Arg Arg Gln Ser Phe Ala Asn Asp Leu
            115                 120                 125

Thr Asn Pro Gln Leu Ile Ala Val Thr Asp Asn Val Asn Gln Ala Lys
        130                 135                 140

Gly Asp Lys Gly Pro Glu Asp Trp Lys Pro Pro Leu Thr Ser Tyr Tyr
    145                 150                 155

Cys Thr Tyr Ala Lys Met Trp Val Lys Val Lys Ser Val Tyr Ser Leu
160                 165                 170                 175

Thr Ile Thr Ser Ala Glu Lys Ser Ala Leu Thr Met Leu Ala
                180                 185
```

<210> SEQ ID NO 197
<211> LENGTH: 189
<212> TYPE: PRT
<213> ORGANISM: Didymosphaeria futilis

<400> SEQUENCE: 197

```
Leu Pro Thr Pro Asn Thr Leu Glu Ala Arg Ala Pro Pro Asn Ile Pro
1               5                   10                  15
```

```
Ser Thr Ser Ala Ala Gln Ser Gln Leu Ser Ala Leu Thr Val Ala Ala
            20                  25                  30

Gln Gly Pro Gln Thr Gly Tyr Ser Arg Asp Leu Phe Pro His Trp Ile
        35                  40                  45

Thr Gln Ser Gly Thr Cys Asn Thr Arg Glu Thr Val Leu Lys Arg Asp
    50                  55                  60

Gly Thr Asn Val Leu Thr Asp Ser Ala Cys Ala Ser Thr Ser Gly Ser
65                  70                  75                  80

Trp Lys Ser Pro Tyr Asp Gly Ala Thr Trp Thr Ala Ala Ser Asp Val
                85                  90                  95

Asp Ile Asp His Val Val Pro Leu Ser Asn Ala Trp Lys Ser Gly Ala
            100                 105                 110

Ala Ser Trp Thr Thr Ala Arg Arg Gln Ser Phe Ala Asn Asp Leu Thr
        115                 120                 125

Asn Pro Gln Leu Ile Ala Val Thr Asp Asn Val Asn Gln Ala Lys Gly
    130                 135                 140

Asp Lys Gly Pro Glu Asp Trp Lys Pro Pro Leu Thr Ser Tyr Tyr Cys
145                 150                 155                 160

Thr Tyr Ala Lys Met Trp Val Lys Val Lys Ser Val Tyr Ser Leu Thr
                165                 170                 175

Ile Thr Ser Ala Glu Lys Ser Ala Leu Thr Met Leu Ala
            180                 185


<210> SEQ ID NO 198
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Thr (T) or Asp (D) or Ser (S)
<220> FEATURE:
<221> NAME/KEY: MISC_FEATURE
<222> LOCATION: (2)..(2)
<223> OTHER INFORMATION: Xaa = Gly (G) or Asn (N)

<400> SEQUENCE: 198

Xaa Xaa Pro Gln Leu
1               5


<210> SEQ ID NO 199
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Gly (G) or Thr (T)
<220> FEATURE:
<221> NAME/KEY: MISC_FEATURE
<222> LOCATION: (3)..(3)
<223> OTHER INFORMATION: Xaa = Asp (D) or Ser (S)
<220> FEATURE:
<221> NAME/KEY: MISC_FEATURE
<222> LOCATION: (4)..(4)
<223> OTHER INFORMATION: Xaa = Arg (R) or Lys (K) or Leu (L)

<400> SEQUENCE: 199

Xaa Tyr Xaa Xaa
1
```

<210> SEQ ID NO 200
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Glu (E) or Asp (D) or His (H)
<220> FEATURE:
<221> NAME/KEY: MISC_FEATURE
<222> LOCATION: (3)..(3)
<223> OTHER INFORMATION: Xaa = Ile (I) or Val (V) or Leu (L) or Phe (F) or Met (M)
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Pro (P) or Ala (A) or Ser (S)

<400> SEQUENCE: 200

Xaa His Xaa Xaa Xaa
1 5

<210> SEQ ID NO 201
<211> LENGTH: 5
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Phe (F) or Leu (L) or Tyr (Y) or Ile (I)
<220> FEATURE:
<221> NAME/KEY: MISC_FEATURE
<222> LOCATION: (3)..(3)
<223> OTHER INFORMATION: Xaa = Asn (N) or Arg (R)
<220> FEATURE:
<221> NAME/KEY: MISC_FEATURE
<222> LOCATION: (5)..(5)
<223> OTHER INFORMATION: Xaa = Leu (L) or Ile (I) or Pro (P) or Val (V)

<400> SEQUENCE: 201

Xaa Ala Xaa Asp Xaa
1 5

<210> SEQ ID NO 202
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa= Asp (D) or Asn (N)
<220> FEATURE:
<221> NAME/KEY: MISC_FEATURE
<222> LOCATION: (4)..(4)
<223> OTHER INFORMATION: Xaa= Ala (A) or Arg (R)

<400> SEQUENCE: 202

Cys Xaa Thr Xaa
1

<210> SEQ ID NO 203
<211> LENGTH: 4

<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp (D) or Gln (Q)
<220> FEATURE:
<221> NAME/KEY: MISC_FEATURE
<222> LOCATION: (2)..(2)
<223> OTHER INFORMATION: Xaa = Ile (I) or Val (V)

<400> SEQUENCE: 203

Xaa Xaa Asp His
1

<210> SEQ ID NO 204
<211> LENGTH: 7
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Asp (D) or Met (M) or Leu (L)
<220> FEATURE:
<221> NAME/KEY: MISC_FEATURE
<222> LOCATION: (2)..(2)
<223> OTHER INFORMATION: Xaa = Ser (S) or Thr (T)
<220> FEATURE:
<221> NAME/KEY: MISC_FEATURE
<222> LOCATION: (7)..(7)
<223> OTHER INFORMATION: Xaa = Asp (D) or Asn (N)

<400> SEQUENCE: 204

Xaa Xaa Gly Tyr Ser Arg Xaa
1 5

<210> SEQ ID NO 205
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa = any amino acid

<400> SEQUENCE: 205

Ala Ser Xaa Asn Arg Ser Lys Gly
1 5

<210> SEQ ID NO 206
<211> LENGTH: 8
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa = Val (V) or Ile (I)
<220> FEATURE:
<221> NAME/KEY: MISC_FEATURE
<222> LOCATION: (4)..(4)
<223> OTHER INFORMATION: Xaa = Ser (S) or Ala (A)

<400> SEQUENCE: 206

Xaa Pro Leu Xaa Asn Ala Trp Lys
1 5

<210> SEQ ID NO 207
<211> LENGTH: 4
<212> TYPE: PRT
<213> ORGANISM: Artificial sequence
<220> FEATURE:
<223> OTHER INFORMATION: Synthetic construct

<400> SEQUENCE: 207

Asn Pro Gln Leu
1

<210> SEQ ID NO 208
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa = Gln (Q) or Glu(E)
<220> FEATURE:
<221> NAME/KEY: MISC_FEATURE
<222> LOCATION: (4)..(4)
<223> OTHER INFORMATION: Xaa = Trp (W) or Tyr (Y)

<400> SEQUENCE: 208

Pro Xaa Leu Xaa
1

<210> SEQ ID NO 209
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa=Lys (K) or His (H) or Glu (E)

<400> SEQUENCE: 209

Xaa Asn Ala Trp
1

<210> SEQ ID NO 210
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 210

His Xaa Xaa Pro
1

POLYPEPTIDES

CROSS-REFERENCE TO RELATED APPLICATIONS

This application is a 35 U.S.C. 371 national application of PCT/EP2016/074079 filed Oct. 7, 2016, which claims priority or the benefit under 35 U.S.C. 119 of Denmark application nos. PA 2015 00615, PA 2015 00617 and PA 2015 00618, all filed on Oct. 7, 2015, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to new polypeptides having deoxyribonuclease (DNase) activity, nucleotides encoding the polypeptide, as well as methods of producing the polypeptides. The present invention also relates to detergent composition comprising a DNase, a laundering method and the use of DNase.

BACKGROUND OF THE INVENTION

Microorganisms generally live attached to surfaces in many natural, industrial, and medical environments, encapsulated by extracellular substances including biopolymers and macromolecules. The resulting layer of slime encapsulated microorganism is termed a biofilm. Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

A biofilm may include one or more microorganisms, including gram-positive and gram-negative bacteria, algae, protozoa, and/or yeast or filamentous fungi and viruses and/or bacteriophage. Examples of problematic biofilms are dental plaque, infections on medical implants, but also the initial fouling on ship hulls. Biofilms are attributed to the pathogenesis of many infections in humans and are a significant problem in industry in terms of biofouling of exposed surfaces, where biofilm colonization can form the base component of a localized ecosystem which can disrupt and interfere with industrial processes and components.

When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof the laundry item is more "soiled" after wash than before wash. Further, these bacteria are a source of bad odor, which develops after use of the laundry item. The bad odor (malodor) is difficult to remove and may remain even after wash. The reason for this bad odor is adhesion of bacteria to the textile surface. Because of the adhesion to the textile, the bacteria may remain even after wash, and continue to be a source of bad odor.

International patent applications WO 2011/098579 (University of Newcastle) and WO 2014/087011 (Novozymes A/S) relates to deoxyribonuclease compounds and methods for biofilm disruption and prevention.

SUMMARY OF THE INVENTION

The invention relates to novel polypeptides having DNase (deoxyribonuclease) activity and the polynucleotides encoding these. One aspect of the invention relates to a composition comprising at least 0.002 ppm of a polypeptide having DNase activity, wherein the polypeptide comprises the motif HXXP, where H is histidine, P is proline and X is any amino acid, wherein the composition further comprises; one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, and/or ii. optionally one or more enzyme, preferably selected from proteases, amylases or lipases, iii. optionally one or more surfactant, preferably selected from anionic and nonionic surfactants, iv. optionally one or more polymer;

Another aspect of the invention relates to a granule comprising i. a core comprising a polypeptide having DNase activity and optionally, ii. a coating consisting of one or more layer(s) surrounding the core.

In one aspect of the invention the granule comprise a polypeptide having DNase activity and wherein the polypeptide comprises one or more of the motifs selected from the motifs [T/D/S][G/N]PQL (SEQ ID NO 198), [G/T]Y[D/S][R/K/L] (SEQ ID NO 199), [E/D/H]H[I/V/L/F/M]X[P/A/S] (SEQ ID NO 200), [F/L/Y/I]A[N/R]D[L/I/P/V] (SEQ ID NO: 201) and C[D/N]T[A/R] (SEQ ID NO: 202) and wherein the granule comprises a core comprising said polypeptide and a coating.

In one aspect the invention relates to a composition comprising a polypeptide having DNase activity wherein the polypeptide comprises one or more of the motifs selected from the motifs [T/D/S][G/N]PQL (SEQ ID NO 198), [G/T]Y[D/S][R/K/L] (SEQ ID NO 199), [E/D/H]H[I/V/L/F/M]X[P/A/S] (SEQ ID NO 200), [F/L/Y/I]A[N/R]D[L/I/P/V] (SEQ ID NO: 201) and C[D/N]T[A/R] (SEQ ID NO: 202).

In one aspect the invention relates to a composition, wherein the polypeptide having DNase activity belongs to the GYS clade, comprises one or both of the motifs [D/M/L][S/T]GYSR[D/N] (SEQ ID NO: 204) or ASXNRSKG (SEQ ID NO: 205).

In one aspect the composition comprises a polypeptide wherein the polypeptide has DNase activity, wherein the polypeptide comprises one or both of the motifs [D/M/L][S/T]GYSR[D/N] (SEQ ID NO: 204) or ASXNRSKG (SEQ ID NO: 205) and wherein the polypeptide comprises, consists essentially of or consists of an amino acid sequence selected from the group consisting of SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77 and SEQ ID NO 80 or polypeptides having at least 80% sequence identity hereto.

In one aspect the composition comprises a polypeptide has DNase activity and which belongs to the NAWK clade and comprises one or both of the motifs [V/I]PL[S/A]NAWK(SEQ ID NO: 206) or NPQL (SEQ ID NO: 207).

In one aspect the composition comprises a polypeptide wherein the polypeptide has DNase activity, wherein the polypeptide comprises one or both of the motifs [V/I]PL[S/A]NAWK(SEQ ID NO: 206) or NPQL (SEQ ID NO: 207) and wherein the polypeptide comprises, consists essentially of or consists of an amino acid sequence selected from the group consisting of SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 or polypeptides having at least 80% sequence identity hereto.

In one aspect the composition comprises a polypeptide having DNase activity and which belongs to the KNAW clade and comprises one or both of the motifs P[Q/E]L[W/Y] (SEQ ID NO: 208) or [K/H/E]NAW (SEQ ID NO: 209).

In one aspect composition comprises a polypeptide wherein the polypeptide has DNase activity wherein the polypeptide comprises P[Q/E]L[W/Y] (SEQ ID NO: 208) or [K/H/E]NAW (SEQ ID NO: 209) and wherein the polypeptide comprises, consists essentially of or consists of an amino acid sequence selected from the group consisting of SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 80% sequence identity hereto.

In one aspect the composition is a cleaning composition such as a laundry or dish wash composition.

One aspect of the invention relates to a polypeptide having DNase activity, wherein the polypeptide comprises the motif HXXP, where H is histidine and wherein P is proline and X is any amino acid.

In one aspect the polypeptide having DNase activity comprises the one or more motif selected from the group of motifs consisting of [T/D/S][G/N]PQL (SEQ ID NO 198), [G/T]Y[D/S][R/K/L] (SEQ ID NO 199), [E/D/H]H[I/V/L/F/M]X[P/A/S] (SEQ ID NO 200), [F/L/Y/I]A[N/R]D[L/I/P/V] (SEQ ID NO: 201) and C[D/N]T[A/R] (SEQ ID NO: 202).

In one aspect of the invention the polypeptide having DNase activity belongs to the GYS clade and comprises one or both of the motifs [D/M/L][S/T]GYSR[D/N] (SEQ ID NO: 204) or ASXNRSKG (SEQ ID NO:205).

In one aspect the polypeptide is selected from the group consisting of the polypeptides shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77 and SEQ ID NO 80 or polypeptides having at least 98% sequence identity hereto.

In one aspect of the invention the polypeptide having DNase activity belongs to the NAWK clade and wherein the polypeptide comprises one or both of the motifs [V/I]PL[S/A]NAWK (SEQ ID NO: 206) or NPQL (SEQ ID NO: 207).

In one aspect the polypeptide comprises any of the motifs [V/I]PL[S/A]NAWK (SEQ ID NO: 206) or NPQL (SEQ ID NO: 207) and is selected from the group consisting of the polypeptides shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 and polypeptides having at least 95% sequence identity hereto. In one aspect of the invention the polypeptide having DNase activity belongs to the KNAW clade and comprises one or both of the motifs selected from the motifs P[Q/E]L[W/Y] (SEQ ID NO: 208) or [K/H/E]NAW (SEQ ID NO: 209).

In one aspect the polypeptide comprises the motifs P[Q/E]L[W/Y] (SEQ ID NO: 208) or [K/H/E]NAW (SEQ ID NO: 209) and is selected from the group consisting of the polypeptides shown in SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 98% sequence identity hereto.

One aspect of the invention relates to a polynucleotide encoding a polypeptide of the invention. The invention further relates to nucleic acid construct or expression vector comprising the polynucleotide. The invention further relates to a host cell comprising a polypeptide of the invention.

One aspect relates to the use of a polypeptide of the invention for reduction or removal of a biofilm from an item, such as textile, preferably is a cleaning process such as laundry.

One aspect relates to a method of producing the polypeptide of the invention, comprising:

(a) cultivating the recombinant host cell under conditions conducive for production of the polypeptide; and (b) recovering the polypeptide.

The invention further relates to (a) a polypeptide having at least 60% sequence identity to the mature polypeptide of SEQ ID NO: 2, 4 or 6;

(b) a polypeptide encoded by a polynucleotide having at least 60% sequence identity to the mature polypeptide coding sequence of SEQ ID NO: 1, 3 or 5;

(c) a variant of the mature polypeptide of SEQ ID NO: 2, 4 or 6 comprising a substitution, deletion, and/or insertion at one or more positions; and (d) a fragment of the polypeptide of (a), (b) or (c), which has DNase activity.

In another aspect, the invention relates to detergent compositions comprising a polypeptide having DNase activity and preferably a detergent adjunct ingredient. One aspect of the invention relates to a composition comprising a polypeptide having DNases activity with at least 60% sequence identity to the mature polypeptide of SEQ ID NO: 2, 4 or 6 and a detergent adjunct.

The invention further relates to a cleaning or laundering method for cleaning or laundering an item comprising the steps of:

a. Exposing an item to a wash liquor comprising a polypeptide having DNase activity or a detergent composition comprising the polypeptide having DNase activity;

b. Completing at least one wash cycle; and c. Optionally rinsing the item, wherein the item is a textile and wherein the polypeptide having DNase activity is a polypeptide with at least 60% sequence identity to the polypeptide of SEQ ID NO: 8, 9 or 10.

In addition, is claimed the use of DNase for preventing, reducing or removing the biofilm of an item.

The present invention further relates to nucleotides encoding the polypeptides and methods of producing the polypeptides.

Sequences

SEQ ID NO 1 DNA sequence obtained from *Bacillus* sp-62451

SEQ ID NO 2 is the polypeptide sequence derived from SEQ ID NO 1

SEQ ID NO 3 DNA sequence obtained from *Bacillus horikoshii*

SEQ ID NO 4 is the polypeptide sequence derived from SEQ ID NO 3

SEQ ID NO 5 DNA sequence obtained from *Paenibacillus* sp-18057

SEQ ID NO 6 is the polypeptide sequence derived from SEQ ID NO 3

SEQ ID NO 7 mature polypeptide Benzonase DNase (WO 2011/098579)

SEQ ID NO 8 mature polypeptide of SEQ ID NO 2 obtained from *Bacillus* sp-62451

SEQ ID NO 9 mature polypeptide of SEQ ID NO 4 obtained from *Bacillus horikoshii*

SEQ ID NO 10 mature polypeptide of SEQ ID NO 6 obtained from *Paenibacillus* sp-18057

SEQ ID NO 11 mature polypeptide obtained from *Bacillus* sp-62520

SEQ ID NO 12 mature polypeptide obtained from *Bacillus* sp-62520

SEQ ID NO 13 mature polypeptide obtained from *Bacillus horikoshii*

SEQ ID NO 14 mature polypeptide obtained from *Bacillus horikoshii*

SEQ ID NO 15 mature polypeptide obtained from *Bacillus* sp-16840

SEQ ID NO 16 mature polypeptide obtained from *Bacillus* sp-16840

SEQ ID NO 17 mature polypeptide obtained from *Bacillus* sp-62668

SEQ ID NO 18 mature polypeptide obtained from *Bacillus* sp-13395

SEQ ID NO 19 mature polypeptide obtained from *Bacillus horneckiae*

SEQ ID NO 20 mature polypeptide obtained from *Bacillus* sp-11238

SEQ ID NO 21 mature polypeptide obtained from *Bacillus cibi*

SEQ ID NO 22 mature polypeptide obtained from *Bacillus* sp-18318

SEQ ID NO 23 mature polypeptide obtained from *Bacillus idriensis*

SEQ ID NO 24 is *Bacillus clausii* secretion signal

SEQ ID NO 25 DNA sequence obtained from *Bacillus* sp-62520

SEQ ID NO 26 polypeptide sequence derived from SEQ ID NO: 25

SEQ ID NO 27 DNA sequence obtained from *Bacillus* sp-62520

SEQ ID NO 28 polypeptide sequence derived from SEQ ID NO: 27

SEQ ID NO 29 DNA sequence obtained from *Bacillus horikoshii*

SEQ ID NO 30 polypeptide sequence derived from SEQ ID NO: 29

SEQ ID NO 31 DNA sequence obtained from *Bacillus horikoshii*

SEQ ID NO 32 polypeptide sequence derived from SEQ ID NO: 31

SEQ ID NO 33 DNA sequence obtained from *Bacillus* sp-16840

SEQ ID NO 34 polypeptide sequence derived from SEQ ID NO: 33

SEQ ID NO 35 DNA sequence obtained from *Bacillus* sp-16840

SEQ ID NO 36 polypeptide sequence derived from SEQ ID NO: 35

SEQ ID NO 37 DNA sequence obtained from *Bacillus* sp-62668

SEQ ID NO 38 polypeptide sequence derived from SEQ ID NO: 37

SEQ ID NO 39 DNA sequence obtained from *Bacillus* sp-13395

SEQ ID NO 40 polypeptide sequence derived from SEQ ID NO: 39

SEQ ID NO 41 DNA sequence obtained from *Bacillus horneckiae*

SEQ ID NO 42 polypeptide sequence derived from SEQ ID NO: 41

SEQ ID NO 43 DNA sequence obtained from *Bacillus* sp-11238

SEQ ID NO 44 polypeptide sequence derived from SEQ ID NO: 43

SEQ ID NO 45 DNA sequence obtained from *Bacillus cibi*

SEQ ID NO 46 polypeptide sequence derived from SEQ ID NO: 45

SEQ ID NO 47 DNA sequence obtained from *Bacillus* sp-18318

SEQ ID NO 48 polypeptide sequence derived from SEQ ID NO: 47

SEQ ID NO 49 DNA sequence obtained from *Bacillus idriensis*

SEQ ID NO 50 polypeptide sequence derived from SEQ ID NO: 49

SEQ ID NO 51 DNA sequence obtained from *Bacillus algicola*

SEQ ID NO 52 polypeptide sequence derived from SEQ ID NO: 51

SEQ ID NO 53 is the mature polypeptide obtained from *Bacillus algicola*

SEQ ID NO 54 DNA sequence derived from Xanthan alkaline community J

SEQ ID NO 55 polypeptide sequence derived from SEQ ID NO: 54

SEQ ID NO 56 mature polypeptide obtained from Xanthan alkaline community J

SEQ ID NO 57 DNA sequence obtained from *Bacillus vietnamensis*

SEQ ID NO 58 polypeptide sequence derived from SEQ ID NO: 57

SEQ ID NO 59 mature polypeptide obtained from *Bacillus vietnamensis*

SEQ ID NO 60 DNA sequence obtained from *Bacillus hwajinpoensis*

SEQ ID NO 61 polypeptide sequence derived from SEQ ID NO: 60

SEQ ID NO 62 mature polypeptide obtained from *Bacillus hwajinpoensis*

SEQ ID NO 63 DNA sequence obtained from *Paenibacillus mucilaginosus*

SEQ ID NO 64 polypeptide sequence derived from SEQ ID NO: 63

SEQ ID NO 65 mature polypeptide obtained from *Paenibacillus mucilaginosus*

SEQ ID NO 66 DNA sequence obtained from *Bacillus indicus*

SEQ ID NO 67 polypeptide sequence derived from SEQ ID NO: 66

SEQ ID NO 68 mature polypeptide obtained from *Bacillus indicus*

SEQ ID NO 69 DNA sequence obtained from *Bacillus marisflavi*

SEQ ID NO 70 polypeptide sequence derived from SEQ ID NO: 69

SEQ ID NO 71 Mature polypeptide obtained from *Bacillus marisflavi*

SEQ ID NO 72 DNA sequence obtained from *Bacillus luciferensis*

SEQ ID NO 73 polypeptide sequence derived from SEQ ID NO: 72

SEQ ID NO 74 mature polypeptide obtained from *Bacillus luciferensis*

SEQ ID NO 75 DNA sequence obtained from *Bacillus marisflavi*

SEQ ID NO 76 polypeptide sequence derived from SEQ ID NO: 75

SEQ ID NO 77 mature polypeptide obtained from *Bacillus marisflavi*

SEQ ID NO 78 DNA sequence obtained from *Bacillus* sp. SA2-6

SEQ ID NO 79 polypeptide sequence derived from SEQ ID NO: 78

SEQ ID NO 80 mature polypeptide obtained from *Bacillus* sp. SA2-6

SEQ ID NO 81 DNA sequence obtained from *Pyrenochaetopsis* sp.

SEQ ID NO 82 polypeptide sequence derived from SEQ ID NO: 81

SEQ ID NO 83 mature polypeptide obtained from *Pyrenochaetopsis* sp.

SEQ ID NO 84 DNA sequence obtained from *Vibrissea flavovirens*

SEQ ID NO 85 polypeptide sequence derived from SEQ ID NO: 84

SEQ ID NO 86 mature polypeptide obtained from *Vibrissea flavovirens*

SEQ ID NO 87 DNA sequence obtained from *Setosphaeria rostrate*

SEQ ID NO 88 polypeptide sequence derived from SEQ ID NO: 87

SEQ ID NO 89 mature polypeptide obtained from *Setosphaeria rostrate*

SEQ ID NO 90 DNA sequence obtained from *Endophragmiella valdina*

SEQ ID NO 91 polypeptide sequence derived from SEQ ID NO: 90

SEQ ID NO 92 mature polypeptide obtained from *Endophragmiella valdina*

SEQ ID NO 93 DNA sequence obtained from *Corynespora cassiicola*

SEQ ID NO 94 polypeptide sequence derived from SEQ ID NO: 93

SEQ ID NO 95 mature polypeptide obtained from *Corynespora cassiicola*

SEQ ID NO 96 DNA sequence obtained from *Paraphoma* sp. XZ1965

SEQ ID NO 97 polypeptide sequence derived from SEQ ID NO: 96

SEQ ID NO 98 mature polypeptide obtained from *Paraphoma* sp. XZ1965

SEQ ID NO 99 DNA sequence obtained from *Monilinia fructicola*

SEQ ID NO 100 polypeptide sequence derived from SEQ ID NO: 99

SEQ ID NO 101 mature polypeptide obtained from *Monilinia fructicola*

SEQ ID NO 102 DNA sequence obtained from *Curvularia lunata*

SEQ ID NO 103 polypeptide sequence derived from SEQ ID NO: 102

SEQ ID NO 104 mature polypeptide obtained from *Curvularia lunata*

SEQ ID NO 105 DNA sequence obtained from *Penicillium reticulisporum*

SEQ ID NO 106 polypeptide sequence derived from SEQ ID NO: 105

SEQ ID NO 107 mature polypeptide obtained from *Penicillium reticulisporum*

SEQ ID NO 108 DNA sequence obtained from *Penicillium quercetorum*

SEQ ID NO 109 polypeptide sequence derived from SEQ ID NO: 108

SEQ ID NO 110 mature polypeptide obtained from *Penicillium quercetorum*

SEQ ID NO 111 DNA sequence obtained from *Setophaeosphaeria* sp.

SEQ ID NO 112 polypeptide sequence derived from SEQ ID NO: 111

SEQ ID NO 113 mature polypeptide obtained from *Setophaeosphaeria* sp.

SEQ ID NO 114 DNA sequence obtained from *Alternaria* sp. XZ2545

SEQ ID NO 115 polypeptide sequence derived from SEQ ID NO: 114

SEQ ID NO 116 mature polypeptide obtained from *Alternaria* sp. XZ2545

SEQ ID NO 117 DNA sequence obtained from *Alternaria*

SEQ ID NO 118 polypeptide sequence derived from SEQ ID NO: 117

SEQ ID NO 119 mature polypeptide obtained from *Alternaria*

SEQ ID NO 120 DNA sequence obtained from *Trichoderma reesei*

SEQ ID NO 121 polypeptide sequence derived from SEQ ID NO: 121

SEQ ID NO 122 mature polypeptide obtained from *Trichoderma reesei*

SEQ ID NO 123 DNA sequence obtained from *Chaetomium thermophilum*

SEQ ID NO 124 polypeptide sequence derived from SEQ ID NO: 123

SEQ ID NO 125 mature polypeptide obtained from *Chaetomium thermophilum*

SEQ ID NO 126 DNA sequence obtained from *Scytalidium thermophilum*

SEQ ID NO 127 polypeptide sequence derived from SEQ ID NO: 126

SEQ ID NO 128 mature polypeptide obtained from *Scytalidium thermophilum*

SEQ ID NO 129 DNA sequence obtained from *Metapochonia suchlasporia*

SEQ ID NO 130 polypeptide sequence derived from SEQ ID NO: 129

SEQ ID NO 131 mature polypeptide obtained from *Metapochonia suchlasporia*

SEQ ID NO 132 DNA sequence obtained from *Daldinia fissa*

SEQ ID NO 133 polypeptide sequence derived from SEQ ID NO: 132

SEQ ID NO 134 mature polypeptide obtained from *Daldinia fissa*

SEQ ID NO 135 DNA sequence obtained from *Acremonium* sp. XZ2007
SEQ ID NO 136 polypeptide sequence derived from SEQ ID NO: 135
SEQ ID NO 137 mature polypeptide obtained from *Acremonium* sp. XZ2007
SEQ ID NO 138 DNA sequence obtained from *Acremonium dichromosporum*
SEQ ID NO 139 polypeptide sequence derived from SEQ ID NO: 138
SEQ ID NO 140 mature polypeptide obtained from *Acremonium dichromosporum*
SEQ ID NO 141 DNA sequence obtained from *Sarocladium* sp. XZ2014
SEQ ID NO 142 polypeptide sequence derived from SEQ ID NO: 141
SEQ ID NO 143 mature polypeptide obtained from *Sarocladium* sp. XZ2014
SEQ ID NO 144 DNA sequence obtained from *Metarhizium* sp. HNA15-2
SEQ ID NO 145 polypeptide sequence derived from SEQ ID NO: 144
SEQ ID NO 146 mature polypeptide obtained from *Metarhizium* sp. HNA15-2
SEQ ID NO 147 DNA sequence obtained from *Acremonium* sp. XZ2414
SEQ ID NO 148 polypeptide sequence derived from SEQ ID NO: 147
SEQ ID NO 149 mature polypeptide obtained from *Acremonium* sp. XZ2414
SEQ ID NO 150 DNA sequence obtained from *Isaria tenuipes*
SEQ ID NO 151 polypeptide sequence derived from SEQ ID NO: 150
SEQ ID NO 152 mature polypeptide obtained from *Isaria tenuipes*
SEQ ID NO 153 DNA sequence obtained from *Scytalidium circinatum*
SEQ ID NO 154 polypeptide sequence derived from SEQ ID NO: 153
SEQ ID NO 155 mature polypeptide obtained from *Scytalidium circinatum*
SEQ ID NO 156 DNA sequence obtained from *Metarhizium lepidiotae*
SEQ ID NO 157 polypeptide sequence derived from SEQ ID NO: 156
SEQ ID NO 158 mature polypeptide obtained from *Metarhizium lepidiotae*
SEQ ID NO 159 DNA sequence obtained from *Thermobispora bispora*
SEQ ID NO 160 polypeptide sequence derived from SEQ ID NO: 159
SEQ ID NO 161 mature polypeptide obtained from *Thermobispora bispora*
SEQ ID NO 162 DNA sequence obtained from *Sporormia fimetaria*
SEQ ID NO 163 polypeptide sequence derived from SEQ ID NO: 162
SEQ ID NO 164 mature polypeptide obtained from *Sporormia fimetaria*
SEQ ID NO 165 DNA sequence obtained from *Pycnidiophora* cf. *dispera*
SEQ ID NO 166 polypeptide sequence derived from SEQ ID NO: 165
SEQ ID NO 167 mature polypeptide obtained from *Pycnidiophora* cf. *dispera*
SEQ ID NO 168 DNA sequence obtained from Xanthan alkaline community D
SEQ ID NO 169 polypeptide sequence derived from SEQ ID NO: 168
SEQ ID NO 170 mature polypeptide obtained from Xanthan alkaline community D
SEQ ID NO 171 DNA sequence obtained from Xanthan alkaline community 0
SEQ ID NO 172 polypeptide sequence derived from SEQ ID NO: 171
SEQ ID NO 173 mature polypeptide obtained from Xanthan alkaline community 0
SEQ ID NO 174 DNA sequence obtained from *Clavicipitaceae* sp-70249
SEQ ID NO 175 polypeptide sequence derived from SEQ ID NO: 174
SEQ ID NO 176 mature polypeptide obtained from 175 from *Clavicipitaceae* sp-70249
SEQ ID NO 177 DNA sequence obtained from *Westerdykella* sp. AS85-2
SEQ ID NO 178 polypeptide sequence derived from SEQ ID NO: 177
SEQ ID NO 179 mature polypeptide obtained from *Westerdykella* sp. AS85-2
SEQ ID NO 180 DNA sequence obtained from *Humicolopsis cephalosporioides*
SEQ ID NO 181 polypeptide sequence derived from SEQ ID NO: 180
SEQ ID NO 182 mature polypeptide obtained from *Humicolopsis cephalosporioides*
SEQ ID NO 183 DNA sequence obtained from *Neosartorya massa*
SEQ ID NO 184 polypeptide sequence derived from SEQ ID NO: 183
SEQ ID NO 185 mature polypeptide obtained from *Neosartorya massa*
SEQ ID NO 186 DNA sequence obtained from *Roussoella intermedia*
SEQ ID NO 187 polypeptide sequence derived from SEQ ID NO: 186
SEQ ID NO 188 mature polypeptide obtained from 187
SEQ ID NO 189 DNA sequence obtained from *Pleosporales*
SEQ ID NO 190 polypeptide sequence derived from SEQ ID NO: 189
SEQ ID NO 191 mature polypeptide obtained from *Pleosporales*
SEQ ID NO 192 DNA sequence obtained from *Phaeosphaeria*
SEQ ID NO 193 polypeptide sequence derived from SEQ ID NO: 192
SEQ ID NO 194 mature polypeptide obtained from *Phaeosphaeria*
SEQ ID NO 195 DNA sequence obtained from *Didymosphaeria futilis*
SEQ ID NO 196 polypeptide sequence derived from SEQ ID NO: 195
SEQ ID NO 197 mature polypeptide obtained from *Didymosphaeria futilis*
SEQ ID NO 198 motif [T/D/S][G/N]PQL
SEQ ID NO 199 motif [G/T]Y[D/S][R/K/L]
SEQ ID NO 200 motif [E/D/H]H[I/V/L/F/M]X[P/A/S]
SEQ ID NO 201 motif [F/L/Y/I]A[N/R]D[L/I/P/V]
SEQ ID NO 202 motif C[D/N]T[A/R]
SEQ ID NO 203 motif [D/Q][I/V]DH
SEQ ID NO 204 motif [D/M/L][S/T]GYSR[D/N]
SEQ ID NO 205 motif ASXNRSKG
SEQ ID NO 206 motif [V/I]PL[S/A]NAWK SEQ ID NO 207 motif NPQL
SEQ ID NO 208 motif P[Q/E]L[W/Y]
SEQ ID NO 209 motif [K/H/E]NAW

Definitions

Figure 1:
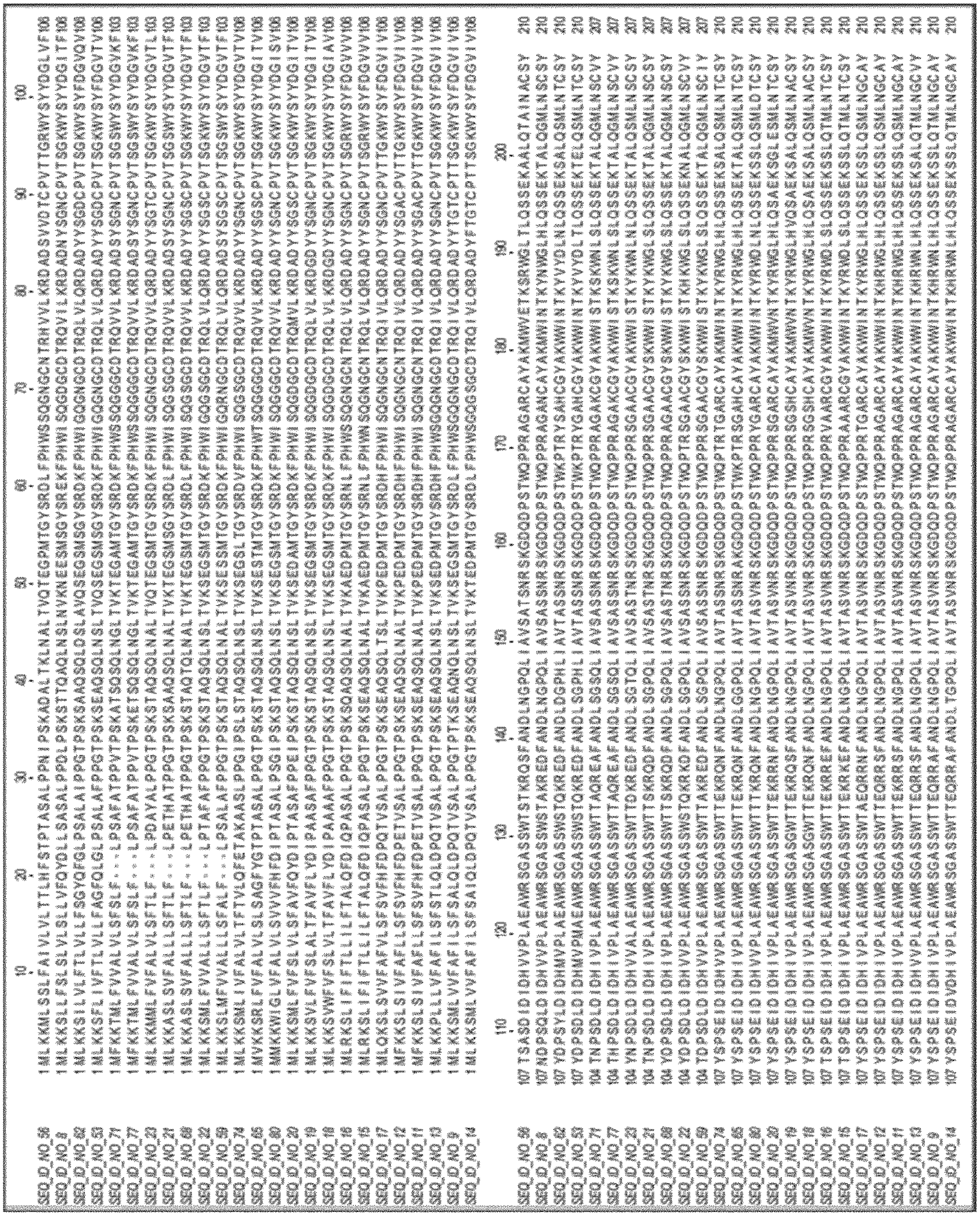
FIG. 1 provides an alignment of the polypeptides of the invention comprised in the GYS clade.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community. On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, synthetic DNA, or a combination thereof.

Color difference (L value): A Lab color space is a color-opponent space with dimension L for lightness. L value, L* represents the darkest black at L*=0, and the brightest white at L*=100. In the context of the present invention L value is also referred to as color difference.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: By the term "deep cleaning" is meant disruption or removal of a biofilm or components of a biofilm such as polysaccharides, proteins, DNA, soil or other components present in the biofilm.

Detergent adjunct ingredient: The detergent adjunct ingredient is different to the DNase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent Composition: The term "detergent composition" refers to compositions that find use in the removal of undesired compounds from items to be cleaned, such as textiles. The detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity that catalyzes the hydrolytic cleavage of phosphodiester linkages in the DNA backbone, thus degrading DNA. The term "DNases" and the expression "a polypeptide with DNase activity" are used interchangeably throughout the application. For purposes of the present invention, DNase activity is determined according to the procedure described in the Assay I. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide of SEQ ID NO:

2, 4 or 6, preferable of SEQ ID NO 2. In one embodiment, the polypeptides of the present invention have improved DNase activity, e.g., such that the DNase activity of the polypeptide is at least 105%, e.g., at least 110%, at least 120%, at least 130%, at least 140%, at least 160%, at least 170%, at least 180%, or at least 200% with reference to the DNase activity of the mature polypeptide of SEQ ID NO: 2, 4 or 6, preferably of SEQ ID NO 2.

In a preferred embodiment, the DNase activity of the polypeptide is at least at least 20%, e.g., at least 40%, at least 50%, at least 60%, at least 70%, at least 80%, at least 90%, at least 95%, at least 100%, at least 105%, at least 110%, at least 120%, at least 130%, at least 140%, at least 160%, at least 170%, at least 180%, or at least 200% with reference to the DNase activity of the mature polypeptide of SEQ ID NO: 2 as determined according to the procedure described in the Assay I.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has DNase activity. In one aspect, a fragment contains at least 206 amino acid residues (e.g., amino acids 1 to 206 of SEQ ID NO: 2), at least 205 amino acid residues (e.g., amino acids 2 to 206 of SEQ ID NO: 2), or at least 204 amino acid residues (e.g., amino acids 3 to 206 of SEQ ID NO: 2). In one aspect, a fragment contains at least 206 amino acid residues (e.g., amino acids 1 to 206 of SEQ ID NO: 4), at least 205 amino acid residues (e.g., amino acids 4 to 206 of SEQ ID NO: 4), or at least 204 amino acid residues (e.g., amino acids 3 to 206 of SEQ ID NO: 4). In one aspect, a fragment contains at least 206 amino acid residues (e.g., amino acids 1 to 206 of SEQ ID NO: 6), at least 205 amino acid residues (e.g., amino acids 2 to 206 of SEQ ID NO: 6), or at least 204 amino acid residues (e.g., amino acids 3 to 206 of SEQ ID NO: 6).

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved wash performance: The term "improved wash performance" is defined herein as an enzyme displaying an increased wash performance in a detergent composition relative to the wash performance of same detergent composition without the enzyme, e.g., by increased stain removal or less redeposition. The term "improved wash performance" includes wash performance in laundry.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g., a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using, e.g., a household or an industrial washing machine or can be carried out by hand.

By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items for example curry or other exotic spices which smells strongly. One way of measuring the ability of an item to adhere malodor is by using Assay II disclosed herein.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 29 to 210 of SEQ ID NO: 2, amino acids 29 to 210 of SEQ ID NO: 4 or amino acids 23 to 202 of SEQ ID NO: 6 and amino acids 1 to 28 of SEQ ID NO: 2, amino acids 1 to 28 of SEQ ID NO: 4 and amino acids 1 to 22 of SEQ ID NO: 6 are signal peptides.

In one aspect, the mature polypeptide is amino acids 1 to 182 of SEQ ID NO: 26.

In one aspect, the mature polypeptide is amino acids 1 to 182 of SEQ ID NO: 28.

In one aspect, the mature polypeptide is amino acids 1 to 182 of SEQ ID NO: 30.

In one aspect, the mature polypeptide is amino acids 1 to 182 of SEQ ID NO: 32.

In one aspect, the mature polypeptide is amino acids 1 to 182 of SEQ ID NO: 34.

In one aspect, the mature polypeptide is amino acids 1 to 182 of SEQ ID NO: 36.

In one aspect, the mature polypeptide is amino acids 1 to 182 of SEQ ID NO: 38.

In one aspect, the mature polypeptide is amino acids 1 to 183 of SEQ ID NO: 40.

In one aspect, the mature polypeptide is amino acids 1 to 185 of SEQ ID NO: 42.

In one aspect, the mature polypeptide is amino acids 1 to 182 of SEQ ID NO: 44.

In one aspect, the mature polypeptide is amino acids 1 to 182 of SEQ ID NO: 46.

In one aspect, the mature polypeptide is amino acids 1 to 182 of SEQ ID NO: 48.

In one aspect, the mature polypeptide is amino acids 1 to 182 of SEQ ID NO: 50.

In one aspect, the mature polypeptide is amino acids 1 to 182 of SEQ ID NO: 52.

In one aspect, the mature polypeptide is amino acids 1 to 182 of SEQ ID NO: 55.

In one aspect, the mature polypeptide is amino acids 1 to 182 of SEQ ID NO: 58.

In one aspect, the mature polypeptide is amino acids 1 to 182 of SEQ ID NO: 61.

In one aspect, the mature polypeptide is amino acids 1 to 182 of SEQ ID NO: 64.

In one aspect, the mature polypeptide is amino acids 1 to 182 of SEQ ID NO: 67.

In one aspect, the mature polypeptide is amino acids 1 to 182 of SEQ ID NO: 70.

In one aspect, the mature polypeptide is amino acids 1 to 184 of SEQ ID NO: 73.

In one aspect, the mature polypeptide is amino acids 1 to 182 of SEQ ID NO: 76.

In one aspect, the mature polypeptide is amino acids 1 to 182 of SEQ ID NO: 79.

In one aspect, the mature polypeptide is amino acids 1 to 191 of SEQ ID NO: 82.

In one aspect, the mature polypeptide is amino acids 1 to 190 of SEQ ID NO: 85.

In one aspect, the mature polypeptide is amino acids 1 to 192 of SEQ ID NO: 88.

In one aspect, the mature polypeptide is amino acids 1 to 192 of SEQ ID NO: 91.

In one aspect, the mature polypeptide is amino acids 1 to 190 of SEQ ID NO: 94.

In one aspect, the mature polypeptide is amino acids 1 to 192 of SEQ ID NO: 97.

In one aspect, the mature polypeptide is amino acids 1 to 186 of SEQ ID NO: 100.

In one aspect, the mature polypeptide is amino acids 1 to 190 of SEQ ID NO: 103.

In one aspect, the mature polypeptide is amino acids 1 to 191 of SEQ ID NO: 106.

In one aspect, the mature polypeptide is amino acids 1 to 191 of SEQ ID NO: 109.

In one aspect, the mature polypeptide is amino acids 1 to 192 of SEQ ID NO: 112.

In one aspect, the mature polypeptide is amino acids 1 to 192 of SEQ ID NO: 115.

In one aspect, the mature polypeptide is amino acids 1 to 192 of SEQ ID NO: 118.

In one aspect, the mature polypeptide is amino acids 1 to 186 of SEQ ID NO: 121.

In one aspect, the mature polypeptide is amino acids 1 to 188 of SEQ ID NO: 124.

In one aspect, the mature polypeptide is amino acids 1 to 190 of SEQ ID NO: 127.

In one aspect, the mature polypeptide is amino acids 1 to 186 of SEQ ID NO: 130.

In one aspect, the mature polypeptide is amino acids 1 to 198 of SEQ ID NO: 133.

In one aspect, the mature polypeptide is amino acids 1 to 188 of SEQ ID NO: 136.

In one aspect, the mature polypeptide is amino acids 1 to 182 of SEQ ID NO: 139

In one aspect, the mature polypeptide is amino acids 1 to 188 of SEQ ID NO: 142.

In one aspect, the mature polypeptide is amino acids 1 to 186 of SEQ ID NO: 145.

In one aspect, the mature polypeptide is amino acids 1 to 188 of SEQ ID NO: 148.

In one aspect, the mature polypeptide is amino acids 1 to 186 of SEQ ID NO: 151.

In one aspect, the mature polypeptide is amino acids 1 to 184 of SEQ ID NO: 154.

In one aspect, the mature polypeptide is amino acids 1 to 186 of SEQ ID NO: 157.

In one aspect, the mature polypeptide is amino acids 1 to 226 of SEQ ID NO: 160.

In one aspect, the mature polypeptide is amino acids 1 to 191 of SEQ ID NO: 163.

In one aspect, the mature polypeptide is amino acids 1 to 193 of SEQ ID NO: 166.

In one aspect, the mature polypeptide is amino acids 1 to 199 of SEQ ID NO: 169.

In one aspect, the mature polypeptide is amino acids 1 to 194 of SEQ ID NO: 172.

In one aspect, the mature polypeptide is amino acids 1 to 186 of SEQ ID NO: 175.

In one aspect, the mature polypeptide is amino acids 1 to 187 of SEQ ID NO: 178.

In one aspect, the mature polypeptide is amino acids 1 to 194 of SEQ ID NO: 181.

In one aspect, the mature polypeptide is amino acids 1 to 190 of SEQ ID NO: 184.

In one aspect, the mature polypeptide is amino acids 1 to 191 of SEQ ID NO: 187.

In one aspect, the mature polypeptide is amino acids 1 to 191 of SEQ ID NO: 190.

In one aspect, the mature polypeptide is amino acids 1 to 192 of SEQ ID NO: 193.

In one aspect, the mature polypeptide is amino acids 1 to 189 of SEQ ID NO: 196.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. The mature polypeptide of SEQ ID NO 2 is SEQ ID NO 8, the mature polypeptide of SEQ ID NO 4 is SEQ ID NO 9 and the mature polypeptide of SEQ ID NO 6 is SEQ ID NO 10.

Mature polypeptide coding sequence: The term "mature polypeptide coding sequence" means a polynucleotide that encodes a mature polypeptide having DNase activity. In one aspect, the mature polypeptide coding sequences are nucleotides 85 to 630 of SEQ ID NO: 1, nucleotides 85 to 630 of SEQ ID NO: 3 and nucleotides 67 to 606 of SEQ ID NO: 5.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pharmaceutical adjunct ingredient means any pharmaceutical excipient suitable for formulating the pharmaceutical compound.

Such excipients, carriers, vehicles etc. are well known to those of skill in the art and are described in text books such as Remington's Pharmaceutical Sciences, Mack Publishing Co., Easton, Pa., 1985.

Pharmaceutically acceptable excipients which are suitable for use in tablet formulations include, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. Tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

For hard gelatin capsule formulations, the active ingredient can be mixed with an inert solid diluent, for example, calcium carbonate, calcium phosphate or kaolin. For soft gelatin capsule formulations the active ingredient can be mixed with water or an oil medium, for example peanut oil, liquid paraffin or olive oil.

Excipients suitable for the manufacture of aqueous suspensions include suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters obtained from fatty acids and a hexitol such as polyoxyethylene sorbitol monooleate, or condensation products of ethylene oxide with partial esters obtained from fatty acids and hexitol anhydrides, for example polyethylene sorbitan monooleate.

Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin The oily suspensions may contain a thickening agent, for example beeswax, hard paraffin or cetyl alcohol. Sweetening agents and flavouring agents may be added. These compositions may be preserved by the addition of an antioxidant such as ascorbic acid.

Remission value: Wash performance is expressed as a Remission value of the stained swatches. After washing and rinsing the swatches were spread out flat and allowed to air dry at room temperature overnight. All washes swatches are evaluated the day after the wash. Light reflectance evaluations of the swatches were done using a Macbeth Color Eye 7000 reflectance spectrophotometer with very small aperture. The measurements were made without UV in the incident light and remission at 460 nm was extracted.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows: (Identical Residues×100)/(Length of Alignment−Total Number of Gaps in Alignment). For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EM-BOSS: The European Molecular Biology Open Software Suite, Rice et al., 2000, supra), prefer-ably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment).

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having DNase activity. In one aspect, a subsequence contains at least 550 nucleotides (e.g., nucleotides 85 to 630 of SEQ ID NO: 1, 3 or 5), at least 400 nucleotides (e.g., nucleotides 100 to 500 of SEQ ID NO: 1, 3 or 5), or at least 300 nucleotides (e.g., nucleotides 200 to 500 of SEQ ID NO: 1, 3 or 5).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g., originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fibre (e.g., polyamide fibre, acrylic fibre, polyester fibre, polyvinyl chloride fibre, polyurethane fibre, polyurea fibre, aramid fibre), and/or cellulose-containing fibre (e.g., rayon/viscose, ramie, flax/linen, jute, cellulose acetate fibre, lyocell). Fabric may be conventional washable laundry, for example stained household laundry. When the term fabric or garment is used it is intended to include the broader term textiles as well. In the context of the present invention, the term "textile" also covers fabrics.

Variant: The term "variant" means a polypeptide having same enzyme activity as the parent enzyme, e.g. in the present context a variant of the invention have DNase activity, wherein the variant comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNase has the enzymatic activity of the parent, i.e. the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g., the mature polypeptide of SEQ ID NO: 2, 4 or 6. In one embodiment, the polypeptide has DNase activity and the variant has increased DNase activity compared to the parent DNase, e.g., the mature polypeptide of SEQ ID NO 2, SEQ ID NO 4, SEQ ID NO 6, SEQ ID NO 26, SEQ ID NO 28, SEQ ID NO 30, SEQ ID NO 32, SEQ ID NO 34, SEQ ID NO 36, SEQ ID NO 38, SEQ ID NO 40, SEQ ID NO 42, SEQ ID NO 44, SEQ ID NO 46, SEQ ID NO 48, SEQ ID NO 50, SEQ ID NO 52, SEQ ID NO 55, SEQ ID NO 58, SEQ ID NO 61, SEQ ID NO 64, SEQ ID NO 67, SEQ ID NO 70, SEQ ID NO 73, SEQ ID NO 76, SEQ ID NO 79, SEQ ID NO 82, SEQ ID NO 85, SEQ ID NO 88, SEQ ID NO 91, SEQ ID NO 94, SEQ ID NO 97, SEQ ID NO 100, SEQ ID NO 103, SEQ ID NO 106, SEQ ID NO 109, SEQ ID NO 112, SEQ ID NO 115, SEQ ID NO 118, SEQ ID NO 121, SEQ ID NO 124, SEQ ID NO 127, SEQ ID NO 130, SEQ ID NO 133, SEQ ID NO 136, SEQ ID NO 139, SEQ ID NO 142, SEQ ID NO 145, SEQ ID NO 148, SEQ ID NO 151, SEQ ID NO 154, SEQ ID NO 157, SEQ ID NO 160, SEQ ID NO 163, SEQ ID NO 166, SEQ ID NO 169, SEQ ID NO 172, SEQ ID NO 175, SEQ ID NO 178, SEQ ID NO 181, SEQ ID NO 184, SEQ ID NO 187, SEQ ID NO 190, SEQ ID NO 193 or SEQ ID NO 196.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is defined herein as the solution or mixture of water and detergent components optionally including the enzyme of the invention.

Wash time: The term "wash time" is defined herein as the time it takes for the entire washing process; i.e. the time for the wash cycle(s) and rinse cycle(s) together.

Whiteness: The term "Whiteness" is defined herein as a broad term with different meanings in different regions and for different consumers. Loss of whiteness can, e.g., be due to greying, yellowing, or removal of optical brighteners/hueing agents. Greying and yellowing can be due to soil redeposition, body soils, colouring from, e.g., iron and copper ions or dye transfer. Whiteness might include one or several issues from the list below: colourant or dye effects;

incomplete stain removal (e.g., body soils, sebum etc.); redeposition (greying, yellowing or other discolorations of the object) (removed soils reassociate with other parts of textile, soiled or unsoiled); chemical changes in textile during application; and clarification or brightening of colours.

Nomenclature

For purposes of the present invention, the nomenclature [E/Q] means that the amino acid at this position may be a glutamic acid (Glu, E) or a glutamine (Gln, Q). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

The present invention relates to novel polypeptides having deoxyribonuclease (DNase) activity which can be used for preventing, reducing or removing biofilm on items such as textiles and/or fabric. A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

Polypeptides

Examples of polypeptides having DNase activity are polypeptides comprising the PFAM domain DUF1524 (http://pfam.xfam.org/), "The Pfam protein families database: towards a more sustainable future", R. D. Finn, et. al. Nucleic Acids Research (2016) Database Issue 44:D279-D285". The DUF1524 domain contains a conserved HXXP sequence motif commonly found in nucleases (M. A. Machnicka, et. al. Phylogenomics and sequence-structure-function relationships in the GmrSD family of Type IV restriction enzymes, BMC Bioinformatics, 2015, 16, 336). DUF means domain of unknown function, and the polypeptide families comprising, e.g., DUF have been collected together in the Pfam database. The Pfam data base provides sequence alignments and hidden Markov models that define the collected protein domains. A protein domain is a conserved part of a given protein sequence and (tertiary) structure that can evolve, function, and exist independently of the rest of the protein chain. Each domain forms a compact three-dimensional structure and often can be independently stable and folded. Many proteins consist of several structural domains. One domain may appear in a variety of different proteins.

A particular DUF may be identified using the prefix DUF followed by a number, e.g., 1524. The DUF1524 is a family of proteins all comprising the HXXP motif, where H is the amino acid histidine, P is the amino acid proline and X is any amino acid.

In one aspect of the invention the polypeptides of the present invention having DNase activity comprise the DUF1524 domain. Thus according to one embodiment the invention relates to polypeptides having DNase activity, wherein the polypeptides comprise the DUF1524 domain and the invention relates to the use of such DNases e.g. for preventing, reducing or removing biofilm on items such as textiles and/or fabric. The invention further relates to compositions comprising polypeptides having DNase activity, which comprises a DUF1524 domain e.g. HXXP. Such compositions may be but is not limited to liquid or powder laundry compositions, tablets, unit dose, spray or soap bars.

In one embodiment the DNases of the invention comprise one or more DUF1524 domains e.g. comprise one or both of the novel motifs [T/D/S][G/N]PQL (SEQ ID NO 198); [G/T]Y[D/S][R/K/L] (SEQ ID NO: 199); where T is threonine, D is aspartic acid, S is serine, G is glycine, N is asparagine, P is proline, Q is glutamine, L is leucine, Y is tyrosine, R is arginine and K is lysine i.e. the amino acids are listed in one letter code. The brackets indicate alternative amino acids within the bracket separated by vertical line or in some instances no line e.g. [TDS]. Thus [T/D/S][G/N]PQL means that either T, D or S could be in the first position and either G or N could be present in the second position followed by PQL. The motifs may then be either of TGPQL, TNPQL, DGPQL, DNPQL, SGPQL or SNPQL. For the motif [G/T]Y[D/S][R/K/L] the conservative amino acid is Y and G or T optional amino acids before and D or S optional amino acids after that position. The motif could then be GYD, TYD, GYS or TYS.

Another domain shared among polypeptides of the DUF1524 is [E/D/H]H[I/V/L/F/M]X[P/A/S] (SEQ ID NO 200), which is located at positions corresponding to positions 87 to 91 in *B. cibi* (SEQ ID NO 21). H88 is a catalytic residue involved in the catalytic activity of DUF1524, and part of the HXXP motif. Modification of H88 to another amino acid will may result in the loss of catalytic activity.

Polypeptides having DNase activity and which comprise these motifs have shown particularly good deep cleaning properties i.e. the polypeptides of the invention having DNase activity are particularly effective in removing or reducing biofilm. One aspect of the invention relates to polypeptides having DNase activity, wherein the polypeptides comprises one or more of the motifs [E/D/H]H[I/V/L/F/M]X[P/A/S] (SEQ ID NO 200), [T/D/S][G/N]PQL (SEQ ID NO: 198) and [G/T]Y[D/S][R/K/L] (SEQ ID NO: 199). One aspect of the invention relates to polypeptides having DNase activity, wherein the polypeptides comprises one or more of the motifs [E/D/H]H[I/V/L/F/M]X[P/A/S] (SEQ ID NO 200), [T/D/S][G/N]PQL (SEQ ID NO: 198) and [G/T]Y[D/S][R/K/L] (SEQ ID NO: 199), with the proviso that the polypeptide is not a DNase comprising SEQ ID NO 2 of WO 2015/155351.

One embodiment of the invention relates to DNases comprising the DUF1524 domain and one or more of the motifs SEQ ID NO: 198, SEQ ID NO 199 or SEQ ID NO: 200, wherein the DNases have deep-cleaning properties i.e. wherein the DNases effectively prevent, reduce or remove biofilm of an item such as a fabric, textile and/or hard surface.

As already described the polypeptides of the invention having DNase activity may comprise the structural domains of DUF1524. A further domain, preferably shared by the DNases of the invention, was identified. This domain has not been described previously, the domain is termed NUC1 and polypeptides of this domain are in addition to having DNase activity, characterized by comprising certain motifs e.g. one or more of the motifs [F/L/Y/I]A[N/R]D[L/I/P/V] (SEQ ID NO: 201) or C[D/N]I[A/R] (SEQ ID NO: 202); as described above the letters indicate amino acids in one letter code thus F is phenylalanine, L is leucine, A is alanine, N is asparagine, D is aspartic acid, I is isoleucine, V is valine, H is histidine, G is glycine, C cysteine, T is threonine, R is arginine and so forth. The brackets indicate that the amino acids within the bracket are alternatives.

One embodiment of the invention relates to polypeptides having DNase activity, wherein the polypeptides comprising one or both of the motifs [F/L/Y/I]A[N/R]D[L/I/P/V] (SEQ ID NO: 201) or C[D/N]T[A/R] (SEQ ID NO: Y). One embodiment of the invention relates to polypeptides having DNase activity, wherein the polypeptides comprising one or both of the motifs [F/L/Y/I]A[N/R]D[L/I/P/V] (SEQ ID NO: 201) or C[D/N]T[A/R] (SEQ ID NO: 202), preferably where the motif [F/L/Y/I]A[N/R]D[L/I/P/V] (SEQ ID NO: 201) is located at positions corresponding to positions 110 to 114 of SEQ ID NO 21 and/or where to motif C[D/N]T[A/R] is located at positions corresponding to positions 43 to 46 of SEQ ID NO 21.

One embodiment of the invention relates to polypeptides having DNase activity, wherein the polypeptides comprising one or both of the motifs [F/L/Y/I]A[N/R]D[L/I/P/V] (SEQ ID NO: 201) or C[D/N]T[A/R] (SEQ ID NO: 202), with the proviso that the polypeptide is not a DNase comprising SEQ ID NO 2 of WO 2015/155351, preferably the motif [F/L/Y/I]A[N/R]D[L/I/P/V] (SEQ ID NO: 201) is located at positions corresponding to positions 110 to 114 of SEQ ID NO 21 and/or where to motif C[D/N]T[A/R] is located at positions corresponding to positions 43 to 46 of SEQ ID NO 21.

The motifs and domains are defined cross-kingdom meaning that the domains and motifs comprise both fungal and bacterial DNases. It is well known that DNases belonging to different taxonomic may share common structural elements, which could be identified by comparing the primary structure e.g. amino acid sequence and grouping the DNases according to sequence homology. However, common structural elements may also be identified by comparing the three dimensional (3D) structure of various DNases. Both approaches have been applied in the present invention.

The structural approach identified DNases, which have different taxonomy but share structural elements common for the identified group. The groups such as e.g. a clade share common functionalities, which may be preference for certain biofilms etc.

From the NUC1 domain a sub-domain has been identified by the inventors and this domain is termed the NUC1_A domain. In addition to comprising any of the domains above the polypeptides having DNase activity belonging to the NUC1_A domain share the common motif [D/Q][I/V]DH (SEQ ID NO 203), corresponding to amino acid 85 to 88 in the reference polypeptide (SEQ ID NO: 21). The D at the position corresponding to position 85 of SEQ ID NO 21 is predicted to be involved in binding of catalytic metal ion cofactor, where the letters define amino acids as described above and the brackets indicate alternative amino acids. In one embodiment the invention relates to polypeptides comprising the motif [D/Q][I/V]DH (SEQ ID NO:203), wherein the polypeptides have DNase activity. In one embodiment the invention relates to polypeptides comprising the motif [D/Q][I/V]DH (SEQ ID NO:203), wherein the polypeptides have DNase activity, with the proviso that the polypeptide is not a DNase comprising SEQ ID NO 2 of WO 2015/155351. One embodiment the invention relates to polypeptides comprising one or more of the motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptides have DNase activity. One embodiment the invention relates to polypeptides comprising one or more of the motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptides have DNase activity, with the proviso that the polypeptide is not a DNase comprising SEQ ID NO 2 of WO 2015/155351.

Polypeptides having DNase activity and comprising one or more or all of the motifs, [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH effectively prevent, remove or reduce biofilm and the DNases are particularly useful in cleaning processes, such as laundry and dish wash. One aspect of the invention relates to a polypeptide having DNase activity, where the polypeptide is selected from the group consisting of polypeptides having the amino acid sequence shown in SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 68, SEQ ID NO: 71, SEQ ID NO: 74, SEQ ID NO: 77, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191 and SEQ ID NO: 197 or polypeptides having at least 80% sequence identity, such as at least 85%, such as at least 90%, such as at least 95% or 100% sequence identity hereto, where the polypeptide further comprises one or more or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. The motifs are novel and have not previously been described. The DNases of the present invention therefore share a novel common inventive concept.

One aspect of the invention relates to a polypeptide having DNase activity, wherein the polypeptide comprises one or more or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, wherein the polypeptide is selected from the group consisting of a) a polypeptide having at least 84% sequence identity to the polypeptide of SEQ ID NO: 8, b) a polypeptide having at least 94% sequence identity to the polypeptide of SEQ ID NO: 9, c) a polypeptide having at least 92% sequence identity to the polypeptide of SEQ ID NO: 11, d) a polypeptide having at least 92% sequence identity to the polypeptide of SEQ ID NO: 12, e) a polypeptide having at least 97% sequence identity to the polypeptide of SEQ ID NO: 13, f) a polypeptide having at least 96% sequence identity to the polypeptide of SEQ ID NO: 14, g) a polypeptide having at least 90% sequence identity to the polypeptide of SEQ ID NO: 15, h) a polypeptide having at least 88% sequence identity to the polypeptide of SEQ ID NO: 16, i) a polypeptide having at least 93% sequence identity to the polypeptide of SEQ ID NO: 17, j) a polypeptide having at least 90% sequence identity to the polypeptide of SEQ ID NO: 18, k) a polypeptide having at least 89% sequence identity to the polypeptide of SEQ ID NO: 19, l) a polypeptide having at least 90% sequence identity to the polypeptide of SEQ ID NO: 20, m) a polypeptide having at least 93% sequence identity to the polypeptide of SEQ ID NO: 21, n) a polypeptide having at least 90% sequence identity to the polypeptide of SEQ ID NO: 22, o) a polypeptide having at least 93% sequence identity to the polypeptide of SEQ ID NO: 23, p) a polypeptide having at least 85% sequence identity to the polypeptide of SEQ ID NO: 53, q) a polypeptide having at least 98% sequence identity to the polypeptide of SEQ ID NO: 56, r) a polypeptide having at least 94% sequence identity to the polypeptide of SEQ ID NO: 59, s) a polypeptide having at least 85% sequence identity to the polypeptide of SEQ ID NO: 62, t) a polypeptide having at least 97% sequence identity to the polypeptide of SEQ ID NO: 68, u) a polypeptide having at least 99% sequence identity to the polypeptide of SEQ ID NO: 71, v) a polypeptide having at least 91% sequence identity to the polypeptide of SEQ ID NO: 74, w) a polypeptide having at least 98% sequence identity to the polypeptide of SEQ ID NO: 77, x) a polypeptide having at least 81% sequence identity to the polypeptide of SEQ ID NO: 83, y) a polypeptide having at least 89% sequence identity to the polypeptide of SEQ ID NO: 86, z) a polypeptide having at least 99% sequence identity to the polypeptide of SEQ ID NO: 89, aa) a polypeptide having at least 91% sequence identity to the polypeptide of SEQ ID NO: 92, bb) a polypeptide having at least 90% sequence identity to the polypeptide of SEQ ID NO: 95, cc) a polypeptide having at least 91% sequence identity to the polypeptide of SEQ ID NO: 98, dd) a polypeptide having at least 92% sequence identity to the polypeptide of SEQ ID NO: 104, ee) a polypeptide having at least 90% sequence identity to the polypeptide of SEQ ID NO: 107.

ff) a polypeptide having at least 91.5% sequence identity to the polypeptide of SEQ ID NO: 110.

gg) a polypeptide having at least 93% sequence identity to the polypeptide of SEQ ID NO: 113, hh) a polypeptide having at least 96% sequence identity to the polypeptide of SEQ ID NO: 116, ii) a polypeptide having at least 99.5% sequence identity to the polypeptide of SEQ ID NO: 119, jj) a polypeptide having at least 99.5% sequence identity to the polypeptide of SEQ ID NO: 128, kk) a polypeptide having at least 93% sequence identity to the polypeptide of SEQ ID NO: 131, ll) a polypeptide having at least 79% sequence identity to the polypeptide of SEQ ID NO: 134, mm) a polypeptide having at least 72% sequence identity to the polypeptide of SEQ ID NO: 137, nn) a polypeptide having at least 77% sequence identity to the polypeptide of SEQ ID NO: 140, oo) a polypeptide having at least 74% sequence identity to the polypeptide of SEQ ID NO: 143, pp) a polypeptide having at least 97% sequence identity to the polypeptide of SEQ ID NO: 146, qq) a polypeptide having at least 71% sequence identity to the polypeptide of SEQ ID NO: 149, rr) a polypeptide having at least 96% sequence identity to the polypeptide of SEQ ID NO: 152, ss) a polypeptide having at least 72% sequence identity to the polypeptide of SEQ ID NO: 155, tt) a polypeptide having at least 93% sequence identity to the polypeptide of SEQ ID NO: 158, uu) a polypeptide having at least 85% sequence identity to the polypeptide of SEQ ID NO: 164, vv) a polypeptide having at least 88% sequence identity to the polypeptide of SEQ ID NO: 167, ww) a polypeptide having at least 87% sequence identity to the polypeptide of SEQ ID NO: 176, xx) a polypeptide having at least 81% sequence identity to the polypeptide of SEQ ID NO: 179, yy) a polypeptide having at least 89% sequence identity to the polypeptide of SEQ ID NO: 182, zz) a polypeptide having at least 96% sequence identity to the polypeptide of SEQ ID NO: 185, aaa) a polypeptide having at least 88% sequence identity to the polypeptide of SEQ ID NO: 188, bbb) a polypeptide having at least 87% sequence identity to the polypeptide of SEQ ID NO: 191, ccc) a polypeptide having at least 94% sequence identity to the polypeptide of SEQ ID NO: 194, and ddd) a polypeptide having at least 90% sequence identity to the polypeptide of SEQ ID NO: 197.

The NUC_1 A domain is identified for the first time in the present invention and described above. The domain may be further divided into different clades. A clade is a group of polypeptides clustered together on the basis of homologous features traced to a common ancestor. Polypeptide clades can be visualized as phylogenetic trees and a clade is a group of polypeptides that consists of a common ancestor and all its lineal descendants. Example 11 describes generation of phylogenetic trees.

The clade of GYS or the GYS-clade is a group of DNases all related to the same ancestor, which share common properties. The hereto unknown clade comprises polypeptides forming a group within a domain e.g. NUC1_A of the phylogenetic tree, which share common properties and are more closely related than other polypeptides in the domain.

The polypeptides of the GYS clade share the conservative motifs [D/M/L][S/T]GYSR[D/N] (SEQ ID NO: 204) or ASXNRSKG (SEQ ID NO:205), where the letters are the amino acids (one letter code), X is any amino acid and the brackets means that the amino acids are alternative. In addition, the polypeptides of the GYS-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][IN]DH.

One aspect of the invention relates to polypeptides of the GYS clade comprising one or more of the motifs [D/M/L][S/T]GYSR[D/N] (SEQ ID NO: 204) or ASXNRSKG (SEQ ID NO:205), wherein the polypeptides have DNase activity. In one aspect the ASXNRSKG motif correspond to pos 125 to 133 of SEQ ID NO 21. In one aspect the [D/M/L][S/T]GYSR[D/N] motif correspond to positions 26 to 32 of SEQ ID NO 21.

The GYS clade comprises polypeptides having DNase activity shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77 and SEQ ID NO 80.

The polypeptides having DNase activity shown in SEQ ID NO 65 and SEQ ID NO 80 are public sequences, with UniProt accession numbers (H6NAU2 and A0A0M2T1U6).

One aspect of the invention relates to a polypeptide of the GYS clade comprising one or both of the motifs [D/M/L][S/T]GYSR[D/N] (SEQ ID NO: 204), ASXNRSKG (SEQ ID NO:205), wherein the polypeptide has DNase activity and wherein the polypeptide is selected from any of the polypeptides shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 68, SEQ ID NO 71, SEQ ID NO 74 and SEQ ID NO 77 or variant hereof having 1-25, such as 1-20, such as 1-15, such as 1-10, such as 1-5 amino acid alterations e.g. substitutions.

One aspect of the invention relates to a polypeptide of the GYS clade comprising one or both of the motifs [D/M/L][S/T]GYSR[D/N], ASXNRSKG and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 68, SEQ ID NO 71, SEQ ID NO 74 and SEQ ID NO 77 or variant hereof having 1-25, such as 1-20, such as 1-15, such as 1-10, such as 1-5 amino acid alterations e.g. substitutions.

One embodiment of the invention relates to a polypeptide of the GYS clade having DNase activity and comprising one or more of the motifs [D/M/L][S/T]GYSR[D/N] (SEQ ID NO: 204), ASXNRSKG (SEQ ID NO: 205), with the proviso that the polypeptide is not the polypeptides shown in SEQ ID NO 65 or SEQ ID NO 80.

One embodiment of the invention relates to a polypeptide of the GYS clade having DNase activity, wherein the polypeptide comprise one or both of the motifs [D/M/L][S/T]GYSR[D/N] (SEQ ID NO: 204), ASXNRSKG (SEQ ID NO: 205) and wherein the polypeptide is selected from the polypeptides:

a) a polypeptide having at least 84% sequence identity to the polypeptide shown in SEQ ID NO: 8, b) a polypeptide having at least 94% sequence identity to the polypeptide shown in SEQ ID NO: 9, c) a polypeptide having at least 92% sequence identity to the polypeptide shown in SEQ ID NO: 11, d) a polypeptide having at least 92% sequence identity to the polypeptide shown in SEQ ID NO: 12, e) a polypeptide having at least 97% sequence identity to the polypeptide shown in SEQ ID NO: 13, f) a polypeptide having at least 96% sequence identity to the polypeptide shown in SEQ ID NO: 14, g) a polypeptide having at least 90% sequence identity to the polypeptide shown in SEQ ID NO: 15, h) a polypeptide having at least 88% sequence identity to the polypeptide shown in SEQ ID NO: 16, i) a polypeptide having at least 93% sequence identity to the polypeptide shown in SEQ ID NO: 17, j) a polypeptide having at least 90% sequence identity to the polypeptide shown in SEQ ID NO: 18, k) a polypeptide having at least 89% sequence identity to the polypeptide shown in SEQ ID NO: 19, l) a polypeptide having at least 90% sequence identity to the polypeptide shown in SEQ ID NO: 20, m) a polypeptide having at least 93% sequence identity to the polypeptide shown in SEQ ID NO: 21, n) a polypeptide having at least 90% sequence identity to the polypeptide shown in SEQ ID NO: 22, o) a polypeptide having at least 93% sequence identity to the polypeptide shown in SEQ ID NO: 23, p) a polypeptide having at least 85% sequence identity to the polypeptide shown in SEQ ID NO: 53, q) a polypeptide having at least 98% sequence identity to the polypeptide shown in SEQ ID NO: 56, r) a polypeptide having at least 94% sequence identity to the polypeptide shown in SEQ ID NO: 59, s) a polypeptide having at least 85% sequence identity to the polypeptide shown in SEQ ID NO: 62, t) a polypeptide having at least 97% sequence identity to the polypeptide shown in SEQ ID NO: 68, u) a polypeptide having at least 99% sequence identity to the polypeptide shown in SEQ ID NO: 71, v) a polypeptide having at least 91% sequence identity to the polypeptide shown in SEQ ID NO: 74, and w) a polypeptide having at least 98% sequence identity to the polypeptide shown in SEQ ID NO: 77.

One embodiment of the invention relates to a polypeptide of the GYS clade having DNase activity and where the polypeptide comprise one or more of the motifs [D/M/L][S/T]GYSR[D/N] (SEQ ID NO: 204), ASXNRSKG (SEQ ID NO: 205), wherein the polypeptide having DNase activity is selected from the group consisting of SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 68, SEQ ID NO 71, SEQ ID NO 74 and SEQ ID NO 77 or a polypeptide having at least 99% sequence identity hereto.

One embodiment of the invention relates to a polypeptide of the GYS clade comprising one or both of the motifs [D/M/L][S/T]GYSR[D/N] (SEQ ID NO: 204) or ASXNRSKG (SEQ ID NO: 205), wherein the polypeptide has DNase activity and wherein the polypeptide is the polypeptide shown in SEQ ID NO 8 or a polypeptide having at least 84%, such as at least 85%, such as at least 90%, such as at least 95% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNRSKG (SEQ ID NO: 205), wherein the polypeptide has DNase activity and wherein the polypeptide is shown in SEQ ID NO 9 or a polypeptide having at least 94%, such as at least 95% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNRSKG (SEQ ID NO:205), wherein the polypeptide has DNase activity and wherein the polypeptide is the polypeptide in SEQ ID NO 11 or a polypeptide having at least 92% such as at least 95%, such as at least 96%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR- SKG (SEQ ID NO: 205), wherein the polypeptide has DNase activity and wherein the polypeptide is the polypeptide shown in SEQ ID NO 12 or a polypeptide having at least 92% such as at least 95%, such as at least 97%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 13 or a polypeptide having at least 97% such as at least 98%, such as at least 99% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 14 or a polypeptide having at least 96% such as at least 97%, such as at least 98%, such as at least 99% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 15 or a polypeptide having at least 90%, such as at least 93%, such as at least 95%, such as at least 97% or such as at least 100% sequence identity hereto.

One embodiment of the invention relates to a polypeptide of the GYS clade comprising one or both of the motifs [D/M/L][S/T]GYSR[D/N] (SEQ ID NO: 204); or ASXNR-SKG (SEQ ID NO: 205), wherein the polypeptide has DNase activity and wherein the polypeptide is the polypeptide shown in SEQ ID NO 16 or a polypeptide having at least 88%, such as at least 90%, such as at least 93%, such as at least 95%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 17 or a polypeptide having at least 93%, such as at least 95%, such as at least 96%, such as at least 97%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 18 or a polypeptide having at least 90%, such as at least 91%, such as at least 93%, such as at least 95%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO:21), wherein the polypeptide has DNase activity and wherein the polypeptide is the polypeptide shown in SEQ ID NO 19 or a polypeptide having at least 89%, such as at least 90%, such as at least 93%, such as at least 95%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 20 or a polypeptide having at least 90%, such as at least 91%, such as at least 93%, such as at least 95%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 21 or a polypeptide having at least 93%, such as at least 94%, such as at least 95%, such as at least 96%, such as at least 97%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 22 or a polypeptide having at least 90%, at least 93%, such as at least 94%, such as at least 95%, such as at least 96%, such as at least 97%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 23 or a polypeptide having at least 93%, at least 94%, such as at least 95%, such as at least 96%, such as at least 97%, such as at least 98%, such as at least 99% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO 53 or a polypeptide having at least 85%, at least 90%, such as at least 93%, such as at least 95%, such as at least 96%, such as at least 97%, such as at least 98% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO 56 or a polypeptide having at least 98%, such as at least 99% or such as at least 100% sequence identity hereto.

One embodiment of the invention relates to a polypeptide of the GYS clade comprising one or both of the motifs [D/M/L][S/T]GYSR[D/N] (SEQ ID NO: 204) or ASXNR-SKG (SEQ ID NO: 205), wherein the polypeptides has DNase activity and wherein the polypeptide is the polypeptide shown in SEQ ID NO 59 or a polypeptide having at least 94%, such as at least 95%, such as at least 96%, such as at least 97%, such as at least 98% or such as at least 100% sequence identity hereto.

One embodiment of the invention relates to a polypeptide of the GYS clade comprising one or more of the motifs [D/M/L][S/T]GYSR[D/N] (SEQ ID NO: 204); or ASXNR-SKG (SEQ ID NO: 205), wherein the polypeptide has DNase activity and wherein the polypeptide is the polypeptide shown in SEQ ID NO 62 or a polypeptide having at least 85%, at least 90%, such as at least 95%, such as at least 95%, such as at least 96%, such as at least 97%, such as at least 98% or such as at least 100% sequence identity hereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 68 or a polypeptide having at least 97%, such as at least 98% or such as at least 100% sequence identity hereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 71 or a polypeptide having at least 99% or 100% sequence identity hereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 74 or a polypeptide having at least 91%, at least 93%, such as at least 94%, such as at least 95%, such as at least 96%, such as at least 97%, such as at least 98% or such as at least 100% sequence identity hereto.

One embodiment of the invention relates to a polypeptide of the GYS clade comprising one or more of the motifs [D/M/L][S/T]GYSR[D/N] (SEQ ID NO: 204) or ASXNR-SKG (SEQ ID NO: 205), wherein the polypeptide has DNase activity and wherein the polypeptide is the polypeptide shown in SEQ ID NO 77 or a polypeptide having at least 98%, such as at least 99% or 100% sequence identity hereto.

Another distinguishable clade is the NAWK-clade. The clade of NAWK or the NAWK-clade is a group of DNases all related to the same ancestor which share common properties. The hereto unknown clade comprises polypeptides forming a group within a domain e.g. NUC1_A of the phylogenetic tree, which may share common properties and are more closely related than other polypeptides in the domain.

The polypeptides of the NAWK-clade share the conservative motifs [V/I]PL[S/A]NAWK (SEQ ID NO: 206), or NPQL (SEQ ID NO: 207), where the letters are the amino acid (one letter code) and the amino acids in the brackets are alternatives. In addition, the polypeptides of the NAWK-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH.

One aspect of the invention relates to polypeptides of the NAWK-clade comprising one or more of the motifs [V/I]PL[S/A]NAWK (SEQ ID NO: 206) or NPQL (SEQ ID NO: 207), wherein the polypeptides have DNase activity. In one aspect the [VI]PL[S/A]NAWK motif correspond to pos 87 to 94 of SEQ ID NO 68. In one aspect the NPQL motif correspond to positions 114 to 117 of SEQ ID NO 68.

The NAWK clade comprises polypeptides having DNase activity shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119.

The polypeptide shown in SEQ ID NO 119 share 99.48% sequence identity with the polypeptide with a UniProt sequence having accession number A0A178DM75.

One aspect of the invention relates to a polypeptide of the NAWK clade comprising one or both of the motifs [V/I]PL[S/A]NAWK (SEQ ID NO: 206) or NPQL (SEQ ID NO: 207), wherein the polypeptide has DNase activity and wherein the polypeptide is selected from any of the polypeptides shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 or a variant hereof having 1-25, such as 1-20, such as 1-15, such as 1-10, such as 1-5 amino acid alterations e.g. substitutions.

One aspect of the invention relates to a polypeptide of the NAWK clade comprising one or both of the motifs [V/I]PL[S/A]NAWK (SEQ ID NO: 206) or NPQL (SEQ ID NO: 207) and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 ora variant hereof having 1-25, such as 1-20, such as 1-15, such as 1-10, such as 1-5 amino acid alterations e.g. substitutions.

One embodiment of the invention relates to a polypeptide of the NAWK clade having DNase activity and comprising one or more of the motifs [V/I]PL[S/A]NAWK (SEQ ID NO: 206), NPQL (SEQ ID NO: 207), with the proviso that the polypeptide is not the polypeptide shown in SEQ ID NO 119.

One embodiment of the invention relates to a polypeptide of the NAWK-clade having DNase activity and where the polypeptide comprise one or both of the motifs [V/I]PL[S/A]NAWK (SEQ ID NO: 206) or NPQL (SEQ ID NO: 207), wherein the polypeptide is selected from the polypeptides:

a) a polypeptide having at least 81% sequence identity to the polypeptide shown in SEQ ID NO: 83, b) a polypeptide having at least 88.5% sequence identity to the polypeptide shown in SEQ ID NO: 86 c) a polypeptide having at least 99% sequence identity to the polypeptide shown in SEQ ID NO: 89 d) a polypeptide having at least 91% sequence identity to the polypeptide shown in SEQ ID NO: 92, e) a polypeptide having at least 90% sequence identity to the polypeptide shown in SEQ ID NO: 95, f) a polypeptide having at least 91% sequence identity to the polypeptide shown in SEQ ID NO: 98, g) a polypeptide having at least 89% sequence identity to the polypeptide shown in SEQ ID NO: 101, h) a polypeptide having at least 92% sequence identity to the polypeptide shown in SEQ ID NO: 104, i) a polypeptide having at least 90% sequence identity to the polypeptide shown in SEQ ID NO: 107 j) a polypeptide having at least 91.5% sequence identity to the polypeptide shown in SEQ ID NO: 110, k) a polypeptide having at least 93% sequence identity to the polypeptide shown in SEQ ID NO: 113, and l) a polypeptide having at least 96% sequence identity to the polypeptide shown in SEQ ID NO: 116, One embodiment of the invention relates to polypeptides of the NAWK clade comprising one or both of the motifs [V/I]PL[S/A]NAWK (SEQ ID NO: 206), NPQL (SEQ ID NO: 207), wherein the polypeptides have DNase activity and wherein the polypeptide is selected from the group consisting of SEQ ID NO 83, SEQ ID NO 86, SEQ ID NO 92, SEQ ID NO 95, SEQ ID NO 98, SEQ ID NO 101, SEQ ID NO 104, SEQ ID NO 107, SEQ ID NO 110, SEQ ID NO 113 and SEQ ID NO 116 or polypeptides having at least 96% sequence identity hereto.

One embodiment of the invention relates to a polypeptide of the NAWK-clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 83 or polypeptides having at least 81%, such as at least 83%, such as at least 85%, such as at least 87%, such as at least 90%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 86 or polypeptides having at least 88.5%, such as at least 90%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 89 or polypeptides having at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 92 or polypeptides having at least 91%, such as at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 95 or polypeptides having at least 90%, such as at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 98 or polypeptides having at least 91%, such as at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 101 or polypeptides having at least 89%, such as at least 90%, such as at least 93%, such as at least 95%, such as at least 97%, such as at least 98%, such as at least 99% or 100% sequence identity hereto.

One embodiment of the invention relates to a polypeptide of the NAWK clade comprising one or more of the motifs [V/I]PL[S/A]NAWK (SEQ ID NO: 68), NPQL (SEQ ID NO: 207), wherein the polypeptide has DNase activity and wherein the polypeptide is the polypeptide shown in SEQ ID NO 104 or polypeptides having at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 107 or polypeptides having at least 90%, such as at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 110 or polypeptides having at least 91.5%, such as at least 92%, such as at least 93%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 113 or polypeptides having at least 93%, such as at least 94%, such as at least 95%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide has DNase activity and wherein the polypeptide is the polypeptide shown in SEQ ID NO 116 or polypeptides having at least 96%, such as at least 97%, such as at least 98%, such as at least 99% or 100% sequence identity hereto.

One embodiment of the invention relates to a polypeptide of the NAWK clade comprising one or both of the motifs [V/I]PL[S/A]NAWK (SEQ ID NO: 206), NPQL (SEQ ID NO: 207), wherein the polypeptide having DNase activity and wherein the polypeptide comprises or consist of the polypeptide shown in SEQ ID NO 119.

A third distinguished clade is the KNAW clade. The clade of KNAW or the KNAW clade is a group of DNases all related to the same ancestor which share common properties. The hereto unknown clade comprises polypeptides forming a group within a domain e.g. NUC1_A of the phylogenetic tree, which may share common properties and are more closely related than other polypeptides in the domain.

The polypeptides of the KNAW-clade share the conservative motifs P[Q/E]L[W/Y] (SEQ ID NO: 208) and [K/H/E]NAW (SEQ ID NO:209), where the letters are the amino acid (one letter code) and the amino acids in the brackets are alternatives. In addition, the polypeptides of the KNAW-clade may comprise any of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH.

One aspect of the invention relates to polypeptides of the KNAW clade where the polypeptides comprise one or both of the motifs P[Q/E]L[W/Y] (SEQ ID NO: 208) and/or [K/H/E]NAW (SEQ ID NO: 209), wherein the polypeptides have DNase activity.

The KNAW clade comprises polypeptides having DNase activity shown in SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158.

The polypeptides shown in SEQ ID NO 122 and SEQ ID NO 125 are public sequences.

One aspect of the invention relates to a polypeptide of the KNAW-clade comprising one or both of the motifs P[Q/E]L[W/Y] (SEQ ID NO: 208) or [K/H/E]NAW (SEQ ID NO: 209), wherein the polypeptide has DNase activity and wherein the polypeptide is selected from any of the polypeptides shown in SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or variant hereof having 1-25, such as 1-20, such as 1-15, such as 1-10, such as 1-5 amino acid alterations e.g. substitutions.

One aspect of the invention relates to a polypeptide of the KNAW-clade comprising one or both the motifs P[Q/E]L[W/Y] (SEQ ID NO: 208) or [K/H/E]NAW (SEQ ID NO: 209) and further comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the polypeptide has DNase activity and wherein the polypeptide is selected from any of the polypeptides shown in SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or variant hereof having 1-25, such as 1-20, such as 1-15, such as 1-10, such as 1-5 amino acid alterations e.g. substitutions.

One embodiment of the invention relates to a polypeptide of the KNAW clade having DNase activity and where the polypeptide comprises one or both of the motifs P[Q/E]L[W/Y] (SEQ ID NO: 208) or [K/H/E]NAW (SEQ ID NO: 209), with the proviso that the polypeptide is not the polypeptides shown in SEQ ID NO 122 and SEQ ID NO 125 and with the proviso that the polypeptide is not the *Trichoderma harzianum* DNase shown in SEQ ID NO 2 of WO 2015/155351.

One embodiment of the invention relates to a polypeptide of the KNAW clade having DNase activity and where the polypeptide comprise one or both of the motifs P[Q/E]L[W/Y] (SEQ ID NO: 208) or [K/H/E]NAW (SEQ ID NO: 209), and wherein the polypeptide is selected from the polypeptides:

a) a polypeptide having at least 99.5% sequence identity to the polypeptide shown in SEQ ID NO: 128, b) a polypeptide having at least 93% sequence identity to the polypeptide shown in SEQ ID NO: 131, c) a polypeptide having at least 79% sequence identity to the polypeptide shown in SEQ ID NO: 134, d) a polypeptide having at least 72% sequence identity to the polypeptide shown in SEQ ID NO: 137, e) a polypeptide having at least 77% sequence identity to the polypeptide shown in SEQ ID NO: 140 f) a polypeptide having at least 74% sequence identity to the polypeptide shown in SEQ ID NO: 143, g) a polypeptide having at least 97% sequence identity to the polypeptide shown in SEQ ID NO: 146, h) a polypeptide having at least 71% sequence identity to the polypeptide shown in SEQ ID NO: 149, i) a polypeptide having at least 96% sequence identity to the polypeptide shown in SEQ ID NO: 152, j) a polypeptide having at least 72% sequence identity to the polypeptide shown in SEQ ID NO: 155, and k) a polypeptide having at least 98% sequence identity to the polypeptide shown in SEQ ID NO: 158.

One embodiment of the invention relates to a polypeptide of the KNAW clade comprising one or both of the motifs P[Q/E]L[W/Y] (SEQ ID NO: 208) or [K/H/E]NAW (SEQ ID NO: 209), wherein the polypeptide having DNase activity is selected from the group consisting of SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 98% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 128 or polypeptides having at least 99.5% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 131 or polypeptides having at least 93%, such as at least 94%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 134 or polypeptides having at least 79%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 137 or polypeptides having at least 72%, such as at least 75%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 140 or polypeptides having at least 77%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 143 or polypeptides having at least 74%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 146 or polypeptides having at least 97%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 149 or polypeptides having at least 71%, such as at least 75%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 152 or polypeptides having at least 96%, such as at least 97%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 155 or polypeptides having at least 72%, such as at least 75%, such as at least 80%, such as at least 85%, such as at least 86%, such as at least 88%, such as at least 90%, such as at least 93%, such as at least 95%, such as at least 98%, such as at least 99% or 100% sequence identity hereto.

One embodiment of the invention relates to a polypeptide of the KNAW clade comprising one or both motifs P[Q/E]L[W/Y] (SEQ ID NO: 208) or [K/H/E]NAW (SEQ ID NO: 209), wherein the polypeptide has DNase activity and wherein the polypeptide is the polypeptide shown in SEQ ID NO 158 or polypeptides having at least 98%, such as at least 99% or 100% sequence identity hereto.

One embodiment of the invention relates to a polypeptide having DNase activity, wherein the polypeptide is selected from the group consisting of:

a) a polypeptide having at least 84% sequence identity to the polypeptide shown in SEQ ID NO: 8, b) a polypeptide having at least 94% sequence identity to the polypeptide shown in SEQ ID NO: 9, c) a polypeptide having at least 92% sequence identity to the polypeptide shown in SEQ ID NO: 11, d) a polypeptide having at least 92% sequence identity to the polypeptide shown in SEQ ID NO: 12, e) a polypeptide having at least 97% sequence identity to the polypeptide shown in SEQ ID NO: 13, f) a polypeptide having at least 96% sequence identity to the polypeptide shown in SEQ ID NO: 14, g) a polypeptide having at least 90% sequence identity to the polypeptide shown in SEQ ID NO: 15, h) a polypeptide having at least 88% sequence identity to the polypeptide shown in SEQ ID NO: 16, i) a polypeptide having at least 93% sequence identity to the polypeptide shown in SEQ ID NO: 17, j) a polypeptide having at least 90% sequence identity to the polypeptide shown in SEQ ID NO: 18, k) a polypeptide having at least 89% sequence identity to the polypeptide shown in SEQ ID NO: 19, l) a polypeptide having at least 90% sequence identity to the polypeptide shown in SEQ ID NO: 20, m) a polypeptide having at least 93% sequence identity to the polypeptide shown in SEQ ID NO: 21, n) a polypeptide having at least 90% sequence identity to the polypeptide shown in SEQ ID NO: 22, o) a polypeptide having at least 93% sequence identity to the polypeptide shown in SEQ ID NO: 23, p) a polypeptide having at least 85% sequence identity to the polypeptide shown in SEQ ID NO: 53, q) a polypeptide having at least 98% sequence identity to the polypeptide shown in SEQ ID NO: 56, r) a polypeptide having at least 94% sequence identity to the polypeptide shown in SEQ ID NO: 59, s) a polypeptide having at least 85% sequence identity to the polypeptide shown in SEQ ID NO: 62, t) a polypeptide having at least 97% sequence identity to the polypeptide shown in SEQ ID NO: 68, u) a polypeptide having at least 99% sequence identity to the polypeptide shown in SEQ ID NO: 71, v) a polypeptide having at least 91% sequence identity to the polypeptide shown in SEQ ID NO: 74, w) a polypeptide having at least 98% sequence identity to the polypeptide shown in SEQ ID NO: 77, x) a polypeptide having at least 81% sequence identity to the polypeptide shown in SEQ ID NO: 83, y) a polypeptide having at least 89% sequence identity to the polypeptide shown in SEQ ID NO: 86, z) a polypeptide having at least 99% sequence identity to the polypeptide shown in SEQ ID NO: 89, aa) a polypeptide having at least 91% sequence identity to the polypeptide shown in SEQ ID NO: 92, bb) a polypeptide having at least 90% sequence identity to the polypeptide shown in SEQ ID NO: 95, cc) a polypeptide having at least 91% sequence identity to the polypeptide shown in SEQ ID NO: 98, dd) a polypeptide having at least 92% sequence identity to the polypeptide shown in SEQ ID NO: 104, ee) a polypeptide having at least 90% sequence identity to the polypeptide shown in SEQ ID NO: 107.

ff) a polypeptide having at least 91.5% sequence identity to the polypeptide shown in SEQ ID NO: 110.

gg) a polypeptide having at least 93% sequence identity to the polypeptide shown in SEQ ID NO: 113, hh) a polypeptide having at least 96% sequence identity to the polypeptide shown in SEQ ID NO: 116, ii) a polypeptide having at least 99.5% sequence identity to the polypeptide shown in SEQ ID NO: 119, jj) a polypeptide having at least 99.5% sequence identity to the polypeptide shown in SEQ ID NO: 128, kk) a polypeptide having at least 93% sequence identity to the polypeptide shown in SEQ ID NO: 131, ll) a polypeptide having at least 79% sequence identity to the polypeptide shown in SEQ ID NO: 134, mm) a polypeptide having at least 72% sequence identity to the polypeptide shown in SEQ ID NO: 137, nn) a polypeptide having at least 77% sequence identity to the polypeptide shown in SEQ ID NO: 140, oo) a polypeptide having at least 74% sequence identity to the polypeptide shown in SEQ ID NO: 143, pp) a polypeptide having at least 97% sequence identity to the polypeptide shown in SEQ ID NO: 146, qq) a polypeptide having at least 71% sequence identity to the polypeptide shown in SEQ ID NO: 149, rr) a polypeptide having at least 96% sequence identity to the polypeptide shown in SEQ ID NO: 152, ss) a polypeptide having at least 72% sequence identity to the polypeptide shown in SEQ ID NO: 155, tt) a polypeptide having at least 93% sequence identity to the polypeptide shown in SEQ ID NO: 158, uu) a polypeptide having at least 85% sequence identity to the polypeptide shown in SEQ ID NO: 164, vv) a polypeptide having at least 88% sequence identity to the polypeptide shown in SEQ ID NO: 167 ww) a polypeptide having at least 99.8% sequence identity to the polypeptide shown in SEQ ID NO: 170, xx) a polypeptide having at least 97% sequence identity to the polypeptide shown in SEQ ID NO: 173, yy) a polypeptide having at least 87% sequence identity to the polypeptide shown in SEQ ID NO: 176 zz) a polypeptide having at least 81% sequence identity to the polypeptide shown in SEQ ID NO: 179, aaa) a polypeptide having at least 89% sequence identity to the polypeptide shown in SEQ ID NO: 182, bbb) a polypeptide having at least 96% sequence identity to the polypeptide shown in SEQ ID NO: 185, ccc) a polypeptide having at least 88% sequence identity to the polypeptide shown in SEQ ID NO: 188, ddd) a polypeptide having at least 87% sequence identity to the polypeptide shown in SEQ ID NO: 191, eee) a polypeptide having at least 94% sequence identity to the polypeptide shown in SEQ ID NO: 194, fff) a polypeptide having at least 90% sequence identity to the polypeptide shown in SEQ ID NO: 197, and optionally ggg) one or more of the motifs [E/D/H]H[I/V/L/F/M]X [P/A/S], [T/D/S][G/N]PQL, [G/T]Y[D/S][R/K/L], [F/L/Y/I]A[N/R]D[L/I/P/V] or C[D/N]T[A/R] and [D/Q][I/V]DH.

In one aspect of the invention, the DNase is obtainable from *Bacillus* sp-62451, *Bacillus horikoshii* or *Paenibacillus* sp-18057. The DNase of the present invention includes the mature polypeptide of SEQ ID NO: 2, 4 or 6 or polypeptides having a sequence identity to the mature polypeptides of SEQ ID NO: 2, 4 or 6 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and wherein the polypeptides have DNase activity.

The group of DNases comprised in the GYS-clade as described above share similar structural and functional properties as described above e.g. common motifs. The DNases of the GYS-clade are preferably obtained from *Bacillus* genus. The individual DNases in the GYS group is described in details below.

The DNase may be obtained from *Bacillus* preferably *Bacillus* sp. sp-62451 The DNase may be a polypeptide comprising the mature polypeptide of SEQ ID NO 2 or a polypeptide closely related hereto such as a polypeptide having at least 60%, such as at least 70%, at least 75%, at least 80%, at least 85%, at least 90% or such as at least 95% sequence identity hereto. A DNase according to the invention may be obtained from *Bacillus*, such as *Bacillus* sp. sp-62451 and comprise a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 8. The polypeptides comprising SEQ ID NO 21 (mature polypeptide obtained from *Bacillus cibi*), SEQ ID NO 22 (mature polypeptide obtained from *Bacillus* sp-18318) and SEQ ID NO 23 (mature polypeptide obtained from *Bacillus idriensis*) are homologue polypeptides within e.g. with at least 80% sequence identity to SEQ ID NO 8.

The polypeptides comprising SEQ ID NO 21 (mature polypeptide obtained from *Bacillus* SEQ ID NO 22 (mature polypeptide obtained from *Bacillus* sp-18318) and SEQ ID NO 23 (mature polypeptide obtained from *Bacillus idriensis*) are also useful for preventing or removing biofilm on items such as textiles and/or fabric as shown in example 2. The DNase may be a polypeptide comprising the mature polypeptide shown in SEQ ID NO 21 or a polypeptide closely related hereto. Thus one aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 21, preferably obtained from *Bacillus cibi*. The DNase may be a polypeptide comprising the mature polypeptide shown in SEQ ID NO 22 or a polypeptide closely related hereto. One aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 22, preferably obtained from *Bacillus* sp-18318. The DNase may be a polypeptide comprising the mature polypeptide shown in SEQ ID NO 23 or a polypeptide closely related hereto. One aspect of the invention relates to a DNase having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 23, preferably obtained from *Bacillus idriensis*.

The DNase may be obtained from *Bacillus* preferably *Bacillus horikoshii*. The DNase may be a polypeptide comprising the mature polypeptide of SEQ ID NO 4 or a polypeptide closely related hereto such as a polypeptides having at least 60% such as at least 70%, at least 75%, at least 80%, at least 85%, at least 90% or such as at least 95% sequence identity hereto. A DNase according to the invention may be obtained from *Bacillus* such as *Bacillus horikoshii* and comprise a polypeptide having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 9. The homologue polypeptides comprised in SEQ ID NO 11 (mature polypeptide obtained from *Bacillus* sp-62520), SEQ ID NO 12 (mature polypeptide obtained from *Bacillus* sp-62520), SEQ ID NO 13 (mature polypeptide obtained from *Bacillus horikoshii*), SEQ ID NO 14 (mature polypeptide obtained from *Bacillus horikoshii*), SEQ ID NO 15 (mature polypeptide obtained from *Bacillus* sp-16840), SEQ ID NO 16 (mature polypeptide obtained from *Bacillus* sp-16840), SEQ ID NO 17 (mature polypeptide obtained from *Bacillus* sp-62668), SEQ ID NO 18 (mature polypeptide obtained from *Bacillus* sp-13395), SEQ ID NO 19 (mature polypeptide obtained from *Bacillus horneckiae*) or SEQ ID NO 20 (mature polypeptide obtained from *Bacillus* sp-11238) are homologue polypeptides within at least 80% sequence identity to SEQ ID NO 9. The polypeptides comprising SEQ ID NO 11 (mature polypeptide obtained from *Bacillus* sp-62520), SEQ ID NO 12 (mature polypeptide obtained from *Bacillus* sp-62520), SEQ ID NO 13 (mature polypeptide obtained from *Bacillus horikoshii*), SEQ ID NO 14 (mature polypeptide obtained from *Bacillus horikoshii*), SEQ ID NO 15 (mature polypeptide obtained from *Bacillus* sp-16840), SEQ ID NO 16 (mature polypeptide obtained from *Bacillus* sp-16840), SEQ ID NO 17 (mature polypeptide obtained from *Bacillus* sp-62668), SEQ ID NO 18 (mature polypeptide obtained from *Bacillus* sp-13395), SEQ ID NO 19 (mature polypeptide obtained from *Bacillus horneckiae*) or SEQ ID NO 20 (mature polypeptide obtained from *Bacillus* sp-11238) are also useful for preventing or removing biofilm on items such as textiles and/or fabric as shown in example 2. The DNase may be a polypeptide comprising the mature polypeptide shown in SEQ ID NO 11 or a polypeptide closely related hereto. Thus one aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 11, preferably obtained from *Bacillus* sp-62520. The DNase may be a polypeptide comprising the mature polypeptide shown in SEQ ID NO 12 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 12, preferably obtained from *Bacillus* sp-62520. The DNase may be a polypeptide comprising the mature polypeptide shown in SEQ ID NO 13 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 13, preferably obtained from *Bacillus horikoshii*. The DNase may be a polypeptide comprising the mature polypeptide shown in SEQ ID NO 14 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 14, preferably obtained from *Bacillus horikoshii*. The DNase may be a polypeptide comprising the mature polypeptide shown in SEQ ID NO 15 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 15, preferably obtained from *Bacillus* sp-16840. The DNase may be a polypeptide comprising the mature polypeptide shown in SEQ ID NO 16 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 16, preferably obtained from *Bacillus* sp-16840. The DNase may be a polypeptide comprising the mature polypeptide shown in SEQ ID NO 17 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 17, preferably obtained from *Bacillus* sp-62668. The DNase may be a polypeptide comprising the mature polypeptide shown in SEQ ID NO 18 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 18, preferably obtained from *Bacillus* sp-13395. The DNase may be a polypeptide comprising the mature polypeptide shown in SEQ ID NO 19 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 19, preferably obtained from *Bacillus horneckiae.*

The DNase may be a polypeptide comprising the mature polypeptide shown in SEQ ID NO 20 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 20, preferably obtained from *Bacillus* sp-11238.

The DNase may be a polypeptide comprising the mature polypeptide shown in SEQ ID NO 53 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 53, preferably obtained from *Bacillus algicola.*

The DNase may be a polypeptide comprising the mature polypeptide shown in SEQ ID NO 56 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 56, preferably obtained from Xanthan community J.

The DNase may be a polypeptide comprising the mature polypeptide shown in SEQ ID NO 59 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 59, preferably obtained from *Bacillus vietnamensis.*

The DNase may be a polypeptide comprising the mature polypeptide shown in SEQ ID NO 62 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 62, preferably obtained from *Bacillus hwajinpoensis.*

The DNase may be a polypeptide comprising the mature polypeptide shown in SEQ ID NO 68 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 68, preferably obtained from *Bacillus indicus.*

The DNase may be a polypeptide comprising the mature polypeptide shown in SEQ ID NO 71 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 71, preferably obtained from *Bacillus marisflavi.*

The DNase may be a polypeptide comprising the mature polypeptide shown in SEQ ID NO 74 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 74, preferably obtained from *Bacillus luciferensis.*

The DNase may be a polypeptide comprising the mature polypeptide shown in SEQ ID NO 77 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 77, preferably obtained from *Bacillus marisflavi.*

The group of DNases comprised in the NAWK-clade as described above share similar structural and functional properties as described above e.g. common motifs. The DNases of the NAWK-clade may be obtained from any of the genus and species listed below. The individual DNases in the NAWK group is described in details below.

The DNase may be a polypeptide comprising the mature polypeptide shown in SEQ ID NO 83 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 83, preferably obtained from *Pyrenochaetopsis* sp.

The DNase may be a polypeptide comprising the mature polypeptide shown in SEQ ID NO 86 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 86, preferably obtained from *Vibrissea flavovirens.*

The DNase may be a polypeptide comprising the mature polypeptide shown in SEQ ID NO 89 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 89, preferably obtained from *Setosphaeria rostrata.*

The DNase may be a polypeptide comprising the mature polypeptide shown in SEQ ID NO 92 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 92, preferably obtained from *Endophragmiella valdina.*

The DNase may be a polypeptide comprising the mature polypeptide shown in SEQ ID NO 95 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 95, preferably obtained from *Corynespora cassiicola.*

The DNase may be a polypeptide comprising the mature polypeptide shown in SEQ ID NO 98 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 98, preferably obtained from *Paraphoma* sp. XZ1965.

The DNase may be a polypeptide comprising the mature polypeptide shown in SEQ ID NO 101 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 101, preferably obtained from *Monilinia fructicola.*

The DNase may be a polypeptide comprising the mature polypeptide shown in SEQ ID NO 104 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 104, preferably obtained from *Curvularia lunata.*

The DNase may be a polypeptide comprising the mature polypeptide shown in SEQ ID NO 107 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 107, preferably obtained from *Penicillium reticulisporum.*

The DNase may be a polypeptide comprising the mature polypeptide shown in SEQ ID NO 110 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 110, preferably obtained from *Penicillium quercetorum.*

The DNase may be a polypeptide comprising the mature polypeptide shown in SEQ ID NO 113 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 113, preferably obtained from *Setophaeosphaeria* sp.

The DNase may be a polypeptide comprising the mature polypeptide shown in SEQ ID NO 116 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 116, preferably obtained from *Alternaria* sp. XZ2545.

The DNase may be a polypeptide comprising the mature polypeptide shown in SEQ ID NO 119 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 119, preferably obtained from *Alternaria* sp.

The group of DNases comprised in the KNAW-clade as described above share similar structural and functional properties as described above e.g. common motifs. The DNases of the NAWK clade are preferably obtained from any of the genus and species listed below. The individual DNases in the NAWK group is described in details below.

The DNase may be a polypeptide comprising the mature polypeptide shown in SEQ ID NO 128 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 128, preferably obtained from *Scytalidium thermophilum.*

The DNase may be a polypeptide comprising the mature polypeptide shown in SEQ ID NO 131 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 131, preferably obtained from *Metapochonia suchlasporia.*

The DNase may be a polypeptide comprising the mature polypeptide shown in SEQ ID NO 134 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 134, preferably obtained from *Daldinia fissa.*

The DNase may be a polypeptide comprising the mature polypeptide shown in SEQ ID NO 137 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 137, preferably obtained from *Acremonium* sp. XZ2007.

The DNase may be a polypeptide comprising the mature polypeptide shown in SEQ ID NO 140 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 140, preferably obtained from *Acremonium dichromosporum.*

The DNase may be a polypeptide comprising the mature polypeptide shown in SEQ ID NO 143 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 143, preferably obtained from *Sarocladium* sp. XZ2014.

The DNase may be a polypeptide comprising the mature polypeptide shown in SEQ ID NO 146 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 146, preferably obtained from *Metarhizium* sp. HNA15-2.

The DNase may be a polypeptide comprising the mature polypeptide shown in SEQ ID NO 149 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 149, preferably obtained from *Acremonium* sp. XZ2414.

The DNase may be a polypeptide comprising the mature polypeptide shown in SEQ ID NO 152 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 152, preferably obtained from *Isaria tenuipes.*

The DNase may be a polypeptide comprising the mature polypeptide shown in SEQ ID NO 155 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 155, preferably obtained from *Scytalidium circinatum.*

The DNase may be a polypeptide comprising the mature polypeptide shown in SEQ ID NO 158 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 158, preferably obtained from *Metarhizium lepidiotae.*

The polypeptides having DNase activity listed below are also useful for deep cleaning e.g. for preventing, reducing or removing biofilm e.g. on fabric e.g. textiles, such as cotton and polyester. The polypeptides having DNase activity listed below comprise the NUC1 and NUC1_A domain and the NUC1 and NUC1_A motifs and have similarity with the polypeptides belonging to either of the clades GYS, NAWK and KNAW, which also comprise the NUC1 and NUC1_A domains and motifs.

The DNase may be a polypeptide comprising the mature polypeptide shown in SEQ ID NO 164 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 164, preferably obtained from *Sporormia fimetaria.*

The DNase may be a polypeptide comprising the mature polypeptide shown in SEQ ID NO 167 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 167, preferably obtained from *Pycnidiophora* cf. *dispera.*

The DNase may be a polypeptide comprising the mature polypeptide shown in SEQ ID NO 170 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 170, preferably obtained from Xanthan alkaline community D.

The DNase may be a polypeptide comprising the mature polypeptide shown in SEQ ID NO 173 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 173, preferably obtained from Xanthan alkaline community 0.

The DNase may be a polypeptide comprising the mature polypeptide shown in SEQ ID NO 176 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 176, preferably obtained from *Clavicipitaceae* sp-70249.

The DNase may be a polypeptide comprising the mature polypeptide shown in SEQ ID NO 179 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 179, preferably obtained from *Westerdykella* sp. AS85-2.

The DNase may be a polypeptide comprising the mature polypeptide shown in SEQ ID NO 182 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 182, preferably obtained from *Humicolopsis cephalosporioides*.

The DNase may be a polypeptide comprising the mature polypeptide shown in SEQ ID NO 185 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 185, preferably obtained from *Neosartorya massa*.

The DNase may be a polypeptide comprising the mature polypeptide shown in SEQ ID NO 188 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 188, preferably obtained from *Roussoella intermedia*.

The DNase may be a polypeptide comprising the mature polypeptide shown in SEQ ID NO 191 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 191, preferably obtained from *Pleosporales*.

The DNase may be a polypeptide comprising the mature polypeptide shown in SEQ ID NO 194 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 194, preferably obtained from *Phaeosphaeria* sp.

The DNase may be a polypeptide comprising the mature polypeptide shown in SEQ ID NO 197 or a polypeptide closely related hereto. One aspect of the invention relates to a DNase having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 197, preferably obtained from *Didymosphaeria futilis*.

The DNase may be obtained from *Paenibacillus* preferably *Paenibacillus* sp-18057. The DNase may be a polypeptide comprising the mature polypeptide of SEQ ID NO 6 or a polypeptide closely related hereto. A DNase according to the invention may be obtained from *Paenibacillus* sp-18057 and comprise a polypeptide having at least 60%, e.g., at least 65%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 10.

In one aspect of the invention, the polypeptide having DNase activity is obtained from *Bacillus*, in particular from *Bacillus* sp-62451. In one aspect of the invention the polypeptide having DNase activity is obtained from *Bacillus*, in particular from *Bacillus horikoshii*. In one aspect of the invention the polypeptide having DNase activity is obtained from *Bacillus*, in particular from *Bacillus* sp-62520. In one aspect of the invention the polypeptide having DNase activity is obtained from *Bacillus*, in particular from *Bacillus* sp-16840. In one aspect of the invention the polypeptide having DNase activity is obtained from *Bacillus*, in particular from *Bacillus* sp-62668. In one aspect of the invention the polypeptide having DNase activity is obtained from *Bacillus*, in particular from *Bacillus* sp-13395. In one aspect of the invention the polypeptide having DNase activity is obtained from *Bacillus*, in particular from *Bacillus* sp-11238. In one aspect of the invention the polypeptide having DNase activity is obtained from *Bacillus*, in particular from *Bacillus cibi*. In one aspect of the invention the polypeptide having DNase activity is obtained from *Bacillus*, in particular from *Bacillus* sp-18318. In one aspect of the invention the polypeptide having DNase activity is obtained from *Bacillus*, in particular from *Bacillus idriensis*. In one aspect of the invention the polypeptide having DNase activity is obtained from *Vibrissea flavovirens* and comprises or consists of the polypeptide shown in SEQ ID NO 86. In one aspect of the invention the polypeptide having DNase activity is obtained from *Acremonium dichromosporum* and comprises or consists of the polypeptide shown in SEQ ID NO 140. In one aspect of the invention the polypeptide having DNase activity is obtained from *Clavicipitaceae* sp-70249 and comprises or consists of the polypeptide shown in SEQ ID NO 176. In one aspect of the invention the polypeptide having DNase activity is obtained from *Penicillium reticulisporum* and comprises or consists of the polypeptide shown in SEQ ID NO 107. In one aspect of the invention the polypeptide having DNase activity is obtained from *Pycnidiophora* cf. *dispera* and comprises or consists of the polypeptide shown in SEQ ID NO 167. In one aspect of the invention the polypeptide having DNase activity is obtained from *Metapochonia suchlasporia* and comprises or consists of the polypeptide shown in SEQ ID NO 131. In one aspect of the invention the polypeptide having DNase activity is obtained from *Acremonium* sp. XZ2007 and comprises or consists of the polypeptide shown in SEQ ID NO 137. In one aspect of the invention the polypeptide having DNase activity is obtained from *Setosphaeria rostrata* and comprises or consists of the polypeptide shown in SEQ ID NO 89. In one aspect of the invention the polypeptide having DNase activity is obtained from *Sarocladium* sp. XZ2014 and comprises or consists of the polypeptide shown in SEQ ID NO 143. In one aspect of the invention the polypeptide having DNase activity is obtained from *Metarhizium* sp. HNA15-2 and comprises or consists of the polypeptide shown in SEQ ID NO 146. In one aspect of the invention the polypeptide having DNase activity is obtained from *Endophragmiella valdina* and comprises or consists of the polypeptide shown in SEQ ID NO 92. In one aspect of the invention the polypeptide having DNase activity is obtained from *Humicolopsis cephalosporioides* and comprises or consists of the polypeptide shown in SEQ ID NO 182. In one aspect of the invention the polypeptide having DNase activity is obtained from *Corynespora cassiicola* and comprises or consists of the polypeptide shown in SEQ ID NO 95. In one aspect of the invention the polypeptide having DNase activity is obtained from *Paraphoma* sp. XZ1965 and comprises or consists of the polypeptide shown in SEQ ID NO 98. In one aspect of the invention the polypeptide having DNase activity is obtained from *Curvularia lunata* and comprises or consists of the polypeptide shown in SEQ ID NO 104. In one aspect of the invention the polypeptide having DNase activity is obtained from *Acremonium* sp. XZ2414 and comprises or consists of the polypeptide shown in SEQ ID NO 149. In one aspect of the invention the polypeptide having DNase activity is obtained from *Isaria tenuipes* and comprises or consists of the polypeptide shown in SEQ ID NO 152. In one aspect of the invention the polypeptide having DNase activity is obtained from *Rous-soella intermedia* and comprises or consists of the polypeptide shown in SEQ ID NO 188. In one aspect of the invention the polypeptide having DNase activity is obtained from *Scytalidium circinatum* and comprises or consists of the polypeptide shown in SEQ ID NO 155. In one aspect of the invention the polypeptide having DNase activity is obtained from *Setophaeosphaeria* sp. and comprises or consists of the polypeptide shown in SEQ ID NO 158. In one aspect of the invention the polypeptide having DNase activity is obtained from *Alternaria* sp. XZ2545 and comprises or consists of the polypeptide shown in SEQ ID NO 116. In one aspect of the invention the polypeptide having DNase activity is obtained from *Alternaria* sp. and comprises or consists of the polypeptide shown in SEQ ID NO 119. In one aspect of the invention the polypeptide having DNase activity is obtained from *Metarhizium lepidiotae* and comprises or consists of the polypeptide shown in SEQ ID NO 158. In one aspect of the invention the polypeptide having DNase activity is obtained from *Pleosporales* and comprises or consists of the polypeptide shown in SEQ ID NO 191. In one aspect of the invention the polypeptide having DNase activity is obtained from *Phaeosphaeria* sp. and comprises or consists of the polypeptide shown in SEQ ID NO 194. In one aspect of the invention the polypeptide having DNase activity is obtained from *Didymosphaeria futilis* and comprises or consists of the polypeptide shown in SEQ ID NO 197. In one aspect of the invention the polypeptide having DNase activity is obtained from *Bacillus vietnamensis* and comprises or consists of the polypeptide shown in SEQ ID NO 59. In one aspect of the invention the polypeptide having DNase activity is obtained from *Bacillus hwajinpoensis* and comprises or consists of the polypeptide shown in SEQ ID NO 62. In one aspect of the invention the polypeptide having DNase activity is obtained from Xanthan alkaline community J and comprises or consists of the polypeptide shown in SEQ ID NO 56. In one aspect of the invention the polypeptide having DNase activity is obtained from *Bacillus indicus* and comprises or consists of the polypeptide shown in SEQ ID NO 68. In one aspect of the invention the polypeptide having DNase activity is obtained from *Bacillus marisflavi* and comprises or consists of the polypeptide shown in SEQ ID NO 71. In one aspect of the invention the polypeptide having DNase activity is obtained from *Bacillus luciferensis* and comprises or consists of the polypeptide shown in SEQ ID NO 74. In one aspect of the invention the polypeptide having DNase activity is obtained from *Bacillus marisflavi* and comprises or consists of the polypeptide shown in SEQ ID NO 77. In one aspect of the invention the polypeptide having DNase activity is obtained from *Sporormia fimetaria* and comprises or consists of the polypeptide shown in SEQ ID NO 164. In one aspect of the invention the polypeptide having DNase activity is obtained from *Daldinia fissa* and comprises or consists of the polypeptide shown in SEQ ID NO.134. In one aspect of the invention the polypeptide having DNase activity is obtained from *Pyrenochaetopsis* sp. and comprises or consists of the polypeptide shown in SEQ ID NO 83. In one aspect of the invention the polypeptide having DNase activity is obtained from *Westerdykella* sp. AS85-2 and comprises or consists of the polypeptide shown in SEQ ID NO 179. In one aspect of the invention the polypeptide having DNase activity is obtained from *Monilinia fructicola* and comprises or consists of the polypeptide shown in SEQ ID NO 101. In one aspect of the invention the polypeptide having DNase activity is obtained from *Neosartorya massa* and comprises or consists of the polypeptide shown in SEQ ID NO 185. In one aspect of the invention the polypeptide having DNase activity is obtained from *Penicillium quercetorum* and comprises or consists of the polypeptide shown in SEQ ID NO 110. In one aspect of the invention the polypeptide having DNase activity is obtained from Xanthan alkaline community D and comprises or consists of the polypeptide shown in SEQ ID NO 170. In one aspect of the invention the polypeptide having DNase activity is obtained from *Bacillus algicola* and comprises or consists of the polypeptide shown in SEQ ID NO 53. In one aspect of the invention the polypeptide having DNase activity is obtained from Xanthan alkaline community 0 and comprises or consists of the polypeptide shown in SEQ ID NO 173. In one aspect of the invention the polypeptide having DNase activity is obtained from *Scytalidium thermophilum* and comprises or consists of the polypeptide shown in SEQ ID NO 128.

In one aspect of the invention the polypeptide having DNase activity is obtained from *Paenibacillus*, in particular from *Paenibacillus* sp-18057. In one aspect of the invention the polypeptide having DNase activity is obtained from *Bacillus* and comprises the mature polypeptide of SEQ ID NOS 2, 4 or 6 i.e. the mature polypeptides with SEQ ID NOS 8, 9 or 10. In a preferred aspect of the invention the DNase is obtained from *Bacillus* sp-62451 and comprises the polypeptide sequence with SEQ ID NO 8. In a preferred aspect of the invention the DNase is obtained from *Bacillus horikoshii* and comprises the polypeptide sequence with SEQ ID NO 9. In a preferred aspect of the invention the DNase is obtained from *Paenibacillus* sp-18057 and comprises any of the polypeptide sequence with SEQ ID NO 10. In a preferred aspect of the invention the DNase is obtained from *Bacillus* sp-62520 and comprises the polypeptide sequence with SEQ ID NO 11. In a preferred aspect of the invention the DNase is obtained from *Bacillus* sp-62520 and comprises the polypeptide sequence with SEQ ID NO 12. In a preferred aspect of the invention the DNase is obtained from *Bacillus horikoshii* and comprises the polypeptide sequence with SEQ ID NO 13. In a preferred aspect of the invention the DNase is obtained from *Bacillus horikoshii* and comprises the polypeptide sequence with SEQ ID NO 14. In a preferred aspect of the invention the DNase is obtained from *Bacillus* sp-16840 and comprises the polypeptide sequence with SEQ ID NO 15. In a preferred aspect of the invention the DNase is obtained from *Bacillus* sp-16840 and comprises the polypeptide sequence with SEQ ID NO 16. In a preferred aspect of the invention the DNase is obtained from *Bacillus* sp-62668 and comprises the polypeptide sequence with SEQ ID NO 17. In a preferred aspect of the invention the DNase is obtained from *Bacillus* sp-13395 and comprises the polypeptide sequence with SEQ ID NO 18. In a preferred aspect of the invention the DNase is obtained from *Bacillus horneckiae* and comprises the polypeptide sequence with SEQ ID NO 19. In a preferred aspect of the invention the DNase is obtained from *Bacillus* sp-11238 and comprises the polypeptide sequence with SEQ ID NO 20. In a preferred aspect of the invention the DNase is obtained from *Bacillus cibi* and comprises the polypeptide sequence with SEQ ID NO 21. In a preferred aspect of the invention the DNase is obtained from *Bacillus* sp-18318 and comprises the polypeptide sequence with SEQ ID NO 22. In a preferred aspect of the invention the DNase is obtained from *Bacillus idriensis* and comprises the polypeptide sequence with SEQ ID NO 23.

In a preferred aspect of the invention the DNase is obtained from *Bacillus* sp-62451 and consists of the polypeptide sequence with SEQ ID NO 8. In another preferred aspect of the invention the DNase is obtained from *Bacillus horikoshii* and consists of the polypeptide sequence with SEQ ID NO 9. In another preferred aspect of the invention the DNase is obtained from *Paenibacillus* sp-18057 and consists of the polypeptide sequence with SEQ ID NO 10. In a preferred aspect of the invention the DNase is obtained from *Bacillus* sp-62520 and consists of the polypeptide sequence with SEQ ID NO 11. In a preferred aspect of the invention the DNase is obtained from *Bacillus* sp-62520 and consists of the polypeptide sequence with SEQ ID NO 12. In a preferred aspect of the invention the DNase is obtained from *Bacillus horikoshii* and consists of the polypeptide sequence with SEQ ID NO 13. In a preferred aspect of the invention the DNase is obtained from *Bacillus horikoshii* and consists of the polypeptide sequence with SEQ ID NO 14. In a preferred aspect of the invention the DNase is obtained from *Bacillus* sp-16840 and consists of the polypeptide sequence with SEQ ID NO 15. In a preferred aspect of the invention the DNase is obtained from *Bacillus* sp-16840 and consists of the polypeptide sequence with SEQ ID NO 16. In a preferred aspect of the invention the DNase is obtained from *Bacillus* sp-62668 and consists of the polypeptide sequence with SEQ ID NO 17. In a preferred aspect of the invention the DNase is obtained from *Bacillus* sp-13395 and consists of the polypeptide sequence with SEQ ID NO 18. In a preferred aspect of the invention the DNase is obtained from *Bacillus horneckiae* and consists of the polypeptide sequence with SEQ ID NO 19. In a preferred aspect of the invention the DNase is obtained from *Bacillus* sp-11238 and consists of the polypeptide sequence with SEQ ID NO 20. In a preferred aspect of the invention the DNase is obtained from *Bacillus cibi* and consists of the polypeptide sequence with SEQ ID NO 21. In a preferred aspect of the invention the DNase is obtained from *Bacillus* sp-18318 and consists of the polypeptide sequence with SEQ ID NO 22. In a preferred aspect of the invention the DNase is obtained from *Bacillus idriensis* and consists of the polypeptide sequence with SEQ ID NO 23.

Biofilm can develop on textile when microorganisms are present on an item and stick together on the item. Some microorganisms tend to adhere to the surface of items such as textiles.

Some microorganisms adhere to such surfaces and form a biofilm on the surface. The biofilm may be sticky and the adhered microorganisms and/or the biofilm may be difficult to remove. Furthermore, the biofilm adhere soil due to the sticky nature of the biofilm. The commercial laundry detergent compositions available on the marked do not remove such adhered microorganisms, microorganism parts or biofilm.

The present invention relates to polypeptides having DNase activity and the use of such polypeptides for preventing, reducing or removing a biofilm from an item, such as textiles. In one embodiment of the invention the polypeptide having DNase activity is used for preventing, reducing or removing the stickiness of an item. In one embodiment of the invention, the polypeptide having DNase activity improves whiteness of an item, such as a textile. In one embodiment the polypeptide of the invention having DNase activity helps maintaining the colour on textiles. When textiles are repeatedly washed the colours tend to be less bright. In one embodiment a polypeptide of the invention having DNase has an improved effect of maintaining the colour of coloured textiles even after repeated washes. In one embodiment the polypeptide of the invention also reduced the colouring of non-coloured part of the same or additional textile present in the wash.

The polypeptide having DNase activity can further be used for pretreating stains on textile such as textile with a pronounced amount of biofilm adhered to the textile.

The polypeptide having DNase activity can further be used for preventing, reducing or removing static electricity from an item on which static electricity may accumulate, such item may be a textile or a hard surface. The polypeptide having DNase activity can further be used for preventing, reducing and/or removing a biofilm from an item, such item may be a hard surface e.g. dishes, cutlery, porcelain, china, crockery etc. Thus in some aspect the polypeptide having DNase activity may be used in an ADW (Automatic dishwash) process.

Additionally, the invention relates to the use of a polypeptide having DNase activity for preventing, reducing or removing redeposition of soil during a wash cycle. When the polypeptide is used for example in the laundering of textile, the polypeptide hinders deposition of soil present in the wash liquor to deposit on the textile.

Further, the invention concerns the use of a polypeptide having DNase activity for preventing, reducing or removing the adherence of soil to an item. In one embodiment, the item is textile. When the soil does not adhere to the item, the item appears cleaner. Thus, the invention further relates to the use of a polypeptide having DNase activity for maintaining or improving the whiteness of the item.

When items like T-shirts or sportswear are used, they are exposed to bacteria from the body of the user and from the rest of the environment in which they are used. This may cause malodor on the item even after the item is washed. The present invention relates to removal or reduction of malodor on textile. The malodor may be caused by bacteria producing compounds with an unpleasant smell. One example of such unpleasant smelling compounds is E-2-nonenal. The malodor can be present on newly washed textile which is still wet or the malodor can be present on newly washed textile, which has subsequently been dried. The malodor may also be present on textile, which has been stored for some time after wash. The present invention concerns the reduction or removal of malodor such as E-2-nonenal from wet or dry textile.

The polypeptides of the invention having DNase activity i.e. the DNases of the invention have very good cleaning performance in powder and liquid detergents. Examples of beneficial effects of the DNases with SEQ ID NO 8, 9 and 10 and homologue DNases, e.g. polypeptides having DNases activity and having a polypeptide sequence shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197. The deep-cleaning effect is shown in examples 2 and 3 one effect is preventing laundry in becoming grey and removal of malodor. The polypeptides comprising SEQ ID NO 8, 9 and 10 are novel polypeptides having DNase activity which have deep cleaning effect in powder detergents and liquid detergents. The polypeptides comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 158, SEQ ID NO 161, SEQ ID NO 164, SEQ ID NO 167, SEQ ID NO 170, SEQ ID NO 176, SEQ ID NO 179, SEQ ID NO 185, SEQ ID NO 188, SEQ ID NO 191 and SEQ ID NO 197, are also polypeptides having DNase activity which have deep cleaning effect in powder detergents and liquid detergents.

Benzonase (SIGMA-E1014) SEQ ID NO 7) is a commercially available DNase. The inventors show that this DNase has also has a deep cleaning effect as could be seen in example 2 The deep cleaning helps preventing greyness of laundry and removing of odor of laundry Yet another embodiment relates to the use of a DNase, selected from the group consisting of SEQ ID NO 7, 8, 9 and 10 for reducing malodor from laundry and/or textile. Another embodiment relates to the use of a DNase, selected from the group consisting of SEQ ID NO 7, 8, 9 and 10 for reducing malodor from laundry and/or textile, for anti-redeposition and for maintaining or improving the whiteness of a textile.

Some aspect of the invention relates to the use of a polypeptide having DNase activity, for prevention, reduction or removing a biofilm from an item, wherein the polypeptide having DNase activity comprises the HXXP motif and wherein H is the amino acid histidine, P is the amino acid proline and X is any amino acid. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity comprises one or more of the motifs [E/D/H]H[I/V/L/F/M]X[P/A/S], [T/D/S][G/N]PQL, [G/T]Y[D/S][R/K/L]. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity comprises one or both of the motifs [F/L/Y/I]A[N/R]D[L/I/P/V], C[D/N]T[A/R]. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the GYS clade and comprises one or both motifs [D/M/L][S/T]GYSR[D/N] (SEQ ID NO: 204) or ASXNRSKG (SEQ ID NO: 205). The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the GYS clade and comprises a polypeptide selected from the polypeptides shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77 and SEQ ID NO 80 or polypeptides having at least 80%, such as at least 85%, such as at least 90%, such as at least 95% or 100% sequence identity hereto. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the NAWK clade and comprises one or both motifs [V/I]PL[S/A]NAWK (SEQ ID NO: 206) or NPQL (SEQ ID NO: 207). The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the NAWK clade and comprises a polypeptides selected from the polypeptides shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 or polypeptides having at least 80%, such as at least 85%, such as at least 90%, such as at least 95% or 100% sequence identity hereto. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the KNAW clade and comprises one or both motifs P[Q/E]L[W/Y] (SEQ ID NO: 208) or [K/H/E]NAW (SEQ ID NO: 209). The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity belongs to the KNAW clade and comprises a polypeptides selected from the polypeptides shown in SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 80%, such as at least 85%, such as at least 90%, such as at least 95% or 100% sequence identity hereto. The item is preferable a fabric e.g. textile e.g. cotton and/or polyester.

Some aspect of the invention relates to the use of a polypeptide having DNase activity, for prevention, reduction or removing a biofilm from an item, wherein the polypeptide having DNase activity comprises the polypeptide shown in SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or polypeptides having at least 80%, such as at least 85%, such as at least 90%, such as at least 95% or 100% sequence identity hereto. The item is preferable a fabric e.g. textile e.g. cotton and/or polyester.

Some aspect of the invention relates to the use of a polypeptide having DNase activity and comprises the amino acid sequence shown in SEQ ID NO 11 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 12 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 13 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 14 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 15 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 16 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 17 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 18 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 19 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 20 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 21 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 22 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 23 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 53 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 56 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 59 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 62 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 65 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 68 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 71 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 74 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 77 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 80 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 83 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 86 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 89 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 92 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 95 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 98 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 101 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 104 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 107 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 110 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 113 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 116 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 119 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 122 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 125 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 128 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 131 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID N0134 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 137 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 140 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 143 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 146 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 149 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 152 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 155 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 158 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 161 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 164 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 167 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 170 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 173 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 176 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 179 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 182 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 185 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 188 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 191 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 194 or a polypeptide having at least 80% sequence identity hereto for reducing malodor from laundry and/or textile, for anti-redeposition and for maintaining or improving the whiteness of a textile.

Some aspect of the invention relates to the use of a polypeptide having DNase activity and comprises the amino acid sequence shown in SEQ ID NO 197 or a polypeptide having at least 80% sequence identity hereto for reducing malodor from laundry and/or textile, for anti-redeposition and for maintaining or improving the whiteness of a textile.

A particular preferred aspect of the invention relates to DNases from the genus of *Bacillus* e.g. a *Bacillus* DNase preferably a *Bacillus* sp. sp-62451 or a DNase selected from the group consisting DNases closely related hereto e.g. *Bacillus cibi, Bacillus* sp-18318 and *Bacillus idriensis* having at least 80% sequence identity the polypeptide having the amino acid sequence shown in SEQ ID NO 8 (*Bacillus* sp. sp-62451). A preferred aspect of the invention relates to the use of a DNase obtained from *Bacillus*, such as *Bacillus* sp. sp-62451 comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 8 for reducing malodor from laundry and/or textile, for anti-redeposition and for maintaining or improving the whiteness of a textile. A preferred aspect of the invention relates to the use of a DNase obtained from *Bacillus*, such as *Bacillus cibi* comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 21 for reducing malodor from laundry and/or textile, for anti-redeposition and for maintaining or improving the whiteness of a textile. A preferred aspect of the invention relates to the use of a DNase obtained from *Bacillus*, such as *Bacillus* sp-18318 comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 22 for reducing malodor from laundry and/or textile, for anti-redeposition and for maintaining or improving the whiteness of a textile. A preferred aspect of the invention relates to the use of a DNase obtained from *Bacillus*, such as *Bacillus idriensis* comprising a polypeptide having at least 60%, e.g., at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO 23 for reducing malodor from laundry and/or textile, for anti-redeposition and for maintaining or improving the whiteness of a textile.

As stated above the DNase polypeptides of the invention have particular deep cleaning powers e.g. the DNases of the invention are particularly effective disruption or removal of a biofilm or components of a biofilm such as polysaccharides, proteins, DNA, soil or other components present in the biofilm. Thus the DNase polypeptides of the invention are particularly effective in preventing, reducing or removing a biofilm from items such as textiles and hard surfaces.

The polypeptide having DNase activity is preferably obtained from *Bacillus* sp. or *Paenibacillus*. The invention relates to polypeptides having a sequence identity to any of the mature polypeptides of SEQ ID NO: 2, 4 or 6 of at least 60% which have DNase activity and wherein the polypeptides are used for preventing, reducing or removing a biofilm from an item. The invention further relates to polypeptides having a sequence identity to any of the mature polypeptides of SEQ ID NO: 2, 4 or 6 of at least 60%, e.g. 70% e.g. 80% or of at least 90%, which have DNase activity and wherein the polypeptides are usable for preventing, reducing or removing a biofilm from an item. The invention further relates to polypeptides having a sequence identity to any of the polypeptides of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22 or SEQ ID NO 23 of at least 60%, e.g. 70% e.g. 80% or of at least 90%, which have DNase activity and wherein the polypeptides are useable for preventing, reducing or removing a biofilm from an item.

In an embodiment, the present invention relates to a polypeptide having a sequence identity to the polypeptide of SEQ ID NO: 8 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 60%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 60%, which have DNase activity and wherein the polypeptide usable for preventing, reducing or removing a biofilm from an item.

In an embodiment, the present invention relates to a polypeptide having a sequence identity to the polypeptide of SEQ ID NO: 8 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 70%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 70%, which have DNase activity and wherein the polypeptide usable for preventing, reducing or removing a biofilm from an item.

In an embodiment, the present invention relates to a polypeptide having a sequence identity to the polypeptide of SEQ ID NO: 8 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 80%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 80%, which have DNase activity and wherein the polypeptide usable for preventing, reducing or removing a biofilm from an item.

In an embodiment, the present invention relates to a polypeptide having a sequence identity to the polypeptide of SEQ ID NO: 8 of at least 85%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 85%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 85%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 85%, which have DNase activity and wherein the polypeptide usable for preventing, reducing or removing a biofilm from an item.

In an embodiment, the present invention relates to a polypeptide having a sequence identity to the polypeptide of SEQ ID NO: 8 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 90%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 90%, which have DNase activity and wherein the polypeptide usable for preventing, reducing or removing a biofilm from an item.

In an embodiment, the present invention relates to a polypeptide having a sequence identity to the polypeptide of SEQ ID NO: 8 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 9 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 10 of at least 95%, which have DNase activity and wherein the polypeptide is used for preventing, reducing or removing a biofilm from an item.

In an embodiment, the present invention relates to a polypeptide having a sequence identity to the polypeptide of SEQ ID NO: 11 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 12 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 13 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 14 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 15 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 16 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 17 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 18 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 19 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 20 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 21 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 22 of at least 95%, which have DNase activity and wherein the polypeptide usable for preventing, reducing or removing a biofilm from an item.

In an embodiment, the present invention relates to a polypeptide having a sequence identity to the polypeptide of SEQ ID NO: 23 of at least 95%, which have DNase activity and wherein the polypeptide usable for preventing, reducing or removing a biofilm from an item.

The preferred polypeptides of the present invention are DNases from *Bacillus* sp-62451

(SEQ ID NO 8 or the mature polypeptide of SEQ ID NO 2) and closely related polypeptides having at least 80% sequence identity to the mature polypeptide with SEQ ID NO 8. The homologue polypeptides also claimed are *Bacillus cibi*, SEQ ID NO 21, *Bacillus* sp-18318 SEQ ID NO 22 and *Bacillus idriensis* SEQ ID NO 23 as well as DNases having at least 80% sequence identity hereto.

The preferred polypeptides of the present invention are DNases from *Bacillus horikoshii* (SEQ ID NO 9, or the mature polypeptide of SEQ ID NO 4) and closely related polypeptides having at least 80% sequence identity to the mature polypeptide with SEQ ID NO 9. The homologue polypeptides also claimed are *Bacillus* sp-62520 SEQ ID NO 11, *Bacillus* sp-62520 SEQ ID NO 12, *Bacillus horikoshii* SEQ ID NO 13, *Bacillus horikoshii* SEQ ID NO 14, *Bacillus* sp-16840 SEQ ID NO 15, *Bacillus* sp-16840 SEQ ID NO 16, *Bacillus* sp-62668 SEQ ID NO 17, *Bacillus* sp-13395 SEQ ID NO 18, *Bacillus horneckiae* SEQ ID NO 19, *Bacillus* sp-11238 SEQ ID NO 20 as well as DNases having at least 80% sequence identity hereto.

The preferred polypeptides of the present invention are DNases from *Paenibacillus* sp-18057 (SEQ ID NO 10, or the mature polypeptide of SEQ ID NO 6) and closely related polypeptides having at least 80% sequence identity to the mature polypeptide with SEQ ID NO 10.

The deep cleaning effect of the polypeptides having DNases activity with SEQ ID NO 8, 9 and 10 and homologue polypeptides having at least 80% identity to SEQ ID NO 8, 9 and 10 is shown in Example 2.

As described By the term "deep cleaning" is meant disruption or removal of a biofilm or components of a biofilm such as polysaccharides, proteins, DNA, soil or other components present in the biofilm.

A polypeptide of the present invention preferably comprises or consists of the amino acid sequence of any of the amino acid sequence shown in SEQ ID NO: 8, 9 or 10 or an allelic variant thereof; or is a fragment thereof having DNase activity. In another aspect, the polypeptide comprises or consists of the mature polypeptide of any of the polypeptides having the amino acid sequence shown in SEQ ID NO: 2, 4 or 6. A polypeptide of the present invention preferably comprises or consists of the amino acid sequence of any of the amino acid sequences shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 or SEQ ID NO 197 or an allelic variant thereof; or is a fragment thereof having DNase activity. In another aspect, the polypeptide comprises or consists of the mature polypeptide of any of the polypeptides having the amino acid sequences shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23 SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 or SEQ ID NO 197.

In an embodiment, the polypeptide has been isolated.

In another embodiment, the present invention relates to variants of the mature polypeptide of SEQ ID NO: 2, 4 or 6 or any of the homologue polypeptides having the amino acid sequence shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 or SEQ ID NO 197, comprising a substitution, deletion, and/or insertion at one or more (e.g., several) positions. In an embodiment, the number of amino acid substitutions, deletions and/or insertions introduced into the mature polypeptide of SEQ ID NO: 2, 4 or 6 is up to 10, e.g., 1, 2, 3, 4, 5, 6, 7, 8, 9, or 10.

In another embodiment, the present invention relates to variants of the mature polypeptide of SEQ ID NO: 8 comprising a substitution, deletion, and/or insertion at one or more (e.g., several) positions. In an embodiment, the number of amino acid substitutions, deletions and/or insertions introduced into the polypeptide of SEQ ID NO: 8 is up to 10, e.g., 1, 2, 3, 4, 5, 6, 7, 8, 9, or 10.

In another embodiment, the present invention relates to variants of the mature polypeptide of SEQ ID NO: 9 comprising a substitution, deletion, and/or insertion at one or more (e.g., several) positions. In an embodiment, the number of amino acid substitutions, deletions and/or insertions introduced into the polypeptide of SEQ ID NO: 9 is up to 10, e.g., 1, 2, 3, 4, 5, 6, 7, 8, 9, or 10.

In another embodiment, the present invention relates to variants of the mature polypeptide of SEQ ID NO: 10 comprising a substitution, deletion, and/or insertion at one or more (e.g., several) positions. In an embodiment, the number of amino acid substitutions, deletions and/or insertions introduced into the polypeptide of SEQ ID NO: 10 is up to 10, e.g., 1, 2, 3, 4, 5, 6, 7, 8, 9, or 10.

In another embodiment, the present invention relates to variants of the mature polypeptide of SEQ ID NO: 11 comprising a substitution, deletion, and/or insertion at one or more (e.g., several) positions. In an embodiment, the number of amino acid substitutions, deletions and/or insertions introduced into the polypeptide of SEQ ID NO: 11 is up to 10, e.g., 1, 2, 3, 4, 5, 6, 7, 8, 9, or 10.

In another embodiment, the present invention relates to variants of the mature polypeptide of SEQ ID NO: 12 comprising a substitution, deletion, and/or insertion at one or more (e.g., several) positions. In an embodiment, the number of amino acid substitutions, deletions and/or insertions introduced into the polypeptide of SEQ ID NO: 12 is up to 10, e.g., 1, 2, 3, 4, 5, 6, 7, 8, 9, or 10.

In another embodiment, the present invention relates to variants of the mature polypeptide of SEQ ID NO: 13 comprising a substitution, deletion, and/or insertion at one or more (e.g., several) positions. In an embodiment, the number of amino acid substitutions, deletions and/or insertions introduced into the polypeptide of SEQ ID NO: 13 is up to 10, e.g., 1, 2, 3, 4, 5, 6, 7, 8, 9, or 10.

In another embodiment, the present invention relates to variants of the mature polypeptide of SEQ ID NO: 14 comprising a substitution, deletion, and/or insertion at one or more (e.g., several) positions. In an embodiment, the number of amino acid substitutions, deletions and/or insertions introduced into the polypeptide of SEQ ID NO: 14 is up to 10, e.g., 1, 2, 3, 4, 5, 6, 7, 8, 9, or 10.

In another embodiment, the present invention relates to variants of the mature polypeptide of SEQ ID NO: 15 comprising a substitution, deletion, and/or insertion at one or more (e.g., several) positions. In an embodiment, the number of amino acid substitutions, deletions and/or insertions introduced into the polypeptide of SEQ ID NO: 15 is up to 10, e.g., 1, 2, 3, 4, 5, 6, 7, 8, 9, or 10.

In another embodiment, the present invention relates to variants of the mature polypeptide of SEQ ID NO: 16 comprising a substitution, deletion, and/or insertion at one or more (e.g., several) positions. In an embodiment, the number of amino acid substitutions, deletions and/or insertions introduced into the polypeptide of SEQ ID NO: 16 is up to 10, e.g., 1, 2, 3, 4, 5, 6, 7, 8, 9, or 10.

In another embodiment, the present invention relates to variants of the mature polypeptide of SEQ ID NO: 17 comprising a substitution, deletion, and/or insertion at one or more (e.g., several) positions. In an embodiment, the number of amino acid substitutions, deletions and/or insertions introduced into the polypeptide of SEQ ID NO: 17 is up to 10, e.g., 1, 2, 3, 4, 5, 6, 7, 8, 9, or 10.

In another embodiment, the present invention relates to variants of the mature polypeptide of SEQ ID NO: 18 comprising a substitution, deletion, and/or insertion at one or more (e.g., several) positions. In an embodiment, the number of amino acid substitutions, deletions and/or insertions introduced into the polypeptide of SEQ ID NO: 18 is up to 10, e.g., 1, 2, 3, 4, 5, 6, 7, 8, 9, or 10.

In another embodiment, the present invention relates to variants of the mature polypeptide of SEQ ID NO: 19 comprising a substitution, deletion, and/or insertion at one or more (e.g., several) positions. In an embodiment, the number of amino acid substitutions, deletions and/or insertions introduced into the polypeptide of SEQ ID NO: 19 is up to 10, e.g., 1, 2, 3, 4, 5, 6, 7, 8, 9, or 10.

In another embodiment, the present invention relates to variants of the mature polypeptide of SEQ ID NO: 20 comprising a substitution, deletion, and/or insertion at one or more (e.g., several) positions. In an embodiment, the number of amino acid substitutions, deletions and/or insertions introduced into the polypeptide of SEQ ID NO: 20 is up to 10, e.g., 1, 2, 3, 4, 5, 6, 7, 8, 9, or 10.

In another embodiment, the present invention relates to variants of the mature polypeptide of SEQ ID NO: 21 comprising a substitution, deletion, and/or insertion at one or more (e.g., several) positions. In an embodiment, the number of amino acid substitutions, deletions and/or insertions introduced into the polypeptide of SEQ ID NO: 21 is up to 10, e.g., 1, 2, 3, 4, 5, 6, 7, 8, 9, or 10.

In another embodiment, the present invention relates to variants of the mature polypeptide of SEQ ID NO: 22 comprising a substitution, deletion, and/or insertion at one or more (e.g., several) positions. In an embodiment, the number of amino acid substitutions, deletions and/or insertions introduced into the polypeptide of SEQ ID NO: 22 is up to 10, e.g., 1, 2, 3, 4, 5, 6, 7, 8, 9, or 10.

In another embodiment, the present invention relates to variants of the mature polypeptide of SEQ ID NO: 23 comprising a substitution, deletion, and/or insertion at one or more (e.g., several) positions. In an embodiment, the number of amino acid substitutions, deletions and/or insertions introduced into the polypeptide of SEQ ID NO: 23 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Left.* 309: 59-64. Use of a polypeptide having DNase activity 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Polynucleotides

The present invention also relates to polynucleotides encoding a polypeptide, as described herein. In an embodiment, the polynucleotide encoding the polypeptide of the present invention has been isolated. In another embodiment, the polynucleotide encoding a polypeptide of the present invention comprises or consists of the polynucleotide sequence set forth in SEQ ID NO: 1, 3 or 5.

In another embodiment, the present invention relates to an isolated polypeptide having DNase activity encoded by a polynucleotide that hybridizes under low stringency conditions with (i) the mature polypeptide coding sequence of SEQ ID NO: 1, 3 or 5 or (ii) the full-length complement of (i) (Sambrook et al., 1989, Molecular Cloning, A Laboratory Manual, 2d edition, Cold Spring Harbor, New York). In an embodiment, the polypeptide has been isolated.

In another embodiment, the present invention relates to an isolated polypeptide having DNase activity encoded by a polynucleotide that hybridizes under low-medium stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under medium stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under medium-high stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under high stringency conditions with (i) the mature polypeptide coding sequence of SEQ ID NO: 1, 3 or 5 or (ii) the full-length complement of (i). In an embodiment, the polypeptide has been isolated.

In another embodiment, the present invention relates to an isolated polypeptide having DNase activity encoded by a polynucleotide that hybridizes under very high stringency conditions with (i) the mature polypeptide coding sequence of SEQ ID NO: 1, 3 or 5 or (ii) the full-length complement of (i). In an embodiment, the polypeptide has been isolated.

The polynucleotide of SEQ ID NO: 1, 3 or 5 or a subsequence thereof, as well as the polypeptides of SEQ ID NO: 2, 4 or 6 or a fragment thereof or the polypeptide of SEQ ID NO: 8, 9 or 10 or a fragment thereof, may be used to design nucleic acid probes to identify and clone DNA encoding polypeptides having DNase activity from strains of different genera or species according to methods well known in the art. In particular, such probes can be used for hybridization with the genomic DNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides or at least 600 nucleotides in length. Both DNA and RNA probes can be used. The probes are typically labelled for detecting the corresponding gene (for example, with $^{32}P$, $^{3}H$, $^{35}S$, biotin, or avidin). Such probes are encompassed by the present invention.

A genomic DNA or cDNA (when polypeptides comprises introns) library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3 or 5 or a subsequence thereof, the carrier material is used in a Southern blot.

For purposes of the present invention, hybridization indicates that the polynucleotide hybridizes to a labelled nucleic acid probe corresponding to (i) SEQ ID NO: 1, 3 or 5; (ii) the mature polypeptide coding sequence of SEQ ID NO: 1, 3 or 5; (iii) the full-length complement thereof; or (iv) a subsequence thereof; under very low, low stringency conditions, low-medium stringency conditions, medium stringency conditions, medium-high stringency conditions, high stringency conditions to very high stringency conditions. Molecules to which the nucleic acid probe hybridizes under these conditions can be detected using, for example, X-ray film or any other detection means known in the art.

In another embodiment, the present invention relates to a polypeptide having DNase activity encoded by a polynucleotide having a sequence identity to the mature polypeptide coding sequence of SEQ ID NO: 1, 3 or 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having DNase activity encoded by a polynucleotide having a sequence identity to the mature polypeptide coding sequence of SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93, SEQ ID NO 96, SEQ ID NO 99, SEQ ID NO 102, SEQ ID NO 105, SEQ ID NO 108, SEQ ID NO 111, SEQ ID NO 114, SEQ ID NO 117, SEQ ID NO 120, SEQ ID NO 123, SEQ ID NO 126, SEQ ID NO 129, SEQ ID NO 132, SEQ ID NO 135, SEQ ID NO 138, SEQ ID NO 141, SEQ ID NO 144, SEQ ID NO 147, SEQ ID NO 150, SEQ ID NO 153, SEQ ID NO 156, SEQ ID NO 159, SEQ ID NO 162, SEQ ID NO 165, SEQ ID NO 168, SEQ ID NO 171, SEQ ID NO 174, SEQ ID NO 177, SEQ ID NO 180, SEQ ID NO 183, SEQ ID NO 186, SEQ ID NO 189, SEQ ID NO 192, SEQ ID NO 195 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

The techniques used to isolate or clone a polynucleotide are known in the art and include isolation from genomic DNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, 3 or 5 or e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals.

In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacifius, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No.* 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Bacillus* sp. or *Paenibacillus* cell. In another aspect, the cell is a *Bacillus* sp. 6245, *bacillus horikoshii* or *Paenibacillus* sp-18057 cell.

The present invention also relates to methods of producing a polypeptide of the present invention, comprising (a) cultivating a recombinant host cell of the present invention under conditions conducive for production of the polypeptide; and optionally, (b) recovering the polypeptide.

One aspect of the invention relates to a method of producing a polypeptide, wherein the polypeptide is selected from the group consisting of polypeptides in shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, wherein the polypeptide has DNase activity (a) cultivating the recombinant host cell under conditions conducive for production of the polypeptide; and (b) recovering the polypeptide.

In one aspect, the cell is a *Bacillus* or *Aspergillus* or any of the host cells mentioned in the section "Host cells".

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

In one embodiment, the invention further comprises producing the polypeptide by cultivating the recombinant host cell further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In one embodiment, the second polypeptide of interest is heterologous or homologous to the host cell.

In one embodiment, the recombinant host cell is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In one embodiment, the recombinant host cell is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus*, or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* host cell.

In one embodiment, a method of producing the second polypeptide of interest comprises cultivating the host cell under conditions conducive for production of the second polypeptide of interest.

In one embodiment, the method further comprises recovering the second polypeptide of interest.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells are removed by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells are grown to saturation, incubated under carbon-limiting conditions to allow protein synthesis. In some embodiments, the cell-killed whole broth or composition contains the spent cell culture medium, extracellular enzymes, and killed bacterial cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Compositions

The present invention relates to compositions comprising a DNase according to the invention.

Some aspect of the invention relates to a composition comprising at least 0.02 ppm of a polypeptide having DNase activity, wherein the polypeptide comprises the motif HXXP, where H is histidine and where P is proline and X is any amino acid.

The amount of DNase is preferably at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. The amount of DNase is preferably at least 0.02 ppm but may be from 0.00008 to 100, in the range of 0.0001-100, in the range of 0.0002-100, in the range of 0.0004-100, in the range of 0.0008-100, in the range of 0.001-100 ppm enzyme protein, 0.01-100 ppm enzyme protein, 0.01-50 ppm enzyme protein, preferably 0.05-50 ppm enzyme protein, preferably 0.02-50 ppm enzyme protein, 0.015-50 ppm enzyme protein, preferably 0.01-50 ppm enzyme protein, preferably 0.1-50 ppm enzyme protein, preferably 0.2-50 ppm enzyme protein, preferably 0.1-30 ppm enzyme protein, preferably 0.5-20 ppm enzyme protein or preferably 0.5-10 ppm enzyme protein per gram composition.

Some aspect of the invention relates to a composition comprising a polypeptide having DNase activity, wherein the polypeptide having DNase activity comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition Some aspect of the invention relates to a composition comprising a polypeptide having DNase activity, wherein the polypeptide having DNase activity comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, with the proviso that the polypeptide is not the *Trichoderma harzianum* DNase shown in SEQ ID NO 2 of WO 2015/155351. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. In some aspects the motif [G/T]Y[D/S][R/K/L][RKL] corresponding to pos 28 to 31 of SEQ ID NO: 21. In some aspects the motif [E/D/H]H[I/V/L/F/M]X[P/A/S] corresponds to positions corresponding to positions 87 to 91 in *B. cibi* (SEQ ID NO 21).

Some aspects of the invention relates to a composition comprising a polypeptide having DNase activity, wherein the polypeptide having DNase activity comprises one, two, three or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition. In some aspects the motif [F/L/Y/I]A[N/R]D[L/I/P/V] (SEQ ID NO: 201) corresponding to positions 110 to 114 of SEQ ID NO 21.

Some aspects of the invention relates to a composition comprising a polypeptide having DNase activity, wherein the polypeptide having DNase activity comprises the motif one, two, three or all of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein the amino acids in brackets are alternatives. Preferably the amount of DNase is at least 0.02 ppm but may be at least 0.00008, at least 0.0001, at least 0.0002 at least 0.0005, at least 0.0008, at least 0.001, at least 0.002, at least 0.005, at least 0.008, at least 0.01, at least 0.02, at least 0.05, at least 0.08, at least 0.1, at least 0.2, at least 0.5 or at least 0.5 ppm enzyme protein per gram composition with the proviso that the polypeptide is not the *Trichoderma harzianum* DNase shown in SEQ ID NO 2 of WO 2015/155351.

Some aspects of the invention relates to a composition comprising a polypeptide having DNase activity, wherein the polypeptide having DNase activity belongs to the GYS-clade, comprises one or more of the motifs selected from the motifs [D/M/L][S/T]GYSR[D/N] (SEQ ID NO: 204) or ASXNRSKG (SEQ ID NO: 205).

Some aspects of the invention relates to a composition comprising a polypeptide having DNase activity, wherein the polypeptide having DNase activity belongs to the GYS clade, comprises one or both motifs selected from the motifs [D/M/IAS/T]GYSR[D/N] (SEQ ID NO: 204) or ASXNRSKG (SEQ ID NO: 205), wherein the polypeptide having DNase activity is selected from the group consisting of the polypeptides shown in SEQ ID NO 8, SEQ ID NO 9, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77 and SEQ ID NO 80 or polypeptides having at least 80%, such as at least 85%, such as at least 90%, such as at least 95% or 100% sequence identity hereto.

Some aspects of the invention relates to a composition comprising a polypeptide having DNase activity, wherein the polypeptide having DNase activity belongs to the NAWK-clade, and where the polypeptide comprises one or both motifs selected from [V/I]PL[S/A]NAWK (SEQ ID NO: 206) or NPQL (SEQ ID NO: 207).

Some aspects of the invention relates to a composition comprising a polypeptide having DNase activity, wherein the polypeptide having DNase activity belongs to the NAWK clade, and wherein the polypeptide comprises one or both motifs selected from the motifs [V/I]PL[S/A]NAWK (SEQ ID NO: 206) or NPQL (SEQ ID NO: 207), wherein the amino acids in brackets are alternatives, wherein X is any amino acid and wherein the polypeptide having DNase activity is selected from the polypeptide shown in SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116 and SEQ ID NO 119 or polypeptides having at least 80%, such as at least 85%, such as at least 90%, such as at least 95% or 100% sequence identity hereto.

Some aspects of the invention relates to a composition comprising a polypeptide having DNase activity, wherein the polypeptide having DNase activity belongs to the KNAW clade, wherein the polypeptide comprises one or both of the motifs selected from the motifs P[Q/E]L[W/Y] (SEQ ID NO: 208) or [K/H/E]NAW (SEQ ID NO: 209), wherein amino acid in brackets are alternatives and wherein the polypeptide having DNase activity is selected from the group consisting of SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 80% such as at least 85%, such as at least 90%, such as at least 95% or 100% sequence identity hereto.

Some aspects of the invention relates to a composition comprising a polypeptide having DNase activity, wherein the polypeptide having DNase activity belongs to the KNAW clade, wherein the polypeptide comprises one or both of the motifs selected from the motifs P[Q/E]L[W/Y] (SEQ ID NO: 208) or [K/H/E]NAW (SEQ ID NO: 209), wherein amino acid in brackets are alternatives and wherein the polypeptide having DNase activity is selected from the group consisting of SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155 and SEQ ID NO 158 or polypeptides having at least 80% such as at least 85%, such as at least 90%, such as at least 95% or 100% sequence identity hereto, with the proviso that the polypeptide is not the *Trichoderma harzianum* DNase shown in SEQ ID NO 2 of WO 2015/155351.

Some aspects of the invention relates to a composition comprising a polypeptide having DNase activity, wherein the polypeptide comprises one or more motifs selected from the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH, wherein amino acid in brackets are alternatives and wherein the polypeptide having DNase activity is selected from the group consisting of SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or polypeptides having at least 80% such as at least 85%, such as at least 90%, such as at least 95% or 100% sequence identity hereto.

Some aspects of the invention relates to a composition comprising a polypeptide having DNase activity, wherein the polypeptide having DNase activity is selected from the group consisting of:

a) a polypeptide having at least 70%, at least 80%, at least 85%, at least 90%, at least 95%, at least 98%, at least 99% or 100% sequence identity to the polypeptide of SEQ ID NO: 8, b) a polypeptide having at least 70%, at least 80%, at least 85%, at least 90%, at least 95%, at least 98%, at least 99% or 100% sequence identity to the polypeptide of SEQ ID NO: 9, c) a polypeptide having at least 70%, at least 80%, at least 85%, at least 90%, at least 95%, at least 98%, at least 99% or 100% sequence identity to the polypeptide of SEQ ID NO: 11, d) a polypeptide having at least 70%, at least 80%, at least 85%, at least 90%, at least 95%, at least 98%, at least 99% or 100% sequence identity to the polypeptide of SEQ ID NO: 12, e) a polypeptide having at least 70%, at least 80%, at least 85%, at least 90%, at least 95%, at least 98%, at least 99% or 100% sequence identity to the polypeptide of SEQ ID NO: 13, f) a polypeptide having at least 70%, at least 80%, at least 85%, at least 90%, at least 95%, at least 98%, at least 99% or 100% sequence identity to the polypeptide of SEQ ID NO: 14, g) a polypeptide having at least 70%, at least 80%, at least 85%, at least 90%, at least 95%, at least 98%, at least 99% or 100% sequence identity to the polypeptide of SEQ ID NO: 15, h) a polypeptide having at least 70%, at least 80%, at least 85%, at least 90%, at least 95%, at least 98%, at least 99% or 100% sequence identity to the polypeptide of SEQ ID NO: 16, i) a polypeptide having at least 70%, at least 80%, at least 85%, at least 90%, at least 95%, at least 98%, at least 99% or 100% sequence identity to the polypeptide of SEQ ID NO: 17, j) a polypeptide having at least 70%, at least 80%, at least 85%, at least 90%, at least 95%, at least 98%, at least 99% or 100% sequence identity to the polypeptide of SEQ ID NO: 18, k) a polypeptide having at least 70%, at least 80%, at least 85%, at least 90%, at least 95%, at least 98%, at least 99% or 100% sequence identity to the polypeptide of SEQ ID NO: 19, l) a polypeptide having at least 70%, at least 80%, at least 85%, at least 90%, at least 95%, at least 98%, at least 99% or 100% sequence identity to the polypeptide of SEQ ID NO: 20, m) a polypeptide having at least 70%, at least 80%, at least 85%, at least 90%, at least 95%, at least 98%, at least 99% or 100% sequence identity to the polypeptide of SEQ ID NO: 21, n) a polypeptide having at least 70%, at least 80%, at least 85%, at least 90%, at least 95%, at least 98%, at least 99% or 100% sequence identity to the polypeptide of SEQ ID NO: 22, o) a polypeptide having at least 70%, at least 80%, at least 85%, at least 90%, at least 95%, at least 98%, at least 99% or 100% sequence identity to the polypeptide of SEQ ID NO: 23, p) a polypeptide having at least 70%, at least 80%, at least 85%, at least 90%, at least 95%, at least 98%, at least 99% or 100% sequence identity to the polypeptide of SEQ ID NO: 53, q) a polypeptide having at least 70%, at least 80%, at least 85%, at least 90%, at least 95%, at least 98%, at least 99% or 100% sequence identity to the polypeptide of SEQ ID NO: 56, r) a polypeptide having at least 70%, at least 80%, at least 85%, at least 90%, at least 95%, at least 98%, at least 99% or 100% sequence identity to the polypeptide of SEQ ID NO: 59, s) a polypeptide having at least 70%, at least 80%, at least 85%, at least 90%, at least 95%, at least 98%, at least 99% or 100% sequence identity to the polypeptide of SEQ ID NO: 62, t) a polypeptide having at least 70%, at least 80%, at least 85%, at least 90%, at least 95%, at least 98%, at least 99% or 100% sequence identity to the polypeptide of SEQ ID NO: 65, u) a polypeptide having at least 70%, at least 80%, at least 85%, at least 90%, at least 95%, at least 98%, at least 99% or 100% sequence identity to the polypeptide of SEQ ID NO: 68, v) a polypeptide having at least 70%, at least 80%, at least 85%, at least 90%, at least 95%, at least 98%, at least 99% or 100% sequence identity to the polypeptide of SEQ ID NO: 71, w) a polypeptide having at least 70%, at least 80%, at least 85%, at least 90%, at least 95%, at least 98%, at least 99% or 100% sequence identity to the polypeptide of SEQ ID NO: 74, x) a polypeptide having at least 70%, at least 80%, at least 85%, at least 90%, at least 95%, at least 98%, at least 99% or 100% sequence identity to the polypeptide of SEQ ID NO: 77, y) a polypeptide having at least 70%, at least 80%, at least 85%, at least 90%, at least 95%, at least 98%, at least 99% or 100% sequence identity to the polypeptide of SEQ ID NO: 80, z) a polypeptide having at least 70%, at least 80%, at least 85%, at least 90%, at least 95%, at least 98%, at least 99% or 100% sequence identity to the polypeptide of SEQ ID NO: 83, aa) a polypeptide having at least 70%, at least 80%, at least 85%, at least 90%, at least 95%, at least 98%, at least 99% or 100% sequence identity to the polypeptide of SEQ ID NO: 86, bb) a polypeptide having at least 70%, at least 80%, at least 85%, at least 90%, at least 95%, at least 98%, at least 99% or 100% sequence identity to the polypeptide of SEQ ID NO: 89, cc) a polypeptide having at least 70%, at least 80%, at least 85%, at least 90%, at least 95%, at least 98%, at least 99% or 100% sequence identity to the polypeptide of SEQ ID NO: 92, dd) a polypeptide having at least 70%, at least 80%, at least 85%, at least 90%, at least 95%, at least 98%, at least 99% or 100% sequence identity to the polypeptide of SEQ ID NO: 95, ee) a polypeptide having at least 70%, at least 80%, at least 85%, at least 90%, at least 95%, at least 98%, at least 99% or 100% sequence identity to the polypeptide of SEQ ID NO: 98, ff) a polypeptide having at least 70%, at least 80%, at least 85%, at least 90%, at least 95%, at least 98%, at least 99% or 100% sequence identity to the polypeptide of SEQ ID NO: 101, gg) a polypeptide having at least 70%, at least 80%, at least 85%, at least 90%, at least 95%, at least 98%, at least 99% or 100% sequence identity to the polypeptide of SEQ ID NO: 104, hh) a polypeptide having at least 70%, at least 80%, at least 85%, at least 90%, at least 95%, at least 98%, at least 99% or 100% sequence identity to the polypeptide of SEQ ID NO: 107, ii) a polypeptide having at least 70%, at least 80%, at least 85%, at least 90%, at least 95%, at least 98%, at least 99% or 100% sequence identity to the polypeptide of SEQ ID NO: 110, jj) a polypeptide having at least 70%, at least 80%, at least 85%, at least 90%, at least 95%, at least 98%, at least 99% or 100% sequence identity to the polypeptide of SEQ ID NO: 113, kk) a polypeptide having at least 70%, at least 80%, at least 85%, at least 90%, at least 95%, at least 98%, at least 99% or 100% sequence identity to the polypeptide of SEQ ID NO: 116, ll) a polypeptide having at least 70%, at least 80%, at least 85%, at least 90%, at least 95%, at least 98%, at least 99% or 100% sequence identity to the polypeptide of SEQ ID NO: 119, mm) a polypeptide having at least 70%, at least 80%, at least 85%, at least 90%, at least 95%, at least 98%, at least 99% or 100% sequence identity to the polypeptide of SEQ ID NO: 122, nn) a polypeptide having at least 70%, at least 80%, at least 85%, at least 90%, at least 95%, at least 98%, at least 99% or 100% sequence identity to the polypeptide of SEQ ID NO: 125, oo) a polypeptide having at least 70%, at least 80%, at least 85%, at least 90%, at least 95%, at least 98%, at least 99% or 100% sequence identity to the polypeptide of SEQ ID NO: 128, pp) a polypeptide having at least 70%, at least 80%, at least 85%, at least 90%, at least 95%, at least 98%, at least 99% or 100% sequence identity to the polypeptide of SEQ ID NO: 131, qq) a polypeptide having at least 70%, at least 80%, at least 85%, at least 90%, at least 95%, at least 98%, at least 99% or 100% sequence identity to the polypeptide of SEQ ID NO: 134, rr) a polypeptide having at least 70%, at least 80%, at least 85%, at least 90%, at least 95%, at least 98%, at least 99% or 100% sequence identity to the polypeptide of SEQ ID NO: 137, ss) a polypeptide having at least 70%, at least 80%, at least 85%, at least 90%, at least 95%, at least 98%, at least 99% or 100% sequence identity to the polypeptide of SEQ ID NO: 140, tt) a polypeptide having at least 70%, at least 80%, at least 85%, at least 90%, at least 95%, at least 98%, at least 99% or 100% sequence identity to the polypeptide of SEQ ID NO: 143, uu) a polypeptide having at least 70%, at least 80%, at least 85%, at least 90%, at least 95%, at least 98%, at least 99% or 100% sequence identity to the polypeptide of SEQ ID NO: 146, vv) a polypeptide having at least 70%, at least 80%, at least 85%, at least 90%, at least 95%, at least 98%, at least 99% or 100% sequence identity to the polypeptide of SEQ ID NO: 149, ww) a polypeptide having at least 70%, at least 80%, at least 85%, at least 90%, at least 95%, at least 98%, at least 99% or 100% sequence identity to the polypeptide of SEQ ID NO: 152, xx) a polypeptide having at least 70%, at least 80%, at least 85%, at least 90%, at least 95%, at least 98%, at least 99% or 100% sequence identity to the polypeptide of SEQ ID NO: 155, yy) a polypeptide having at least 70%, at least 80%, at least 85%, at least 90%, at least 95%, at least 98%, at least 99% or 100% sequence identity to the polypeptide of SEQ ID NO: 158, zz) a polypeptide having at least 70%, at least 80%, at least 85%, at least 90%, at least 95%, at least 98%, at least 99% or 100% sequence identity to the polypeptide of SEQ ID NO: 161, aaa) a polypeptide having at least 70%, at least 80%, at least 85%, at least 90%, at least 95%, at least 98%, at least 99% or 100% sequence identity to the polypeptide of SEQ ID NO: 164, bbb) a polypeptide having at least 70%, at least 80%, at least 85%, at least 90%, at least 95%, at least 98%, at least 99% or 100% sequence identity to the polypeptide of SEQ ID NO: 167, ccc) a polypeptide having at least 70%, at least 80%, at least 85%, at least 90%, at least 95%, at least 98%, at least 99% or 100% sequence identity to the polypeptide of SEQ ID NO: 170, ddd) a polypeptide having at least 70%, at least 80%, at least 85%, at least 90%, at least 95%, at least 98%, at least 99% or 100% sequence identity to the polypeptide of SEQ ID NO: 173, eee) a polypeptide having at least 70%, at least 80%, at least 85%, at least 90%, at least 95%, at least 98%, at least 99% or 100% sequence identity to the polypeptide of SEQ ID NO: 176, fff) a polypeptide having at least 70%, at least 80%, at least 85%, at least 90%, at least 95%, at least 98%, at least 99% or 100% sequence identity to the polypeptide of SEQ ID NO: 179, ggg) a polypeptide having at least 70%, at least 80%, at least 85%, at least 90%, at least 95%, at least 98%, at least 99% or 100% sequence identity to the polypeptide of SEQ ID NO: 182, hhh) a polypeptide having at least 70%, at least 80%, at least 85%, at least 90%, at least 95%, at least 98%, at least 99% or 100% sequence identity to the polypeptide of SEQ ID NO: 185, iii) a polypeptide having at least 70%, at least 80%, at least 85%, at least 90%, at least 95%, at least 98%, at least 99% or 100% sequence identity to the polypeptide of SEQ ID NO: 188, jjj) a polypeptide having at least 70%, at least 80%, at least 85%, at least 90%, at least 95%, at least 98%, at least 99% or 100% sequence identity to the polypeptide of SEQ ID NO: 191, kkk) a polypeptide having at least 70%, at least 80%, at least 85%, at least 90%, at least 95%, at least 98%, at least 99% or 100% sequence identity to the polypeptide of SEQ ID NO: 194, lll) a polypeptide having at least 70%, at least 80%, at least 85%, at least 90%, at least 95%, at least 98%, at least 99% or 100% sequence identity to the polypeptide of SEQ ID NO: 197, optionally the polypeptide comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]f[A/R] and [D/Q][I/V]DH and optionally the composition comprises one or more of the following;

i. one or more polyol(s), preferably selected from glycerol, (mono, di, or tri) propylene glycol, ethylene glycol, polyethylene glycol, sugar alcohols, sorbitol, mannitol, erythritol, dulcitol, inositol, xylitol and adonitol, ii. optionally one or more enzyme, preferably selected from proteases, amylases or lipases, iii. optionally one or more surfactant, preferably selected from anionic and nonionic surfactants, iii. optionally one or more polymer.

A polyol (or polyhydric alcohol) used according to the invention is an alcohol with two or more hydroxyl groups, for example alcohols with many hydroxyl groups. The polyol typically includes less than 10 carbons, such as 9, 8, 7, 6, 5, 4, or 3 carbons. The molecular weight is typically less than 500 g/mol, such as 400 g/mol or 300 g/mol. Examples of suitable polyols include, but are not limited to, glycerol, (mono, di, or tri) propylene glycol, ethylene glycol, polyethylene glycol (for example PEG 200-PEG 800), sugar alcohols, sorbitol, mannitol, erythritol, dulcitol, inositol, xylitol and adonitol.

The present invention further concerns a detergent composition comprising a polypeptide having DNase activity and preferably a detergent adjunct ingredient. The detergent composition can be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item, such as E-2-nonenal as described in Assay II. The detergent compositions comprising the polypeptides of the present invention overcomes the problems of the prior art.

The polypeptides of the invention having DNase activity are useful in powder and liquid detergent and show high performance in both types of detergents. This is surprising since the composition and condition of such detergents are very diverse and it shows the broad performance range of the polypeptides of the invention.

In one embodiment of the invention, the detergent composition comprises a DNase, selected from the group consisting of SEQ ID NO 7, 8, 9 and 10, or a DNase having at least 60%, e.g. 70% e.g. 80% e.g. at least 90% sequence identity hereto and a detergent adjunct.

In one embodiment of the invention, the detergent composition comprises a DNase, selected from the group consisting of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 75% e.g. at least 80% e.g. at least 85% e.g. at least 90%, e.g. at least 95%, e.g. at least 98%, e.g. at least 99% sequence identity hereto and a detergent adjunct.

In one embodiment of the invention, the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

The detergent adjunct ingredient may preferably be a surfactant. One advantage of including a surfactant in a detergent composition comprising a DNase is that the wash performance is improved. In one embodiment, the detergent adjunct ingredient is a builder. In another embodiment, the detergent adjunct is a clay soil removal/anti-redeposition agent.

In one embodiment, detergent adjunct ingredient is an enzyme. The detergent composition may in addition to a DNase of the invention comprise one or more enzymes, as specified below. The one or more enzymes may be selected from the group consisting of proteases, lipases, cutinases, amylases, carbohydrases, cellulases, pectinases, mannanases, arabinases, galactanases, xylanases and oxidases. Specific enzymes suitable for the detergent compositions of the invention are described below.

In one embodiment, the detergent composition is capable of reducing adhesion of bacteria selected from the group consisting of *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. to a surface, or releasing the bacteria from a surface to which they adhere.

Biofilm growth in laundry items may originate from many organisms as described previously. One particular abundant bacterium in biofilm originates from *Brevundimonas*. The DNases of the invention are particularly effective in reducing the growth of the bacterium and reducing the malodor, stickiness and re-deposition coursed by these bacteria. One embodiment of the invention relates to the use of a DNase, selected from the group consisting of SEQ ID NO 7, 8, 9 and 10 or a DNase having at least 60%, e.g. 70% e.g. 80% e.g. at least 90% sequence identity hereto in reduction of malodor and reducing stickiness and re-deposition. One embodiment relates to the use in laundering of a DNase, selected from the group consisting of SEQ ID NO 7, 8, 9 and 10 or a DNase having at least 60%, e.g. 70% e.g. 80% e.g. at least 90% sequence identity hereto, wherein the DNase reducing adhesion of bacteria e.g. from *Brevundimonas*.

One embodiment of the invention relates to the use of a DNase, selected from the group consisting of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, ora DNase having at least 70% e.g. at least 80% e.g. at least 85% e.g. at least 90% or 100% sequence identity hereto for reduction of malodor, stickiness and/or re-deposition. One embodiment relates to the use in laundering of a DNase, selected from the group consisting of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto, wherein the DNase reducing adhesion of bacteria e.g. from *Brevundimonas.*

In one embodiment of the invention, the surface is a textile surface. The textile can be made of cotton, Cotton/Polyester, Polyester, Polyamide, Polyacryl and/or silk.

One embodiment relates to a method for laundering a textile comprising the steps of:

a) Contacting the textile with a wash liquor comprising a DNase selected from the group consisting of the polypeptides having the amino acids sequence shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto and a surfactant; and b) optionally rinsing the textile, wherein the textile comprises at least 20% polyester.

The detergent composition may be formulated as a bar, a homogenous tablet, and a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The DNases of the invention are suitable for use in cleaning processes such as laundry. The invention further relates a method for laundering an item, which method comprises the steps of:

a. Exposing an item to a wash liquor comprising a polypeptide selected from the group consisting of polypeptides comprising SEQ ID NOS 7, 8, 9 and 10 or a DNase having at least 70% e.g. at least 80% e.g. at least 85% e.g. at least 90% or 100% sequence identity hereto which have DNase activity or a detergent composition comprising the polypeptide;

b. Completing at least one wash cycle; and c. Optionally rinsing the item, wherein the item is a textile.

The invention further relates a method for laundering an item, which method comprises the steps of:

a. Exposing an item to a wash liquor comprising a polypeptide selected from the group consisting of polypeptides having the amino acid sequence shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23 SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto, which have DNase activity or a detergent composition comprising the polypeptide;

b. Completing at least one wash cycle; and c. Optionally rinsing the item, wherein the item is a textile.

The pH of the liquid solution is in the range of 1 to 11, such as in the range 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment the item is rinsed after being exposed to the wash liquor. The item can be rinsed with water or with water comprising a conditioner.

The invention further concerns an item washed according to the inventive method.

The detergent composition comprising a polypeptide selected from the group consisting of polypeptides comprising SEQ ID NO 7, 8, 9 and 10 or a DNase having at least 60%, e.g. 70% e.g. 80% e.g. 90% sequence identity hereto having DNase activity can be used for releasing or removing a biofilm or preventing biofilm formation.

The detergent composition comprising a polypeptide selected from the group consisting of polypeptides having the amino acid sequence shown in SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto, which have DNase activity, may be used for releasing or removing a biofilm or preventing biofilm formation.

The DNases of the invention may be added to a wash liquor.

Thus, one embodiment of the invention relates to a detergent composition comprising one or more anionic surfactants; an enzyme selected from the group consisting of: a protease, a lipase, a cutinase, an amylase, a carbohydrase, a cellulase, a pectinase, a mannanase, an arabinase, a galactanase, a xylanase, and an oxidase; and a DNase, selected from the group consisting of SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto.

One embodiment further relates to a washing method for textile comprising:

a. exposing a textile to a wash liquor comprising a DNase or a detergent composition comprising at least one of the DNases, b. completing at least one wash cycle; and c. optionally rinsing the textile, wherein the DNase is selected from the group consisting of SEQ ID NO 7, 8, 9 and 10 or a DNase having at least 60%, e.g. 70% e.g. 80% e.g. at least 90% sequence identity hereto.

One embodiment further relates to a washing method for textile comprising:

a. exposing a textile to a wash liquor comprising a DNase or a detergent composition comprising at least one of the DNases, b. completing at least one wash cycle; and c. optionally rinsing the textile, wherein the DNase is selected from the group consisting of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23 and SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto.

Another embodiment relates to a textile washed according to the inventive method.

The concentration of the DNase in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

Enzymes e.g. protease present in a detergent of the invention may be stabilized using conventional stabilizing agents, e.g. a polyols such as propylene glycol or glycerol, a sugar or sugar alcohol, different salts such as NaCl or KCl. A polyol (or polyhydric alcohol) used according to the invention is an alcohol with two or more hydroxyl groups, for example alcohols with many hydroxyl groups. The polyol typically includes less than 10 carbons, such as 9, 8, 7, 6, 5, 4, or 3 carbons. The molecular weight is typically less than 500 g/mol, such as 400 g/mol or 300 g/mol. Examples of suitable polyols include, but are not limited to, glycerol, (mono, di, or tri) propylene glycol, ethylene glycol, polyethylene glycol (for example PEG 200-PEG 800), sugar alcohols, sorbitol, mannitol, erythritol, dulcitol, inositol, xylitol and adonitol. DNases present in the detergent of the invention may be stabilized by lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-$B^0$—R wherein, R is H, CH3, CX3, CHX2, or CH2X (X=halogen), $B^0$ is a single amino acid residue (preferably with an optionally substituted aliphatic or aromatic side chain); and B1 consists of one or more amino acid residues (preferably one, two or three), optionally comprising an N-terminal protection group, or as described in WO 2009/118375, WO 98/13459) or a protease inhibitor of the protein type such as RASI, BASI, WASI (bifunctional alpha-amylase/subtilisin inhibitors of rice, barley and wheat) or 012 or SSI. The composition may be formulated as described in e.g. WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In one embodiment, the polypeptides are stabilized using peptide aldehydes or ketones Suitable peptide aldehydes are described in WO 94/04651, WO 95/25791, WO 98/13458, WO 98/13459, WO 98/13460, WO 98/13461, WO 98/13462, WO 2007/141736, WO 2007/145963, WO 2009/118375, WO 2010/055052 and WO 2011/036153. A polypeptide of the present invention may also be incorporated in the detergent formulations disclosed in WO 97/07202, which is hereby incorporated by reference.

In another embodiment, the polypeptides are stabilized using a phenyl boronic acid derivative is 4-formylphenylboronic acid (4-FPBA) with the following formula:

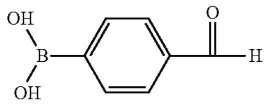

The detergent compositions may comprise two or more stabilizing agents e.g. such as those selected from the group consisting of propylene glycol, glycerol, 4-formylphenyl boronic acid and borate.

The detergent compositions may comprise two or more stabilizing agents e.g. such as those selected from the group consisting of propylene glycol, glycerol, 4-formylphenyl boronic acid and borate.

The stabilizing agent(s) is preferably present in the detergent composition in a quantity of from 0.001 to about 5.0 wt %, from 0.01 to about 2.0 wt %, from 0.1 to about 3 wt % or from 0.5% to about 1.5 wt %.

Liquid Detergent Composition

The DNases of the invention may also be formulated in liquid laundry compositions such as a liquid laundry compositions composition comprising:

a) at least 0.002 mg, preferably at least 0.005 mg of active DNase protein per litre detergent wherein the DNase is a polypeptide selected from a list consisting of SEQ ID NO 7, SEQ ID NO 8, SEQ ID NO 9 and SEQ ID NO 10 or a DNase having at least 70% e.g. at least 80% e.g. at least 85% e.g. at least 90% or 100% sequence identity hereto, b) 2 wt % to 60 wt % of at least one surfactant, and/or c) 5 wt % to 50 wt % of at least one builder The DNases of the invention may also be formulated in liquid laundry compositions such as a liquid laundry compositions composition comprising:

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto, b) 2 wt % to 60 wt % of one or more surfactants, and/or c) 5 wt % to 50 wt % of one or more builders.

One aspect of the invention relates to a liquid laundry compositions composition comprising:

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 70% e.g. at least 80% e.g. at least 85% e.g. at least 90% or 100% sequence identity hereto, b) 2 wt % to 60 wt % of one or more surfactants, and/or c) 5 wt % to 50 wt % of one or more builders, with the proviso that the polypeptide is not the *Trichoderma harzianum* DNase shown in SEQ ID NO 2 of WO 2015/155351.

The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants includes Plurafac™, Lutensol™ and Pluronic™ range from BASF, Dehypon™ series from Cognis and Genapol™ series from Clariant.

The builder is preferably selected among phosphates, sodium citrate builders, sodium carbonate, sodium silicate, sodium aluminosilicate (zeolite). Suitable builders are alkali metal or ammonium phosphates, polyphosphates, phosphonates, polyphosphates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In a laundry detergent, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl) inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N"-(2-hydroxyethyl)ethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis(methylenephosphonic acid) (EDTMPA), diethylenetriaminepentakis(methylenephosphonic acid) (DTMPA or DTPMPA or DTPMP), nitrilotris(methylenephosphonic acid) (ATMP or NTMP), 2-phosphonobutane-1,2,4-tricarboxylic acid (PBTC), hexamethylenediaminetetrakis(methylenephosphonic acid) (HDTMP).

The composition may also contain 0-50% by weight, such as about 5% to about 30%, of a detergent co-builder.

The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA) or polyaspartic acid.

Further exemplary builders and/or co-builders are described in, e.g., WO 2009/102854, U.S. Pat. No. 5,977,053.

In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

The laundry composition may also be phosphate free in the instance the preferred builders includes citrate and/or methylglycine-N,N-diacetic acid (MGDA) and/or glutamic-N,N-diacetic acid (GLDA) and/or salts thereof.

One embodiment of the invention concerns a liquid laundry compositions composition comprising:

a) at least 0.002 ppm active DNase, wherein the DNase is selected from a polypeptide comprising SEQ ID NO 7, SEQ ID NO 8, SEQ ID NO 9, SEQ ID NO 10 or DNases having at least 60%, e.g. 70% e.g. 80%, e.g. at least 90% sequence identity hereto, b) 1% to 15% by weight of one or more surfactant wherein the surfactant is LAS, AEOS and/or SLES, and/or c) 5% to 50% by weight of one or more builder selected from HEDP, DTMPA or DTPMPA.

One embodiment of the invention concerns a liquid laundry compositions composition comprising:

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or DNases having at least 60%, e.g. 70% e.g. 80% e.g. at least 90% sequence identity hereto, b) 1% to 15% by weight of at least one surfactant wherein the surfactant is LAS, AEOS and/or SLES, and/or c) 5% to 50% by weight of at least one builder selected from HEDP, DTMPA or DTPMPA.

The liquid detergent composition may typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Powder Compositions

The detergent composition may also be formulated into a granular detergent for laundry or dish wash. One embodiment of the invention concerns a granular detergent composition comprising a) at least 0.002 ppm active DNase, wherein the DNase is selected from a polypeptide comprising SEQ ID NO 7, SEQ ID NO 8, SEQ ID NO 9, SEQ ID NO 10, or a DNase having at least 60%, e.g. 70% e.g. 80%, at least 90% sequence identity hereto, b) 5 wt % to 50 wt % anionic surfactant, and/or c) 1 wt % to 8 wt % nonionic surfactant, and/or d) 5 wt % to 40 wt % builder such as carbonates, zeolites, phosphate builder, calcium sequestering builders or complexing agents.

One embodiment of the invention concerns a granular detergent composition comprising a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or a DNase having at least 60%, e.g. 70% e.g. 80%, at least 90% sequence identity hereto, b) 5 wt % to 50 wt % anionic surfactant and/or c) 1 wt % to 8 wt % nonionic surfactant, and/or d) 5 wt % to 40 wt % builder such as carbonates, zeolites, phosphate builder, calcium sequestering builders or complexing agents.

The surfactant may be selected among nonionic, anionic and/or amphoteric surfactants as described above, preferably anionic or nonionic surfactants but also amphoteric surfactants may be used. In general, bleach-stable surfactants are preferred. Preferred anionic surfactants are sulphate surfactants and in particular alkyl ether sulphates, especially C-9-15 alcohol ethersulfates, C12-15 primary alcohol ethoxylate, C8-C16 ester sulphates and C10-C14 ester sulphates, such as mono dodecyl ester sulphates Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl)ammonium, bis(2-hydroxyethyl)ammonium and tris(2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Commercially available nonionic surfactants includes Plurafac™, Lutensol™ and Pluronic™ range from BASF, Dehypon™ series from Cognis and Genapol™ series from Clariant.

The builder is may be non-phosphate such as citrate preferably as a sodium salt and/or zeolites. Phosphonate builder may be any of those described above.

The builder is preferably selected among phosphates and sodium citrate builders, sodium carbonate, sodium silicate, sodium aluminosilicate (zeolite) as described above. Suitable builders are described above and include alkali metal or ammonium phosphates, polyphosphates, phosphonates, polyphosphonates, carbonates, bicarbonates, borates, polyhydroxysulfonates, polyacetates, carboxylates, citrates, and polycarboxylates. Citrate builders, e.g., citric acid and soluble salts thereof (particularly sodium salt), are polycarboxylate builders. The builder is preferably added in an amount of about 0-65% by weight, such as about 5% to about 50% by weight, such as 5 to 40% by weight, such as 10 to 40% by weight, such as 10 to 30% by weight, such as 15 to 20% by weight or such as 20 to 40% by weight. The builder may be a phosphonate builder including 1-hydroxyethane-1,1-diphosphonic acid (HEDP), ethylenediaminetetra (methylenephosphonic acid) (EDTMPA), diethylenetriaminepentakis (methylenephosphonic acid) (DTMPA or DTPMPA), diethylenetriamine penta (methylenephosphonic acid) (DTPMP), aminotris(methylenephosphonic acid) (ATMP), 2-phosphonobutane-1,2,4-tricarboxylic acid (PBTC) and hexamethylenediaminetetra (methylenephosphonic acid) (HDTMP). Preferred phosphonates includes 1-hydroxyethane-1,1-diphosphonic acid (HEDP) and/or diethylenetriaminepentakis (methylenephosphonic acid) (DTMPA or DTPMPA). The phosphonate is preferably added in an amount of about in a level of from about 0.01% to about 10% by weight, preferably from 0.1% to about 5% by weight, more preferably from 0.5% to 3% by weight of the composition.

The laundry composition may also be phosphate free in the instance the preferred builders includes citrate, carbonates and/or sodium aluminosilicate (zeolite).

The detergent may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of hydrogen peroxide: Suitable sources of hydrogen peroxide are inorganic persalts, including alkali metal salts such as sodium percarbonate and sodium perborates (usually mono- or tetrahydrate), and hydrogen peroxide-urea (1/1).

Sources of peracids: Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those bebnging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder.

Bleach catalysts and boosters: The bleaching system may also include a bleach catalyst or booster. Some non-limiting examples of bleach catalysts that may be used in the compositions of the present invention include manganese oxalate, manganese acetate, manganese-collagen, cobalt-amine catalysts and manganese triazacyclononane (Mn-TACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

(i)

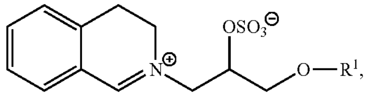

(ii)

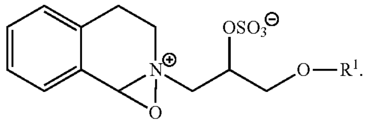

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO 2007/087258, WO 2007/087244, WO 2007/087259, EP 1867708 (Vitamin K) and WO 2007/087242. Suitable photobleaches may for example be sulfonated zinc or aluminium phthalocyanines.

According to one embodiment and any of the previous embodiments the invention also relates to a cleaning composition comprising;

a) at least 0.002 mg, preferably at least 0.005 mg of active DNase per gram of composition wherein the DNase is selected from a polypeptide comprising SEQ ID NO 7, SEQ ID NO 8, SEQ ID NO 9 and SEQ ID NO 10 or a DNase having at least 60%, e.g. 70% e.g. 80% e.g. at least 90% sequence identity hereto, b) 10-50 wt % builder and/or c) at least one bleach component, wherein the bleach is a peroxide and the bleach catalyst is a manganese compound.

According to one embodiment and any of the previous embodiments the invention also relates to a cleaning composition comprising;

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 ora DNase having at least 60%, e.g. 70% e.g. 80% e.g. at least 90% sequence identity hereto, b) 5-50 wt % builder and/or c) at least one bleach component, wherein the bleach is a peroxide and the bleach catalyst is a manganese compound.

The oxygen bleach is preferably percarbonate and the manganese catalyst preferably 1,4,7-trimethyl-1,4,7-triazacyclononane or manganese (III) acetate tetrahydrate.

According to one embodiment and any of the previous embodiments the invention also relates to a cleaning composition comprising:

a) at least 0.002 ppm active DNase, wherein the DNase is selected from a polypeptide comprising SEQ ID NO 7, SEQ ID NO 8, SEQ ID NO 9 and SEQ ID NO 10 ora DNase having at least 60%, e.g. 70% e.g. 80% e.g. at least 90% sequence identity hereto, b) 10-50 wt % builder selected from citric acid, methyl glycine-N,N-diacetic acid (MGDA) and/or glutamic-N,N-diacetic acid (GLDA) and mixtures thereof, and/or c) at least one bleach component, wherein the bleach is an oxygen bleach and the bleach catalyst is a manganese compound.

According to one embodiment and any of the previous embodiments the invention also relates to a cleaning composition comprising;

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 ora DNase having at least 60%, e.g. 70% e.g. 80% e.g. at least 90% sequence identity hereto, b) 10-50 wt % builder selected from citric acid, methyl glycine-N,N-diacetic acid (MGDA) and/or glutamic-N,N-diacetic acid (GLDA) and mixtures thereof, and/or c) at least one bleach component, wherein the bleach is an oxygen bleach and the bleach catalyst is a manganese compound.

The oxygen bleach is preferably percarbonate and the manganese catalyst preferably 1,4,7-trimethyl-1,4,7-triaza-cyclo-nonane or manganese (II) acetate tetrahydrate.

According to one embodiment and any of the previous embodiments the invention also relates to a cleaning composition comprising;

a) at least 0.002 ppm active DNase, wherein the DNase is selected from a polypeptide comprising SEQ ID NO 7, SEQ ID NO 8, SEQ ID NO 9 and SEQ ID NO 10 or a DNase having at least 60%, e.g. 70% e.g 80% e.g. at least 90% sequence identity hereto, b) 10-50 wt % builder selected from citric acid, methyl glycine-N,N-diacetic acid (MGDA) and/or glutamic-N,N-diacetic acid (GLDA) and mixtures thereof, and/or c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

According to one embodiment and any of the previous embodiments the invention also relates to a cleaning composition comprising;

a) at least 0.002 ppm active DNase, wherein the DNase is selected from a polypeptide comprising SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 ora DNase having at least 60%, e.g. 70% e.g 80% e.g. at least 90% sequence identity hereto, b) 10-50 wt % builder selected from citric acid, methyl glycine-N,N-diacetic acid (MGDA) and/or glutamic-N,N-diacetic acid (GLDA) and mixtures thereof, and/or c) 0.1-40 wt %, preferably from 0.5-30 wt %, of bleaching components, wherein the bleach components are a peroxide, preferably percabonate and a metal-containing bleach catalyst preferably 1,4,7-trimethyl-1,4,7-triazacyclononane or manganese (II) acetate tetrahydrate (MnTACN).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan, including the exemplary non-limiting components set forth below.

Hydrotropes

The cleaning composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly (vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The cleaning compositions of the invention may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO 2009/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/16285, WO 02/026024 and WO 02/016547. Examples of trypsin-like proteases are trypsin (e.g. of porcine or bovine origin) and the *Fusarium* protease described in WO 89/06270, WO 94/25583 and WO 2005/040372, and the chymotrypsin proteases obtained from Cellulomonas described in WO 2005/052161 and WO 2005/052146.

A further preferred protease is the alkaline protease from *Bacillus lentus* DSM 5483, as described for example in WO 95/23221, and variants thereof which are described in WO92/21760, WO 95/23221, EP 1921147 and EP 1921148.

Examples of metalloproteases are the neutral metalloprotease as described in WO 2007/044993 (Genencor Int.) such as those obtained from *Bacillus amyloliquefaciens*.

Examples of useful proteases are the variants described in: WO 92/19729, WO 96/34946, WO 98/20115, WO 98/20116, WO 99/11768, WO 01/44452, WO 03/06602, WO 2004/03186, WO 2004/041979, WO 2007/006305, WO 2011/036263, WO 2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Specific examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus Lentus* protease shown in SEQ ID NO 1 of WO 2016/001449. More preferred the subtilase variants may comprise the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A, R269H. The protease variants are preferably variants of the *Bacillus Lentus* protease (Savinase®) shown in SEQ ID NO 1 of WO 2016/001449, the *Bacillus amylolichenifaciens* protease (BPN') shown in SEQ ID NO 2 of WO 2016/001449. The protease variants preferably have at least 80% sequence identity to SEQ ID NO 1 or SEQ ID NO 2 of WO 2016/001449.

Or a protease selected from a protease variant comprising a substitution at one or more positions corresponding to positions 171, 173, 175, 179, or 180 of SEQ ID NO: 1 of WO 2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Some aspect of the invention relates to a composition, such as a detergent e.g. cleaning composition comprising a polypeptide having DNase activity, wherein the polypeptide having DNase activity is selected from the group consisting of the polypeptides shown in: SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or polypeptides having at least 60%, e.g. 70% e.g. 80% e.g. at least 90% sequence identity hereto, wherein the composition further comprises: at least 0.01 ppm of one or more protease variant comprising a substitution in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO 1 of WO 2011/036263.

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP 258068 and EP 305216, cutinase from *Humicola*, e.g. *H. insolens* (WO 96/13580), lipase from strains of *Pseudomonas* (some of these now renamed to *Burkholderia*), e.g. *P. alcaligenes* or *P. pseudoalcaligenes* (EP 218272), *P. cepacia* (EP 331376), P. sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO07/87508 and WO 2009/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the 554V variant used in the commercial product Gentle Power Bleach from Huntsman Textile Effects Pte Ltd (WO 2010/100028).

Some aspect of the invention relates to a composition, such as a detergent e.g. cleaning composition comprising a polypeptide having DNase activity, wherein the polypeptide having DNase activity is selected from the group consisting of the polypeptides shown in: SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, or polypeptides having at least 60%, e.g. 70% e.g. 80% e.g. at least 90% sequence identity hereto, wherein the composition further comprises:

a) at least 0.01 ppm one or more lipase.

Amylases

Suitable amylases which can be used together with the DNases of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, 1201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, 1206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K, wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar/Effectenz™, Powerase and Preferenz S100 (from Genencor International Inc./DuPont).

Some aspect of the invention relates to a composition, such as a detergent e.g. cleaning composition comprising a polypeptide having DNase activity, wherein the polypeptide having DNase activity is selected from the group consisting of the polypeptides shown in: SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, or polypeptides having at least 60%, e.g. 70% e.g. 80% e.g. at least 90% sequence identity hereto, wherein the composition further comprises:

a) at least 0.01 ppm of one or more amylase variant, wherein the variant comprises:

(i) one or more substitutions in the following positions: 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484, wherein the positions corresponds to positions of SEQ ID NO 2 of WO2000/060060;

(ii) exhibiting at least 90 percent identity with SEQ ID NO 2 of WO96/023873, with deletions in the 183 and 184 positions; or (iii) variants exhibiting at least 95 percent identity with SEQ ID NO 3 of WO2008/112459, comprising mutations in one or more of the following positions M202, M208, S255, R172 and/or M261.

Peroxidases/Oxidases

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In a preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885).

Suitable examples from bacteria include a laccase derivable from a strain of *Bacillus*. A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Other Materials

Any detergent components known in the art for use in the cleaning composition of the invention may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The cleaning compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The cleaning compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2,2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4,4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Anti-Parasitic/Viral Compounds

The cleaning composition may further comprise an anti-parasitic compound can be one or more of a benzazole, such as albendazole, mebendazole and tiabendazole; an azole, such as metronidazole and tinidazole; a macrocycle, such as amphotericin B, rifampin and ivermectin; pyrantel pamoate; diethylcarbamazine; niclosamide; praziquantel; melarsopro; and eflornithine.

The antiviral compound can be one or more of a nucleoside analog reverse transcriptase inhibitor, such as acyclovir, didanosine, stavudine, zidovudine, lamivudine, abacavir, emtricitabine and entecavir; an uncoating inhibitor such as amantadine, rimantadine and pleconaril; a protease inhibitor such as saquinavir, ritonavir, indinavir, nelfinavir and amprenavir; zanamivir; oseltamivir; and rifampin. The anti-bacterial compound can be one or more of an aminoglycoside such as gentamicin, kanamycin and streptomycin; a beta-lactam such as penicillin, ampicillin and imipenem; a cephalosporin such as ceftazidime, a quinolone such as ciprofloxacin; a macrolide such as azithromycin, clarithromycin, dirithromycin, erythromycin, roxithromycin and telithromycin; an oxazolidinone such as linezolid; an ansamycin such as rifamycin; a sulphonamide; a tetracycline such as doxycycline; a glycopeptide such as vancomycin; sulfisoxazole, trimethoprim, novobiocin, daptomycin and linezolid.

The antifungal compound can be one or more of an azole, such as miconazole, ketoconazole, clotrimazole, econazole, omoconazole, bifonazole, butoconazole, fenticonazole, isoconazole, sertaconazole, sulconazole, tioconazole, fluconazole, itraconazole, isavuconazole, ravuconazole, posaconazole, voriconazole, terconazole and abafungin; a macrocycle, such as natamycin, rimocidin, filipin, nystatin, amphotericin B, candicin, hamycin; an allyl amine such as terbinafine, naftifine and butenafine; an echinocandin such as andidulafungin, caspofungin and micafungin; or others such as polygodial, ciclopirox, tolnaftate, benzoic acid, undecylenic acid, flucytosine and griseofulvin.

Formulation of DNases in Microcapsule

The DNases of the invention may be formulated in microcapsules or in liquid detergents comprising microcapsules. A liquid cleaning composition of the invention may comprise a surfactant and a detergent builder in a total concentration of at least 3% by weight, and an enzyme, which may be a DNase, containing microcapsule, wherein the membrane of the microcapsule is produced by cross-linking of a polybranched polyamine having a molecular weight of more than 1 kDa. Encapsulating of enzymes such as DNases in a microcapsule with a semipermeable membrane having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability.

This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of enzymes such as DNases in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes such as the DNases of the invention against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g. CMC) (cellulase), and dextrin and cyclodextrin (amylase).

Also, sensitive detergent ingredients can be encapsulated, and thus stabilized, in the microcapsules of the invention. Sensitive detergent ingredients are prone to degradation during storage. Such detergent ingredients include bleaching compounds, bleach activators, perfumes, polymers, builder, surfactants, etc.

Generally, the microcapsules can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:

Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

A microcapsule may be a small aqueous sphere with a uniform membrane around it. The material inside the microcapsule is referred to as the core, internal phase, or fill, whereas the membrane is sometimes called a shell, coating, or wall. The microcapsules typically have diameters between 0.5 μm and 2 millimeters. Preferably, the mean diameter of the microcapsules is in the range of 1 μm to 1000 μm, more preferably in the range of 5 μm to 500 μm, even more preferably in the range of 10 μm to 500 μm, even more preferably in the range of 50 μm to 500 μm, and most preferably in the range of 50 μm to 200 μm. Alternatively, the diameter of the microcapsules is in the range of 0.5 μm to 30 μm; or in the range of 1 μm to 25 μm. The diameter of the microcapsule is measured in the oil phase after polymerization is complete. The diameter of the capsule may change depending on the water activity of the surrounding chemical environment.

Microencapsulation of enzymes may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favourable properties of the invention. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared—it is not formed in situ from other starting materials. To obtain the attractive properties, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear di-amine will allow one or more primary amine(s) to be introduced at the end of the introduced branch(es). In this context we the primary amino group is understood as part of the branch, i.e., the endpoint of the branch. For example, both tris(2-aminoethyl)amine and 1,2,3-propanetriamine is considered as molecules having one branching point. The polyamine preferably has at least four primary amines. Branching points can be introduced from an aliphatic hydrocarbon chain from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

The reactive amino groups preferably constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

The polybranched polyamine may be a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa. Combinations of different polybranched polyamines may be used for preparing the microcapsule.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

The liquid detergent composition may comprise a microcapsule, and thus form part of, any detergent composition in any form, such as liquid and powder detergents, and soap and detergent bars.

The microcapsule, as described above, may be added to the liquid detergent composition in an amount corresponding to from 0.0001/0 to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be either isotropic or structured, preferably isotropic. It may be a formulation useful for washing in automatic washing machines or for hand washing. It may also be a personal care product, such as a shampoo, toothpaste, or hand soap. The microcaplsule is further described in WO 2014/177709 which is incorporated by reference.

Formulation of Enzyme in Granules

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000;

ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the DNase of the invention. The granule is composed of a core, and optionally one or more coatings (outer layers) surrounding the core. Typically the granule/particle size, measured as equivalent spherical diameter (volume based average particle size), of the granule is 20-2000 μm, particularly 50-1500 μm, 100-1500 μm or 250-1200 μm.

The core may include additional materials such as fillers, fibre materials (cellulose or synthetic fibres), stabilizing agents, solubilising agents, suspension agents, viscosity regulating agents, light spheres, plasticizers, salts, lubricants and fragrances.

The core may include binders, such as synthetic polymer, wax, fat, or carbohydrate.

The core may comprise a salt of a multivalent cation, a reducing agent, an antioxidant, a peroxide decomposing catalyst and/or an acidic buffer component, typically as a homogenous blend.

The core may consist of an inert particle with the enzyme absorbed into it, or applied onto the surface, e.g., by fluid bed coating.

The core may have a diameter of 20-2000 μm, particularly 50-1500 μm, 100-1500 μm or 250-1200 μm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 μm thick, particularly at least 0.5 μm, at least 1 μm or at least 5 μm. In a particular embodiment the thickness of the coating is below 100 μm. In a more particular embodiment the thickness of the coating is below 60 μm. In an even more particular embodiment the total thickness of the coating is below 40 μm.

The coating should encapsulate the core unit by forming a substantially continuous layer. A substantially continuous layer is to be understood as a coating having few or no holes, so that the core unit it is encapsulating/enclosing has few or none uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w.

The salt may be added from a salt solution where the salt is completely dissolved or from a salt suspension wherein the fine particles is less than 50 μm, such as less than 10 μm or less than 5 μm.

The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate).

The salt coating may be as described in WO 00/01793 or WO 2006/034710.

Specific examples of suitable salts are NaCl ($CH_{20° C.}$=76%), $Na_2CO_3$ ($CH_{20° C.}$=92%), $NaNO_3$ ($CH_{20° C.}$=73%), $Na_2HPO_4$ ($CH_{20° C.}$=95%), $Na_3PO_4$ ($CH_{25° C.}$=92%), $NH_4Cl$ ($CH_{20° C.}$=79.5%), $(NH_4)_2HPO_4$ ($CH_{20° C.}$=93.0%), $NH_4H_2PO_4$ ($CH_{20° C.}$=93.1%), $(NH_4)_2SO_4$ ($CH_{20° C.}$=81.1%), KCl ($CH_{20° C.}$=85%), $K_2HPO_4$ ($CH_{20° C.}$=92%), $KH_2PO_4$($CH_{20° C.}$=96.5%), $KNO_3$ ($CH_{20° C.}$=93.5%), $Na_2SO_4$ ($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{25° C.}$=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate.

Preferably the salt is applied as a solution of the salt, e.g., using a fluid bed.

Thus, in a further aspect, the present invention provides a granule, which comprises:

(a) a core comprising a DNase according to the invention, and (b) optionally a coating consisting of one or more layer(s) surrounding the core. Some aspect of the invention relates to a granule, which comprises:

(a) a core comprising a polypeptide having DNase activity wherein the polypeptide is selected from the group consisting of polypeptides shown in SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or polypeptides having at least 60%, e.g. 70% e.g. 80%, e.g. at least 90%, e.g. at least 95%, e.g. at least 98%, e.g. at least 99% sequence identity hereto, and (b) optionally a coating consisting of one or more layer(s) surrounding the core.

One embodiment of the invention relates to a granule comprising a polypeptide having DNase activity, wherein the polypeptide has at least 80% sequence identity to the polypeptide comprising one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] or [D/Q][I/V]DH, with the proviso that the polypeptide is not the *Trichoderma harzianum* DNase shown in SEQ ID NO 2 of WO 2015/155351 and wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [D/M/L]

[S/T]GYSR[D/N] (SEQ ID NO: 204) or ASXNRSKG (SEQ ID NO: 205), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs [V/I]PL [S/A]NAWK (SEQ ID NO: 206) or NPQL (SEQ ID NO: 207), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs P[Q/E]L [W/Y] (SEQ ID NO: 208) or [K/H/E]NAW (SEQ ID NO: 209), wherein the granule comprises a core comprising said polypeptide and a coating.

One embodiment of the invention relates to a granule comprising a polypeptide having DNase activity, wherein the polypeptide has at least 80% sequence identity to the polypeptide comprising one or more of the motifs P[Q/E]L [W/Y] (SEQ ID NO: 208) or [K/H/E]NAW (SEQ ID NO: 209), with the proviso that the polypeptide is not the *Trichoderma harzianum* DNase shown in SEQ ID NO 2 of WO 2015/155351 and wherein the granule comprises a core comprising said polypeptide and a coating.

One embodiment of the invention relates to a granule comprising a polypeptide having DNase activity, wherein the polypeptide is selected from the group consisting of:

a) a polypeptide having at least 70%, at least 80%, at least 85%, at least 90%, at least 95%, at least 98%, at least 99% or 100% sequence identity to the polypeptide of SEQ ID NO: 8, b) a polypeptide having at least 70%, at least 80%, at least 85%, at least 90%, at least 95%, at least 98%, at least 99% or 100% sequence identity to the polypeptide of SEQ ID NO: 9, c) a polypeptide having at least 70%, at least 80%, at least 85%, at least 90%, at least 95%, at least 98%, at least 99% or 100% sequence identity to the polypeptide of SEQ ID NO: 11, d) a polypeptide having at least 70%, at least 80%, at least 85%, at least 90%, at least 95%, at least 98%, at least 99% or 100% sequence identity to the polypeptide of SEQ ID NO: 12, e) a polypeptide having at least 70%, at least 80%, at least 85%, at least 90%, at least 95%, at least 98%, at least 99% or 100% sequence identity to the polypeptide of SEQ ID NO: 13, f) a polypeptide having at least 70%, at least 80%, at least 85%, at least 90%, at least 95%, at least 98%, at least 99% or 100% sequence identity to the polypeptide of SEQ ID NO: 14, g) a polypeptide having at least 70%, at least 80%, at least 85%, at least 90%, at least 95%, at least 98%, at least 99% or 100% sequence identity to the polypeptide of SEQ ID NO: 15, h) a polypeptide having at least 70%, at least 80%, at least 85%, at least 90%, at least 95%, at least 98%, at least 99% or 100% sequence identity to the polypeptide of SEQ ID NO: 16, i) a polypeptide having at least 70%, at least 80%, at least 85%, at least 90%, at least 95%, at least 98%, at least 99% or 100% sequence identity to the polypeptide of SEQ ID NO: 17, j) a polypeptide having at least 70%, at least 80%, at least 85%, at least 90%, at least 95%, at least 98%, at least 99% or 100% sequence identity to the polypeptide of SEQ ID NO: 18, k) a polypeptide having at least 70%, at least 80%, at least 85%, at least 90%, at least 95%, at least 98%, at least 99% or 100% sequence identity to the polypeptide of SEQ ID NO: 19, l) a polypeptide having at least 70%, at least 80%, at least 85%, at least 90%, at least 95%, at least 98%, at least 99% or 100% sequence identity to the polypeptide of SEQ ID NO: 20, m) a polypeptide having at least 70%, at least 80%, at least 85%, at least 90%, at least 95%, at least 98%, at least 99% or 100% sequence identity to the polypeptide of SEQ ID NO: 21, n) a polypeptide having at least 70%, at least 80%, at least 85%, at least 90%, at least 95%, at least 98%, at least 99% or 100% sequence identity to the polypeptide of SEQ ID NO: 22, o) a polypeptide having at least 70%, at least 80%, at least 85%, at least 90%, at least 95%, at least 98%, at least 99% or 100% sequence identity to the polypeptide of SEQ ID NO: 23, p) a polypeptide having at least 70%, at least 80%, at least 85%, at least 90%, at least 95%, at least 98%, at least 99% or 100% sequence identity to the polypeptide of SEQ ID NO: 53, q) a polypeptide having at least 70%, at least 80%, at least 85%, at least 90%, at least 95%, at least 98%, at least 99% or 100% sequence identity to the polypeptide of SEQ ID NO: 56, r) a polypeptide having at least 70%, at least 80%, at least 85%, at least 90%, at least 95%, at least 98%, at least 99% or 100% sequence identity to the polypeptide of SEQ ID NO: 59, s) a polypeptide having at least 70%, at least 80%, at least 85%, at least 90%, at least 95%, at least 98%, at least 99% or 100% sequence identity to the polypeptide of SEQ ID NO: 62, t) a polypeptide having at least 70%, at least 80%, at least 85%, at least 90%, at least 95%, at least 98%, at least 99% or 100% sequence identity to the polypeptide of SEQ ID NO: 65, u) a polypeptide having at least 70%, at least 80%, at least 85%, at least 90%, at least 95%, at least 98%, at least 99% or 100% sequence identity to the polypeptide of SEQ ID NO: 68, v) a polypeptide having at least 70%, at least 80%, at least 85%, at least 90%, at least 95%, at least 98%, at least 99% or 100% sequence identity to the polypeptide of SEQ ID NO: 71, w) a polypeptide having at least 70%, at least 80%, at least 85%, at least 90%, at least 95%, at least 98%, at least 99% or 100% sequence identity to the polypeptide of SEQ ID NO: 74, x) a polypeptide having at least 70%, at least 80%, at least 85%, at least 90%, at least 95%, at least 98%, at least 99% or 100% sequence identity to the polypeptide of SEQ ID NO: 77, y) a polypeptide having at least 70%, at least 80%, at least 85%, at least 90%, at least 95%, at least 98%, at least 99% or 100% sequence identity to the polypeptide of SEQ ID NO: 80, z) a polypeptide having at least 70%, at least 80%, at least 85%, at least 90%, at least 95%, at least 98%, at least 99% or 100% sequence identity to the polypeptide of SEQ ID NO: 83, aa) a polypeptide having at least 70%, at least 80%, at least 85%, at least 90%, at least 95%, at least 98%, at least 99% or 100% sequence identity to the polypeptide of SEQ ID NO: 86, bb) a polypeptide having at least 70%, at least 80%, at least 85%, at least 90%, at least 95%, at least 98%, at least 99% or 100% sequence identity to the polypeptide of SEQ ID NO: 89, cc) a polypeptide having at least 70%, at least 80%, at least 85%, at least 90%, at least 95%, at least 98%, at least 99% or 100% sequence identity to the polypeptide of SEQ ID NO: 92, dd) a polypeptide having at least 70%, at least 80%, at least 85%, at least 90%, at least 95%, at least 98%, at least 99% or 100% sequence identity to the polypeptide of SEQ ID NO: 95, ee) a polypeptide having at least 70%, at least 80%, at least 85%, at least 90%, at least 95%, at least 98%, at least 99% or 100% sequence identity to the polypeptide of SEQ ID NO: 98, ff) a polypeptide having at least 70%, at least 80%, at least 85%, at least 90%, at least 95%, at least 98%, at least 99% or 100% sequence identity to the polypeptide of SEQ ID NO: 101, gg) a polypeptide having at least 70%, at least 80%, at least 85%, at least 90%, at least 95%, at least 98%, at least 99% or 100% sequence identity to the polypeptide of SEQ ID NO: 104, hh) a polypeptide having at least 70%, at least 80%, at least 85%, at least 90%, at least 95%, at least 98%, at least 99% or 100% sequence identity to the polypeptide of SEQ ID NO: 107, ii) a polypeptide having at least 70%, at least 80%, at least 85%, at least 90%, at least 95%, at least 98%, at least 99% or 100% sequence identity to the polypeptide of SEQ ID NO: 110, jj) a polypeptide having at least 70%, at least 80%, at least 85%, at least 90%, at least 95%, at least 98%, at least 99% or 100% sequence identity to the polypeptide of SEQ ID NO: 113, kk) a polypeptide having at least 70%, at least 80%, at least 85%, at least 90%, at least 95%, at least 98%, at least 99% or 100% sequence identity to the polypeptide of SEQ ID NO: 116, ll) a polypeptide having at least 70%, at least 80%, at least 85%, at least 90%, at least 95%, at least 98%, at least 99% or 100% sequence identity to the polypeptide of SEQ ID NO: 119, mm) a polypeptide having at least 70%, at least 80%, at least 85%, at least 90%, at least 95%, at least 98%, at least 99% or 100% sequence identity to the polypeptide of SEQ ID NO: 122, nn) a polypeptide having at least 70%, at least 80%, at least 85%, at least 90%, at least 95%, at least 98%, at least 99% or 100% sequence identity to the polypeptide of SEQ ID NO: 125, oo) a polypeptide having at least 70%, at least 80%, at least 85%, at least 90%, at least 95%, at least 98%, at least 99% or 100% sequence identity to the polypeptide of SEQ ID NO: 128, pp) a polypeptide having at least 70%, at least 80%, at least 85%, at least 90%, at least 95%, at least 98%, at least 99% or 100% sequence identity to the polypeptide of SEQ ID NO: 131, qq) a polypeptide having at least 70%, at least 80%, at least 85%, at least 90%, at least 95%, at least 98%, at least 99% or 100% sequence identity to the polypeptide of SEQ ID NO: 134, rr) a polypeptide having at least 70%, at least 80%, at least 85%, at least 90%, at least 95%, at least 98%, at least 99% or 100% sequence identity to the polypeptide of SEQ ID NO: 137, ss) a polypeptide having at least 70%, at least 80%, at least 85%, at least 90%, at least 95%, at least 98%, at least 99% or 100% sequence identity to the polypeptide of SEQ ID NO: 140, tt) a polypeptide having at least 70%, at least 80%, at least 85%, at least 90%, at least 95%, at least 98%, at least 99% or 100% sequence identity to the polypeptide of SEQ ID NO: 143, uu) a polypeptide having at least 70%, at least 80%, at least 85%, at least 90%, at least 95%, at least 98%, at least 99% or 100% sequence identity to the polypeptide of SEQ ID NO: 146, vv) a polypeptide having at least 70%, at least 80%, at least 85%, at least 90%, at least 95%, at least 98%, at least 99% or 100% sequence identity to the polypeptide of SEQ ID NO: 149, ww) a polypeptide having at least 70%, at least 80%, at least 85%, at least 90%, at least 95%, at least 98%, at least 99% or 100% sequence identity to the polypeptide of SEQ ID NO: 152, xx) a polypeptide having at least 70%, at least 80%, at least 85%, at least 90%, at least 95%, at least 98%, at least 99% or 100% sequence identity to the polypeptide of SEQ ID NO: 155, yy) a polypeptide having at least 70%, at least 80%, at least 85%, at least 90%, at least 95%, at least 98%, at least 99% or 100% sequence identity to the polypeptide of SEQ ID NO: 158, zz) a polypeptide having at least 70%, at least 80%, at least 85%, at least 90%, at least 95%, at least 98%, at least 99% or 100% sequence identity to the polypeptide of SEQ ID NO: 161, aaa) a polypeptide having at least 70%, at least 80%, at least 85%, at least 90%, at least 95%, at least 98%, at least 99% or 100% sequence identity to the polypeptide of SEQ ID NO: 164, bbb) a polypeptide having at least 70%, at least 80%, at least 85%, at least 90%, at least 95%, at least 98%, at least 99% or 100% sequence identity to the polypeptide of SEQ ID NO: 167, ccc) a polypeptide having at least 70%, at least 80%, at least 85%, at least 90%, at least 95%, at least 98%, at least 99% or 100% sequence identity to the polypeptide of SEQ ID NO: 170, ddd) a polypeptide having at least 70%, at least 80%, at least 85%, at least 90%, at least 95%, at least 98%, at least 99% or 100% sequence identity to the polypeptide of SEQ ID NO: 173, eee) a polypeptide having at least 70%, at least 80%, at least 85%, at least 90%, at least 95%, at least 98%, at least 99% or 100% sequence identity to the polypeptide of SEQ ID NO: 176, fff) a polypeptide having at least 70%, at least 80%, at least 85%, at least 90%, at least 95%, at least 98%, at least 99% or 100% sequence identity to the polypeptide of SEQ ID NO: 179, ggg) a polypeptide having at least 70%, at least 80%, at least 85%, at least 90%, at least 95%, at least 98%, at least 99% or 100% sequence identity to the polypeptide of SEQ ID NO: 182, hhh) a polypeptide having at least 70%, at least 80%, at least 85%, at least 90%, at least 95%, at least 98%, at least 99% or 100% sequence identity to the polypeptide of SEQ ID NO: 185, iii) a polypeptide having at least 70%, at least 80%, at least 85%, at least 90%, at least 95%, at least 98%, at least 99% or 100% sequence identity to the polypeptide of SEQ ID NO: 188, jjj) a polypeptide having at least 70%, at least 80%, at least 85%, at least 90%, at least 95%, at least 98%, at least 99% or 100% sequence identity to the polypeptide of SEQ ID NO: 191, kkk) a polypeptide having at least 70%, at least 80%, at least 85%, at least 90%, at least 95%, at least 98%, at least 99% or 100% sequence identity to the polypeptide of SEQ ID NO: 194, lll) a polypeptide having at least 70%, at least 80%, at least 85%, at least 90%, at least 95%, at least 98%, at least 99% or 100% sequence identity to the polypeptide of SEQ ID NO: 197, wherein the granule comprises a core comprising said polypeptide and a coating and optionally the polypeptide comprises one or more of the motifs [E/D/H]H[I/V/L/F/M]X[P/A/S], [T/D/S][G/N]PQL, [G/T]Y[D/S][R/K/L], [F/L/Y/I]A[N/R]D[L/I/P/V], C[D/N]T[A/R] and [D/Q][I/V]DH.

One embodiment of the invention relates to a granule comprising a polypeptide having DNase activity, wherein the polypeptide has at least 60%, e.g. 70% e.g. 80%, e.g. at least 90%, e.g. at least 95%, e.g. at least 98%, e.g. at least 99% sequence identity to the polypeptide shown in SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, wherein the granule comprises a core comprising the polypeptide and a coating.

Formulation of Detergent

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing soap, DNase, optionally one or more additional enzymes, a protease inhibitor, and a salt of a monovalent cation and an organic anion may be prepared and the mixture is then plodded. The DNase and optional additional enzymes may be added at the same time as the protease inhibitor for example in liquid form. Besides the mixing step and the plodding step, the process may further comprise the steps of milling, extruding, cutting, stamping, cooling and/or wrapping.

Pharmaceutical Compositions and Uses

The invention further concerns a pharmaceutical composition comprising a polypeptide having DNase activity and a pharmaceutical adjunct ingredient, wherein the polypeptide having DNase activity. The adjunct ingredient may be any excipient suitable for pharmaceutical compositions. The adjunct/excipient are within the choice of the skilled artisan. The pharmaceutical composition further comprise a polypeptide selected from the group consisting of polypeptides comprising SEQ ID NOS 8, 9, 10 and 11, or DNases having at least 80% sequence identity hereto. The pharmaceutical compositions can be used for releasing or removing a biofilm or preventing biofilm formation on surfaces such as medical devices.

The use may be indwelling medical device characterized in that at least a portion of a patient-contactable surface of said device is coated with the pharmaceutical composition comprising the DNases of the invention.

The device can be a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a scleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

The pharmaceutical composition can be formulated as a liquid, lotion, cream, spray, gel or ointment.

The pharmaceutical composition can be for administration to an animal patient. The animal patient can be a mammalian patient. The mammalian patient can be a human The invention is further summarized in the following paragraphs:

1. Use of a polypeptide having DNase activity, wherein the polypeptide is selected from the group consisting of SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197, or a DNase having at least 80% sequence identity hereto for preventing, reducing or removing a biofilm from an item, wherein the item is a textile.

2. Use according to paragraph 1 for preventing, reducing or removing stickiness of the item.

3. Use according to any of paragraphs 1 or 2 for pretreating stains on the item.

4. Use according to any of paragraphs 1-3 for preventing, reducing or removing redeposition of soil during a wash cycle.

5. Use according to any of paragraphs 1-4 for preventing, reducing or removing adherence of soil to the item.

6. Use according to any of the preceding paragraphs for maintaining or improving the whiteness of the item.

7. Use according to any of the preceding paragraphs, wherein the polypeptide is the polypeptide of paragraphs 45-54.

8. Use according to any of the preceding paragraphs, wherein a malodor is reduced or removed from the item.

9. Use according to any of the preceding paragraphs, wherein the malodor is caused by E-2-nonenal.

10. Use according to any of the preceding paragraphs, wherein the amount of E-2-nonenal present on a wet textile is reduced or removed.

11. Use according to any of the preceding paragraphs, wherein the amount of E-2-nonenal present on a dry textile is reduced or removed.

12. A detergent composition comprising a polypeptide having deoxyribonuclease (DNase) activity selected from the group consisting of SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197 or DNases having at least 80% sequence identity hereto and a detergent adjunct ingredient.

13. Detergent composition according to paragraph 12, wherein the polypeptide is obtained from *Bacillus* sp. or *Paenibacillus*.

14. Detergent composition according to any of the preceding composition paragraphs, wherein the polypeptides with SEQ ID NOS 7, 8, 9 or 10 are obtained from *Bacillus* sp-62451, *Bacillus horikoshii* or *Paenibacillus* sp-18057 respectively and wherein SEQ ID NO 11 is obtained from *Bacillus* sp-62520, SEQ ID NO 12 is obtained from *Bacillus* sp-62520, SEQ ID NO 13 is obtained from *Bacillus horikoshii*, SEQ ID NO 14 is obtained from *Bacillus horikoshii*, SEQ ID NO 15 is obtained from *Bacillus* sp-16840, SEQ ID NO 16 is obtained from *Bacillus* sp-16840, SEQ ID NO 17 is obtained from *Bacillus* sp-62668, SEQ ID NO 18 is obtained from *Bacillus* sp-13395, SEQ ID NO 19 is obtained from *Bacillus horneckiae*, SEQ ID NO 20 is obtained from *Bacillus* sp-11238, SEQ ID NO 21 is obtained from *Bacillus cibi*, SEQ ID NO 22 is obtained from *Bacillus* sp-18318 and SEQ ID NO 23 is obtained from *Bacillus idriensis* or is one of the following In one aspect of the invention the polypeptide having DNase activity is obtained from *Vibrissea flavovirens* and comprises or consists of the polypeptide shown in SEQ ID NO 86. In one aspect of the invention the polypeptide having DNase activity is obtained from *Acremonium dichromosporum* and comprises or consists of the polypeptide shown in SEQ ID NO 140. In one aspect of the invention the polypeptide having DNase activity is obtained from *Clavicipitaceae* sp-70249 and comprises or consists of the polypeptide shown in SEQ ID NO 176. In one aspect of the invention the polypeptide having DNase activity is obtained from *Penicillium reticulisporum* and comprises or consists of the polypeptide shown in SEQ ID NO 107. In one aspect of the invention the polypeptide having DNase activity is obtained from *Pycnidiophora* cf. *dispera* and comprises or consists of the polypeptide shown in SEQ ID NO 167. In one aspect of the invention the polypeptide having DNase activity is obtained from *Metapochonia suchlasporia* and comprises or consists of the polypeptide shown in SEQ ID NO 131. In one aspect of the invention the polypeptide having DNase activity is obtained from *Acremonium* sp. XZ2007 and comprises or consists of the polypeptide shown in SEQ ID NO 137. In one aspect of the invention the polypeptide having DNase activity is obtained from *Setosphaeria rostrata* and comprises or consists of the polypeptide shown in SEQ ID NO 89. In one aspect of the invention the polypeptide having DNase activity is obtained from *Sarocladium* sp. XZ2014 and comprises or consists of the polypeptide shown in SEQ ID NO 143. In one aspect of the invention the polypeptide having DNase activity is obtained from *Metarhizium* sp. HNA15-2 and comprises or consists of the polypeptide shown in SEQ ID NO 146. In one aspect of the invention the polypeptide having DNase activity is obtained from *Endophragmiella valdina* and comprises or consists of the polypeptide shown in SEQ ID NO 92. In one aspect of the invention the polypeptide having DNase activity is obtained from *Humicolopsis cephalosporioides* and comprises or consists of the polypeptide shown in SEQ ID NO 182. In one aspect of the invention the polypeptide having DNase activity is obtained from *Corynespora cassiicola* and comprises or consists of the polypeptide shown in SEQ ID NO 95. In one aspect of the invention the polypeptide having DNase activity is obtained from *Paraphoma* sp. XZ1965 and comprises or consists of the polypeptide shown in SEQ ID NO 98. In one aspect of the invention the polypeptide having DNase activity is obtained from *Curvularia lunata* and comprises or consists of the polypeptide shown in SEQ ID NO 104. In one aspect of the invention the polypeptide having DNase activity is obtained from *Acremonium* sp. XZ2414 and comprises or consists of the polypeptide shown in SEQ ID NO 149. In one aspect of the invention the polypeptide having DNase activity is obtained from *Isaria tenuipes* and comprises or consists of the polypeptide shown in SEQ ID NO 152. In one aspect of the invention the polypeptide having DNase activity is obtained from *Roussoella intermedia* and comprises or consists of the polypeptide shown in SEQ ID NO 188. In one aspect of the invention the polypeptide having DNase activity is obtained from *Scytalidium circinatum* and comprises or consists of the polypeptide shown in SEQ ID NO 155. In one aspect of the invention the polypeptide having DNase activity is obtained from *Setophaeosphaeria* sp. and comprises or consists of the polypeptide shown in SEQ ID NO 158. In one aspect of the invention the polypeptide having DNase activity is obtained from *Alternaria* sp. XZ2545 and comprises or consists of the polypeptide shown in SEQ ID NO 116. In one aspect of the invention the polypeptide having DNase activity is obtained from *Alternaria* sp. and comprises or consists of the polypeptide shown in SEQ ID NO 119. In one aspect of the invention the polypeptide having DNase activity is obtained from *Metarhizium lepidiotae* and comprises or consists of the polypeptide shown in SEQ ID NO 158. In one aspect of the invention the polypeptide having DNase activity is obtained from *Pleosporales* and comprises or consists of the polypeptide shown in SEQ ID NO 191. In one aspect of the invention the polypeptide having DNase activity is obtained from *Phaeosphaeria* sp. and comprises or consists of the polypeptide shown in SEQ ID NO 194. In one aspect of the invention the polypeptide having DNase activity is obtained from *Didymosphaeria futilis* and comprises or consists of the polypeptide shown in SEQ ID NO 197. In one aspect of the invention the polypeptide having DNase activity is obtained from *Bacillus vietnamensis* and comprises or consists of the polypeptide shown in SEQ ID NO 59. In one aspect of the invention the polypeptide having DNase activity is obtained from *Bacillus hwajinpoensis* and comprises or consists of the polypeptide shown in SEQ ID NO 62. In one aspect of the invention the polypeptide having DNase activity is obtained from Xanthan alkaline community J and comprises or consists of the polypeptide shown in SEQ ID NO 56. In one aspect of the invention the polypeptide having DNase activity is obtained from *Bacillus indicus* and comprises or consists of the polypeptide shown in SEQ ID NO 68. In one aspect of the invention the polypeptide having DNase activity is obtained from *Bacillus marisflavi* and comprises or consists of the polypeptide shown in SEQ ID NO 71. In one aspect of the invention the polypeptide having DNase activity is obtained from *Bacillus luciferensis* and comprises or consists of the polypeptide shown in SEQ ID NO 74. In one aspect of the invention the polypeptide having DNase activity is obtained from *Bacillus marisflavi* and comprises or consists of the polypeptide shown in SEQ ID NO 77. In one aspect of the invention the polypeptide having DNase activity is obtained from *Sporormia fimetaria* and comprises or consists of the polypeptide shown in SEQ ID NO 164. In one aspect of the invention the polypeptide having DNase activity is obtained from *Daldinia fissa* and comprises or consists of the polypeptide shown in SEQ ID NO.134. In one aspect of the invention the polypeptide having DNase activity is obtained from *Pyrenochaetopsis* sp. and comprises or consists of the polypeptide shown in SEQ ID NO 83. In one aspect of the invention the polypeptide having DNase activity is obtained from *Westerdykella* sp. AS85-2 and comprises or consists of the polypeptide shown in SEQ ID NO 179. In one aspect of the invention the polypeptide having DNase activity is obtained from *Monilinia fructicola* and comprises or consists of the polypeptide shown in SEQ ID NO 101. In one aspect of the invention the polypeptide having DNase activity is obtained from *Neosartorya massa* and comprises or consists of the polypeptide shown in SEQ ID NO 185. In one aspect of the invention the polypeptide having DNase activity is obtained from *Penicillium quercetorum* and comprises or consists of the polypeptide shown in SEQ ID NO 110. In one aspect of the invention the polypeptide having DNase activity is obtained from Xanthan alkaline community D and comprises or consists of the polypeptide shown in SEQ ID NO 170. In one aspect of the invention the polypeptide having DNase activity is obtained from *Bacillus algicola* and comprises or consists of the polypeptide shown in SEQ ID NO 53. In one aspect of the invention the polypeptide having DNase activity is obtained from Xanthan alkaline community 0 and comprises or consists of the polypeptide shown in SEQ ID NO 173. In one aspect of the invention the polypeptide having DNase activity is obtained from *Scytalidium thermophilum* and comprises or consists of the polypeptide shown in SEQ ID NO 128.

15. Detergent composition according to any of the preceding paragraphs, wherein the polypeptide is the polypeptide of paragraphs 45-54.

16. Detergent composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

17. Detergent composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

18. Detergent composition according to any of the preceding composition paragraphs, wherein the enzyme is a protease, which is of animal, vegetable or microbial origin.

19. Detergent composition according to any of the preceding composition paragraphs, wherein the protease is chemically modified or protein engineered.

20. Detergent composition according to any of the preceding composition paragraphs, wherein the protease is a serine protease or a metalloprotease, preferably an alkaline microbial protease or a trypsin-like protease.

21. Detergent composition according to any of the preceding composition paragraphs, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.

22. Detergent composition according to any of the preceding composition paragraphs, wherein the detergent composition is capable of reducing adhesion of bacteria selected from the group consisting of *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. to a surface, or releasing the bacteria from a surface to which they adhere.

23. Detergent composition according to any of the preceding composition paragraphs, wherein the surface is a textile surface.

24. Detergent composition according to any of the preceding composition paragraphs, wherein the textile is made of cotton, Cotton/Polyester, Polyester, Polyamide, Polyacryl and/or silk.

25. Detergent composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

26. Detergent composition according to any of the preceding composition paragraphs, wherein the composition is a liquid detergent, a powder detergent or a granule detergent.

27. A laundering method for laundering an item comprising the steps of:

a. Exposing an item to a wash liquor comprising a polypeptide of paragraphs 45-54 or a detergent composition according to any of paragraphs 12-26;
b. Completing at least one wash cycle; and
c. Optionally rinsing the item, wherein the item is a textile.

28. Method according to paragraph 27, wherein the pH of the wash liquor is in the range of 1 to 29. Method according to any of the preceding method paragraphs, wherein the pH of the wash liquor is in the range 5.5 to 11, such as in the range of 7 to 9, in the range of 7 to 8 or in the range of 7 to 8.5.

30. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.

31. Method according to any of the preceding method paragraphs, wherein the temperature of the wash liquor is 30° C.

32. Method according to any of the preceding method paragraphs, wherein the method further comprises draining of the wash liquor or part of the wash liquor after completion of a wash cycle.

33. Method according to any of the preceding method paragraphs, wherein the item is exposed to the wash liquor during a first and optionally a second or a third wash cycle.

34. Method according to any of the preceding method paragraphs, wherein the item is rinsed after being exposed to the wash liquor.

35. Method according to any of the preceding method paragraphs, wherein the item is rinsed with water or with water comprising a conditioner.

36. Method according to any of the preceding method paragraphs, wherein stickiness of the item is reduced.

37. Method according to any of the preceding method paragraphs, wherein stains present on the item is pretreated with a polypeptide of paragraphs 45-54 or a detergent composition according to any of paragraphs 12-26.

38. Method according to any of the preceding method paragraphs, wherein redeposition of soil is reduced.

39. Method according to any of the preceding method paragraphs, wherein adherence of soil to the item is reduced or removed.

40. Method according to any of the preceding method paragraphs, wherein whiteness of the item is maintained or improved.

41. Method according to any of the preceding method paragraphs, wherein malodor is reduced or removed from the item.
42. Method according to any of the preceding method paragraphs, wherein the malodor is caused by E-2-nonenal.
43. Method according to any of the preceding method paragraphs, wherein the amount of E-2-nonenal present on a wet or dry textile is reduced or removed.
44. Method according to any of the preceding method paragraphs, wherein the concentration of the polypeptide in the wash liquor is at least 1 mg of DNase protein, such as at least 5 mg of protein, preferably at least 10 mg of protein, more preferably at least 15 mg of protein, even more preferably at least 20 mg of protein, most preferably at least 30 mg of protein, and even most preferably at least 40 mg of protein per liter of wash liquor.
45. A polypeptide having DNase activity, selected from the group consisting of:

a. a polypeptide having at least 60% sequence identity to the mature polypeptide of SEQ ID NO: 2, 4 or 6 or a polypeptide having at least 80% sequence identity to the polypeptide shown in SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 53, SEQ ID NO 56, SEQ ID NO 59, SEQ ID NO 62, SEQ ID NO 65, SEQ ID NO 68, SEQ ID NO 71, SEQ ID NO 74, SEQ ID NO 77, SEQ ID NO 80, SEQ ID NO 83, SEQ ID NO 86, SEQ ID NO 89, SEQ ID NO 92, SEQ ID NO 95, SEQ ID NO 98, SEQ ID NO 101, SEQ ID NO 104, SEQ ID NO 107, SEQ ID NO 110, SEQ ID NO 113, SEQ ID NO 116, SEQ ID NO 119, SEQ ID NO 122, SEQ ID NO 125, SEQ ID NO 128, SEQ ID NO 131, SEQ ID NO 134, SEQ ID NO 137, SEQ ID NO 140, SEQ ID NO 143, SEQ ID NO 146, SEQ ID NO 149, SEQ ID NO 152, SEQ ID NO 155, SEQ ID NO 158, SEQ ID NO 161, SEQ ID NO 164, SEQ ID NO 167, SEQ ID NO 170, SEQ ID NO 173, SEQ ID NO 176, SEQ ID NO 179, SEQ ID NO 182, SEQ ID NO 185, SEQ ID NO 188, SEQ ID NO 191, SEQ ID NO 194 and SEQ ID NO 197;
b. a polypeptide encoded by a polynucleotide that hybridizes under low stringency conditions with
   i. the mature polypeptide coding sequence of SEQ ID NO: 1, or
   ii. the full-length complement of (i) or (ii);
c. a polypeptide encoded by a polynucleotide having at least 80% sequence identity to the mature polypeptide coding sequence of SEQ ID NO: 1, 3 or 5; or SEQ ID NO 25, SEQ ID NO 27, SEQ ID NO 29, SEQ ID NO 31, SEQ ID NO 33, SEQ ID NO 35, SEQ ID NO 37, SEQ ID NO 39, SEQ ID NO 41, SEQ ID NO 43, SEQ ID NO 45, SEQ ID NO 47, SEQ ID NO 49, SEQ ID NO 51, SEQ ID NO 54, SEQ ID NO 57, SEQ ID NO 60, SEQ ID NO 63, SEQ ID NO 66, SEQ ID NO 69, SEQ ID NO 72, SEQ ID NO 75, SEQ ID NO 78, SEQ ID NO 81, SEQ ID NO 84, SEQ ID NO 87, SEQ ID NO 90, SEQ ID NO 93, SEQ ID NO 96, SEQ ID NO 99, SEQ ID NO 102, SEQ ID NO 105, SEQ ID NO 108, SEQ ID NO 111, SEQ ID NO 114, SEQ ID NO 117, SEQ ID NO 120, SEQ ID NO 123, SEQ ID NO 126, SEQ ID NO 129, SEQ ID NO 132, SEQ ID NO 135, SEQ ID NO 138, SEQ ID NO 141, SEQ ID NO 144, SEQ ID NO 147, SEQ ID NO 150, SEQ ID NO 153, SEQ ID NO 156, SEQ ID NO 159, SEQ ID NO 162, SEQ ID NO 165, SEQ ID NO 168, SEQ ID NO 171, SEQ ID NO 174, SEQ ID NO 177, SEQ ID NO 180, SEQ ID NO 183, SEQ ID NO 186, SEQ ID NO 189, SEQ ID NO 192, SEQ ID NO 195
d. a variant of the mature polypeptide of SEQ ID NO: 2, 4 or 6 comprising a substitution, deletion, and/or insertion at one or more positions or a variant of the mature polypeptide of SEQ ID NO: 8, 9 or 10 comprising a substitution, deletion, and/or insertion at one or more positions; and
e. a fragment of the polypeptide of (a), (b), (c), or (d) that has DNase activity;

46. The polypeptide of paragraph 45 having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, 4 or 6 or to the mature polypeptide of SEQ ID NO: 8, 9 or 10.
47. The polypeptide according to paragraph 45 or 46, which is encoded by a polynucleotide that hybridizes under low stringency conditions, low-medium stringency conditions, medium stringency conditions, medium-high stringency conditions, high stringency conditions, or very high stringency conditions with i. the mature polypeptide coding sequence of SEQ ID NO: 1, or
   ii. the full-length complement of (i) or (ii).

48. The polypeptide according to any of paragraphs 45-47, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1, 3 or 5 or.
49. The polypeptide according to any of paragraphs 45-48, comprising or consisting of SEQ ID NO: 8, 9 or 10 or the mature polypeptide of SEQ ID NO: 2, 4 or 6.
50. The polypeptide according to any of paragraphs 45-49, which is a variant of the mature polypeptide of SEQ ID NO: 8, 9 or 10 comprising a substitution, deletion, and/or insertion at one or more positions
51. The polypeptide according to paragraph 50, which is a fragment of SEQ ID NO: 2, 4 or 6, wherein the fragment has DNase activity or a fragment of SEQ ID NO: 9, wherein the fragment has DNase activity.
52. A polynucleotide encoding the polypeptide according to any of paragraphs 45-51.
53. A nucleic acid construct or expression vector comprising the polynucleotide of paragraph 52 operably linked to one or more control sequences that direct the production of the polypeptide in an expression host.
54. A recombinant host cell comprising the polynucleotide of paragraph 52-53 operably linked to one or more control sequences that direct the production of the polypeptide.
55. A method of producing the polypeptide of any of paragraphs 45-51, comprising cultivating a cell, which in its wild-type form produces the polypeptide, under conditions conducive for production of the polypeptide.
56. The method of paragraph 55, further comprising recovering the polypeptide.
57. A method of producing a polypeptide having DNase activity, comprising cultivating the host cell of paragraph 56 under conditions conducive for production of the polypeptide.
58. The method of paragraph 57, further comprising recovering the polypeptide.

59. A method of producing a protein, comprising cultivating the recombinant host cell comprising a gene encoding a protein operably linked to the polynucleotide of paragraph 52, wherein the gene is foreign to the polynucleotide encoding the propeptide, under conditions conducive for production of the protein.

60. The method of paragraph 59, further comprising recovering the protein.

61. A whole broth formulation or cell culture composition comprising a polypeptide of any of paragraphs 45-51.

62. An Item laundered according to the method of any of paragraphs 27-44.

63. A pharmaceutical composition comprising a polypeptide having DNase activity and a pharmaceutical adjunct ingredient, wherein the polypeptide is obtained from a bacterial source.

64. Pharmaceutical composition according to paragraph 63, wherein the polypeptide having DNase activity is obtained from *Bacillus* or *Paenibacillus*.

65. Pharmaceutical composition according to any of paragraphs 63-64, wherein the polypeptide having DNase activity is obtained from *Bacillus* sp-62451, *Bacillus horikoshii* or *Paenibacillus* sp-18057.

66. Pharmaceutical composition according to any of paragraphs 63-65, wherein the polypeptide is the polypeptide of paragraphs 45-51.

67. Pharmaceutical composition according to any of paragraphs 63-66, wherein the composition is formulated as a dental paste, a liquid dentifrice, a mouthwash, a troche or a gingival massage ointment.

68. Pharmaceutical composition according to any of paragraphs 63-66, further comprising one or more of an antimicrobial compound, such as an antibacterial compound, an antiparasitic compound, an antifungal compound and an antiviral compound.

69. An indwelling medical device characterized in that at least a portion of a patient-contactable surface of said device is coated with the pharmaceutical composition of any of paragraphs 63-68.

70. The device according to paragraph 69 wherein said device is a catheter such as a central venous catheter, intravascular catheter, urinary catheter, Hickman catheter, peritoneal dialysis catheter, endrotracheal catheter, or wherein the device is a mechanical heart valve, a cardiac pacemaker, an arteriovenous shunt, a schleral buckle, a prosthetic joint, a tympanostomy tube, a tracheostomy tube, a voice prosthetic, a penile prosthetic, an artificial urinary sphincter, a synthetic pubovaginal sling, a surgical suture, a bone anchor, a bone screw, an intraocular lens, a contact lens, an intrauterine device, an aortofemoral graft, a vascular graft, a needle, a Luer-Lok connector, a needleless connector or a surgical instrument.

71. A method of producing the polypeptide of any of paragraphs 45-51, comprising cultivating the host cell of paragraph 54 under conditions conducive for production of the polypeptide.

72. The method of paragraph 71, further comprising recovering the polypeptide.

73. The recombinant host cell of paragraph 54 further comprising a polynucleotide encoding a second polypeptide of interest; preferably an enzyme of interest; more preferably a secreted enzyme of interest; even more preferably a hydrolase, isomerase, ligase, lyase, oxidoreductase, or a transferase; and most preferably the secreted enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

74. The recombinant host cell of paragraph 73, wherein the second polypeptide of interest is heterologous or homologous to the host cell.

75. The recombinant host cell of paragraph 73 or 74, which is a fungal host cell; preferably a filamentous fungal host cell; more preferably an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell; most preferably an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

76. The recombinant host cell of paragraph 73 or 74, which is a bacterial host cell; preferably a prokaryotic host cell; more preferably a Gram-positive host cell; even more preferably a *Bacillus, Clostridium, Enterococcus, Geobacillus, Lactobacillus, Lactococcus, Oceanobacillus, Staphylococcus, Streptococcus*, or *Streptomyces* host cell; and most preferably a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* host cell.

77. A method of producing the second polypeptide of interest as defined in any of paragraphs 71-72, comprising cultivating the host cell of any of paragraphs 73-76 under conditions conducive for production of the second polypeptide of interest.

78. The method of paragraph 77, further comprising recovering the second polypeptide of interest.

79. Detergent composition according to any of the preceding composition paragraphs, wherein the detergent adjunct ingredient is a surfactant.

80. Detergent composition according to any of the preceding composition paragraphs, wherein the detergent adjunct ingredient is a builder.
81. Detergent composition according to any of the preceding composition paragraphs, wherein the detergent adjunct ingredient is a clay soil removal/anti-redeposition agents.
82. Detergent composition according to paragraphs 12-26, wherein the composition is a liquid detergent composition, comprising a surfactant and a detergent builder in a total concentration of at least 3% by weight, and a detergent enzyme containing microcapsule, wherein the membrane of the microcapsule is produced by cross-linking of a polybranched polyamine having a molecular weight of more than 1 kDa.
83. Detergent composition according to any of paragraphs 79-82, wherein the reactive amino groups of the polybranched polyamine constitute at least 15% of the molecular weight.
84. Detergent composition according to any of paragraphs 79-83, wherein the microcapsule is produced by using an acid chloride as crosslinking agent.
85. Detergent composition according to any of paragraphs 79-84, wherein the diameter of the microcapsule is at least, or above, 50 micrometers.
86. Detergent composition according to any of paragraphs 79-85, wherein the microcapsule contains at least 1% by weight of active enzyme.
87. Detergent composition according to any of paragraphs 79-86, which further includes an alcohol, such as a polyol.
88. Detergent composition according to any of paragraphs 79-87, wherein the surfactant is an anionic surfactant.
89. Detergent composition according to any of paragraphs 79-88, which is a liquid laundry composition.
90. Detergent composition according to any of paragraphs 79-89, which contains less than 90% by weight of water.
91. Detergent composition according to any of paragraphs 79-90, wherein the detergent enzyme is a polypeptide having DNase activity, protease, amylase, lipase, cellulase, mannanase, pectinase, or oxidoreductase.
92. Detergent composition according to any of paragraphs 79-91, wherein the protease is a metalloprotease or an alkaline serine protease, such as a subtilisin.
93. Detergent composition according to any of paragraphs 79-92, wherein the polypeptide having DNase activity is the polypeptide according to any of claims 45-51.
94. Detergent composition according to any of paragraphs 79-93, wherein the microcapsule is produced by interfacial polymerization using an acid chloride as crosslinking agent.
95. Detergent composition according to any of paragraphs 79-94, wherein the polybranched polyamine is a polyethyleneimine.
96. Detergent composition according to any of paragraphs 79-95, wherein the microcapsule comprises a source of Mg2+, Ca2+, or Zn2+ ions, such as a poorly soluble salt of Mg2+, Ca2+, or Zn2+.

Assays and Detergent Compositions

Detergent Compositions

The below mentioned detergent composition can be used in combination with the enzyme of the invention.

Biotex Black (Liquid)

5-15% Anionic surfactants, <5% Nonionic surfactants, perfume, enzymes, DMDM and hydantoin.

Composition of Ariel Sensitive White & Color, Liquid Detergent Composition

Aqua, Alcohol Ethoxy Sulfate, Alcohol Ethoxylate, Amino Oxide, Citric Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent a (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour & Style (Liquid)

Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.

Composition of Persil Small & Mighty (Liquid)

Ingredients: 15-30% Anionic surfactants, Non-ionic surfactants, 5-15% Soap, <5% Polycarboxylates, Perfume, Phosphates, Optical Brighteners Persil 2 Int with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Perfume, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Perfume, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin.

Persil Colour Care Biological Powder

Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Perfume, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Perfume, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 Int with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinyl-aminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2in1 with Comfort Sunshiny Days

Aqua, 012-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl lonone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl lonone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour & Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase.

Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:

Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:

Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:

Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:

Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:

Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:

Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:

Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:

Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:

Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:

Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide boost with Oxi:

Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:

Polyvinyl Alcoholpouch film, wherein there is packed a liquid part and a powder part:

Liquid Ingredients:

Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:

Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:

Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:

Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Pwdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

HEY SPORT TEX WASH Detergent

Aqua, dodecylbenzenesulfonsaure, laureth-11, peg-75 lanolin, propylene glycol, alcohol denat., potassium soyate, potassium hydroxide, disodium cocoamphodiacetate, ethylendiamine triacetate cocosalkyl acetamide, perfume, zinc ricinoleate, sodium chloride, benzisothiazolinone, methylisothiazolinone, ci 16255, benzyl alcohol.

The products named Tide, Ariel, Gain and Fairy are commercially available products supplied by Procter & Gamble. The products named Persil are commercially available products supplied by Unilever and Henkel. The products named Hey Sport are commercially available products supplied by Hey Sport.

| Ingredient | Amount (in wt %) |
|---|---|
| Anionic detersive surfactant (such as alkyl benzene sulphonate, alkyl ethoxylated sulphate and mixtures | from 8 wt % to 15 wt % thereof) |
| Non-ionic detersive surfactant (such as alkyl ethoxylated alcohol) | from 0.5 wt % to 4 wt % |
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 wt % to 4 wt % |
| Carboxylate polymer (such as co-polymers of maleic acid and acrylic acid) | from 1 wt % to 4 wt % |
| Polyethylene glycol polymer (such as a polyethylene glycol polymer comprising poly vinyl acetate side chains) | from 0.5 wt % to 4 wt % |
| Polyester soil release polymer (such as Repel-o-tex from and/or Texcare polymers) | 0.1 to 2 wt % |
| Cellulosic polymer (such as carboxymethyl cellulose, methyl cellulose and combinations thereof) | from 0.5 wt % to 2 wt % |
| Other polymer (such as amine polymers, dye transfer inhibitor polymers, hexamethylenediamine derivative polymers, and mixtures thereof) | from 0 wt % to 4 wt % |
| Zeolite builder and phosphate builder (such as zeolite 4A and/or sodium tripolyphosphate) | from 0 wt % to 4 wt % |
| Other builder (such as sodium citrate and/or citric acid) | from 0 wt % to 3 wt % |
| Carbonate salt (such as sodium carbonate and/or sodium bicarbonate) | from 15 wt % to 30 wt % |
| Silicate salt (such as sodium silicate) | from 0 wt % to 10 wt % |
| Filler (such as sodium sulphate and/or bio-fillers) | from 10 wt % to 40 wt % |
| Source of available oxygen (such as sodium percarbonate) | from 10 wt % to 20 wt % |
| Bleach activator (such as tetraacetylethylene diamine (TAED) and/or nonanoyloxybenzenesulphonate (NOBS) | from 2 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre-formed peracid) | from 0 wt % to 10 wt % |
| Chelant (such as ethylenediamine-N'N'-disuccinic acid (EDDS) and/or hydroxyethane diphosphonic acid (HEDP) | from 0.2 wt % to 1 wt % |
| Photobleach (such as zinc and/or aluminium sulphonated phthalocyanine) | from 0 wt % to 0.1 wt % |
| Hueing agent (such as direct violet 99, acid red 52, acid blue 80, direct violet 9, solvent violet 13 and any combination thereof) | from 0 wt % to 1 wt % |

-continued

| | |
|---|---|
| Brightener (such as brightener 15 and/or brightener 49) | from 0.1 wt % to 0.4 wt % |
| Protease (such as Savinase, Savinase Ultra, Purafect, FN3, FN4 and any combination thereof) | from 0.1 wt % to 0.4 wt % |
| Amylase (such as Termamyl, Termamyl ultra Natalase, Optisize, Stainzyme, Stainzyme Plus, and any combination thereof) | from 0.05 wt % to 0.2 wt % |
| Cellulase (such as Carezyme and/or Celluclean) | from 0.05 wt % to 0.2 wt % |
| Lipase (such as Lipex, Lipolex, Lipoclean and any combination thereof) | from 0.2 to 1 wt % |
| Other enzyme (such as xyloglucanase, cutinase, pectate lyase, mannanase, bleaching enzyme) | from 0 wt % to 2 wt % |
| Fabric softener (such as montmorillonite clay and/or polydimethylsiloxane (PDMS) | from 0 wt % to 4 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | Balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO 2014/032269. | from about 0.5 wt % to about 1.5 wt % |
| Amylase (Stainzyme Plus(R), having an enzyme activity of 14 mg active enzyme/g) | from about 0.1 wt % to about 0.5 wt % |
| Anionic detersive surfactant (such as alkyl benzene sulphonate, alkyl ethoxylated sulphate and mixtures thereof) | from about 8 wt % to about 15 wt % |
| Non-ionic detersive surfactant (such as alkyl ethoxylated alcohol) | from about 0.5 wt % to 4 wt % |
| Cationic detersive surfactant (such as quaternary ammonium compounds) | from about 0 wt % to about 4 wt % |
| Other detersive surfactant (such as zwiterionic detersive surfactants, amphoteric surfactants and mixtures thereof) | from about 0 wt % to 4 wt % |
| Carboxylate polymer (such as co-polymers of maleic acid and acrylic acid) | from about 1 wt % to about 4 wt % |
| Polyethylene glycol polymer (such as a polyethylene glycol polymer comprising poly vinyl acetate side chains) | from about 0 wt % to about 4 wt % |
| Polyester soil release polymer (such as Repel-O-Tex(R) and/or Texcare(R) polymers) | from about 0.1 wt % to about 2 wt % |
| Cellulosic polymer (such as carboxymethyl cellulose, methyl cellulose and combinations thereof) | from about 0.5 wt % to about 2 wt % |
| Other polymer (such as amine polymers, dye transfer inhibitor polymers, hexamethylenediamine derivative polymers, and mixtures thereof) | from about 0 wt % to about 4 wt % |
| Zeolite builder and phosphate builder (such as zeolite 4A and/or sodium tripolyphosphate) | from about 0 wt % to about 4 wt % |
| Other builder (such as sodium citrate and/or citric acid) | from about 0 wt % to about 3 wt % |
| Carbonate salt (such as sodium carbonate and/or sodium bicarbonate) | from about 15 t % to about 30 wt % |
| Silicate salt (such as sodium silicate) | from about 0 wt % to about 10 wt % |
| Filler (such as sodium sulphate and/or bio-fillers) | from about 10 wt % to about 40 wt % |
| Source of available oxygen (such as sodium percarbonate) | from about 10 wt % to about 20 wt % |
| Bleach activator (such as tetraacetylethylene diamine (TAED) and/or nonanoyloxybenzenesulphonate (NOBS) | from about 2 wt % to about 8 wt % |
| Bleach catalyst (such as oxaziridinium-based bleach catalyst and/or transition metal bleach catalyst) | from about 0 wt % to about 0.1 wt % |
| Other bleach (such as reducing bleach and/or pre formed peracid) | from about 0 wt % to about 10 wt % |
| Chelant (such as ethylenediamine-N'N'-disuccinic acid (EDDS) and/or hydroxyethane diphosphonic acid (HEDP) | from about 0.2 wt % to about 1 wt % |
| Photobleach (such as zinc and/or aluminium sulphonated phthalocyanine) | from about 0 wt % to about 0.1 wt % |
| Hueing agent (such as direct violet 99, acid red 52, acid blue 80, direct violet 9, solvent violet 13 and any combination thereof) | from about 0 wt % to about 0.5 wt % |
| Brightener (such as brightener 15 and/or brightener 49) | from about 0.1 wt % to about 0.4 wt % |
| Protease (such as Savinase, Polarzyme, Purafect, FN3, FN4 and any combination thereof, typically having an enzyme activity of from about 20 mg to about 100 mg active enzyme/g) | from about 0.1 wt % to about 1.5 wt % |

-continued

| | |
|---|---|
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 wt % to about 0.2 wt % |
| Cellulase (such as Carezyme(R), Celluzyme(R) and/or Celluclean(R), typically having an enzyme activity of about from 10 to 50 mg active enzyme/g) | from about 0.05 wt % to 0.5 wt % |
| Lipase (such as Lipex(R), Lipolex(R), Lipoclean(R) and any combination thereof, typically having an enzyme activity of from about 10 mg to about 50 mg active enzyme/g) | from about 0.2 wt % to about 1 wt % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 wt % to 2 wt % |
| Fabric softener (such as montmorillonite clay and/or polydimethylsiloxane (PDMS)) | from 0 wt % to 15 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as colored soap rings and/or colored speckles/noodles) | from 0 wt % to 1 wt % |
| Miscellaneous | Balance |

All enzyme levels expressed as rug active enzyme protein per 100 g detergent composition. Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®).

Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Basel, Switzerland. NOBS is sodium nonanoyloxybenzenesulfonate, supplied by Eastman, Batesville, Ark., USA.

TAED is tetraacetylethylenediamine, supplied under the Peractive® brand name by Clariant GmbH, Sulzbach, Germany.

Sodium carbonate and sodium bicarbonate can be obtained from Solvay, Brussels, Belgium.

Polyacrylate, polyacrylate/maleate copolymers can be obtained from BASF, Ludwigshafen, Germany.

Repel-O-Tex® can be obtained from Rhodia, Paris, France.

Texcare® can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK.

Hydroxy ethane di phosphonate (HEDP) was supplied by Dow Chemical, Midland, Mich., USA.

Enzymes Savinase®, Savinase® Ultra, Stainzyme® Plus, Lipex®, Lipolex®, Lipoclean®, Celluclean®, Carezyme®, Natalase®, Stainzyme®, Stainzyme® Plus, Termamyl®, Termamyl® ultra, and Mannaway® can be obtained from Novozymes, Bagsvaerd, Denmark.

Enzymes Purafect®, FN3, FN4 and Optisize can be obtained from Genencor International Inc., Palo Alto, Calif., US.

Direct violet 9 and 99 can be obtained from BASF DE, Ludwigshafen, Germany. Solvent violet 13 can be obtained from Ningbo Lixing Chemical Co., Ltd. Ningbo, Zhejiang, China. Brighteners can be obtained from Ciba Specialty Chemicals, Basel, Switzerland.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Terg-O-Timeter (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.). All beakers shall be clean and without traces of prior test material.

The wash solution with desired amount of detergent, temperature and water hardness is prepared in a bucket. The detergent is allowed to dissolve during magnet stirring for 10 min. Wash solution shall be used within 30 to 60 min after preparation.

800 ml wash solution is added into a TOM beaker. The wash solution is agitated at 120 rpm and optionally one or more enzymes are added to the beaker. The swatches are sprinkled into the beaker and then the ballast load. Time measurement starts when the swatches and ballast are added to the beaker. The swatches are washed for 20 minutes after which agitation is terminated.

The wash load is subsequently transferred from the TOM beaker to a sieve and rinse with cold tap water. The soiled swatches are separated from the ballast load. The soil swatches are transferred to a 5 L beaker with cold tap water under running water for 5 minutes. The ballast load is kept separately for the coming inactivation. The water is gently pressed out of the swatches by hand and placed on a tray covered with a paper. Another paper is placed on top of the swatches. The swatches are allowed to dry overnight before subjecting the swatches to analysis, such as measuring the color intensity using a Color Eye as described herein.

Enzyme Assays

Assay I: Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 μl of enzyme solutions are added and DNase activity is observed as colorless zones around the spotted enzyme solutions.

Assay II

Analysis of E-2-nonenal on textile using an electronic nose.

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyse 5 mL headspace from the capped vials in a Heracles II Electronic nose from Alpha M.O.S., France (double column gas chromatograph with 2 FIDs, column 1: MXT5 and column 2: MXT1701) after 20 minutes incubation at 40° C.

EXAMPLES

Methods

General methods of PCR, cloning, ligation nucleotides etc. are well-known to a person skilled in the art and may for example be found in in “Molecular cloning: A laboratory manual”, Sambrook et al. (1989), Cold Spring Harbor lab., Cold Spring Harbor, N.Y.; Ausubel, F. M. et al. (eds.); “Current protocols in Molecular Biology”, John Wiley and Sons, (1995); Harwood, C. R., and Cutting, S. M. (eds.); “DNA Cloning: A Practical Approach, Volumes I and II”, D. N. Glover ed. (1985); “Oligonucleotide Synthesis”, M. J. Gait ed. (1984); “Nucleic Acid Hybridization”, B. D. Hames & S. J. Higgins eds (1985); “A Practical Guide To Molecular Cloning”, B. Perbal, (1984).

Example 1 Cloning and Expression of Bacterial DNases

The DNases were derived from bacterial strains isolated from environmental samples by standard microbiological isolation techniques. Strains were identified and taxonomy was assigned based on DNA sequencing of the 16S ribosomal genes (Table 1).

TABLE 1

| Strain | Source Country | Mature protein SEQ ID: |
|---|---|---|
| *Bacillus* sp-62520 | United states | 11 |
| *Bacillus* sp-62520 | United states | 12 |
| *Bacillus horikoshii* | United states | 13 |
| *Bacillus horikoshii* | Denmark | 14 |
| *Bacillus* sp-16840 | China | 15 |
| *Bacillus* sp-16840 | United states | 16 |
| *Bacillus* sp-62668 | United states | 17 |
| *Bacillus* sp-13395 | Denmark | 18 |
| *Bacillus horneckiae* | Turkey | 19 |
| *Bacillus cibi* | Japan | 21 |
| *Bacillus* sp-18318 | Japan | 22 |
| *Bacillus* sp-11238 | Nepal | 20 |
| *Bacillus idriensis* | Antarctica | 23 |
| *Bacillus* sp-62451 | United States | 8 |
| *Bacillus horikoshii* | Japan | 9 |
| *Paenibacillus* sp-18057 | New Zeeland | 10 |

Chromosomal DNA was isolated from pure cultures of the individual strains with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) is known to the person skilled in the art and the service can be purchased commercially.

The genome sequences were analyzed for putative DNases from the PFAM database families PF14040 and PF07510 (R. D. Finn et al. Nucleic Acids Research (2014), 42:D222-D230) this analysis identified sixteen genes encoding putative DNases which were subsequently cloned and recombinantly expressed in *Bacillus subtilis*. PF07510 corresponds to the DUF1524 domain.

The genes encoding the DNases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two *Bacillus subtilis* chromosomal regions along with strong promoters and a chloramphenicol resistance marker. The SOE PCR method is also described in patent application WO 2003/095658.

The genes were expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The genes were fused with DNA encoding a *Bacillus clausii* secretion signal (encoding the following amino acid sequence: MKKPLGKIVASTALLISVAFSSSIASA (SEQ ID NO 24)) replacing the native secretion signal. Furthermore the expression construct results in the addition of a carboxy-terminal poly histidine tail consisting of 6 consecutive histidine residues.

The SOE-PCR products were transformed into *Bacillus subtilis* and integrated in the chromosome by homologous recombination into the pectate lyase locus. Subsequently a recombinant *Bacillus subtilis* clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 2 MiniLOM Liquid Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted. The color difference (L value, L*) represents the darkest black at L*=0, and the brightest white at L*=100. Data is represented as Delta L values meaning the L value of the swatch washed with DNase minus the L value of swatch washed without DNase.

TABLE 2

| Deep cleaning effect of the DNase from *Bacillus horikoshii* with SEQ ID NO 9 and closely related homologues | | |
|---|---|---|
| Host name | L-value$_{Model\ detergent\ A}$ | $\Delta L_{Model\ detergent\ A}$ |
| No enzyme | 83.59 | n/a |
| *Bacillus horikoshii* | 88.50 | 4.91 |
| *Bacillus* sp-62520 | 92.77 | 3.50 |
| *Bacillus* sp-62520 | 93.17 | 3.90 |
| *Bacillus horikoshii* | 93.41 | 4.14 |
| *Bacillus horikoshii* | 93.28 | 4.01 |
| *Bacillus* sp-16840 | 93.74 | 4.47 |
| *Bacillus* sp-16840 | 92.47 | 3.20 |
| *Bacillus* sp-62668 | 92.95 | 3.68 |
| *Bacillus* sp-13395 | 92.31 | 3.04 |
| *Bacillus horneckiae* | 90.01 | 0.74 |

TABLE 3

| Deep cleaning effect of the DNase from *Bacillus* sp-62451with SEQ ID NO 8 and closely related homologues. | | |
|---|---|---|
| Host name | L-value$_{Model\ detergent\ A}$ | $\Delta L_{Model\ detergent\ A}$ |
| No enzyme | 83.59 | n/a |
| *Bacillus* sp-62451 | 88.71 | 5.13 |
| *Bacillus cibi* | 91.80 | 2.53 |
| *Bacillus* sp-18318 | 92.91 | 3.64 |
| *Bacillus idriensis* | 92.41 | 3.14 |

TABLE 4

| Deep cleaning effect of the DNase from *Paenibacillus* sp-18057 with SEQ ID NO 10 | | |
|---|---|---|
| Host name | L-value$_{Model\ detergent\ A}$ | $\Delta L_{Model\ detergent\ A}$ |
| No enzyme | 83.59 | n/a |
| *Paenibacillus* sp-18057 | 88.82 | 5.24 |

Tables 2, 3 and 4 show that all the tested DNases have "deep cleaning" effect meaning that they disrupt, reduce or remove the biofilm or components of the biofilm swatches in a liquid detergent.

Below is shown the cleaning effect of Benzonase (SEQ ID NO 7) another polypeptide having DNase activity.

TABLE 5

| Deep-cleaning of Benzonase (SEQ ID NO 7). | | | |
|---|---|---|---|
| Detergent | DNase conc. (ppm) | L-value | L-value$_{with\ DNase}$ − L-value$_{without\ DNase}$ |
| No enzyme | 0 | 83.5 | n/a |
| Benzonase | 0.5 | 88.1 | 4.6 |

Table 5 shows that Benzonase DNase also has deep cleaning effect in liquid detergent.

Example 3 MiniLOM Wash in Powder Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of powder model detergent T without bleach and powder model detergent T with bleach were prepared by weighing out and dissolving detergents in water with water with hardness 15° dH. Dosing of detergent T without bleach and model detergent T with bleach model detergent was 5.30 g/L. The AEO Biosoft N25-7 (NI) (0.16 g/l) component of model detergent T without bleach and model detergent T with bleach was added separately. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Color difference (L values) was measured using a Color Eye (Macbeth Color Eye 7000 reflectance spectrophotometer). The measurements were made without UV in the incident light and the L value from the CIE Lab color space was extracted. The color difference (L value, L*) represents the darkest black at L*=0, and the brightest white at L*=100. Data is represented as Delta L values meaning the L value of the swatch washed with DNase minus the L value of swatch washed without DNase.

TABLE 6

| Host name | $\Delta L_{Model\ detergent\ T\ w/o\ bleach}$ | $L\text{-value}_{Model\ detergent\ T\ w\ bleach}$ | $\Delta L_{Model\ detergent\ T\ w\ bleach}$ |
|---|---|---|---|
| No enzyme | n/a | 83.49 | n/a |
| Bacillus sp-62451 | 4.47 | 87.01 | 3.51 |
| Bacillus horikoshii | 3.61 | 85.58 | 2.08 |
| Paenibacillus sp-18057 | 4.82 | 87.40 | 3.91 |

Example 4 Cloning and Expression of Bacterial DNases

The DNases were derived from bacterial strains isolated from environmental samples by standard microbiological isolation techniques or from mixed bacterial communities. Isolated pure strains were identified and taxonomy was assigned based on DNA sequencing of the 16S ribosomal genes (Table 7).

TABLE 7

| Strain or community | Source Country | Mature protein SEQ ID: |
|---|---|---|
| Bacillus algicola | Denmark | 53 |
| Xanthan alkaline community J | United States | 56 |
| Xanthan alkaline community D | Spain | 170 |
| Paenibacilus mucilaginosus 3016 | Public China SWISSPROT:H6NAU2 | 65 |
| Bacillus vietnamensis | Himalaya | 59 |
| Bacillus hwajinpoensis | Denmark | 62 |
| Xanthan alkaline community O | Denmark | 173 |
| Bacillus indicus | United States | 68 |
| Bacillus marisflavi | United States | 71 |
| Bacillus luciferensis | United States | 74 |
| Bacillus marisflavi | United States | 77 |
| Bacillus sp. SA2-6 | Public India UNIPROT:A0A0M2T1U6 | 80 |
| Thermobispora bispora DSM 43833 | Public Germany SWISSPROT:D6Y838 | 161 |

Chromosomal DNA was isolated from either pure cultures of the individual strains or from mixed cultured communities in the case of Xanthan alkaline community J, D and O with the DNeasy Blood & Tissue Kit from Qiagen (Hilden, Germany) and subjected to full genome sequencing using Illumina technology. Genome sequencing, the subsequent assembly of reads and the gene discovery (i.e. annotation of gene functions) is known to the person skilled in the art and the service can be purchased commercially.

The genome sequences of the strains Paenibacilus mucilaginosus 3016, Bacillus sp. SA2-6 and Thermobispora bispora DSM 43833 are publically available in the Genbank database under accession numbers NC_016935.1, NZ_LAYY00000000.1 and NC_014165.1 respectively.

The genome sequences were analyzed for putative DNases from the PFAM database families PF14040 and PF07510 (R. D. Finn et al. Nucleic Acids Research (2014), 42:D222-D230) this analysis identified twenty-nine genes encoding putative DNases which were subsequently cloned and recombinantly expressed in Bacillus subtilis. The PF07510 corresponds to the DUF1524 family.

The genes encoding the DNases were amplified by PCR or in the case of Paenibacilus mucilaginosus 3016, Bacillus sp. SA2-6 and Thermobispora bispora ordered as synthetic genes and fused with regulatory elements, affinity purification tag and homology regions for recombination into the pel locus of the B. subtilis genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two Bacillus subtilis chromosomal regions along with strong promoters and a chloramphenicol resistance marker. The SOE PCR method is also described in patent application WO2003/095658.

The genes were expressed under the control of a triple promoter system (as described in WO 99/43835), consisting of the promoters from Bacillus licheniformis alpha-amylase gene (amyL), Bacillus amyloliquefaciens alpha-amylase gene (amyQ), and the Bacillus thuringiensis cryIIIA promoter including stabilizing sequence.

The genes were fused with DNA encoding a Bacillus clausii secretion signal (encoding the following amino acid sequence: MKKPLGKIVASTALLISVAFSSSIASA (SEQ ID NO 24)) replacing the native secretion signal. Furthermore the expression construct results in the addition of a carboxy-terminal poly histidine tail consisting of 6 consecutive histidine residues.

The SOE-PCR products were transformed into Bacillus subtilis and integrated in the chromosome by homologous recombination into the pectate lyase locus. Subsequently a recombinant Bacillus subtilis clone containing the integrated expression construct was grown in liquid culture. The culture broth was centrifuged (20000×g, 20 min) and the supernatant was carefully decanted from the precipitate and used for purification of the enzyme or alternatively sterile filtered supernatant was used directly for assays.

Example 5 Cloning and Expression of Fungal DNases

Strains

Escherichia coli Top-10 strain purchased from TIANGEN (TIANGEN Biotech Co. Ltd., Beijing, China) was used to propagate the expression vector. Aspergillus oryzae MT3568 strain was used for heterologous expression of the gene encoding a polypeptide having homology with polypeptides with phospholipase activity. A. oryzae MT3568 is an amdS (acetamidase) disrupted gene derivative of A. oryzae JaL355 (WO 02/40694) in which pyrG auxotrophy was restored by disrupting the A. oryzae acetamidase (amdS) gene with the pyrG gene.

Media

YPM medium composition: 10 g yeast extract, 20 g Bacto-peptone, 20 g maltose, and deionised water to 1000 ml.

LB plates composed of: 10 g of Bacto-tryptone, 5 g of yeast extract, 10 g of sodium chloride, 15 g of Bacto-agar, and deionised water to 1000 ml.

LB medium composed of: 1 g of Bacto-tryptone, 5 g of yeast extract, and 10 g of sodium chloride, and deionised water to 1000 ml.

COVE sucrose plates were composed of: 342 g of sucrose, 20 g of agar powder, 20 ml of COVE salt solution, and deionized water to 1 liter.

The medium was sterilized by autoclaving at 15 psi for 15 minutes. The medium was then cooled to 60° C. and 10 mM acetamide, 15 mM CsCl, Triton X-100 (50 μl/500 ml) were added.

COVE-2 plate/tube for isolation: 30 g/L sucrose, 20 ml/L COVE salt solution, 10 mM acetamide, 30 g/L noble agar (Difco, Cat #214220).

COVE salt solution composed of: 26 g of $MgSO_4.7H_2O$, 26 g of KCL, 26 g of $KH_2PO_4$, 50 ml of COVE trace metal solution, and deionised water to 1000 ml.

COVE trace metal solution composed of: 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_4.2H_2O$, 10 g of $ZnSO_4.7H_2O$, and deionised water to 1000 ml.

Methyl green DNA test agar plates was made by suspending 42.05 g "DNase Test Agar Base w/methyl green" (HiMedia Laboratories Pvt. Ltd., Inida) in 1000 ml distilled water and sterilized by autoclaving.

Example 6: Cloning, Expression and Fermentation of Fungal DNases

The DNases were derived from fungal strains isolated from environmental samples by standard microbiological isolation techniques. Strains were identified and taxonomy was assigned based on DNA sequencing (Table 6).

TABLE 6

| Donor Organism name | source country | Mature protein SEQ ID: |
|---|---|---|
| *Scytalidium circinatum* | China | 155 |
| *Metarhizium* sp. HNA15-2 | China | 146 |
| *Humicolopsis cephalosporioides* | Argentina | 182 |
| *Alternaria* sp. XZ2545 | China | 116 |
| *Alternaria* sp. | China | 119 |
| *Corynespora cassiicola* | China | 95 |
| *Curvularia lunata* | China | 104 |
| *Endophragmiella valdina* | China | 92 |
| *Setophaeosphaeria* sp. | China | 113 |
| *Setosphaeria rostrate* | China | 89 |
| *Paraphoma* sp. XZ1965 | China | 98 |
| *Metapochonia suchlasporia* | China | 131 |
| *Acremonium* sp. XZ2007 | China | 137 |
| *Acremonium* sp. XZ2414 | China | 149 |
| Isaria tenuipes | China | 152 |
| *Metarhizium lepidiotae* | China | 158 |
| *Sarocladium* sp. XZ2014 | China | 143 |
| *Didymosphaeria futilis* | China | 197 |
| *Pycnidiophora* cf. dispera | China | 167 |
| Pleosporales | China | 191 |
| *Phaeosphaeria* sp. | China | 194 |
| *Roussoella intermedia* | China | 188 |
| *Monilinia fructicola* | Australia | 101 |
| *Westerdykella* sp. AS85-2 | China | 179 |
| *Sporormia fimetaria* | China | 164 |
| *Chaetomium thermophilum* var. *thermophilum* | United kingdom | 125 |

TABLE 6-continued

| Donor Organism name | source country | Mature protein SEQ ID: |
|---|---|---|
| *Daldinia fissa* | China | 134 |
| *Scytalidium thermophilum* | China | 128 |

Chromosomal DNA from individual strains (Table. 6) was isolated by QIAamp DNA Blood Mini Kit (Qiagen, Hilden, Germany). 5 μg of chromosomal DNA were sent for full genome sequencing using Illumina technology. Genomic DNA was isolated from the strains and the genomic sequences were determined, assembled and annotated by standard methods or by purchasing the services commercially.

The genome sequences were analyzed for putative DNases from the PFAM database families DUF1524 (R. D. Finn et al. 2014, *Nucleic Acids Research* 42:D222-D230). This analysis identified 29 genes encoding putative DNases which were subsequently cloned and recombinantly expressed in *Aspergillus oryzae*.

Those 29 genes were amplified by PCR from above isolated fungal genomic DNA. The purified PCR product was cloned into the expression vector pCaHj505 by ligation with an IN-FUSION™ CF Dry-down Cloning Kit (Clontech Laboratories, Inc., Mountain View, Calif., USA) according to the manufacturer's instructions. The ligation mixture was used to transform *E. coli* TOP10 chemically competent cells (described in Strains). Correct colonies containing DNases were selected and verified by DNA sequencing (by SinoGenoMax Company Limited, Beijing, China). The DNase comprising colonies were cultivated overnight in 3 ml of LB medium supplemented with 100 μg of ampicillin per ml. Plasmid DNA was purified using a Qiagen Spin Miniprep kit (Cat. 27106) (QIAGEN GmbH, Hilden, Germany) according to the manufacturer's instructions. Using the SignalP program v.3 (Nielsen et al., 1997, *Protein Engineering* 10: 1-6), the signal peptide and accordingly the mature peptide were predicted.

Protoplasts of *Aspergillus oryzae* MT3568 were prepared according to WO 95/02043. 100 μl of protoplasts were respectively mixed with 2.5-10 μg of each *Aspergillus* expression vector comprising DNases and 250 μl of 60% PEG 4000, 10 mM $CaCl_2$, and 10 mM Tris-HCl pH 7.5 and gently mixed. The mixture was incubated at 37° C. for 30 minutes and the protoplasts were spread onto COVE sucrose plates for selection. After incubation for 4-7 days at 37° C. spores of 4 transformants were inoculated into 3 ml of YPM medium. After 3 days cultivation at 30° C., the culture broths were analyzed by SDS-PAGE using Novex® 4-20% Tris-Glycine Gel (Invitrogen Corporation, Carlsbad, Calif., USA) to identify the transformants producing the largest amount of recombinant DNases with respective estimated mature peptide size.

The hydrolytic activity of the DNase produced by the *Aspergillus* transformants was investigated using methyl green DNA test agar plates. 20 μl aliquots of the culture broth from the different transformants, or buffer (negative control) were distributed into punched holes with a diameter of 3 mm and incubated for 1 hour at 37° C. The plates were subsequently examined for the presence or absence of a white zone around the holes corresponding to phospholipase activity.

Based on those two selection criteria, spores of the best transformant were spread on COVE-2 plates for re-isolation in order to isolate single colonies. Then a single colony was spread on a COVE-2 tube until sporulation. Spores from the best expressed transformant were cultivated in 2400 ml of YPM medium in shake flasks during 3 days at a temperature of 30° C. under 80 rpm agitation. Culture broth was harvested by filtration using a 0.2 μm filter device. The filtered fermentation broth was used for enzyme characterization.

Example 7 Purification of Recombinant DNase by Metal Ion Affinity Chromatography (IMAC)

The culture broth harvested in example 7 was precipitated with ammonium sulfate (80% saturated). Precipitates were re-dissolved in 50 ml of 20 mM PBS pH 7.0, and then filtered through a 0.45 μm filter. The filtered crude protein solution was applied to a 50 ml self-packed Ni sepharose excel affinity column (GE Healthcare, Buckinghamshire, UK) equilibrated with 20 mM PBS pH 7.0 and 300 mM sodium chloride. Proteins were eluted with a linear 0-0.5 M imidazole gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 8: Purification of Recombinant DNase by Hydrophobic Interaction Chromatography (HIC)

The culture broth harvested in example 7 was precipitated with ammonium sulfate (80% saturated). Precipitates were re-dissolved in 50 ml of 20 mM PBS pH 7.0, and ammonium sulfate was replenished to get final concentration 1.8 M. Crude protein solution was filtered through a 0.45 μm filter, and then applied to a 20 ml pre-packed Hiprep Phenyl HP 16/10 column (GE Healthcare, Buckinghamshire, UK) equilibrated with 20 mM PBS pH 7.0 and 1.8 M ammonium sulfate buffer. Proteins were eluted with a linear 1.8 M-0 M ammonium sulfate gradient. Fractions were analyzed by SDS-PAGE using a Mini-PROTEAN TGX Stain-Free 4-15% Precast Gel (Bio-Rad Laboratories, CA, United States). DNase activities of fractions were assessed on BD Difco™ DNase Test Agar with Methyl Green (Becton, Dickinson and Company, New Jersey, United States) at pH 8.0, 40° C. Fractions were pooled containing recombinant protein bands and showing positive activities. Then the pooled solution was concentrated by ultrafiltration.

Example 9: Cloning, Expression and Fermentation of DNases

The DNases were cloned from fungal strains obtained from a variety of sources. *Pyrenochaetopsis* sp. was isolated in Denmark and received from the University of Copenhagen and is the source of the mature polypeptide SEQ ID NO 83. *Penicillium quercetorum* was isolated from a soils sample in Japan and is the source for the mature peptide with SEQ ID NO 110. *Trichoderma reesei* strain RUT-C30 was obtained from Rutgers University and is available from the ATCC, Manassas, Va., USA, as ATCC56765, and is the source for the mature peptide with SEQ ID NO 122. *Neosartorya massa* strain CBS117265 was purchased from the CBS-KNAW Fungal Biodiversity Centre, Utrecht, The Netherlands, and is the source for the mature peptide with SEQ ID NO 185. Genomic DNA was isolated from the strains and the genomic sequences were determined, assembled and annotated by standard methods or by purchasing the services commercially. The annotated genomes were searched for putative DNases with the NUC1_A domain. The predicted peptides with SEQ ID NO: 82, 109, 121, and 184 were found to have a NUC1_A domain and the corresponding DNA sequences encoding them with SEQ ID NO: 81, 108, 120, and 183 were PCR amplified from genomic DNA isolated from *Pyrenochaetopsis* sp., *Penicillium quercetorum, Trichoderma reesei* and *Neosartorya massa* and cloned into the *Aspergillus* expression vector pMStr57(WO04/032648). The sequences of the NUC1_A encoding genes cloned in the expression vector were confirmed, and the expression constructs were transformed into the *Aspergillus oryzae* strain MT3568 (WO 11/057140). Transformants were selected on acetamide during regeneration from protoplasts and subsequently re-isolated under selection (Christensen et al., 1988, *Biotechnology* 6, 1419-1422 and WO 04/032648). For production of the recombinant DNases, a single *Aspergillus* transformant was selected for each DNase and the transformants were cultured in 500 ml baffled flasks containing 150 ml of DAP-4C-1 medium (WO 12/103350). The cultures were shaken on a rotary table at 150 RPM at 30° C. for 4 days. The culture broth was subsequently separated from cellular material by passage through a 0.22 um filter.

Example 10 Chromatographic Purification of Recombinant DNases pH of the filtered sample was adjusted to around pH 7.5 and 1.8M ammonium sulfate was added. The sample was applied to a 5 ml HiTrap™ Phenyl (HS) column on an Akta Explorer. Prior to loading, the column had been equilibrated in 5 column volumes (CV) of 50 mM HEPES+1.8M AMS pH 7. In order to remove unbound material, the column was washed with 5 CV of 50 mM HEPES+1.8M AMS pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min. Protein concentration in the final sample was estimated by measuring absorption at 280 nm.

Example 11 Construction of Phylogenetic Trees

The NUC1 domain includes the polypeptides of the invention having DNase activity and comprises the NUC1_A domain as well as the clusters such as the clades.

A phylogenetic tree was constructed, of polypeptide sequences containing a DUF1524 domain, as defined in PFAM (PF07510, Pfam version 30.0 Finn (2016). Nucleic Acids Research, Database Issue 44:D279-D285). The phylogenetic tree was constructed from a multiple alignment of mature polypeptide sequences containing at least one DUF1524 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

The polypeptide comprises of the DUF1524 domain comprises several motifs one example is [E/D/H]H[I/V/L/F/M]

X[P/A/S] (SEQ ID NO 200) situated in positions corresponding to positions 87 to 91 in *B. cibi* (SEQ ID NO 21). H88 is a catalytic residue involved in the catalytic activity of DUF1524, and part of the HXXP motif. Residue N128 (SEQ ID NO 21) is predicted to bind catalytic metal ions. Another motif which may be comprised by the polypeptides of the invention is [T/D/S][G/N]PQL (SEQ ID NO: 198), where Q is involved in stabilizing backbone of HXXP motif. Yet another motif is [G/T]Y[D/S][R/K/L] (SEQ ID NO 199) corresponding to pos 28 to 31 of SEQ ID NO: 21, where R31 is part of catalytic motif of GYS clade, described below.

The polypeptides in DUF1524 can be separated into distinct sub-clusters, where we denoted one sub-cluster comprising the motif [F/L/Y/I]A[N/R]D[L/I/P/V][(SEQ ID NO 201) as family NUC1. The motif is located at positions corresponding to positions 110 to 114 of SEQ ID NO 21. Another motif characteristic of this domain is C[D/N]T[A/R] (SEQ ID NO 202), located at positions corresponding to positions 43 to 46 of (SEQ ID NO 21).

Generation of NUC1_A Domain

A phylogenetic tree was constructed, of polypeptide sequences containing a NUC1 domain, as defined above. The phylogenetic tree was constructed from a multiple alignment of mature polypeptide sequences containing at least one NUC1 domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *P/oS one* 5(3)) and visualized using iTOL (Letunic & Bork, 2007. *Bioinformatics* 23(1): 127-128). The polypeptides in NUC1 can be separated into at least distinct sub-clusters, one where denoted NUC1_A. A characteristic motif for this subgroup is the motif [DQ][IV]D[H] (SEQ ID NO 203) corresponding to amino acid 85 to 88 in the reference polypeptide (SEQ ID NO: 21). The D at the position corresponding to position 85 of SEQ ID NO 21 is predicted to be involved in binding of catalytic metal ion cofactor.

Generation of Phylogenetic Trees

A phylogenetic tree was constructed, of polypeptide sequences containing a NUC1_A domain, as defined above. The phylogenetic tree was constructed from a multiple alignment of mature polypeptide sequences containing at least one NUC1_A domain. The sequences were aligned using the MUSCLE algorithm version 3.8.31 (Edgar, 2004. *Nucleic Acids Research* 32(5): 1792-1797), and the tree was constructed using FastTree version 2.1.8 (Price et al., 2010, *P/oS one* 5(3)) and visualized using iTOL (Letunic & Bork, 2007, *Bioinformatics* 23(1): 127-128). The polypeptides in NUC1_A can be separated into multiple distinct sub-clusters, or clades, where we denoted the clades listed below. The distinct motifs for each clade are described in details below.

(a) GYS Clade

The GYS clade comprises NUC1_A polypeptides having DNase activity, primarily bacterial class of *bacillus*. The polypeptides of the clade comprises several motifs one example is ASXNRSKG (SEQ ID NO: 205), corresponding to pos 125 to 133 of SEQ ID NO 21, where R (corresponding to position 129 of SEQ ID NO 21) is fully conserved in GYS clade. The motif is located on the surface of the protein, and is putatively involved in DNA binding. The N (corresponding to position 128 of SEQ ID NO 21) is predicted to be involved in catalytic metal ion binding. Another example on a motif within the GYS clade [D/M/L][S/T]GYSR[D/N] (SEQ ID NO: 204) corresponding to positions 26 to 32 of SEQ ID NO 21. The R located at a position corresponding to position 31 of SEQ ID NO 21 is part of catalytic motif of GYS clade. An alignment of the polypeptides of the invention comprised in the clade is shown in FIG. 1.

(b) NAWK Clade

Figure 2:
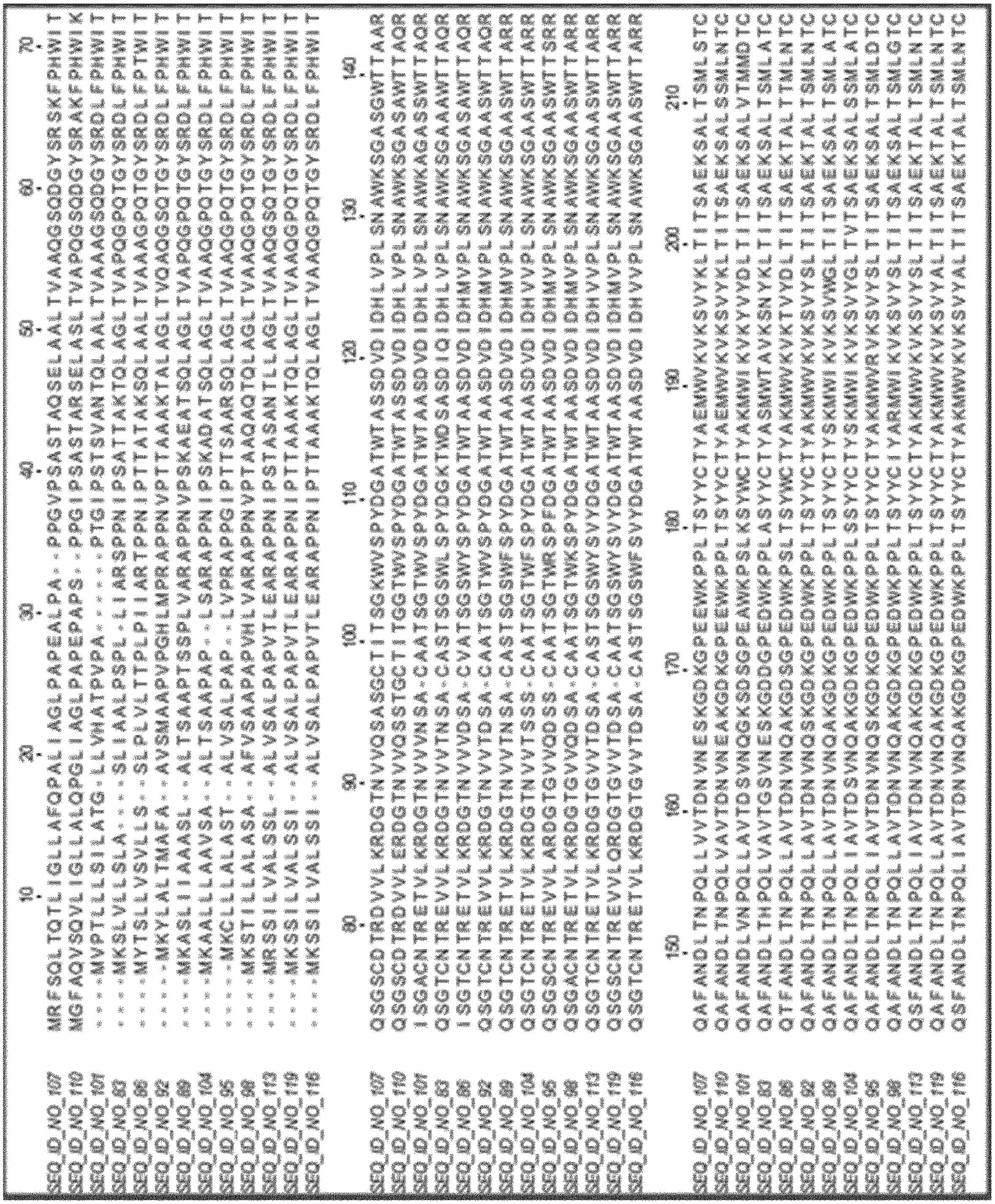
FIG. 2 provides an alignment of the polypeptides of the invention comprised in the NAWK clade.
Figure 3:
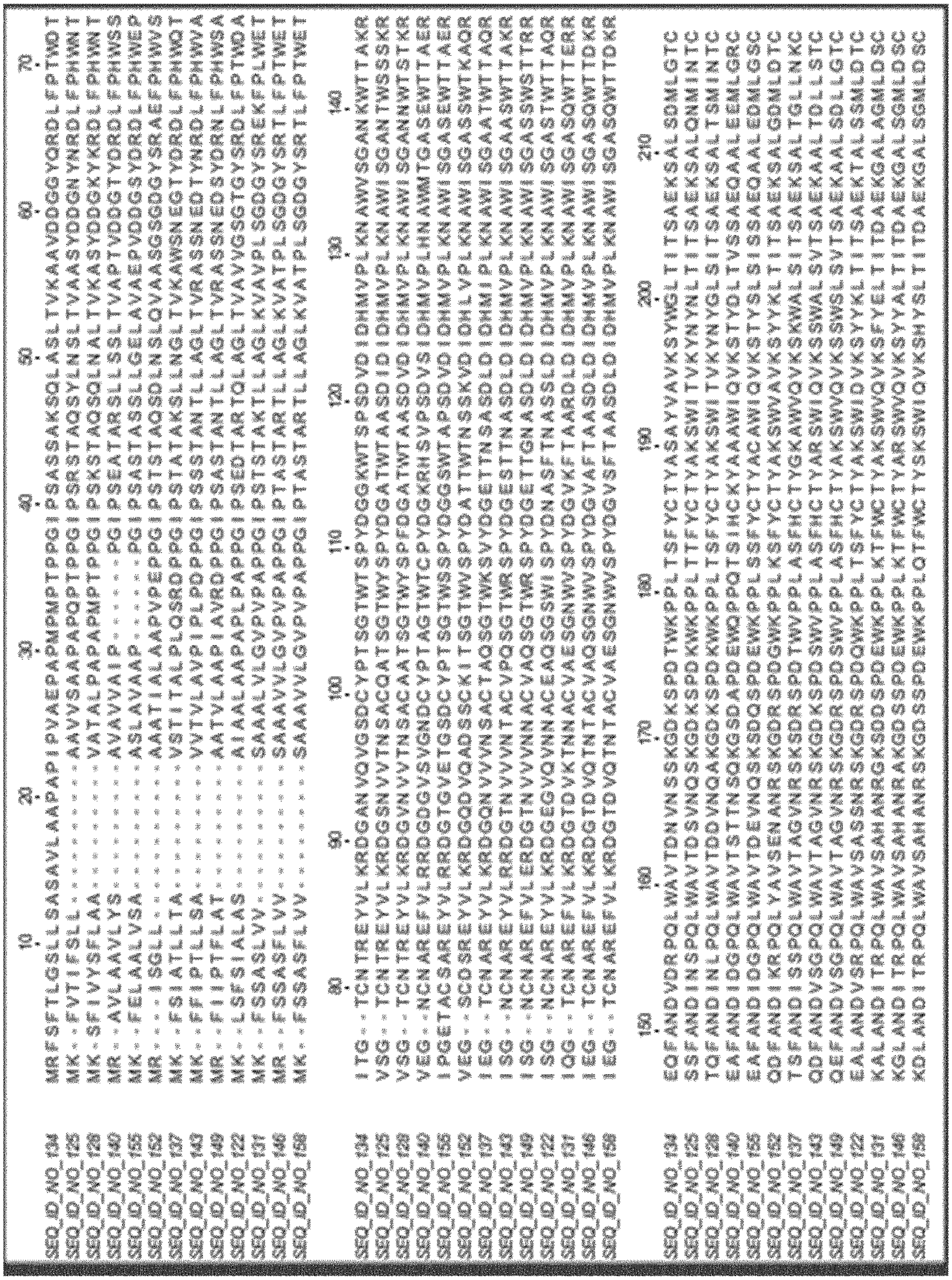
FIG. 3 provides an alignment of the polypeptides of the invention comprised in the KNAW clade.

This clade comprises polypeptides having DNase activity and which comprises primarily of fungal DNases, particularly from the class of dothideomycetes. The polypeptides of this clade comprises one or more motifs, examples of such motifs are [V/I]PL[S/A]NAWK (SEQ ID NO: 206) and NPQL (SEQ ID NO: 207). An alignment of the polypeptides of the invention comprised in the clade is shown in FIG. 2.

(c) KNAW Clade

The polypeptides of this clade comprises primarily polypeptides originating from fungal source e.g. Sordariomycetes taxonomic group. The polypeptides of the clade comprise one or more motifs. Examples of such motifs are P[Q/E]L[W/Y] (SEQ ID NO: 208), which is predicted to be involved in calcium binding. Another motif is [K/H/E]NAW (SEQ ID NO: 209).

Hidden Markov Model (HMM):

The strategy for creating the Hidden Markov Model is as indicated below. The polypeptide sequences of the experimentally verified functional NUC1_A endo-nucleases were analyzed using the HMMER software package (available at http://hmmer.orq; the theory behind profile HMMs is described in R. Durbin, S. Eddy, A. Krogh, and G. Mitchison, Biological sequence analysis: probabilistic models of proteins and nucleic acids, Cambridge University Press, 1998; Krogh et al., 1994; *J. Mol. Biol.* 235:1501-1531), following the user guide which is available from HMMER (Janelia Farm Research Campus, Ashburn, Va., http://hmmer.org). Hidden Markov models are used in a number of databases that aim at classifying proteins, for review see Bateman A and Haft D H (2002) Brief Bioinform 3; 236-245. The output of the HMMER hmmbuild software program is a profile Hidden Markov Model (profile HMM) that characterizes the input sequences. As stated in the user guide, profile HMMs are statistical descriptions of the consensus of a multiple sequence alignment. They use position-specific scores for amino acids (or nucleotides) and position specific scores for opening and extending an insertion or deletion. Compared to other profile based methods, HMMs have a formal probabilistic basis. Profile HMMs for a large number of protein families are publicly available in the PFAM database (Janelia Farm Research Campus, Ashburn, Va.).

The profile HMM was built as follows:

Step 1. Build a Sequence Alignment

The polypeptides shown in SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 113, SEQ ID NO: 116, SEQ ID NO: 119, SEQ ID NO: 122, SEQ ID NO: 125, SEQ ID NO: 128, SEQ ID NO: 131, SEQ ID NO: 134, SEQ ID NO: 137, SEQ ID NO: 140, SEQ ID NO: 143, SEQ ID NO: 146, SEQ ID NO: 149, SEQ ID NO: 152, SEQ ID NO: 155, SEQ ID NO: 158, SEQ ID NO: 161, SEQ ID NO: 164, SEQ ID NO: 167, SEQ ID NO: 170, SEQ ID NO: 173, SEQ ID NO: 176, SEQ ID NO: 179, SEQ ID NO: 182, SEQ ID NO: 185, SEQ ID NO: 188, SEQ ID NO: 191, SEQ ID NO: 194, SEQ ID NO: 197 were aligned using the MUSCLE algorithm version 3.8.31 with default parameters (Edgar, R. C. (2004). *Nucleic Acids Research,* 32(5), 1792-1797), and from this multiple sequence alignment the HMM was built with the software program hmmbuild version 3.1b2 (available at http://hmmer.org). hmmbuild reads the multiple sequence alignment file created by MUSCLE, builds a new profile HMM, and saves the profile HMM to a HMMER profile file. A profile HMM is completely described in a HMMER profile file, which contains all the probabilities that are used to parameterize the HMM. The profile HMM for the set of NUC1_A polypeptides.

Step 2. Test the Specificity and Sensitivity of the Built Profile HMMs

The Profile HMM was evaluated using hmmsearch version 3.1b2 software program with default settings, which reads a Profile HMM file and searches a sequence file for significantly similar sequence matches. The sequence file searched contained all Uniprot sequences annotated with DUF1524 (Pfam DUF1524, Trusted domain cut-off 21.2 Pfam family PF07510, database version 30.0 UniProt annotated 1412 sequences). During the search, the size of the database (Z parameter) was set to 1 billion. This size setting ensures that significant E-values against the current database will remain significant in the foreseeable future. The hmmsearch domT trusted cutoff was set at 157.0.

A hmmer search, using hmmsearch, with the profile HMM generated from the alignment of the 64 NUC1_A experimentally active endo-nucleases, matched 2966 sequences in UniProt above a Trusted domain cut-off of 157.0; all matching pFam domain DUF1524 and all comprising NUC1_A motif [D/Q][IN]DH. This result indicates that members of the NUC1_A family share significant sequence similarity. A hmmer search with a Trusted domain cut-off of 157 was used to separate NUC1_A from other proteins.

Example 12: Wash Assay

Preparation of Biofilm Swatches

Biofilm swatches were made by growing *Brevundimonas* sp. on polyester swatches for two days. The biofilm swatches were rinsed twice in water and dried for 1 h under a flow and subsequently punched into small circles and stored at 4° C. for further use.

Washing Experiment

Biofilm swatches punctures were placed in a deep well 96 format plate. The 96 well plate was placed in a Hamilton robot and subjected to a wash simulation program using the following conditions: Shaking speed: 30 sec at 1000 rpm. Duration of wash cycle: 30 minutes with shaking; temperature 30° C.; Volume of wash liquor (total): 0.5 ml per well. (490 wash liquor+10 ul sample). For screening of wash performance of WT DNases, Model detergent A (3.3 g/L) dissolved in water hardness 15° dH was used. Soil was subsequently added to reach a concentration of 0.7 g soil/L (WFK 09V pigment soil). A 96 well plate was filled with each enzyme sample, and the program was started on the robot. DNases were tested in on concentration 0.05 ppm. The blank consisted of biofilm swatches without any enzyme addition. After completion of the wash simulation cycle, the swatch punctures were removed from the wash liquor and dried on a filter paper. The dried swatch punctures were fixed on a sheet of white paper for scanning. The scanned picture was further used with the software colour-analyzer. Each sample will have an intensity measurement, from the colour analyzer software analysis, that will be used to calculate the delta intensity (remission), by subtracting the intensity of the blank, without enzyme. Values over 70 are visual for the human eye.

Data for KNAW:

TABLE 7

| | REM Without enzyme | REM With enzyme | ΔREM |
|---|---|---|---|
| *Trichoderma reesei* SEQ ID NO 122 | 285 | 372 | 87 |
| *Chaetomium thermophilum* var. SEQ ID NO 125 | 285 | 382 | 97 |
| *Scytalidium thermophilum* SEQ ID NO 128 | 285 | 356 | 71 |
| *Daldinia Fissa* SEQ ID NO 134 | 285 | 391 | 106 |

Data for NAWK:

TABLE 8

| | REM Without enzyme | REM With enzyme | ΔREM |
|---|---|---|---|
| *Pyrenochaetopsis* sp. SEQ ID NO 83 | 285 | 393 | 108 |
| *Monilinia fructicola* SEQ ID NO 101 | 285 | 385 | 100 |

Data for NUC1_A

TABLE 9

| | REM Without enzyme | REM With enzyme | ΔREM |
|---|---|---|---|
| *Sporormia fimetaria* SEQ ID NO 164 | 285 | 378 | 93 |
| *Neosartorya massa* SEQ ID NO 185 | 285 | 383 | 98 |

Example 13 MiniLOM Liquid Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquor of liquid model detergent A were prepared by weighing out and dissolving detergent in water with water with hardness 15° dH. Dosing of model detergent A was 3.33 g/L. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 10

Deep cleaning of biofilm established on polyester by DNases in miniLOM.

| Host name | L-value$_{Model\ detergent\ A}$ | ΔL$_{Model\ detergent\ A}$ |
|---|---|---|
| No enzyme | 88.09 | 0 |
| *Vibressea flavovirens* (SEQ ID NO 86) | 83.48 | 4.61 |
| *Penicillium reticulisporum* (SEQ ID NO 107) | 88.00 | 4.41 |

Example 14 MiniLOM Wash in Powder Detergent

Isolating Laundry Specific Bacterial Strains

One strain of *Brevundimonas* sp. isolated from laundry was used in the present example. The *Brevundimonas* sp. was isolated during a study, where the bacterial diversity in laundry after washing at 15, 40 and 60° C., respectively, was investigated. The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 or 60° C. For washing at 15 and 40° C., Ariel Sensitive White & Colour was used, whereas WFK IEC-A* model detergent was used for washing at 60° C. Ariel Sensitive White & Colour was prepared by weighing out 5.1 g and adding tap water up to 1000 ml followed by stirring for 5 minutes. WFK IEC-A* model detergent (which is available from WFK Testgewebe GmbH) was prepared by weighing out 5 g and adding tap water up to 1300 ml followed by stirring for 15 min. Washing was performed for 1 hour at 15, 40 and 60° C., respectively, followed by 2 times rinsing with tap water for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (TSA) (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Bacterial colonies were selected from countable plates and purified by restreaking twice on TSA. For long time storage, purified isolates were stored at −80° C. in TSB containing 20% (w/v) glycerol (49779; Sigma).

Preparation of Swatches with Biofilm

*Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 1 day at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with water. Optical density (OD) at 600 nm was measured using a spectophometer (POLARstar Omega (BMG Labtech, Ortenberg, Germany). Fresh TSB diluted twice with water was inoculated to an $OD_{600\ nm}$ of 0.03, and 1.6 mL was added into each well of a 12-well polystyrene flat-bottom microplate (3512; Corning Incorporated, Corning, N.Y., USA), in which a round swatch (diameter 2 cm) of sterile Polyester WFK30A was placed. After incubation (24 h at 15° C. with shaking (100 rpm), swatches were rinsed twice with 0.9% (w/v) NaCl.

Wash Experiment

Wash liquors of powder model detergent T without bleach and powder model detergent T with bleach were prepared by weighing out and dissolving detergents in water with water with hardness 15° dH. Dosing of detergent T without bleach and model detergent T with bleach model detergent was 5.30 g/L. The AEO Biosoft N25-7 (NI) (0.16 g/I) component of model detergent T without bleach and model detergent T with bleach was added separately. Pigment soil (Pigmentschmutz, 09V, wfk, Krefeld, Germany) (0.7 g/L) was added to the wash liquor. DNase (0.5 ppm) was added to the wash liquor. As control, wash liquor without DNase was made. Wash liquor (10 ml) was added to a 50 ml test tube, in which five rinsed swatches with *Brevundimonas* sp. biofilm and five sterile polyester (WFK30A) swatches were placed. Test tubes were placed in a Stuart rotator (Mini LOM) for 1 hour at 30° C. Swatches were rinsed twice with tap water and dried on filter paper over night. Colour difference (L values) was measured using a Colour Eye (Macbeth Colour Eye 7000 reflectance spectrophotometer). The measurements were made without UV in the incident light and the L value from the CIE Lab colour space was extracted. The colour difference (L value, L*) represents the darkest black at L*=0, and the brightest white at L*=100. Data is represented as Delta L values meaning the L value of the swatch washed with DNase minus the L value of swatch washed without DNase.

TABLE 11

Deep cleaning of biofilm by *Vibressea flavovirens* DNase in miniLOM.

| Detergent | Type of textile | Soil (g/L) | DNase conc. (ppm) | L-value | $L\text{-value}_{with\ DNase} - L\text{-value}_{without\ DNase}$ |
|---|---|---|---|---|---|
| Model detergent T w/o bleach | Polyester | 0.7 | 0 | 85.58 | |
| Model detergent T w/o bleach | Polyester | 0.7 | 0.5 | 82.39 | 3.19 |
| Model detergent T w bleach | Polyester | 0.7 | 0 | 85.62 | |
| Model detergent T w bleach | Polyester | 0.7 | 0.5 | 84.95 | 0.67 |

The invention claimed is:

1. A composition comprising (a) at least 0.002 ppm of a polypeptide having DNase activity, wherein the polypeptide comprises the motif HXXP and has at least 95% sequence identity to the polypeptide shown in SEQ ID NO: 21, (b) one or more polyol(s) selected from the group consisting of glycerol, (mono, di, or tri) propylene glycol, ethylene glycol, polyethylene glycol, sugar alcohols, sorbitol, mannitol, erythritol, dulcitol, inositol, xylitol and adonitol, and (c) a surfactant, wherein the composition is formulated as a bar, a homogenous tablet, and a tablet having two or more layers, a pouch having one or more compartments, a regular or compact powder, a granule, a paste, a gel, or a liquid.

2. The composition of claim 1, wherein the polypeptide having DNase activity has at least 97% sequence identity to the polypeptide shown in SEQ ID NO: 21.

3. The composition of claim 1, wherein the polypeptide having DNase activity comprises the amino acid sequence of SEQ ID NO: 21.

4. The composition of claim 1, wherein the polypeptide having DNase activity consists of the amino acid sequence of SEQ ID NO: 21.

5. The composition of claim 1, wherein the polypeptide having DNase activity is a variant of the polypeptide of SEQ ID NO: 21, wherein the variant has DNase activity and comprises one or more amino acid substitutions, or one or more amino acid deletions, or one or more amino acid insertions or any combination thereof in 1, 2, 3, 4, 5, 6, 7, 8, 9 or 10 positions.

6. The composition of claim 1, wherein the polypeptide having DNase activity comprises one or more of the motifs selected from the group consisting of

```
                                   (SEQ ID NO 198)
[T/D/S][G/N]PQL,

                                   (SEQ ID NO 199)
[G/T]Y[D/S][R/K/L],

                                   (SEQ ID NO 200)
[E/D/H]H[I/V/L/F/M]X[P/A/S],

                                  (SEQ ID NO: 201)
[F/L/Y/I]A[N/R]D[L/I/P/V]
and

                                  (SEQ ID NO: 202)
C[D/N]T[A/R].
```

7. The composition of claim 1, wherein the polypeptide having DNase activity comprises a GYS motif and one or both of the motifs [D/M/L][S/T]GYSR[D/N] (SEQ ID NO: 204) or ASXNRSKG (SEQ ID NO: 205).

8. The composition of claim 1, further comprising a second enzyme.

9. The composition of claim 8, wherein the second enzyme is a protease.

10. The composition of claim 8, wherein the second enzyme is an amylase.

11. The composition of claim 8, wherein the second enzyme is a lipase.

12. The composition of claim 1, wherein the surfactant is an anionic or a nonionic surfactant.

13. The composition of claim 1, further comprising a polymer.

14. The composition of claim 1, wherein the composition is in the form of a granule comprising a core and a coating that has one or more layer(s) surrounding the core.

15. The composition of claim 1, wherein the composition is in the form of a liquid.

* * * * *